US007667041B2

(12) United States Patent
Kimura et al.

(10) Patent No.: US 7,667,041 B2
(45) Date of Patent: Feb. 23, 2010

(54) CINNAMIDE COMPOUND

(75) Inventors: Teiji Kimura, Tsukuba (JP); Koki Kawano, Tsukuba (JP); Eriko Doi, Tsukuba (JP); Noritaka Kitazawa, Tsukuba (JP); Kogyoku Shin, Tsukuba (JP); Takehiko Miyagawa, Tsukuba (JP); Toshihiko Kaneko, Tsukuba (JP); Koichi Ito, Tsukuba (JP); Mamoru Takaishi, Tsukuba (JP); Hiroaki Hagiwara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 555 days.

(21) Appl. No.: 11/136,355

(22) Filed: May 25, 2005

(65) Prior Publication Data

US 2006/0004013 A1 Jan. 5, 2006

(30) Foreign Application Priority Data

May 26, 2004 (JP) ............................. 2004-155790
Oct. 26, 2004 (JP) ............................. 2004-310909

(51) Int. Cl.
*C07D 401/00* (2006.01)
*A61K 31/54* (2006.01)

(52) U.S. Cl. ....................................... 546/210; 514/326

(58) Field of Classification Search ................. 546/194, 546/207, 208, 209; 514/317, 318, 319
See application file for complete search history.

(56) References Cited

U.S. PATENT DOCUMENTS 4,910,200 A 3/1990 Curtze et al.
5,281,626 A 1/1994 Oinuma et al.
5,563,162 A 10/1996 Oku et al.
5,985,856 A 11/1999 Stella et al.
6,235,728 B1 5/2001 Golik et al.
6,306,870 B1 10/2001 Bombrun
7,053,087 B1 5/2006 Beatch et al.
7,138,414 B2 11/2006 Schoenafinger et al.
7,300,936 B2 11/2007 Parker et al.
2001/0051642 A1 12/2001 Ahn et al.
2002/0128263 A1 9/2002 Mutel et al.
2003/0195201 A1 10/2003 Bo et al.
2003/0208082 A1 11/2003 Mutel et al.
2003/0225070 A1 12/2003 Mutel et al.
2004/0034096 A1 2/2004 Jolidon et al.
2004/0038969 A1 2/2004 Doherty et al.
2004/0063770 A1 4/2004 Ahn
2004/0087798 A1 5/2004 Yamada
2004/0127494 A1 7/2004 Parker et al.
2004/0127555 A1 7/2004 Snow et al.
2004/0152743 A1 8/2004 Schoenafinger et al.
2004/0192743 A1 9/2004 Mjalli et al.
2004/0235864 A1 11/2004 Graczyk et al.
2005/0070538 A1 3/2005 Cheng et al.
2005/0131043 A1 6/2005 Mutel et al.
2005/0187277 A1 8/2005 Mjalli et al.
2006/0004013 A1 1/2006 Kimura et al.
2007/0117798 A1* 5/2007 Kimura et al. ........... 514/230.5
2007/0117839 A1 5/2007 Kimura et al.
2007/0219181 A1* 9/2007 Kimura et al. ......... 514/211.09
2008/0070902 A1* 3/2008 Kimura et al. ......... 514/217.09
2008/0085894 A1 4/2008 Parker et al.
2008/0096892 A1 4/2008 Cheng et al.
2008/0280948 A1 11/2008 Baumann et al.
2009/0048213 A1 2/2009 Kimura et al.

FOREIGN PATENT DOCUMENTS

DE 3541716 A1 5/1987
EP 0219756 A1 4/1987
EP 0 973 768 B1 7/2003
EP 1 757 591 A1 2/2007
EP 1 808 432 A1 7/2007
EP 1 953 151 A1 8/2008
EP 1 953 158 A1 8/2008

(Continued)

OTHER PUBLICATIONS

Foreign Search Report: Application #2006146070/04(050338) dated 2008.*

(Continued)

*Primary Examiner*—Rita J Desai
*Assistant Examiner*—John Mabry
(74) *Attorney, Agent, or Firm*—Birch, Stewart, Kolasch & Birch, LLP

(57) ABSTRACT

The present invention relates to a compound represented by Formula (I):

(I)

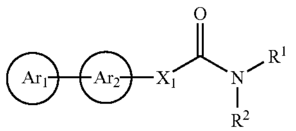

(wherein $Ar_1$ represents an imidazolyl group which may be substituted with 1 to 3 substituents; $Ar_2$ represents a pyridinyl group, a pyrimidinyl group, or a phenyl group which may be substituted with 1 to 3 substituents; $X_1$ represents (1) —C≡C— or (2) a double bond etc. which may be substituted; $R^1$ and $R^2$ represent, for example, a C1-6 alkyl group or C3-8 cycloalkyl group which may be substituted)

or a pharmacologically acceptable salt thereof and to the use thereof as pharmaceutical agents. The object of the present invention is to find a therapeutic or preventive agent for diseases caused by Aβ. According to the present invention, a therapeutic or preventive agents for diseases caused by Aβ can be provided.

4 Claims, No Drawings

FOREIGN PATENT DOCUMENTS

| | | | |
|---|---|---|---|
| GE | P 2006 3920 | B | 5/2006 |
| JP | 3-206042 | A | 9/1991 |
| JP | 7-2780 | A | 1/1995 |
| JP | 8283219 | A | 10/1996 |
| JP | 10-510512 | A | 10/1998 |
| JP | 11-228548 | A | 8/1999 |
| JP | 3176365 | B2 | 4/2001 |
| JP | 2001-508767 | A | 7/2001 |
| JP | 2001-527083 | A | 12/2001 |
| JP | 2003-206280 | A | 7/2003 |
| JP | 2004-531519 | A | 10/2004 |
| JP | 2005-518371 | A | 6/2005 |
| JP | 2005-526807 | A | 9/2005 |
| JP | 2005-531596 | A | 10/2005 |
| JP | 2005-533092 | A | 11/2005 |
| JP | 2006-502247 | T | 1/2006 |
| JP | 2007-504282 | T | 3/2007 |
| WO | WO91/12237 | A1 | 8/1991 |
| WO | WO-96/10559 | A1 | 4/1996 |
| WO | WO97/43287 | A1 | 11/1997 |
| WO | WO-98/24785 | A1 | 6/1998 |
| WO | WO-00/07993 | A1 | 2/2000 |
| WO | WO-00/50391 | A1 | 8/2000 |
| WO | WO-00/51981 | A1 | 9/2000 |
| WO | WO-01/68585 | A1 | 9/2001 |
| WO | WO01/81312 | A2 | 11/2001 |
| WO | WO-03/053912 | A1 | 7/2003 |
| WO | WO-03/082292 | A1 | 10/2003 |
| WO | WO-03/101927 | A1 | 12/2003 |
| WO | WO-2004/007455 | A1 | 1/2004 |
| WO | WO-2005/020921 | A2 | 3/2005 |
| WO | WO-2005/115990 | A1 | 12/2005 |
| WO | WO-2006/046575 | A1 | 5/2006 |
| WO | WO-2006/112550 | A2 | 10/2006 |
| WO | WO-2007/034282 | A2 | 3/2007 |
| WO | WO-2007/060810 | A1 | 5/2007 |
| WO | WO-2008/013213 | A1 | 1/2008 |
| WO | WO-2008-097538 | A1 | 8/2008 |
| WO | WO-2008/137139 | A1 | 11/2008 |
| WO | WO-2008/156580 | A1 | 12/2008 |
| WO | WO-2009/020580 | A1 | 2/2009 |

OTHER PUBLICATIONS

W. J. Ross et al., Journal of Medicinal Chemistry, 1973, vol. 16, No. 4, pp. 347-352.

D. C. Guiroy et al., Acta Neuropathol (1991) 82: 87-92.

Office Action dated Jul. 11, 2008, that issued in connection with copending U.S. Appl. No. 11/594,150.

Masahiko Kato et al., Chem. Pharm. Bull., 42 (12), 2546-2555 (1994).

Yuesong Gong et al.; Proceeding National Academy of Science, vol. 100, No. 18, pp. 10417-10422, Sep. 2, 2003.

Christoph Hock et al.; Neuron, vol. 38, No. 4, pp. 547-554, May 22, 2003.

Joseph T. Jarrett et al.; Biochemistry; vol. 32, No. 18, pp. 4693-4697, May 11, 1993.

George G. Glenner et al.; Biochemical and Biophysical Research Communications; vol. 120, No. 3, pp. 885-890, May 16, 1984.

Colin L. Masters et al.; Proceeding National Academy of Science; vol. 82, No. 12, pp. 4245-4249, Jun. 1985.

Gunnar K. Gouras et al.; American Journal of Pathology, vol. 156, No. 1, pp. 15-20, Jan. 2000.

D. Scheuner et al.; Nature Medicine, vol. 2, No. 8, pp. 864-870, Aug. 1996.

Mark S. Forman et al.; The Journal of Biological Chemistry; vol. 272, No. 51, pp. 32247-32253, Dec. 19, 1997.

Mark S. Shearman et al.; Biochemistry; vol. 39, No. 30, pp. 8698-8704, 2000.

Huw D. Lewis et al.; Biochemistry, vol. 42, No. 24, pp. 7580-7586, 2003.

Thomas A. Lanz et al., The Journal of Pharmacology and Experimental Therapeutics; vol. 39, No. 1, pp. 49-55, 2004.

Gwendolyn T. Wong et al.; The Journal of Biological Chemistry, vol. 279, No. 13, pp. 12876-12882, Mar. 26, 2004.

John P. Blass; Journal of Neuroscience Research, vol. 66, No. 1, pp. 851-856, 2001.

Genevieve Evin et al.; NeuroReport; vol. 13, No. 5, pp. 719-723, Apr. 16, 2002.

Osamu Yasuhara et al.; Neuroscience Letters, vol. 171, Nos. 1 and 2, pp. 63-66, 1994.

Jan T. Keller et al.; Nature Medicine, vol. 2, No. 1, pp. 93-95, Jan. 1996.

Takahiko Tokuda et al.; Annals Neurology, vol. 41, No. 2, pp. 271-273, Feb. 1997.

Yorihide Hayashi et al.; Brain Research; vol. 789, No. 2, pp. 307-314, 1998.

Helene Barelli et al.; Molecular Medicine, vol. 3, No. 10, pp. 695-707, Oct. 1997.

Michael E. Calhoun et al.; Proceeding National Academy of Science, vol. 96, No. 24, pp. 14088-14093, Nov. 23, 1999.

B. Dermaut et al.; Brain, vol. 124, No. 12, pp. 2383-2392, 2001.

P. Cras et al.; Acta Neuropathol, vol. 96, No. 3, pp. 253-260, 1998.

Martin C. Herzig et al.; Nature Neuroscience, vol. 7, No. 9, pp. 954-960, Sep. 2004.

Sjoerd G. Van Duinen et al.; Proceeding National Academy of Science, vol. 84, No. 16, pp. 5991-5994, Aug. 1987.

Efrat Levy et al.; Science, vol. 248, No. 4959, pp. 1124-1126, 1990.

Simon M. Laws et al.; Neurobiology of Aging, vol. 23, No. 1, pp. 55-58, 2002.

E. Vaucher et al.; Experimental Neurology, vol. 175, No. 2, pp. 398-406, 2002.

Dave Morgan et al.; Nature, vol. 408, No. 6815, pp. 982-985, Dec. 2000.

Paula M. Moran et al.; Proceeding National Academy of Science, vol. 92, No. 12, pp. 5341-5345, 2002.

Milla Koistinaho et al.; Proceeding National Academy of Science, vol. 99, No. 3, pp. 1610-1615, Feb. 5, 2002.

Fangyi Zhang et al.; The Journal of Neuroscience, vol. 17, No. 20, pp. 7655-7661, Oct. 15, 1997.

Marcin Sadowski et al.; Neurochemical Research, vol. 29, No. 6, pp. 1257-1266, Jun. 2004.

S. O'Riordan et al.; Neurology, vol. 59, No. 7, pp. 1108-1110, Oct. 2002.

Jochen Gehrmann et al.; Glia; vol. 15, No. 2, pp. 141-151, 1995.

Wanda F. Reynolds et al.; Experimental Neurology, vol. 155, No. 1, pp. 31-41, 1999.

Douglas H. Smith et al.; NeuroMolecular Medicine, vol. 4, No. 1 and 2, pp. 59-72, 2003.

Miho Matsubara-Tsutsui et al.; American Journal of Medical Genetics, vol. 114, No. 3, pp. 292-298, 2002.

Marina D. Kirkitadze et al.; Journal of Neuroscience Research, vol. 69, No. 5, pp. 567-577, 2002.

Bernd O. Evert et al.; The Journal of Neuroscience, vol. 21, No. 15, pp. 5389-5396, Aug. 1, 2001.

D.M.A. Mann et al.; Neuroscience Letters, vol. 109, No. 1 and 2, pp. 68-75, 1990.

James Primavera et al.; Journal of Alzheimer's Disease, vol. 1, No. 3, pp. 183-193, 1999.

Benoit I. Giasson et al.; NeuroMolecular Medicine, vol. 4, No. 1 and 2, pp. 49-58, 2003.

Eliezer Masliah et al.; Proceeding National Academy of Science; vol. 98, No. 21, pp. 12245-12250, Oct. 9, 2001.

Marta Barrachina et al.; Neurochemistry International; vol. 46, No. 3, pp. 253-260, 2005.

M.L. Schmidt et al.; Acta Neuropathol, vol. 95, No. 2, pp. 117-122, 1998.

H. Ito et al.; Neuropathology and Applied Neurobiology, vol. 17, No. 5, pp. 365-373, 1991.

S.M. Rosso et al.; Annals of the New York Academy of Science, vol. 920, pp. 115-119, 2000.

M. Tolnay et al.; Neuropathology and Applied Neurobiology, vol. 25, No. 4, pp. 295-305, 1999.

Lee-Way Jin et al., American Journal of Pathology, vol. 164, No. 3, pp. 975-985, Mar. 2004.
Shoichi Sasaki et al.; Acta Neuropathol, vol. 97, No. 5, pp. 463-468, 1999.
A. Tamaoka et al.; Journal of Neurology, vol. 247, No. 8, pp. 633-635, 2000.
Ronald L. Hamilton et al.; Acta Neuropathol, vol. 107, No. 6, pp. 515-522, 2004.
Bradley J. Turner et al.; Neurochemical Research, vol. 29, No. 12, pp. 2281-2286, 2004.
Roy O. Weller; Journal of Neuropathology and Experimental Neurology, vol. 57, No. 10, pp. 885-894, Oct. 1998.
Gerald D. Silverberg et al.; Lancet Neurology, vol. 2, No. 8, pp. 506-511, Aug. 2003.
Roy O. Weller et al.; Annals of the New York Academy of Science, vol. 903, pp. 110-117, 2000.
H. Y. Yow et al.; Neuropathology and Applied Neurobiology; vol. 28, p. 149, 2002.
Roy O. Weller et al.; Annals of the New York Academy of Science, vol. 977, pp. 162-168, 2002.
Margaret J. Smith et al.; Annals of Neurology, vol. 49, No. 1, pp. 125-129, 2001.
Richard Crook et al.; Nature Medicine, vol. 4, No. 4, pp. 452-455, Apr. 1998.
Craig S. Atwood, Brain Research Review; vol. 43, No. 1, pp. 164-178, 2003.
Jonathan D. Lowenson et al.; Trends in Cardiovascular Medicine, vol. 4, No. 1, pp. 3-8, 1994.
Andrew B. Singleton et al.; vol. 123, No. 12, pp. 2467-2474, 2000.
W.F. Gattaz et al.; Journal of Neural Transmission, vol. 111, No. 5, pp. 591-601, 2004.
A. Assini et al.; Neurology, vol. 63, No. 5, pp. 828-831, 2004.
Guido R.Y. DeMeyer et al.; Circulation Research, vol. 90, No. 11, pp. 1197-1204, 2002.
J. G. Varnes et al., Bioorganic & Medicinal Chemistry Letters 14 (2004) 1645-1649.
H. Stark et al., Pharmazie 52 (1997) 6, 419-423.
M. Kajbaf et al., Journal of Chromatography, 575 (1992) 75-85.
S. L. Marcus et al., Cancer Research 45, 112-115, Jan. 1985.
H. L. Yale et al., Yale et al., 1966. vol. 9. No. 1, 42-46.
S. M. Catalano et al., Current Topics in Medicinal Chemistry, vol. 6, 597-608.
T. A. Comery et al., "Acute γ-Secretase Inhibition Improves Contextual Fear Conditioning in the Tg2576 Mouse Model of Alzheimer's Disease," The Journal of Neuroscience, Sep. 28, 2005, vol. 25, No. 39, pp. 8898-8902.
T. A. Comery et al., "Acute γ-secretase inhibition improves condition in the TG2576 mouse model of Alzheimer's disease," Society for Neurological Annual Meeting (2003) Abstracts, Program No. 525. 21.
Search Report issued May 27, 2009, in connection with Georgia Patent Application No. AP 2006 010709 (with English translation).
International Search Report issued on Sep. 19, 2008, in connection with PCT Internatiional Application No. PCT/JP2008/053887.
Office Action issued on Jul. 16, 2009, in connection with U.S. Appl. No. 11/715,440.
Office Action issued on Jul. 30, 2009, in connection with U.S. Appl. No. 12/200,731.
Office Action issued on Jul. 1, 2009, in connection with Russian Application No. 2008125426/04(030920).

* cited by examiner

CINNAMIDE COMPOUND

CROSS-REFERENCE TO RELATED APPLICATION

This application claims priority dates under the Paris Convention based on Japanese Patent Applications No. 2004-155790 and No. 2004-310909 filed in Japan on May 26, 2004 and Oct. 26, 2004, respectively. Therefore, the contents of those Japanese applications are hereby incorporated by reference.

BACKGROUND OF THE INVENTION

1. Field of the Invention

The present invention relates to a pharmaceutical agent, particularly an agent of reducing amyloid beta (hereinafter referred to as Aβ) production, which is effective in the treatment of neurodegenerative diseases caused by Aβ, such as Alzheimer's disease and Down syndrome.

2. Description of the Related Art

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, and seven others, Related Articles, Links Alzheimer's disease-affected brain: presence of oligomeric Aβ ligands (ADDLs) suggests a molecular basis for reversible memory loss, Proceeding National Academy of Science USA, Sep. 2, 2003, 100(18), p. 10417-22;

Nitsch R M, and 16 others, Antibodies against β-amyloid slow cognitive decline in Alzheimer's disease, Neuron, 22, May, 2003, 38(4), p. 547-554.). The main components of Aβ protein are Aβ40 consisting of 40 amino acids and Aβ42 having two additional amino acids at the C-terminal. The Aβ40 and Aβ42 tend to aggregate (for example, see Jarrett J T, and 2 others, The carboxy terminus of the β amyloid protein is critical for the seeding of amyloid formation: implications for the pathogenesis of Alzheimer's disease, Biochemistry, 11, May, 1993, 32(18), p. 4693-4697) and constitute main components of senile plaques (for example, Glenner GG, and another, Alzheimer's disease: initial report of the purification and characterization of a novel cerebrovascular amyloid protein, Biochemical and Biophysical Research Communications, 1984, May 16, 120(3), p. 885-90; and Masters C L, and six others, Amyloid plaque core protein in Alzheimer disease and Down syndrome, Proceeding National Academy of Science USA, 1985, June, 82(12), p. 4245-4249.), and furthermore, it is known that mutations of APP and presenelin genes, which is observed in familial Alzheimer's disease, increase production of Aβ40 and Aβ42

(for example, see Gouras G K, and eleven others, Intraneuronal Aβ42 accumulation in human brain, American Journal of Pathology, 2000, January, 156(1), p. 15-20;

Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870;

Forman M S, and 4 others, Differential effects of the swedish mutant amyloid precursor protein on β-amyloid accumulation and secretion in neurons and nonneuronal cells, Journal of Biological Chemistry, 1997, Dec. 19, 272(51), p. 32247-32253.). Therefore, compounds which reduce production of Aβ40 and Aβ42 are expected as an agent for controlling progress of Alzheimer's disease or for preventing the disease.

These Aβs are produced when APP is cleaved by beta secretase and subsequently clipped by gamma secretase. In consideration of this, creation of inhibitors of γ secretase and β secretase has been attempted for the purpose of reducing production of Aβs. Many of these secretase inhibitors already known are peptides or peptidomimetics such as L-685,458 (for example, see Shearman M S, and nine others, L-685,458, an aspartyl protease transition state mimic, is a potent inhibitor of amyloid β-protein precursor γ-secretase activity, Biochemistry, Aug. 1, 2000, 39(30), p. 8698-8704.) and LY-411575 (for example, see Shearman MS, and six others, Catalytic site-directed γ-secretase complex inhibitors do not discriminate pharmacologically between Notch S3 and β-APP cleavages, Biochemistry, 2003, Jun. 24, 42(24), p. 7580-7586;

Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), Journal of Pharmacology and Experimental Therapeutics, 2004, April, 309(1), p. 49-55; and Wong G T, and twelve others, Chronic treatment with the γ-secretase inhibitor LY-411,575 inhibits β-amyloid peptide production and alters lymphopoiesis and intestinal cell differentiation, Journal of Biological Chemistry, 2004, Mar. 26, 279(13), p. 12876-12882.).

BRIEF SUMMARY OF THE INVENTION

As mentioned above, compounds which prevent production of Aβ40 and Aβ42 from APP are expected as an preventive or therapeutic agent for diseases caused by Aβ represented by Alzheimer's disease. However, non-peptide compounds which prevent production of Aβ40 and Aβ42 and have an excellent medicinal effect have not been known. Therefore, a novel low molecular compound that inhibits production of Aβ40 and Aβ42 is demanded.

The present inventors have conducted intensive studies and first discovered non-peptidic cinnamide compounds which inhibit production of Aβ40 and Aβ42 from APP and discovered preventive or therapeutic agents for diseases caused by Aβ, represented by Alzheimer's disease, thereby completed the present invention.

That is, the present invention relates to the followings:

1) A compound or a pharmacologically acceptable salt thereof represented by Formula (I):

(I)

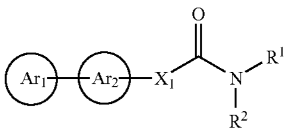

(wherein $Ar_1$ represents an imidazolyl group which may be substituted with 1 to 3 substituents selected from Substituent Group A1 shown below; $Ar_2$ represents a pyridinyl group, a pyrimidinyl group, or a phenyl group which may be substituted with 1 to 3 substituents selected from Substituent Group A2 shown below; $X_1$ represents (1) —C≡C— or (2) —$CR^3$═$CR^4$— (wherein $R^3$ and $R^4$ represents a substituent selected from Substituent Group A3 shown below); and (1) $R^1$ and $R^2$ represent groups selected from Substituent Group A4 shown below or $R^1$ and $R^2$, together with a nitrogen atom to which they bind, form one of the following groups:

(2-1) a 5- to 11-membered non-aromatic heterocyclic group represented by Formula (II):

(II)

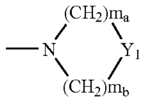

(wherein $Y_1$ represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$═$CR^6$— (wherein $R^5$ and $R^6$ represent substituents selected from Substituent Group A4 shown below), (11) a single bond or (12) >C═$CR^{13}R^{14}$ (wherein $R^{13}$ and $R^{14}$ represent substituents selected from Substituent Group A4 shown below); and $m_a$ and $m_b$ represent an integer of 0 to 4) which may be substituted with 1 to 4 substituents selected from Substituent Group A4;

(2-2) a 6- to 20-membered non-aromatic heterocyclic group represented by Formula (III):

(III)

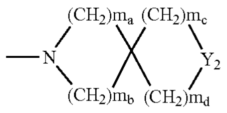

(wherein $Y_2$ represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$═$CR^6$— (wherein $R^5$ and $R^6$ represent substituents selected from Substituent Group A4 shown below or $R^5$ and $R^6$, together with a carbon atom to which they bind, form a 6- to 14-membered aromatic hydrocarbon ring group or a 6- to 14-membered non-aromatic hydrocarbon ring group) or (11) a single bond; and $m_a$, $m_b$, $m_c$ and $m_d$ represent an integer of 0 to 4) which may be substituted with 1 to 4 substituents selected from Substituent Group A4;

(2-3) a 9- to 16-membered non-aromatic heterocyclic group represented by Formula (IV):

(IV)

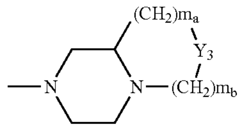

(wherein $Y_3$ represents (1) —NH—, (2) —O—, (3) —S—, (4) —SO—, (5) —$SO_2$—, (6) —$CH_2$—, (7) —CO—, (8) —CONH—, (9) —NHCO— or (10) a single bond; and $m_a$ and $m_b$ are the same as defined above) which may be substituted with 1 to 4 substituents selected from Substituent Group A4;

(2-4) a group represented by the following formula:

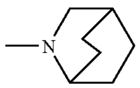,
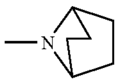,
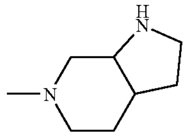
or
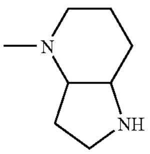

which may be substituted with 1 to 4 substituents selected from Substituent Group A4 shown below;

(2-5) a group represented by the following formula:

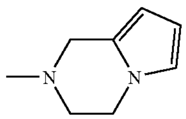,
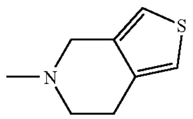,
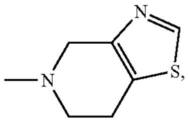,
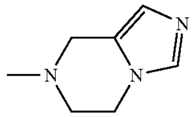,
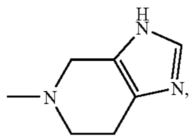,
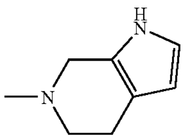,
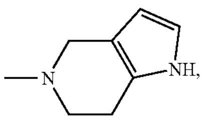,
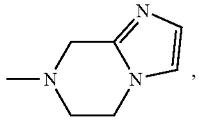,
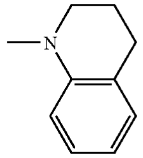,
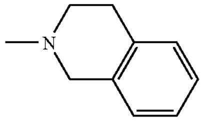, -continued

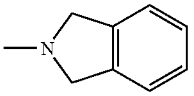

or

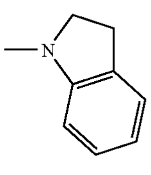

which may be substituted with 1 to 4 substituents selected from Substituent Group A4 shown below; or $R^1$ and $R^2$, together with —$X_1$—CO—N—, form one of the following ring structures:

(3-1) a cyclic group represented by Formula (V):

(V)

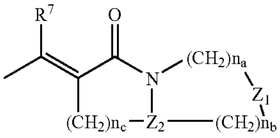

(wherein $Z_1$ represents (1) —NH—, (2) —O—, (3) —S—, (4) —SO—, (5) —$SO_2$—, (6) —$CH_2$—, (7) —CO—, (8) —CONH—, (9) —NHCO— or (10) a single bond; $Z_2$ represents (1) a methine group or (2) a nitrogen atom; $R^7$ represents a substituent selected from Substituent Group A3 shown below; and $n_a$, $n_b$ and $n_c$ represent an integer of 0 to 4) which may be substituted with 1 to 4 substituents selected from Substituent Group A4;

(3-2) a cyclic group represented by Formula (VI):

(VI)

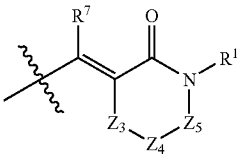

(wherein $Z_3$ represents (1) a single bond, (2) —CO—, (3) —$(CH_2)n_d$— (wherein $n_d$ represents an integer of 1 to 3) or (4) —$CR^8R^9$— (wherein $R^8$ and $R^9$ represent a substituent selected from Substituent Group A4 shown below;

$Z_4$ represents (1) a single bond, (2) —O—, (3) —NRCO—, (4) —CONR—, (5) —CSNR— (6) —NRCS— (wherein R represents a substituent selected from Substituent Group A4 shown below) or (7) —S—;

$Z_5$ represents (1) a single bond, (2) an imino group which may be substituted with a substituent selected from Substituent Group A4 shown below, (3) —$(CH_2)n_e$— (wherein $n_e$ represents an integer of 1 to 3), (4) —$CR^8R^9$— (wherein $R^8$ and $R^9$ are the same as defined above) or (5) —O—; and $R^1$ and $R^7$ are the same as defined above); or (3-3) a cyclic group represented by the following formula:

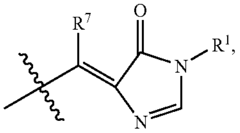

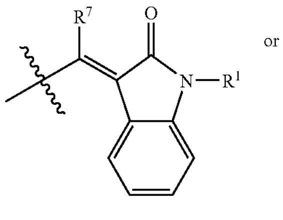

or

-continued

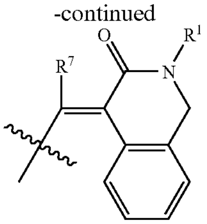

(wherein $R^1$ and $R^7$ are the same as defined above) which may be substituted with 1 to 4 substituents selected from Substituent Group A4 shown below.

Substituent Group A1: (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group, and (12) a C1-6 alkyl group (wherein said C1-6 alkyl group may be substituted with 1 to 3 substituents selected from the group consisting of a halogen atom, a hydroxyl group, a cyano group, a C1-6 alkoxy group, a C3-8 cycloalkyl group and a C1-6 alkylcarbonyl group).

Substituent Group A2: (1) a hydrogen atom, (2) a halogen atom, (3) a hydroxyl group, (4) a cyano group, (5) a C1-6 alkoxy group (wherein said C1-6 alkoxy group may be substituted with 1 to 3 substituents selected from the group consisting of a halogen atom, a cyano group, a C1-6 alkoxy group, a C2-6 alkeny group, a C2-6 alkyny group and a C3-8 cycloalkyl group), (6) a C3-8 cycloalkoxy group, (7) a C2-6 alkenyloxy group and (8) a C2-6 alkynyloxy group.

Substituent Group A3: (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4) and (6) a C1-6 alkoxyl group.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) ═CH-A (wherein A is the same as defined above).

2) The compound or pharmacologically acceptable salt thereof according to above 1) wherein $Ar_1$ is an imidazolyl group which may be substituted with 1 to 2 substituents selected from the group consisting of (1) a hydrogen atom, (2) a halogen atom, (3) a C3-8 cycloalkyl group, (4) a C2-6 alkeny group, (5) a C2-6 alkyny group, (6) a C1-6 alkyl group (wherein said C1-6 alkyl group may be substituted with 1 to 3 halogen atoms)

3) The compound or pharmacologically acceptable salt thereof according to above 1) wherein $Ar_2$ is a phenyl group which may be substituted with 1 to 3 substituents selected from the group consisting of (1) a hydrogen atom, (2) a halogen atom, (3) a hydroxyl group, (4) a cyano group, (6) a C1-6 alkoxy group (wherein said C1-6 alkoxy group may be substituted with 1 to 3 substituents selected from a C2-6 alkenyl group, a C2-6 alkyny group and a C3-8 cycloalkyl group), (7) a C2-6 alkenyloxy group and (8) a C2-6 alkynyloxy group.

4) The compound or pharmacologically acceptable salt thereof according to above 2) wherein $Ar_1$ is an imidazolyl group which may be substituted with 1 to 2 substituents selected from the group consisting of (1) a hydrogen atom, (2) a halogen atom, (3) a C3-8 cycloalkyl group and (4) a C1-6 alkyl group.

5) The compound or pharmacologically acceptable salt thereof according to above 3) wherein $Ar_2$ is a phenyl group which may be substituted with 1 to 3 substituents selected from the group consisting of (1) a hydrogen atom, (2) a halogen atom, (3) a cyano group and (4) a C1-6 alkoxy group.

6) The compound or pharmacologically acceptable salt thereof according to above 1) wherein $X_1$ is —C≡C—.

7) The compound or pharmacologically acceptable salt thereof according to above 1) wherein $X_1$ is —$CR^3$═$CR^4$— (wherein $R^3$ and $R^4$ represent substituents selected from Substituent Group A3 shown below).

Substituent Group A3: (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4) and (6) a C1-6 alkoxy group.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

8) The compound or pharmacologically acceptable salt thereof according to above 7) wherein $X_1$ is $—CR^{31}=CR^{41}—$ (wherein $R^{31}$ is a group selected from the group consisting of (1) a hydrogen atom, (2) a halogen atom, (3) a C1-6 alkyl group and (4) a C1-6 alkoxy group; and $R^{41}$ represents a group selected from the group consisting of (1) a hydrogen atom, (2) a halogen atom, (3) a 6- to 14-membered aromatic hydrocarbon ring group which may be substituted with 1 to 3 substituents selected from Substituent Group A5, (4) a 5- to 14-membered aromatic heterocyclic group which may be substituted with 1 to 3 substituents selected from Substituent Group A5 and (5) a C1-6 alkyl group (wherein said C1-6 alkyl group may be substituted with 1 to 3 substituents selected from the group consisting of a halogen atom, a hydroxyl group, a cyano group, a C3-8 cycloalkyl group, a C1-6 alkyl group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A5, a 5- to 14-membered aromatic heterocyclic group which may be substituted with 1 to 3 substituents selected from Substituent Group A5, a 5- to 14-membered non-aromatic heterocyclic group which may be substituted with 1 to 3 substituents selected from Substituent Group A5 and $—O-A^1$ (wherein $A^1$ represents a 6- to 14-membered aromatic hydrocarbon ring group which may be substituted with 1 to 3 substituents selected from Substituent Group A5 or a 5- to 14-membered aromatic heterocyclic group which may be substituted with 1 to 3 substituents selected from Substituent Group A5))).

Substituent Group A5: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkyl group (wherein said C1-6 alkyl group may be substituted with 1 to 5 halogen atoms), (8) a C1-6 alkoxy group (wherein said C1-6 alkoxy group may be substituted with 1 to 5 halogen atoms) and (9) an amino group (wherein said amino group may be substituted with C1-6 alkyl groups optionally having 1 to 5 halogen atoms).

9) The compound or pharmacologically acceptable salt thereof according to above 8) wherein $X_1$ is $—CR^{32}=CR^{42}—$ (wherein $R^{32}$ represents a hydrogen atom or a halogen atom, and $R^{42}$ represents a substituent selected from the group consisting of a hydrogen atom, a halogen atom, a C1-6 alkyl group (wherein said C1-6 alkyl group may be substituted with a C3-8 cycloalkyl group or a phenyl group) and a phenyl group).

10) The compound or pharmacologically acceptable salt thereof according to above 1) wherein $R^1$ and $R^2$ are groups selected from substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

11) The compound or pharmacologically acceptable salt thereof according to above 10) wherein $R^1$ is a group selected from Substituent Group A8 shown below and $R^2$ is a group selected from Substituent Group A6 shown below.

Substituent Group A6: (1) a hydrogen atom, (2) a C3-8 cycloalkyl group, (3) a C3-8 cycloalkoxy group, (4) a C1-6 alkyl group (wherein said C1-6 alkyl group may be substituted with 1 to 3 substituents selected from the group consisting of a halogen atom, a hydroxyl group, a cyano group, a C3-8 cycloalkyl group, a C3-8 cycloalkoxy group, a formyl group, a C1-6 alkylthio group, a hydroxyimino group, a C1-6 alkoxyimino group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A7 shown below, a 5- to 14-membered aromatic heterocyclic group which may be substituted with 1 to 3 substituents selected from Substituent Group A7 shown below, a 5- to 14-membered non-aromatic heterocyclic group which may be substituted with 1 to 3 substituents selected from Substituent Group A7 shown below and $—O-A^2$ (wherein $A^2$ represents a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below)) and (5) a C1-6 alkoxy group (wherein said C1-6 alkoxy group may be substituted with 1 to 3 substituents selected from the group consisting of a halogen atom, a hydroxyl group, a cyano group, a C3-8 cycloalkyl group, a C3-8 cycloalkoxy group, a formyl group, a C1-6 alkylthio group, a hydroxyimino group, a C1-6 alkoxyimino group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A7 shown below, a 5- to 14-membered aromatic heterocyclic group which may be substituted with 1 to 3 substituents selected from Substituent Group A7 shown below, a 5- to 14-membered non-aromatic heterocyclic group which may be substituted with 1 to 3 substituents selected from Substituent Group A7 shown below and —O-$A^2$ (wherein $A^2$ is the same as defined above)).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group)), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 and (17) —CO-$A^3$ (wherein $A^3$ is the same as defined above).

Substituent Group A8: (1) a hydrogen atom, (2) C1-6 alkyl group (wherein said C1-6 alkyl group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 5 substituents selected from Substituent Group A7, a 5- to 14-membered aromatic heterocyclic group which may be substituted with 1 to 3 substituents selected from Substituent Group A7, a 5- to 14-membered non-aromatic heterocyclic group which may be substituted with 1 to 3 substituents selected from Substituent Group A7 and —X-$A^2$ (wherein X represents an imino group, —O— or —S— and $A^2$ represents a 6- to 14-membered aromatic hydrocarbon ring group which may be substituted with 1 to 5 substituents selected from Substituent Group A7 or a 5- to 14-membered aromatic heterocyclic group which may be substituted with 1 to 3 substituents selected from Substituent Group A7)), (3) a 6- to 14-membered aromatic hydrocarbon ring group which may be substituted with 1 to 3 substituents selected from Substituent Group A7, (4) a 5- to 14-membered aromatic heterocyclic group which may be substituted with 1 to 3 substituents selected from Substituent Group A7 and (5) —X-$A^2$ (wherein X and $A^2$ are the same as defined above).

12) The compound or pharmacologically acceptable salt thereof according to above 11) wherein $R^1$ is a C1-6 alkyl group (wherein said C1-6 alkyl group is a hydrogen atom, a C3-8 cycloalkoxy group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, a 6- to 14-membered aromatic hydrocarbon ring group which may be substituted with 1 to 3 substituents selected from Substituent Group A9, a 5- to 14-membered aromatic heterocyclic group which may be substituted with 1 to 3 substituents selected from Substituent Group A9 and —O-$A^4$ (wherein $A^4$ represents a 6- to 14-membered aromatic hydrocarbon ring group which may be substituted with 1 to 3 substituents selected from Substituent Group A9 or a 5- to 14-membered aromatic heterocyclic group which may be substituted with 1 to 3 substituents selected from Substituent Group A9)), and $R^2$ is (1) a hydrogen atom or (2) a C1-6 alkyl group (wherein said C1-6 alkyl group may be substituted with 1 to 3 substituents selected from the group consisting of a hydroxyl group, a C3-8 cycloalkyl group, a C3-8 cycloalkoxy group, a C1-6 alkylthio group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A9, a 5- to 14-membered aromatic heterocyclic group which may be substituted with 1 to 3 substituents selected from Substituent Group A9 and a 5- to 14-membered non-aromatic heterocyclic group which may be substituted with 1 to 3 substituents selected from Substituent Group A9).

Substituent Group A9: (1) a hydrogen atom, (2) a halogen atom, (3) a C3-8 cycloalkyl group, (4) a C3-8 cycloalkoxy group, (5) a C1-6 alkyl group (wherein said C1-6 alkyl group may be substituted with 1 to 5 substituents selected from the group consisting of a halogen atom and a C1-6 alkyl group), (6) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (7) an amino group (wherein said amino group may be substituted with C1-6 alkyl groups optionally having 1 to 5 halogen atoms), (8) a 5- to 14-membered non-aromatic heterocyclic group which may be substituted with 1 to 3 substituents selected from Substituent Group A9, (9) —CO-$A^3$ (wherein $A^3$ represents a 6- to 14-membered aromatic hydrocarbon ring group), (10) a 6- to 14-membered aromatic hydrocarbon ring group which may be substituted with 1 to 3 substituents selected from Substituent Group A9 and (11) a 5- to 14-membered aromatic heterocyclic group which may be substituted with 1 to 3 substituents selected from Substituent Group A9.

13) The compound or pharmacologically acceptable salt thereof according to above 1) wherein $R^1$ and $R^2$, together with a nitrogen atom to which they bind, form a 5- to 11-membered heterocyclic group represented by Formula (II):

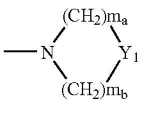

(II)

(wherein Y, represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$=$CR^6$— (wherein $R^5$ and $R^5$ represent groups selected from Substituent Group A4 shown below), (11) a single bond or (12) >C=$CR^{13}R^{14}$ (wherein $R^{13}$ and $R^{14}$ represent substituents selected from Substituent Group A4 shown below); and; $m_a$ and $m_b$ represent an integer of 0 to 4) which may be substituted with 1 to 4 substituents selected from Substituent Group A4 shown below.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

14) The compound or pharmacologically acceptable salt thereof according to above 13) wherein a 5- to 11-membered heterocyclic group is a piperidinyl group, a pyrrolidinyl group, an azepinyl group, an azocanyl group, a piperazinyl group, a 1,4-diazepanyl group, a morpholinyl group or a thiomorpholinyl group.

15) The compound or pharmacologically acceptable salt thereof according to above 14) wherein $R^1$ and $R^2$, together with a nitrogen atom to which they bind, form a piperidinyl group, a pyrrolidinyl group, an azepinyl group, an azocanyl group, a piperazinyl group, a 1,4-diazepanyl group, a morpholinyl group or a thiomorpholinyl group which may be substituted with 1 to 3 substituents selected from the group consisting of (1) a hydrogen atom, (2) a halogen atom, (3) a hydroxyl group, (4) a formyl group, (5) a hydroxyimino group, (6) a C1-6 alkoxyimino group, (7) a C1-6 alkyl group (wherein said C1-6 alkyl group may be substituted with 1 to 3 hydroxyl groups or 1 to 3 substituents selected from the group consisting of a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below), (8) 6- to 14-membered aromatic hydrocarbon ring group which may be substituted with 1 to 3 substituents selected from substituents of A7 shown below, (9) a 5- to 14-membered aromatic heterocyclic group which may be substituted with 1 to 3 substituents selected from Substituent Group A7 shown below, (10) —O-$A^2$ (wherein $A^2$ represents a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below), (11) —CO-$A^2$ (wherein $A^2$ is the same as defined above) and (12) =CH-$A^2$ (wherein $A^2$ is the same as defined above).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group)), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 and (17) —CO-$A^3$ (wherein $A^3$ is the same as defined above).

16) The compound or pharmacologically acceptable salt thereof according to above 15) wherein $R^1$ and $R^2$, together with a nitrogen atom to which they bind, form a piperidinyl group, a pyrrolidinyl group, an azepinyl group, an azocanyl group, a piperazinyl group, a 1,4-diazepanyl group, a morpholinyl group or a thiomorpholinyl group which may be substituted with 1 to 4 substituents selected from the group consisting of (1) a hydrogen atom, (2) a halogen atom, (3) a hydroxyl group, (4) a C1-6 alkyl group (wherein said C1-6 alkyl group may be substituted with 1 to 3 hydroxyl groups or 1 to 3 substituents selected from the group consisting of a 6- to 14-membered aromatic hydrocarbon ring group which may be substituted with 1 to 3 substituents selected from Substituent Group A10 shown below), (5) a 6- to 14-membered aromatic hydrocarbon ring group which may be substituted with 1 to 3 substituents selected from substituents of A10 shown below, (6) a 5- to 14-membered aromatic heterocyclic group which may be substituted with 1 to 3 substituents selected from Substituent Group A10 shown below, (7) —O-$A^6$ (wherein $A^6$ represents a 6- to 14-membered aromatic hydrocarbon ring group which may be substituted with 1 to 3 substituents selected from Substituent Group A10 shown below), (8) =CH-$A^6$ (wherein $A^6$ has the same above).

Substituent Group A10: (1) a hydrogen atom, (2) a halogen atom, (3) a C1-6 alkyl group (wherein said C1-6 alkyl group may be substituted with 1 to 5 halogen atoms), (4) a C1-6 alkoxy group and (5) a 6- to 14-membered aromatic hydrocarbon ring group.

17) The compound or pharmacologically acceptable salt thereof according to above 1) wherein $R^1$ and $R^2$, together with a nitrogen atom to which they bind, form a 6- to 20-membered non-aromatic heterocyclic group represented by Formula (III):

(III)

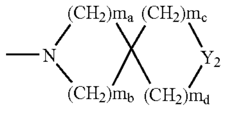

(wherein $Y_2$ represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$═$CR^6$— (wherein $R^5$ and $R^6$ represent groups selected from Substituent Group A4 shown below or $R^5$ and $R^6$, together with a nitrogen atom to which they bind, form a 6- to 14-membered aromatic hydrocarbon ring group or a 6- to 14-membered non-aromatic hydrocarbon ring group) or (11) a single bond;

and $m_a$, $m_b$, $m_c$ and $m_d$ represent an integer of 0 to 4) which may be substituted with 1 to 4 substituents selected from Substituent Group A4 shown below.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) ═CH-A (wherein A is the same as defined above).

18) The compound or pharmacologically acceptable salt thereof according to above 1) wherein $R^1$ and $R^2$, together with a nitrogen atom to which they bind, form a 9- to 16-membered non-aromatic heterocyclic group represented by Formula (IV):

(IV)

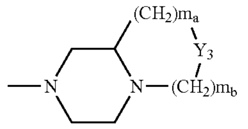

(wherein $Y_3$ represents (1) —NH—, (2) —O—, (3) —S—, (4) —SO—, (5) —$SO_2$—, (6) —$CH_2$—, (7) —CO—, (8) —CONH—, (9) —NHCO— or (10) a single bond; and $m_a$ and $m_b$ represent an integer of 0 to 4) which may be substituted with 1 to 4 substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) ═CH-A (wherein A is the same as defined above).

19) The compound or pharmacologically acceptable salt thereof according to above 1) wherein $R^1$ and $R^2$, together with a nitrogen atom to which they bind, form a group represented by the following formula:

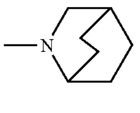
,
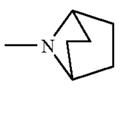
,
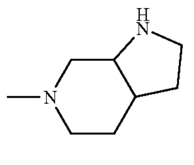
or

-continued

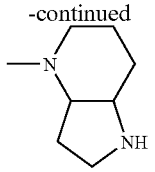

which may be substituted with 1 to 4 substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4 and (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

20) The compound or pharmacologically acceptable salt thereof according to above 1) wherein $R^1$ and $R^2$, together with a nitrogen atom to which they bind, form a group represented by the following formula:

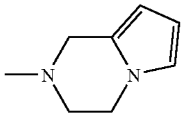
,
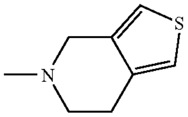
,
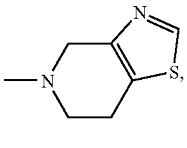
,
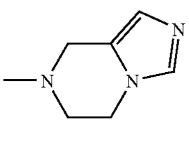
,

-continued

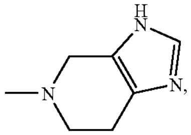
,
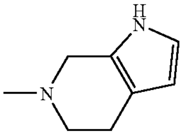
,
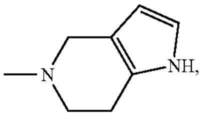
,
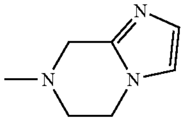
,
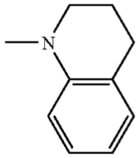
,
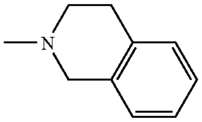
,
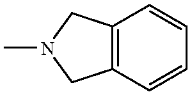
or
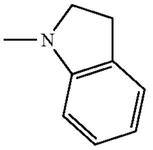

which may be substituted with 1 to 4 substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

21) The compound or pharmacologically acceptable salt thereof according to above 20) wherein $R^1$ and $R^2$, together with a nitrogen atom to which they bind, form a group represented by the following formula:

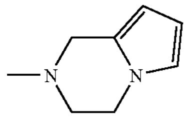
,
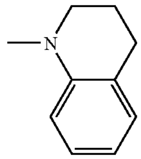
,
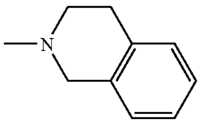
,
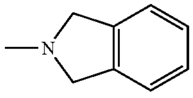
or
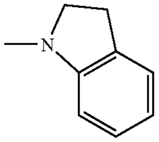

which may be substituted with 1 to 4 substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 3 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

22) The compound or pharmacologically acceptable salt thereof according to above 21) wherein the group formed by $R^1$ and $R^2$, together with a nitrogen atom to which they bind, may be substituted with 1 to 4 fluorine atoms.

23) The compound or pharmacologically acceptable salt thereof according to above 1) wherein $R^1$ and $R^2$, together with —$X_1$—CO—N—, form a cyclic group represented by Formula (V):

(V)

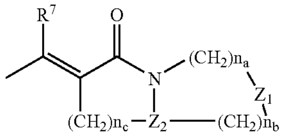

(wherein $Z_1$ represents (1) —NH—, (2) —O—, (3) —S—, (4) —SO—, (5) —$SO_2$—, (6) —$CH_2$—, (7) —CO—, (8) —CONH—, (9) —NHCO— or (10) a single bond; $Z_2$ represents (1) a methine group or (2) a nitrogen atom; $R^7$ represents a substituent selected from Substituent Group A3 shown below; and $n_a$, $n_b$ and $n_c$ represent an integer of 0 to 4) which may be substituted with 1 to 4 substituents selected from Substituent Group A4.

Substituent Group A3: (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4)) and (6) a C1-6 alkoxy group.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) ═CH-A (wherein A is the same as defined above).

24) The compound or pharmacologically acceptable salt thereof according to above 1) wherein $R^1$ and $R^2$ together with —$X_1$—CO—N—, form a cyclic group represented by Formula (VI):

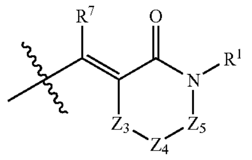

(VI)

(wherein $Z_3$ represents (1) a single bond, (2) —CO—, (3) —$(CH_2)n_d$— (wherein $n_d$ represents an integer of 1 to 3) or (4) —$CR^8R^9$— (wherein $R^8$ and $R^9$ represent a substituent selected from Substituent Group A4 shown below;

$Z_4$ represents (1) a single bond, (2) —O—, (3) —NRCO—, (4) —CONR—, (5) —CSNR—, (6)-NRCS-(wherein R represents a substituent selected from Substituent Group A4 shown below) or (7) —S—;

$Z_5$ represents (1) a single bond, (2) an imino group which may be substituted with a substituent selected from Substituent Group A4 shown below, (3) —$(CH_2)n_e$— (wherein $n_e$ represents an integer of 1 to 3), (4) —$CR^8R^9$— (wherein $R^8$ and $R^9$ are the same as defined above) or (5) —O—; and $R^1$ represents a substituent selected from Substituent Group A4 and $R^7$ represents a substituent selected from Substituent Group A3) which may be substituted with 1 to 4 substituents selected from Substituent Group A4.

Substituent Group A3: (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4)) and (6) a C1-6 alkoxy group.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group, which may be substituted with 1 to 3 substituents selected from Substituent Group A4), (31) —CO-A (wherein A is the same as defined above) and (32) ═CH-A (wherein A is the same as defined above).

25) The compound or pharmacologically acceptable salt thereof according to above 24) wherein Formula (VI) is a cyclic group:

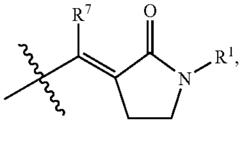

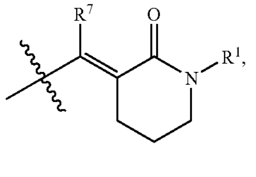

-continued

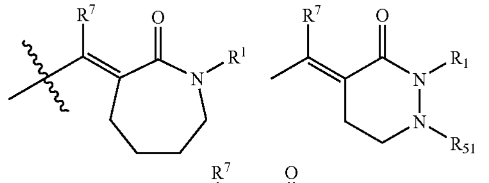

or

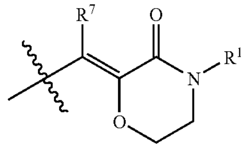

(wherein $R^1$ and $R_{51}$ represents a substituent selected from Substituent Group A4 and $R^7$ represents a substituent selected from Substituent Group A3) which may be substituted with 1 to 4 substituents selected from Substituent Group A7.

Substituent Group A3: (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4)) and (6) a C1-6 alkoxy group.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group)), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with a C1-6 alkyl group optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected-from Substituent Group A7 and (17) —CO-$A^3$ (wherein $A^3$ is the same as defined above).

26) The compound or pharmacologically acceptable salt thereof according to above 1) wherein $R^1$ and $R^2$, together with —$X_1$—CO—N—, form a cyclic group represented by the following formula:

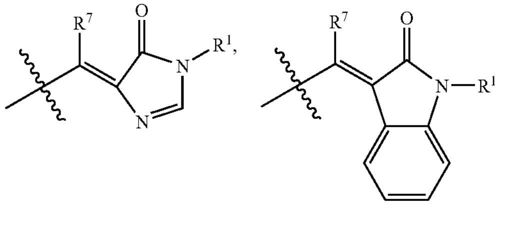

or

-continued

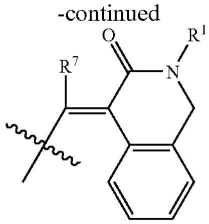

(wherein $R^1$ and $R^7$ are the same as defined above) which may be substituted with 1 to 4 substituents selected from Substituent Group A4.

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

27) The compound or pharmacologically acceptable salt thereof according to any one of above 24) and 26) wherein $R^1$ is a substituent selected from Substituent Group A8.

Substituent Group A8: (1) a hydrogen atom, (2) C1-6 alkyl group (wherein said C1-6 alkyl group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A7, a 5- to 14-membered aromatic heterocyclic group which may be substituted with 1 to 3 substituents selected from Substituent Group A7, a 5- to 14-membered non-aromatic heterocyclic group which may be substituted with 1 to 3 substituents selected from Substituent Group A7 and —X-$A^2$ (wherein X represents an imino group, —O— or —S— and $A^2$ represents a 6- to 14-membered aromatic hydrocarbon ring group which may be substituted with 1 to 3 substituents selected from Substituent Group A7 or a 5- to 14-membered aromatic heterocyclic group which may be substituted with 1 to 3 substituents selected from Substituent Group A7)), (3) a 6- to 14-membered aromatic hydrocarbon ring group which may be substituted with 1 to 3 substituents selected from Substituent Group A7, (4) a 5- to 14-membered aromatic heterocyclic group which may be substituted with 1 to 3 substituents selected from Substituent Group A7 and (5) —X-$A^2$ (wherein X and $A^2$ are the same as defined above).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic-heterocyclic group), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 and (17) —CO-$A^3$ (wherein $A^3$ is the same as defined above).

28) The compound or pharmacologically acceptable salt thereof according to above 27) wherein $R^1$ is a C1-6 alkyl group (wherein said C1-6 alkyl group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A9, a 5- to 14-membered aromatic heterocyclic group which may be substituted with 1 to 3 substituents selected from Substituent Group A9, a 5- to 14-membered non-aromatic heterocyclic group which may be substituted with 1 to 3 substituents selected from Substituent Group A9 and —X-$A^4$ (wherein X represents an imino group, —O— or —S— and $A^4$ represents a 6- to 14-membered aromatic hydrocarbon ring group which may be substituted with 1 to 3 substituents selected from Substituent Group A9 or 5- to 14-membered aromatic heterocyclic group which may be substituted with 1 to 3 substituents selected from Substituent Group A9)).

Substituent Group A9: (1) a hydrogen atom, (2) a halogen atom, (3) a C3-8 cycloalkyl group, (4) a C3-8 cycloalkoxy group, (5) a C1-6 alkyl group (wherein said C1-6 alkyl group may be substituted with 1 to 5 substituents selected from the group consisting of a halogen atom and a C1-6 alkyl group), (6) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (7) an amino group (wherein said amino group may be substituted with a C1-6 alkyl group optionally having 1 to 5 halogen atoms), (8) a 5- to 14-membered non-aromatic heterocyclic group which may be substituted with 1 to 3 substituents selected from Substituent Group A9, (9) —CO-$A^3$ (wherein $A^3$ represents a 6- to 14-membered aromatic hydrocarbon ring group), (10) a 6- to 14-membered aromatic hydrocarbon ring group which may be substituted with 1 to 3 substituents selected from Substituent Group A9 and (11) a 5- to 14-membered aromatic heterocyclic group which may be substituted with 1 to 3 substituents selected from Substituent Group A9.

29) The compound or pharmacologically acceptable salt thereof according to any one of above 10), 24) and 26) wherein $R^1$ is —$X_{21}$—$X_{22}$—$Ar_3$ (wherein $X_{21}$ represents 1) a C1-6 alkylene group (wherein said C1-6 alkylene group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl), a 5- to 14-membered non-aromatic heterocyclic group which may be substituted with 1 to 3 substituents selected from Substituent Group A7) or 2) a single bond, and $X_{22}$ represents a single bond, an imino group which may be substituted with a substituent selected from Substituent Group A7, —O— or —S— and $Ar_3$ represents a 6- to 14-membered aromatic hydrocarbon ring group which may be-substituted with 1 to 3 substituents selected from Substituent Group A7 or a 5- to 14-membered aromatic heterocyclic group which may be substituted with 1 to 3 substituents selected from Substituent Group A7).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 and (17) —CO-$A^3$ (wherein $A^3$ is the same as defined above).

30) The compound or pharmacologically acceptable salt thereof according to above 29) wherein $R^1$ is —$X_{21a}$—$X_{22a}$—$Ar_{3a}$ (wherein $X_{21a}$ represents a C1-6 alkylene group (wherein said C1-6 alkylene group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with C1-6 alkyl groups optionally having 1 to 5 halogen atoms), a 5- to 14-membered non-aromatic heterocyclic group which may be substituted with 1 to 3 substituents selected from Substituent Group A9), and $X_{22a}$ represents a single bond or an oxygen atom and $Ar_{3a}$ represents a 6- to 14-membered aromatic hydrocarbon ring group which may be substituted with 1 to 3 substituents selected from Substituent Group A9 or a 5- to 14-membered aromatic heterocyclic group which may be substituted with 1 to 3 substituents selected from Substituent Group A9).

Substituent Group A9: (1) a hydrogen atom, (2) a halogen atom, (3) a C3-8 cycloalkyl group, (4) a C3-8 cycloalkoxy group, (5) a C1-6 alkyl group (wherein said C1-6 alkyl group may be substituted with 1 to 5 substituents selected from the group consisting of a halogen atom and a C1-6 alkyl group), (6) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (7) an amino group (wherein said amino group may be substituted with a C1-6 alkyl group optionally having 1 to 5 halogen atoms), (8) a 5- to 14-membered non-aromatic heterocyclic group which may be substituted with 1 to 3 substituents selected from Substituent Group A9, (9) —CO-$A^3$ (wherein $A^3$ represents a 6- to 14-membered aromatic hydrocarbon ring group), (10) a 6- to 14-membered aromatic hydrocarbon ring group which may be substituted with 1 to 3 substituents selected from Substituent Group A9 and (11) a 5- to 14-membered aromatic heterocyclic group which may be substituted with 1 to 3 substituents selected from Substituent Group A9.

31) The compound or pharmacologically acceptable salt thereof according to above 30) wherein $Ar_{3a}$ is a 6- to 14-membered aromatic hydrocarbon ring group selected from the group consisting of a phenyl group, a naphthyl group and a fluorenyl group or a 5- to 14-membered aromatic heterocyclic group selected from the group consisting of a thienyl group, a pyridyl group, a quinolyl group, an isoquinolyl group, an indolyl group, a benzothiazolyl group, a benzoxazolyl group and a furyl group, which may be substituted with 1 to 3 substituents selected from Substituent Group A9.

Substituent Group A9: (1) a hydrogen atom, (2) a halogen atom, (3) a C3-8 cycloalkyl group, (4) a C3-8 cycloalkoxy group, (5) a C1-6 alkyl group (wherein said C1-6 alkyl group may be substituted with 1 to 5 substituents selected from the group consisting of a halogen atom and a C1-6 alkyl group), (6) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (7) an amino group (wherein said amino group may be substituted with a C1-6 alkyl group optionally having 1 to 5 halogen atoms), (8) a 5- to 14-membered non-aromatic heterocyclic group which may be substituted with 1 to 3 substituents selected from Substituent Group A9, (9) —CO-$A^3$ (wherein $A^3$ represents a 6- to 14-membered aromatic hydrocarbon ring group), (10) a 6- to 14-membered aromatic hydrocarbon ring group which may be substituted with 1 to 3 substituents selected from Substituent Group A9 and (11) a 5- to 14-membered aromatic heterocyclic group which may be substituted with 1 to 3 substituents selected from Substituent Group A9.

32) The compound or pharmacologically acceptable salt thereof according to above 1) wherein $R^1$ is a 6- to 14-membered non-aromatic hydrocarbon ring group or a 5- to 14-membered non-aromatic heterocyclic group represented by Formula (VII):

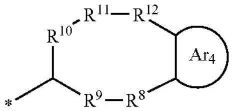
(VII)

(wherein $R^8$ to $R^{12}$ represent 1) a single bond, 2) —CO—, 3) a methylene group which may be substituted with 1 or 2 substituents selected from Substituent Group A4, 4) —O—, 5) an imino group which may have a substituent selected from Substituent Group A4 or 6) —S—, and $Ar_4$ represents a 6- to 14-membered aromatic hydrocarbon ring group which may be substituted with 1 to 3 substituents selected from Substituent Group A4 shown below or a 5- to 14-membered aromatic heterocyclic group which may be substituted with 1 to 3 substituents selected from Substituent Group A4 shown below).

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) and (32) =CH-A (wherein A is the same as defined above).

33) The compound or pharmacologically acceptable salt thereof according to above 32) wherein $Ar_4$ represents a phenyl group or a 5- to 14-membered aromatic heterocyclic group selected from the group consisting of a pyridinyl group, a pyrimidinyl group, a pyrazinyl group, a thienyl group, an oxazolyl group, a pyrrolyl group, a thiazolyl group and a furyl group, which may be substituted with 1 to 3 substituents selected from the group consisting of a halogen atom, a C1-6 alkyl group (wherein said C1-6 alkyl group may be substituted with 1 to 3 substituents selected from the group consisting of a halogen atom and a C1-6 alkyl group), a C1-6 alkoxy group (wherein said C1-6 alkoxy group may be substituted with 1 to 3 halogen atoms), an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A7, a 5- to 14-membered aromatic heterocyclic group which may be substituted with 1 to 3 substituents selected from Substituent Group A7, a 5- to 14-membered non-aromatic heterocyclic group which may be substituted with 1 to 3 substituents selected from Substituent Group A7 and —CO-$A^2$ (wherein $A^2$ represents a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below).

Substituent Group A7: (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 and (17) —CO-$A^3$ (wherein $A^3$ is the same as defined above).

34) The compound or pharmacologically acceptable salt thereof according to above 33) wherein $R^1$ is an indanyl group, an azaindanyl group, a tetrahydronaphthyl group, an azatetrahydronaphthyl group, a chromanyl group, an azachromanyl group, a tetrahydrobenzofuranyl group or a tetrahydrobenzothienyl group, which may be substituted with 1 to 3 substituents selected from the group consisting of (1) a halogen atom, (2) a hydroxyl group, (3) a cyano group, (4) a C3-8 cycloalkyl group, (5) a C3-8 cycloalkoxy group, (6) a C1-6 alkyl group (wherein said C1-6 alkyl group may be substituted with 1 to 3 halogen atoms or C1-6 alkyl groups), (7) a C1-6 alkoxy group (wherein said C1-6 alkoxy group may be substituted with 1 to 3 halogen atoms), (8) an amino group (wherein said amino group may be substituted with a C1-6 alkyl group optionally having 1 to 5 halogen atoms), and (9) a 5- to 14-membered non-aromatic heterocyclic group.

35) The compound or pharmacologically acceptable salt thereof according to above 1) selected from the following group:

1) (E)-N-biphenyl-3-ylmethyl-3-[3-methoxy-4-(4-methyl-1H-imidazol-1-yl)phenyl]acrylamide,
2) (E)-N-((1S)-indan-1-yl)-3-(3-methoxy-4-(4-methyl-1H-imidazol-1-yl)phenyl)acrylamide,
3) (E)-N-(chroman-4-yl)-3-(3-methoxy-4-(4-methyl-1H-imidazol-1-yl)phenyl)acrylamide,
4) (E)-1-(3,4-difluorobenzyl)-3-(3-methoxy-4-(4-methyl-1H-imidazol-1-yl)benzylidene)piperidin-2-one,
5) (E)-1-indan-2-yl-3-(3-methoxy-4-(4-methyl-1H-imidazol-1-yl)benzylidene)piperidin-2-one,
6) (E)-1-(chroman-4-yl)-3-(3-methoxy-4-(4-methyl-1H-imidazol-1-yl)benzylidene)piperidin-2-one,
7) (E)-1-((1S)-1-(4-fluorophenyl)ethyl)-3-(3-methoxy-4-(4-methyl-1H-imidazol-1-yl)benzylidene)piperidin-2-one,
8) (E)-1-((6-chloropyridin-2-yl)methyl)-3-(3-methoxy-4-(4-methyl-1H-imidazol-1-yl)benzylidene)piperidin-2-one,
9) (E)-1-(4-tert-butylbenzyl)-3-(3-methoxy-4-(4-methyl-1H-imidazol-1-yl)benzylidene)piperidin-2-one,
10) (E)-1-(3,4-difluorobenzyl)-3-((5-methoxy-6-(4-methyl-1H-imidazol-1-yl)pyridin-3-yl)methylene)piperidin-2-one,
11) (E)-1-((1H-indol-3-yl)ethyl)-3-(3-methoxy-4-(4-methyl-1H-imidazol-1-yl)benzylidene)piperidin-2-one,
12) (E)-1-(5-fluoroindan-2-yl)-3-(3-methoxy-4-(4-methyl-1H-imidazol-1-yl)benzylidene)piperidin-2-one,
13) (E)-1-(7-fluorochroman-4-yl)-3-(3-methoxy-4-(4-methyl-1H-imidazol-1-yl)benzylidene)piperidin-2-one,
14) (E)-3-(3-methoxy-4-(4-methyl-1H-imidazol-1-yl)benzylidene)-1-(1,2,3,4-tetrahydronaphthalen-2-yl) piperidin-2-one and
15) (E)-1-((2,4-difluorophenyl)ethyl)-3-(3-methoxy-4-(4-methyl-1H-imidazol-1-yl)benzylidene)piperidin-2-one.

36) A preventive or therapeutic agent for a disease resulting from amyloid betas comprising a compound represented by general formula (I) or pharmacologically acceptable salt thereof as an active ingredient.

37) The preventive or therapeutic agent according to above 36) wherein the disease resulting from amyloid betas is Alzheimer's disease, senile dementia, Down syndrome or amyloidosis.

The compound of the general formula (I) of the present invention or pharmacologically acceptable salt thereof and preventive or therapeutic agent of diseases caused by Aβs are new inventions not described in documents.

Hereinbelow, symbols, terms and the like used in the present specification are explained and the present invention is described in detail.

DETAILED DESCRIPTION OF THE INVENTION

Although a structural formula of a compound may express a certain isomer for the sake of convenience in the present specification, the present invention encompasses all the isomers such as geometric isomers which can be generated from the structure of a compound, optical isomers based on chiral carbon(s), stereoisomers and tautomers and a mixture of isomers and the invention is not limited to the formula described for the sake of convenience and may be either one of isomers or mixtures thereof. Therefore, although some molecules may have a chiral carbon atom therein and there may be an optically-active substance and racemate, the present invention is not limited to a certain one of them and includes either one of them. Furthermore, crystal polymorphs, which may exist, are not limited, and may be either one of single crystal type thereof or a mixture thereof, and may be hydrate or may be an anhydride.

The term "disease(s) caused by Aβ" encompasses a wide variety of diseases includeing Alzheimer's disease (for example, see Klein W L, and seven others, Alzheimer's disease-affected brain: presence of oligomeric Aβ ligands (ADDLs) suggests a molecular basis for reversible memory loss, Proceeding National Academy of Science USA, 2003, Sep. 2, 100(18), p. 10417-10422;

Nitsch R M, and 16 others, Antibodies against β-amyloid slow cognitive decline in Alzheimer's disease, Neuron, 2003, May, 22, 38(4), p. 547-554;

Jarrett J T, and 2 others, The carboxy terminus of the β amyloid protein is critical for the seeding of amyloid formation: implications for the pathogenesis of Alzheimer's disease, Biochemistry, 1993, May 11, 32(18), p. 4693-4697;

Glenner G G, and another, Alzheimer's disease: initial report of the purification and characterization of a novel cerebrovascular amyloid protein, Biochem Biophys Res Commun, 1984, May 16, 120(3), p. 885-890;

Masters C L, and six others, Amyloid plaque core protein in Alzheimer disease and Down syndrome, Proceeding National Academy of Science USA, 1985, June 82(12), p. 4245-4249;

Gouras G K, and eleven others, Intraneuronal Aβ42 accumulation in human brain, American Journal of Pathology, 2000, January 156(1), p. 15-20;

Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and 4 others, Differential effects of the swedish mutant amyloid precursor protein on β-amyloid accumulation and secretion in neurons and nonneuronal cells, Journal of Biological Chemistry, 1997, Dec. 19, 272(51), p. 32247-32253.), senile dementia (for example, see Blass J P, Brain metabolism and brain disease: is metabolic deficiency the proximate cause of Alzheimer dementia? Journal of Neuroscience Research, 2001, Dec. 1, 66(5), p. 851-6.), frontotemporal dementia (for example, see Evin G, and eleven others, Alternative transcripts of presenilin-1 associated with frontotemporal dementia, Neuroreport, 2002, Apr. 16, 13(5), p. 719-723.), Pick disease (for example, see Yasuhara O, and three others, Accumulation of amyloid precursor protein in brain lesions of patients with Pick disease, Neuroscience Letters, 1994, Apr. 25, 171(1-2), p. 63-66.), Down syndrome (for example, see Teller J K, and ten others, Presence of soluble amyloid β-peptide precedes amyloid plaque formation in Down's syndrome, Nature Medicine, 1996, January, 2(1), p. 93-95; and Tokuda T, and six others, Plasma levels of amyloid β proteins Aβ1-40 and Aβ1-42(43) are elevated in Down's syndrome, Annals of Neurology, 1997, February, 41(2), p. 271-273.), cerebral amyloid angiopathy (for example, see Hayashi Y, and nine others, Evidence for presenilin-1 involvement in amyloid angiopathy in the Alzheimer's disease-affected brain, Brain Research, 1998, Apr. 13, 789(2), p. 307-314;

Barelli H, and fifteen others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, 1997, October, 3(10), p. 695-707;

Calhoun M E, and ten others, Neuronal overexpression of mutant amyloid precursor protein results in prominent deposition of cerebrovascular amyloid, Proceeding National Academy of Science USA, 1999, Nov. 23, 96(24), p. 14088-14093; and Dermaut B, and ten others, Cerebral amyloid angiopathy is a pathogenic lesion in Alzheimer's disease due to a novel presenilin 1 mutation, Brain, 2001, December, 124(Pt 12), p. 2383-2392.), hereditary cerebral hemorrhage with amyloidosis-Dutch type (for example, see Cras P, and nine others, Presenile Alzheimer dementia characterized by amyloid angiopathy and large amyloid core type senile plaques in the APP 692Ala→Gly mutation, Acta Neuropathologica (Berl), 1998, September, 96(3), p. 253-260;

Herzig M C, and fourteen others, Aβ is targeted to the vasculature in a mouse model of hereditary cerebral hemorrhage with amyloidosis, Nature Neuroscience, 2004, September, 7(9), p. 954-960;

Van Duinen S G, and five others, Hereditary cerebral hemorrhage with amyloidosis in patients of Dutch origin is related to Alzheimer disease, Proceeding National Academy of Science USA, 1987, August, 84(16), p. 5991-5994; and Levy E, and eight others, Mutation of the Alzheimer's disease amyloid gene in hereditary cerebral hemorrhage, Dutch type, Science, 1990, Jun. 1, 248(4959), p. 1124-1126.), cognitive impairment (for example, see Laws S M, and seven others, Association between the presenilin-1 mutation Glu318Gly and complaints of memory impairment, Neurobiology of Aging, 2002, January-February, 23(1), p. 55-58.), memory disorder/learning disorder (for example, see Vaucher E, and five others, Object recognition memory and cholinergic parameters in mice expressing human presenilin 1 transgenes, Experimental Neurology, 2002, June, 175(2), p. 398-406;

Morgan D, and fourteen others, Aβ peptide vaccination prevents memory loss in an animal model of Alzheimer's disease, Nature, 2000, Dec. 21-28, 408(6815), p. 982-985; and Moran P M, and three others, Age-related learning deficits in transgenic mice expressing the 751-amino acid isoform of human β-amyloid precursor protein, Proceeding National Academy of Science USA, 1995, Jun. 6, 92(12), p. 5341-5345.), amyloidosis, cerebral ischemia (for example, see Laws S M, and seven others, Association between the presenilin-1 mutation Glu318Gly and complaints of memory impairment, Neurobiology of Aging, 2002, January-February, 23(1), p. 55-58;

Koistinaho M, and ten others. β-amyloid precursor protein transgenic mice that harbor diffuse Aβ deposits but do not form plaques show increased ischemic vulnerability: role of inflammation, Proceeding National Academy of Science USA, 2002, Feb. 5, 99(3), p. 1610-1615; and Zhang F, and four others, Increased susceptibility to ischemic brain damage in transgenic mice overexpressing the amyloid precursor protein, Journal of Neuroscience, 1997, Oct. 15, 17(20), p. 7655-7661.), vascular dementia (for example, see Sadowski M, and six others, Links between the pathology of Alzheimer's disease and vascular dementia, Neurochemical Research, 2004, June, 29(6), p. 1257-1266.), ophthalmoplegia(eye muscle paralysis) (for example, see O'Riordan S, and seven others, Presenilin-1 mutation (E280G), spastic paraparesis, and cranial MRI white-matter abnormalities, Neurology, 2002, Oct. 8, 59(7), p. 1108-1110.), multiple sclerosis (for example, see Gehrmann J, and four others, Amyloid precursor protein (APP) expression in multiple sclerosis lesions, Glia, 1995, October, 15(2), p. 141-151; and Reynolds, W F, and six others, Myeloperoxidase polymorphism is associated with gender specific risk for Alzheimer's disease, Experimental Neurology, 1999, January, 155(1), p. 31-41.), head trauma, cranial damage (for example, see Smith D H, and four others, Protein accumulation in traumatic brain injury, Neuromolecular Medicine, 2003, 4(1-2), p. 59-72.), apraxia (for example, see Matsubara-Tsutsui M, and seven others, Molecular evidence of presenilin 1 mutation in familial early onset dementia, American Journal of Medical Genetics, 2002, Apr. 8, 114(3), p. 292-298.), prion disease, familial amyloid neuropathy, triplet repeat disease (for example, see Kirkitadze M D, and two others, Paradigm shifts in Alzheimer's disease and other neurodegenerative disorders: the emerging role of oligomeric assemblies, Journal of Neuroscience Research, 2002, Sep. 1, 69(5), p. 567-577;

Evert B O, and eight others, Inflammatory genes are upregulated in expanded ataxin-3-expressing cell lines and spinocerebellar ataxia type 3 brains, Journal of Neuroscience, 2001, Aug. 1, 21(15), p. 5389-5396; and Mann D M, and another, Deposition of amyloid (A4) protein within the brains of persons with dementing disorders other than Alzheimer's disease and Down's syndrome, Neuroscience Letters, 1990, Feb. 5, 109(1-2), p. 68-75.), Parkinson's disease (for example, see Primavera J, and four others, Brain Accumulation of Amyloid-β in Non-Alzheimer Neurodegeneration, Journal of Alzheimer's Disease, 1999, October, 1(3), p. 183-193.), Dementia with Lewy bodies (for example, see Giasson B I, and two others, Interactions of amyloidogenic proteins, Neuromolecular Medicine, 2003, 4(1-2), p. 49-58;

Masliah E, and six others, β-amyloid peptides enhance alpha-synuclein accumulation and neuronal deficits in a transgenic mouse model linking Alzheimer's disease and Parkinson's disease, Proceeding National Academy of Science USA, 2001, Oct. 9, 98(21), p. 12245-12250;

Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain Accumulation of Amyloid-β in Non-Alzheimer Neurodegeneration, Journal of Alzheimer's Disease, 1999, October, 1(3), p. 183-193.), Parkinsonism-dementia complex (PDC) (for example, see Schmidt M L, and six others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), February, 1998, February, 95(2), p. 117-122; and Ito H, and three others, Demonstration of β amyloid protein-containing neurofibrillary tangles in parkinsonism-dementia complex on Guam, Neuropathology and Applied Neurobiology, 1991, October, 17(5), p. 365-373.), frontotemporal dementia-parkinsonism linked to chromosome 17 (FTDP-17) (for example, see Rosso S M, and three others, Coexistent tau and amyloid pathology in hereditary frontotemporal dementia with tau mutations, Annals of the New York Academy of Science, 2000, 920, p. 115-119.), dementia with argyrophilic grains (for example, see Tolnay M, and four others, Low amyloid (Aβ) plaque load and relative predominance of diffuse plaques distinguish argyrophilic grain disease from Alzheimer's disease, Neuropathology and Applied Neurobiology, 1999, August, 25(4), p. 295-305.), Niemann-Pick disease (for example, see Jin L W, and three others, Intracellular accumulation of amyloidogenic fragments of amyloid-β precursor protein in neurons with Niemann-Pick type C defects is associated with endosomal abnormalities, American Journal of Pathology, 2004, March, 164(3), p. 975-985.), amyotrophic lateral scleraosis (for example, see Sasaki S, and another, Immunoreactivity of β-amyloid precursor protein in amyotrophic lateral sclerosis, Acta Neuropathologica (Berl), May, 1999, 97(5), p. 463-468;

Tamaoka A, and four others, Increased amyloid β protein in the skin of patients with amyotrophic lateral sclerosis, Journal of Neurology, August, 2000, 247(8), p. 633-635;

Hamilton R L, and another, Alzheimer disease pathology in amyotrophic lateral sclerosis, Acta Neuropathologica (Berl), June, 2004, 107(6), p. 515-522; and Turner B J, and six others, Brain β-amyloid accumulation in transgenic mice expressing mutant superoxide dismutase 1, Neurochemical Research, December, 2004, 29(12), p. 2281-2286.), hydrocephalus (for example, see Weller R O, Pathology of cerebrospinal fluid and interstitial fluid of the CNS: significance for Alzheimer disease, prion disorders and multiple sclerosis, Journal of Neuropathology and Experimental Neurology, October, 1998, 57(10), p. 885-894;

Silverberg G D, and four others, Alzheimer's disease, normal-pressure hydrocephalus, and senescent changes in CSF circulatory physiology: a hypothesis, Lancet Neurology, August, 2003, 2(8), p. 506-511;

Weller R O, and three others, Cerebral amyloid angiopathy: accumulation of Aβ in interstitial fluid drainage pathways in Alzheimer's disease, Annals of the New York Academy of Sciences, April, 2000, 903, p. 110-117;

Yow H Y, and another, A role for cerebrovascular disease in determining the pattern of β-amyloid deposition in Alzheimer's disease, Neurology and applied neurobiology, 2002, 28, p. 149; and Weller R O, and four others, Cerebrovascular disease is a major factor in the failure of elimination of A from the aging human brain, Annals of the New York Academy of Sciences, November 2002, 977, p. 162-168.), incomplete parapalegia (for example, see O'Riordan S, and seven others, Presenilin-1 mutation (E280G), spastic paraparesis, and cranial MRI white-matter abnormalities, Neurology, Oct. 8, 2002, 59(7), p. 1108-10;

Matsubara-Tsutsui M, and seven others, Molecular evidence of presenilin 1 mutation in familial early onset dementia, American Journal of Medical Genetics, Apr. 8, 2002, 114(3), p. 292-8;

Smith M J, and eleven others, Variable phenotype of Alzheimer's disease with spastic paraparesis, Ann Neurol. January, 2001 49(1), p. 125-129; and Crook R, and seventeen others, A variant of Alzheimer's disease with spastic paraparesis and unusual plaques due to deletion of exon 9 of presenilin 1, Nature Medicine, April, 1998, 4(4), p. 452-455.), progressive supranuclear palsy (PSP) (for example, see Masliah E, and six others, β-amyloid peptides enhance alpha-synuclein accumulation and neuronal deficits in a transgenic mouse model linking Alzheimer's disease and Parkinson's disease, Proceeding National Academy of Science USA, Oct. 9, 2001, 98(21), p. 12245-12250; and Primavera J, and four others, Brain Accumulation of Amyloid-β in Non-Alzheimer Neurodegeneration, Journal of Alzheimer's Disease, October, 1999, 1(3), p. 183-193.), cerebral hemorrhage (for example, see Atwood C S, and three others, Cerebrovascular requirement for sealant, anti-coagulant and remodeling molecules that allow for the maintenance of vascular integrity and blood supply, Brain Research Review, September, 2003 43(1), p. 164-178; and Lowenson J D, and 2 others, Protein Aging: Extracellular amyloid formation and intracellular repair, Trends in Cirdiovascular medicine, 1994, 4(1), p. 3-8.), spasm (for example, see Singleton A B, and thirteen others, Pathology of early-onset Alzheimer's disease cases bearing the Thr113-114ins presenilin-1 mutation, Brain, December, 2000, 123 Pt 12, p. 2467-2474.), mild cognitive impairment (for example, see Gattaz W F, and four others, Platelet phospholipase A(2) activity in Alzheimer's disease and mild cognitive impairment, Journal of Neural Transmission, 2004, May, 111(5), p. 591-601; and Assini A, and four others, Plasma levels of amyloid β-protein 42 are increased in women with mild cognitive impairment, Neurology, 2004, Sep. 14, 63(5), p. 828-831.), atherosclerosis (for example, see De Meyer G R, and eight others, Platelet phagocytosis and processing of β-amyloid precursor protein as a mechanism of macrophage activation in atherosclerosis, Circulation Research, 2002, Jun. 14, 90(11), p. 1197-1204.), etc.

The "6- to 14-membered aromatic hydrocarbon ring group," "5- to 14-membered aromatic heterocyclic group," "6- to 14-membered non-aromatic hydrocarbon ring group" and "5- to 14-membered non-aromatic heterocyclic group" in the above-mentioned formula (I) contained in the therapeutic or preventive agent of diseases caused by Aβs according to the present invention have the following meanings.

The "6- to 14-membered aromatic hydrocarbon ring group" means a monocyclic, bicyclic or tricyclic aromatic hydrocarbon ring group having 6 to 14 carbon atoms and preferable groups include a monocyclic, bicyclic or tricyclic 6- to 14-membered aromatic hydrocarbon ring group, for example, a phenyl group, an indenyl group, a naphthyl group, an azulenyl group, a heptalenyl group, a biphenyl group, a fluorenyl group, a phenalenyl group, a phenanthrenyl group, an anthracenyl group, etc.

The "5- to 14-membered aromatic heterocyclic group" refers to a monocyclic, bicyclic or tricyclic aromatic heterocyclic group having 5 to 14 atoms and preferable groups include, for example, (1) nitrogen-containing aromatic heterocyclic groups such as a pyrrolyl group, a pyridyl group, a pyridazinyl group, a pyrimidinyl group, a pyrazinyl group, a pyrazolinyl group, an imidazolyl group, an indolyl group, an isoindolyl group, an indolizinyl group, a purinyl group, an indazolyl group, a quinolyl group, an isoquinolyl group, a quinolizinyl group, a phthalazinyl group, a naphthylizinyl group, a quinoxalinyl group, a quinazolinyl group, a cinnolinyl group, a pteridinyl group, an imidazotriazinyl group, a pyrazinopyridazinyl group, an acridinyl group, a phenantholizinyl group, a carbazolyl group, a perimidinyl group, a phenanthrolinyl group and a phenacyl group; (2) sulfur-containing aromatic heterocyclic groups such as a thienyl group and a benzothienyl group; (3) oxygen-containing aromatic heterocyclic groups such as a furyl group, a pyranyl group, a cyclopentapyranyl group, a benzofuranyl group and an isobenzofuranyl group; (4) aromatic heterocyclic groups containing two or more hetero atoms selected from the group consisting of a nitrogen atom, a sulfur atom, and an oxygen atom such as a thiazolyl group, an isothiazolyl group, a benzothiazolyl group, a benzothiadiazolyl group, a phenothiazinyl group, an isoxazolyl group, a furazanyl group, a phenoxazinyl group, a pyrazoloxazolyl group, imidazothiazolyl group, a thienofuryl group, a furopyrrolyl group, a pyridoxazinyl group, etc.

The "6- to 14-membered non-aromatic hydrocarbon ring group" refers to a cyclic, aliphatic hydrocarbon group having 6 to 14 carbon atoms, and means, for example, a cyclopropyl group, a cyclobutyl group, a cyclopentyl group, a cyclohexyl group, a cycloheptyl group, a cyclooctyl group, a spiro[3.4]octanyl group, a decanyl group, an indanyl group, 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group, 1,4-dihydronaphthalenyl group and the other cyclic, aliphatic hydrocarbon groups having 6 to 14 carbon atoms.

The "5- to 14-membered non-aromatic heterocyclic group" means not only a 5- to 14-membered non-aromatic hetero monocyclic group but also a saturated heterocyclic group condensed with aromatic hydrocarbon ring groups, or a saturated hydrocarbon ring group or a saturated heterocyclic group condensed with aromatic heterocyclic group(s), which 1) has 5 to 14 ring-constituting atoms, 2) contains 1 to 5 hetero atoms such as a nitrogen atom, —O— or —S— in the ring-constituting atoms and 3) may contain one or more carbonyl groups, double bonds, or triple bonds in the ring. Specific examples of 5- to 14-membered non-aromatic heterocyclic group include an azetidinyl ring, a pyrrolidinyl ring, a piperidinyl ring, an azepanyl ring, an azocanyl ring, a tetrahydrofuranyl ring, a tetrahydropyranyl ring, a morpholinyl ring, a thiomorpholinyl ring, a piperazinyl ring, a thiadiazolidinyl ring, a dioxanyl ring, an imidazolinyl ring, a thiadiazolinyl ring, 1,2-benzopyranyl ring, an isochromanyl ring, a chromanyl ring, an indolinyl ring, an isoindolinyl ring, an azaindanyl group, an azatetrahydronaphthyl group, an azachromanyl group, a tetrahydrobenzofuranyl group, a tetrahydrobenzothienyl group, a 2,3,4,5- tetrahydrobenzo[b]thienyl group, a 3,4-dihydro-2H-benzo[b][1,4]dioxepinyl group, an indan-1-onyl group, a 6,7-dihydro-5H-cyclopentapyrazinyl group, a 6,7-dihydro-5H-[1]-pyridinyl group, a 6,7-dihydro-5H-[1]-pyridinyl group, a 5,6-dihydro-4H-cyclopenta[b]thienyl group, a 4,5,6,7-tetrahydro-benzo[b]thienyl group, a 3,4-dihydro-2H-naphthale-1-onyl group, a 2,3-dihydro-isoindol-1-onyl group, a 3,4-dihydro-2H-isoquinoline-1-onyl group, a 3,4-dihydro-2H-benzo[1,4]oxapinyl group, etc.

The substituent group A1, substituent group A2, substituent group A3, substituent group A4, substituent group A5, substituent group A6, substituent group A7, substituent group A8, substituent group A9 and substituent group A10 represent the following groups.

Substituent Group Al refers to (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group, or (12) a C1-6 alkyl group (wherein the above described C1-6 alkyl group may be substituted with 1 to 3 substituents selected from the group consisting of a halogen atom, a hydroxyl group, a cyano group, a C1-6 alkoxy group, a C3-8 cycloalkyl group and a C1-6 alkylcarbonyl group).

Substituent Group A2 refers to (1) a hydrogen atom, (2) a halogen atom, (3) a hydroxyl group, (4) a cyano group, (5) a C1-6 alkoxy group (wherein the C1-6 alkoxy group may be substituted with 1 to 3 substituents selected from the group consisting of a halogen atom, a cyano group, a C1-6 alkoxy group, a C2-6 alkeny group, a C2-6 alkyny group and a C3-8 cycloalkyl group), (6) a C3-8 cycloalkoxy group, (7) a C2-6 alkenyloxy group or (8) a C2-6 alkynyloxy group.

Substituent Group A3 refers to (1) a hydrogen atom, (2) a halogen atom, (3) a 6- to 14-membered aromatic hydrocarbon ring group which may be substituted with 1 to 3 substituents selected from Substituent Group A4, (4) a 5- to 14-membered aromatic heterocyclic group which may be substituted with 1 to 3 substituents selected from Substituent Group A4, (5) a C1-6 alkyl group (wherein said C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A4, a 5- to 14-membered aromatic heterocyclic group which may be substituted with 1 to 3 substituents selected from Substituent Group A4, a 6- to 14-membered non-aromatic hydrocarbon ring group which may be substituted with 1 to 3 substituents selected from Substituent Group A4, a 5- to 14-membered non-aromatic heterocyclic group which may be substituted with 1 to 3 substituents selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4)) or (6) a C1-6 alkoxy group.

Substituent Group A4 refers to (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituents selected from Substituent Group A4, (19) a C1-6 alkoxy group which may be substituted with 1 to 3 substituents selected from Substituent Group A4, (20) an amino group which may be substituted with 1 to 2 substituents selected from Substituent Group A4, (21) a carbamoyl group which may be substituted with 1 to 2 substituents selected from Substituent Group A4, (22) a 6- to 14-membered aromatic hydrocarbon ring group which may be substituted with 1 to 5 substituents selected from Substituent Group A4, (23) a 5- to 14-membered aromatic heterocyclic group which may be substituted with 1 to 3 substituents selected from Substituent Group A4, (24) a 6- to 14-membered non-aromatic hydrocarbon ring group which may be substituted with 1 to 3 substituents selected from Substituent Group A4, (25) a 5- to 14-membered non-aromatic heterocyclic group which may be substituted with 1 to 3 substituents selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituents selected from Substituent Group A4), (31) —CO-A (wherein A is the same as defined above) or (32) =CH-A (wherein A is the same as defined above).

Substituent Group A5 refers to (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkyl group (wherein said C1-6 alkyl group may be substituted with 1 to 5 halogen atoms) (8) a C1-6 alkoxy group (wherein said alkoxy group may be substituted with 1 to 5 halogen atoms) or (9) an amino group (wherein said amino group may be substituted with a C1-6 alkyl group optionally having 1 to 5 halogen atoms).

Substituent Group A6 refers to (1) a hydrogen atom, (2) a C3-8 cycloalkyl group, (3) a C3-8 cycloalkoxy group, (4) a C1-6 alkyl group (wherein said C1-6 alkyl group may be substituted with 1 to 3 substituents selected from the group consisting of a halogen atom, a hydroxyl group, a cyano group, a C3-8 cycloalkyl group, a C3-8 cycloalkoxy group, a formyl group, a C1-6 alkylthio group, a hydroxyimino group, a C1-6 alkoxyimino group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A7 shown below, a 5- to 14-membered aromatic heterocyclic group which may be substituted with 1 to 3 substituents selected from Substituent Group A7 shown below, a 5- to 14-membered non-aromatic heterocyclic group which may be substituted with 1 to 3 substituents selected from Substituent Group A7 shown below and —O-$A^2$ (wherein $A^2$ represents a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below)) or (5) a C1-6 alkoxy group (wherein said C1-6 alkoxy group may be substituted with 1 to 3 substituents selected from the group consisting of a halogen atom, a hydroxyl group, a cyano group, a C3-8 cycloalkyl group, a C3-8 cycloalkoxy group, a formyl group, a C1-6 alkylthio group, a hydroxyimino group, a C1-6 alkoxyimino group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A7 shown below, a 5- to 14-membered aromatic heterocyclic group which may be substituted with 1 to 3 substituents selected from Substituent Group A7 shown below, a 5- to 14-membered non-aromatic heterocyclic group which may be substituted with 1 to 3 substituents selected from Substituent Group A7 shown below and —O-$A^2$ (wherein $A^2$ is the same as defined above)).

Substituent Group A7 refers to (1) a hydrogen atom, (2) a halogen atom, (3) a hydroxyl group, (4) a cyano group, (5) a C3-8 cycloalkyl group, (6) a C3-8 cycloalkoxy group, (7) a C1-6 alkylcarbonyl group, (8) a C1-6 alkylthio group, (9) a C1-6 alkylsulfinyl group, (10) a C1-6 alkylsulfonyl group, (11) a C1-6 alkyl group (wherein said C1-6 alkyl group may be substituted with 1 to 5 substituents selected from the group consisting of a halogen atom, a C1-6 alkyl group, a 6- to 14-membered aromatic hydrocarbon ring group, a 5- to 14-membered aromatic heterocyclic group and —O-$A^3$ (wherein $A^3$ represents a 6- to 14-membered aromatic hydrocarbon ring group or a 5- to 14-membered aromatic heterocyclic group)), (12) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (13) an amino group (wherein said amino group may be substituted with C1-6 alkyl groups optionally having 1 to 5 halogen atoms), (14) a 6- to 14-membered aromatic hydrocarbon ring group which may be substituted with 1 to 3 substituents selected from Substituent Group A7, (15) a 5- to 14-membered aromatic heterocyclic group which may be substituted with 1 to 3 substituents selected from Substituent Group A7, (16) a 5- to 14-membered non-aromatic heterocyclic group which may be substituted with 1 to 3 substituents selected from Substituent Group A7 or (17) —CO-$A^3$ (wherein $A^3$ is the same as defined above).

Substituent Group A8 refers to (1) a hydrogen atom, (2) C1-6 alkyl group (wherein said C1-6 alkyl group may be substituted with 1 to 3 substituents selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A7, a 5- to 14-membered aromatic heterocyclic group which may be substituted with 1 to 3 substituents selected from Substituent Group A7, a 5- to 14-membered non-aromatic heterocyclic group which may be substituted with 1 to 3 substituents selected from Substituent Group A7 and —X-$A^2$ (wherein X represents an imino group, —O— or —S— and $A^2$ represents a 6- to 14-membered aromatic hydrocarbon ring group or 5- to 14-membered aromatic heterocyclic group which may be substituted with 1 to 3 substituents selected from Substituent Group A7)), (3) a 6- to 14-membered aromatic hydrocarbon ring group which may be substituted with 1 to 3 substituents selected from Substituent Group A7, (4) a 5- to 14-membered aromatic heterocyclic group which may be substituted with 1 to 3 substituents selected from Substituent Group A7 or (5) —X-$A^2$ (wherein X and $A^2$ are the same as defined above).

Substituent Group A9 refers to (1) a hydrogen atom, (2) a halogen atom, (3) a C3-8 cycloalkyl group, (4) a C3-8 cycloalkoxy group, (5) a C1-6 alkyl group (wherein said C1-6 alkyl group may be substituted with 1 to 5 substituents selected from the group consisting of a halogen atom and a C1-6 alkyl group), (6) a C1-6 alkoxy group (wherein said C1-6 alkoxy group may be substituted with 1 to 5 halogen atoms or may, together with a carbon atom to which said adjacent C1-6 alkoxy groups bind, form a cyclic group), (7) an amino group (wherein said amino group may be substituted with C1-6 alkyl groups optionally having 1 to 5 halogen atoms), (8) a 5- to 14-membered non-aromatic heterocyclic group which may be substituted with 1 to 3 substituents selected from Substituent Group A9, (9) —CO-$A^3$ (wherein $A^3$ represents a 6- to 14-membered aromatic hydrocarbon ring group), (10) a 6- to 14-membered aromatic hydrocarbon ring group which may be substituted with 1 to 3 substituents selected from Substituent Group A9 or (11) a 5- to 14-membered aromatic heterocyclic group which may be substituted with 1 to 3 substituents selected from Substituent Group A9.

Substituent Group A10 refers to (1) a hydrogen atom, (2) a halogen atom, (3) a C1-6 alkyl group (wherein said C1-6 alkyl group may be substituted with 1 to 5 halogen atoms), (4) a C1-6 alkoxy group and (5) a 6- to 14-membered aromatic hydrocarbon ring group.

The term "halogen atom" refers to a fluorine atom, a chlorine atom, a bromine atom, an iodine atom, etc., and preferably a fluorine atom, a chlorine atom and a bromine atom.

The term "C1-6 alkyl group" refers to an alkyl group having 1 to 6 carbon atoms and preferable groups include linear or branched alkyl groups, for example, methyl group, ethyl group, n-propyl group, iso-propyl group, n-butyl group, isobutyl group, tert-butyl group, n-pentyl group, iso-pentyl group, neopentyl group, n-hexyl group, 1-methylpropyl group, 1,2-dimethylpropyl group, 1-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, 3-methylpentyl group, etc.

The term "C1-6 alkoxy group" refers to a group in which a hydrogen atom has been substituted with an oxygen atom in an alkyl group having 1 to 6 carbon atoms and preferable groups include, for example, methoxy group, ethoxy group, n-propoxy group, an i-propoxy group, n-butoxy group, i-butoxy group, sec-butoxy group, tert-butoxy group, n-pentoxy group, i-pentoxy group, sec-pentoxy group, tert-pentoxy group, n-hexoxy group, i-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group, 3-methylpentoxy group, a hexyloxy group, etc.

The term "C1-6 alkylsulfonyl group" refers to a group in which a hydrogen atom has been substituted with a sulfonyl group in an alkyl group having 1 to 6 carbon atoms and preferable groups include, for example, methanesulfonyl group, ethanesulfonyl group, etc.

The term "amino group which may be substituted with C1-6 alkyl groups" refers to an amino group which may be substituted with alkyl groups having 1 to 6 carbon atoms and preferable groups include, for example, amino group, methylamino group, ethylamino group, propylamino group, dimethylamino group, etc.

The term "C2-6 alkenyl group" refers to an alkenyl group having 2 to 6 carbon atoms and preferable groups include linear or branched alkenyl groups, for example, vinyl group, allyl group, 1-propenyl group, isopropenyl group, 1-buten-1-yl group, 1-buten-2-yl group, 1-buten-3-yl group, 2-buten-1-yl group, 2-buten-2-yl group, etc.

The term "C2-6 alkynyl group" refers to an alkynyl group having 2 to 6 carbon atoms and preferable groups include linear or branched alkynyl groups, for example, ethynyl group, 1-propynyl group, 2-propynyl group, butynyl group, pentynyl group, hexynyl group, etc.

The term "C3-8 cycloalkyl group" refers to a cyclic alkyl group having 3 to 8 carbon atoms and preferable groups include, for example, cyclopropyl group, cyclobutyl group, cyclopentyl group, cyclohexyl group, cycloheptyl group, cyclooctyl group, etc.

The term "C1-6 alkylthio group" refers to a group in which a hydrogen atom has been substituted with a sulfur atom in an alkyl group having 1 to 6 carbon atoms and preferable groups include, for example, methylthio group, ethylthio group, n-propylthio group, i-propylthio group, n-butylthio group, i-butylthio group, tert-butylthio group, n-pentylthio group, i-pentylthio group, neopentylthio group, n-hexylthio group, 1-methylpropylthio group, etc.

The term "C1-6 alkylsulfinyl group" refers to a group in which a hydrogen atom has been substituted with a sulfinyl group in an alkyl group having 1 to 6 carbon atoms and preferable groups include, for example, methylsulfinyl group, ethyl methylsulfinyl group, n-propylsulfinyl group, i-propylsulfinyl group, n-butylsulfinyl group, i-butylsulfinyl group, tert-butylsulfinyl group, n-pentylsulfinyl group, i-pentylsulfinyl group, neopentylsulfinyl group, n-hexylsulfinyl group, 1-methyl propyl sulfinyl group, etc.

The term "C1-6 alkylcarbonyl group" refers to a group in which a hydrogen atom has been substituted with a carbonyl group in an alkyl group having 1 to 6 carbon atoms and preferable groups include, for example, acetyl group, propionyl group, butyryl group, etc.

The term "C3-8 cycloalkoxy group" refers to a group in which a hydrogen atom has been substituted with an oxygen atom in a cyclic alkyl group having 3 to 8 carbon atoms and preferable groups include, for example, cyclopropoxy group, cyclobutoxy group, cyclopentoxy group, cyclohexoxy group, cycloheptyloxy group, cyclooctyloxy group, etc.

The term "C3-8 cycloalkylthio group" refers to a group in which a hydrogen atom has been substituted with a sulfur atom in a cyclic alkyl group having 3 to 8 carbon atoms and preferable groups include, for example, cyclopropylthio group, cyclobutylthio group, cyclopentylthio group, cyclohexylthio group, cycloheptylthio group, cyclooctylthio group, etc.

The term "C1-6 alkoxyimino group" refers to a group in which a hydrogen atom has been substituted with a C1-6 alkoxy group in an imino group and preferable groups include, for example, methoxyimino group, ethoxyimino group, etc.

The term "C2-6 alkenyloxy group" refers to a group in which a hydrogen atom has been substituted with an oxygen atom in an alkenyl group having 2 to 6 carbon atoms and preferable groups include linear or branched alkenyloxy groups, for example, vinyloxy group, allyloxy group, 1-propenyloxy group, isopropenyloxy group, 1-buten-1-yloxy group, 1-buten-2-yloxy group, 1-buten-3-yloxy group, 2-buten-1-yloxy group, 2-buten-2-yloxy group.

The term "C2-6 alkynyloxy group" refers to a group in which a hydrogen atom has been substituted with an oxygen atom in an alkynyl group having 2 to 6 carbon atoms and preferable groups include linear or branched alkynyloxy groups, for example, ethynyloxy group, 1-propynyloxy group, 2-propynyloxy group, butynyloxy group, pentynyloxy group, hexynyloxy group, etc.

The term "C3-8 cycloalkylsulfinyl group" refers to a group in which a hydrogen atom has been substituted with a sulfinyl group in a cyclic alkyl group having 3 to 8 carbon atoms and preferable groups include, for example, cyclopropylsulfinyl group, cyclobutylsulfinyl group, cyclopentylsulfinyl group, cyclohexylsulfinyl group, cycloheptylsulfinyl group, cyclooctylsulfinyl group, etc.

The term "C3-8 cycloalkylsulfonyl group" refers to a group in which a hydrogen atom has been substituted with a sulfonyl group in a cyclic alkyl group having 3 to 8 carbon atoms and preferable groups include, for example, cyclopropylsulfonyl group, cyclobutylsulfonyl group, cyclopentylsulfonyl group, cyclohexylsulfonyl group, cycloheptylsulfonyl group, cyclooctylsulfonyl group, etc.

Preferable examples of "hydroxyl group having a protecting group" include methoxymethyl ether group, tetrahydropyranyl ether group, tert-butyl ether group, allyl ether group, benzoate group, acetate group, formate group, crotonate group, p-phenylbenzoate group or pivaloate group, tert-butydimethyl silyl group, tert-butyldiphenyl silyl group, trityl group, benzyl group, etc.

Preferable examples of C1-6 alkoxy group in "C1-6 alkoxy group (wherein said C1-6 alkoxy group may be substituted with 1 to 5 halogen atoms or may, together with a carbon atom to which said adjacent C1-6 alkoxy groups bind, form a cyclic group)" include a C1-6 alkoxy group substituted with 1 to 5 halogen atoms or a cyclic group can be formed together with a carbon atom to which said adjacent C1-6 alkoxy groups bind. The expression "a cyclic group can be formed together with a carbon atom to which said adjacent C1-6 alkoxy groups bind" means, for example, a methylenedioxy group, ethylenedioxy group, etc. and it can be specifically illustrated by, for example, a formula:

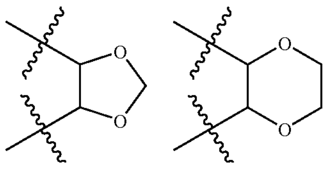

and the like.

The substituent in a "C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom))" can be specifically illustrated by, for example, a formula:

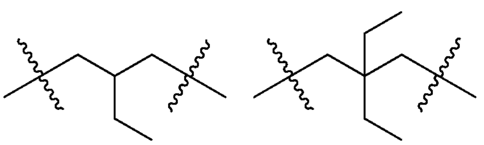

-continued

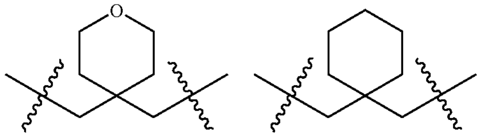

and the like.

Next, the compound of Formula (I) of the present invention is described.

Among the compounds represented by Formula (I), preferred is a compound or a pharmacologically acceptable salt thereof in which $Ar_1$ is an imidazolyl group which may be substituted with 1 to 2 substituents selected from Substituent Group A1;

more preferred is a compound or a pharmacologically acceptable salt thereof in which $Ar_1$ is an imidazolyl group which may be substituted with 1 to 2 substituents selected from a hydrogen atom, a halogen atom, a C3-8 cycloalkyl group, a C2-6 alkeny group, a C2-6 alkyny group and a C1-6 alkyl group (wherein said C1-6 alkyl group may be substituted with 1 to 3 halogen atoms); and the most preferred is a compound or a pharmacologically acceptable salt thereof in which $Ar_1$ is an imidazolyl group which may be substituted with 1 to 2 substituents selected from the group consisting of a hydrogen atom, a halogen atom, a C3-8 cycloalkyl group and a C1-6 alkyl group.

Among the compounds represented by Formula (I), preferred is a compound or a pharmacologically acceptable salt thereof in which $Ar_2$ is a pyridinyl group, a pyrimidinyl group, or a phenyl group which may be substituted with 1 to 3 substituents selected from Substituent Group A2;

more preferred is a compound or a pharmacologically acceptable salt thereof in which $Ar_2$ is a pyridinyl group, a pyrimidinyl group or a phenyl group which may be substituted with 1 to 3 substituents selected from the group consisting of a hydrogen atom, a halogen atom, a cyano group, a hydroxyl group, a C1-6 alkoxy group (wherein said C1-6 alkoxy group may be substituted with 1 to 3 substituents selected from a C2-6 alkeny group, a C2-6 alkyny group and a C3-8 cycloalkyl group), a C2-6 alkenyloxy group and a C2-6 alkynyloxy group; and the most preferred is a compound or a pharmacologically acceptable salt thereof in which $Ar_2$ is a pyridinyl group, a pyrimidinyl group or a phenyl group which may be substituted with 1 to 3 substituents selected from the group consisting of (1) a hydrogen atom, (2) a halogen atom, (3) a cyano group and (4) a C1-6 alkoxy group.

Among the compounds represented by Formula (I), preferred is a compound or a pharmacologically acceptable salt thereof in which $X_1$ represents (1) $—C≡C—$ or (2) $—CR^3═CR^4—$ (wherein $R^3$ and $R^4$ represents a substituent selected from Substituent Group A3;

more preferred is a compound or a pharmacologically acceptable salt thereof in which $X_1$ is $—CR^{31}═CR^{41}—$ (wherein $R^{31}$ is a group selected from the group consisting of (1) a hydrogen atom, (2) a halogen atom, (3) a C1-6 alkyl group and (4) a C1-6 alkoxyl group;

and $R^{41}$ represents a group selected from the group consisting of (1) a hydrogen atom, (2) a halogen atom, (3) a 6- to 14-membered aromatic hydrocarbon ring group which may be substituted with 1 to 3 substituents selected from Substituent Group A5, (4) a 5- to 14-membered aromatic heterocyclic group which may be substituted with 1 to 3 substituents selected from Substituent Group A5 and (5) a C1-6 alkyl group (wherein said C1-6 alkyl group may be substituted with 1 to 3 substituents selected from the group consisting of a halogen atom, a hydroxy group, a cyano group, a C3-8 cycloalkyl group, a C1-6 alkyl group, a C1-6 alkoxy group, an amino group (wherein said amino group may be substituted with C1-6 alkyl groups optionally having 1 to 5 halogen atoms), a 6- to 14-membered aromatic hydrocarbon ring group which may be substituted with 1 to 3 substituents selected from Substituent Group A5, a 5- to 14-membered aromatic heterocyclic group which may be substituted with 1 to 3 substituents selected from Substituent Group A5, a 5- to 14-membered non-aromatic heterocyclic group which may be substituted with 1 to 3 substituents selected from Substituent Group A5 and —O-$A^1$ (wherein $A^1$ represents a 6- to 14-membered aromatic hydrocarbon ring group which may be substituted with 1 to 3 substituents selected from Substituent Group A5 or a 5- to 14-membered aromatic heterocyclic group which may be substituted with 1 to 3 substituents selected from Substituent Group A5))); and the most preferred is a compound or a pharmacologically acceptable salt thereof in which $X_1$ is —$CR^{32}$=$CR^{42}$— (wherein $R^{32}$ represents a hydrogen atom or a halogen atom, and $R^{42}$ represents a substituent selected from the group consisting of a hydrogen atom, a halogen atom and a C1-6 alkyl group (wherein said C1-6 alkyl group may be substituted with a C3-8 cycloalkyl group or a phenyl group) and a phenyl group).

Among the compounds represented by Formula (I), a compound or a pharmacologically acceptable salt thereof in which $R^1$ and $R^2$ represent groups selected from Substituent Group A4 or the group formed by $R^1$ and $R^2$, together with a nitrogen atom is a 5- to 11-membered heterocyclic group represented by Formula (II) which may be substituted with 1 to 4 substituents selected from Substituent Group A4; a 6- to 20-membered non-aromatic heterocyclic group represented by Formula (III) which may be substituted with 1 to 4 substituents selected from Substituent Group A4, a 9- to 16-membered non-aromatic heterocyclic group represented by Formula (IV) which may be substituted with 1 to 4 substituents selected from Substituent Group A4, a group represented by the following formula:

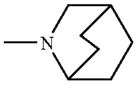,
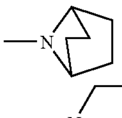,
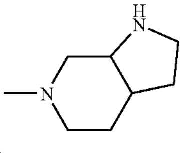
or
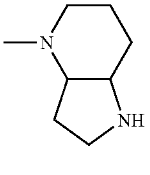

which may be substituted with 1 to 4 substituents selected from Substituent Group A4, a group represented by the following formula:

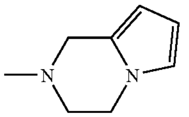,
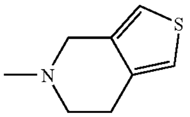,
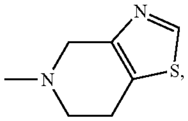
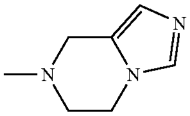,
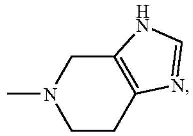,
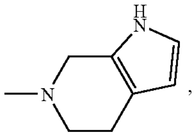,
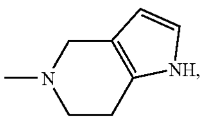
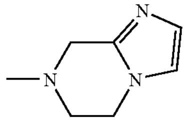,
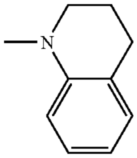,
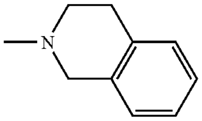,
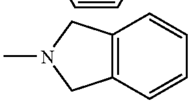
or
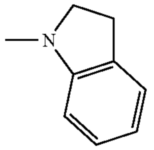

which may be substituted with 1 to 4 substituents selected from Substituent Group A4, a cyclic group represented by Formula (V) which may be substituted with 1 to 4 substituents selected from Substituent Group A4, a cyclic group represented by Formula (VI) which may be substituted with 1 to 4 substituents selected from Substituent Group A4 and a cyclic group represented by the following formula:

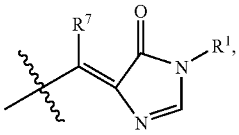
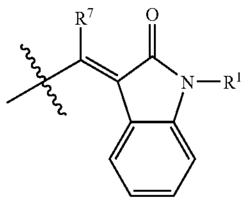
or
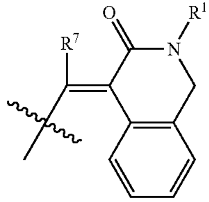

which may be substituted with 1 to 4 substituents selected from Substituent Group A4 can be exemplified as a preferable compound.

Among the compounds represented by Formula (I), preferred is a compound or a pharmacologically acceptable salt thereof in which $R^1$ and $R^2$ are groups selected from Substituent Group A4;

more preferred is a compound or a pharmacologically acceptable salt thereof in which $R^1$ is a group selected from Substituent Group A8 and $R^2$ is a group selected from Substituent Group A6; and the most preferred is a compound or a pharmacologically acceptable salt thereof in which $R^1$ is a C1-6 alkyl group (wherein said C1-6 alkyl group is a hydrogen atom, a C3-8 cycloalkoxy group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, a 6- to 14-membered aromatic hydrocarbon ring group which may be substituted with 1 to 3 substituents selected from Substituent Group A9, a 5- to 14-membered aromatic heterocyclic group which may be substituted with 1 to 3 substituents selected from Substituent Group A9 and —O— $A^4$ (wherein $A^4$ represents a 6- to 14-membered aromatic hydrocarbon ring group or 5- to 14-membered aromatic heterocyclic group which may be substituted with 1 to 3 substituents selected from Substituent Group A9)), and $R^2$ is (1) a hydrogen atom or (2) a C1-6 alkyl group (wherein said C1-6 alkyl group may be substituted with 1 to 3 substituents selected from the group consisting of a hydroxyl group, a C3-8 cycloalkyl group, a C3-8 cycloalkoxy group, a C1-6 alkylthio group, an amino group (wherein said amino group may be substituted with a C1-6 alkyl group optionally having 1 to 5 halogen atoms), a 6- to 14-membered aromatic hydrocarbon ring group which may be substituted with 1 to 3 substituents selected from Substituent Group A9, a 5- to 14-membered aromatic heterocyclic group which may be substituted with 1 to 3 substituents selected from Substituent Group A9 and a 5- to 14-membered non-aromatic heterocyclic group which may be substituted with 1 to 3 substituents selected from Substituent Group A9).

Among the compounds represented by Formula (I), a 5- to 11-membered heterocyclic group represented by Formula (II) formed by $R^1$ and $R^2$, together with a nitrogen atom to which they bind, refers to a hetero atom containing cyclic group having 5 to 11 total members and preferable examples include a piperidinyl group, a pyrrolidinyl group, an azepinyl group, an azocanyl group, a piperazinyl group, a 1,4-diazepanyl group, a morpholinyl group or a thiomorpholinyl group.

Among the compounds represented by Formula (I), preferred is a compound or a pharmacologically acceptable salt thereof in which $R^1$ and $R^2$ form a 5- to 11-membered heterocyclic group represented by Formula (II), together with a nitrogen atom to which they bind, which may be substituted with 1 to 4 substituents selected from Substituent Group A4;

more preferred is a compound or a pharmacologically acceptable salt thereof in which $R^1$ and $R^2$ form a 5- to 11-membered heterocyclic group represented by Formula (II), together with a nitrogen atom to which they bind, which may be substituted with 1 to 4 substituents selected from the group consisting of a hydrogen atom, a halogen atom, a hydroxyl group, a formyl group, a hydroxyimino group, a C1-6 alkoxyimino group, a C1-6 alkyl group (wherein said C1-6 alkyl group may be substituted with 1 to 3 substituents selected from the group consisting of a hydroxyl group, a 6- to 14-membered aromatic hydrocarbon ring group which may be substituted with 1 to 3 substituents selected from Substituent Group A7 shown below, a 5- to 14-membered aromatic heterocyclic group which may be substituted with 1 to 3 substituents selected from Substituent Group A7 shown below), 6- to 14-membered aromatic hydrocarbon ring group which may be substituted with 1 to 3 substituents selected from substituents of A7 shown below, a 5- to 14-membered aromatic heterocyclic group which may be substituted with 1 to 3 substituents selected from Substituent Group A7 shown below, —O-$A^2$ (wherein $A^2$ represents a 6- to 14-membered aromatic hydrocarbon ring group which may be substituted with 1 to 3 substituents selected from Substituent Group A7 shown below or a 5- to 14-membered aromatic heterocyclic group which may be substituted with 1 to 3 substituents selected from Substituent Group A7 shown below), —CO-$A^2$ (wherein $A^2$ is the same as defined above) and =CH-$A^2$ (wherein $A^2$ is the same as defined above); and the most preferred is a compound or a pharmacologically acceptable salt thereof in which $R^1$ and $R^2$ form a 5- to 11-membered heterocyclic group represented by Formula (II), together with a nitrogen atom to which they bind, which may be substituted with 1 to 4 substituents selected from the group consisting of a hydrogen atom, a halogen atom, a hydroxyl group, a C1-6 alkyl group (wherein said C1-6 alkyl group may be substituted with 1 to 3 substituents selected from the group consisting of a hydroxyl group or a 6- to 14-membered aromatic hydrocarbon ring group which may be substituted with 1 to 3 substituents selected from Substituent Group A10), a 6- to 14-membered aromatic hydrocarbon ring group which may be substituted with 1 to 3 substituents selected from substituents of A10, a 5- to 14-membered aromatic heterocyclic group which may be substituted with 1 to 3 substituents selected from Substituent Group A10, —O-$A^6$ (wherein $A^6$ represents a 6- to 14-membered aromatic hydrocarbon ring group which may be substituted with 1 to 3 substituents selected from Substituent Group A10 shown below) and =CH-$A^6$ (wherein $A^6$ is the same as defined above).

Among the compounds represented by Formula (I), the "6- to 20-membered non-aromatic heterocyclic group" represented by Formula (III) formed by $R^1$ and $R^2$, together with a nitrogen atom to which they bind, refers to a hetero atom containing spiro cyclic group having 6 to 20 total members and preferable examples include

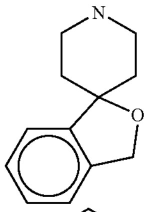
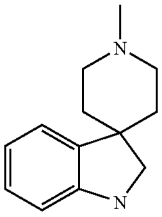
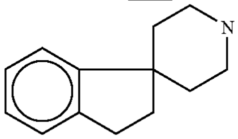
or
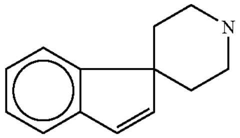

and the like.

In addition, among the compounds represented by Formula (I), preferred is a compound or a pharmacologically acceptable salt thereof in which $R^1$ and $R^2$ form a 6- to 20-membered non-aromatic heterocyclic group represented by Formula (III), together with a nitrogen atom to which they bind, which may be substituted with 1 to 4 substituents selected from Substituent Group A4.

Among the compounds represented by Formula (I), preferred is a compound in which the group formed by $R^1$ and $R^2$, together with a nitrogen atom to which they bind is a 9- to 16-membered non-aromatic heterocyclic group represented by Formula (IV) which may be substituted with 1 to 4 substituent groups selected from Substituent Group A4 or a pharmaceutically acceptable salt thereof.

The "9- to 16-membered non-aromatic heterocyclic group" represented by Formula (IV) refers to a hetero atom containing cyclic group having 9 to 16 members in total.

Among the compounds represented by Formula (I), preferred is a compound in which the group formed by $R^1$ and $R^2$, together with a nitrogen atom to which they bind, is a group represented by the following formula:

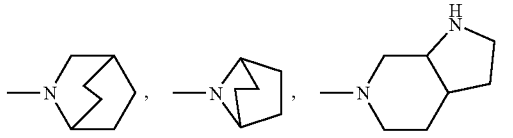

or

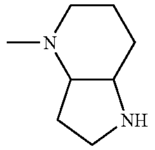

which may be substituted with 1 to 4 substituent groups selected from Substituent Group A4 or a pharmaceutically acceptable salt thereof.

Among the compounds represented by Formula (I), preferred is a compound in which the group formed by $R^1$ and $R^2$, together with a nitrogen atom to which they bind, is a group represented by the following formula:

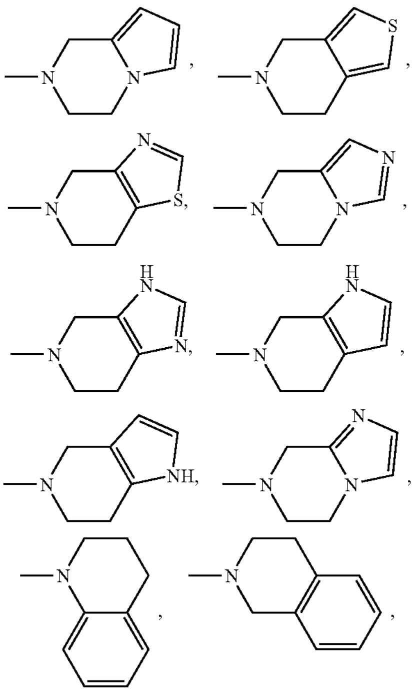

-continued

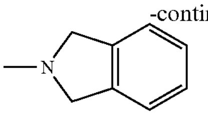

or

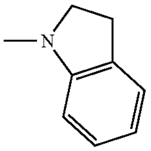

which may be substituted with 1 to 4 substituent groups selected from Substituent Group A4 or a pharmaceutically acceptable salt thereof.

Among the compounds represented by Formula (I), more preferred is a compound in which $R^1$ and $R^2$, together with a nitrogen atom to which they bind, form a group represented by the following formula:

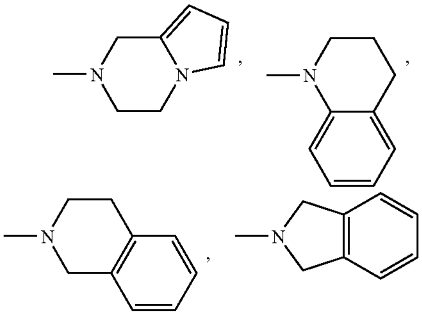

or

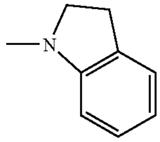

which may be substituted with 1 to 4 substituent groups selected from Substituent Group A4 or a pharmaceutically acceptable salt thereof.

Among the compounds represented by Formula (I), preferred is a compound in which the group formed by $R^1$ and $R^2$, together with a nitrogen atom to which they bind, may be substituted with 1 to 4 substituent groups selected from Substituent Group A4 or a pharmaceutically acceptable salt thereof.

Among the compounds represented by Formula (I), more preferred is a compound in which the group formed by $R^1$ and $R^2$, together with a nitrogen atom to which they bind, may be substituted with 1 to 4 fluorine atoms and the like or a pharmaceutically acceptable salt thereof.

Among the compounds represented by Formula (I), preferred is a compound in which the group formed by $R^1$ and $R^2$, together with —$X_1$—CO—N, is a cyclic group (wherein $R^7$ represents a substituent selected from substituent-Group A3) represented by Formula (V) in which may be substituted with 1 to 4 substituents selected from Substituent Group A4 or a pharmaceutically acceptable salt thereof.

Among the compounds represented by Formula (I), preferred is a compound in which the group formed by $R^1$ and $R^2$, together with —$X_1$—CO—N, is a cyclic group represented by Formula (VI) in which may be substituted with 1 to 4 substituents selected from Substituent Group A4 (wherein R1 represents a substituent selected from Substituent Group A4, and R7 represents a substituent selected from Substituent Group A3) or a pharmaceutically acceptable salt thereof.

Among the compounds represented by Formula (I), more preferred is a compound in which the group formed by $R^1$ and $R^2$, together with —$X_1$—CO—N, is a cyclic group represented by the following formula:

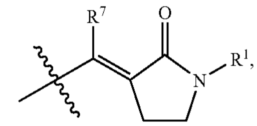,
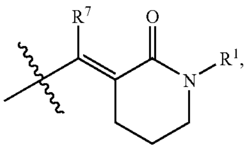,
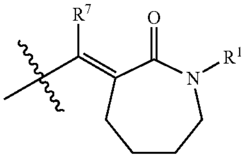
or
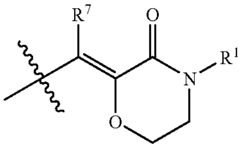

which may be substituted with 1 to 4 substituent groups selected from Substituent Group A7 (wherein, R1 represents a substituent selected from Substituent Group A4, and R7 represents Substituent Group A3) or a pharmaceutically acceptable salt thereof.

Among the compounds represented by Formula (I), preferred is a compound in which $R^1$ in the above described cyclic group is a substituent selected from Substituent Group A4 or a pharmaceutically acceptable salt thereof.

Among the compounds represented by Formula (I), more preferred is a compound in which $R^1$ in the above described cyclic group is a substituent selected from Substituent Group A8 or a pharmaceutically acceptable salt thereof.

Among the compounds represented by Formula (I), the most preferred is a compound in which $R^1$ in the above described cyclic group is a substituent selected from the group consisting of a C1-6 alkyl group (wherein said C1-6 alkyl group may be substituted with 1 to 3 substituent groups selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 3 substituent groups selected from Substituent Group A9, a 5- to 14-membered aromatic heterocyclic group which may be substituted with 1 to 3 substituent groups selected from Substituent Group A9, a 5- to 14-membered non-aromatic heterocyclic group which may be substituted with 1 to 3 substituent groups selected from Substituent Group A9 and —X-$A^4$ (wherein X represents an imino group, —O— or —S— and $A^4$ represents a 6- to 14-membered aromatic hydrocarbon ring group which may be substituted with 1 to 3 substituent groups selected from Substituent Group A9 or 5- to 14-membered aromatic heterocyclic group which may be substituted with 1 to 3 substituent groups selected from Substituent Group A9)) or a pharmaceutically acceptable salt thereof.

Among the compounds represented by Formula (I), preferred is a compound in which the group formed by $R^1$ and $R^2$, together with —$X_1$—CO—N, is a cyclic group represented by the following formula:

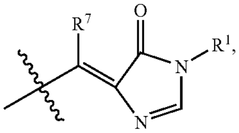,
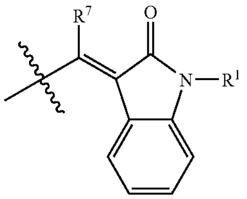
or
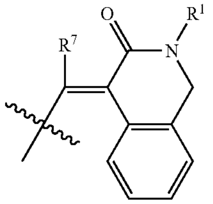

which may be substituted with 1 to 4 substituent groups selected from Substituent Group A4 or a pharmaceutically acceptable salt thereof.

Among the compounds represented by Formula (I), preferred is a compound in which $R^1$ in the above described cyclic group is a substituent selected from Substituent Group A4 or a pharmaceutically acceptable salt thereof.

Among the compounds represented by Formula (I), more preferred is a compound in which $R^1$ in the above described cyclic group is a substituent selected from Substituent Group A8 or a pharmaceutically acceptable salt thereof.

Among the compounds represented by Formula (I), the most preferred is a compound in which $R^1$ in the above described cyclic group is a substituent selected from the group consisting of a C1-6 alkyl group (wherein said C1-6 alkyl group may be substituted with 1 to 3 substituent groups selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl group optionally having 1 to 5 halogen atoms), a 6- to 14-membered aromatic hydrocarbon ring group which may be substituted with 1 to 3 substituent groups selected from Substituent Group A9, a 5- to 14-membered aromatic heterocyclic group which may be substituted with 1 to 3 substituent groups selected from Substituent Group A9, a 5- to 14-membered non-aromatic heterocyclic group which may be substituted with 1 to 3 substituent groups selected from Substituent Group A9 and —X-$A^4$ (wherein X represents an imino group, —O— or —S— and $A^4$ represents a 6- to 14-membered aromatic hydrocarbon ring group which may be substituted with 1 to 3 substituent groups selected from Substituent Group A9 or 5- to 14-membered aromatic heterocyclic group which may be substituted with 1 to 3 substituent groups selected from Substituent Group A9)) or a pharmaceutically acceptable salt thereof.

Among the compounds represented by Formula (I), preferred is a compound in which $R^1$ in Formula (I), $R^1$ in Formula (VI) and $R^1$ in the cyclic group represented by the following formula:

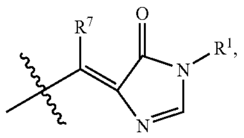

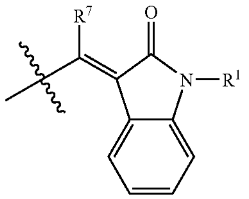

or

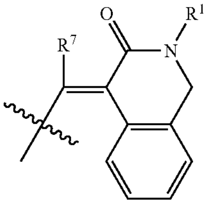

is $—X_{21}—X_{22}—Ar_3$ wherein $X_{21}$ represents a C1-6 alkylene group (wherein said C1-6 alkylene group may be substituted with 1 to 3 substituent groups selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl), a 5- to 14-membered non-aromatic heterocyclic group which may be substituted with 1 to 3 substituent groups selected from Substituent Group A7) or a single bond, and $X_{22}$ represents a single bond, an imino group which may be substituted with a substituent selected from Substituent Group A7, —O— or —S— and $Ar_3$ represents a 6- to 14-membered aromatic hydrocarbon ring group which may be substituted with 1 to 3 substituent groups selected from Substituent Group A7 or a 5- to 14-membered aromatic heterocyclic group which may be substituted with 1 to 3 substituent groups selected from Substituent Group A7 or a pharmaceutically acceptable salt thereof.

Among the compounds represented by Formula (I), more preferred is a compound in which $R^1$ is $—X_{21a}—X_{22a}—Ar_{3a}$ wherein $X_{21a}$ represents a C1-6 alkylene group (wherein said C1-6 alkylene group may be substituted with 1 to 3 substituent groups selected from the group consisting of a hydrogen atom, a halogen atom, a hydroxyl group, a cyano group, a C3-8 cycloalkyl group, a C3-8 cycloalkoxy group, a formyl group, a C1-6 alkyl group (wherein 1 or 2 of said C1-6 alkyl group may substitute the same carbon atom in the C1-6 alkylene group and said two C1-6 alkyl groups may, together with the carbon atom to which they bind, form a cyclic group (wherein a methylene group in the cyclic group which constitutes the ring may be substituted with one oxygen atom)), a C1-6 alkoxy group, an amino group (wherein said amino group may be substituted with a C1-6 alkyl having 1 to 5 halogen atoms), a 5- to 14-membered non-aromatic heterocyclic group which may be substituted with 1 to 3 substituent groups selected from Substituent Group A9), and $X_{22a}$ represents a single bond or an oxygen atom and $Ar_{3a}$ represents a 6- to 14-membered aromatic hydrocarbon ring group which may be substituted with 1 to 3 substituent groups selected from Substituent Group A9 or a 5- to 14-membered aromatic heterocyclic group which may be substituted with 1 to 3 substituent groups selected from Substituent Group A9 or a pharmaceutically acceptable salt thereof.

Furthermore, $Ar_{3a}$ in "$—X_{21a}—X_{22a}—Ar_{3a}$" represents a 6- to 14-membered aromatic hydrocarbon ring group or a 5- to 14-membered aromatic heterocyclic group and preferably a group selected from a phenyl group, a naphthyl group and a fluorenyl group or a group selected from a thienyl group, a pyridinyl group, a guinolinyl group, an isoquinolinyl group, an indolyl group, a benzothiazolyl group, a benzoxazolyl group and a furyl group.

Among the compounds represented by Formula (I), preferred is a compound in which $R^1$ is a 6- to 14-membered non-aromatic hydrocarbon ring group or a 5- to 14-membered non-aromatic heterocyclic group represented by Formula (VII) or a pharmaceutically acceptable salt thereof.

Among the compounds represented by Formula (I), preferred is a compound in which $R^1$ is represented by Formula (VII) wherein $Ar_4$ represents a phenyl group, a pyridinyl group, a pyrimidinyl group, a pyrazinyl group, a thienyl group, an oxazolyl group, a pyrrolyl group, a thiazolyl group and a furyl group, which may be substituted with 1 to 3 substituent groups selected from the group consisting of a halogen atom, a C1-6 alkyl group (wherein said C1-6 alkyl group may be substituted with 1 to 3 substituent groups selected from the group consisting of a halogen atom and a C1-6 alkyl group), a C1-6 alkoxy group (wherein said C1-6 alkoxy group may be substituted with 1 to 3 halogen atoms), an amino group (wherein said amino group may be substituted with a C1-6 alkyl group optionally having 1 to 5 halogen atoms), a 6- to 14-membered aromatic hydrocarbon ring group which may be substituted with 1 to 3 substituent groups selected from Substituent Group A7, a 5- to 14-membered aromatic heterocyclic group which may be substituted with 1 to 3 substituent groups selected from Substituent Group A7, a 5- to 14-membered non-aromatic heterocyclic group which may be substituted with 1 to 3 substituent groups selected from Substituent Group A7 and $—CO-A^2$ (wherein $A^2$ represents a 6- to 14-membered aromatic hydrocarbon ring group which may be substituted with 1 to 3 substituent groups selected from Substituent Group A7 or a 5- to 14-membered aromatic heterocyclic group which may be substituted with 1 to 3 substituent groups selected from Substituent Group A7) or a pharmaceutically acceptable salt thereof.

Among the compounds represented by Formula (I), the most preferred is a compound in which $R^1$ is represented by Formula (VII) wherein $R^1$ is an indanyl group, an azaindanyl group, a tetrahydronaphthyl group, an azatetrahydronaphthyl group, a chromanyl group, an azachromanyl group, a tetrahydrobenzofuranyl group or a tetrahydrobenzothienyl group, which may be substituted with 1 to 3 substituent groups selected from the group consisting of, for example, a halogen atom, a hydroxyl group, a cyano group, a C3-8 cycloalkyl group, a C3-8 cycloalkoxy group, a C1-6 alkyl group (wherein said C1-6 alkyl group may be substituted with 1 to 3 halogen atoms or C1-6 alkyl groups), a C1-6 alkoxy group (wherein said C1-6 alkoxy group may be substituted with 1 to 3 halogen atoms), an amino group (wherein said amino group may be substituted with a C1-6 alkyl having 1 to 5 halogen atoms), and a 5- to 14-membered non-aromatic heterocyclic group or a pharmaceutically acceptable salt thereof.

Particularly, preferred are compounds selected from the following group, for example, or a pharmaceutically acceptable salt thereof, which are useful as a preventive or therapeutic agent for diseases caused by amyloid beta, for example, Alzheimer's disease, senile dementia, Down syndrome, amyloidosis, etc.

1) (E)-N-Biphenyl-3-ylmethyl-3-[3-methoxy-4-(4-methyl-1H-imidazol-1-yl)phenyl]acrylamide,
2) (E)-N-((1S)-Indan-1-yl)-3-[3-methoxy-4-(4-methyl-1H-imidazol-1-yl)phenyl]acrylamide,
3) (E)-N-(Chroman-4-yl)-3[3-methoxy-4-(4-methyl-1H-imidazol-1-yl)phenyl]acrylamide,
4) (E)-1-(3,4-Difluorobenzyl)-3-[3-methoxy-4-(4-methyl-1H-imidazol-1-yl)benzylidene]piperidin-2-one,
5) (E)-1-Indan-2-yl-3[3-methoxy-4-(4-methyl-1H-imidazol-1-yl)benzylidene]piperidin-2-one,
6) (E)-1-(Chroman-4-yl)-3-[3-methoxy-4-(4-methyl-1H-imidazol-1-yl)benzylidene]piperidin-2-one,
7) (E)-1-[(1S)-1-(4-Fluorophenyl)ethyl]-3-(3-methoxy-4-(4-methyl-1H-imidazol-1-yl)benzylidene]piperidin-2-one,
8) (E)-1-[(6-Chloropyridin-2-yl)methyl]-3-[3-methoxy-4-(4-methyl-1H-imidazol-1-yl)benzylidene]piperidin-2-one,
9) (E)-1-(4-Tert-butylbenzyl)-3-[3-methoxy-4-(4-methyl-1H-imidazol-1-yl)benzylidene]piperidin-2-one,
10) (E)-1-(3,4-Difluorobenzyl)-3-{[5-methoxy-6-(4-methyl-1H-imidazol-1-yl)pyridin-3-yl]methylene}piperidin-2-one,
11) (E)-1-[(1H-Indole-3-yl)ethyl]-3-[3-methoxy-4-(4-methyl-1H-imidazol-1-yl)benzylidene]piperidin-2-one,
12) (E)-1-(5-Fluoroindan-2-yl)-3-[3-methoxy-4-(4-methyl-1H-imidazol-1-yl)benzylidene]piperidin-2-one,
13) (E)-1-(7-Fluorochroman-4-yl)-3-[3-methoxy-4-(4-methyl-1H-imidazol-1-yl)benzylidene]piperidin-2-one,
14) (E)-3-[3-Methoxy-4-(4-methyl-1H-imidazol-1-yl)benzyliden]-1-(1,2,3,4-tetrahydronaphthalen-2-yl)piperidin-2-one and,
15) (E)-1-[(2,4-Difluorophenyl)ethyl]-3-[3-methoxy-4-(4-methyl-1H-imidazol-1-yl)benzylidene]piperidin-2-one.

Although the above are preferable embodiments of the compound of the above-mentioned general formula (I), the active ingredient of a pharmaceutical agent according to the present invention is not limited to a specific compound described in this specification, and any embodiment can be selected from the full extent contained in the range of the compound of general formula (I).

The production process of the compound of the general formula (I) of the present invention is described below.

The compound represented by the general formula (I)

(I)

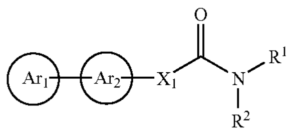

(wherein $Ar_1$, $Ar_2$, $X_1$, $R^1$ and $R^2$ have the same meanings as above and if necessary, $Ar_1$ and $Ar_2$ may contain protecting group(s) for functional groups such as hydroxy group(s), amino group(s) or carboxylic acid group(s).) can be synthesized according to the following General Production Processes 1 to 5.

(General Production Process 1)

A typical production process (General Production Process 1) of the compound of the general formula (I) according to the present invention is described below.

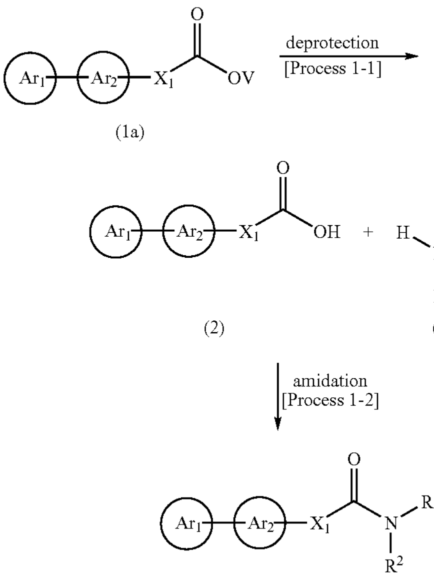

(1a) (2) (3) (I)

(wherein $Ar_1$, $Ar_2$ and $X_1$ is the same as defined above; V represents a protecting group for carboxyl group such as a methyl group, an ethyl group, a benzyl group, an allyl group, a triphenylmethyl group, a tert-butyl group, a methoxymethyl group or a tert-butyldimethylsilyl group, and (1) $R^1$ and $R^2$ represent groups selected from Substituent Group A4 shown below or $R^1$ and $R^2$, together with a nitrogen atom to which they bind, form one of the following groups:

(2-1) a 5- to 11-membered non-aromatic heterocyclic group represented by Formula (II):

(II)

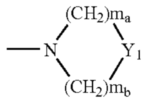

(wherein $Y_1$ represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$=$CR^6$— (wherein $R^5$ and $R^6$ represent groups selected from Substituent Group A4 shown below), (11) a single bond or (12) >C=$CR^{13}R^{14}$ (wherein $R^{13}$ and $R^{14}$ represent groups selected from Substituent Group A4 shown below); and $m_a$ and $m_b$ represent an integer of 0 to 4) which may be substituted with 1 to 4 substituent groups selected from Substituent Group A4;

(2-2) a 6- to 20-membered non-aromatic heterocyclic group represented by Formula (III):

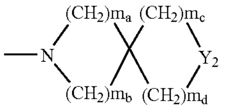

(III)

(wherein $Y_2$ represents (1) —NH—, (2) —O—, (3) —S—, (4) —SO—, (5) —$SO_2$—, (6) —$CH_2$—, (7) —CO—, (8) —CONH—, (9) —NHCO—, (10) —$CR^5$=$CR^6$— (wherein $R^5$ and $R^6$ represent groups selected from Substituent Group A4 shown below or $R^5$ and $R^6$, together with a carbon atom to which they bind, form a 6- to 14-membered aromatic hydrocarbon ring group or a 6- to 14-membered non-aromatic hydrocarbon ring group) or (11) a single bond; and $m_a$, $m_b$, $m_c$ and $m_d$ represent an integer of 0 to 4) which may be substituted with 1 to 4 substituent groups selected from Substituent Group A4;

(2-3) a 9- to 16-membered non-aromatic heterocyclic group represented by Formula (IV):

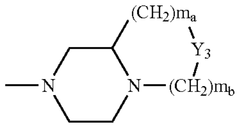

(IV)

(wherein $Y_3$ represents (1) —NH—, (2) —O—, (3) —S—, (4) —S—, (5) —$SO_2$—, (6) —$CH_2$—, (7) —CO—, (8) —CONH—, (9) —NHCO— or (10) a single bond; and $m_a$ and $m_b$ represent an integer of 0 to 4) which may be substituted with 1 to 4 substituent groups selected from Substituent Group A4;

(2-4) a group represented by the following formula:

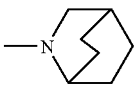 , 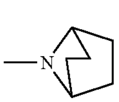 , 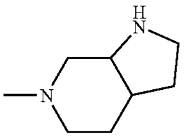 or

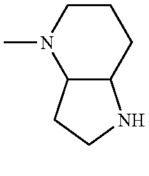

which may be substituted with 1 to 4 substituent groups selected from Substituent Group A4;

(2-5) a group represented by the following formula:

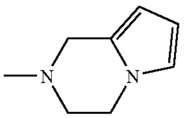 , 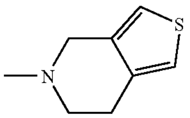 ,

-continued

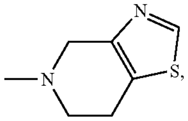 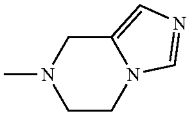 ,

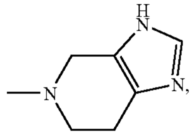 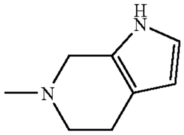 ,

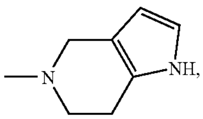 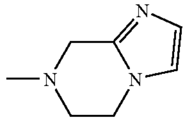 ,

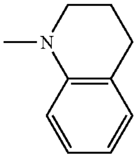 , 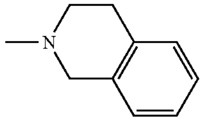 ,

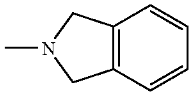 or 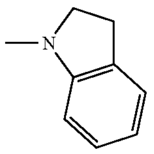

which may be substituted with 1 to 4 substituent groups selected from Substituent Group A4 shown below.

Substituent group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituent groups selected from Substituent Group A4, (19) a C1-6 alkoxy group which may be substituted with 1 to 3 substituent groups selected from Substituent Group A4, (20) an amino group which may be substituted with 1 to 2 substituent groups selected from Substituent Group A4, (21) a carbamoyl group which may be substituted with 1 to 2 substituent groups selected from Substituent Group A4, (22) 6- to 14-membered aromatic hydrocarbon ring group which may be substituted with 1 to 5 substituent groups selected from Substituent Group A4, (23) a 5- to 14-membered aromatic heterocyclic group which may be substituted with 1 to 3 substituent groups selected from Substituent Group A4, (24) a 6- to 14-membered non-aromatic hydrocarbon ring group which may be substituted with 1 to 3 substituent groups selected from Substituent Group A4, (25) a 5- to 14-membered non-aromatic heterocyclic group which may be substituted with 1 to 3 substituent groups selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituent groups selected from Substituent Group A4), (31) —CO-A (wherein A is the same as defined above) and (32) =CH-A (wherein A is the same as defined above).

The above described "General Production Process 1" is an example of production process of the compound of the general formula (I) in which an ester compound (1a) is subjected to deprotection reaction in "step 1-1" to be converted into a carboxylic acid compound (2) and subsequently the carboxylic acid compound (2) is subjected to amidation reaction together with an amine compound (3).

(Preparation of Carboxylic Acid Compound (2))

The carboxylic acid compound (2) can be prepared, for example, by subjecting an ester compound (1a) to the "step 1-1". That is, although the deprotection reaction in "step 1-1" may vary depending on the starting material, no particular limitation is imposed upon it as long as the reaction is conducted under conditions similar to those in this reaction by methods known in the art (for example, methods as described in T. W. Green. "Protective Groups in Organic Synthesis" John Wiley & Sons. Inc., 1981, p 154-186) can be employed. Preferably, it is a hydrolysis reaction of an ester compound, and techniques described in many known references can be used (for example, such methods are described in "Composition and Reaction of Organic Compound [II]," New Experiment Chemistry Series, vol. 14, edited by the Chemical Society of Japan, Maruzen Co., Ltd., February, 1978, p. 930-943). Preferably, a desired carboxylic acid compound (2) can be obtained by reacting an ester compound (1a) using a water-containing solvent (mixed solvent of water with, for example, methanol, ethanol and/or tetrahydrofuran, etc.) at room temperature to 100° C. in the presence of 1.0 to 5.0 equivalents of metal hydroxide (preferably, for example, sodium hydroxide, potassium hydroxide or lithium hydroxide etc.). Moreover, depending on a corresponding ester compound (1a), a carboxylic acid compound (2) can also be suitably obtained under an acidic condition (preferably with trifluoroacetic acid). Under a preferable reaction condition, the reaction completes in 1 to 24 hours, and the progress of reaction can be monitored by known chromatography technology. Undesirable by-products can be removed by techniques in the art such as conventional chromatography technology, extraction procedure and/or crystallization.

(Preparation of Compound of General Formula (I))

The compound of general formula (I) can be prepared, for example, by subjecting carboxylic acid compound (2) to the "step 1-2". That is, although the amidation reaction of "step 1-2" may vary depending on the starting material, no particular limitation is imposed upon it as long as the reaction is conducted under conditions similar to those in this reaction by known techniques described in many references (for example, such methods are described in "Composition and Reaction of Organic Compound [II]," New Experiment Chemistry Series, vol. 14, edited by the Chemical Society of Japan, Maruzen Co., Ltd., February, 1978, p. 1136-1162) can be employed. Preferable examples include i) a process comprising converting a carboxylic acid compound (2) to an acid halide followed by reacting the acid halide with an amine compound under a basic condition (for example, such a process is described in "Composition and Reaction of Organic Compound [II]," New Experiment Chemistry Series, vol. 14, edited by the Chemical Society of Japan, Maruzen Co., Ltd., February, 1978, p. 1142-1145), ii) a process comprising reacting a carboxylic acid compound (2) and an amine compound using a condensation agent (for example, such a process is described in "Guide to Organic Chemistry Experiment (4)," KagakuDojin, September, 1990, p. 27-52), etc.

In the case of above i), the base, solvent and reaction temperature to be used may vary depending on the starting material and are not particularly limited, and (i) a technique using, for example, pyridine, lutidine, quinoline, isoquinoline, etc. as a basic solvent; (ii) a technique using, for example, pyridine, triethylamine, N,N-diisopropylethylamine etc. as a base and preferably, for example, tetrahydrofuran, 1,4-dioxane etc. as a solvent which dissolves the starting substance(s) to some extent but does not prevent the reaction or a mixed solvent thereof; or (iii) a technique using a two-layer distribution system comprising of an alkali solution, preferably, for example, an aqueous solution of a base, such as sodium hydroxide, potassium hydroxide, etc., and a halogenated solvent preferably, for example, methylene chloride, 1,2-dichloroethane, etc. can be used. The reaction temperature should be a temperature which is sufficient for completing the reaction without promoting formation of undesired by-products and is preferably an ice-cooling temperature to 100° C. In preferable reaction conditions, the reaction completes in 1 to 24 hours, and the progress of the reaction can be monitored by known chromatography technology. Although the technique of converting the carboxylic acid compound (2) to an acid halide may vary depending on the starting material, no particular limitation is imposed upon it as long as the reaction is conducted under conditions similar to those in this reaction by methods known in the art can be used. Preferably, a chlorination agent such as thionyl chloride and oxalyl chloride can be used in an inert solvent such as methylene chloride, toluene and tetrahydrofuran. A catalytic amount of N,N-dimethylformamide, etc. may be suitably added to advance the reaction. The reaction temperature should be a temperature which is sufficient for completing the reaction without promoting formation of undesired by-products and is an ice-cooling temperature to 100° C. preferably.

In the case of above ii), the condensation agent to be used may vary depending on the starting material and is not particularly limited, and it is preferable to use suitably 1.0 equivalent to 2.0 equivalents of 1,3-dicyclohexylcarbodiimide, 1-ethyl-3-(3'-dimethylaminopropyl)carbodiimide, benzotriazol-1-yloxytris(dimethylamino)phosphonium hexafluorophosphate etc., for example, to the carboxylic acid compound (2). In order to advance the reaction efficiently, 1.0 equivalents to 2.0 equivalents of N-hydroxysuccinimide, N-hydroxybenzotriazol, etc., for example, may be added. It is preferable from a viewpoint of operativity and stirring efficiency to perform this reaction in the presence of a solvent, and although the solvent to be used may vary depending on the starting material and the condensation agent to be used and is not particularly limited as long as it dissolves the starting substance(s) to some extent but does not prevent the reaction, a halogen solvent such as methylene chloride and 1,2-dichloroethane, or a polar solvent such as tetrahydrofuran and N,N-dimethylformamide are preferable. The reaction temperature should be a temperature which is sufficient for completing the reaction without promoting formation of undesired by-products and is an ice-cooling temperature to 100° C. preferably. In preferable reaction conditions, the reaction completes in 1 to 24 hours, and the progress of the reaction can be monitored by known chromatography technique. Undesirable by-products can be removed by any technique known in the art, such as conventional chromatography technique and/or crystallization. It is also possible to obtain a desired compound of the general formula (I) by forming an amide bond and subsequently converting $R^1$ and $R^2$ by a usual method using a technique known and it is also possible to obtain a desired compound of the general formula (I) by suitably modifying the substituent groups of $Ar_1$, $Ar_2$ and $X_1$.

(Preparation of Amine Compound (3))

The amine compound (3) is commercially available or can be obtained by a technique known in the art. Preferable examples thereof include i) a method of converting a corresponding alcohol compound or alkyl halide compound to the amine compound by a known technique; ii) a method of converting a corresponding nitro compound, nitrile compound, oxime compound, azide compound or acid amide compound by a known reduction reaction, iii) a method of converting a corresponding carbonyl compound by a known reductive amidation reaction, iv) a method of obtaining amine compound by subjecting the nitrogen atom protected by a protecting group to deprotection reaction, etc.

In the case of above i), conversion can be effected by methods described in many known references; and for example, methods of obtaining the amine compound from a corresponding alcohol compound by Mitsunobu method (see, for example, O. Mitsunobu, "Synthesis," p. 1, 1981) or from a alkyl halide compound by Gabriel method (see, for example, M. M. S. Gibson et al., "Angew. Chem.," vol. 80, p. 986, 1968) are preferable. In the case of Mitsunobu method, the desired amine compound can be efficiently obtained preferably by a two-step reaction comprising condensing a corresponding alcohol compound with an imide compound using 1.0 to 3.0 equivalents of diethyl azodicarboxylate under the coexistence of 1.0 to 3.0 equivalents of triphenylphosphine and treating a product obtained from the first step with 1.0 to 3.0 equivalents of hydrazine, for example. The reaction temperature should be a temperature which is sufficient for completing the reaction without promoting formation of undesired by-products and it is preferably an ice-cooling temperature to 100° C. for the condensation reaction with an imide compound at the first step and 50° C. to 100° C. for the hydrazine treatment at the second step. Although the solvent to be used in this reaction may vary depending on the starting material and the condensation agent to be used and is not particularly limited as long as it dissolves the starting substance(s) to some extent but does not prevent the reaction, diethyl ether, tetrahydrofuran, etc., for example, are preferable for the reaction of the first step and methanol, ethanol, etc., for example, are preferable for the reaction of the second step. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization. In the case of Gabriel method, the desired amine compound can be efficiently obtained preferably by a two-step reaction comprising condensing a corresponding alkyl halide compound with an imide compound by any technique known in the art and treating a product obtained from the first step with 1.0 to 3.0 equivalents of hydrazine for example. The reaction temperature should be a temperature which is sufficient for completing the reaction without promoting formation of undesired by-products and it is preferably an ice-cooling temperature to 100° C. for the condensation reaction with an imide compound in the first step and 50° C. to 100° C. for the hydrazine treatment in the second step. Although the solvent to be used in this reaction may vary depending on the starting material and the condensation agent to be used and is not particularly limited as long as it dissolves the starting substance(s) to some extent but does not prevent the reaction, diethyl ether, tetrahydrofuran, N,N-dimethylformamide, etc., for example, are preferable for the reaction of the first step and methanol, ethanol, etc., for example, are preferable for the reaction of the second step. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

In the case of above ii), reduction processes described in many known references can be used (for example, such a process is described in "Composition and Reaction of Organic Compound [III]," New Experiment Chemistry Series, vol. 14, edited by the Chemical Society of Japan, Maruzen Co., Ltd., February, 1978, p. 1333-1341), and the desired amine compound can be efficiently obtained by catalytic hydrogenation method which preferably uses, for example, a metal catalyst, a reduction method using a metal hydride, etc. The catalytic hydrogenation method is preferably conducted at ordinary pressure to 100 atm under hydrogen atmosphere. The metal catalysts usable in this reaction are preferably, for example, platinum, platinum oxide, platinum black, Raney nickel, palladium-carbon, etc. Although the solvent to be used in this reaction may vary depending on the starting material and is not particularly limited as long as it dissolves the starting substance(s) to some extent but does not prevent the reaction, methanol, ethanol, diethyl ether, tetrahydrofuran, methylene chloride, chloroform, ethyl acetate, etc., for example, are preferable. In order to advance the reaction efficiently, acidic substances such as acetic acid or hydrochloric acid may be added. As for the reduction method using a metal hydride, the desired amine compound (3) will be obtained efficiently by preferably using lithium aluminum hydride or diborane. The solvent to be used in this reaction may vary depending on the starting material and is not particularly limited as long as it dissolves the starting substance(s) to some extent but does not prevent the reaction, diethyl ether, tetrahydrofuran, etc. are preferable, for example. The temperature for the reduction reaction of ii) should be a temperature which is sufficient for completing the reaction without promoting formation of undesired by-products, and it is preferably an ice-cooling temperature to 100° C. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

In the case of above iii), reductive amination reaction known in the art (for example, such a process is described in "Composition and Reaction of Organic Compound [III]," New Experiment Chemistry Series, vol. 14, edited by the Chemical Society of Japan, Maruzen Co., Ltd., February, 1978, p. 1380-1384) can be used, and a preferable process comprises obtaining an imine compound by dehydration reaction from a corresponding carbonyl compound and an amine compound by heat-refluxing in the presence of an acid catalyst (preferably, for example, an inorganic acid such as hydrochloric acid or sulfuric acid, an organic acid such as methanesulfonic acid, p-toluenesulfonic acid, and camphorsulfonic acid or an organic acid salt such as pyridinium p-toluenesulfonate) and reducing the imine compound with a metal hydride such as lithium aluminum hydride, sodium borohydride, etc. to obtain a desired amine compound. Alternatively, a process comprising treating an imine compound in an inert solvent such as tetrahydrofuran in the presence of a Lewis acid catalyst (preferably titanium (IV) isopropoxide) and reducing the imine compound with a metal hydride such as sodium borohydride is also preferable. Alternatively, for example, a technique of reducing a carbonyl compound and 0.5 to 5.0 equivalents of an amine compound with a metal hydride such as sodium triacetoxy borohydride and sodium cyano borohydride in an inert solvent such as methylene chloride, 1,2-dichloroethane, tetrahydrofuran, methanol and ethanol to obtain a desired amine compound is also preferable. It is preferable to suitably add an acidic substance such as acetic acid or hydrochloric acid in order to advance the reaction efficiently. The progress of the reductive amination reaction iii) can be monitored by known chromatography technique. Undesirable by-products can be removed by any technique known in the art such as conventional chromatography technique and/or crystallization.

In the case of above iv), deprotection reactions described in many known references can be used (see, for example, T. W. Green, "Protective Groups in Organic Synthesis," John Wiley & Sons. Inc., 1981), and a method of obtaining a desired amine compound from a corresponding carbamate compound (preferably, for example, a tert-butylcarbamate compound, a benzylcarbamate compound, a 9-fluorenylmethylcarbamate compound etc.), or a method of obtaining such a desired amine compound from a corresponding amide compound (preferably, for example, a formamide compound, an acetamide compound, a trifluoroacetamide compound, etc.) are preferable. Alternatively, a method of deprotecting a corresponding imide compound according to the above described Gabriel method to obtain a desired amine compound is also preferable. Although the conditions of deprotecting reaction may vary depending on the starting material and no particular limitation is imposed upon it as long as the reaction is conducted under conditions similar to those in this reaction and any known method can be used. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

(Preparation-1 of an Ester Compound (1a))

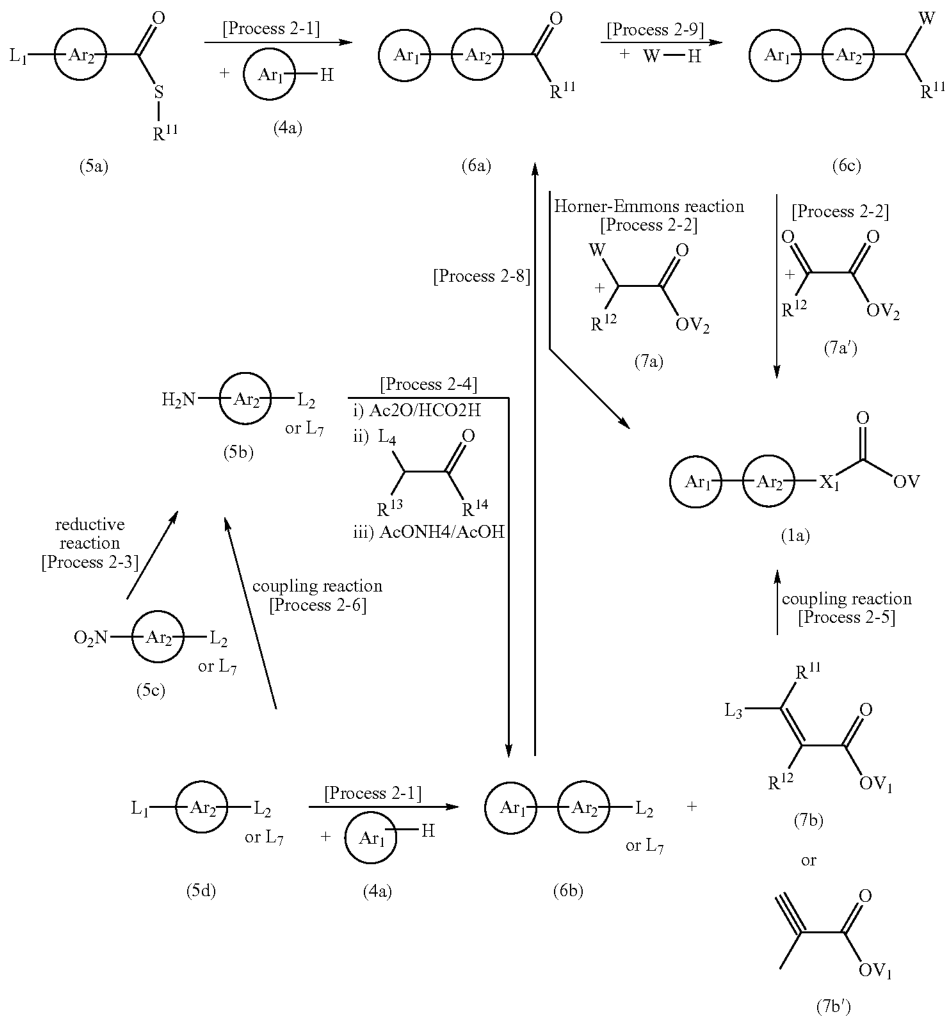

(wherein $Ar_1$, $Ar_2$, $X_1$ and V represent the same meaning as above;

V, $V_1$ and $V_2$ are the same or different and represent protecting groups for a carboxyl group such as a methyl group, an ethyl group, a benzyl group, an allyl group, a triphenylmethyl group, a tert-butyl group or a tert-butyldimethylsilyl group;

$L_1$, $L_2$, $L_3$ and $L_4$ represent leaving groups such as a hydrogen atom, a fluorine atom, a chlorine atom, a bromine atom, an iodine atom, a sulfonate such as triflate, a trialkyltin group, boronic acid or boronic acid ester ($B(OV_1)_2$);

$L_7$ represents ester groups such as methylester, ethylester or benzylester, or cyano group;

W represents a diethylphosphonyl group, a diphenyl phosphonyl group or a bis(2,2,2-trifluoroethyl)phosphonyl group;

$R^{13}$ and $R^{14}$ represent groups selected from Substituent Group Al shown below; and $R^{11}$ and $R^{12}$ represent groups selected from Substituent Group A3 shown below.

Substituent group A1: (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group, and (12) a C1-6 alkyl group (wherein said C1-6 alkyl group may be substituted with 1 to 3 substituent groups selected from the group consisting of a halogen atom, a hydroxyl group, a cyano group, a C1-6 alkoxy group, a C3-8 cycloalkyl group and a C1-6 alkylcarbonyl group).

Substituent group A3: (1) a hydrogen atom, (2) a halogen atom, (3) a 6- to 14-membered aromatic hydrocarbon ring group which may be substituted with 1 to 3 substituent groups selected from Substituent Group A4, (4) a 5- to 14-membered aromatic heterocyclic group which may be substituted with 1 to 3 substituent groups selected from Substituent Group A4, (5) a C1-6 alkyl group (wherein said C1-6 alkyl group may be substituted with 1 to 3 substituent groups selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with C1-6 alkyl group(s) optionally having 1 to 5 halogen atoms), a 6- to 14-membered aromatic hydrocarbon ring group which may be substituted with 1 to 3 substituent groups selected from Substituent Group A4, a 5- to 14-membered aromatic heterocyclic group which may be substituted with 1 to 3 substituent groups selected from Substituent Group A4, a 6- to 14-membered non-aromatic hydrocarbon ring group which may be substituted with 1 to 3 substituent groups selected from Substituent Group A4, a 5- to 14-membered non-aromatic heterocyclic group which may be substituted with 1 to 3 substituent groups selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted group with 1 to 3 substituted groups selected from Substituent Group A4) and (6) a C1-6 alkoxyl group.

Although the ester compound (1a) may vary depending on the starting material, it can be obtained by a technique known in the art. Preferably, for example, the ester compound (1a) can be prepared as shown in the above-mentioned reaction formula, but the preparation is not limited thereto. That is, the ester compound (1a) can be prepared, for example, by reacting a compound (4a) and a compound (5a) at "Step 2-1" to obtain a carbonyl compound (6a), and subjecting the carbonyl compound to Horner-Emmons reaction at "Step 2-2" to yield the ester compound (1a). Alternatively, starting from a carbonyl compound (6a) through "step 2-9" to obtain a compound (6c), and subjecting the compound (6c) to Horner-Emmons reaction with a compound (7a') at "Step 2-2" to yield the ester compound (1a). Alternatively, the ester compound (1a) can be also prepared through a three-step reaction of "step 2-4" using an amino compound (5b) as the starting material to build $Ar_1$ of a compound (6b) followed by a coupling reaction with a compound (7b) or (7b') according to "step 2-5". The ester compound (1a) can be also prepared by using a compound (5d) as the starting material and converting it into a compound (6b) according to "Step 2-1" to yield an ester compound (1a) at "Step 2-5".

(Preparation of Carbonyl Compound (6a))

The carbonyl compound (6a) is commercially available or can be acquired with technique known in the art. When not marketed, the carbonyl compound (6a) can be prepared according to "Step 2-1" by using a compound (5a), for example, as the starting material. That is, the reaction of "Step 2-1" may vary depending on the starting material and no particular limitation is imposed upon it as long as the reaction is conducted under conditions similar to those in this reaction and any method known in the art can be used. For example, it is preferable to conduct a coupling reaction of a compound (4a) and a compound (5a) under neutral or basic conditions (see, for example, D. D. Davey et al., "J. Med. Chem.," vol. 39, p. 2671-2677, 1991). That is, it is preferable to use 1.0 to 5.0 equivalents of compound (4a) to compound (5a). In order to perform the reaction efficiently, the base is preferably used in 1.0 to 5.0 equivalents, and preferable examples include sodium hydride, sodium hydroxide, potassium hydroxide, potassium carbonate, sodium carbonate, cesium carbonate, barium carbonate, etc. The solvent to be used in this reaction may vary depending on the starting material and is not particularly limited as long as it dissolves the starting substance(s) to some extent but does not prevent the reaction, acetonitrile, tetrahydrofuran, dimethylsulfoxide, N,N-dimethylformamide, N-methylpyrrolidine, etc. are preferable, for example. The reaction temperature should be a temperature which is sufficient for completing the reaction without promoting formation of undesired by-products and it is preferably 50° C. to 200° C. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

The carbonyl compound (6a) can be prepared according to "Step 2-8" by using a compound (6b) as the starting material. That is, the reaction of "Step 2-8" may vary depending on the starting material and no particular limitation is imposed upon it as long as the reaction is conducted under conditions similar to those in this reaction and any method known in the art can be used. For example, a two-step technique comprising subjecting a compound (6b) (wherein $L_2$ is preferably a chlorine atom, a bromine atom, an iodine atom, and a sulfonate such as triflate) and a vinyl tin compound to Stille coupling reaction to convert the former to a vinyl compound and subjecting the vinyl compound to ozone oxidation reaction (see, for example, S. S. Chandran et al., "Bioorg. Med. Chem. Lett.," vol. 11, p. 1493-1496, 2001) can also be used. Alternatively, carbon monoxide insertion reaction (see, for example, T. Okano et al., "Bull. Chem. Soc. Jpn.," vol. 67, p. 2329-2332, 1994) using a transition metal catalyst can also be used.

Additionally, for example, in case the carbonyl compound (6b) has L7 group, the compound 6a can be prepared by reductive reaction which methods are known in the art.

(Preparation of a Compound (5a))

The compound (5a) used in this step is commercially available, or can be obtained by a technique known in the art. When not marketed, a preferable compound (5a) (wherein, $L_1$ represents a fluorine atom, a chlorine atom or a bromine atom) can be obtained as a corresponding alcohol by an oxidation reaction known in the art, and an ester can be subjected to a known reduction reaction to yield a carbonyl compound.

(Preparation of a Compound (4a))

The compound (4a) used at this step is commercially available, or can be obtained by a technique known in the art (see, for example, M. Komoto et al., "Agr. Biol. Chem.," vol. 32, p. 983-987, 1968 or J. M. Kokosa et al., "J. Org. Chem.," vol. 48, p. 3605-3607, 1983).

(Conversion of Carbonyl Compound (6a) to Ester Compound (1a)

Although the conversion of the carbonyl compound (6a) to an ester compound (1a) may vary depending on the starting material, known technique described in many references can be used (such a process is described, for example, in H. O. House, "Modern synthetic reactions," W. A. Benjamin Inc., p 629-733, 1972, or W. Carrthers, "Some modern methods of organic synthesis," Cambridge University press, p. 125-144, 1986). For example, an ester compound (1a) can be prepared by converting a carbonyl compound (6a) according to "Step 2-2". That is, although the Horner-Emmons reaction of "Step 2-2" may vary depending on the starting material, no particular limitation is imposed upon it as long as the reaction is conducted under conditions similar to those in this reaction and methods known in the art (see, for example, W. S. Wadsworth, Jr. "Org. Reactions.," vol. 25, p. 73, 1997) can be used. That is, the carbonyl compound (6a) and the phosphonic acid ester compound (7a) can be subjected to a reaction condensation and converted into a corresponding ester compound (1a) under basic conditions. The base is preferably used in 1.0 to 2.0 equivalents to carbonyl compound (6a), and preferable examples include sodium hydride, sodium hydroxide, potassium hydroxide, lithium hydroxide, n-butyl lithium, lithium diisopropyl amide, lithium bis(trimethylsilyl)amide, sodium bis(trimethylsilyl)amide, triethylamine, diisopropylethylamine, etc. The solvent to be used in this reaction may vary depending on the starting material and is not particularly limited as long as it dissolves the starting substance(s) to some extent but does not prevent the reaction, diethyl ether, tetrahydrofuran, dimethylsulfoxide, toluene, benzene, ethanol, methanol, etc. are preferable, for example. The reaction temperature should be a temperature which is sufficient for completing the reaction without promoting formation of undesired by-products and it is preferably −78° C. to 100° C., and more preferably −78° C. to room temperature. In preferable reaction conditions, the reaction completes in 1 to 24 hours, and the progress of the reaction can be monitored by known chromatography technique. As for the geometric isomers formed during this reaction, the desired geometric isomer can be selectively prepared by a suitable selection of a phosphonic acid ester compound (7a), base, reaction temperature and/or solvent, and undesirable by-products and geometric isomers can be removed by any technique known in the art such as conventional chromatography technique and/or crystallization.

For example, conversion of a carbonyl compound (6a) to an ester compound (1a) can be effected through a compound (6c) by subjecting the compound (7a') to Horner-Emmons reaction of "Step 2-2" to yield an ester compound (1a). For example, well-known technique described in many references can be used in the "Step 2-9" to prepare the compound (6c) (for example, as described in O. Pamies et al., J. Org. Chem., p. 4815-4818, 2003, etc.). That is, it is preferable to use a carbonyl compound (6a) and a phosphate compound such as diethyl phosphite, etc. under basic conditions. As a base, it is preferable to use 1.0 to 2.0 equivalent to the carbonyl compound (6a), preferable examples of which include 1,8-diazabicyclo[5.4.0]undec-7-ene, triethylamine, piridine, sodium methoxide, etc. The solvent used for this reaction may vary depending on the starting material, and is not particularly limited as long as it dissolves the starting substance(s) to some extent but does not prevent the reaction. Preferable examples include diethyl ether, tetrahydrofuran, dimethylsulfoxide, toluene, benzene, ethanol, methanol, etc. The reaction temperature should be a temperature which is sufficient for completing the reaction without promoting formation of undesired by-product and it is preferably −78° C. to 100° C., and more preferably −78° C. to room temperature. In preferable reaction conditions, the reaction completes in 1 to 24 hours, and the progress of the reaction can be monitored by known chromatography technique. Undesirable by-products formed in this reaction can be removed by any technique known in the art such as conventional chromatography technique and/or crystallization. Moreover, the prepared compound (6c) can be modified by a technology well-known to those skilled in the art into a desired compound (for example, as described in T.-J. Tsai. Tetrahedron Letters, vol. 37, No. 5, p. 629-632, 1996).

(Preparation of Compound (7a'))

The compound (7a') used at this step is commercially available, or can be obtained by a technique known in the art. When not marketed, a preferable compound (7a') can be obtained by subjecting a corresponding alcohol to an oxidation reaction well-known to those skilled in the art or by subjecting a corresponding ester to well-known oxidation reaction to obtain an α-ketoester compound.

(Preparation of Amine Compound (5b))

The amine compound (5b) is commercially available, or can be obtained by a technique known in the art. Preferably, it can be prepared according to "Step 2-3" using a nitro compound (5c) as the starting material. That is, although the reduction reaction of "Step 2-3" may vary depending on the starting material, no particular limitation is imposed upon it as long as the reaction is conducted under conditions similar to those in this reaction and methods known in the art (for example, such a process is described in "Composition and Reaction of Organic Compound [III]," New Experiment Chemistry Series, vol. 14, edited by the Chemical Society of Japan, Maruzen Co., Ltd., February, 1978, p. 1333-1341) can be used. Preferably, they are catalytic hydrogenation method which preferably uses, for example, a metal catalyst, or a reduction method using a metal, etc. The catalytic hydrogenation method is preferably conducted at ordinary pressure to 100 atm under hydrogen atmosphere. The metal catalysts usable in this reaction are preferably, for example, platinum, platinum oxide, platinum black, Raney nickel, palladium-carbon, etc. Although the solvent to be used in this reaction may vary depending on the starting material and is not particularly limited as long as it dissolves the starting substance(s) to some extent but does not prevent the reaction, methanol, ethanol, diethyl ether, tetrahydrofuran, methylene chloride, chloroform, ethyl acetate, etc., for example, are preferable. In order to advance the reaction efficiently, acidic substances such as acetic acid or hydrochloric acid may be added. As for the reduction method using a metal, it is preferable to use zinc, iron, tin, etc. and to carry out under acidic conditions using, for example, hydrochloric acid, acetic acid, and ammonium chloride, preferably. Although the solvent to be used in this reaction may vary depending on the starting material and is not particularly limited as long as it dissolves the starting substance(s) to some extent but does not prevent the reaction, methanol, ethanol, 2-propanol, etc. are preferable, for example. The reaction temperature should be a temperature which is sufficient for completing the reaction without promoting formation of undesired by-products and it is preferably room temperature to 100° C. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

The preferable amine compound (5b) can also be prepared according to the coupling reaction in "Step 2-6" by using as a starting material the compound (5d) which is commercially available or can be obtained by a technique known in the art. That is, although the coupling reaction of "Step 2-6" may vary depending on the starting material, no particular limitation is imposed upon it as long as the reaction is conducted under conditions similar to those in this reaction and methods known in the art can be used. Preferably, two-step technique of carrying out known de-benzophenone reaction processing after coupling reaction of benzophenone imine using a transition metal catalyst can be used (see, for example, S. L. Buchwald et al., "Tetrahedron Lett.," vol. 38, p. 6367-6370, 1997 or J. F. Hartwig et al., "J. Am. Chem. Soc.," vol. 120, p. 827-828, 1998). In the coupling reaction of benzophenone imine, a catalytic amount (0.01 to 0.2 equivalents to compound (5d)) of a conventional palladium catalyst such as palladium (II) acetate, dichlorobis(triphenylphosphine)palladium (II), tetrakis(triphenylphosphine)palladium (0) or tris (dibenzylideneacetone)dipalladium (0), or a conventional nickel catalyst such as (1,5-cyclooctadien) nickel (0), etc. can be preferably used as a catalyst. In addition, it is also preferable to suitably add a phosphorus ligand (preferably, for example, triphenylphosphine, tri-o-tolylphosphine, tri-tert-butylphosphine, 2-(di-tert-butylphosphino)-biphenyl, 2,2'-bis(diphenylphosphino)-1,1'-binaphthyl, 1,2-bis(diphenylphosphino)ethane, or 1,1'-bis(diphenylphosphino) ferrocene, etc. in order to advance the reaction efficiently. Moreover, the reaction may give a preferable result in the presence of a base, and although the base to be used is not particularly limited as long as it can be used in a similar coupling reactions as this reaction, and preferable examples include sodium hydroxide, barium hydroxide, potassium fluoride, cesium fluoride, sodium carbonate, potassium carbonate, cesium carbonate, potassium phosphate, sodium tert-butoxide, etc. This reaction is preferably conducted in the presence of a solvent from a viewpoint of operativity and stirring efficiency, and although the solvent to be used in this reaction may vary depending on the starting material and the transition metal catalyst to be used and is not particularly limited as long as it dissolves the starting substance(s) to some extent but does not prevent the reaction, acetonitrile, tetrahydrofuran, 1,4-dioxane, 1,2-dimethoxyethane, benzene, toluene, xylene, 1-methyl-2-pyrrolidone, N,N-dimethylformamide etc. are preferable, for example. The reaction temperature should be a temperature which is sufficient for completing the coupling reaction and it is preferably room temperature to 100° C. It is preferable to carry out this reaction under an inactive gas atmosphere, and more preferably under nitrogen or argon atmosphere. Post-processing of the second step can use a technique known in the art (see, for example, T. W. Green. "Protective Groups in Organic Synthesis" John Wiley & Sons. Inc., 1981). Undesirable by-products can be removed by any technique known in the art such as conventional chromatography technique and/or crystallization.

As for the preferable amine compound (5b), $L_2$ can be modified by a technique known in the art, and preferably conversion from a hydrogen atom to a halogen substituent group is possible at $L_2$ (for example, as described in "Composition and Reaction of Organic Compound [I]," New Experiment Chemistry Series, vol. 14, edited by the Chemical Society of Japan, Maruzen Co., Ltd., November, 1977, p. 354-360).

(Preparation of Nitro Compound (5c))

The nitro compound (5c) used at this step is commercially available, or can be obtained by a technique known in the art. When not marketed, a preferable compound (5c) (wherein $L_2$ represents a fluorine atom, a chlorine atom, a bromine atom, or iodine) can be efficiently obtained by subjecting a corresponding precursor to a nitration known to those skilled in the art (for example, as described in "Composition and Reaction of Organic Compound [III]," New Experiment Chemistry Series, vol. 14, edited by the Chemical Society of Japan, Maruzen Co., Ltd., February, 1978, p. 1261-1300).

(Preparation of a Compound (6b))

A compound (6b) can be obtained by a technique known in the art. It is preferably prepared through the above "Step 2-1," using a compound (5d) as the starting material, or it can also be prepared according to "step 2-4" using an amine compound (5b) as the starting material. For example, the "step 2-4" can be conducted by treating the compound (5b) with a mixed solvent of acetic anhydride and formic acid in the first phase, effecting condensation with an α-haloketone (in which $L_4$ is a chlorine atom, a bromine atom, or iodine) under a basic condition in the second phase, and heat-treating with ammonium acetate and acetic acid in the third phase to efficiently convert into a compound (6b). It is preferable in the first phase to conduct treatment with a mixed solvent of 2.0 to 10.0 equivalents of acetic anhydride and 10.0 to 20.0 equivalents of formic acid to the compound (5b) at a temperature of ice-cooling temperature to 50° C. The base used in the second phase is preferably used in 1.0 to 5.0 equivalents to the compound (5b), and, for example, sodium hydride, sodium hydroxide, potassium hydroxide, lithium hydroxide, n-butyl lithium, lithium diisopropyl amide, lithium bis(trimethylsilyl)amide, sodium bis(trimethylsilyl)amide, etc. are preferable. Although the solvent to be used in this reaction may vary depending on the starting material and is not particularly limited as long as it dissolves the starting substance(s) to some extent but does not prevent the reaction, diethyl ether, tetrahydrofuran, dimethylsulfoxide, N,N-dimethylformamide, etc. are preferable, for example. It is preferable to suitably add, for example, potassium iodide, sodium iodide, etc. in order to advance the reaction efficiently. The reaction temperature should be a temperature which is sufficient for completing the reaction without promoting formation of undesired by-products and it is preferably room temperature to 100° C. It is preferable in the third phase to conduct treatment with a mixed solvent of 5.0 to 10.0 equivalents of ammonium acetate and 10.0 to 20.0 equivalents of acetic acid to the compound (5b) at a temperature of 50° C. to 150° C. In preferable reaction conditions, the reaction completes in 1 to 24 hours, and the progress of the reaction can be monitored by known chromatography technique. Undesirable by-products can be removed by any technique known in the art such as conventional chromatography technique and/or crystallization.

The α-haloketone used in the second phase of this step is commercially available, or can be acquired with technique known in the art. When not marketed, preferable α-haloketone (in which $L_4$ is a chlorine atom, a bromine atom, or iodine) can be efficiently obtained by subjecting a corresponding precursor to a halogenation reaction known to those skilled in the art (for example, as described in "Composition and Reaction of Organic Compound [I]," New Experiment Chemistry Series, vol. 14, edited by the Chemical Society of Japan, Maruzen Co., Ltd., February, 1977, p. 307-450).

As for the compound (6b), $L_2$ can be modified by a technique known in the art, and preferably conversion to an iodine group (see, for example, S. L. Buchwald et al. "J. Am. Chem. Soc.," vol. 124, p. 14844-14845, 2002), to a lower alkyl tin group (see; for example, J. Marti et al., "Synth. Commun.," vol. 30, p. 3023-3030, 2000), and to a boron group (see, for example, N. Miyaura et al., "J. Org. Chem.," vol. 60, p. 7508-7510, 1995), etc. is possible.

(Conversion from Compound (6b) to Ester Compound (1a))

The conversion from a compound (6b) to an ester compound (1a) can be conducted by using a known technique in the art. For example, an ester compound (1a) can be prepared by subjecting a compound (6b) to "Step 2-5" together with a compound (7b) or a compound (7b'). That is, although the coupling reaction of "Step 2-5" may vary depending on the starting material, no particular limitation is imposed upon it as long as the reaction is conducted under conditions similar to those in this reaction and methods known in the art can be used, and Mizoroki-Heck reaction (see, for example, R. F. Heck, "Org. Reactions.," vol. 27, p. 345, 1982), Suzuki-Miyaura reaction (see, for example, A. Suzuki, "Chem. Rev.," vol. 95, p. 2457, 1995), Sonogashira reaction (see, for example, K. Sonogashira, "Comprehensive Organic Synthesis," vol. 3, p. 521, 1991), Stille coupling reaction (J. K. Stille, "Angew. Chem. Int. Ed. Engl.," vol. 25, p. 508, 1986), etc. are preferable.

In Mizoroki-Heck reaction preferably performed is a coupling reaction of a halide, a triflate compound (6b) (wherein $L_2$ represents a chlorine atom, a bromine atom, an iodine atom, or a triflate), with an alkene compound (7b; $L_3$ is a hydrogen atom) in 1.0 to 5.0 equivalents to the compound (6b) in the presence of 0.01 to 0.2 equivalents of a transition metal catalyst, for example. This reaction is preferably conducted in the presence of a solvent from a viewpoint of operativity and stirring efficiency, and although the solvent to be used in this reaction may vary depending on the starting material and the transition metal catalyst to be used and is not particularly limited as long as it dissolves the starting substance(s) to some extent but does not prevent the reaction, acetonitrile, tetrahydrofuran, 1,4-dioxane, 1,2-dimethoxyethane, benzene, toluene, xylene, 1-methyl-2-pyrrolidone, N,N-dimethylformamide, etc. are preferable, for example. The reaction temperature should be a temperature which is sufficient for completing the coupling reaction and it is preferably room temperature to 150° C. It is preferable to carry out this reaction under an inactive gas atmosphere, and more preferably under nitrogen or argon atmosphere. The transition metal catalyst is preferably a palladium complex, for example, and more preferably includes a conventional palladium complex such as palladium (II) acetate, dichlorobis (triphenylphosphine)palladium (II), tetrakis(triphenylphosphine)palladium (0) or tris(dibenzylideneacetone) dipalladium (0). In addition, it is also preferable to suitably add a phosphorus ligand (preferably, for example, triphenylphosphine, tri-o-tolylphosphine, tri-tert-butylphosphine, 2-(di-tert-butylphosphino)biphenyl, etc.) in order to advance the reaction efficiently. Moreover, the reaction may give a preferable result in the presence of a base, and although the base to be used is not particularly limited as long as it can be used in a similar coupling reactions as this reaction, and preferable examples include triethylamine, N,N-diisopropylethylamine, N,N-dicyclohexylmethylamine, tetrabutylammonium chloride, etc. In preferable reaction conditions, the reaction completes in 1 to 24 hours, and the progress of the reaction can be monitored by known chromatography technique.

Suzuki-Miyaura reaction is preferably carried out by coupling, for example, a halide or a triflate compound (6b), wherein $L_2$ represents a chlorine atom, a bromine atom, an iodine atom or a triflate, with, for example, a boronic acid compound or a boronic ester compound (7b), wherein $L_3$ represents $B(OH)_2$ or $B(OV_1)_2$, in the presence of 0.01 to 0.5 equivalent of a transition metal catalyst based on the triflate compound. This reaction is preferably carried out in the presence of a solvent in order to achieve easy operation and stirring. The solvent used differs according to the starting material and the transition metal catalyst used, and is not specifically limited insofar as the solvent does not inhibit the reaction and allows the starting material to be solved therein to a certain extent. Preferable examples include acetonitrile, tetrahydrofuran, 1,4-dioxane, 1,2-dimethoxyethane, benzene, toluene, xylene, 1-methyl-2-pyrrolidone and N,N-dimethylformamide, and mixtures of water with these solvents. The reaction temperature should be a temperature that can complete the coupling reaction, and is preferably room temperature to 200° C. The reaction is carried out preferably in an inert gas atmosphere, and more preferably in a nitrogen or argon atmosphere. Under preferable reaction conditions, the reaction is completed in 1 to 24 hours, and the progress of the reaction can be monitored using a known chromatography technology. The transition metal catalyst is preferably a known palladium catalyst, and more preferably a known palladium catalyst such as, for example, palladium (II) acetate, dichlorobis(triphenylphosphine)palladium (II), tetrakis (triphenylphosphine)palladium (0) or tris(dibenzylideneacetone)dipalladium (0). In order to proceed the reaction efficiently, a phosphorus ligand (preferably, for example, triphenylphosphine, tri-o-tolylphosphine, tricyclohexylphosphine or tri-tert-butylphosphine) or the like may be appropriately added. Further, in order to proceed the reaction efficiently, a quaternary ammonium salt, preferably, for example, tetrabutylammonium chloride or tetrabutylammonium bromide may be appropriately added. This reaction can bring about preferable results in the presence of a base. The base used in this case differs according to the starting material, the solvent used, and the like, and is not specifically limited. Preferable examples include sodium hydroxide, barium hydroxide, potassium fluoride, cesium fluoride, sodium carbonate, potassium carbonate, cesium carbonate and potassium phosphate. Under preferable reaction conditions, the reaction is completed in 1 to 24 hours, and the progress of the reaction can be monitored using a known chromatography technology. In this reaction, even if the compound (7b) is, for example, a halide or a triflate compound (7b), wherein $L_3$ represents a chlorine atom, a bromine atom, an iodine atom or a triflate, and the compound (6b) is, for example, a boronic acid compound or a boronic ester compound (6b), wherein $L_2$ represents $B(OH)_2$ or $B(OV_1)_2$, a desired coupling product (1a) can be efficiently obtained.

The reaction conditions for Sonogashira reaction differ according to the starting material, the solvent and the transition metal catalyst, but are not specifically limited insofar as the reaction conditions are those used in a reaction like this reaction. A technique known to a person skilled in the art may be used for the reaction. As the starting material, an alkyne compound (7b') is preferably used. Examples of preferable solvents include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. Examples of more preferable solvents include tetrahydrofuran, 1,4-dioxane, 1-methyl-2-pyrrolidone and N,N-dimethylformamide. The reaction temperature should be a temperature that can complete the coupling reaction, and is preferably room temperature to 100° C. The reaction is carried out preferably in an inert gas atmosphere, and more preferably in a nitrogen or argon atmosphere. Under preferable reaction conditions, the reaction is completed in 1 to 24 hours, and the progress of the reaction can be monitored using a known chromatography technology. The transition metal catalyst is preferably, for example, a known palladium catalyst, and more preferably a known palladium catalyst such as, for example, palladium (II) acetate, dichlorobis(triphenylphosphine)palladium (II), tetrakis(triphenylphosphine) palladium (0) or tris(dibenzylideneacetone)dipalladium (0). In order to proceed the reaction efficiently, a phosphorus ligand (preferably, for example, triphenylphosphine, tri-o-tolylphosphine or tri-tert-butylphosphine) may be appropriately added, for example. In this reaction, a metal halide, a quaternary ammonium salt, or the like, preferably, for example, copper (I) iodide, lithium chloride, tetrabutylammonium fluoride or silver (I) oxide may be added. The reaction can bring about preferable results in the presence of a base. The base used in this case is not specifically limited insofar as the base can be used in a coupling reaction like this reaction. Preferable examples include basic solvents such as diethylamine, triethylamine, N,N-diisopropylethylamine, piperidine and pyridine.

Stille coupling reaction is preferably carried out by reacting 1.0 equivalent or more of a trialkyltin compound (6b), wherein $L_2$ represents $(V_1)Sn$, with a halide or a triflate compound (7b), wherein $L_3$ represents a chlorine atom, a bromine atom, an iodine atom or a triflate, in the presence of 0.01 to 0.2 equivalent of a transition metal catalyst. In order to proceed the reaction efficiently, it is preferable to use 0.1 to 5.0 equivalents of copper (I) halide and/or lithium chloride appropriately. Examples of preferable solvents used in this reaction include toluene, xylene, N,N-dimethylformamide, N,N-dimethylacetamide, 1-methyl-2-pyrrolidone and dimethyl sulfoxide. The reaction temperature should be a temperature that can complete the coupling reaction, and is preferably room temperature to 100° C. The transition metal catalyst is preferably a palladium catalyst, more preferably a known palladium catalyst such as, for example, palladium (II) acetate, dichlorobis(triphenylphosphine)palladium. (II), tetrakis (triphenylphosphine)palladium (0) or tris(dibenzylideneacetone)dipalladium (0), and still more preferably, for example, tetrakis(triphenylphosphine)palladium (0) or tris(dibenzylideneacetone)dipalladium (0). The reaction is carried out preferably in an inert gas atmosphere, and more preferably in a nitrogen or argon atmosphere. Under preferable reaction conditions, the reaction is completed in 1 to 24 hours, and the progress of the reaction can be monitored using a known chromatography technology.

[Preparation of Compound (7b) and Compound (7b')]

The compound (7b) and the compound (7b') used in this step are commercially available or can be obtained by a technique known to a person skilled in the art. When such a compound is not commercially available, a preferable compound (7b), wherein $L_3$ represents $B(OH)_2$ or $B(OV_1)_2$, and $V_1$ represents the same as defined above, can be efficiently obtained, for example, from a corresponding precursor by a coupling reaction known to a person skilled in the art (as described in, for example, C. R. Deloge et al., "Bull. Soc. Chim. Fr.", 1992, vol. 129, pp. 285-290). Alternatively, a preferable compound (7b), wherein $L_3$ is a triflate, can be efficiently obtained from, for example, a corresponding precursor by a method known to a person skilled in the art (as described in, for example, B. Dupre et al., "J. Org. Chem.", 1991, vol. 56, pp. 3197-3198.

(Preparation of Phosphonic Acid Ester Compound (7a))

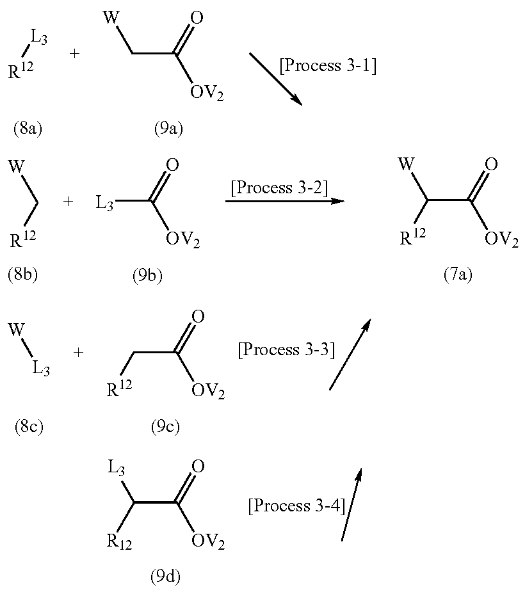

(8a) (9a) (8b) (9b) (7a) (8c) (9c) (9d)

(wherein $V_2$ and $R^{12}$ is the same as defined above, W represents $(EtO)_2PO$, $(PhO)_2PO$ or $(CF_3CH_2O)_2PO$, and $L_3$ represents a chlorine atom, a bromine atom or an iodine atom.)

The above-mentioned formula shows an example of the method of preparing a phosphonic acid ester compound (7a). That is, a phosphonic acid ester compound (7a) is commercially available or can be obtained by a method known to those skilled in the art shown above as "Step 3-1" to "Step 3-3" (see, for example, C. Patois et al., Synth. Commun., vol. 22, p. 2391, 1991 or J. A. Jackson et al., J. Org. Chem., vol. 20, p. 5556, 1989). For example, "Step 3-1" is a process in which a desired phosphonic acid ester compound (7a) is obtained by processing a phosphonic acid ester compound (9a) with an alkyl halide compound (8a) 1.0 to 2.0 equivalent to the phosphonic acid ester compound (9a) under basic conditions and introducing $R^{12}$. "Step 3-2" is a process in which a desired phosphonic acid ester compound (7a) is obtained by processing a phosphonic acid ester compound (8b) with a halogenated formic acid ester compound (9b) 1.0 to 2.0 equivalent to the phosphonic acid ester compound (8b) under basic conditions. "Step 3-3" is a process in which a desired phosphonic acid ester compound (7a) is obtained by processing a phosphonic acid halide (8c) with an ester compound (9c) 1.0 to 2.0 equivalent to the phosphonic acid halide (8c) under basic conditions. "Step 3-4" is a process in which a desired phosphonic acid ester compound (7a) is obtained by processing on α-haloester compound (9d) with trialkylphosphite 1.0 to 10.0 equivalent to the α-haloester compound (9d). Although the base compounds used at this step vary depending on the starting materials, it is preferable to use sodium hydride, n-butyl lithium, lithium diisopropyl amide, lithium bis(trimethylsilyl)amide, sodium bis(trimethylsilyl)amide etc., in an amount of 1.0 to 1.5 equivalent, for example. Although the trialkyl phosphites used at this step vary depending on the starting materials, it is preferable to use trimethyl phosphite, triethylphosphite etc., in an amount of 1.0 to 10.0 equivalent, for example. The solvent used for this reaction may vary depending on the starting material, and is not particularly limited as long as it dissolves the starting substance(s) to some extent but does not prevent the reaction. Preferable examples include hexane, toluene, diethyl ether, tetrahydrofuran, N,N-dimethylformamide, hexamethyl phosphoric acid triamide, or a mixed solvent of thereof. Reaction temperature should be a temperature which is sufficient for completing the reaction without promoting formation of undesired by-products and is preferably −78° C. to 150° C. In preferable reaction conditions, the reaction completes in 1 to 24 hours, and the progress of the reaction can be monitored by known chromatography technique. Undesirable by-products formed in this reaction can be removed by any technique known in the art such as conventional chromatography technique and/or crystallization. Moreover, as for the phosphonic acid ester compound (7a), $R^{12}$ can be modified by a technology well-known to those skilled in the art into a desired phosphonic acid ester compound (7a) efficiently.

The alkyl halide compound (8a), phosphonic acid ester compound (8b), phosphonic acid halide (8c), phosphonic acid ester compound (9a), halogenated formic acid ester compound (9b) ester compound (9c) and α-habester compound (9d) used at this step are commercially available or can be obtained by a technique known in the art.

(Preparation-2 of Ester Compound (1a))

The above described formula shows an example of the method of preparing an ester compound (1a) as an alternative method. That is, it is (i) a process in which the above described compound (5a) is used as a starting material, which is converted to an ester compound (1b) following the above described "Step 2-2" to prepare an ester compound (1a) in the above-mentioned "Step 2-1"; (ii) a process in which an ester compound (1b) is converted to an amine compound (1d) at "Step 2-6" from which an ester compound (1a) is prepared according to the above described "Step 2-4" or (iii) a process in which the above described nitro compound (5c) is used as a starting material, which is subjected to the three of the above "Step 2-5", "Step 2-3" and "Step 2-4" to prepare an ester compound (1a). In addition, it is shown that the amine compound (1d) can be also converted to an ester compound (1b) at the Sandmeyer reaction of "Step 2-7" and then converted to an ester compound (1a) according to the above "Step 2-1".

(Conversion from Ester Compound (1b) to Amine Compound (1d))

The conversion to an amine compound (1d) from an ester compound (1b) can be effected using a technique known in the art. Preferably, the same technique as the above "Step 2-6" can be used.

(Conversion from Amine Compound (1d) to Ester Compound (1b))

The conversion from an amine compound (1d) to an ester compound (1b) may vary depending on the starting material, and is not particularly limited as long as it can be effected

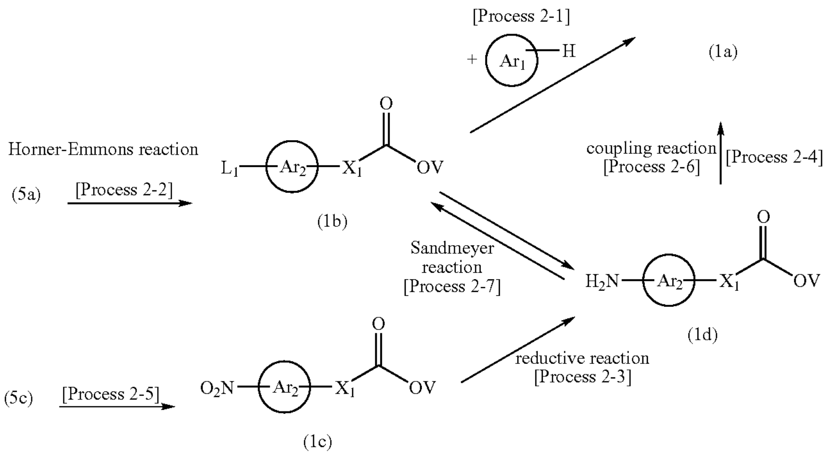

(wherein $Ar_2$, $X_1$, V and $L_1$ have the same meaning as in formula (I);

V represents an methyl group, an ethyl group, a benzyl group, an allyl group, a triphenylmethyl group, a tert-butyl group, or a protecting group such as a tert-butyldimethylsilyl group, a methoxymethyl group;

$L_1$ represents a hydrogen atom, a fluorine atom, a chlorine atom, a bromine atom, an iodine atom, and a triflate such as a sulfonate, a trialkyltin group, boronic acid or boronic acid ester ($B(OV_1)_2$.)

under similar conditions as in this process and processes known in the art can be used. Preferably, the Sandmeyer reaction of "Step 2-7" etc. can be used, and a preferable ester compound (1b) can be efficiently obtained by the technique known in the art (for example, as described in "Composition and Reaction of Organic Compound [I]", New Experiment Chemistry Series, vol. 14, edited by the Chemical Society of Japan, Maruzen Co., Ltd., November, 1977, p. 383-388)

(General Preparing Process 2)

The "general preparing process 2" for preparing typical compound of general formula (I) is explained below.

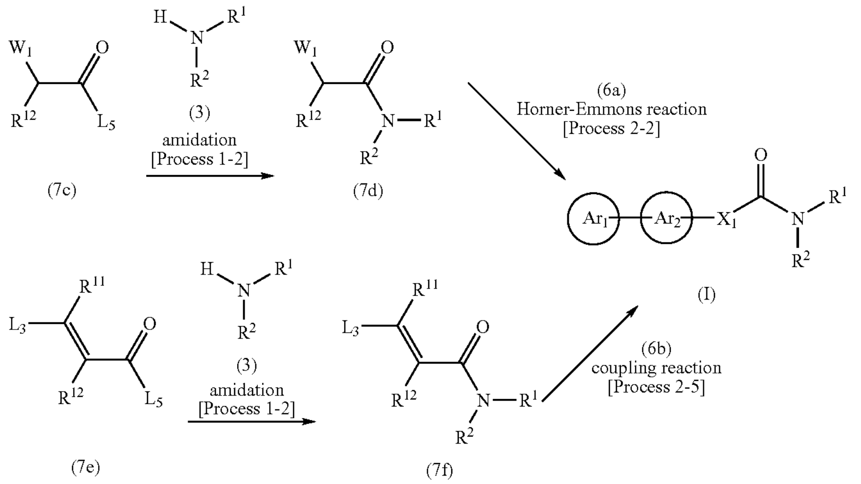

(7c) (7d) (I) (7e) (7f)

(wherein $Ar_1$, $Ar_2$, $X_1$, $R^1$, $R^2$, $R^{11}$, $R^{12}$ and $L_3$ is the same as defined above;

$W_1$ has the same meaning as W and $L_5$ represents a hydroxyl group, a chlorine atom and a bromine atom).

The compound of general formula (I) can be prepared by, for example, converting a compound (7c) to a compound (7d) according to the above "Step 1-2", and then performing "Step 2-2" with a carbonyl compound (6a) as described above, or by converting a compound (7e) to a compound (7f) according to the above "Step 1-2", and then performing "Step 2-5" with a carbonyl compound (6b) as described above.

(Preparation of Compound (7d))

The compound (7d) is commercially available or can be prepared by subjecting a compound (7c) to a similar step as the above "Step 1-2" with an amine compound (3) as described above.

(Preparation of Compound (7c))

The compound (7c) is commercially available or can be prepared by a technique known in the art. Preferably, compound (7c) can be efficiently obtained by using the above described phosphonic acid ester (7a) as the starting material and subjecting it to a similar deprotection reaction as in above "step 1-1".

(Preparation of Compound (7f))

The compound (7f) is commercially available or can be prepared by subjecting a compound (7e) to a similar step as in above "Step 1-2" together with an amine compound (3) as described above.

(Preparation of Compound (7e))

The compound (7e) is commercially available or can be obtained by a technique known in the art. Preferably, compound (7e) can be efficiently obtained by using the above described compound (7b) as the starting material and subjecting it to a similar deprotection reaction as in above "step 1-1".

(General Manufacturing Process 3)

The typical (general manufacturing process 3) of the compound of general formula (I) is explained below.

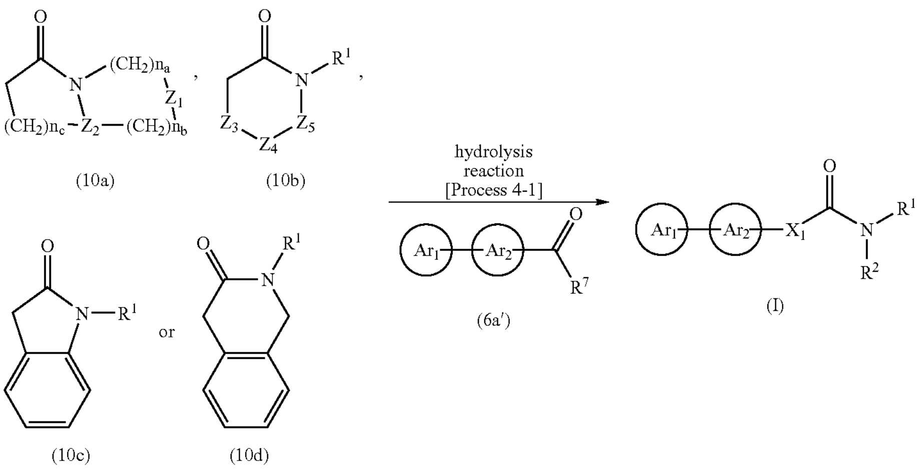

(10a), (10b), (10c) or (10d) (6a') (I)

(wherein, $Ar_1$, Ar2 and $X_1$ is the same as defined above;

$R^1$ and $R^2$, together with —$X_1$—CO—N—, form one of the following ring structures:

(3-1) a cyclic group represented by Formula (V):

(V)

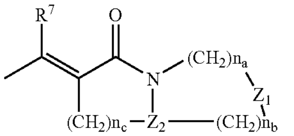

(wherein $Z_1$ represents (1) —NH—, (2) —O—, (3) —S—, (4) —SO—, (5) —$SO_2$—, (6) —$CH_2$—, (7) —CO—, (8) —CONH—, (9) —NHCO— or (10) a single bond; $Z_2$ represents (1) a methine group or (2) a nitrogen atom; $R^7$ represents a substituent selected from Substituent Group A3 shown below; and $n_a$, $n_b$ and $n_c$ represent an integer of 0 to 4) which may be substituted with 1 to 4 substituent groups selected from Substituent Group A4;

(3-2) a cyclic group represented by Formula (VI):

(VI)

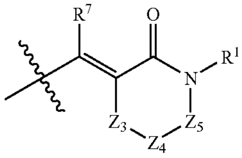

(wherein $Z_3$ represents (1) a single bond, (2) —CO—, (3) —$(CH_2)n_d$- (wherein nd represents an integer of 1 to 3) or (4) —$CR^8R^9$— (wherein $R^8$ and $R^9$ represent a substituent selected from Substituent Group A4 shown below;

$Z_4$ represents (1) a single bond, (2) —O—, (3) —NRCO—, (4) —CONR—, (5) —CSNR— or (6) —NRCS— (wherein R represents a substituent selected from Substituent Group A4 shown below) or (7) —S—;

$Z_5$ represents (1) a single bond, (2) an imino group which may be substituted with a substituent selected from Substituent Group A4 shown below, (3) —$(CH_2)n_e$-(wherein $n_e$ represents an integer of 1 to 3), (4) —$CR^8R^9$— (wherein $R^8$ and $R^9$ is the same as defined above) or (5) —O—; and $R^1$ to $R^7$ are the same as defined above); or (3-3) a cyclic group represented by the following formula:

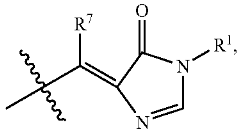

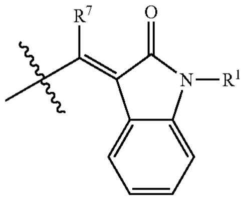

or

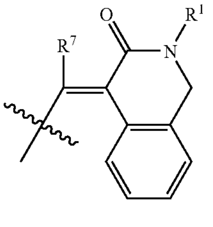

(wherein $R^1$ and $R^7$ are the same as defined above) which may be substituted with 1 to 4 substituent groups selected from Substituent Group A4 shown below. Substituent group A3: (1) a hydrogen atom, (2) a halogen atom, (3) a 6- to 14-membered aromatic hydrocarbon ring group which may be substituted with 1 to 3 substituent groups selected from Substituent Group A4, (4) a 5- to 14-membered aromatic heterocyclic group which may be substituted with 1 to 3 substituent groups selected from Substituent Group A4, (5) a C1-6 alkyl group (wherein said C1-6 alkyl group may be substituted with 1 to 3 substituent groups selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein said amino group may be substituted with a C1-6 alkyl group optionally having 1 to 5 halogen atoms), a 6- to 14-membered aromatic hydrocarbon ring group which may be substituted with 1 to 3 substituent groups selected from Substituent Group A4, a 5- to 14-membered aromatic heterocyclic group which may be substituted with 1 to 3 substituent groups selected from Substituent Group A4, a 6- to 14-membered non-aromatic hydrocarbon ring group which may be substituted with 1 to 3 substituent groups selected from Substituent Group A4, a 5- to 14-membered non-aromatic heterocyclic group which may be substituted with 1 to 3 substituent groups selected from Substituent Group A4 and —X-A (wherein X represents an imino group, —O— or —S— and A represents a 6- to 14-membered aromatic hydrocarbon ring group or 5- to 14-membered aromatic heterocyclic group which may be substituted with 1 to 3 substituent groups selected from Substituent Group A4) and (6) a C1-6 alkoxyl group.

Substituent group A4: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group which may be substituted with 1 to 3 substituent groups selected from Substituent Group A4, (19) a C1-6 alkoxy group which may be substituted with 1 to 3 substituent groups selected from Substituent Group A4, (20) an amino group which may be substituted with 1 to 2 substituent groups selected from Substituent Group A4, (21) a carbamoyl group which may be substituted with 1 to 2 substituent groups selected from Substituent Group A4, (22) 6- to 14-membered aromatic hydrocarbon ring group which may be substituted with 1 to 3 substituent groups selected from Substituent Group A4, (23) a 5- to 14-membered aromatic heterocyclic group which may be substituted with 1 to 3 substituent groups selected from Substituent Group A4, (24) a 6- to 14-membered non-aromatic hydrocarbon ring group which may be substituted with 1 to 3 substituent groups selected from Substituent Group A4, (25) a 5- to 14-membered non-aromatic heterocyclic group which may be substituted with 1 to 3 substituent groups selected from Substituent Group A4, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or 5- to 14-membered aromatic heterocyclic group which may be substituted with 1 to 3 substituent groups selected from Substituent Group A4), (31) —CO-A (wherein A is the same as defined above) and (32) =CH-A (wherein A is the same as defined above).

The above-mentioned formula is given to illustrate an example of a process using a compound (10a), a compound (10b), a compound (10c) or a compound (10d) as starting materials, and subjecting them to a dehydration reaction of "Step 4-1" with a carbonyl compound (6a') to prepare the compound of general formula (I). That is, although the dehydration reaction of "Step 4-1" may vary depending on the starting material, and is not particularly limited as long as it can be effected under similar conditions as in this process and processes known in the art can be used (for example, as described in H. O. House."Modern synthetic reactions" W. A. Benjamin, Inc., p. 629-653, 1972). Preferably, the compound of Formula (I) can be efficiently obtained by carrying out dehydrating condensation reaction of the acidic hydrogen of a compound (10a), a compound (10b), a compound (10c) or a compound (10d) and the oxygen atom of a carbonyl compound (6a') on basic conditions. Preferable examples of base usable in this reaction include piperidine, pyrrolidine, sodium methoxide, sodium ethoxide, potassium tert-butoxide, sodium hydride, sodium hydroxide, potassium hydroxide, lithium hydroxide, sodium carbonate, potassium carbonate, calcium carbonate, cesium carbonate, n-butyl lithium, lithium diisopropyl amide, lithium bis(trimethylsilyl)amide, sodiumbis(trimethylsilyl)amide, etc. The equivalent of the base may vary depending on the base to be used, starting material and the solvent to be used, and is not limited. The solvent used for this reaction may vary depending on the starting material and base, and is not particularly limited as long as it dissolves the starting substance(s) to some extent but does not prevent the reaction. Preferable examples include diethyl ether, tetrahydrofuran, benzene, toluene, xylene, methanol, ethanol or tert-butyl alcohol. Reaction temperature should be a temperature which is sufficient for completing the reaction without promoting formation of undesired by-products and is preferably −78° C. to 150° C. In preferable reaction conditions, the reaction completes in 1 to 24 hours, and the progress of the reaction can be monitored by known chromatography technique.

In addition, the compound of general formula (I) can also be obtained two-step process wherein compounds (10a), (10b), (10c) or (10d) which have been processed under basic conditions and a carbonyl compound (6a') form an alcohol compound through aldol reaction and then the hydroxyl group thereof is eliminated by a known technique. As a base used at the first step of this technique, sodium hydride, n-butyl lithium, lithium diisopropyl amide, lithium bis(trimethylsilyl)amide, sodium bis(trimethylsilyl)amide, sodium ethoxide, tert-butoxide, etc. are mentioned preferably. The equivalent of these bases may vary depending on the starting material, and although it is not limited, 1.0 to 2.0 equivalent is preferable. In order to advance the reaction efficiently, titanium (IV) isopropoxide or boron trifluoride may be added, for example. The solvent used for the first step may vary depending on the starting material and base and is not particularly limited as long as it dissolves the starting substance(s) to some extent but does not prevent the reaction. Preferable examples include diethyl ether, tetrahydrofuran, etc. Reaction temperature should be a temperature which is sufficient for completing the reaction without promoting formation of undesired by-products and is preferably −78° C. to room temperature. As the second step of this reaction any technique known in the art can be used (for example, as described in "Composition and Reaction of Organic Compound [I]", New Experiment Chemistry Series, vol. 14, edited by the Chemical Society of Japan, Maruzen Co., Ltd., November, 1977, p. 115-127). The progress of the reaction can be monitored by known chromatography technique. Undesirable by-products formed in this reaction can be removed by any technique known in the art such as conventional chromatography technique and/or crystallization.

(Preparation of Carbonyl Compound (6a'))

The carbonyl compound (6a') can be prepared by the same technique as for the above described carbonyl compound (6a), for example.

(Preparation of compound (10a), compound (10b), compound (11c) and compound (11d))

The compound (10a), compound (10b), compound (11c) and compound (11d) are commercially available or can be prepared by the technique known in the art. Preferably, they can be prepared efficiently by introducing $R^1$ group into the secondary amide nitrogen under basic conditions (see J. A. Campbell et al., J. Org. Chem., vol. 60, p. 4602-4616, 1995).

(General Manufacturing Process 4)

The typical (general manufacturing process 4) of the compound of general formula (I) is explained below.

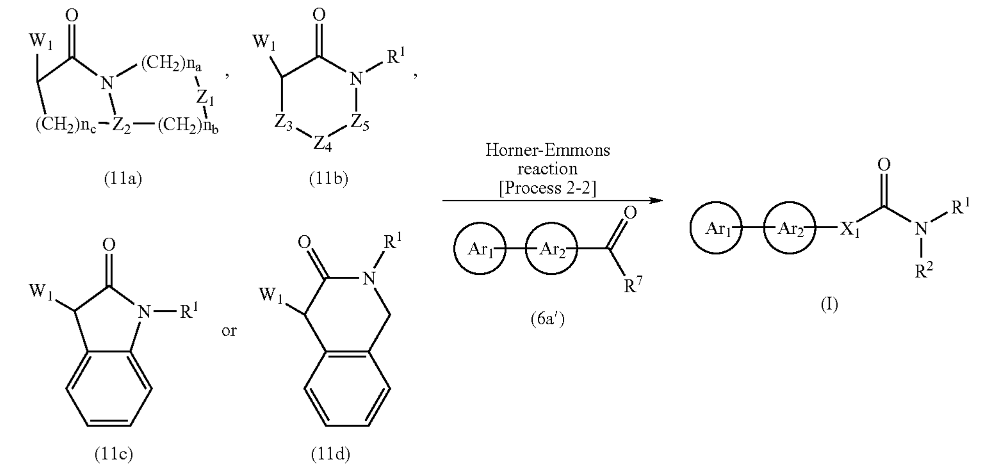

(11a), (11b), (11c) or (11d); (6a'); (I)

(wherein, $Ar_1$, $Ar_2$, $X_1$, $R^1$, $R^2$, $R^7$, $Z_1$, $Z_2$, $Z_3$, $Z_4$, $Z_5$, $n_a$, $n_b$, $n_c$ and $W_1$ is the same as defined above).

The above described formula illustrates an example of a process using a compound (11a), a compound (11b), a compound (11c) or a compound (11d) as starting materials, and subjecting them to the reaction of "Step 2-2" with a carbonyl compound (6a') to prepare the compound of general formula (I).

(Preparation of Compound (11a), Compound (11b), Compound (11c), and Compound (11d))

The compound (11a), the compound (11b), the compound (11c), and the compound (11d) are commercially available, or can be prepared by the technique known in the art. Preferably, according to the "Step 3-3" of the above (Preparation of a phosphonic acid ester compound (7a)), they can be prepared efficiently by using a corresponding amide compound as starting materials.

(General Manufacturing Process 5)

The typical (general manufacturing process 5) of the compound of general formula (I) is explained below.

preferably suitably modified using a technique known to those skilled in the art in order to advances the reaction efficiently at each step.

(Preparation of Compound (12a))

The compound (12a) is commercially available or can be prepared by the technique known in the art. When the carboxylic acid compound is not marketed, a corresponding compound, for example, can be obtained by subjecting a corresponding carboxylic acid compound to a protection reaction known in the art (see T. W. Green."Protective Groups in Organic Synthesis" John Wiley & Sons. Inc., 1981).

(Preparation of the Amine Compound (3b))

The amine compound (3b) is commercially available or can be prepared by the technique known in the art. Preferably,

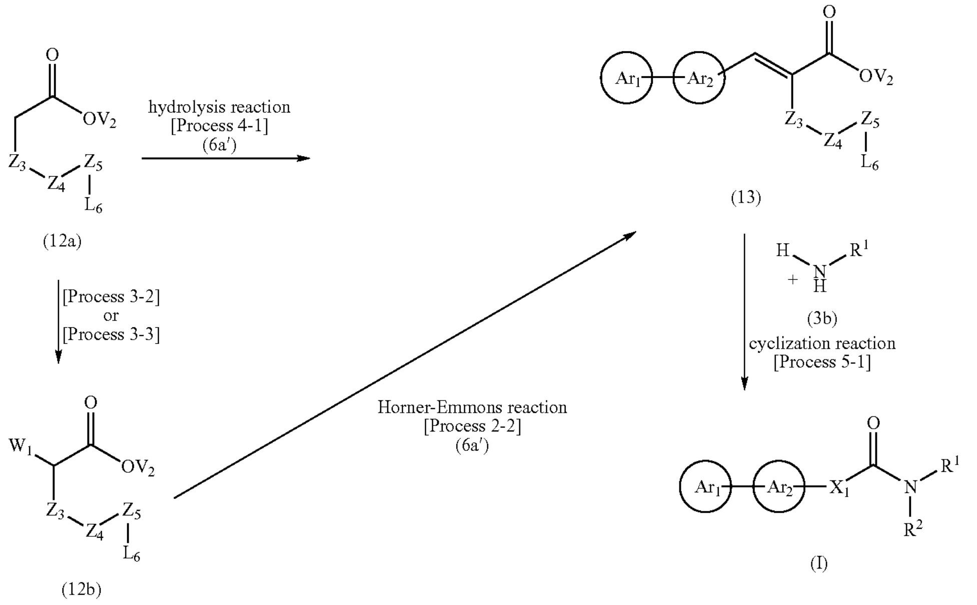

(wherein, $Ar_1$, $Ar_2$, $X_1$, $R^1$, $R^2$, $R^7$, $Z_3$, $Z_4$, $Z_5$, $W_1$ and $V_2$ is the same as defined above and $L_6$ is selected from the above-mentioned substituent group A4).

The above described formula illustrates an example of a process using an ester compound (12a) as the starting material, and subjecting it to the reaction of "Step 4-1" with a carbonyl compound (6a') to convert to a compound (13) which is then converted to a compound of general formula (I) by cyclization reaction of "Step 5-1" or a process using a compound (12b) as the starting material, and subjecting it to the reaction of "Step 2-2" with a carbonyl compound (6a') to convert to a compound (13) which is then subjected to "Step 5-1". For example, the cyclization of "Step 5-1" may vary depending on the starting material, and is not particularly limited as long as it can be effected under similar conditions as in this process and processes known in the art can be used. For example, cyclization can be effected by (i) reacting the compound (13) with an amine compound (3b) through two of the above "step 1-1" and "Step 1-2" to form an amide bond and cyclize while eliminating the substituent group $L_6$ or (ii) introducing an amine compound (3b) into the substituent group $L_6$ and subjecting the product to the above "step 1-1" and 2 of "Step 1-2" to form an intramolecular amide bond to effect cyclization. The substituent groups $L_6$ or $V_2$ may be it can be prepared by the same technique as in the above (Preparation of the amine compound (3)).

(Preparation of Compound (12b))

The compound (12b) is commercially available or can be prepared by the technique known in the art. Preferably, it can be prepares by the same technique as in the above (phosphonic acid ester compound (7a)).

[Effect of Invention]

The present inventors performed the following tests in order to demonstrate the usefulness of the compound of the general formula (I) of the present invention.

Test Example 1

[Quantification of Aβ Peptide in Neuronal Culture from Rat Fetus Brain](1)

Rat Primary Neuronal Culture

Primary neuronal cultures were prepared from cerebral cortices from embryonic day 18 Wistar rat (Charles River Japan, Yokohama, Japan). The embryos were aseptically removed from a pregnant rat under ether anesthesia. The brain was isolated from the embryo, and immersed in ice-cold L-15 medium (for example, Invitrogen Corp. Cat #11415-064, Carlsbad, Calif., USA, or SIGMA L1518, St. Louis. Mo., USA). The cerebral cortex was collected under a stereoscopic microscope from the brain. The cerebral cortex fragments collected were subjected to enzyme treatment in an enzyme solution containing 0.25% trypsin (for example, Invitrogen Corp., Cat #15050-065, Carlsbad, Calif., USA) and 0.01% DNase (for example, Sigma D5025, St. Louis. Mo., USA) at 37 C for 30 minutes to allow for cell dispersion. The enzyme reaction was terminated by addition of same volume of heat-inactivated horse serum. After centrifugation at 1500 rpm for 5 minutes, the supernatant was removed and 5-10 ml of medium was added to the cell pellet. Neurobasal medium™ (Invitrogen Corp., Carlsbad, Calif., USA) supplemented with 2% B-27 supplement (Invitrogen Corp., Carlsbad, Calif., USA), 25 μM 2-mercaptoethanol (2-ME, WAKO, 139-06861, Osaka, Japan), 0.5 mM L-glutamine (for example, Invitrogen Corp., Cat # 25030-081, Carlsbad, Calif., USA), and 1% antibiotics-antimycotics (Invitrogen Corp., Cat # 15240-062, Carlsbad, Calif., USA) was used as the culture medium (Neurobasal/B27/2-ME). At the compound evaluation, the medium of the same composition not to add 2-ME alone (Neurobasal/B27) was used. The cell pellet was triturated by mild pipetting. Remaining cell pellet was removed by filtering through a 40-μm nylon mesh (Cell Strainer, Cat # 35-2340, Becton Dickinson Labware, Franklin Lakes, N.J., USA) and a neuronal cell suspension was obtained. The neuronal cell suspension was diluted with the Neurobasal/B27/2-ME medium and then plated in a volume of 100 μl/well to obtain an initial cell density of $5\times10^5$ cells/$cm^2$ in a 96-well polystyrene plate pre-coated with poly-L or D-lysine (for example, Falcon MICROTEST™ Tissue culture plate 96 well flat bottom with low evaporation lid (Cat # 35-3075, Becton Dickinson Labware, Franklin Lakes, N.J., USA) coated with poly-L-lysine using the method shown below, or BIOCOAT™ cell environments Poly-D-lysine cell ware 96-well plate, Cat # 35-6461, Becton Dickinson Labware, Franklin Lakes, N.J., USA). Poly-L-lysine coating was carried out as follows. Poly-L-lysine (SIGMA P2636, St. Louis, Mo., USA) solution at 100 μg/ml was prepared aseptically with 0.15 M Borate buffer (pH 8.5). The solution was added to a 96-well polystyrene incubator at 50-100 μl/well and incubated at room temperature for one hour or more, or at 4 C overnight or longer. This was rinsed 4 or more times with sterile water, and then dried or rinsed with, for example, sterile PBS or medium, and used for plating cells. Cells were cultured for one day in an incubator of 5% $CO_2$-95% air at 37 C, the entire amount of the medium was exchanged with fresh Neurobasal/B27/2-ME, and the cells were then cultured for further 3 days.

Addition of Compounds

Drugs were added on day 4 of culture as follows. The entire amount of the medium was removed from culture well, and Neurobasal/B27 medium was added at 180 μl/well. The test compound dimethyl sulfoxide (hereinafter abbreviated as DMSO) solution was diluted with Neurobasal/B27 so than it would be 10-fold of the desired final concentration. A diluent was added at 20 μl/well and mixed well. The final concentration of DMSO was 1% or less. Only DMSO was added to the control group.

Sampling

After incubation for 3 days, the entire amount of the medium was collected as ELISA sample. This was used, without any dilution for Aβx-42 measurement, by ELISA assay.

Evaluation of Cell Survival

Cell survival was evaluated by MTT assay. MTT assay was carried out according to the following protocols. Pre-warmed medium of 100 μl/well was added to the wells after collecting the medium. A solution of 8 mg/ml of MTT (SIGMA M2128, St. Louis, Mo., USA) dissolved in D-PBS(−) (Dulbecco's phosphate buffered Saline, SIGMA D8537, ST. Louis, Mo., USA) was added at 8 μl/well, and this was incubated in an incubator of 5% CO2-95% air at 37 C for 20 minutes. MTT solubilizing buffer was added to this at 100 μl/well, MTT formazan crystals were dissolved well in an incubator of 5% $CO_2$-95% air at 37 C, and absorbance was measured at 550 nm. MTT solubilizing buffer was prepared as follows. N,N'-dimethylformamide (for example, WAKO 045-02916, Osaka, Japan) and distilled water 250 ml each were mixed together. To this 100 g of SDS (sodium dodecyl sulfate (for example, sodium lauryl sulfate, WAKO 191-07145, Osaka, Japan)) was dissolved. Conc. HCl and conc. Acetic acid 350 μl each were added to allow for a final pH of about 4.7.

Upon measurement, wells without plating any cells containing only the medium and MTT solution were set as background (bkg). Individual measured values were subjected to the following formula and calculate the proportion against the control group (group without treatment with drugs, CTRL) (% of CTRL), to compare and evaluate cell survival.

$$\%\ \text{of}\ CTRL=(A550\_\text{sample}—A550\_bkg)/(A550\_CTRL—A550\_bkg)\times100$$

(A550_sample: absorbance at 550 nm of sample well, A550_bkg: absorbance at 550 nm of background well, A550_CTRL: absorbance at 550 nm of control group well)

Aβ ELISA

For Aβ ELISA, Human Amyloid beta (1-42) Assay Kit (#17711 or #27711) from Immuno-Biological Laboratories, Co., Ltd. (IBL Co., Ltd.) was used. The methods were as described in the protocols recommended by the manufacturer (methods described in the attached document), except that Aβ calibration curve was created using beta-amyloid peptide 1-42, rat (Calbiochem, #171596 [Aβ42]). The results are shown as percentage to the Aβ concentration in the medium of control group (% of CTRL). The results are shown in Table 1.

(2) Accordingly, the compound of the present invention was proved to have effect to reduce Aβ42 production. Consequently, as the compound of the general formula (I) or a pharmaceutically acceptable salt thereof have effect to reduce Aβ42 production, according to the present an invention, they can provide a preventive or therapeutic agent particularly for neurodegenerative diseases caused by Aβ such as Alzheimer's disease and Down syndrome.

TABLE 1

| Test Compound | Effect to Reduce Aβ42 Production IC50(nM) |
|---|---|
| Example 153 | 190 |
| Example 121 | 70 |
| Example 173 | 190 |
| Example 175 | 60 |
| Example 186 | 190 |
| Example 86 | 320 |
| Example 122 | 190 |
| Example 139 | 200 |
| Example 398 | 220 |
| Example 96 | 220 |
| Example 338 | 330 |
| Example 90 | 240 |

TABLE 1-continued

| Test Compound | Effect to Reduce Aβ42 Production IC50(nM) |
|---|---|
| Example 402 | 70 |
| Example 403 | 90 |
| Example 366 | 330 |
| Example 353 | 220 |
| Example 414 | 130 |
| Example 416 | 100 |
| Example 418 | 109 |
| Example 420 | 120 |
| Example 425 | 80 |
| Example 427 | 780 |
| Example 430 | 119 |
| Example 611 | 265 |
| Example 639 | 56 |
| Example 908 | 68 |
| Example 976 | 80 |
| Example 1014 | 60 |
| Example 1027 | 71 |
| Example 965 | 87 |
| Example 991 | 60 |
| Example 1025 | 70 |
| Example 621 | 100 |

"Salt" indicates a pharmaceutically acceptable salt, and is not particularly limited provided that it forms a pharmaceutically acceptable salt with a compound of the general formula (I) which would be a preventive or therapeutic agent for diseases caused by Aβ. Particular examples which can be mentioned are, for example, preferably hydrohalic acid salts (such as for example hydrofluorides, hydrochlorides, hydrobromides, and hydroiodides), inorganic acid salts (such as for example sulfates, nitrates, perchlorates, phosphates, carbonates, and bicarbonates), organic carboxylates (such as for example acetates, oxalates, maleates, tartrates, fumarates, and citrates), organic sulfonates (such as for example methanesulfonates, trifluoromethanesulfonates, ethanesulfonates, benzenesulfonates, toluenesulfonates, and camphorsulfonates), amino acid salts (such as for example aspartates and glutamates), quaternary amine salts, alkaline metal salts (such as for example sodium salts and potassium salts), alkaline earth metal salts (such as for example magnesium salts and calcium salts) etc.

The preventive agent for diseases caused by Aβ according to the present invention can be formulated by customary methods. Preferred dosage forms are, for example, tablets, powders, subtle granules, granules, coated tablets, capsules, syrups, troches, inhalants, suppositories, injections, ointments, ophthalmic solutions, ophthalmic ointments, nasal drops, ear drops, cataplasms, lotions, etc. For formulation, commonly used excipients, such as for example binders, lubricants, colorants, and correctives, and where necessary stabilizers, emulsifiers, absorbefacients, surfactants, pH adjusters, preservatives, and antioxidants, can be used, and components generally used as ingredients for pharmaceuticals can be blended to formulate by customary methods. Such components which can be mentioned are animal and plant oils such as for example soybean oil, beef tallow, and synthetic glycerides; hydrocarbons such as for example liquid paraffin, squalane, solid paraffin; ester oils such as for example octyldodecyl myristate, isopropyl myristate; higher alcohols such as for example cetostearyl alcohol, behenyl alcohol; silicone resin; for example silicone oil; surfactants such as polyoxyethylene fatty acid ester, sorbitan fatty acid ester, glycerine fatty acid ester, polyoxyethylene sorbitan fatty acid ester, polyoxyethylene hydrogenated castor oil, polyoxyethylene polyoxypropylene block copolymer; water-soluble polymers such as for example hydroxyethylcellulose, polyacrylate, carboxyvinyl polymer, polyethyleneglycol, polyvinylpyrrolidone, methylcellulose; lower alcohols such as for example ethanol, isopropanol; polyols such as for example glycerine, propylene glycol, dipropylene glycol, sorbitol; sugars such as glucose, sucrose; inorganic powders such as for example silicic anhydride, aluminium magnesium silicate, aluminium silicate; and purified water, etc. Excipients used are for example lactose, corn starch, white soft sugar, dextrose, mannitol, sorbitol, crystalline cellulose, and silicone dioxide etc. Binders used are for example polyvinyl alcohol, polyvinyl ether, methylcellulose, ethylcellulose, gum arabic, tragacanth, gelatin, shellac, hydroxypropyl methylcellulose, hydroxypropylcellulose, polyvinylpyrrolidone, polypropylene glycol/polyoxyethylene block polymer, and meglumine etc. Disintegrators used are for example starch, agar, gelatin powders, crystalline cellulose, calcium carbonate, sodium bicarbonate, calcium citrate, dextrin, pectin, and carboxymethylcellulose calcium etc. Lubricants used are for example magnesium stearate, talc, polyethyleneglycol, silica, and hydrogenated plant oils etc. As colorants, those approved as additives to pharmaceuticals are used. Correctives used are cocoa powder, peppermint camphor, empasm, mentha oil, borneol, and cinnamon powder etc.

Oral formulations, for example, are formulated by adding a compound which is an active ingredient or a salt thereof or a hydrate thereof and excipients, and further for example binders, disintegrators, lubricants, colorants, and correctives etc. as necessary, then by customary methods formulating into for example powders, subtle granules, granules, tablets, coated tablets, and capsules etc. In case of tablets/granules, needless to say, it is acceptable to coat them accordingly as necessary with for example sugar coating. In case of syrups or injection formulation, for example pH adjusters, solubilizers, and tonicity adjusting agents etc., and when necessary solubilization facilitators and stabilizers etc. are added, and formulated by customary methods. In case of external preparations, formulation methods are not particularly limited and can be manufactured by customary methods. As base materials used, various materials commonly used such as for pharmaceuticals, quasi drugs, and cosmetics can be used. Examples of such which can be mentioned are animal and plant oils, mineral oils, ester oils, waxes, higher alcohols, fatty acids, silicone oils, surfactants, phospholipids, alcohols, polyols, water-soluble polymers, clay minerals, and purified water etc., and pH adjuster, antioxidants, chelators, preservatives and fungicides, colorants, and fragrances etc. can also be added as necessary. In addition, ingredients having differentiation inducing effect, such as for example blood flow facilitating agents, bactericides, anti-inflammatory agents, cell stimulants, vitamins, amino acids, humectants, and keratolytic agents can be formulated as necessary. Amount of the therapeutic/preventive agents according to the present invention administered varies according to for example degree of symptoms, age, gender, weight, mode of administration, type of salt, and particular type of disease etc. A typical amount for an adult is about 30 μg to 10 g, preferably 100 μg to 5 g, more preferably 100 μg to 3 g per day for oral administration, and about 30 μg to 1 g, preferably 100 μg to 500 mg, more preferably 100 μg to 30 mg for injection administration, which are either administered in a single or multiple dose(s).

The present invention will now be described in further detail with reference to Examples. These are illustrative, and are in no means to limit the preventive or therapeutic agents for diseases caused by Aβ of the present invention to the particular Examples below. Those having ordinary skills in the art are capable of applying different variations to the reference examples and Examples below as well as Claims according to the present invention to carry out the invention to its full. Such variations are within the scope of Claims according to the present invention.

EXAMPLES

The following symbols are used in the following Examples.

DMF: N,N'-dimethylformamide
THF: tetrahydrofuran
LAH: lithium aluminum hydride
EDC: 1-ethyl-3-(3-dimethylaminopropyl)carbodiimide hydrochloride
HOBT: 1-hydroxybenzotriazol
IPEA: diisopropylethylamine
TEA: triethylamine
DPPF: 1,1-bis(diphenylphosphino)ferrocene
CDI: N,N'-carbonyldiimidazole
TBAF: tetrabutylammonium fluoride
PYBOP: benzotriazol-1-yloxytris(pyridino)phosphonium-hexafluorophosphonic acid ester
DBU: 1,8-diazabicyclo[5.4.0]undec-7-ene
DAST: diethylamino sulfur trifluoride
BOP: benzotriazol-1-yloxy-tris(dimethylamino)phosphoniumhexafluorophosphate
DIBAL-H: diisobutyl aluminum hydride
Dess-Martin reagent: Dess-Martin Periodinane Chromatography was conducted using BW-300 (product of Fuji Silysia Chemical Ltd.) as a carrier unless otherwise stated.

LC-MS: High-performance liquid chromatography for preparative isolation of the object compound using mass spectrometry. As an elution solvent, 10 to 99% of linear gradient system of water containing 0.1% trifluoroacetic acid and acetonitrile containing 0.1% trifluoroacetic acid was used.

Example 1

Synthesis of (E)-N-indan-1-yl-3-[3-methoxy-4-(4-methyl-1H-imidazol-1-yl)phenyl]acrylamide

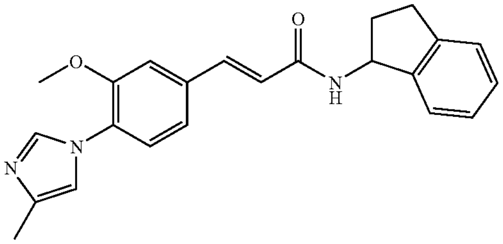

Synthesis of 3-methoxy-4-(4-methyl-1H-imidazol-1-yl)benzaldehyde and 3-methoxy-4-(5-methyl-1H-imidazol-1-yl)benzaldehyde To a DMF (50 mL) solution of 4-fluoro-3-methoxybenzaldehyde (3.00 g) and 4-methylimidazole (3.307 g), potassium carbonate (4.05 g) was added and the reaction mixture was agitated at 100° C. overnight. The obtained reaction mixture was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (elution solvent: hexane-ethyl acetate system), and 3-methoxy-4-(4-methyl-1H-imidazol-1-yl)benzaldehyde (856 mg) and 3-methoxy-4-(5-methyl-1H-imidazol-1-yl)benzaldehyde (44 mg) were obtained.

The physical properties of 3-methoxy-4-(4-methyl-1H-imidazol-1-yl)benzaldehyde:

$^1$H-NMR ($CDCl_3$) δ (ppm): 2.31 (s, 3H), 3.97 (s, 3H), 7.02 (brs, 1H), 7.44 (d, J=8.0 Hz, 1H), 7.55 (dd, J=1.6 Hz, 8.0 Hz, 1H), 7.58 (d, J=1.6 Hz, 1H), 7.84 (brs, 1H), 10.00 (s, 1H).

The physical properties of 3-methoxy-4-(5-methyl-1H-imidazol-1-yl)benzaldehyde:

$^1$H-NMR ($CDCl_3$) δ (ppm): 2.10 (s, 3H), 3.90 (s, 3H), 6.91 (brs, 1H), 7.40 (d, J=8.0 Hz, 1H), 7.50 (d, J=1.2 Hz, 1H), 7.57-7.59 (m, 1H), 7.84 (s, 1H), 10.05 (s, 1H).

In addition, 3-methoxy-4-(4-methy-1H-limidazol-1-yl) benzaldehyde can be synthesized also in the following alternative method.

Synthesis of 3-methoxy-4-nitrobenzoic acid methyl ester

Methyl iodide (463 g) was dropped to a mixture of 3-hydroxy-4-nitrobenzoic acid (199 g) and potassium carbonate (450 g) in DMF (1 L) at room temperature. After agitating the reaction solution at room temperature overnight, methyl iodide (230 g) was further added to the reaction mixture, and the reaction mixture was further agitated at room temperature for 6 hours. The reaction mixture was added to ice water and the deposited solids were obtained by filtration. 178 g of the title compound was obtained by drying the obtained solid at 50° C. overnight. The physical properties was in agreement with the reported values (CAS#5081-37-8).

Synthesis of 4-amino-3-methoxybenzoic acid methyl ester

To a solution of 3-methoxy-4-nitrobenzoic acid methyl ester (150 g) in methanol (600 mL) and THF (300 mL), 10% palladium-carbon (15 g) was added and the reaction mixture was agitated at 50° C. to 64° C. under hydrogen pressure of 0.9 MPa(s) for 6.5 hours. After allowing cool the reaction solution to room temperature, 134 g of the title compound was obtained by filtering the reaction solution on celite and condensing the obtained filtrate under reduced pressure. The physical properties was in agreement with the reported values (CAS#41608-64-4).

Synthesis of 4-formylamino-3-methoxybenzoic acid methyl ester

Anhydrous acetic acid (268 mL) was added dropwise to formic acid (401 mL) at room temperature, and the reaction solution was agitated for 40 minutes at room temperature. To this reaction solution, a THF (600 mL) solution of 4-amino-3-methoxybenzoic acid methyl ester (134 g) was added dropwise at room temperature, and the reaction solution was agitated for 1 hour. 3.8 L of iced water was added to the reaction solution, and the deposited solids were separated by filtering, and further washed with water (2 L). 111 g of the title compound was obtained by drying the obtained solid at 50° C. overnight. The physical properties was in agreement with the reported values (CAS#700834-18-0).

Synthesis of 4-[formyl-(2-oxopropyl)amino]-3-methoxybenzoic acid methyl ester

Chloroacetone (84.5 mL) was added dropwise to the DMF (497 mL) mixture of 4-formylamino-3-methoxybenzoic acid methyl ester (111 g), cesium carbonate (346 g), and potassium iodide (8.78 g) at room temperature, and the reaction mixture was agitated for 3 hours. Cesium carbonate (173 g) and chloroacetone (42.0 mL) were added to the reaction mixture, and the reaction mixture was agitated at room temperature for 2 hours. Iced water and ethyl acetate were added to the reaction mixture, and the organic layer was partitioned. Ethyl acetate was added to the aqueous layer and the organic layer was partitioned. The organic layers were combined, washed with water and a saturated saline solution in this order, and the obtained organic layer was dried over anhydrous magnesium sulfate and then concentrated under reduced pressure. The residue was diluted with toluene and the solution was concentrated under reduced pressure. Tert-butylmethyl ether and heptane were added to the resulted residue and the deposited solids were separated by filtering and washed with a 50% heptane solution of tert-butylmethyl ether. 118 g of the title compound was obtained by air-drying the obtained solids overnight.

$^1$H-NMR ($CDCl_3$) δ (ppm): 2.19 (s, 3H), 3.91 (s, 3H), 3.94 (s, 3H), 4.49 (s, 2H), 7.31 (d, J=8.0 Hz, 1H), 7.63 (d, J=2.0 Hz, 1H), 7.69 (dd, J=8.0, 2.0 Hz, 1H), 8.33 (s, 1H).

Synthesis of 3-methoxy-4-(4-methyl-1H-imidazol-1-yl)benzoic acid methyl ester

An acetic acid (255 mL) solution of 4-(formyl-(2-oxopropyl)amino)-3-methoxybenzoic acid methyl ester (118 g) and ammonium acetate (172 g) was heated under stirring at 140° C. for 1 hour. The reaction solution was neutralized with an ammoniac solution under ice-cooling after the reaction completed. Ethyl acetate was added to the reaction solution, and the organic layer was partitioned. The obtained organic layer was filtered with a silica gel pad after dried over anhydrous magnesium sulfate, and the filtrate was concentrated under reduced pressure. Tert-butylmethyl ether and heptane were added to the residue and the deposited solids were separated by filtering and washed with a 50% heptane solution of tert-butylmethyl ether. 68.4 g of the title compound was obtained by air-drying the obtained solids overnight. Furthermore, crystallization mother liquid was concentrated under reduced pressure, the residue was purified by silica gel column chromatography (elution solvent:heptane-ethyl acetate system), and 22.3 g of the title compound was obtained.

$^1$H-NMR ($CDCl_3$) δ (ppm): 2.30 (s, 3H), 3.94 (s, 3H), 3.96 (s, 3H), 6.98 (brs, 1H), 7.32 (d, J=8.4 Hz, 1H), 7.71-7.73 (m, 2H), 7.79 (brs, 1H).

Synthesis of 3-methoxy-4-(4-methyl-1H-imidazol-1-yl)benzaldehyde

To a THF (60 mL) solution of sodium bis(2-methoxyethoxy)aluminum hydride (65% toluene solution, 56 mL), a THF (45 mL) solution of pyrrolidine (18 mL) was added dropwise for 15 minutes at −5° C. or less. The reaction solution was agitated at room temperature for 1 hour, a THF (15 mL) suspension of tert-butoxide (2.10 g) was added dropwise to the reaction solution at room temperature and the reaction mixture was agitated for 15 minutes. The reaction mixture was added dropwise to a THF (50 mL) solution of 3-methoxy-4-(4-methyl-1H-imidazol-1-yl)benzoic acid methyl ester (20 g) under ice-cooling for 30 minutes. The reaction mixture was agitated at room temperature for 2 hours and a 5N sodium hydroxide solution (150 mL) was added dropwise to the reaction solution. Ethyl acetate was added to the reaction solution and the organic layer was partitioned. The organic layer was washed with a saturated ammonium chloride solution and a saturated saline solution in this order. The organic layer was dried over anhydrous magnesium sulfate, and the filtrate was concentrated under reduced pressure after filtration with a silica gel pad. The residue was diluted with ethyl acetate and the deposited solids were separated by filtering. 7.10 g of the title compound was obtained by air-drying the obtained solids overnight. Furthermore, crystallization mother liquid was concentrated under reduced pressure, the residue was purified by silica gel column chromatography (elution solvent:heptane-ethyl acetate-2-propanol system), and 2.65 g of the title compound was obtained.

Synthesis of indan-1-ylcarbamoylmethylphosphonic acid diethyl ester

After adding thionyl chloride (6.07 g) to a methylene chloride (20 mL) solution of diethoxyphosphoryl acetic acid (5.00 g), this reaction mixture was agitated at room temperature for 2 hours and the reaction solution was concentrated under reduced pressure. THF (40 mL) solution of the obtained residue was added dropwise to a THF (80 mL) solution of 1-aminoindane (3.40 g) and TEA (3.5 mL) under ice-cooling, and the reaction solution was agitated at the temperature. Water and ethyl acetate were added to this reaction mixture, and the organic layer was partitioned. The organic layer was washed with a saturated saline solution, dried over anhydrous magnesium sulfate, and concentrated under reduced pressure. The residue was purified by silica gel column chromatography (elution solvent:hexane-ethyl acetate system), and 4.2 g of the title compound was obtained.

$^1$H-NMR ($CDCl_3$) δ (ppm): 1.31-1.36 (m, 6H), 1.79-1.89 (m, 1H), 2.56-2.63 (m, 1H), 2.83-3.03 (m, 4H), 4.09-4.18 (m, 4H), 5.47 (q, J=7.6 Hz, 1H), 6.83-6.89 (brd, 1H), 7.19-7.32 (m, 4H).

Synthesis of (E)-N-indan-1-yl-3-[3-methoxy-4-(4-methyl-1H-imidazol-1-yl)phenyl]acrylamide Lithium hydroxide monohydrate (9 mg) was added to a THF (2 mL) solution of 3-methoxy-4-(4-methyl-1H-imidazol-1-yl)benzaldehyde (21 mg) and indan-1-ylcarbamoylmethylphosphonic acid diethyl ester (30 mg) obtained above, and the reaction solution was agitated at room temperature overnight. After the reaction mixture was concentrated under reduced pressure, the residue was purified by silica gel column chromatography (Carrier: Chromatorex™ NH, elution solvent:hexane-ethyl acetate system), and 13 mg of the title compound was obtained.

$^1$H-NMR ($CDCl_3$) δ (ppm): 1.86-1.95 (m, 1H), 2.29 (s, 3H), 2.63-2.72 (m, 1H), 2.88-3.06 (m, 2H), 3.88 (s, 3H), 5.65 (q, J=7.6 Hz, 1H), 5.88 (d, J=8.4 Hz, 1H), 6.41 (d, J=15.4 Hz, 1H), 6.92 (t, J=1.2 Hz, 1H), 7.13-7.35 (m, 7H), 7.67 (d, J=15.4 Hz, 1H), 7.71 (d, J=1.6 Hz, 1H)

Example 1-1

Synthesis of (E)-3-[4-(4-bromo-1H-imidazol-1-yl)-3-methoxyphenyl]-N-(9H-fluoren-9-yl)acrylamide

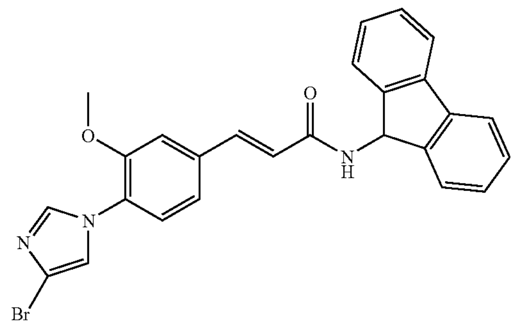

Synthesis of 4-(4-bromo-1H-imidazol-1-yl)-3-methoxybenzaldehyde

Potassium carbonate (1.74 g) was added to a DMF solution of 4-fluoro-3-methoxybenzaldehyde (1.94 g) and 4-bromoimidezole(1.85 g), and the reaction solution was agitated at 100° C. overnight. The obtained reaction mixture was concentrated under reduced pressure, water and ethyl acetate were added to the obtained residue, and the organic layer was partitioned. The organic layer was washed with a saturated saline solution, dried over anhydrous magnesium sulfate, and concentrated under reduced pressure. The residue was purified by silica gel chromatography (elution solvent:hexane: ethyl acetate system), and 1.21 g of the title compound was obtained. The physical properties of the compound are as follows.

$^1$H-NMR ($CDCl_3$) δ (ppm): 3.93 (s, 3H), 7.24 (s, 1H), 7.43 (d, J=7.6 Hz, 1H), 7.52-7.55 (m, 2H), 7.74 (s, 1H), 9.97 (s, 1H).

Synthesis of (E)-3-[4-(4-bromo-1H-imidazol-1-yl)-3-methoxyphenyl]-N-(9H-fluoren-9-yl)acrylamide By the same method as in Example 121, the title compound was synthesized from 3-(4-(4-bromo-1H-imidazol-1-yl)-3-methoxyphenyl)acrylic acid (100 mg) obtained from 4-(4-bromo-1H-imidazol-1-yl)-3-methoxybenzaldehyde and 9-fluoren-9-ylamine hydrochloride (81 mg).

$^1$H-NMR ($CDCl_3$) δ (ppm): 1.83-1.97 (m, 1H), 2.60-2.74 (m, 1H), 2.84-3.08 (m, 2H), 3.89 (s, 3H), 5.64 (q, J=7.6 Hz, 1H), 6.05 (d, J=8.4 Hz, 1H), 6.46 (d, J=15.2 Hz, 1H), 7.10-7.30 (m, 7H), 7.34 (d, J=6.8 Hz, 1H), 7.61 (d, J=6.0 Hz, 1H), 7.67 (d, J=15.6 Hz, 1H).

Example 2

Synthesis of (E)-3-[3-ethoxy-4-(4-methyl-1H-imidazol-1-yl)phenyl]-N-indan-1-yl-acrylamide

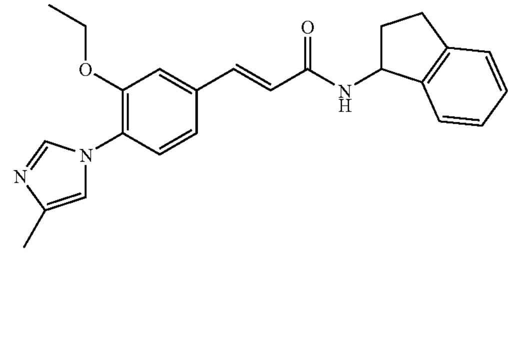

Synthesis of 4-fluoro-3-hydroxybenzaldehyde

Boron tribromide (1M methylene chloride solution, 100 mL) was gradually added dropwise to a methylene chloride (100 mL) solution of 3-methoxy-4-fluoro benzaldehyde (4.4 g) under ice-cooling. The reaction solution was agitated at room temperature for 2 hours after the dropping ended. The reaction solution was again cooled with ice, iced water was gradually added to the reaction solution to terminate the reaction, and further 5N hydrochloride solution was added until the pH reached 1. After condensing the reaction solution under reduced pressure, water and ethyl acetate were added to the residue, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 4:1), and 3.18 g (79%) of 4-fluoro-3-hydroxybenzaldehyde was obtained. The physical properties of the compound are as follows.

$^1$H-NMR ($CDCl_3$) δ (ppm): 5.70 (s, 1H), 7.24 (dd, J=8.4, 10.0 Hz, 1H), 7.40-7.50 (m, 1H), 7.55 (dd, J=2.0, 8.4 Hz, 1H), 9.91 (s, 1H).

Synthesis of 3-ethoxy-4-fluorobenzaldehyde

Sodium hydride (171 mg) was added to a DMF (10 mL) solution of 4-fluoro-3-hydroxybenzaldehyde (300 mg) obtained above at room temperature, and the reaction solution was agitated for 30 minutes. Then, iodoethane (0.26 mL) was added dropwise to the reaction solution, and the reaction mixture was agitated at room temperature for 1 hour. After the reaction ended, water and ethyl acetate were added to the reaction solution under ice-cooling and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 5:1), and 250 mg (70%) 3-ethoxy-4-fluorobenzaldehyde was obtained. The physical properties of the compound are as follows.

$^1$H-NMR ($CDCl_3$) δ (ppm): 1.49 (t, J=6.8 Hz, 3H), 4.19 (q, J=6.8 Hz, 2H), 7.23 (dd, J=8.0, 10.4 Hz, 1H), 7.43 (m, 1H), 7.50 (dd, J=2.0, 8.0 Hz, 1H), 9.91 (s, 1H).

Synthesis of 3-ethoxy-4-(4-methyl-1H-imidazol-1-yl)benzaldehyde 4-methylimidazole (244 mg) was added to a DMF (3 mL) solution of 3-ethoxy-4-fluorobenzaldehyde (250 mg) obtained above, and the reaction solution was agitated at 150° C. for 4 hours. The reaction solution was concentrated as it was after the reaction ended, water and ethyl acetate were added to the obtained reaction residue, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 1:4), and 60 mg (18%) of 3-ethoxy-4-(4-methyl-1H-imidazol-1-yl)benzaldehyde was obtained. The physical properties of the compound are as follows.

$^1$H-NMR ($CDCl_3$) δ (ppm): 1.46 (t, J=8.4 Hz, 3H), 2.31 (s, 3H), 4.20 (q, J=8.4 Hz, 2H), 7.00-7.06 (m, 1H), 7.43 (d, J=8.0 Hz, 1H), 7.53 (dd, J=1.6, 8.0 Hz, 1H), 7.55 (d, J=1.6 Hz, 1H), 7.90 (d, J=1.2 Hz, 1H), 9.99 (s, 1H).

Synthesis of (E)-3-[3-ethoxy-4-(4-methyl-1H-imidazol-1-yl)phenyl]-N-indan-1-yl-acrylamide To a THF (8 mL) solution of 3-ethoxy-4-(4-methyl-1H-imidazole-1-yl)benzaldehyde (60 mg), (indan-1-ylcarbamoylmethyl)phosphonic acid diethyl ester (81 mg) and lithium hydroxide monohydrate (22 mg) were added, and the reaction mixture was agitated at room temperature for 14 hours. Water and ethyl acetate were added to the reaction solution after the reaction ended, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 1:4), and 23 mg (23%) of the title compound was obtained. The physical properties of the compound are as follows.

ESI-MS; m/z388 [$M^{+}$+H]. $^{1}$H-NMR ($CDCl_3$) δ (ppm): 1.41 (t, J=6.8 Hz, 3H), 1.82-1.97 (m, 1H), 2.30 (s, 3H), 2.60-2.74 (m, 1H), 2.84-3.10 (m, 2H), 4.10 (q, J=6.8 Hz, 2H), 5.64 (q, J=7.6 Hz, 1H), 5.88 (d, J=8.4 Hz, 1H), 6.39 (d, J=15.6 Hz, 1H), 6.95 (s, 1H), 7.10-7.19 (m, 2H), 7.20-7.31 (m, 4H), 7.34 (d, J=6.8 Hz, 1H), 7.66 (d, J=15.6 Hz, 1H), 7.78 (d, J=1.6 Hz, 1H).

Example 3

Synthesis of (E)-3-[3-cyclopropyl methoxy-4-(4-methyl-1H-imidazol-1-yl)phenyl]-N-indan-1-yl-acrylamide

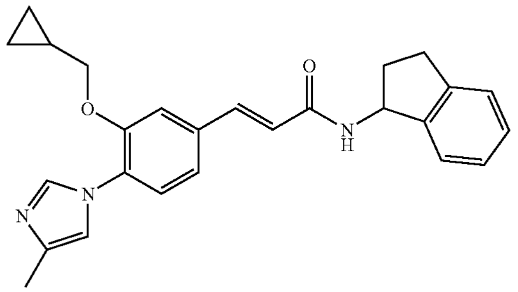

By the same method as in Example 2, 22 mg (3.6%) of the title compound was obtained from 4-fluoro-3-hydroxybenzaldehyde (200 mg). The physical properties of the compound are as follows.

ESI-MS; m/z414 [$M^{+}$+H]. $^{1}$H-NMR ($CDCl_3$) δ (ppm): 0.24-0.38 (m, 2H), 0.56-0.70 (m, 2H), 1.16-1.32 (m, 1H), 1.82-1.98 (m, 1H), 2.30 (s, 3H), 2.60-2.74 (m, 1H), 2.84-3.10 (m, 2H), 3.87 (d, J=6.8 Hz, 2H), 5.63 (q, J=7.6 Hz, 1H), 5.93 (d, J=8.4 Hz, 1H), 6.39 (d, J=15.6 Hz, 1H), 6.98 (s, 1H), 7.11 (d, J=1.7 Hz, 1H), 7.16 (dd, J=1.7, 8.4 Hz, 1H), 7.19-7.30 (m, 4H), 7.34 (d, J=6.8 Hz, 1H), 7.65 (d, J=15.2 Hz, 1H), 7.84 (m, 1H)

Example 4

Synthesis of (E)-3-[3-(2-butynyloxy)-4-(4-methyl-1H-imidazol-1-yl)phenyl]-N-indan-1-yl-acrylamide

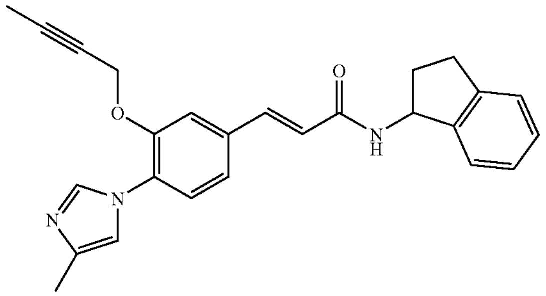

By the same method as in Example 2, 58 mg (7.8%) of the title compound was obtained from 4-fluoro-3-hydroxybenzaldehyde (250 mg). The physical properties of the compound are as follows.

ESI-MS; m/z412 [$M^{+}$+H]. $^{1}$H-NMR ($CDCl_3$) δ (ppm): 1.85 (t, J=3.0 Hz, 3H), 1.82-1.98 (m, 1H), 2.45 (s, 3H), 2.62-2.74 (m, 1H), 2.86-3.10 (m, 2H), 4.71 (d, J=3.0 Hz, 2H), 5.65 (q, J=7.6 Hz, 1H), 5.93 (d, J=8.0 Hz, 1H), 6.41 (d, J=15.6 Hz, 1H), 6.92-6.97 (m, 1H), 7.18-7.32 (m, 6H), 7.35 (d, J=7.6 Hz, 1H), 7.69 (d, J=15.6 Hz, 1H), 7.74 (d, J=11.6 Hz, 1H)

Example 5

Synthesis of (E)-N-indan-2-yl-3-[4-(4-methyl-1H-imidazol-1-yl)-3-(2-propynyloxy)phenyl]acrylamide

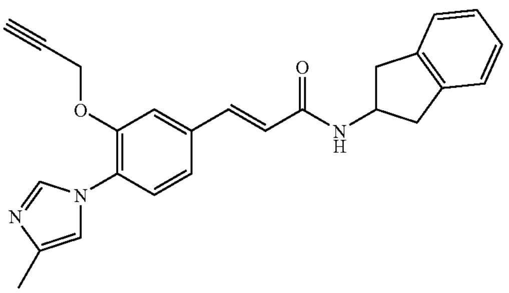

By the same method as the Example 2, 96 mg (9.5%) of the title compound was obtained from 4-fluoro-3-hydroxybenzaldehyde (350 mg). The physical properties of the compound are as follows.

ESI-MS; m/z398 [$M^{+}$+H]. $^{1}$H-NMR ($CDCl_3$) δ (ppm): 2.29 (d, J=1.0 Hz, 3H), 2.55 (t, J=2.0 Hz, 1H), 2.99 (dd, J=4.0, 16.4 Hz, 2H), 3.39 (dd, J=6.8, 16.4 Hz, 2H), 4.73 (d, J=2.0 Hz, 2H), 4.85-4.95 (m, 1H), 5.94 (d, J=8.0 Hz, 1H), 6.33 (d, J=15.6 Hz, 1H), 6.91-6.95 (m, 1H), 7.16-7.32 (m, 7H), 7.63 (d, J=15.6 Hz, 1H), 7.71 (d, J=1.6 Hz, 1H).

Example 6

Synthesis of (E)-N-indan-1-yl-3-[4-(4-methyl-1H-imidazol-1-yl)-3-vinyloxyphenyl]acrylamide

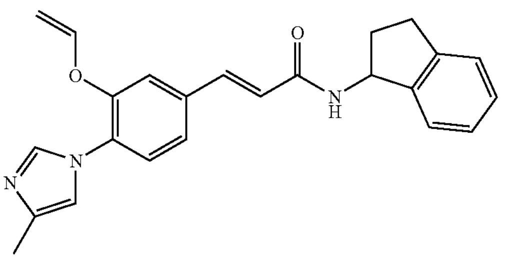

Synthesis of 3-(2-bromoethoxy)-4-fluoro benzaldehyde

Sodium hydride (1.14 g) was added to a DMF (30 mL) solution of 4-fluoro-3-hydroxybenzaldehyde (2.00 g) at room temperature., and the reaction solution was agitated for 30 minutes. Then, dibromoethane (2.46 mL) was added dropwise to the reaction solution, and the reaction solution was heated at 140° C. for 3 hours after the dropping ended. Water and ethyl acetate were added to the reaction solution under ice-cooling, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 6:1), and 606 mg (20%) 3-(2-bromoethoxy)-4-fluoro benzaldehyde was obtained. The physical properties of the compound are as follows.

$^1$H-NMR ($CDCl_3$) δ (ppm): 3.69 (t, J=6.4 Hz, 2H), 4.42 (t, J=6.4 Hz, 2H), 7.27 (dd, J=8.4, 9.6 Hz, 1H), 7.46-7.56 (m, 2H), 9.92 (s, 1H).

Synthesis of 4-fluoro-3-vinyloxybenzaldehyde

A 50% sodium hydroxide solution (5 mL) and tetrabutylammonium hydrogen sulfate (859 mg) were added to the toluene (8 mL) solution of 3-(2-bromoethoxy)-4-fluorobenzaldehyde derivative (606 mg) obtained above, and the reaction solution was agitated at room temperature for 1 hour. Water and ethyl acetate were added to the reaction solution after the reaction ended, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:heptane-ethyl acetate 6:1), and 200 mg (49%) of 4-fluoro-3-vinyloxybenzaldehyde was obtained. The physical properties of the compound are as follows.

$^1$H-NMR ($CDCl_3$) δ (ppm): 4.60 (dd, J=2.0, 6.0 Hz, 1H), 4.84 (dd, J=2.0, 13.6 Hz, 1H), 6.67 (dd, J=6.0, 13.6 Hz, 1H), 7.30 (dd, J=8.4, 10.0 Hz, 1H), 7.50-7.70 (m, 2H), 9.93 (s, 1H)

Synthesis of 4-(4-methyl-1H-imidazol-1-yl)-3-vinyloxybenzaldehyde

By the same method as in Example 2, 66 mg (24%) of 4-(4-methyl-1H-imidazol-1-yl)-3-vinyloxybenzaldehyde was obtained from 4-fluoro-3-vinyloxybenzaldehyde (200 mg) obtained above. The physical properties of the compound are as follows.

$^1$H-NMR ($CDCl_3$) δ (ppm): 2.31 (s, 3H), 4.64 (dd, J=2.0, 6.0 Hz, 1H), 4.87 (dd, J=2.0, 13.6 Hz, 1H), 6.63 (dd, J=6.0, 13.6 Hz, 1H), 7.03 (s, 1H), 7.50 (d, J=8.4 Hz, 1H), 7.64-7.74 (m, 2H), 7.85 (s, 1H), 10.00 (s, 1H).

Synthesis of (E)-N-indan-1-yl-3-[4-(4-methyl-1H-imidazol-1-yl)-3-vinyloxyphenyl]acrylamide By the same method as in Example 2, 60 mg (54%) of (E)-N-indan-1-yl-3-(4-(4-methyl-1H-imidazol-1-yl)-3-vinyloxyphenyl)acrylamide was obtained from 4-(4-methyl-1H-imidazol-1-yl)-3-vinyloxybenzaldehyde (66 mg) obtained above. The physical properties of the compound are as follows.

ESI-MS; m/z386 [M$^+$+H]. $^1$H-NMR ($CDCl_3$) δ (ppm): 1.89-1.98 (m, 1H), 2.30 (s, 3H), 2.60-2.74 (m, 1H), 2.84-3.10 (m, 2H), 4.53 (dd, J=2.8, 5.6 Hz, 1H), 4.76 (dd, J=2.8, 14.0 Hz, 1H), 5.64 (q, J=7.2 Hz, 1H), 5.91 (d, J=8.4 Hz, 1H), 6.41 (d, J=15.6 Hz, 1H), 6.55 (dd, J=6.4, 14.0 Hz, 1H), 6.95 (s, 1H), 7.20-7.37 (m, 6H), 7.34 (d, J=6.8 Hz, 1H), 7.65 (d, J=15.6 Hz, 1H), 7.73 (d, J=1.6 Hz, 1H).

Example 7

Synthesis of (E)-3-[3-ethoxy-4-(4-methyl-1H-imidazol-1-yl)phenyl]-1-(4-indol-1-yl-piperidin-1-yl)propenone

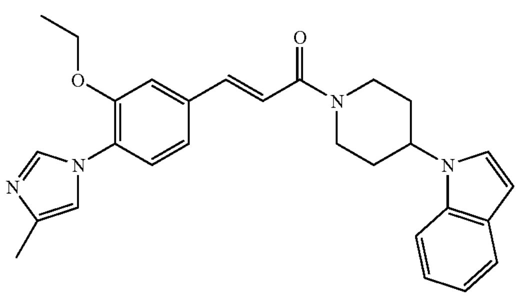

By the same method as in Example 121, 60 mg (26%) of the title compound was obtained from (E)-(3-ethoxy-4-(4-methyl-1H-imidazol-1-yl)phenyl)acrylic acid (140 mg). The physical properties of the compound are as follows.

ESI-MS; m/z477 [M$^+$+Na]. $^1$H-NMR ($CDCl_3$) δ (ppm): 1.42 (t, J=6.8 Hz, 3H), 1.90-2.10 (m, 2H), 2.19-2.29 (m, 2H), 2.30 (s, 3H), 2.80-3.06 (m, 1H), 3.25-3.50 (m, 1H), 4.12 (q, J=6.8 Hz, 2H), 4.24-4.40 (m, 1H), 4.46-4.60 (m, 1H), 4.90-5.08 (m, 1H), 6.54 (dd, J=0.8, 3.2 Hz, 1H), 6.92-6.97 (m, 1H), 7.08-7.30 (m, 7H), 7.39 (d, J=8.0 Hz, 1H), 7.64 (d, J=7.6 Hz, 1H), 7.68 (d, J=15.6 Hz, 1H), 7.78 (d, J=1.6 Hz, 1H).

Example 8

Synthesis of (E)-3-[3-allyloxy-4-(4-methyl-1H-imidazol-1-yl)phenyl]-N-indan-2-yl-acrylamide

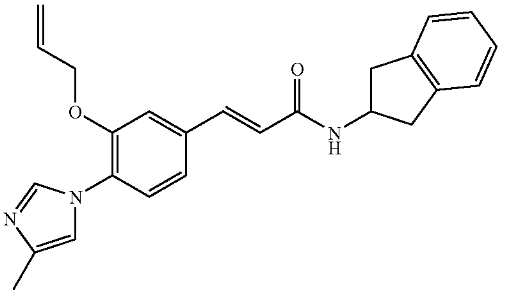

By the same method as in Example 121, 48 mg (17%) of the title compound was obtained from (E)-(3-allyloxy-4-(4-methyl-1H-imidazol-1-yl)phenyl)acrylic acid (512 mg). The physical properties of the compound are as follows.

$^1$H-NMR ($CDCl_3$) δ: 2.29 (s, 3H), 2.89 (dd, J=4.0, 16.0 Hz, 2H), 3.38 (dd, J=6.8, 16.0 Hz, 2H), 4.58 (d, J=5.2 Hz, 2H), 4.82-4.98 (m, 1H), 5.27 (dd, J=1.2, 10.8 Hz, 1H), 5.35 (dd, J=1.2, 15.6 Hz, 1H), 5.90-6.10 (m, 1H), 6.04 (d, J=8.0 Hz, 1H), 6.32 (d, J=15.2 Hz, 1H), 6.94 (s, 1H), 7.07-7.17 (m, 2H), 7.18-7.30 (m, 5H), 7.59 (d, J=15.6 Hz, 1H), 7.74 (d, J=0.8 Hz, 1H)

Example 9

Synthesis of (E)-3-[3-cyano-4-(4-methyl-1H-imidazol-1-yl)phenyl]-N-indan-1-ylacrylamide

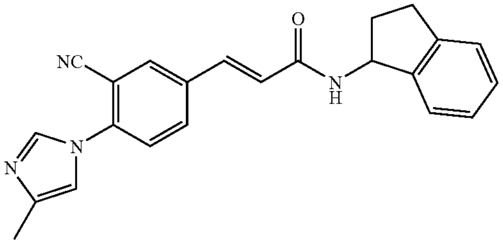

Synthesis of 5-bromo-2-(4-methyl-1H-imidazol-1-yl)benzonitrile and 5-bromo-2-(5-methyl-1H-imidazol-1-yl)benzonitrile Potassium carbonate (2.07 g) was added to a DMF (20 mL) solution of 5-bromo-2-fluorobenzonitrile (2.00 g) and 4-methylimidazole (1.23 g) and the reaction solution was agitated at 100° C. for 4.5 hours. The reaction mixture was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (elution solvent:hexane-ethyl acetate system), and 5-bromo-2-(4-methyl-1H-imidazol-1-yl)benzonitrile (962 mg) and 5-bromo-2-(5-methyl-1H-imidazol-1-yl)benzonitrile (60 mg) were obtained.

The physical properties of 5-bromo-2-(4-methyl-1H-imidazol-1-yl)benzonitrile are as follows.

$^1$H-NMR ($CDCl_3$) δ (ppm): 2.32 (s, 3H), 7.05 (t, J=1.2 Hz, 1H), 7.31 (d, J=8.8 Hz, 1H), 7.74 (d, J=1.2 Hz, 1H), 7.83 (dd, J=2 Hz, 8.8 Hz, 1H), 7.93 (d, J=1.2 Hz, 1H).

The physical properties of 5-bromo-2-(5-methyl-1H-imidazol-1-yl)benzonitrile are as follows.

$^1$H-NMR ($CDCl_3$) δ (ppm): 2.15 (s, 3H), 6.97 (t, J=1.2 Hz, 1H), 7.28 (d, J=8.4 Hz, 1H), 7.56 (d, J=1.2 Hz, 1H), 7.89 (dd, J=2.4 Hz, 8.4 Hz, 1H), 7.97 (d, J=2.4 Hz, 1H).

Synthesis of N-indan-1-yl-acrylamide

A THF (10 mL) solution of acrylic acid chloride (2.04 g) was added dropwise to a THF (30 mL) solution of 1-aminoindane (3.00 g) and TEA (2.28 g) under ice-cooling, and the reaction solution was agitated for 20 minutes at the temperature. Water and ethyl acetate were added to this reaction mixture, and the organic layer was partitioned. The organic layer was washed with a saturated saline solution, dried over anhydrous magnesium sulfate, and concentrated under reduced pressure. 2.23 g of the title compound was obtained by adding ether to the residue and filtering insoluble matter.

$^1$H-NMR ($CDCl_3$) δ (ppm): 1.81-1.90 (m, 1H), 2.61-2.69 (m, 1H), 2.86-3.05 (m, 2H), 5.58 (q, J=7.6 Hz, 1H), 5.68 (dd, J=1.6 Hz, 10.4 Hz, 1H), 5.70-5.78 (brs, 1H), 6.10 (dd, J=10.4 Hz, 17.2 Hz, 1H), 6.34 (dd, J=1.6 Hz, 17.2 Hz, 1H), 7.20-7.32 (m, 4H).

Synthesis of (E)-3-[3-cyano-4-(4-methyl-1H-imidazol-1-yl)phenyl]-N-indan-1-ylacrylamide To a DMF (2 mL) solution of 5-bromo-2-(4-methyl-1H-imidazol-1-yl)benzonitrile (50 mg) and N-indan-1-yl-acrylamide (43 mg) obtained above, palladium acetate (2.2 mg), ortho-tritolylphosphine (6 mg) and TEA (0.5 mL) were added, and the reaction solution was agitated at 70° C. under nitrogen atmosphere overnight. The reaction mixture was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (Carrier: Chromatorex®NH, elution solvent:hexane-ethyl acetate system), and 31 mg of the title compound was obtained.

$^1$H-NMR ($CDCl_3$) δ (ppm): 1.86-1.95 (m, 1H), 2.32 (s, 3H), 2.64-2.72 (m, 1H), 2.89-3.08 (m, 2H), 5.64 (q, J=7.6 Hz, 1H), 5.96 (d, J=8.4 Hz, 1H), 6.44 (d, J=16 Hz, 1H), 7.10 (t, J=1.2 Hz, 1H), 7.22-7.30 (m, 3H), 7.34 (d, J=7.6 Hz, 1H), 7.43 (d, J=8.4 Hz, 1H), 7.69 (d, J=16 Hz, 1H), 7.78-7.80 (m, 2H), 7.90 (d, J=2 Hz, 1H).

Example 10

Synthesis of (E)-N-biphenyl-3-ylmethyl-3-[3-cyano-4-(4-methyl-1H-imidazol-1-yl)phenyl]acrylamide

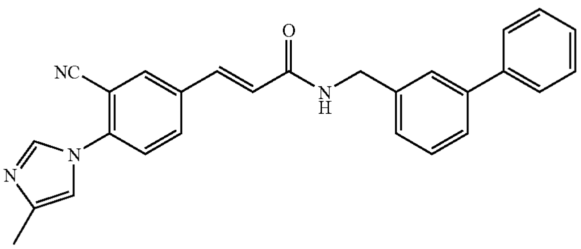

Synthesis of (E)-3-[3-cyano-4-(4-methyl-1H-imidazol-1-yl)phenyl]acrylic acid

To a DMF (10 mL) solution of 5-bromo-2-(4-methyl-1H-imidazol-1-yl)benzonitrile (700 mg) and acrylic acid ethyl ester (362 mg), palladium acetate (31 mg), tri-ortho-tolylphosphine (85 mg) and TEA (2 mL) were added, and the reaction solution was agitated at 80° C. under nitrogen-atmosphere overnight. The reaction mixture was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (elution solvent:hexane-ethyl acetate system), fractions of the object substance were combined, and concentrated under reduced pressure. The obtained substance was dissolved by SN sodium hydroxide solution (5 mL) and ethanol (30 mL), and the reaction mixture was agitated at 60° C. for 3 hours. The reaction mixture was concentrated under reduced pressure, water was added to the residue, and was made neutral with 5N hydrochloric acid. Insoluble matter consequently deposited was separated by filtering, washed with ether, and 498 mg of the title compound was obtained.

ESI-MS; m/z254 [$M^+$+H].

Synthesis of (E)-N-biphenyl-3-ylmethyl-3-[3-cyano-4-(4-methyl-1H-imidazol-1-yl)phenyl]acrylamide To a DMF (0.2 mL) solution of (E)-3-[3-cyano-4-(4-methyl-1H-imidazol-1-yl)phenyl]acrylic acid (15 mg) and 3-phenylbenzylamine monohydrochloride (16 mg), TEA (0.007 mL), HOBT (10 mg) and EDC (14 mg) were added one by one, and the reaction mixture was agitated at room temperature overnight. The reaction mixture was concentrated under reduced pressure, the residue was purified by silica gel column chromatography (Carrier: Chromatorex®NH, elution solvent:hexane-ethyl acetate system), and 5 mg of the title compound was obtained.

$^1$H-NMR ($CDCl_3$) δ (ppm): 2.32 (s, 3H), 4.67 (d, J=6 Hz, 2H), 6.04-6.08 (m, 1H), 6.49 (d, J=15.6 Hz, 1H), 7.09 (s, 1H), 7.32-7.60 (m, 10H), 7.68 (d, J=15.6 Hz, 1H), 7.76-7.79 (m, 2H), 7.89 (d, J=2 Hz, 1H).

Example 11

Synthesis of (E)-3-[3-chloro-4-(1H-imidazol-1-yl-phenyl]-N-indan-1-yl-acrylamide

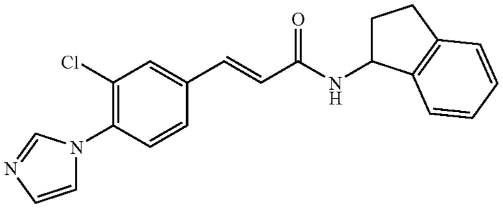

Synthesis of 3-chloro-4-(1H-imidazol-1-yl)benzaldehyde

To a DMF (20 mL) solution of 3-chloro-4-fluorobenzaldehyde (500 mg), potassium carbonate (1.20 g) and imidazole (275 mg) were added one by one, and the reaction solution was agitated at 80° C. overnight. Water and ethyl acetate were added to the reaction solution, and the organic layer was partitioned. After the obtained organic layer was washed with a saturated saline solution, it was dried over anhydrous magnesium sulfate and concentrated under reduced pressure. The obtained residue was purified by silica gel chromatography (elution solvent:ethyl acetate→ethyl acetate:methanol=10:1), and 548 mg of the title compound was obtained. The physical properties of the compound are as follows.

$^1$H-NMR ($CDCl_3$) δ (ppm): 10.0 (s, 1H), 8.09 (d, J=2.0 Hz, 1H), 7.91 (dd, J=2.0, 8.0 Hz, 1H), 7.80 (s, 1H), 7.54 (d, J=8.0 Hz, 1H), 7.24-7.27 (m, 2H).

Synthesis of (E)-3-[3-chloro-4-(1H-imidazol-1-yl-phenyl]acrylic acid

To a THF (13 mL) solution of 3-chloro-4-(1H-imidazol-1-yl)benzaldehyde (545 mg) dimethylphosphonoacetic acid methyl ester (513 µL) and lithium hydroxide monohydrate (133 mg) were added one by one, and the reaction solution was agitated overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure to obtain 442 mg of crude ester product. 2N sodium hydroxide solution (5.0 mL) was added to the reaction solution obtained by which dissolving the obtained ester product in THF (5.0 mL), and the reaction solution was agitated at room temperature overnight. The reaction solution was cooled to 0° C., 2N hydrochloric acid was added to the reaction solution, and the deposited precipitation was separated by filtering with Kiriyama funnel. The obtained precipitation was washed with water and ethyl acetate, and 218 mg of the title compound was obtained. The physical properties of the compound are as follows.

$^1$H-NMR (DMSO-d6) δ (ppm): 8.08 (d, J=2.0 Hz, 1H), 7.93 (s, 1H), 7.82 (dd, J=2.0, 8.4 Hz, 1H), 7.61 (d, J=16 Hz, 1H), 7.56 (d, J=8.4 Hz, 1H), 7.48 (s, 1H), 7.11 (s, 1H), 6.70 (d, J=16 Hz, 1H).

Synthesis of (E)-3-[3-chloro-4-(1H-imidazol-1-yl) phenyl]-N-indan-1-yl-acrylamide 17.0 mg of the title compound was obtained from (E)-3-[3-chloro-4-(1H-imidazol-1-yl)phenyl]acrylic acid (20.0 mg) and 1-aminoindan (15.0 µL) by the same method as in Example 324. The physical properties of the compound are as follows.

ESI-MS; m/z364[$M^+$+H].

Example 12

Synthesis of (E)-3-[4(1H-imidazol-1-yl)phenyl]-N-indan-1-yl-acrylamide

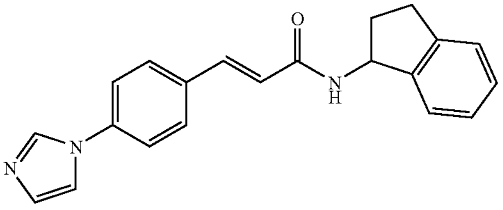

Synthesis of (E)-3-[4(1H-imidazol-1-yl)phenyl]acrylic acid

To a THF (3.0 mL) solution of 4-imidazol-1-yl-benzaldehyde (100 mg), dimethylphosphonoacetic acid methyl ester (103 µL) and lithium hydroxide monohydrate (27.0 mg) were added to one by one, and the reaction solution was agitated overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure to obtain 143 mg of crude ester product. 2N sodium hydroxide solution (2.0 mL) was added to a THF (2.0 mL) solution of the obtained ester product, and the reaction solution was agitated at room temperature overnight. The reaction solution was cooled to 0° C., and 2N hydrochloric acid was added to the reaction solution, and the deposited precipitation was separated by filtering with Kiriyama funnel. The obtained precipitation was washed with water and ethyl acetate, and 98.0 mg of the title compound was obtained. The physical properties of the compound are as follows.

$^1$H-NMR (DMSO-d6) δ (ppm): 8.35 (s, 1H), 7.83 (d, J=8.4 Hz, 2H), 7.82 (s, 1H), 7.71 (d, J=8.4 Hz, 2H), 7.60 (d, J=16 Hz, 1H), 7.11 (s, 1H), 6.58 (d, J=16 Hz, 1H).

Synthesis of (E)-3-[4-(1H-imidazol-1-yl)phenyl]-N-indan-1-yl-acrylamide 11.0 mg of the title compound was obtained from (E)-3-[4-(1H-imidazol-1-yl)phenyl]acrylic acid (20.0 mg) and 1-aminoindan (17.0 μL) by the same method as in Example 324. The physical properties of the compound are as follows.

1H-NMR ($CDCl_3$) δ (ppm): 7.91 (s, 1H), 7.70 (d, J=16 Hz, 1H), 7.62 (d, J=8.4 Hz, 2H), 7.40 (d, J=8.4 Hz, 2H), 7.22-7.37 (m, 5H), 7.20 (s, 1H), 6.43 (d, J=16 Hz, 1H), 5.88 (d, J=7.2 Hz, 1H), 5.64 (q, J=7.2 Hz, 1H), 3.03 (ddd, J=4.4, 8.8, 16 Hz, 1H), 2.92 (td, J=8.0, 16 Hz, 1H), 2.64-2.72 (m, 1H), 1.86-1.95 (m, 1H)

Example 12-1

Synthesis of (E)-N-(9H-fluoren-9-yl)-3-[4-(1H-imidazol-1-yl)phenyl]acrylamide

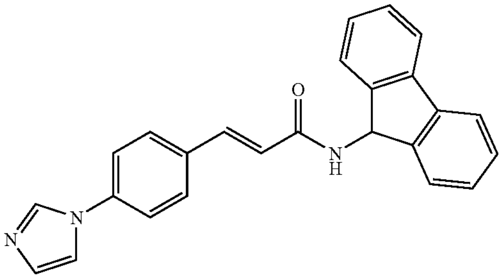

By the same method as in Example 12, 3.6 mg of the title compound was obtained from (E)-3-[4-(1H-imidazol-1-yl-phenyl)acrylic acid (13 mg) and 9-aminofluorene hydrochloride (20 mg). The physical properties of the compound are as follows.

ESI-MS; m/z 378 $[M^{+}+H]$

Example 13

Synthesis of (E)-3-[4-(1H-imidazol-1-yl)-3-trifluoromethylphenyl]-N-indan-1-yl-acrylamide

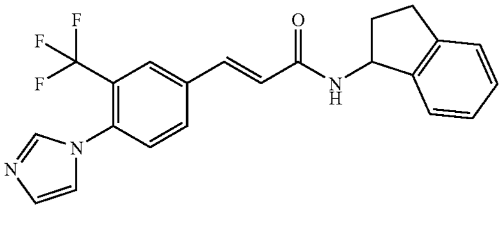

To a DMF (2.0 mL) solution of 4-fluoro-3-trifluoromethylbenzaldehyde (400 mg), potassium carbonate (414 mg) and imidazole (136 mg) were added one by one, and the reaction solution was agitated at 80° C. for 6 hours. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate 3:1→ethyl acetate) and 13.7 mg of 4-(1H-imidazol-1-yl)-3-trifluoromethylbenzaldehyde was obtained. Next, malonic acid (11.0 mg) and piperidine (53.0 mg) were added to an ethanol (1.0 mL) solution of the obtained aldehyde compound (13.0 mg), and the reaction solution was refluxed for 5 hours. Pyridine (2.0 mL) and malonic acid (11.0 mg) were added to the reaction solution, and the reaction solution was refluxed for one and a half hour. Water and ethyl acetate were added to the reaction solution, and the organic layer was partitioned. After the obtained organic layer was washed with a saturated saline solution, it was dried over anhydrous magnesium sulfate and 15.0 mg of crude carboxylic acid was obtained by condensing under reduced pressure. By the same method as in Example 324, 10.7 mg of the title compound was obtained from the obtained carboxylic acid and 1-aminoindan. The physical properties of the compound are as follows.

$^1$H-NMR ($CDCl_3$) δ (ppm): 7.94 (dd, J=2.0, 8.4 Hz, 1H), 7.76 (d, J=16 Hz, 1H), 7.75-7.78 (m, 1H), 7.64 (s, 1H), 7.41 (d, J=8.4 Hz, 1H), 7.34 (d, J=7.2 Hz, 1H), 7.26-7.31 (m, 3H), 7.21 (s, 1H), 7.13 (s, 1H), 6.53 (d, J=16 Hz, 1H), 5.97 (brs, 1H), 5.65 (q, J=7.6 Hz, 1H), 3.04 (ddd, J=4.4, 8.8, 16 Hz, 1H), 2.95 (td, J=8.0, 16 Hz, 1H), 2.69 (dtd, 4.4, 8.0, 13 Hz, 1H), 1.87-1.96 (m, 1H)

Example 14

Synthesis of (E)-N-biphenyl-3-ylmethyl-3-[3-hydroxy-4-(4-methyl-1H-imidazol-1-yl)phenyl]acrylic acid amide

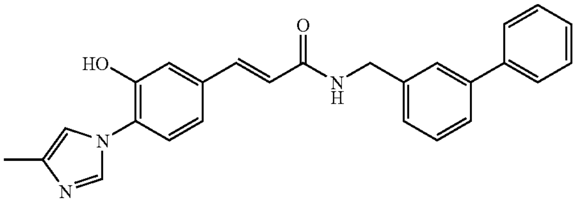

To a methylene chloride solution (3 mL) of (E)-N-biphenyl-3-ylmethyl-3-(3-methoxy-4-(4-methyl-1H-imidazol-1-yl)phenyl)acrylic acid amide (100 mg) obtained in Example 121, boron tribromide (1M pentane solution, 1.18 mL) was added dropwise at −78° C. and the reaction solution was agitated at room temperature for 6 hours. The reaction solution was diluted with a saturated sodium bicarbonate solution and ethyl acetate, and the organic layer was partitioned. The organic layer was concentrated under reduced pressure after dried over anhydrous magnesium sulfate. The residue was purified by silica gel column chromatography (elution solvent:chloroform-methanol system), and 16.5 mg of the title compound was obtained.

ESI-MS; m/z410 $[M^{+}+H]$. $^1$H-NMR (DMSO-$d_6$) δ(ppm): 2.15 (s, 3H), 4.49 (d, J=6.0 Hz, 1H), 6.63 (d, J=15.6 Hz, 1H), 7.11 (d, J=8.0 Hz, 1H), 7.19-7.20 (m, 2H), 7.30-7.66 (m, 11H), 7.86 (s, 1H), 8.72 (t, J=6.0 Hz, 1H), 10.43 (s, 1H).

Example 15

Synthesis of (E)-3-[4-(1H-imidazol-1-yl)-2-methoxyphenyl]-N-indan-1-yl-acrylamide

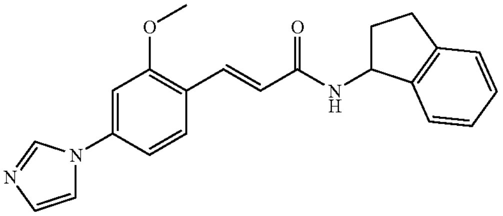

Synthesis of 4-(1H-imidazol-1-yl)-2-methoxybenzoic acid methyl ester

To an acetone (10 mL) solution of 4-fluoro-2-hydroxy benzoic acid methyl ester (1.0 g), potassium carbonate (1.2 g) and iodomethane (732 μL) were added one by one, and the reaction solution was concentrated under reduced pressure, after refluxing for 4 hours. Potassium carbonate (1.20 g) and imidazole (479 mg) were added to a DMF (10 mL) solution of the obtained residue (1.08 g) one by one, and the reaction solution was agitated at 80° C. overnight. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate=3:1→ethyl acetate:methanol=10:1), and 370 mg of the title compound was obtained. The physical properties of the compound are as follows.

$^1$H-NMR ($CDCl_3$) δ (ppm): 7.92-7.96 (m, 2H), 7.34 (s, 1H), 7.23 (s, 1H), 6.97-7.04 (m, 2H), 3.98 (s, 3H), 3.91 (s, 3H)

Synthesis of (E)-3-[4-(1H-imidazol-1-yl-2-methoxyphenyl]-N-indan-1-yl-acrylamide DIBAL-H (1.0M toluene solution, 3.27 mL) was added to a methylene chloride (5.0 mL) solution of 4-(1H-imidazol-1-yl)-2-methoxybenzoic acid methyl ester (253 mg) at −78° C., and the reaction solution was agitated for 1 hour. Saturated Rochelle salt aqueous solution was added to the reaction solution, and the reaction solution was agitated at room temperature overnight. Ethyl acetate was added to the reaction solution and the organic layer was partitioned. After the obtained organic layer was washed with a saturated saline solution, it was dried over anhydrous magnesium sulfate and 216 mg of crude alcohol compound was obtained by condensing under reduced pressure.

To a methylene chloride (4.0 mL) solution of oxalyl chloride (277 μL), dimethylsulfoxide (451 μL) was added at −78° C. and the reaction solution was agitated for 15 minutes. Next, a methylene chloride (3.0 mL) solution of alcohol compound (216 mg) obtained at a precedent step was added to the above-mentioned reaction solution at −78° C., and was agitated for 25 more minutes. Then, TEA (1.0 mL) was added to the reaction solution, heated to 0° C., and agitated for 3 hours. Water and ethyl acetate were added to the reaction solution, and the organic layer was partitioned. After the obtained organic layer was washed with a saturated saline solution, it was dried over anhydrous magnesium sulfate and obtained 214 mg of crude aldehyde compounds by condensing under reduced pressure. To a THF (2.0 mL) solution of the obtained aldehyde (25.5 mg), sodium hydride (8.0 mg) and (indan-1-ylcarbamoylmethyl)phosphonic acid diethyl ester (63.0 mg) obtained in Example 1 were added at 0° C., and the reaction solution was agitated at room temperature for one hour and 40 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate=1:1→ethyl acetate→ethyl acetate:methanol=10:1), and 28.4 mg of the title compound was obtained. The physical properties of the compound are as follows.

$^1$H-NMR ($CDCl_3$) δ (ppm): 7.89 (d, J=16 Hz, 1H), 7.88 (s, 1H), 7.56 (d, J=8.4 Hz, 1H), 7.35 (d, J=6.4 Hz, 1H), 7.20-7.30 (m, 5H), 6.98 (dd, J=2.0, 8.4 Hz, 1H), 6.89 (d, J=2.0 Hz, 1H), 6.57 (d, J=16 Hz, 1H), 5.93 (brd, J=8.0 Hz, 1H), 5.65 (q, J=8.0 Hz, 1H), 3.94 (s, 3H), 3.02 (ddd, J=4.4, 8.8, 16 Hz, 1H), 2.87-2.96 (m, 1H), 2.67 (dtd, J=4.4, 8.0, 16 Hz, 1H), 1.85-1.95 (m, 1H)

Example 16

Synthesis of (E)-3-[3-fluoro-4-(1H-imidazol-1-yl)-5-methoxyphenyl]-N-indan-1-yl-acrylamide

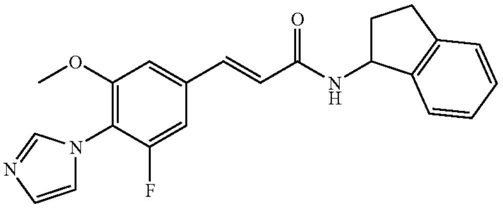

Synthesis of 1-(4-bromo-2-fluoro-6-methoxyphenyl)-1H-imidazole

To an acetone (10 mL) solution of 5-bromo-2,3-difluoro phenol (600 μL), potassium carbonate (1.10 g) and iodomethane (654 μL) were added one by one, and the reaction solution was refluxed for 4 hours. The reaction solution was concentrated under reduced pressure and the crude bromo compound was obtained. Potassium carbonate (1.10 g) and imidazole (429 mg) were added to a DMF (10 mL) solution of the obtained bromo compound (1.17 g) one by one, and the reaction solution was agitated at 80° C. overnight. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate=3:1→ethyl acetate:ethanol=10:1), and 510 mg of the title compound was obtained. The physical properties of the compound are as follows.

$^1$H-NMR ($CDCl_3$) δ (ppm): 7.82 (s, 1H), 7.24 (s, 1H), 7.21 (s, 1H), 7.05-7.08 (m, 2H), 3.98 (s, 3H).

Synthesis of (E)-3-[3-fluoro-4-(1H-imidazol-1-yl)-5-methoxyphenyl]-N-indan-1-yl-acrylamide By the same method as in Example 9, 3.80 mg of the title compound was obtained from 1-(4-bromo-2-fluoro-6-methoxyphenyl)-1H-imidazole (86.0 mg) and N-indan-1-yl-acrylamide (90.0 mg). The physical properties of the compound are as follows.

$^1$H-NMR ($CDCl_3$) δ (ppm): 7.84 (s, 1H), 7.64 (d, J=16 Hz, 1H), 7.34 (d, J=7.2 Hz, 1H), 7.23-7.29 (m, 5H), 7.11 (t, J=8.0 Hz, 1H), 6.40 (d, J=16.0 Hz, 1H), 5.95 (d, J=8.0 Hz, 1H), 5.64 (q, J=8.0 Hz, 1H), 3.98 (s, 3H), 3.04 (ddd, J=4.4, 8.8, 16.0 Hz, 1H), 2.93 (td, J=8.0, 16.0 Hz, 1H), 2.64-2.72 (m, 1H), 1.86-1.95 (m, 1H)

Example 17

Synthesis of (E)-3-[3-(1H-imidazol-1-yl)-4-methoxyphenyl]-N-indan-1-yl-acrylamide

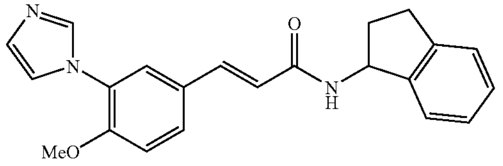

Synthesis of 3-(1H-imidazol-1-yl-4-methoxybenzaldehyde

To an aqueous solution (15 mL) of imidazole (5.69 g), 3-bromo-4-methoxybenzaldehyde (3.00 g) and copper powder (86 mg) were added, and the reaction solution was agitated for three days at 100° C. under nitrogen atmosphere. A concentrated ammonia water and ethyl acetate were added to the reaction mixture, and the organic layer was partitioned. The organic layer was washed with a saturated saline solution, dried over anhydrous magnesium sulfate, and concentrated under reduced pressure. The residue was purified by silica gel column chromatography (elution solvent:ethyl acetate), and 321 mg of the title compound was obtained.

$^1$H-NMR ($CDCl_3$) δ (ppm): 3.98 (s, 3H), 7.11-7.28 (m, 3H), 7.84-7.93 (m, 3H), 9.94 (s, 1H)

Synthesis of (E)-3-[3-(1H-imidazol-1-yl)-4-methoxyphenyl]-N-indan-1-yl-acrylamide By the same method as in Example 1, 44 mg of the title compound was obtained from 3-imidazol-1-yl-4-methoxybenzaldehyde (33 mg)

$^1$H-NMR ($CDCl_3$) δ (ppm): 1.84-1.93 (m, 1H), 2.60-2.68 (m, 1H), 2.85-3.04 (m, 2H), 3.87 (s, 3H), 5.61 (q, J=7.6 Hz, 1H), 6.28 (d, J=8 Hz, 1H), 6.37 (d, J=15.6 Hz, 1H), 7.03 (d, J=8.8 Hz, 1H), 7.13-7.34 (m, 6H), 7.41 (d, J=2 Hz, 1H), 7.47 (dd, J=2.4 Hz, 8.8 Hz, 1H), 7.64 (d, J=15.6 Hz, 1H), 7.72 (s, 1H).

Example 18

Synthesis of (E)-3-[2-fluoro-5-methoxy-4-(4-methyl-1H-imidazol-1-yl)phenyl]-N-indan-1-yl-acrylamide

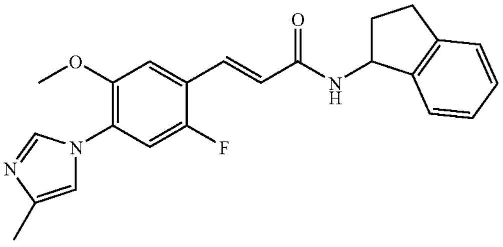

Synthesis of 4-bromo-5-fluoro-2-methoxyaniline

To a THF (20 mL) solution of 5-fluoro-2-methoxyaniline (1.76 g), a THF (30 mL) solution of pyridinium bromide perbromide (4.36 g) was added dropwise under ice-cooling, and the reaction solution was agitated for 30 minutes at room temperature. The solid which deposited from the reaction mixture was separated by filtering and the solid was washed by THF. After the obtained solid was dissolved with water and ethyl acetate, the aqueous layer was neutralized with a saturated sodium bicarbonate water, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane-ethyl acetate system), and 1.83 mg of the title compound was obtained.

$^1$H-NMR ($CDCl_3$) δ (ppm): 3.82 (s, 3H), 3.91 (brs, 2H), 6.50 (d, J=9.6 Hz, 1H), 6.84 (d, J=6.0 Hz, 1H).

Synthesis of 1-(4-bromo-5-fluoro-2-methoxyphenyl)-4-methyl-1H-imidazole

By the same method as in Example 23, 326 mg of the title compound was obtained from 4-bromo-5-fluoro-2-methoxyaniline (500 mg).

$^1$H-NMR ($CDCl_3$) δ (ppm): 2.29 (s, 3H), 3.85 (s, 3H), 6.89 (s, 1H), 7.09 (d, J=8.4 Hz, 1H), 7.19 (d, J=6.0 Hz, 1H), 7.70 (s, 1H).

Synthesis of (E)-3-[2-fluoro-5-methoxy-4-(4-methyl-1H-imidazol-1-yl)phenyl]-N-indan-1-yl-acrylamide By the same method as in Example 9, 31 mg of the title compound was obtained from 1-(4-bromo-5-fluoro-2-methoxyphenyl)-4-methyl-1H-imidazole (44 mg).

$^1$H-NMR ($CDCl_3$) δ (ppm): 1.86-1.95 (m, 1H), 2.29 (s, 3H), 2.63-2.72 (m, 1H), 2.88-3.07 (m, 2H), 3.86 (s, 3H), 5.65 (q, J=7.6 Hz, 1H), 5.97 (d, J=8.4 Hz, 1H), 6.57 (d, J=15.6 Hz, 1H), 6.93 (s, 1H), 7.05 (d, J=10.4 Hz, 1H), 7.08 (d, J=6.8 Hz, 1H), 7.21-7.27 (m, 3H), 7.34 (d, J=6.4 Hz, 1H), 7.71 (d, J=15.6 Hz, 1H), 7.76 (s, 1H).

Example 19

Synthesis of (E)-3-[2-fluoro-3-methoxy-4-(4-methyl-1H-imidazol-1-yl)phenyl]-N-indan-1-yl-acrylamide

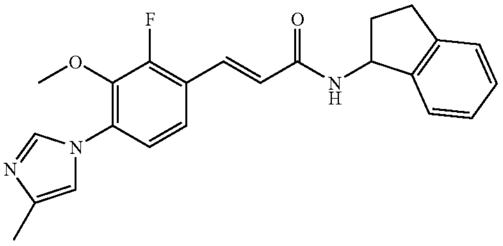

Synthesis of 2,4-difluoro-3-methoxybenzaldehyde

Lithium diisopropyl amide (1.5M cyclohexane solution, 5.6 mL) was added dropwise to a THF (10 mL) solution of 2,6-difluoroanisole (1.00 g) at −72° C. under nitrogen atmosphere, and the reaction solution was agitated for 30 minutes. DMF (2.7 mL) was added to the reaction mixture, the reaction solution was agitated for 30 minutes at −78° C., and then agitated at room temperature for 1 hour. Water and ethyl acetate were added to the reaction mixture, and the organic layer was partitioned. The organic layer was washed with a saturated saline solution, dried over anhydrous magnesium sulfate, and concentrated under reduced pressure. The residue was purified by silica gel column chromatography (elution solvent:hexane-ethyl acetate system) and 433 mg of the title compound was obtained.

$^1$H-NMR ($CDCl_3$) δ (ppm): 4.05 (s, 3H), 6.99-7.05 (m, 1H), 7.54-7.60 (m, 1H), 10.27 (s, 1H).

Synthesis of (E)-3-[2-fluoro-3-methoxy-4-(4-methyl-1H-imidazol-1-yl)phenyl]-N-indan-1-yl-acrylamide By the same method as in Example 1, 5 mg of the title compound was obtained from 2,4-difluoro-2-methoxybenzaldehyde (443 mg).

$^1$H-NMR ($CDCl_3$) δ (ppm): 1.86-1.95 (m, 1H), 2.30 (s, 3H), 2.64-2.73 (m, 1H), 2.89-3.07 (m, 2H), 3.81 (s, 3H), 5.65 (q, J=7.6 Hz, 1H), 5.88 (d, J=8.4 Hz, 1H), 6.54 (d, J=15.6 Hz, 1H), 6.98 (s, 1H), 7.08 (dd, J=2 Hz, 8.4 Hz, 1H), 7.21-7.27 (m, 4H), 7.35 (d, J=7.6 Hz, 1H), 7.76 (d, J=15.6 Hz, 1H), 7.78 (s, 1H).

Example 20

Synthesis of (E)-3-[4-(2-chloro-1H-imidazol-1-yl)-3-methoxyphenyl]-N-indan-1-ylacrylamide

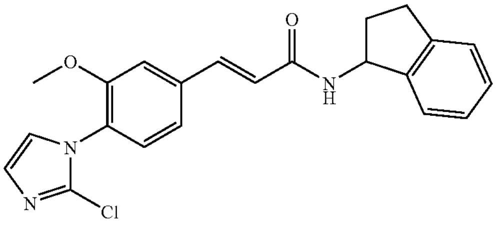

Synthesis of 4-(2-chloro-1H-imidazol-1-yl)-3-methoxybenzaldehyde and 4-(5-chloro-1H-imidazol-1-yl)-3-methoxybenzaldehyde To a chloroform (3 mL) solution of the 4-(1H-imidazol-1-yl)-3-methoxybenzaldehyde (50 mg) obtained in Example 111, N-chlorosuccinimide (35 mg) was added, and the reaction solution was heated to reflux for 1.5 hours. The reaction mixture was allowed to be cooled and then purified by silica gel column chromatography (elution solvent:hexane-ethyl acetate system), and 4-(2-chloro-1H-imidazol-1-yl)-3-methoxybenzaldehyde (13 mg) and 4-(5-chloro-1H-imidazol-1-yl)-3-methoxybenzaldehyde (14 mg) were obtained.

The physical properties of 4-(2-chloro-1H-imidazol-1-yl)-3-methoxybenzaldehyde are as follows.

$^1$H-NMR ($CDCl_3$) δ (ppm): 3.92 (s, 3H), 7.04 (d, J=1.4 Hz, 1H), 7.10 (d, J=1.4 Hz, 1H), 7.48 (d, J=8 Hz, 1H), 7.57-7.59 (m, 2H), 10.6 (s, 1H).

The physical properties of 4-(5-chloro-1H-imidazol-1-yl)-3-methoxybenzaldehyde are as follows.

$^1$H-NMR ($CDCl_3$) δ (ppm): 3.92 (s, 3H), 7.10 (s, 1H), 7.47 (d, J=8 Hz, 1H), 7.58-7.60 (m, 3H), 10.6 (s, 1H) Synthesis of (E)-3-[4-(2-chloro-1H-imidazol-1-yl)-3-methoxyphenyl]-N-indan-1-ylacrylamide By the same method as in Example 1, 18 mg of the title compound was obtained from 4-(2-chloro-1H-imidazol-1-yl)-3-methoxybenzaldehyde (13 mg).

$^1$H-NMR ($CDCl_3$) δ (ppm): 1.86-1.96 (m, 1H), 2.63-2.72 (m, 1H), 2.88-3.07 (m, 2H), 3.84 (s, 3H), 5.64 (q, J=7.6 Hz, 1H), 5.94 (d, J=8.4 Hz, 1H), 6.46 (d, J=15.4 Hz, 1H), 7.00 (d, J=1.0 Hz, 1H), 7.06 (d, J=1.0 Hz, 1H), 7.14-7.36 (m, 7H), 7.70 (d, J=15.4 Hz, 1H).

Example 21

Synthesis of (E)-3-[4-(5-chloro-1H-imidazol-1-yl)-3-methoxyphenyl]-N-indan-1-ylacrylamide

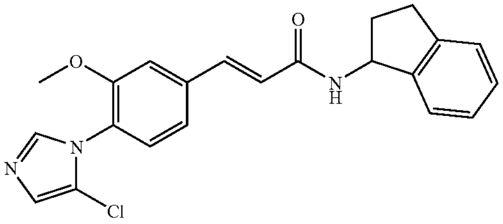

By the same method as in Example 1, 19 mg of the title compound was obtained from 4-(5-chloro-1H-imidazol-1-yl)-3-methoxybenzaldehyde (14 mg).

$^1$H-NMR ($CDCl_3$) δ (ppm): 1.86-1.96 (m, 1H), 2.63-2.72 (m, 1H), 2.86-3.07 (m, 2H), 3.84 (s, 3H), 5.65 (q, J=7.6 Hz, 1H), 6.01 (d, J=8.4 Hz, 1H), 6.47 (d, J=15.4 Hz, 1H), 7.05 (s, 1H), 7.15-7.36 (m, 7H), 7.53 (s, 1H), 7.70 (d, J=15.4 Hz, 1H).

Example 22

Synthesis of (E)-N-indan-1-yl-3-[5-methoxy-6-(4-methyl-1H-imidazol-1-yl)pyridine-3-yl]acrylamide

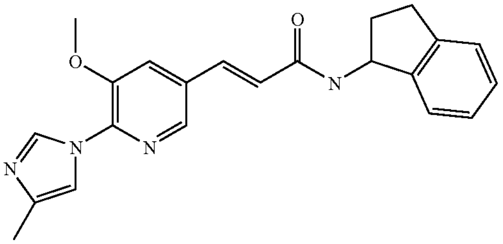

Synthesis of (E)-3-(5-methoxy-6-nitropyridin-3-yl) acrylic acid ethyl ester

To a DMF (20 mL) solution of 5-bromo-3-methoxy-2-nitropyridine (726 mg) synthesized according to the method described in Acta Chemica Scandinavica vol. 47, p. 805, 1993, ethyl acrylate (0.44 mL), palladium acetate (35 mg), 2-(di-tert-butylphosphino) biphenyl (93 mg) and TEA (0.87 mL) were added, and the reaction solution was agitated at 80° C. for 3 hours. After the reaction solution was allowed to be cooled to room temperature, ethyl acetate and a saturated ammonium chloride solution were added to the reaction solution to separate an organic layer. After the obtained organic layer was dried over anhydrous magnesium sulfate, solvent was evaporated under reduced pressure. The residue was purified by silica gel column chromatography (elution solvent:heptane-ethyl acetate 2:1), and 787 mg (69%) of (E)-3-(5-methoxy-6-nitropyridin-3-yl)acrylic acid ethyl ester was obtained. The physical properties of the compound are as follows.

$^1$H-NMR ($CDCl_3$) δ (ppm): 1.35 (t, J=7.6 Hz, 3H), 4.01 (s, 3H), 4.28 (q, J=7.6 Hz, 2H), 6.58 (d, J=16.4 Hz, 1H), 7.56 (d, J=1.6 Hz, 1H), 7.67 (d, J=16.4 Hz, 1H), 8.20 (d, J=1.6 Hz, 1H).

Synthesis of (E)-3-(6-amino-5-methoxypyridin-3-yl) acrylic acid ethyl ester

Iron (1.6 g) and ammonium chloride (3 g) were added to the suspension of (E)-3-(5-methoxy-6-nitropyridin-3-yl)acrylic acid ethyl ester (787 mg) in ethanol (40 mL) and water (8 mL) obtained above, and the reaction solution was heated to reflux for 1 hour. After the reaction solution was allowed to be cooled to room temperature, deposited substance was filtered by celite. Ethyl acetate and saturated sodium bicarbonate water were added to the filtrate, and the organic layer was partitioned. After drying the obtained organic layer with anhydrous magnesium sulfate, the solvent was evaporated under reduced pressure. The obtained residue was purified by silica gel column chromatography (elution solvent:heptane-ethyl acetate 2:1), and 506 mg (66%) (E)-3-(6-amino-5-methoxypyridin-3-yl)acrylic acid ethyl ester was obtained. The physical properties of the compound are as follows.

$^{1}$H-NMR ($CDCl_3$) δ (ppm): 1.33 (t, J=7.2 Hz, 3H), 3.88 (s, 3H), 4.25 (q, J=7.2 Hz, 2H), 5.02 (brs, 2H), 6.23 (d, J=16.0 Hz, 1H), 7.06 (d, J=1.6 Hz, 1H), 7.60 (d, J=16.0 Hz, 1H), 7.78 (d, J=1.6 Hz, 1H).

Synthesis of (E)-3-(6-chloro-5-methoxypyridin-3-yl) acrylic acid ethyl ester

Sodium nitrite (124 mg) was added to a concentrated hydrochloric acid (10 mL) solution of (E)-3-(6-chloro-5-methoxypyridin-3-yl)acrylic acid ethyl ester (200 mg) obtained above at 0° C. The reaction solution was agitated for 1 hour and 30 minutes at 0° C. and further for 1 hour and 30 minutes at room temperature. Then, the reaction solution was neutralized with 8N sodium hydroxide solution, and extracted with ethyl acetate. After drying the organic layer over anhydrous magnesium sulfate, the solvent was evaporated under reduced pressure. The obtained residue was purified by silica gel column chromatography (elution solvent: heptane-ethyl acetate 2:1), and 57 mg (26%) (E)-3-(6-chloro-5-methoxypyridin-3-yl)acrylic acid ethyl ester was obtained. The physical properties of the compound are as follows.

$^{1}$H-NMR ($CDCl_3$) δ (ppm): 1.35 (t, J=7.2 Hz, 3H), 3.96 (s, 3H), 4.28 (q, J=7.2 Hz, 2H), 6.48 (d, J=16.4 Hz, 1H), 7.29 (d, J=1.6 Hz, 1H), 7.64 (d, J=16.4 Hz, 1H), 8.11 (d, J=1.6 Hz, 1H)

Synthesis of (E)-3-[5-methoxy-6-(4-methyl-1H-imidazol-1-yl)pyridine-3-yl]acrylic acid ethyl ester 4-methylimidazole (39 mg) and potassium carbonate (65 mg) were added to a DMF (5 mL) solution of (E)-3-[5-methoxy-6-(4-methyl-1H-imidazol-1-yl)pyridin-3-yl] acrylic acid ethyl ester (57 mg) obtained above, and agitated at 120° C. for 32 hours. After the reaction solution was allowed to be cooled to room temperature, ethyl acetate was added to the reaction solution and the organic layer was washed with a saturated sodium bicarbonate water. After drying the organic layer over anhydrous magnesium sulfate, the solvent was evaporated under reduced pressure. The obtained residue was purified by silica gel column chromatography (elution solvent:ethyl acetate), and 12 mg (18%) (E)-3-[5-methoxy-6-(4-methyl-1H-imidazol-1-yl)pyridine-3-yl]acrylic acid ethyl ester was obtained. The physical properties of the compound are as follows.

$^{1}$H-NMR ($CDCl_3$) δ (ppm): 1.35 (t, J=7.2 Hz, 3H), 2.29 (s, 3H), 4.04 (s, 3H), 4.29 (q, J=7.2 Hz, 2H), 6.48 (d, J=15.6 Hz, 1H), 7.45 (d, J=1.6 Hz, 1H), 7.56 (s, 1H), 7.67 (d, J=15.6 Hz, 1H), 8.18 (d, J=1.6 Hz, 1H), 8.39 (s, 1H).

Synthesis of (E)-N-indan-1-yl-3-[5-methoxy-6-(4-methyl-1H-imidazol-1-yl)pyridine-3-yl]acrylamide 1N sodium hydroxide solution (0.2 mL) was added to a methanol (0.5 mL) solution of (E)-3-[5-methoxy-6-(4-methyl-1H-imidazol-1-yl)pyridine-3-yl]acrylic acid ethyl ester (12 mg) obtained above, and agitated at room temperature for 12 hours. After adding 1N hydrochloric acid water (0.2 mL) to the reaction solution for neutralizing the reaction solution, it was extracted with ethyl acetate, the organic layer was dried over anhydrous magnesium sulfate, and 11 mg (100%) of (E)-3-[5-methoxy-6-(4-methy-1H-limidazol-1-yl)pyridine-3-yl]acrylic acid was obtained for by evaporating the solvent under reduced pressure. 4 mg (23%) of the title compound was obtained for by condensing 1-aminoindane (7.5 mg) with an acrylic acid compound obtained by the same method as in Example 121. The physical properties of the compound are as follows.

$^{1}$H-NMR ($CDCl_3$) δ (ppm): 1.86-1.97 (m, 1H), 2.29 (s, 3H), 2.63-2.74 (m, 1H), 2.88-3.09 (m, 2H), 3.99 (s, 3H), 5.65 (q, J=7.6 Hz, 1H), 5.87 (brd, J=7.6 Hz, 1H), 6.46 (d, J=15.6 Hz, 1H), 7.20-7.35 (m, 4H), 7.42 (d, J=1.6 Hz, 1H), 7.56 (s, 1H), 7.68 (d, J=15.6 Hz, 1H), 8.20 (d, J=1.6 Hz, 1H), 8.39 (s, 1H).

Example 23

Synthesis of (E)-N-indan-1-yl-3-[6-methoxy-5-(4-methyl-1H-imidazol-1-yl)pyridin-2-yl]acrylamide

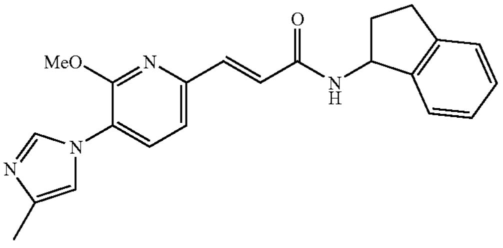

Synthesis of 6-chloro-2-methoxy-3-nitropyridine

Sodium methoxide (1.40 g) was gradually added to a THF (50 mL) solution of 2,6-dichloro-3-nitropyridine (5.00 g) over 30 minutes under ice-cooling. Then, the reaction solution was agitated at 0° C. for 1 hour, and agitated at room temperature for further 12 hours. The reaction solution was poured into a saturated ammonium chloride solution (50 mL), and extracted with ethyl acetate. After drying the organic layer over anhydrous magnesium sulfate, the solvent was evaporated under reduced pressure. The obtained residue was purified by silica gel column chromatography (elution solvent:heptane-ethyl acetate 2:1), and 2.90 g (58%) of 6-chloro-2-methoxy-3-nitropyridine was obtained. The physical properties of the compound are as follows.

$^{1}$H-NMR ($CDCl_3$) δ (ppm): 4.16 (s, 3H), 7.03 (d, J=8.8 Hz, 1H), 8.25 (d, J=8.8 Hz, 1H).

Synthesis of (E)-3-(6-methoxy-5-nitropyridin-2-yl) acrylic acid tert-butyl ester To a DMF (10 mL) solution of 6-chloro-2-methoxy-3-nitropyridine (440 mg) obtained above, acrylic acid tert-butyl ester (0.44 mL), palladium acetate (26 mg), 2-(di-tert-butylphosphino)biphenyl (70 mg) and TEA (0.65 mL) were added, and the reaction solution was agitated at 120° C. for 3 hours. After the reaction solution was allowed to be cooled to room temperature, ethyl acetate and a saturated ammonium chloride solution were added and the reaction solution was partitioned. After drying the organic layer over anhydrous magnesium sulfate, the solvent was evaporated under reduced pressure. The obtained residue was purified by silica gel column chromatography (elution solvent:heptane-ethyl acetate 2:1), and 491 mg (75%) (E)-3-(6-methoxy-5-nitropyridin-2-yl)acrylic acid tert-butyl ester was obtained. The physical properties of the compound are as follows.

$^{1}$H-NMR ($CDCl_3$) δ (ppm): 1.55 (s, 9H), 4.16 (s, 3H), 6.93 (d, J=15.6 Hz, 1H), 7.08 (d, J=8.8 Hz, 1H), 7.47 (d, J=15.6 Hz, 1H), 8.29 (d, J=8.8 Hz, 1H).

Synthesis of (E)-3-(5-amino-6-methoxypyridin-2-yl) acrylic acid tert-butyl ester Iron (780 mg) and ammonium chloride (1.5 g) were added to a suspension of (E)-3-(5-amino-6-methoxypyridin-2-yl) acrylic acid tert-butyl ester (491 mg) obtained above in ethanol (40 mL) and water (8 mL), and heating refluxing of the reaction solution was carried out for 7 hours. After the reaction solution was allowed to be cooled to room temperature, deposited substance was filtered by celite. Ethyl acetate and saturated sodium bicarbonate water were added to the filtrate and the organic layer was partitioned. After drying the organic layer over anhydrous magnesium sulfate, the solvent was evaporated under reduced pressure. The obtained residue was purified by silica gel column chromatography (elution solvent:heptane-ethyl acetate 2:1), and 340 mg (78%) (E)-3-(5-amino-6-methoxypyridin-2-yl)acrylic acid tert-butyl ester was obtained. The physical properties of the compound are as follows.

$^1$H-NMR ($CDCl_3$) δ (ppm): 1.56 (s, 9H), 4.01 (s, 3H), 4.03 (brs, 2H), 6.63 (d, J=15.6 Hz, 1H), 6.77 (d, J=8.8 Hz, 1H), 6.81 (d, J=8.8 Hz, 1H), 7.40 (d, J=15.6 Hz, 1H).

Synthesis of (E)-3-(5-formylamino-6-methoxypyridin-2-yl)acrylic acid tert-butyl ester A methylene chloride (3 mL) solution of (E)-3-(5-formylamino-6-methoxypyridin-2-yl)acrylic acid tert-butyl ester (136 mg) obtained above was added dropwise to a mixed solution of acetic anhydride (0.2 mL) and formic acid (0.4 mL) agitated at room temperature for 10 minutes. After agitating reaction solution at room temperature for 20 minutes, ethyl acetate and a saturated sodium bicarbonate water were added to the reaction solution and the organic layer was partitioned. After drying the organic layer over anhydrous magnesium sulfate, the solvent was evaporated under reduced pressure. The obtained residue was purified by silica gel column chromatography (elution solvent:heptane-ethyl acetate 1:1), and 151 mg (69%) (E)-3-(5-formylamino-6-methoxypyridin-2-yl)acrylic acid tert-butyl ester was obtained. The physical properties of the compound are as follows.

$^1$H-NMR ($CDCl_3$) δ (ppm): 1.54 (s, 9H), 4.06 (s, 3H), 6.76 (d, J=15.6 Hz, 1H), 6.99 (d, J=8.8 Hz, 1H), 7.45 (d, J=15.6 Hz, 1H), 7.79 (brs, 1H), 8.50 (s, 1H), 8.57 (d, J=8.8 Hz, 1H).

Synthesis of (E)-3-{5-[formyl(2-oxopropyl)amino]-6-methoxypyridin-2-yl}acrylic acid tert-butyl ester Cesium carbonate (490 mg), potassium iodide (13 mg) and chloroacetone (0.12 mL) were added to a DMF (2 mL) solution of (E)-3-{5-formyl(2-oxopropyl)amino]-6-methoxypyridin-2-yl}acrylic acid tert-butyl ester (104 mg) obtained above, and the reaction solution was agitated at room temperature for 10 hours. Then, ethyl acetate and saturated sodium bicarbonate water were added to the reaction solution and the organic layer was partitioned, and the solvent was evaporated under reduced pressure after the organic layer was dried over anhydrous magnesium sulfate. The obtained residue was purified by silica gel column chromatography (elution solvent:heptane-ethyl acetate=1:1), and 116 mg (93%) of (E)-3-{5-[formyl(2-oxopropyl)amino]-6-methoxypyridin-2-yl}acrylic acid tert-butyl ester was obtained. The physical properties of the compound are as follows.

$^1$H-NMR ($CDCl_3$) δ (ppm): 1.53 (s, 9H), 2.16 (s, 3H), 4.00 (s, 3H), 4.50 (s, 2H), 6.81 (d, J=15.6 Hz, 1H), 7.00 (d, J=8.8 Hz, 1H), 7.43 (d, J=15.6 Hz, 1H), 7.55 (d, J=8.8 Hz, 1H), 8.28 (s, 1H).

Synthesis of (E)-3-[6-methoxy-5-(4-methyl-1H-imidazol-1-yl)pyridin-2-yl]acrylic acid tert-butyl ester Ammonium acetate (130 mg) was added to an acetic acid (2 mL) solution of (E)-3-[6-methoxy-5-(4-methyl-1H-imidazol-1-yl)pyridin-2-yl]acrylic acid tert-butyl ester (116 mg) obtained above, and the reaction solution was agitated at 120° C. for 3 hours. Then, after the reaction solution was allowed to be cooled to room temperature, the reaction solution was diluted with ethyl acetate and the resultant mixture was neutralized with a saturated sodium bicarbonate water. After separating and drying the organic layer with anhydrous magnesium sulfate, the solvent was evaporated under reduced pressure. The obtained residue was purified by silica gel column chromatography (elution solvent:ethyl acetate), and 40 mg (37%) (E)-3-[6-methoxy-5-(4-methyl-1H-imidazol-1-yl)pyridin-2-yl]acrylic acid tert-butyl ester was obtained. The physical properties of the compound are as follows.

$^1$H-NMR ($CDCl_3$) δ (ppm): 1.55 (s, 9H), 2.30 (s, 3H), 4.06 (s, 3H), 6.86 (d, J=15.6 Hz, 1H), 6.99 (s, 1H), 7.05 (d, J=8.8 Hz, 1H), 7.48 (d, J=15.6 Hz, 1H), 7.52 (d, J=8.8 Hz, 1H), 7.82 (s, 1H).

Synthesis of (E)-N-indan-1-yl-3-[6-methoxy-5-(4-methyl-1H-imidazol-1-yl)pyridin-2-yl]acrylamide An ethyl acetate solution (3 mL) of 4N hydrochloric acid was added to (E)-N-indan-1-yl-3-[6-methoxy-5-(4-methyl-1H-imidazol-1-yl)pyridin-2-yl]acrylamide (20 mg) obtained above, and the reaction solution was agitated at room temperature for 3 hours. Then, the reaction solution was concentrated under reduced pressure. 20 mg (69%) of the title compound was obtained by condensing the obtained crude acrylic acid compound with 1-aminoindane (0.015 mL) by the same method as in Example 121. The physical properties of the compound are as follows.

$^1$H-NMR ($CDCl_3$) δ (ppm): 1.86-1.97 (m, 1H), 2.30 (s, 3H), 2.64-2.74 (m, 1H), 2.88-3.09 (m, 2H), 4.04 (s, 3H), 5.65 (q, J=7.6 Hz, 1H), 5.95 (brd, J=7.6 Hz, 1H), 6.95 (d, J=15.6 Hz, 1H), 6.98 (brs, 1H), 7.06 (d, J=8.8 Hz, 1H), 7.20-7.39 (m, 4H), 7.56 (d, J=8.8 Hz, 1H), 7.60 (d, J=15.6 Hz, 1H), 7.81 (brs, 1H).

Example 24

Synthesis of (E)-N-indan-1-yl-3-[4-methoxy-5-(4-methyl-1H-imidazol-1-yl)pyridin-2-yl]acrylamide

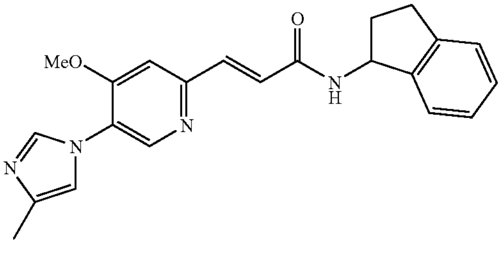

Synthesis of 5-bromo-4-methoxypyridine-2-carbaldehyde

Dess-Martin reagent (1.14 g) was added at 0° C. to a methylene chloride (5 mL) solution of (5-bromo-4-methoxypyridin-2-yl)methanol (450 mg) synthesized by the method described in organic Process Research & Development 2000 4,473. The reaction solution was agitated at 0° C. for 1 hour and further agitated at room temperature for 1 hour. 1N sodium hydroxide solution was added to the reaction solution, the organic layer was separated, and washed with a saturated sodium chloride solution. After the organic layer was dried over anhydrous magnesium sulfate, the solvent was evaporated under reduced pressure. The obtained residue was purified by silica gel column chromatography (elution solvent:heptane-ethyl acetate 1:1), and 300 mg (67%) 5-bromo-4-methoxypyridine-2-carbaldehyde was obtained. The physical properties of the compound are as follows.

$^1$H-NMR ($CDCl_3$) δ (ppm): 4.04 (s, 3H), 7.48 (s, 1H), 8.75 (s, 1H), 10.1 (s, 1H).

Synthesis of (E)-3-(5-bromo-4-methoxypyridin-2-yl) acrylic acid tert-butyl ester Diethylphosphonoacetic acid tert-butyl ester (0.26 mL) was added to a THF (4 mL) suspension of sodium hydride (45 mg), and the reaction solution was agitated at room temperature for 1 hour. Then, the reaction solution was cooled to 0° C., and a THF (1 mL) solution of 5-bromo-4-methoxypyridine-2-carbaldehyde (200 mg) obtained above was added dropwise to the reaction solution. The reaction solution was agitated for 1 h at 0° C. and further agitated for 12 h at room temperature. A saturated ammonium chloride solution was added to the reaction solution after the reaction ended, and the reaction solution was extracted with ethyl acetate to separate an organic layer. After drying the organic layer over anhydrous magnesium sulfate, the solvent was evaporated under reduced pressure. The obtained residue was purified by silica gel column chromatography (elution solvent:heptane-ethyl acetate 2:1), and 116 mg (40%) (E)-3-(5-bromo-4-methoxypyridin-2-yl)acrylic acid tert-butyl ester was obtained. The physical properties of the compound are as follows.

$^1$H-NMR ($CDCl_3$) δ (ppm): 1.53 (s, 9H), 3.98 (s, 3H), 6.82 (d, J=15.6 Hz, 1H), 6.92 (s, 1H), 7.49 (d, J=15.6 Hz, 1H), 8.56 (s, 1H).

Synthesis of (E)-3-(5-amino-4-methoxypyridin-2-yl) acrylic acid tert-butyl ester Benzophenone imine (0.04 mL), sodium tert-butoxide (26 mg) and DPPF (13 mg), and bis(1,5-cyclooctadiene) nickel (0) were added to a toluene (3 mL) solution of (E)-3-(5-bromo-4-methoxypyridin-2-yl)acrylic acid tert-butyl ester (70 mg) obtained above, and heating refluxing of the solution was carried out for 14 hours. After the reaction solution was allowed to be cooled to room temperature, the solvent was evaporated under reduced pressure. The obtained residue was purified by silica gel column chromatography (elution solvent:heptane-ethyl acetate 3:1), and 45 mg of (49%) imine compound was obtained. Hydroxylamine hydrochloride (15 mg) and sodium acetate (30 mg) were added to a methanol (3 mL) solution of the obtained imine compound, and the reaction solution was agitated at room temperature for 1 hour. A saturated sodium bicarbonate water and ethyl acetate were added to the reaction solution after the reaction ended, and the organic layer was separated. After drying the organic layer with anhydrous magnesium sulfate, the solvent was evaporated under reduced pressure. The obtained residue was purified by silica gel column chromatography (elution solvent: heptane-ethyl acetate=1:2), and 20 mg (73%) (E)-3-(5-amino-4-methoxypyridin-2-yl)acrylic acid tert-butyl ester was obtained. The physical properties of the compound are as follows.

$^1$H-NMR ($CDCl_3$) δ (ppm): 1.52 (s, 9H), 3.91 (s, 3H), 3.93 (brs, 2H), 6.54 (d, J=15.6 Hz, 1H), 6.88 (s, 1H), 7.49 (d, J=15.6 Hz, 1H), 8.00 (s, 1H).

Synthesis of (E)-3-[4-methoxy-5-(4-methyl-1H-imidazol-1-yl)pyridin-2-yl]acrylic acid tert-butyl ester By the same method as in Example 23, 15 mg (60%) of (E)-3-(4-methoxy-5-(4-methylimidazol-1-yl)pyridin-2-yl) acrylic acid tert-butyl ester was obtained from (E)-3-(5-amino-4-methoxypyridin-2-yl)acrylic acid tert-butyl ester (20 mg) obtained above. The physical properties of the compound are as follows.

$^1$H-NMR ($CDCl_3$) δ: 1.54 (s, 9H), 2.31 (s, 3H), 3.97 (s, 3H), 6.83 (d, J=15.6 Hz, 1H), 6.93 (s, 1H), 7.07 (s, 1H), 7.55 (d, J=15.6 Hz, 1H), 7.74 (s, 1H), 8.45 (s, 1H).

Synthesis of (E)-N-indan-1-yl-3-[4-methoxy-5-[4-methyl-1H-imidazol-1-yl)pyridin-2-yl]acrylamide By the same method as in Example 23, 4 mg (27%) (E)-N-indan-1-yl-3-[4-methoxy-5-(4-methylimidazol-1-yl)pyridin-2-yl)acrylamide was obtained from (E)-3-(4-methoxy-5-(4-methyl-1H-imidazol-1-yl)pyridin-2-yl)acrylic acid tert-butyl ester (15 mg) obtained above and 1-aminoindan. The physical properties of the compound are as follows.

$^1$H-NMR ($CDCl_3$) δ (ppm): 1.84-1.96 (m, 1H), 2.30 (s, 3H), 2.65-2.74 (m, 1H), 2.88-3.08 (m, 2H), 3.98 (s, 3H), 5.65 (q, J=7.6 Hz, 1H), 6.00 (brd, J=7.6 Hz, 1H), 6.93 (s, 1H), 7.01 (d, J-15.6 Hz, 1H), 7.05 (s, 1H), 7.21-7.37 (m, 4H), 7.66 (d, J=15.6 Hz, 1H), 7.72 (s, 1H), 8.43 (s, 1H).

Example 24-1

Synthesis of (E)-N-(9H-fluoren-9-yl)-3-(3-fluoro-4-(1H-imidazol-1-yl)phenyl]acrylamide

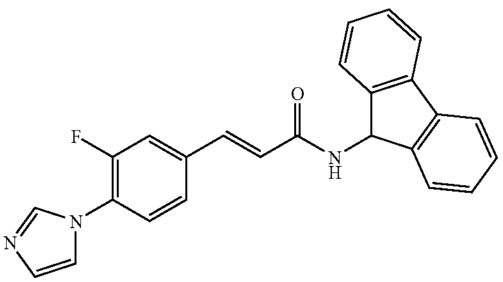

By the same method as in Example 12, 7.6 mg of the title compound was obtained from (E)-3-(3-fluoro-4-(1H-imidazol-1-yl)phenyl]acrylic acid (14 mg) and 9-aminofluorene hydrochloride (20 mg). The physical properties of the compound are as follows.

ESI-MS; m/z396 [$M^+$+H]

According to the Example 1, the combination of an imidazole derivative and a benzaldehyde derivative was changed, and the compounds shown in Table 2 were synthesized. The structural formulae and physicochemical properties are shown in Table 2, respectively.

TABLE 2

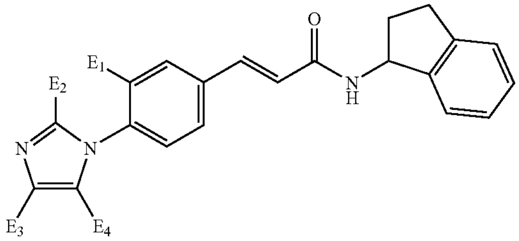

| Example | $E_1$ | $E_2$ | $E_3$ | $E_4$ | Data:MS m/z |
|---|---|---|---|---|---|
| 25 | Me | H | H | H | $M^+$ + H:344 (ESI) |
| 26 | F | Me | H | H | $M^+$ + H:362 (ESI) |
| 27 | F | H | Me | H | $M^+$ + H:362 (ESI) |
| 28 | F | H | 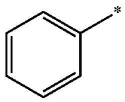 | H | $M^+$ + H:424 (ESI) |
| 29 | F | H | $NO_2$ | H | $M^+$ + H:393 (ESI) |
| 30 | F | H | $HOCH_2$— | H | $M^+$ + H:378 (ESI) |
| 31 | MeO | H | H | Me | $M^+$ + H:374 (ESI) |
| 32 | F | H | Br | H | $M^+$ + H:426 (ESI) |
| 33 | F | H | Me | H | $M^+$ + H:376 (ESI) |
| 34 | MeO | H | Br | H | $M^+$ + H:438 (ESI) |
| 35 | MeO | Me | H | H | $M^+$ + H:374 (ESI) |
| 36 | MeO | H | Et | H | $M^+$ + H:388 (ESI) |
| 37 | MeO | H | $CF_3$ | H | $M^+$ + H:428 (ESI) |
| 38 | MeO | H | NC— | H | $M^+$ + H:385 (ESI) |
| 39 | 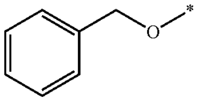 | H | H | H | $M^+$ + H:436 (ESI) |
| 40 | 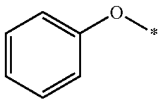 | H | H | H | $M^+$ + H:422 (ESI) |
| 41 | 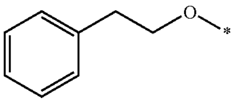 | H | H | H | $M^+$ + H:450 (ESI) |
| 42 | Br | H | H | H | $M^+$ + H:408 (ESI) |
| 43 | Cl | H | Me | H | $M^+$ + H:378 (ESI) |
| 44 | Br | H | Me | H | $M^+$ + H:422 (ESI) |
| 45 | MeO | H | $HOCH_2$— | H | $M^+$ + H:390 (ESI) |
| 46 | MeO | H | 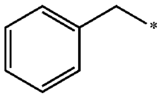 | H | $M^+$ + H:450 (ESI) |
| 47 | MeO | H | F | H | $M^+$ + H:378 (ESI) |

TABLE 2-continued
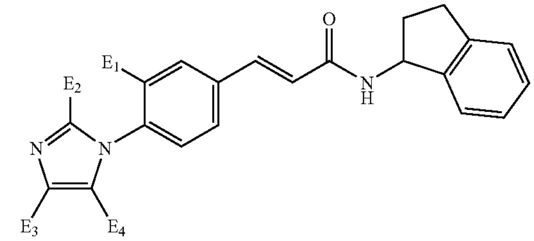
| Example | $E_1$ | $E_2$ | $E_3$ | $E_4$ | Data:MS m/z |
|---|---|---|---|---|---|
| 48 | MeO | H | 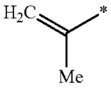 | H | $M^+$ + H:400 (ESI) |
| 49 | MeO | H | i-Pr | H | $M^+$ + H:402 (ESI) |
| 50 | MeO | H | 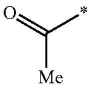 | H | $M^+$ + H:402 (ESI) |
| 51 | H | Me | Me | H | $M^+$ + H:358 (ESI) |
| 52 | H | H | Me | H | $M^+$ + H:344 (ESI) |
| 53 | MeO | H | Cl | H | $M^+$ + H:394 (ESI) |
| 54 | 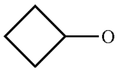 | H | H | H | $M^+$ + H:400 (ESI) |
| 55 | SMe | H | H | H | $M^+$ + H:376 (ESI) |
| 56 | $SO_2Me$ | H | H | H | $M^+$ + H:408 (ESI) |
| 57 | 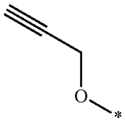 | H | Me | H | $M^+$ + H:398 (ESI) |
| 58 | 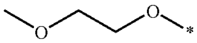 | H | Me | H | $M^+$ + H:418 (ESI) |
| 59 | 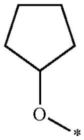 | H | Me | H | $M^+$ + H:428 (ESI) |
| 60 | 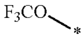 | H | Me | H | $M^+$ + H:428 (ESI) |
| 61 | 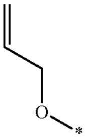 | H | Me | H | $M^+$ + H:400 (ESI) |
| 62 | 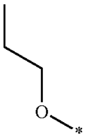 | H | Me | H | $M^+$ + H:402 (ESI) |

TABLE 2-continued

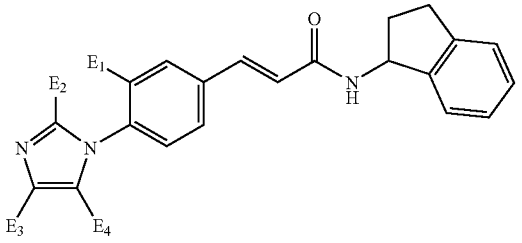

| Example | $E_1$ | $E_2$ | $E_3$ | $E_4$ | Data:MS m/z |
|---|---|---|---|---|---|
| 63 | MeO | H | 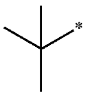 | H | M$^+$ + H:416 (ESI) |
| 64 | MeO | H | 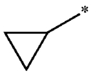 | H | M$^+$ + H:400 (ESI) |
| 65 | MeO | H | 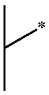 | H | M$^+$ + H:486 (ESI) |

The compound shown in Table 3 were synthesized as in Example 10. These structural formulae and physicochemical properties are shown in Table 3, respectively.

TABLE 3

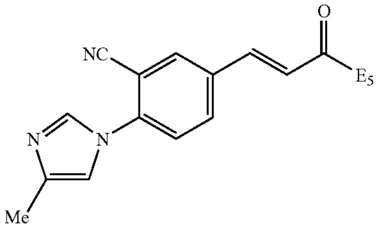

| Example | $E_5$ | DATA: MS m/z |
|---|---|---|
| 66 | 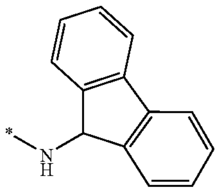 | M$^+$ + H:417 (ESI) |
| 67 | 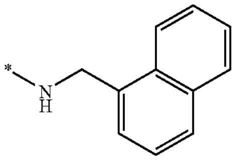 | M$^+$ + H:393 (ESI) |
| 68 | 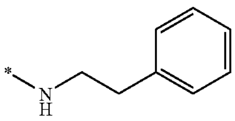 | M$^+$ + H:357 (ESI) |

TABLE 3-continued

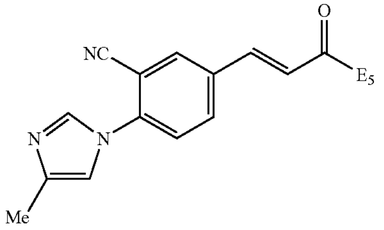

| Example | $E_5$ | DATA: MS m/z |
|---|---|---|
| 69 | 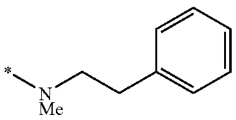 | M$^+$ + H:371 (ESI) |
| 70 | 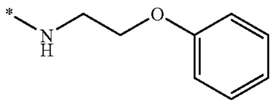 | M$^+$ + H:373 (ESI) |
| 71 | 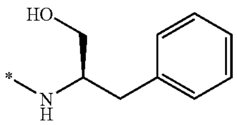 | M$^+$ + H:387 (ESI) |
| 72 | 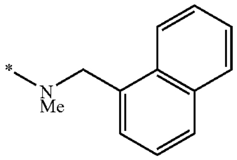 | M$^+$ + H:407 (ESI) |

TABLE 3-continued

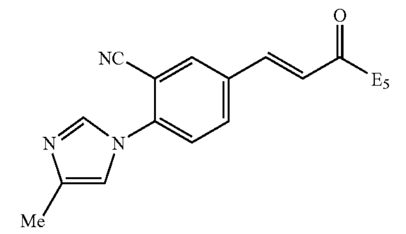

| Example | $E_5$ | DATA: MS m/z |
|---|---|---|
| 73 | 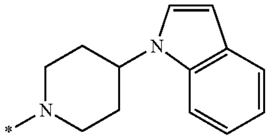 | $M^+$ + H:436 (ESI) |
| 74 | 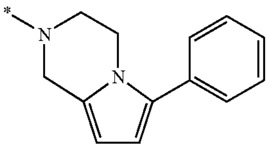 | $M^+$ + H:434 (ESI) |

Example 75

Synthesis of N-(9H-fluoren-9-yl)-3-(3-methoxy-4-(4-methyl-1H-imidazol-1-yl)phenyl)propiolic acid amide

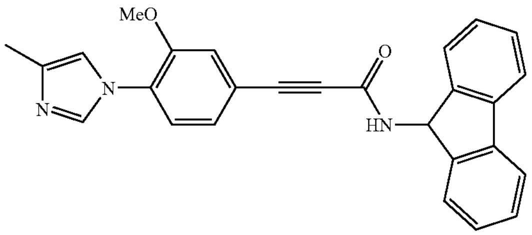

Synthesis of N-(4-bromo-2-methoxyphenyl)-2,2,2-trifluoroacetamide

Trifluoroacetic anhydride (24 mL) was added dropwise to a pyridine (48 mL) solution of 4-bromo-2-methoxyaniline (23.4 g) under ice-cooling. The reaction solution was stirred for an hour and iced water was added thereto. Crystals deposited were separated by filtering, and air-dried overnight. 32.4 g of the title compound was obtained.

$^1$H-NMR ($CDCl_3$) δ(ppm): 3.93 (s, 3H), 7.07 (d, J=2.4 Hz, 1H), 7.16 (dd, J=8.8, 2.4 Hz, 1H), 8.21 (d, J=8.8 Hz, 1H), 8.47 (brs, 1H).

Synthesis of 1-(4-bromo-2-methoxyphenyl)aminopropan-2-one

Chloroacetone (20 g) was added dropwise to a DMF (160 mL) suspension of N-(4-bromo-2-methoxyphenyl)-2,2,2-trifluoroacetamide (32.4 g), cesium carbonate (71 g) and potassium iodide (1.8 g), and the reaction solution was agitated at room temperature for 2 hours. Then, The reaction solution was stirred for 1 hour and iced water was added thereto. Crystals deposited were separated by filtering. The obtained crystal was suspended in methanol (360 mL) and 2N sodium hydroxide solution (55 mL), and the suspension was agitated for 30 minutes. An iced water was added thereto. Crystals deposited were separated by filtering, and air-dried overnight. 25.2 g of the title compound was obtained.

$^1$H-NMR ($CDCl_3$) δ(ppm): 2.25 (s, 3H), 3.85 (s, 3H), 3.97 (d, J=5.2 Hz, 2H), 5.05 (brs, 1H), 6.29 (d, J=8.4 Hz, 1H), 6.85 (d, J=2.0 Hz, 1H), 6.94 (dd, J=8.4, 2.0 Hz, 1H).

Synthesis of N-(4-bromo-2-methoxyphenyl)-N-(2-oxopropyl)acetamide

A mixture of acetic anhydride (40 g) and formic acid (90 g) was agitated under ice-cooling for 30 minutes. A methylene chloride (65 mL) solution of 1-(4-bromo-2-methoxyphenyl) propan-2-one(25.2 g) was added dropwise to the solution, and the reaction solution was agitated for 30 minutes. The reaction solution was extracted with ether after neutralized with a sodium hydroxide solution. The organic layer was washed with a saturated saline solution, dried over anhydrous magnesium sulfate, and concentrated under reduced pressure. The residue was filtered, washed with ether and air-dried, and 23.4 g of the title compound was obtained.

$^1$H-NMR ($CDCl_3$) δ(ppm): 2.17 (s, 3H), 3.84 (s, 3H), 4.43 (s, 2H), 7.09 (d, J=2.0 Hz, 1H), 7.13 (dd, J=8.0, 2.0 Hz, 1H), 7.19 (d, J=8.0 Hz, 1H), 8.23 (s, 1H).

Synthesis of 1-(4-bromo-2-methoxyphenyl)-4-methyl-1H-imidazole

A mixture of N-(4-bromo-2-methoxyphenyl)-N-(2-oxopropyl)acetamide (23.4 g), ammonium acetate-(31.5 g), and acetic acid (49 g) was agitated under heating at 120° C. for 30 minutes. After the reaction solution was neutralized with sodium hydroxide under ice-cooling, the reaction solution was extracted with ethyl acetate. The organic layer was washed with a saturated saline solution, dried over anhydrous magnesium sulfate, and concentrated under reduced pressure. The residue was purified by silica gel column chromatography (elution solvent:hexane-ethyl acetate system), and 19.4 g of the title compound was obtained.

$^1$H-NMR ($CDCl_3$) δ(ppm): 2.29 (s, 3H), 3.85 (s, 3H), 6.87 (s, 1H), 7.10-7.18 (m, 3H), 7.65 (s, 1H).

Synthesis of 1-(4-iodine-2-methoxyphenyl)-4-methyl-1H-imidazole

A 1,4-dioxane (50 mL) suspension of 1-(4-bromo-2-methoxyphenyl)-4-methyl-1H-imidazole (10.0 g) and copper iodide (I) (I) (7.13 g), sodium iodide (11.2 g) and N,N'-dimethyl ethylene diamine (6.59 g) was agitated at 110° C. for 9 hours. Ethyl acetate and a saturated ammonium chloride solution were added to the reaction solution after cooling reaction solution to room temperature, and the reaction solution was agitated for 30 minutes. After celite filtration, the organic layer of the filtrate was washed with a saturated saline solution, and the reaction solution was concentrated under reduced pressure after dried over anhydrous magnesium sulfate. The residue was purified by silica gel column chromatography (elution solvent:heptane-ethyl acetate system), and 4.07 g of the title compound was obtained.

$^1$H-NMR ($CDCl_3$) δ(ppm): 2.29 (s, 3H), 3.86 (s, 3H), 6.82 (s, 1H), 6.97 (d, J=8.0 Hz, 1H), 7.34 (d, J=2.0 Hz, 1H), 7.36 (dd, J=8.0, 2.0 Hz, 1H), 7.73 (s, 1H).

Synthesis of tert-butyl(3-methoxy-4-(4-methyl-1H-imidazol-1-yl)phenyl]propiolic acid ester A DMF (17 mL) suspension of 1-(4-iodine-2-methoxyphenyl)-4-methyl-1H-imidazole (2.67 g) and tert-butyl propiolate (2.14 g), dichlorobis(triphenylphosphine)palladium (II) (300 mg), potassium carbonate (2.35 g) and iodation copper (I) (162 mg) was agitated under heating at 100° C. for 20 minutes. Ethyl acetate and a saturated ammonium chloride solution were added to the reaction solution after cooling reaction solution to room temperature, and the reaction solution was agitated for 30 minutes. After washed with a saturated saline solution, reaction solution was dried over anhydrous magnesium sulfate and the separated organic layer was concentrated under reduced pressure. The residue was purified by silica gel column chromatography (heptane-ethyl acetate system), and 2.45 g of the title compound was obtained.

$^1$H-NMR ($CDCl_3$) δ(ppm): 1.56 (s, 9H), 2.29 (s, 3H), 3.87 (s, 3H), 6.93 (s, 1H), 7.21-7.24 (m, 3H), 7.78 (s, 1H).

Synthesis of [3-methoxy-4-(4-methyl-1H-imidazol-1-yl)phenyl]propiolic acid

Trifluoroacetic acid (6.0 mL) was added to a methylene chloride (30 mL) solution of tert-butyl (3-methoxy-4-(4-methyl-1H-imidazol-1-yl)phenyl)propiolic acid ester (2.45 g) under ice-cooling, and the reaction solution was agitated at room temperature overnight. The reaction solution was concentrated under reduced pressure and diluted with ethyl acetate. Crystals deposited were separated by filtering, and air-dried overnight. 1.45 g of the title compound was obtained.

$^1$H-NMR (DMSO-$d_6$) δ(ppm): 2.32 (s, 3H), 3.92 (s, 3H), 7.44 (dd, J=8.0, 1.6 Hz, 1H), 7.61 (d, J=1.6 Hz, 1H), 7.66 (d, J=8.0 Hz, 1H), 7.71 (s, 1H), 9.18 (s, 1H).

Synthesis of N-(9H-fluoren-9-yl)-3-[3-methoxy-4-(4-methyl-1H-imidazol-1-yl)phenyl]propiolic acid amide A DMF (2 mL) solution of [3-methoxy-4-(4-methyl-1H-imidazol-1-yl)phenyl]propiolic acid (74 mg) and 9-aminofluorene (65 mg) and BOP (133 mg) and N,N'-IPEA (77 μL) was agitated at room temperature overnight. Water and chloroform were added to the reaction solution, the organic layer was partitioned and concentrated under reduced pressure. The residue was purified by silica gel column chromatography (Carrier: Chromatorex NH, elution solvent:heptane-ethyl acetate system), and 45 mg of the title compound was obtained.

ESI-MS; m/z420 [$M^+$+H].

$^1$H-NMR (DMSO-$d_6$) δ(ppm): 2.14 (s, 3H), 3.86 (s, 3H), 6.11 (d, J=8.0 Hz, 1H), 7.18 (s, 1H), 7.26 (d, J=6.4 Hz, 1H), 7.34-7.47 (m, 6H), 7.55 (d, J=7.6 Hz, 2H), 7.84 (s, 1H), 7.88 (d, J=7.6 Hz, 2H), 9.47 (d, J=8.0 Hz, 1H).

ESI-MS; m/z420 [$M^+$+H].

The compounds shown in Table 4 were synthesized as in Example 75. The structural formulae and physicochemical properties are shown in Table 4, respectively.

TABLE 4

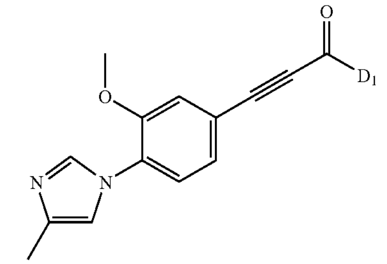

| Example | $D_1$ | DATA: MS m/z |
|---|---|---|
| 76 | 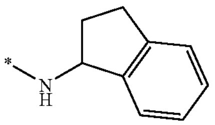 | $M^+$ + H:372 (ESI) |
| 77 | 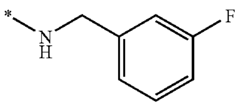 | $M^+$ + H:364 (ESI) |
| 78 | 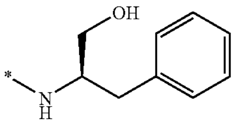 | $M^+$ + H:390 (ESI) |
| 79 | 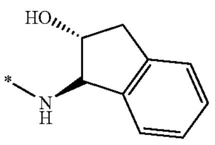 | $M^+$ + H:388 (ESI) |
| 79-1 | 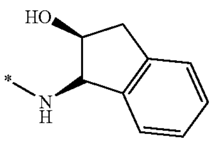 | $M^+$ + H:388 (ESI) |
| 80 | 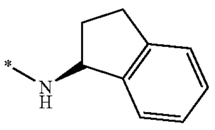 | $M^+$ + H:372 (ESI) |
| 81 | 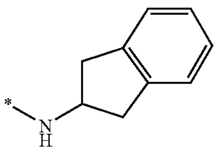 | $M^+$ + H:372 (ESI) |
| 82 | 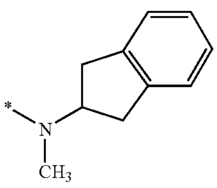 | $M^+$ + H:386 (ESI) |

TABLE 4-continued

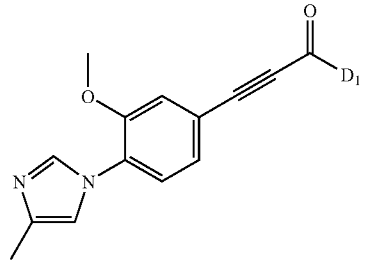

| Example | $D_1$ | DATA: MS m/z |
|---|---|---|
| 83 | 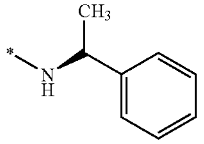 | $M^+ + H$:360 (ESI) |
| 84 | 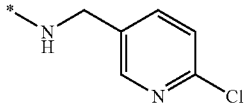 | $M^+ + H$:381 (ESI) |

Example 85

Synthesis of (E)-2-fluoro-N-[(1R)-hydroxymethyl-2-phenylethyl)-3-[3-methoxy-4-(4-methyl-1H-imidazol-1-yl)phenyl]acrylamide

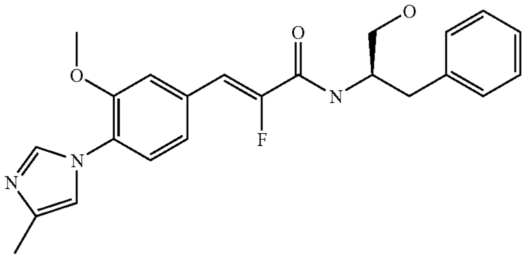

Synthesis of (E)-3-[3-methoxy-4-(4-methyl-1H-imidazol-1-yl)phenyl]acrylic acid ethyl ester To a THF (15 mL) solution of sodium hydride (814 mg) triethylphosphonoacetic acid (4.1 mL) was added at 0° C., and the reaction solution was agitated at 0° C. for 30 minutes and at room temperature for 1 hour. After cooling the reaction solution at 0° C., the THF (5 mL) solution of 3-methoxy-4-(4-methyl-1H-imidazol-1-yl)benzaldehyde (4.0 g) synthesized in Example 1 was added dropwise to the reaction solution. The reaction solution was further agitated at 0° C. for 30 minutes and then at room temperature for 2 hours. Ethyl acetate and water was added to the reaction solution, and the organic layer was separated and washed with a saturated ammonium chloride solution. After drying with anhydrous magnesium sulfate, the solvent was evaporated under reduced pressure. By re-crystallizing the obtained solid using a mixed solution of hexane and ethyl acetate, the 4.55 g (86%) title compound was obtained. The physical properties of the compound are as follows.

$^1$H-NMR ($CDCl_3$) δ(ppm): 1.71 (t, J=7.8 Hz, 3H), 2.60 (s, 3H), 3.79 (s, 3H), 4.58 (q, J=7.8 Hz, 2H), 6.45 (d, J=16.2 Hz, 1H), 6.95 (m, 1H), 7.17 (d, J=1.6 Hz, 1H), 7.19 (dd, J=8.4, 1.6 Hz, 1H), 7.28 (d, J=8.4 Hz 1H), 7.68 (d, J=16.2 Hz, 1H), 7.72 (d, J=1.2 Hz, 1H).

Synthesis of (E)-2-fluoro-3-[3-methoxy-4-(4-methyl-1H-imidazol-1-yl)phenyl]acrylic acid ethyl ester 2-fluoro malonic acid diethyl ester (670 μL) was added to a THF (8 mL) suspension of sodium hydride (170 mg) under ice-cooling, and the reaction solution was agitated under ice-cooling for 20 minutes and further agitated at room temperature for 1 hour. After dropping the THF (2 mL) solution of (E)-3-(3-methoxy-4-(4-methyl-1H-imidazol-1-yl)phenyl) acrylic acid ethyl ester (1 g) obtained above to the reaction solution over 10 minutes and the reaction solution was agitated at room temperature for 30 minutes, and heated to reflux for 8 hours. After the reaction solution was allowed to be cooled to room temperature, ethyl acetate and water was added and the organic layer was washed with a saturated ammonium chloride solution. After drying the organic layer over anhydrous magnesium sulfate, the solvent was evaporated under reduced pressure. The obtained residue was purified by silica gel column chromatography (Carrier: Chromatorex™ NH, elution solvent:from hexane to hexane:ethyl acetate=1:1), and 593 mg (56%) of (E)-2-fluoro-3-(3-methoxy-4-(4-methyl-1H-imidazol-1-yl)phenyl)acrylic acid ethyl ester was obtained. The physical properties of the compound are as follows.

ESI-MS; m/z305 [$M^+$+H]. $^1$H-NMR ($CDCl_3$) δ(ppm): 1.42 (t, J=7.8 Hz, 3H), 2.31 (s, 3H), 3.89 (s, 3H), 4.38 (q, J=7.8 Hz, 2H), 6.92 (d, J=36 Hz, 1H), 6.95 (m, 1H), 7.26 (d, J=8.4 Hz, 1H), 7.31 (dd, J=8.4, 1.6 Hz, 1H), 7.37 (brs, 1H), 7.76 (d, J=1.6 Hz, 1H).

Synthesis of (E)-2-fluoro-3-[3-methoxy-4-(4-methyl-1H-imidazol-1-yl)phenyl]acrylic acid 2N sodium hydroxide solution (2 mL) was added to a solution of (E)-2-fluoro-3-[3-methoxy-4-(4-methyl-1H-imidazol-1-yl)phenyl]acrylic acid diethyl ester (593 mg) in THF (1 mL) and ethanol (4 mL). The reaction solution was agitated at room temperature for 15 hours, neutralized with 2N hydrochloric acid (2 mL). The solid deposited from the reaction solution was separated by filtering and 512 mg (95%) of (E)-2-fluoro-3-[3-methoxy-4-(4-methyl-1H-imidazol-1-yl) phenyl]acrylic acid was obtained by washing the solid with ethanol. The physical properties of the compound are as follows.

$^1$H-NMR (DMSO-$d_6$) δ(ppm): 2.15 (s, 3H), 3.85 (s, 3H), 7.06 (d, J=36.0 Hz, 1H), 7.18 (m, 1H), 7.38 (dd, J=8.4, 1.6 Hz, 1H), 7.44 (dd, J=8.4, 1H), 7.51 (brs, 1H), 7.84. (d, J=1.6 Hz, 1H).

Synthesis of (E)-2-fluoro-N-[(1R)-hydroxymethyl-2-phenylethyl]-3-[3-methoxy-4-(4-methyl-1H-imidazol-1-yl)phenyl]acrylamide 71 mg (74%) of the title compound was obtained from (E)-2-fluoro-3-(3-methoxy-4-(4-methyl-1H-imidazol-1-yl) phenyl)acrylic acid (65 mg) and D-phenylalanilol (43 mg) which were obtained by the same method as in Example 121. The physical properties of the compound are as follows.

ESI-MS; m/z410 [$M^+$+H]. $^1$H-NMR ($CDCl_3$) δ: 2.30 (s, 3H), 2.98 (d, J=7.2 Hz, 2H), 3.69 (dd, J=6.8, 4.8 Hz, 1H), 3.77 (dd, J=6.8, 4.8 Hz, 1H), 3.87 (s, 3H), 4.30-4.39 (m, 1H), 6.64 (brd, 1H), 6.90 (d, J=36.0 Hz, 1H), 6.94 (brs, 1H), 7.38 (dd, J=8.4, 1.6 Hz, 1H), 7.25-7.38 (m, 8H), 7.74 (d, J=1.6 Hz, 1H).

Example 86

Synthesis of N-(9H-fluoren-9-yl)-2-fluoro-3-[3-methoxy-4-(4-methyl-1H-imidazol-1-yl)phenyl] acrylamide

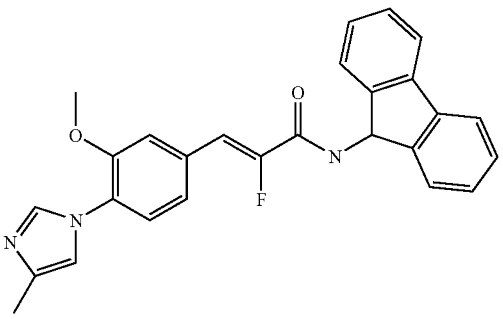

By the same method as in Example 86, 46 mg (36%) of the title compound was obtained from the 2-fluoro-3-(3-methoxy-4-(4-methyl-imidazol-1-yl)phenyl)acrylic acid (80 mg) obtained in the Example 85 and 9-aminofluorene hydrochloride (64 mg). The physical properties of the compound are as follows.

$^1$H-NMR (DMSO-$d_6$) δ(ppm): 2.15 (s, 3H), 3.85 (s, 3H), 6.17 (brd, 1H), 7.10 (d, J=38.0 Hz, 1H), 7.18 (brs, 1H), 7.28-7.55 (m, 9H), 7.83 (d, J=1.6 Hz, 1H), 7.88 (d, J=7.6, 2H), 9.30 (d, J=8.8 Hz, 1H).

Example 87

Synthesis of (E)-2-fluoro-N-(4-fluoro-3-morpholin-4-yl-benzyl)-3-[3-methoxy-4-(4-methyl-1H-imidazol-1-yl)phenyl]acrylamide

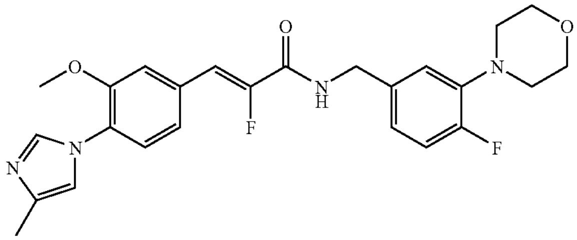

By the same method as in Example 85, 43.8 mg of the title compound was obtained from (E)-2-fluoro-3-(3-methoxy-4-(4-methyl-1H-imidazol-1-yl)phenyl)acrylic acid (40.0 mg) and 4-fluoro-3-morpholin-4-yl-benzylamine (32.0 mg). The physical properties of the compound are as follows.

$^1$H-NMR ($CDCl_3$) δ (ppm): 7.74 (d, J=1.6 Hz, 1H), 7.27-7.29 (m, 3H), 7.00-7.05 (m, 2H), 6.89-6.95 (m, 3H), 6.61-6.67 (br, 1H), 4.54 (d, J=6.0 Hz, 2H), 3.88 (s, 3H), 3.86-3.89 (m, 4H), 3.09-3.11 (m, 4H), 2.30 (s, 3H).

Example 88

Synthesis of (E)-2-fluoro-3-[3-methoxy-4-(4-methyl-1H-imidazol-1-yl)-phenyl]-N-methyl-N-(2-morpholin-4-yl-1-phenylethyl)acrylamide

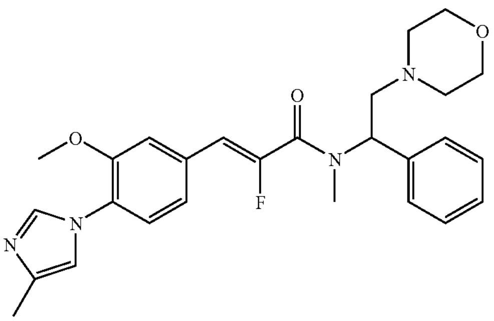

By the same method as in Example 85, 51.5 mg of the title compound was obtained from (E)-2-fluoro-3-[3-methoxy-4-(4-methyl-1H-imidazol-1-yl)phenyl]acrylic acid (45.0 mg) and methyl-(2-morpholin-4-yl-phenylethyl)amine (1M DMF solution, 245 μL). The physical properties of the compound are as follows.

$^1$H-NMR ($CDCl_3$) δ (ppm): 7.74 (s, 1H), 7.30-7.42 (m, 4H), 7.21-7.28 (m, 4H), 6.94 (s, 1H), 6.62 (d, J=38 Hz 1H), 3.88 (s, 3H), 3.64-3.74 (m, 4H), 2.94-3.20 (m, 1H), 2.80-2.90 (m, 4H), 2.62-2.74 (br, 2H), 2.43-2.50 (m, 3H), 2.30 (s, 3H)

Example 89

Synthesis of (E)-2-fluoro-N-[(1R,2S)-2-hydroxy-indan-1-yl]-3-[3-methoxy-4-(4-methyl-1H-imidazol-1-yl)phenyl]-N-methyl-acrylamide

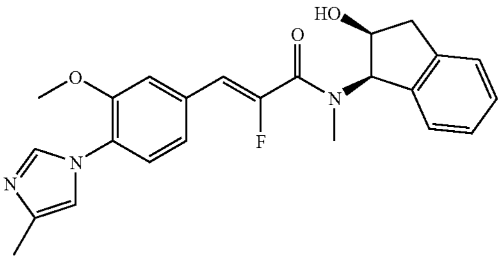

By the same method as in Example 85, 76.0 mg of the title compound was obtained from (E)-2-fluoro-3-[3-methoxy-4-(4-methyl-1H-imidazol-1-yl)phenyl]acrylic acid (60.0 mg) and (1R,2S)1-methylamino-indan-2-ol (42.5 mg). The physical properties of the compound are as follows.

$^1$H-NMR ($CDCl_3$) δ (ppm): 7.74 (s, 1H), 7.24-7.34 (m, 7H), 6.95 (s, 1H), 6.73 (d, J=37 Hz, 1H), 5.66-5.74 (m, 1H), 4.90-4.96 (m, 1H), 3.89 (s, 3H), 3.35 (dd, J=7.2, 17 Hz, 1H), 2.94-3.02 (m, 1H), 2.86-2.90 (m, 3H), 2.30 (s, 3H).

Example 90

Synthesis of (E)-2-fluoro-N-[(1R,2S)-2-hydroxy-indan-1-yl]-3-[3-methoxy-4-(4-methyl-1H-imidazol-1-yl)phenyl]acrylamide

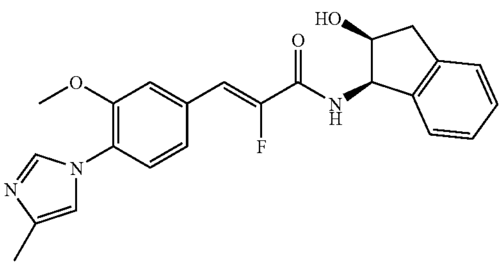

By the same method as in Example 85, (E)-2-fluoro-3-(3-methoxy-4-(4-methyl-1H-imidazol-1-yl)phenyl)acrylic acid (60.0 mg) and 76.0 mg of (1R,2S)1-amino-2-indanol (38.8 mg) title compounds were obtained. The physical properties of the compound are as follows.

$^1$H-NMR ($CDCl_3$) δ (ppm): 7.72 (s, 1H), 7.25-7.35 (m, 7H), 7.16 (d, J=8.4 Hz, 1H), 6.98 (d, J=38 Hz, 1H), 6.94 (s, 1H), 5.54 (dd, J=5.2, 8.4 Hz, 1H), 4.77 (dt, J=2.0, 5.2 Hz, 1H), 3.86 (s, 3H), 3.26 (dd, J=5.2, 16 Hz, 1H), 3.05 (dd, J=2.0, 16 Hz, 1H), 2.29 (s, 3H)

Example 91

Synthesis of (E)-3-(4-imidazol-yl-3-methoxyphenyl)-N-indan-yl-2-methyl-acrylamide

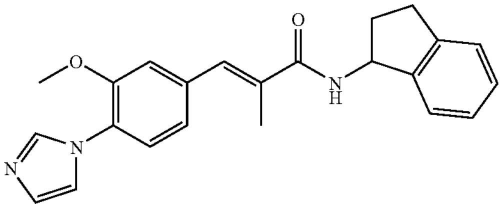

Triethyl-2-phosphonopropionic acid ester (116 μL) and sodium hydride (43.0 mg) were added at 0° C. one by one to a DMF (5.0 mL) solution of 4-(1H-imidazol-1-yl)-3-methoxybenzaldehyde (100 mg) obtained in the Example 111. The reaction solution was warmed to room temperature and agitated overnight. Then, water and ethyl acetate were added to the reaction solution, and the organic layer was partitioned. After the obtained organic layer was washed with a saturated saline solution, it was dried over anhydrous magnesium sulfate and 68.0 mg of crude carboxylic acid was obtained by condensing under reduced pressure. Next, 25.3 mg of the title compound was obtained from the obtained carboxylic acid (30.5 mg) and 1-aminoindan (24.0 μL) by the same method as in Example 324. The physical properties of the compound are as follows.

$^1$H-NMR ($CDCl_3$) δ (ppm): 7.82 (s, 1H), 7.41 (s, 1H), 7.37 (d, J=6.0 Hz, 1H), 7.247.30 (m, 4H), 7.23 (s, 1H), 7.18 (3, 1H), 7.02 (d, J=8.4 Hz, 1H), 7.01 (s, 1H), 6.14 (d, J=7.6 Hz, 1H), 5.64 (q, J=7.6 Hz, 1H), 3.86 (s, 3H), 3.05 (ddd, J=4.0, 8.8, 16 Hz, 1H), 2.94 (td, J=8.0, 16 Hz, 1H), 2.71 (dtd, J=4.0, 8.0, 12 Hz, 1H), 2.16 (s, 3H), 1.86-1.96 (m, 1H)

Example 92

Synthesis of (E)-2-cyano-3-[4-(1H-imidazol-1-yl)-3-methoxyphenyl)-N-indan-1-yl-acrylamide

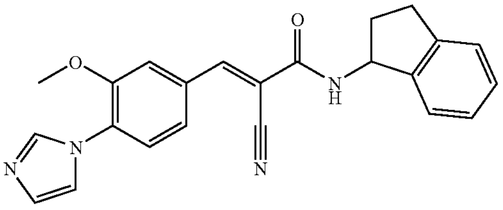

Cyano ethyl acetate (76.0 μL) and piperidine were added one by one to an ethanol solution (5.0 mL) of 4-(1H-imidazol-1-yl-3-methoxybenzaldehyde (144 mg) obtained in Example 111 (35.0 μL). The reaction solution was refluxed for 3.5 hours, water and ethyl acetate were added to the reaction solution, and the organic layer was partitioned. After the obtained organic layer was washed with a saturated saline solution, it was dried over anhydrous magnesium sulfate and concentrated under reduced pressure to obtain the crude ester product. 2N sodium hydroxide solution (1.0 mL) was added to a THF (2 mL) solution of the obtained ester product, and the reaction solution was agitated for 45 minutes at room temperature. Then, the reaction solution was warmed up to 50° C., it was agitated for further 9 hours. Crude carboxylic acid sodium salt was obtained by condensing the reaction solution as it was under reduced pressure. 1.0 mg of the title compound was obtained from the obtained carboxylic acid sodium salt and 1-aminoindan (41.0 μL) by the same method as in Example 324. The physical properties of the compound are as follows.

$^1$H-NMR ($CDCl_3$) δ (ppm): 8.11 (s, 1H), 7.68 (s, 1H), 7.24-7.38 (m, 9H), 6.41 (d, J=7.6 Hz, 1H), 5.73 (q, J=7.6 Hz, 1H), 3.96 (s, 3H), 3.08 (ddd, J=4.0, 8.8, 16 Hz, 1H), 2.88-3.00 (m, 1H), 2.75 (tdt, J=4.0, 8.0, 13 Hz, 1H), 1.93-2.02 (m, 1H).

Example 93

Synthesis of (E)-3-[3-fluoro-4-(1H-imidazol-1-yl)-phenyl]-2-butenone acid indan-1-ylamide

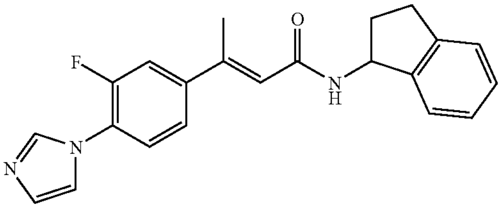

Synthesis of 1-[3-fluoro-4-(1H-imidazol-1-yl)-phenyl]ethanone

Imidazole (543 mg) and potassium carbonate (1.80 g) were added to a DMF (15 mL) solution of 3,4-difluoroacetophenone (1.0 mL). After agitating reaction solution at 80° C. for 4 hours, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane: ethyl acetate=5:1→ethyl acetate), and 1.40 g of the title compound was obtained. The physical properties of the compound are as follows.

$^1$H-NMR ($CDCl_3$) δ (ppm): 7.95 (s, 1H), 7.86-7.92 (m, 2H), 7.52-7.59 (m, 1H), 7.39 (s, 1H), 7.25 (s, 1H), 2.65 (s, 3H).

Synthesis of (E)-3-(3-fluoro-4-(1H-imidazol-1-yl)-phenyl]crotonic acid indan-1-ylamide Dimethylphosphonoacetic acid methyl ester (308 μL) and sodium hydride (44.0 mg) were added to a THF (5.0 mL) solution of 1-[3-fluoro-4-(1H-imidazol-1-yl)phenyl]ethanone (390 mg), and the reaction solution was refluxed for 2 hours. Sodium hydride (40.0 mg) was further added to the reaction solution, the reaction solution was refluxed for 5 hours. Water and ethyl acetate were added to the reaction solution, and the organic layer was partitioned. After the obtained organic layer was washed with a saturated saline solution, it was dried over anhydrous magnesium sulfate and concentrated under reduced pressure to yield 525 mg of crude ester product as an isomer mixture (E:Z=2.4:1). 2N sodium hydroxide solution (3.0 mL) was added to a THF (3.0 mL) solution of the obtained ester product (260 mg). The reaction solution was warmed to 50° C., and was agitated for 1 hour and 40 minutes. By condensing reaction solution under reduced pressure, 235 mg of crude carboxylic acid sodium salt was obtained as an isomer mixture. 22.0 mg of the title compound was obtained from the obtained carboxylic acid sodium salt and 1-aminoindan (234 μL) by the same method as in Example 324. The physical properties of the compound are as follows.

$^1$H-NMR ($CDCl_3$) δ (ppm): 7.80 (s, 1H), 7.31-7.38 (m, 4H), 7.20-7.28 (m, 5H), 6.30 (d, J=7.6 Hz, 1H), 6.12-6.13 (m, 1H), 5.58 (q, J=7.6 Hz, 1H), 3.01 (ddd, J=4.8, 8.8, 16 Hz, 1H), 2.93 (td, J=8.0, 16 Hz, 1H), 2.60-2.69 (m, 1H), 2.60 (s, 3H), 1.85-1.94 (m, 1H)

Example 94

Synthesis of (E)-N-[(1R,1S)-2-hydroxy-indan-1-yl]-3-[3-methoxy-4-(4-methyl-1H-imidazol-1-yl)phenyl]-2-methyl acrylamide trifluoroacetic acid salt

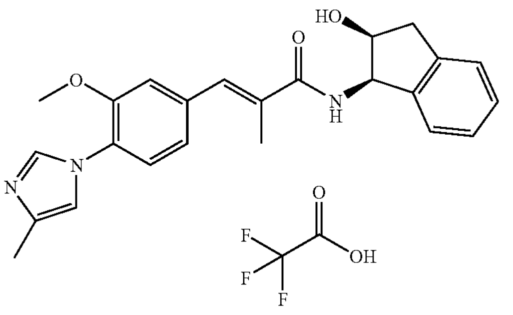

Synthesis of (E)-[3-methoxy-4-(4-methyl-1H-imidazol-1-yl)phenyl]-2-methyl-acrylic acid 250 mg of the title compound was obtained from 3-methoxy-4-(4-methyl-1H-imidazol-1-yl)benzaldehyde (200 mg) obtained in Example 1 and diethyl-2-phosphonopropionic acidethyl ester (238 μL) by the same method as in Example 111. The physical properties of the compound are as follows.

$^1$H-NMR (DMSO-d6) δ (ppm): 7.80 (d, J=1.2 Hz, 1H), 7.61 (d, J=1.2 Hz, 1H), 7.41 (d, J=7.4 Hz, 1H), 7.29 (d, J=1.6 Hz, 1H), 7.16 (dd, J=1.6 Hz, 7.4 Hz, 1H), 7.14-7.15 (m, 1H), 3.85 (s, 3H), 2.15 (s, 3H), 2.07 (s, 3H).

Synthesis of (E)-N-[(1R, 2S)-2-hydroxy-indan-1-yl]-3-[3-methoxy-4-(4-methyl-1H-imidazol-1-yl)-phenyl]-2-methylacrylamide trifluoroacetic-acid salt To a DMF (3 mL) solution of (E)-[3-methoxy-4-(4-methyl-1H-imidazol-1-yl)phenyl]-2-methylacrylic acid (60.0 mg), (1R,2S)-1-amino-2-indanol (39.4 mg), IPEA (0.05 mL), EDC (58 mg) and HOBT (41 mg) were added one by one, and the reaction solution was agitated at room temperature overnight. 55.5 mg of the title compound was obtained by purifying reaction solution by LC-MS as it was. The physical properties of the compound are as follows.

$^1$H-NMR ($CDCl_3$) δ (ppm): 8.66 (s, 1H), 7.48 (s, 1H), 7.24-7.39 (m, 5H), 7.02-7.15 (m, 3H), 6.68 (d, J=7.6 Hz, 1H), 5.53-5.57 (m, 1H), 4.76 (brs, 1H), 3.90 (s, 3H), 3.27 (dd, J=4.8, 16 Hz, 1H), 3.02 (d, J=16 Hz, 1H), 2.48 (s, 3H), 2.18 (s, 3H).

Example 95

Synthesis of (E)-N-[(1R,2S)-2-hydroxy-indan-1-yl]-3-[3-methoxy-4-(4-methyl-1H-imidazol-1-yl)benzylidene]butyl amide trifluoroacetic acid salt

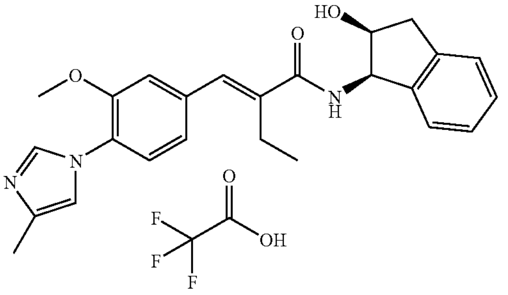

Synthesis of (E)-2-[3-methoxy-4-(4-methyl-1H-imidazol-1-yl)benzylidene]butyric acid 269 mg of the title compound was obtained from (348 mg) by the same method as in Example 111 from 3-methoxy-4-(4-methyl-1H-imidazol-1-yl)benzaldehyde (200 mg) and 2-(diethoxyphosphoryl)butyric acid ethyl ester obtained in Example 1. The physical properties of the compound are as follows.

$^1$H-NMR (DMSO-d6) δ (ppm): 7.81 (d, J=1.2 Hz, 1H), 7.59 (s, 1H), 7.43 (d, J=8.0 Hz, 1H), 7.25 (d, J=1.2 Hz, 1H), 7.16 (s, 1H), 7.11 (d, J=8.0 Hz, 1H), 3.86 (s, 3H), 2.16 (s, 3H), 1.11-1.19 (m, 5H)

Synthesis of (E)-N-[(1R,2S)-2-hydroxy-indan-1-yl]-3-[3-methoxy-4-(4-methyl-1H-imidazol-1-yl)benzylidene]butylamide trifluoroacetic acid salt 26.0 mg of the title compound was obtained by the same method as in Example 111 from (E)-2-(3-methoxy-4-(4-methyl-1H-imidazol-1-yl)benzylidene)butyl acid (20.0 mg) and (1R,2S)-1-amino-2-indanol (15.6 mg). The physical properties of the compound are as follows.

$^1$H-NMR ($CDCl_3$) δ (ppm): 8.69 (d, J=1.6 Hz, 1H), 7.28-7.36 (m, 6H), 7.04-7.06 (m, 3H), 6.68 (brd, J=7.6 Hz, 1H), 5.56 (dd, J=4.8, 7.6 Hz, 1H), 4.76 (dt, J=2.0, 4.8 Hz, 1H), 3.90 (s, 3H), 3.28 (dd, J=4.8, 16 Hz, 1H), 3.01 (dd, J=2.0, 16 Hz, 1H), 2.56-2.65 (m, 2H), 2.48 (s, 3H), 1.21 (t, J=7.6 Hz, 3H).

Example 96

Synthesis of (E)-2-benzyl-N-[(1R,2S)-2-hydroxy-indan-1-yl]-3-[3-methoxy-4-(4-methyl-1H-imidazol-1-yl)phenyl]acrylamide trifluoroacetic acid salt

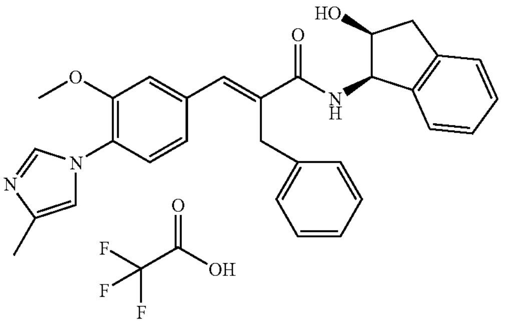

Synthesis of (E)-2-benzyl-3-[3-methoxy-4-(4-methyl-1H-imidazol-1-yl)phenyl]acrylic acid 315 mg of the title compound was obtained by the same method as in Example 111 from 3-methoxy-4-(4-methyl-1H-imidazol-1-yl)benzaldehyde (200 mg) and 2-(diethoxyphosphoryl)-3-phenylpropionic acid ethyl ester (434 mg) obtained in Example 1. The physical properties of the compound are as follows.

$^1$H-NMR (DMSO-d6) δ (ppm): 7.92 (s, 1H), 7.64 (s, 1H), 7.56 (d, J=7.6 Hz, 1H), 7.28-7.35 (m, 3H), 7.16-7.23 (m, 5H), 3.92 (s, 2H), 3.69 (s, 3H), 2.30 (s, 3H).

Synthesis of (E)-2-benzyl-N[(1R,2S)-2-hydroxy-indan-1-yl]-3-[3-methoxy-4-(4-methyl-1H-imidazol-1-yl)phenyl]acrylamide trifluoroacetic acid salt 19.3 mg of the title compound was obtained from (E)-2-benzyl-3-[3-methoxy-4-(4-methyl-1H-imidazol-1-yl)phenyl]acrylic acid (25.0 mg) and (1R,2S)1-amino-2-indanol (16.1 mg) by the same method as in Example 94. The physical properties of the compound are as follows.

$^1$H-NMR ($CDCl_3$) δ (ppm): 8.64 (s, 1H), 7.76 (s, 1H), 7.22-7.37 (m, 8H), 7.15 (td, J=3.6, 7.6 Hz, 1H), 7.10 (d, J=8.4 Hz, 1H), 7.02-7.06 (m, 2H), 6.93 (d, J=7.2 Hz, 1H), 6.49 (brd, J=8.0 Hz, 1H), 5.44 (dd, J=5.2, 8.0 Hz, 1H), 4.59 (dt, J=1.6, 5.2 Hz, 1H), 4.00 (d, J=17 Hz, 1H), 3.99 (d, J=17 Hz, 1H), 3.71 (s, 3H), 3.16 (dd, J=5.2, 16 Hz, 1H), 2.90 (dd, J=1.6, 16 Hz, 1H), 2.46 (s, 3H).

Example 97

Synthesis of (E)-2-cyclopropylmethyl-N-[(1R,2S)-2-hydroxy-indan-1-yl]-3-[3-methoxy-4-(4-methyl-1H-imidazol-1-yl)phenyl]acrylamide trifluoroacetic acid salt

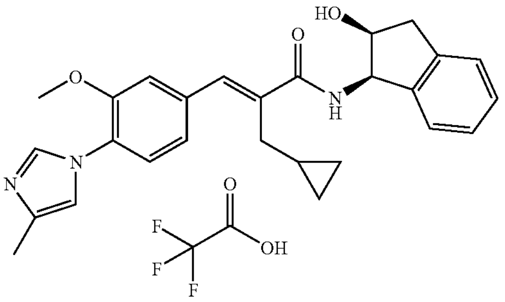

Synthesis of (E)-2-cyclopropylmethyl-3-[3-methoxy-4-(4-methyl-1H-imidazol-1-yl)phenyl]acrylic acid 102 mg of the title compound was by the same method as in Example 111 from 3-methoxy-4-(4-methylimidazol-1-yl)benzaldehyde (200 mg) obtained in Example 1 and 3-cyclopropyl-2-(diethoxyphosphoryl)propionic acid ethyl ester (384 mg). The physical properties of the compound are as follows.

$^1$H-NMR (DMSO-d6) δ (ppm): 7.82 (s, 1H), 7.61 (s, 1H), 7.43 (d, J=8.0 Hz, 1H), 7.31 (s, 1H), 7.17-7.18 (m, 2H), 3.86 (s, 3H), 2.15 (s, 3H), 2.45-2.50 (m, 2H), 0.90-0.98 (m, 1H), 0.39-0.43 (m, 2H), 0.12-0.16 (m, 2H).

Synthesis of (E)-2-cyclopropylmethyl-N-[(1R,2S)-2-hydroxy-indan-1-yl]-3-[3-methoxy-4-(4-methyl-1H-imidazol-1-yl)phenyl]acrylamide trifluoroacetic acid salt 11.5 mg of the title compound was obtained from (E)-2-cyclopropylmethyl-3-(3-methoxy-4-(4-methyl-1H-imidazol-1-yl)phenyl)acrylic acid (20.0 mg) and (1R,2S)1-amino-2-indanol (11.5 mg) by the same method as in Example 94. The physical properties of the compound are as follows.

$^1$H-NMR ($CDCl_3$) δ (ppm): 8.72 (s, 1H), 7.28-7.40 (m, 6H), 7.07-7.10 (m, 3H), 6.79 (d, J=8.4 Hz, 1H), 5.56 (dd, J=5.2, 8.4 Hz, 1H), 4.77 (dt, J=2.4, 5.2 Hz, 1H), 3.91 (s, 3H), 3.28 (dd, J=5.2, 16 Hz, 1H), 3.02 (dd, J=2.4, 16 Hz, 1H), 2.54 (d, J=6.4 Hz, 2H), 2.48 (s, 3H), 0.88-0.96 (m, 1H), 0.50-0.60 (m, 2H), 0.18-0.26 (m, 2H).

Example 98

Synthesis of (E)-2-benzyl-N-(2-hydroxy ethyl)-3-[3-methoxy-4-(4-methyl-1H-imidazol-1-yl)phenyl] acrylamide trifluoroacetic acid salt

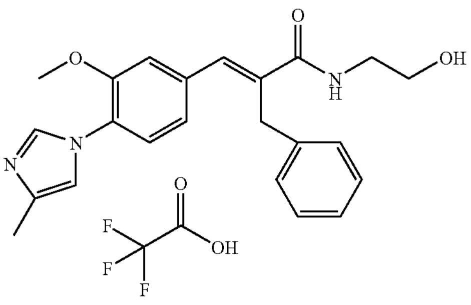

15.3 mg of the title compound was obtained from (E)-2-benzyl-3-(3-methoxy-4-(4-methyl-1H-imidazol-1-yl)phenyl)acrylic acid (25.0 mg) and ethanolamine (8.8 mg) by the same method as in Example 94. The physical properties of the compound are as follows.

ESI-MS; m/z392 [$M^+$+H].

Example 99

Synthesis of (E)-1-(4-indol-1-yl-piperidin-1-yl)-2-[3-methoxy-4-(4-methyl-1H-imidazol-1-yl)benzylidene]butan-1-one

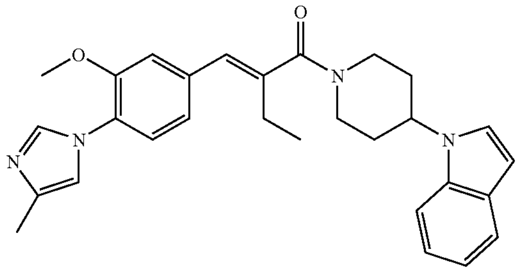

76.8 mg of the title compound was obtained from (E)-2-(3-methoxy-4-(4-methyl-1H-imidazol-1-yl)benzylidene)butyric acid (60.0 mg) and 4-(1-indole)piperidine hydrochloride (74.6 mg) by the same method as in Example 111. The physical properties of the compound are as follows.

$^1$H-NMR ($CDCl_3$) δ (ppm): 7.69 (s, 1H), 7.64 (d, J=8.0 Hz, 1H), 7.38 (d, J=8.0 Hz, 1H), 7.18-7.25 (m, 3H), 7.12 (t, J=7.6 Hz, 1H), 6.92-6.96 (m, 3H), 6.53 (d, J=10 Hz, 2H), 4.65-4.95 (brs, 1H), 4.49-4.55 (m, 1H), 4.20-4.50 (br, 1H), 3.85 (s, 3H), 2.80-3.40 (br, 2H), 2.62-2.67 (m, 2H), 2.99 (s, 3H), 2.22-2.25 (m, 2H), 1.80-2.10 (br, 2H), 1.18 (t, J=7.2 Hz, 3H)

Example 100

Synthesis of (E)-N-indan-1-yl-2-[3-methoxy-4-(4-methyl-1H-imidazol-1-yl]benzylidene)butyl amide trifluoroacetic acid salt

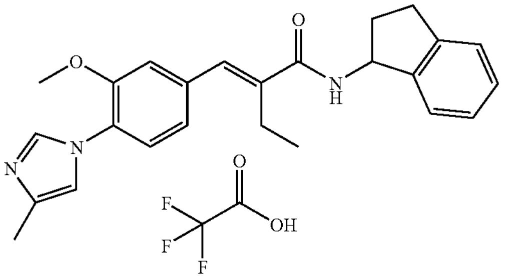

6.95 mg of the title compound was obtained from (E)-2-(3-methoxy-4-(4-methyl-1H-imidazol-1-yl)benzylidene)butyric acid (13.8 mg) and 1-aminoindane (9.6 mg) by the same method as in Example 111. The physical properties of the compound are as follows.

$^1$H-NMR ($CDCl_3$) δ (ppm): 8.63 (s, 1H), 7.22-7.35 (m, 5H), 7.17 (s, 1H), 7.00-7.02 (m, 3H), 6.08 (brd, J=7.6 Hz, 1H), 5.63 (q, J=7.6 Hz, 1H), 3.48 (s, 3H), 3.05 (ddd, J=4.0, 8.8, 16 Hz, 1H), 2.94 (dt, J=7.6, 16 Hz, 1H), 2.71 (dtd, J=4.0, 7.6, 16 Hz, 1H), 2.51-2.59 (m, 2H), 2.47 (s, 3H), 1.86-1.95 (m, 1H), 1.20 (t, J=7.6 Hz, 3H).

Example 101

Synthesis of (E)-2-cyclopropyl methyl-N-indan-1-yl-3-[3-methoxy-4-(4-methyl-1H-imidazol-1-yl)phenyl]acrylamide trifluoroacetic acid salt

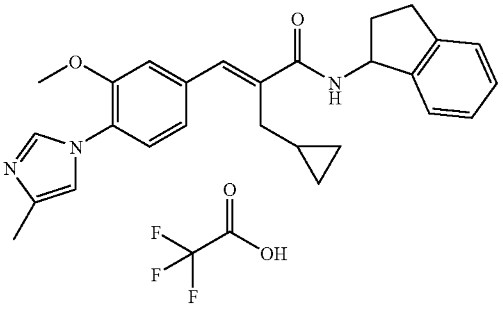

6.23 mg of the title compound was obtained from (E)-2-cyclopropyl methyl-3-(3-methoxy-4-(4-methyl-1H-imidazol-1-yl)phenyl)acrylic acid (15.0 mg) and 1-aminoindane (9.6 mg) by the same method as in Example 94. The physical properties of the compound are as follows.

$^1$H-NMR ($CDCl_3$) δ (ppm): 8.67 (s, 1H), 7.22-7.36 (m, 5H), 7.18 (s, 1H), 7.04-7.05 (m, 3H), 6.24 (brd, J=7.6 Hz, 1H), 5.62 (q, J=7.6 Hz, 1H), 3.89 (s, 3H), 3.05 (ddd, J=4.0, 8.4, 16 Hz, 1H), 2.93 (dt, J=8.0, 16 Hz, 1H), 2.71 (dtd, J=4.0, 7.6, 16 Hz, 1H), 2.50 (d, J=6.4 Hz, 2H), 2.47 (s, 3H), 1.88-1.97 (m, 1H), 0.82-0.91 (m, 1H), 0.52-0.56 (m, 2H), 0.18-0.22 (m, 2H)

Example 102

Synthesis of (E)-2-benzyl-N-indan-1-yl-3-[3-methoxy-4-(4-methyl-1H-imidazol-1-yl)phenyl]acrylamide trifluoroacetic acid salt

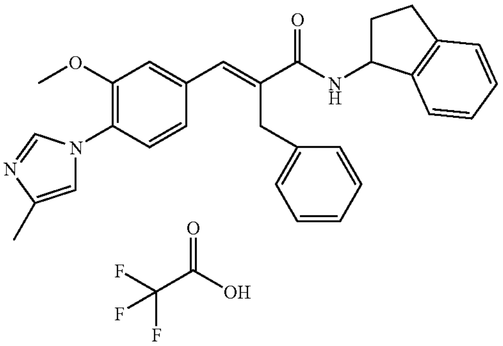

6.76 mg of the title compound was obtained from (E)-2-benzyl-3-(3-methoxy-4-(4-methyl-1H-imidazol-1-yl)phenyl)acrylic acid (17.0 mg) and 1-aminoindane (9.6 mg) by the same method as in Example 94. The physical properties of the compound are as follows.

$^1$H-NMR ($CDCl_3$) δ (ppm): 8.61 (d, J=2.0 Hz, 1H), 7.71 (s, 1H), 7.20-7.37 (m, 7H), 7.05-7.13 (m, 3H), 6.99-7.01 (m, 2H), 6.87 (d, J=7.2 Hz, 1H), 5.95 (brd, J=7.6 Hz, 1H), 5.50 (q, J=7.6 Hz, 1H), 3.98 (d, J=16 Hz, 1H), 3.88 (d, J=16 Hz, 1H), 3.68 (s, 3H), 2.80-2.94 (m, 2H), 2.59 (dtd, J=4.0, 7.2, 13 Hz, 1H), 2.46 (s, 3H), 1.62-1.71 (m, 1H).

The compounds shown in Table 5 were synthesized as in Example 85.

The structural formulae and physicochemical properties are shown in Table 5, respectively.

TABLE 5

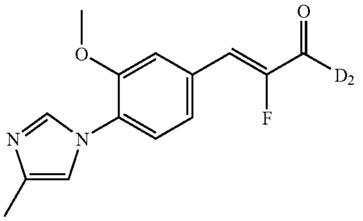

| Example | $D_2$ | DATA: MS m/z |
|---|---|---|
| 103 | 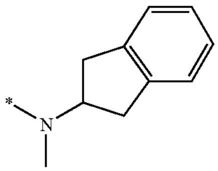 | $M^+$ + H:406 (ESI) |
| 104 | 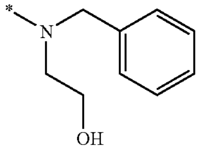 | $M^+$ + H:410 (ESI) |
| 105 | 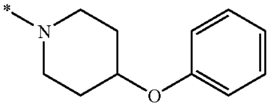 | $M^+$ + H:436 (ESI) |

The compounds shown in Table 6 were synthesized as in Example 474. The structured formulae and physicochemical properties are shown in Table 6, respectively.

TABLE 6

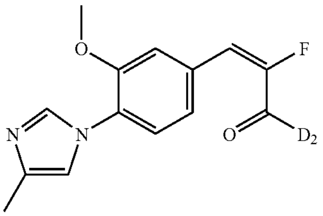

| Example | $D_2$ | DATA: MS m/z |
|---|---|---|
| 106 | 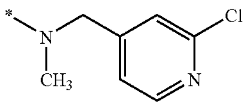 | $M^+$ + H:415 (ESI) |
| 107 | 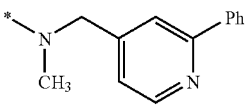 | $M^+$ + H:457 (ESI) |
| 108 | 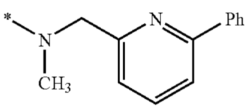 | $M^+$ + H:457 (ESI) |

TABLE 6-continued

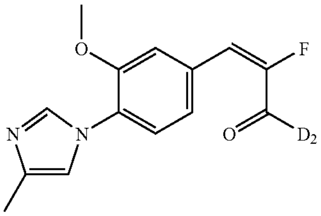

| Example | $D_2$ | DATA: MS m/z |
|---|---|---|
| 109 | 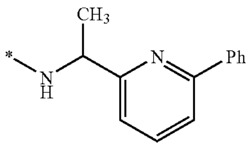 | $M^+$ + H:457 (ESI) |
| 110 | 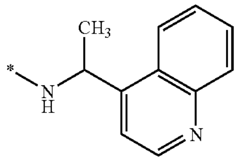 | $M^+$ + H:431 (ESI) |

Example 111

Synthesis of (E)-N-(9H-fluoren-9-yl)-3-[4-(1H-imidazol-1-yl)-3-methoxyphenyl]acrylamide

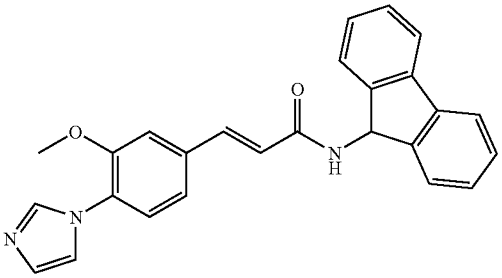

Synthesis of 4-(1H-imidazol-1-yl)-3-methoxybenzaldehyde

Potassium carbonate (6.70 g) and imidazole (2.60 g) were added to a DMF (30 mL) solution of 4-fluoro-3-methoxybenzaldehyde (5.00 g) one by one, and the reaction solution was agitated at 130° C. overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and 4.76 g of crude aldehyde compounds was obtained by condensing under reduced pressure. The physical properties of the compound are as follows.

$^1$H-NMR ($CDCl_3$) δ (ppm): 10.01 (s, 1H), 7.92 (s, 1H), 7.57-7.60 (m, 2H), 7.49 (d, J=7.6 Hz, 1H), 7.29 (s, 1H), 7.21 (s, 1H), 3.98 (s, 3H).

Synthesis of (E)-3-[4-(1H-imidazol-1-yl)-3-methoxyphenyl)acrylic acid

Dimethylphosphonoacetic acid methyl ester (3.80 mL) and lithium hydroxide monohydrate (1.20 g) were added one by one to a THF (20 mL) solution of the crude aldehyde compound (4.76 g) obtained above, and the reaction solution was agitated overnight at the room temperature. 2N sodium hydroxide solution was added to the reaction solution after confirming disappearance of the starting materials (20 mL), and the reaction solution was agitated at 50° C. for 2 hours. The reaction solution was cooled to 0° C., 2N hydrochloric acid was added to the reaction solution (20 mL), and deposited precipitation was separated by filtering with Kiriyama funnel. The obtained precipitation was washed with water and ethyl acetate, and 4.2 g of the title compound was obtained. The physical properties of the compound are as follows.

$^1$H-NMR (DMSO-d6) δ (ppm): 7.96 (s, 1H), 7.63 (d, J=16 Hz, 1H), 7.60 (d, J=1.6 Hz, 1H), 7.48 (s, 1H), 7.45 (d, J=8.0 Hz, 1H), 7.39 (dd, J=1.6, 8.0 Hz, 1H), 7.06 (s, 1H), 6.68 (d, J=16 Hz, 1H), 3.90 (s, 3H).

(E)-N-(9H-fluoren-9-yl)-3-[4-(1H-imidazol-1-yl)-3-methoxyphenyl]acrylicamide

To a DMF (70 mL) solution of (E)-3-[4-(1H-imidazol-1-yl)-3-methoxyphenyl)acrylic acid (3.50 g), 9-aminofluorene (2.40 g), IPEA (7.5 mL), EDC (3.00 g) and HOBT (2.10 g) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate=1:1→ethyl acetate→ethyl acetate:ethanol=10:1), and 2.20 g of the title compound was obtained. The physical properties of the compound are as follows.

$^1$H-NMR ($CDCl_3$) δ (ppm): 7.80 (s, 1H), 7.76 (d, J=16 Hz, 1H), 7.72 (d, J=7.2 Hz, 2H), 7.63 (d, J=7.2 Hz, 2H), 7.42 (t, J=7.2 Hz, 2H), 7.32 (dt, J=1.2 Hz, 7.2 Hz, 2H), 7.28 (d, J=8.4 Hz, 1H), 7.19-7.22 (m, 2H), 7.16-7.17 (m, 2H), 6.47 (d, J=16 Hz, 1H), 6.39 (d, J=8.8 Hz, 1H), 6.00 (d, J=8.8 Hz, 1H), 3.88 (s, 3H).

Example 112

Synthesis of (E)-{3-[4-(1H-imidazol-1-yl)-3-methoxyphenyl]acryloylamino}-(S)-phenylacetic acid tert-butyl ester trifluoroacetic acid salt

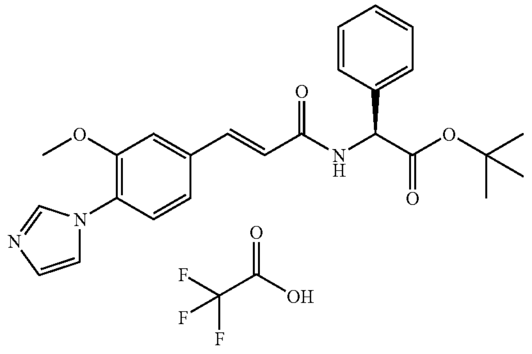

By the same method as in Example 94, 14.0 mg of the title compound was obtained from (E)-3-[4-(1H-imidazol-1-yl)-3-methoxyphenyl]acrylic acid (20.0 mg) and (S)-2-phenylglycine-tert-butyl ester (25.0 mg). The physical properties of the compound are as follows.

$^1$H-NMR ($CD_3OD$) δ (ppm): 9.19 (t, J=1.6 Hz, 1H), 7.79 (t, J=1.6 Hz, 1H), 7.63 (t, J=1.6 Hz, 1H), 7.52 (d, J=16 Hz, 1H), 7.50 (d, J=8.4 Hz, 1H), 7.40 (d, J=1.6 Hz, 1H), 7.26-7.36 (m, 6H), 7.32 (d, J=16 Hz, 1H), 5.38 (s, 1H), 3.88 (s, 3H), 1.32 (s, 9H).

Example 113

Synthesis of (E)-3-[4-(1H-imidazol-1-yl)-3-methoxyphenyl]-N-(3-iodo-benzyl)acrylamide

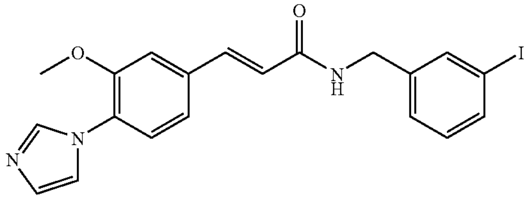

By the same method as in Example 111, 1.40 g of the title compound was obtained from (E)-3-(4-1H-imidazol-1-yl-3-methoxyphenyl)acrylic acid (1.00 g) and 3-iodobenzylamine (550 μL). The physical properties of the compound are as follows.

$^1$H-NMR ($CDCl_3$) δ (ppm): 7.76 (s, 1H), 7.65 (s, 1H), 7.64 (d, J=15.2 Hz, 1H), 7.58 (d, J=8.0 Hz, 1H), 7.28 (d, J=8.0 Hz, 1H), 7.23 (d, J=8.0 Hz, 1H), 7.20 (t, J=1.6 Hz, 1H), 7.11-7.16 (m, 3H), 7.04 (t, J=8.0 Hz, 1H), 6.94 (brs, 1H), 6.54 (d, J=15.2 Hz, 1H), 4.51 (d, J=6.0 Hz, 2H), 3.84 (s, 3H).

Example 114

Synthesis of (E)-3-[4-(1H-imidazol-1-yl)-3-methoxyphenyl]-N-(3-phenethyl-benzyl)acrylamide trifluoroacetic acid salt

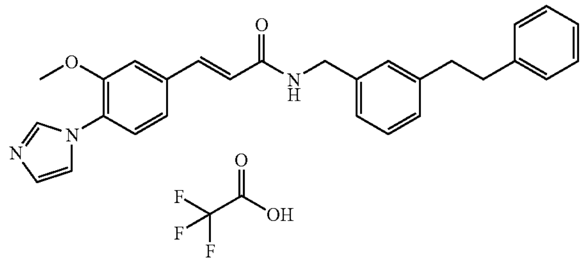

By the same method as in Example 94, 2.30 mg of the title compound was obtained from (E)-3-[4-(1H-imidazol-1-yl)-3-methoxyphenyl]acrylic acid (10.0 mg) and 3-phenethylbenzylamine hydrochloride (14.0 mg). The physical properties of the compound are as follows.

$^1$H-NMR ($CD_3OD$) δ (ppm): 9.29 (t, J=1.6 Hz, 1H), 7.89 (t, J=1.6 Hz, 1H), 7.73 (t, J=1.6 Hz, 1H), 7.62 (d, J=16 Hz, 1H), 7.59 (d, J=8.0 Hz, 1H), 7.50 (d, J=1.6 Hz, 1H), 7.40 (dd, J=1.2, 8.0 Hz, 1H), 7.08-7.25 (m, 9H), 6.78 (d, J=16 Hz, 1H), 4.48 (s, 2H), 3.98 (s, 3H), 2.90 (s, 4H).

Example 115

Synthesis of (E)-3-[4-(1H-imidazol-1-yl)-3-methoxyphenyl]-N-(5-methyl-6-oxo-6,7-dihydro-5H-dibenzo[b,d]azepin-7-yl)acrylamide trifluoroacetic acid salt

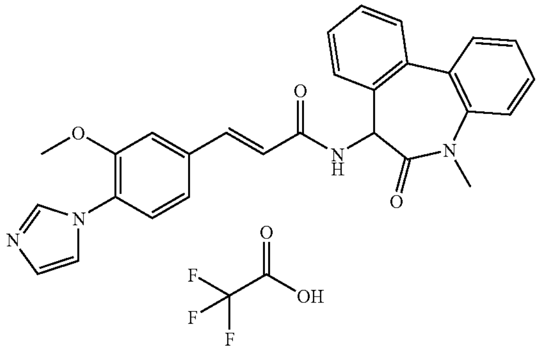

By the same method as in Example 94, 2.7 mg of the title compound was obtained from (E)-3-(4-1H-imidazol-1-yl-3-methoxyphenyl)acrylic acid (6.20 mg) and 7-amino-5-methyl-5H,7H-dibenzo[b,d]azepin-6-one (6.00 mg). The physical properties of the compound are as follows.

$^1$H-NMR ($CD_3OD$) δ (ppm): 9.31 (t, J=1.6 Hz, 1H), 7.90 (t, J=1.6 Hz, 1H), 7.74 (t, J=1.6 Hz, 1H), 7.71 (d, J=8.0 Hz, 1H), 7.67 (d, J=3.6, 5.6 Hz, 1H), 7.62 (d, J=8.0 Hz, 1H), 7.61 (d, J=16 Hz, 1H), 7.55-7.58 (m, 3H), 7.40-7.50 (m, 5H), 7.20 (d, J=16 Hz, 1H), 5.46 (s, 1H), 4.00 (s, 3H), 3.37 (s, 3H).

Example 116

Synthesis of (E)-N-(2-benzylbenzyl)-3-[4-(1H-imidazol-1-yl)-3-methoxyphenyl]acrylamide trifluoroacetic acid salt

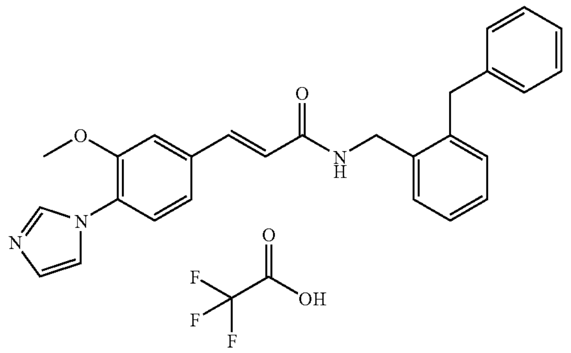

By the same method as in Example 94, 7.2 mg of the title compound was obtained from (E)-3-[4-(1H-imidazol-1-yl)-3-methoxyphenyl]acrylic acid (10.0 mg) and 2-benzylbenzylamine (12.0 mg). The physical properties of the compound are as follows.

$^1$H-NMR ($CD_3OD$) δ (ppm): 9.29 (t, J=1.6 Hz, 1H), 7.88 (t, J=1.6 Hz, 1H), 7.73 (t, J=1.6 Hz, 1H), 7.58 (d, J=8.0 Hz, 1H), 7.55 (d, J=16 Hz, 1H), 7.45 (d, J=1.6 Hz, 1H), 7.36 (dd, J=1.6, 8.0 Hz, 1H), 7.32-7.34 (m, 1H), 7.19-7.27 (m, 5H), 7.12-7.15 (m, 3H), 6.65 (d, J=16 Hz, 1H), 4.49 (s, 2H), 4.10 (s, 2H), 3.97 (s, 3H).

Example 117

Synthesis of (E)-N-(9H-fluoren-1-yl)-3-[4-(1H-imidazol-1-yl)-3-methoxyphenyl]acrylamide trifluoroacetic acid salt

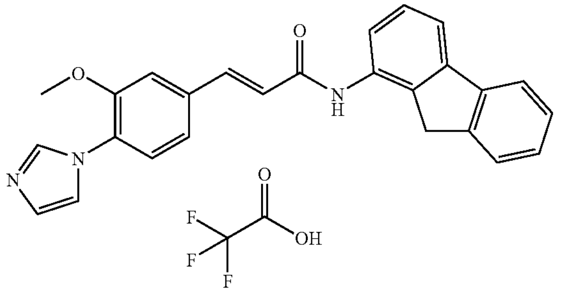

By the same method as in Example 94, 14.0 mg of the title compound was obtained from (E)-3-[4-(1H-imidazol-1-yl)-3-methoxyphenyl]acrylic acid (20.0 mg) and 1-aminofluorene (22 mg). The physical properties of the compound are as follows.

$^1$H-NMR ($CD_3OD$) δ (ppm): 9.29 (s, 1H), 7.98 (s, 1H), 7.89 (t, J=1.6 Hz, 1H), 7.72-7.80 (m, 3H), 7.74 (t, J=1.6 Hz, 1H), 7.63 (d, J=8.0 Hz, 2H), 7.53-7.54 (m, 2H), 7.46 (d, J=8.0 Hz, 1H), 7.35 (t, J=7.6 Hz, 1H), 7.26 (dt, J=1.2, 7.6 Hz, 1H), 6.96 (d, J=16 Hz, 1H), 4.01 (s, 3H), 3.92 (s, 2H).

Example 118

Synthesis of (E)-N-(1H-benzoimidazol-2-ylmethyl)-3-[4-(1H-imidazol-1-yl)-3-methoxyphenyl]acrylamide nitrilofluoroacetic acid salt

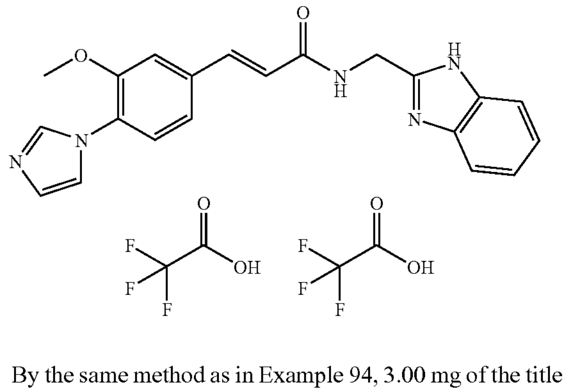

By the same method as in Example 94, 3.00 mg of the title compound was obtained from (E)-3-[4-(1H-imidazol-1-yl)-3-methoxyphenyl]acrylic acid (20.0 mg) and 2-(aminomethyl)benzimidazole dihydrochloride (26.0 mg). The physical properties of the compound are as follows.

$^1$H-NMR ($CD_3OD$) δ (ppm): 9.28 (d, J=1.6 Hz, 1H), 7.89 (t, J=1.6 Hz, 1H), 7.55-7.61 (m, 2H), 7.74 (t, J=1.6 Hz, 1H), 7.70 (d, J=16 Hz, 1H), 7.63 (d, J=8.0 Hz, 1H), 7.73-7.78 (m, 2H), 7.53 (d, J=1.6, 1H), 7.44 (dd, J=1.6, 8.0 Hz, 1H), 6.90 (d, J=16 Hz, 1H), 4.98 (s, 2H), 3.99 (s, 3H).

Example 119

Synthesis of (E)-3-[4-(1H-imidazol-1-yl)-3-methoxyphenyl]-N-naphthalen-1-ylmethyl-acrylamide

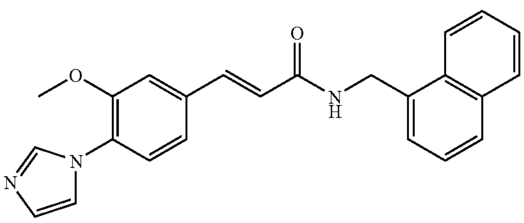

By the same method as in Example 111, 1.90 mg of the title compound was obtained from (E)-3-[4-(1H-imidazol-1-yl)-3-methoxyphenyl]acrylic acid (20.0 mg) and 1-naphthalenemethylamine (19.0 mg). The physical properties of the compound are as follows.

$^1$H-NMR ($CDCl_3$) δ (ppm): 8.06 (d, J=8.4 Hz, 1H), 7.89 (d, J=7.6 Hz, 1H), 7.86 (d, J=12.4 Hz, 1H), 7.79 (s, 1H), 7.68 (d, J=15.6 Hz, 1H), 7.42-7.58 (m, 4H), 7.11-7.30 (m, 5H), 6.38 (d, J=15.6 Hz, 1H), 5.86 (brs, 1H), 5.05 (d, J=5.2 Hz, 2H), 3.85 (s, 3H)

Example 120

Synthesis of (E)-3-[4-(1H-imidazol-1-yl)-3-methoxyphenyl]-N-(1H-imidazole-2-ylmethyl)acrylamide nitrilofluoroacetic acid salt

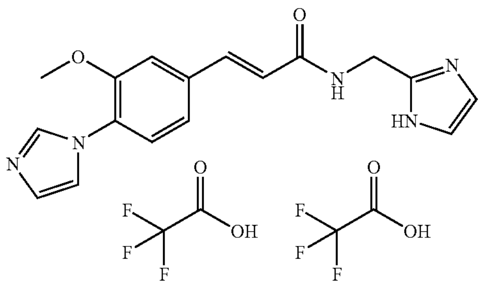

15.7 mg of the title compound was obtained from (E)-3-[4-(1H-imidazol-1-yl)-3-methoxyphenyl]acrylic acid (15.0 mg) and (1H-imidazole-2-yl)-methylamine dihydrochloride (15.3 mg) by the same method as in Example 94. The physical properties of the compound are as follows.

$^1$H-NMR ($CD_3OD$) δ (ppm): 9.29 (t, J=1.6 Hz, 1H), 7.88 (t, J=1.6 Hz, 1H), 7.74 (t, J=1.6 Hz, 1H), 7.66 (d, J=16 Hz, 1H), 7.61 (d, J=8.0 Hz, 1H), 7.51 (d, J=1.6 Hz, 1H), 7.48 (s, 2H), 7.42 (dd, J=1.6, 8.0 Hz, 1H), 6.84 (d, J=16 Hz, 1H), 4.78 (s, 2H), 3.99 (s, 3H)

Example 121

Synthesis of (E)-N-biphenyl-3-ylmethyl-3-[3-methoxy-4-(4-methyl-1H-imidazol-1-yl)phenyl]acrylamide

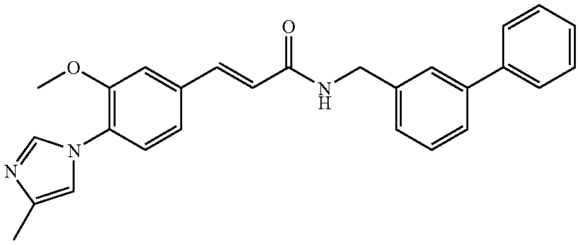

Synthesis of (E)-3-[3-methoxy-4-(4-methyl-1H-imidazol-1-yl)phenyl]acrylic acid

To a THF (40 mL) solution of 3-methoxy-4-(4-methyl-1H-imidazol-1-yl)benzaldehyde (4.00 g) obtained in Example 1, diethylphosphonoacetic acid ethyl ester (4.00 mL) and lithium hydroxide monohydrate (932 mg) were added one by one, and the reaction solution was agitated overnight at room temperature. 2N sodium hydroxide solution (30 mL) and ethanol (5 mL) were added to the reaction solution after confirming disappearance of the starting materials, and the reaction solution was agitated at room temperature overnight. The reaction solution was cooled to 0° C., 2N hydrochloric acid (30 mL) was added to the reaction solution, and the precipitation consequently deposited was separated by filtering with Kiriyama funnel. The obtained precipitation was washed with water and ethyl acetate, and 4.61 g of the title compound was obtained. The physical properties of the compound are as follows.

$^1$H-NMR (DMSO-d6) δ (ppm): 7.81 (s, 1H), 7.60 (d, J=16 Hz, 1H), 7.56 (s, 1H), 7.39 (d, J=8.0 Hz, 1H), 7.35 (d, J=8.0 Hz, 1H), 7.16 (s, 1H), 6.66 (d, J=16 Hz, 1H), 3.88 (s, 3H), 2.15 (s, 3H).

Synthesis of (E)-N-biphenyl-3-ylmethyl-3-[3-methoxy-4-(4-methyl-1H-imidazol-1-yl)phenyl]acrylamide To a DMF (30 mL) solution of (E)-3-(3-methoxy-4-(4-methyl-1H-imidazol-1-yl)phenyl)acrylic acid (2.20 g), 3-phenylbenzylamine hydrochloride (2.30 g), IPEA (4.57 mL), EDC (1.96 g) and HOBT (1.38 g) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate ethanol=10:1), and 3.30 g of the title compound was obtained. The physical properties of the compound are as follows.

$^1$H-NMR ($CDCl_3$) δ (ppm): 7.71 (d, J=1.2 Hz, 1H), 7.67 (d, J=16 Hz, 1H), 7.52-7.60 (m, 4H), 7.42-7.46 (m, 3H), 7.37 (td, J=1.2, 7.6 Hz, 1H), 7.33 (brd, J=7.6 Hz, 1H), 7.24 (d, J=8.0 Hz, 1H), 7.17 (dd, J=1.6 Hz, 6.4 Hz, 1H), 7.13 (d, J=1.6 Hz, 1H), 6.93 (t, J=1.2 Hz, 1H), 6.45 (d, J=16,Hz, 1H), 6.09 (brs, 1H), 4.67 (d, J=5.6 Hz, 2H), 3.87 (s, 3H), 2.29 (s, 3H).

Example 122

Synthesis of (E)-N-[(1S)-indan-1-yl]-3-[3-methoxy-4-(4-methyl-1H-imidazol-1-yl)phenyl]acrylamide trifluoroacetic acid salt

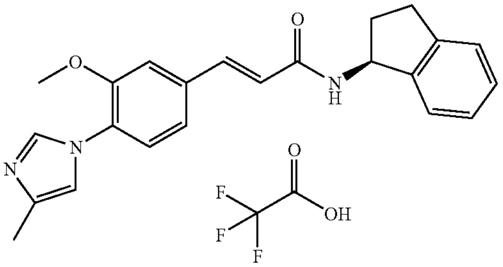

To a DMF (0.8 mL) solution of (E)-3-(3-methoxy-4-(4-methyl-1H-imidazol-1-yl)phenyl)acrylic acid (15.0 mg), (S)-

(+)-1-aminoindan (12.0 mg), IPEA (30 EL), EDC (16.7 mg), and HOBT (11.8 mg) were added one by one, and the reaction solution was agitated at room temperature for 3 hours. After confirming disappearance of the starting materials, the reaction solution was purified by LC-MS, and 6.6 mg of the title compound was obtained. The physical properties of the compound are as follows.

$^1$H-NMR ($CDCl_3$) δ (ppm): 9.15 (d, J=2.0 Hz, 1H), 8.57 (d, J=8.4 Hz, 1H), 7.65 (d, J=16 Hz, 1H), 7.59 (t, J=1.2 Hz, 1H), 7.56 (d, J=8.0 Hz, 1H), 7.48 (d, J=1.6 Hz, 1H), 7.34 (dd, J=1.6, 6.8 Hz, 1H), 7.18-7.29 (m, 4H), 6.77 (d, J=16 Hz, 1H), 5.50-5.55 (m, 1H), 3.97 (s, 3H), 3.05 (ddd, J=4.4, 8.8, 16 Hz, 1H), 2.90 (td, J=7.6, 16 Hz, 1H), 2.57 (dtd, J=4.4, 7.6, 16 Hz, 1H), 2.43 (s, 3H), 1.88-1.97 (m, 1H).

Example 123

Synthesis of (E)-3-[3-methoxy-4-(4-methyl-1H-imidazol-1-yl)phenyl]-N-(2-pheoxy ethyl)acrylamide trifluoroacetic acid salt

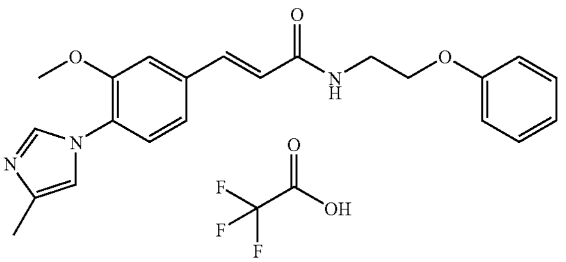

By the same method as in Example 94, 5.3 mg of the title compound was obtained from (E)-3-[3-methoxy-4-(4-methyl-1H-imidazol-1-yl)phenyl]acrylic acid (15.0 mg) and 2-pheoxyethylamine (13.0 μL). The physical properties of the compound are as follows.

$^1$H-NMR ($CD_3OD$) δ (ppm): 9.13 (d, J=1.6 Hz, 1H), 8.50 (t, J=5.6 Hz, 1H), 7.54-7.61 (m, 3H), 7.47 (d, J=2.0 Hz, 1H), 7.37 (dd, J=2.0, 8.4 Hz, 1H), 7.20-7.31 (m, 2H), 6.90-6.98 (m, 3H), 6.79 (d, J=15.6 Hz, 1H), 4.12 (t, J=5.6 Hz, 2H), 3.97 (s, 3H), 3.69-3.74 (m, 2H), 2.43 (s, 3H)

Example 124

Synthesis of (E)-N-[(1R)-1-hydroxymethyl-2-phenylethyl]-3-[3-methoxy-4-(4-methyl-1H-imidazol-1-yl)phenyl]acrylamide

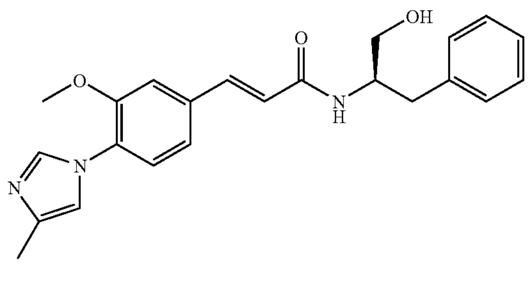

By the same method as in Example 121, 262 mg of the title compound was obtained from (E)-3-[3-methoxy-4-(4-methyl-1H-imidazol-1-yl)phenyl]acrylic acid (200 mg) and D-phenylalanilol (176 mg). The physical properties of the compound are as follows.

$^1$H-NMR ($CDCl_3$) δ (ppm): 7.69 (d, J=1.6 Hz, 1H), 7.56 (d, J=15.6 Hz, 1H), 7.20-7.33 (m, 5H), 7.18 (d, J=8.0 Hz, 1H), 7.06-7.10 (m, 2H), 6.91 (t, J=1.2 Hz, 1H), 6.34 (d, J=15.6 Hz, 1H), 6.18 (d, J=7.6 Hz, 1H), 4.31-4.36 (m, 1H), 3.84 (s, 3H), 3.79 (dd, J=3.2, 11 Hz, 1H), 3.68 (dd, J=4.8, 11 Hz, 1H), 2.98 (d, J=7.2 Hz, 2H), 2.29 (s, 3H).

Example 125

Synthesis of (E)-N-[2-(3-fluoro-pheoxy)-ethyl]-3-[3-methoxy-4-(4-methyl-1H-imidazol-1-yl)phenyl]acrylamide trifluoroacetic acid salt

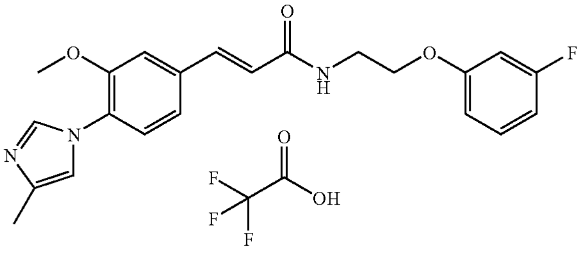

By the same method as in Example 94, 2.10 mg of the title compound was obtained from (E)-3-[3-methoxy-4-(4-methyl-1H-imidazol-1-yl)phenyl]acrylic acid (15.0 mg) and 2-(3-fluoropheoxy) ethyl amine (13.0 mg). The physical properties of the compound are as follows.

$^1$H-NMR ($CD_3OD$) δ (ppm): 8.89 (s, 1H), 7.59 (d, J=16 Hz, 1H), 7.52 (d, J=8.0 Hz, 1H), 7.49 (m, 1H), 7.45 (d, J=1.6 Hz, 1H), 7.36 (dd, J=1.6, 8.4 Hz, 1H), 7.26 (dt, J=6.8, 8.0 Hz, 1H), 6.76-6.79 (m, 1H), 6.65-6.75 (m, 3H), 4.12 (t, J=5.2 Hz, 2H), 3.96 (s, 3H), 3.72 (t, J=5.2 Hz, 2H), 2.39 (s, 3H).

Example 126

Synthesis of (E)-N-[(1S,2R)-2-hydroxy-indan-1-yl]-3-[3-methoxy-4-(4-methyl-1H-imidazol-1-yl)-phenyl]acrylamide trifluoroacetic acid salt

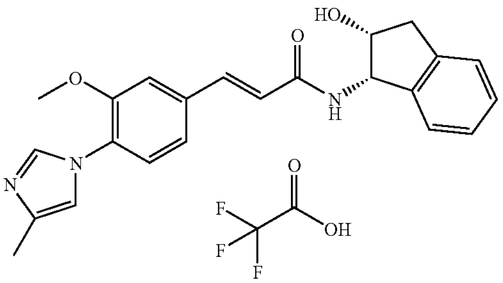

By the same method as in Example 94, 8.40 mg of the title compound was obtained from (E)-3-[3-methoxy-4-(4-methyl-1H-imidazol-1-yl)phenyl)acrylic acid (15.0 mg) and (1S, 2R)-1-amino-2-indanol (13.0 mg). The physical properties of the compound are as follows.

$^1$H-NMR ($CD_3OD$) δ (ppm): 9.14 (d, J=1.2 Hz, 1H), 8.26 (d, J=8.8 Hz, 1H), 7.67 (d, J=16 Hz, 1H), 7.59 (m, 1H), 7.56

(d, J=8.0 Hz, 1H), 7.52 (d, J=1.6 Hz, 1H), 7.41 (dd, J=1.2, 8.8 Hz, 1H), 7.21-7.29 (m, 3H), 6.98 (d, J=16 Hz, 1H), 5.47 (q, J=5.6 Hz, 1H), 4.63 (dt, J=2.0, 5.6 Hz, 1H), 3.98 (s, 3H), 3.20 (dd, J=5.6, 16 Hz, 1H), 2.87 (dd, J=2.0, 16 Hz, 1H), 2.44 (s, 3H).

Example 127

Synthesis of (E)-N-[(1R)-1-hydroxymethyl-2-phenyl-ethyl]-3-[3-methoxy-4-(4-methyl-1H-imidazol-1-yl)phenyl]-N-(2-morpholin-4-yl-ethyl)acrylamide

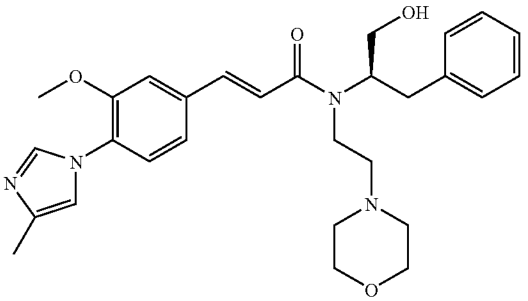

Synthesis of (2R)-2-(2-morpholin-4-yl-ethylamino)-3-phenylpropan-1-ol

Sodium iodide (84.5 mg) and sodium hydride (676 mg) and 4-(2-chloroethyl)morpholine hydrochloride (2.1 g) were added to a DMF (20 mL) solution of (R)-4-benzyl-2-oxazolidinone (1.0 g) at 0° C., and the reaction solution was warmed to 60° C. and agitated for 3 hours. After agitating the reaction solution at room temperature overnight, water and ethyl acetate were added to the reaction solution and the organic layer was partitioned. After the obtained organic layer was washed with a saturated saline solution, it was dried over anhydrous magnesium sulfate and concentrated under reduced pressure. The obtained residue was purified by silica gel chromatography (Carrier: Chromatorex™ NH, elution solvent:heptane-ethyl acetate=2:1), and 1.62 g of oxazolidinone compound was obtained. Next, lithium hydroxide (1.61 g) was added to a solution of the obtained oxazolidinone in ethanol (14 mL) and water (6.0 mL), and the reaction solution was refluxed for 6 hours and 30 minutes. Water and ethyl acetate were added to the reaction solution, and the organic layer was partitioned. The obtained organic layer was washed with a saturated salt solution, dried over anhydrous magnesium sulfate, and 549 mg of crude amine compounds was obtained by condensing under reduced pressure. The physical properties of the compound are as follows.

$^1$H-NMR ($CDCl_3$) δ (ppm): 7.14-7.32 (m, 5H), 3.67-3.76 (m, 1H), 3.64 (dd, J=4.8, 10 Hz, 1H), 3.51-3.62 (m, 3H), 3.39 (dd, J=5.6, 10 Hz, 1H), 2.86-2.92 (m, 1H), 2.70-2.80 (m, 2H), 2.62-2.68 (m, 2H), 2.42-2.54 (m, 2H), 2.28-2.36 (m, 6H).

Synthesis of (E)-N-[(1R)-1-hydroxymethyl-2-phenyl-ethyl]-3-[3-methoxy-4-(4-methyl-1H-imidazol-1-yl)phenyl]-N-(2-morpholin-4-yl-ethyl)-acrylamide 18.1 mg of the title compound was obtained by the same method as the in Example 111 from (E)-3-[3-methoxy-4-(4-methyl-1H-imidazol-1-yl)phenyl]acrylic acid (15.0 mg) and (2R)-2-(2-morpholin-4-yl-ethylamino)-3-phenyl-propan-1-ol (23.0-mg). The physical properties of the compound are as follows.

$^1$H-NMR ($CDCl_3$) δ (ppm): 7.71 (d, J=1.2 Hz, 1H), 7.25-7.29 (m, 1H), 7.14-7.22 (m, 4H), 6.92-7.05 (m, 5H), 6.48 (d, J=15 Hz, 1H), 4.27-4.36 (m, 1H), 3.87 (s, 3H), 3.60-3.86 (m, 7H), 3.52-3.58 (m, 1H), 3.06-3.26 (m, 2H), 2.63-2.76 (m, 4H), 2.42-2.54 (m, 3H), 2.30 (s, 3H).

Example 128

Synthesis of (E)-3-[3-methoxy-4-(4-methyl-1H-imidazol-1-yl)phenyl]-N-[3-(morpholin-4-yl-benzyl) acrylamide

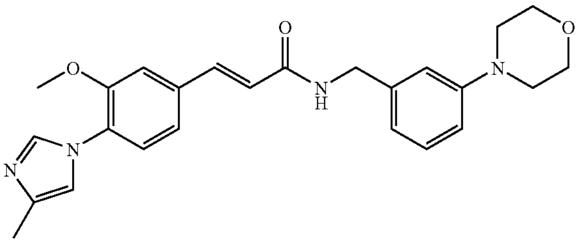

By the same method as in Example 121, 12.0 mg of the title compound was obtained from (E)-3-[3-methoxy-4-(4-methyl-1H-imidazol-1-yl)phenyl]acrylic acid (15.0 mg) and (3-morpholin-4-yl)benzylamine (17.0 mg). The physical properties of the compound are as follows.

$^1$H-NMR ($CDCl_3$) δ (ppm): 7.70 (d, J=1.2 Hz, 1H), 7.65 (d, J=16 Hz, 1H), 7.23-7.27 (m, 2H), 7.16 (dd, J=1.6, 8.4 Hz, 1H), 7.11 (d, J=1.6 Hz, 1H), 6.91 (t, J=1.2 Hz, 1H), 6.836.88 (m, 3H), 6.40 (d, J=16 Hz, 1H), 5.93 (brs, 1H), 4.54 (d, J=5.6 Hz, 2H), 3.87 (s, 3H), 3.85 (t, J=4.8 Hz, 4H), 3.16 (t, J=4.8 Hz, 4H), 2.29 (s, 3H)

Example 129

Synthesis of (E)-N-(4-fluoro-3-morpholin-4-yl-benzyl)-3-[3-methoxy-4-(4-methyl-1H-imidazol-1-yl) phenyl]acrylamide oxalic acid salt

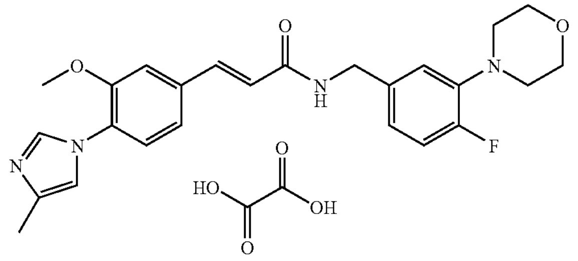

By the same method as in Example 121, free compound of the title compound was obtained from (E)-3-[3-methoxy-4-(4-methyl-1H-imidazol-1-yl)phenyl]acrylic acid (200 mg) and 4-fluoro-3-morpholin-4-yl-benzylamine (165 mg). 221 mg of the title compound was obtained by adding 1 equivalent of oxalic acid to a methanol (2 mL) solution of the obtained free compound, and reaction solvent was removed. The physical properties of the compound are as follows.

$^1$H-NMR (DMSO-d6) δ (ppm): 8.59 (t, J=6.0 Hz, 1H), 8.07 (brs, 1H), 7.50 (d, J=15.6 Hz, 1H), 7.427.44 (m, 2H), 7.27 (dd, J=1.6, 8.4 Hz, 1H), 7.26-7.28 (m, 1H), 7.09 (dd, J=8.4, 12.8 Hz, 1H), 6.98 (dd, J=1.6, 8.4 Hz, 1H), 6.88-6.91 (m, 1H), 6.75 (d, J=15.6 Hz, 1H), 4.35 (d, J=5.6 Hz, 2H), 3.87 (s, 3H), 3.74 (t, J=4.8 Hz, 4H), 2.99 (t, J=4.8 Hz, 4H), 2.18 (s, 3H).

Example 130

Synthesis of (E)-N-[2-(3-fluorophenyl)ethyl]-3-[3-methoxy-4-(4-methyl-1H-imidazol-1-yl)phenyl] acrylamide trifluoroacetic acid salt

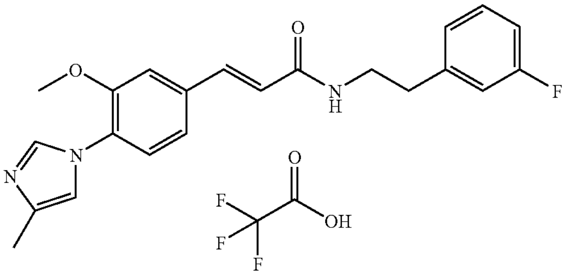

By the same method as in Example 94, 3.1 mg of the title compound was obtained from (E)-3-[3-methoxy-4-(4-methyl-1H-imidazol-1-yl)phenyl]acrylic acid (15.0 mg) and 2-(3-fluorophenyl)ethyl amine (12.0 μL). The physical properties of the compound are as follows.

$^1$H-NMR ($CD_3OD$) δ (ppm): 9.05 (s, 1H), 7.56 (d, J=15.6 Hz, 1H), 7.54 (dd, J=8.4 Hz, 1H), 7.45 (d, J=1.6 Hz, 1H), 7.35 (dd, J=1.6, 8.4 Hz, 1H), 7.29 (dd, J=6.0, 8.0 Hz, 1H), 7.07 (d, J=8.0 Hz, 1H), 7.00 (d, J=10.0 Hz, 1H), 6.94 (dt, J=1.6, 8.0 Hz, 1H), 6.68 (d, J=15.6 Hz, 1H), 3.96 (s, 3H), 3.56 (t, J=7.2 Hz, 2H), 2.89 (t, J=7.2 Hz, 2H), 2.41 (s, 3H).

Example 131

Synthesis of (E)-N-(benzo[B]thiophen-3-ylmethyl)-3-[3-methoxy-4-(4-methyl-1H-imidazol-1-yl)phenyl] acrylamide trifluoroacetic acid salt

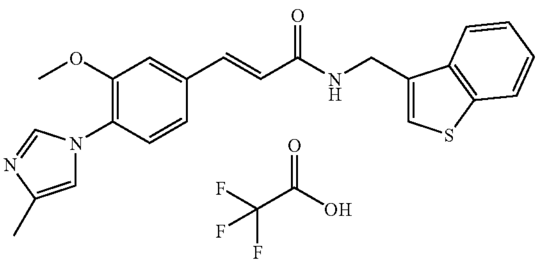

By the same method as in Example 94, 1.40 mg of the title compound was obtained from (E)-3-[3-methoxy-4-(4-methyl-1H-imidazol-1-yl)phenyl]acrylic acid (15.0 mg) and 1-benzo[B]thiophen-3-ylmethylamine hydrochloride (17.0 mg). The physical properties of the compound are as follows.

$^1$H-NMR ($CD_3OD$) δ (ppm): 9.05 (s, 1H), 7.86-7.90 (m, 2H), 7.64 (d, J=16 Hz, 1H), 7.51-7.54 (m, 3H), 7.46 (d, J=1.2 Hz, 1H), 7.35-7.42 (m, 3H), 6.75 (d, J=16 Hz, 1H), 4.78 (s, 2H), 3.96 (s, 3H), 2.41 (s, 3H).

Example 132

Synthesis of (E)-N-(biphenyl-3-ylmethyl)-3-[3-fluoro-4-(4-methyl-1H-imidazol-1-yl)phenyl]acrylamide 1/2 oxalic acid salt

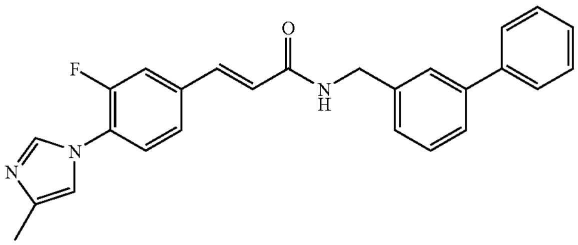

½ $(COOH)_2$

By the same method as in Example 121, 118 mg of the title compound was obtained from (E)-3-[3-fluoro-4-(4-methyl-1H-imidazol-1-yl)phenyl]acrylic acid (60.0 mg) and 3-phenylbenzylamine hydrochloride (80.0 m). The physical properties of the compound are as follows.

$^1$H-NMR ($CD_3OD$) δ (ppm): 8.75 (t, J=4.8 Hz, 1H), 8.48 (5, 1H), 7.527.68 (m, 8H), 7.41-7.44 (m, 4H), 7.31-7.35 (m, 2H), 6.76 (d, J=16 Hz, 1H), 4.86 (s, 3H), 4.58 (d, J=4.8 Hz, 2H).

Example 133

Synthesis of (E)-3-[3-methoxy-4-(4-methyl-1H-imidazol-1-yl)phenyl]-N-methyl-N-(2-pheoxy ethyl) acrylamide trifluoroacetic acid salt

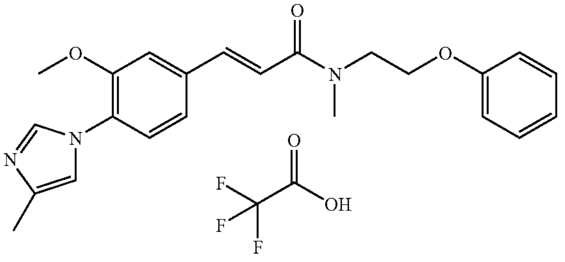

By the same method as in Example 94, 41.0 mg of the title compound was obtained from (E)-3-[3-methoxy-4-(4-methyl-1H-imidazol-1-yl)phenyl)acrylic acid (70.0 mg) and methyl-(2-pheoxy ethyl)amine (61.0 mg). The physical properties of the compound are as follows.

$^1$H-NMR ($CD_3OD$) δ (ppm): 9.12 (s, 1H), 7.21-7.63 (m, 8H), 6.87-6.95 (m, 3H), 4.20-4.24 (m, 2H), 4.02 (t, J=4.8 Hz, 1H), 3.98 (3, 1.5H), 3.95 (s, 1.5H), 3.89 (t, J=5.6 Hz, 1H), 3.38 (s, 1.5H), 3.15 (s, 1.5H), 2.42 (s, 3H)

Example 134

Synthesis of (E)-3-[3-methoxy-4-(4-methyl-1H-imidazol-1-yl)phenyl]-N-methyl-N-(2-morpholin-4-yl-1-phenylethyl)acrylamide trifluoroacetic acid salt

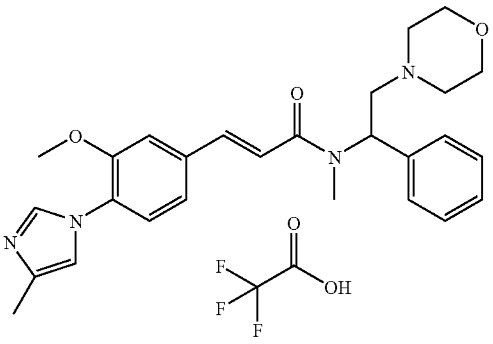

By the same method as in Example 94, 139 mg of the title compound was obtained from (E)-3-[3-methoxy-4-(4-methyl-1H-imidazol-1-yl)phenyl]acrylic acid (70.0 mg) and a DMF solution (405 μL) of methyl-(2-morpholin-4-yl-phenylethyl)amine of 10 mM(s). The physical properties of the compound are as follows.

$^1$H-NMR ($CD_3OD$) δ (ppm): 9.16 (d, J=1.2 Hz, 1H), 7.74 (d, J=16 Hz, 1H), 7.56-7.59 (m, 3H), 7.35-7.47 (m, 6H), 7.2 (d, J=15 Hz, 1H), 6.49 (dd, J=2.8, 12 Hz, 1H), 4.16 (t, J=12 Hz, 1H), 3.98 (s, 3H), 3.83 (dd, J=2.8, 12 Hz, 1H), 3.81-4.20 (m, 8H), 2.94 (s, 3H), 2.43. (s, 3H)

Example 135

Synthesis of (E)-3-[3-methoxy-4-(4-methyl-1H-imidazol-1-yl)phenyl]-N-methyl-N-(3-morpholin-4-yl-1-benzyl)acrylamide 1/2 oxalic acid salt

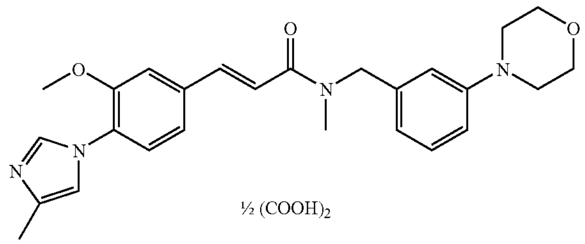

½ $(COOH)_2$

By the same method as in Example 121, 132 mg of the title compound was obtained from (E)-3-[3-methoxy-4-(4-methyl-1H-imidazol-1-yl)phenyl]acrylic acid (68.0 mg) and N-methyl-N-[3-morpholin-4-yl)benzyl]amine (76.0 mg). The physical properties of the compound are as follows.

$^1$H-NMR (DMSO-d6) δ (ppm): 8.01 (brs, 1H), 7.55-7.60 (m, 2H), 7.40-7.44 (m, 2H), 7.32-7.36 (m, 1H), 7.18-7.26 (m, 2H), 6.84-6.86 (m, 2H), 6.65-6.71 (m, 1H), 4.78 (s, 1H), 4.58 (s, 1H), 3.90 (s, 1.5H), 3.87 (s, 1.5H), 3.69-3.74 (m, 4H), 3.12 (s, 1.5H), 3.07-3.10 (m, 4H), 2.93 (s, 1.5H), 2.18 (s, 3H)

Example 136

Synthesis of (E)-N-[3-(2-hydroxy-ethoxy)-benzyl]-3-[3-methoxy-4-(4-methyl-1H-imidazol-1-yl)phenyl]-N-methyl-acrylamide trifluoroacetic acid salt

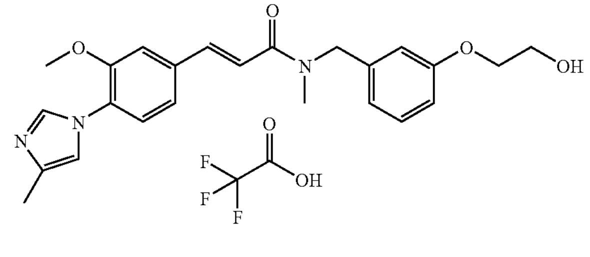

By the same method as in Example 94, 36.1 mg of the title compound was obtained from (E)-3-[3-methoxy-4-(4-methyl-1H-imidazol-1-yl)phenyl]acrylic acid (20.0 mg) and 2-(3-methylaminomethylpheoxy) ethanol (21.0 mg). The physical properties of the compound are as follows.

$^1$H-NMR ($CDCl_3$) δ (ppm): 8.72 (s, 0.5H), 8.69 (s, 0.5H), 7.75 (d, J=12 Hz, 0.5H), 7.72 (d, J=12 Hz, 0.5H), 7.28-7.36 (m, 2H), 7.20-7.21 (m, 1H), 6.97-7.12 (m, 2H), 6.79-6.91 (m, 4H), 4.71 (s, 1H), 4.69 (s, 1H), 4.07-4.12 (m, 2H), 3.96-4.00 (m, 2H), 3.95 (s, 1.5H), 3.90 (s, 1.5H), 3.13 (s, 1.5H), 3.12 (s, 1.5H), 2.48 (s, 1.5H), 2.47 (s, 1.5H).

Example 137

Synthesis of (E)-N-[1-(3-fluorophenyl)ethyl]-3-[3-methoxy-4-(4-methyl-1H-imidazol-1-yl)phenyl]acrylamide trifluoroacetic acid salt

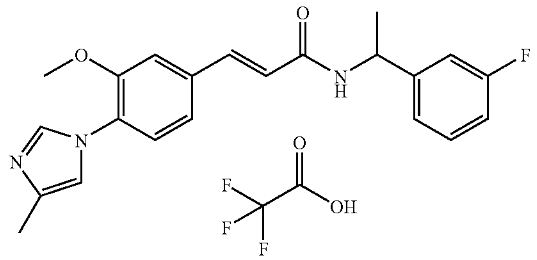

By the same method as in Example 94, 17.3 mg of the title compound was obtained from (E)-3-[3-methoxy-4-(4-methyl-1H-imidazol-1-yl)phenyl]acrylic acid (20.0 mg) and 1-(3-fluorophenyl)ethyl amine (16.2 mg). The physical properties of the compound are as follows.

$^1$H-NMR ($CDCl_3$) δ (ppm): 8.68 (d, J=1.6 Hz, 1H), 7.63 (d, J=16 Hz, 1H), 7.30-7.35 (m, 2H), 7.22-7.26 (m, 1H), 7.19 (d, J=1.6 Hz, 1H), 7.15 (dd, J=1.2, 8.4 Hz, 1H), 6.99-7.08 (m, 2H), 6.97 (dt, J=2.4, 8.4 Hz, 1H), 6.55 (d, J=16 Hz, 1H), 6.02-6.08 (brs, 1H), 5.27 (qu, J=7.2 Hz, 1H), 3.99 (s, 3H), 2.47 (s, 3H), 1.57 (d, J=7.2 Hz, 3H).

Example 139

Synthesis of (E)-N-[(1R)-fluoromethyl-2-phenylethyl]-3-[3-methoxy-4-(4-methyl-1H-imidazol-1-yl)phenyl]acrylic acid amide

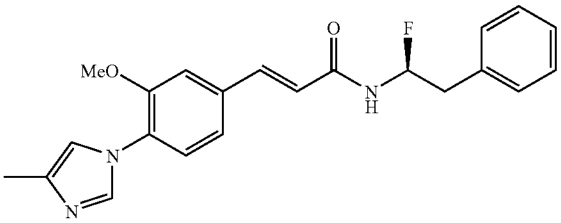

Synthesis of (R)-2-(1-fluoromethyl-2-phenylethyl)isoindol-1,3-dione (R)-2-(1-hydroxymethyl-2-phenylethyl)isoindole-1,3-dione (1.20 g) was added to a methylene chloride (20 mL) solution of DAST (825 mg) at −78° C. and the reaction solution was agitated at room temperature. DAST (500 mg) was added to the reaction solution after 2 hours, and the reaction solution was agitated at 50° C. for 3 hours. Saturated sodium bicarbonate solution was added for reaction solution to the reaction solution after allowing the reaction solution to be cooled to room temperature, and the organic layer was partitioned. The organic layer was concentrated under reduced pressure after dried over anhydrous magnesium sulfate. The residue was purified by silica gel column chromatography (heptane-ethyl acetate system), and 52 mg of the title compound was obtained.

$^1$H-NMR ($CDCl_3$) δ(ppm): 3.16 (dd, J=14.0, 6.4 Hz, 1H), 3.28 (dd, J=14.0, 9.6 Hz, 1H), 4.67 (ddd, J=40.8, 8.8, 4.8 Hz, 1H), 4.82-4.94 (m, 1H), 4.98 (dt, J=47.2, 8.8 Hz, 1H), 7.13-7.24 (m, 5H), 7.67-7.70 (m, 2H), 7.77-7.79 (m, 2H).

Synthesis of (R)-1-fluoromethyl-2-phenylethylamine on

A mixture of (R)-2-(1-fluoromethyl-2-phenylethyl)isoindol-1,3-dione (52 mg) and hydrazine hydrate (two drops) and ethanol (1 mL) was heated to reflux for 2 hours. The reaction solution was allowed to be cooled to room temperature, and the deposited crystal was separated by filtration and concentrated under reduced pressure. The residue was purified by LC-MS and 6.0 mg of the title compound was obtained.

$^1$H-NMR ($CDCl_3$) δ(ppm): 2.61 (dd, J=13.2, 8.4 Hz, 1H), 2.82 (dd, J=13.2, 5.6 Hz, 1H), 3.23-3.39 (m, 1H), 4.20-4.47 (m, 2H), 7.20-7.34 (m, 5H).

ESI-MS; m/z154 [$M^+$+H].

Synthesis of (R)-(E)-[(1R)-fluoromethyl-2-phenylethyl]-3-[3-methoxy-4-(4-methyl-1H-imidazol-1-yl)phenyl]acrylic acid amide By the same method as in Example 121, 1.38 mg of the title compound was obtained from 3-[3-methoxy-4-(4-methyl-1H-imidazol-1-yl)phenyl]acrylic acid (10.0 mg) and (R)-1-fluoromethyl-2-phenylethylamine (6.0 mg).

ESI-MS; m/z394 [$M^+$+H]. $^1$H-NMR ($CDCl_3$) δ(ppm): 2.29 (s, 3H), 2.92-3.06 (m, 2H), 3.89 (s, 3H), 4.34-4.56 (m, 3H), 5.85 (d, J=8.2 Hz, 1H), 6.38 (d, J=15.2 Hz, 1H), 6.92 (s, 1H), 7.11-7.17 (m, 2H), 7.23-7.27 (m, 4H), 7.31-7.35 (m, 2H), 7.60 (d, J=15.2 Hz, 1H), 7.71 (s, 1H).

Example 140

Synthesis of (E)-3-[3-methoxy-4-(4-methyl-1H-imidazol-1-yl)phenyl]-N-(6-phenylpyridin-2-ylmethyl)acrylic acid amide

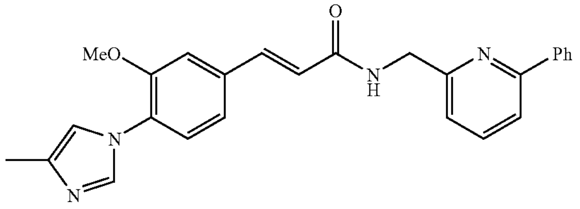

By the same method as in Example 121, the title compound (83 mg) was obtained from (E)-3-[3-methoxy-4-(4-methyl-1H-imidazol-1-yl)phenyl]acrylic acid (71 mg) and (6-phenylpyridin-2-ylmethyl)amine (61 mg).

ESI-MS; m/z425 [$M^+$+H]. $^1$H-NMR ($CDCl_3$) δ(ppm): 2.30 (s, 3H), 3.90 (s, 3H), 4.79 (d, J=4.8 Hz, 2H), 6.57 (d, J=15.6 Hz, 1H), 6.94 (s, 1H), 7.10-7.29 (m, 5H), 7.43-7.56 (m, 3H), 7.64-7.80 (m, 4H), 8.01 (d, J=15.6 Hz, 1H), 8.03 (s, 1H).

Example 141

Synthesis of (E)-3-[3-methoxy-4-(4-methyl-1H-imidazol-1-yl)phenyl]-N-methyl-N-(quinoline-4-ylmethyl)acrylic acid amide

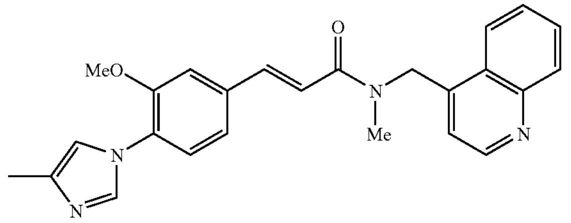

By the same method as in Example 121 The title compound (18 mg) was obtained from (E)-3-[3-methoxy-4-(4-methyl-1H-imidazol-1-yl)phenyl]acrylic acid (71 mg) and N-(methylquinoline-4-yl)methylamine (57 mg).

ESI-MS; m/z413 [$M^+$+H]. $^1$H-NMR ($CDCl_3$) δ(ppm): 2.26 (s, 0.9H), 2.30 (s, 2.1H), 3.17 (s, 2.1H), 3.24 (s, 0.9H), 3.75 (s, 0.9H), 3.91 (s, 2.1H), 5.20 (s, 0.6H), 5.24 (s, 1.4H), 6.60-7.29 (m, 6H), 7.59-7.83 (m, 4H), 8.08-8.25 (m, 2H), 8.88-8.94 (m, 1H).

Example 142-1 and Example 142-2

Synthesis of (E)-N-[(1R,2S) and (1S,2R)-(2-fluoroindan-1-yl)]-3-[3-methoxy-4-(4-methyl-1H-imidazol-1-yl)phenyl]-N-methyl acrylic acid amide

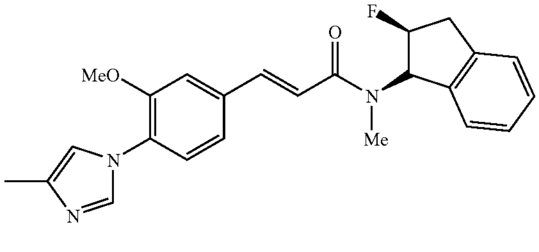

Synthesis of methylamine(1R*,2S*)-(2-fluoroindan-1-yl)

To a THF (1.0 mL) solution of 2-fluoroindan-1-one(100 mg) synthesized according to the method described in Tetrahedron Letters, vol. 37, No. 20, p. 3591, 1996, 2M methylamine THF solution (0.67 mL), acetic acid (400 mg) and triacetoxy sodium borohydride (282 mg) were agitated under ice-cooling and the reaction solution was agitated at room temperature after addition. After 5 hours, 2M methylamine THF solution (0.67 mL) was added to the reaction solution, and the reaction solution was agitated overnight. The organic layer was diluted with a saturated sodium bicarbonate solution and ethyl acetate and partitioned. After drying the organic layer over anhydrous magnesium sulfate the organic layer was washed with a saturation sodium chloride solution and concentrated under reduced pressure. The residue was purified by silica gel column chromatography (elution solvent: from ethyl acetate to ethyl acetate:methanol=20:1), and the title compound (57 mg) was obtained.

ESI-MS; m/z166 [$M^+$+H]. $^1$H-NMR ($CDCl_3$) δ(ppm): 2.67 (s, 3H), 3.09 (ddd, J=37.6, 17.2, 4.4 Hz, 1H), 3.22 (dd, J=23.2, 17.2 Hz, 1H), 4.12 (dd, J=23.2, 4.0 Hz, 1H), 5.48 (dt, J=54.0, 4.0 Hz, 1H), 7.23-7.27 (m, 3H), 7.41-7.45 (m, 1H).

Synthesis of (E)-N-[(1R*,2S*)-(2-fluoroindan-1-yl)]-3-[3-methoxy-4-(4-methyl-1H-imidazol-1-yl) phenyl]-N-methyl acrylamide By the same method as the in Example 121, the title compound (81 mg) was obtained from (E)-3-(4-1H-imidazol-1-yl-3-methoxyphenyl)acrylic acid (74 mg) and (1R*,2S*)(2-fluoroindan-1-yl)methylamine (57 mg).

ESI-MS; m/z406 [$M^+$+H]. $^1$H-NMR ($CDCl_3$) δ(ppm): 2.31 (s, 3H), 3.10 (s, 3H), 3.18-3.28 (m, 2H), 3.92 (s, 3H), 5.46-5.63 (m, 1H), 6.29 (dd, J=27.2, 4.8 Hz, 1H), 6.95 (s, 1H), 7.04 (d, J=15.2 Hz, 1H), 7.18-7.24 (m, 2H), 7.25-7.38 (m, 5H) 7.75 (s, 1H), 7.81 (d, J=15.2 Hz, 1H).

Synthesis of (E)-N-[(1R,2S) and (1S,2R)-(2-fluoroindan-1-yl]3-[3-methoxy-4-(4-methyl-1H-imidazol-1-yl)phenyl]-N-methyl acrylic acid amide N-[(1R*,2S*)-(2-fluoroindan-1-yl))-3-(3-methoxy-4-(4-methyl-1H-imidazol-1-yl)phenyl]-N-methyl acrylic acid amide racemate (80 mg) was separated by CHIRALCEL OD available from Daicel Chemical Industries, Ltd. (2 cm×25 cm :mobile phase; ethanol). The title optically-active substance with a retention time of 17 minutes (Example 142-1:35.8 mg; 99% e.e) and the title optically-active substance with a retention time of 22 minutes (Example 142-2:30.9 mg; 99% e.e) were obtained.

Example 143

Synthesis of (E)-N-[(1R*,2S*)-(2-fluoroindan-1-yl)]-3-[3-methoxy-4-(4-methyl-1H-imidazol-1-yl) phenyl]acrylic acid amide

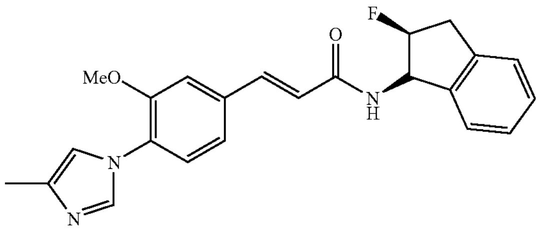

By the same method as in Example 121, the title compound (6.2 mg) was obtained from (E)-3-(4-methyl-1H-imidazol-1-yl-3-methoxyphenyl)acrylic acid (24 mg) and (1R*,2S*)-(2-fluoroindan-1-yl)amine (17 mg).

ESI-MS; m/z392 [$M^+$+H]. $^1$H-NMR ($CDCl_3$) δ(ppm): 2.31 (s, 3H), 3.14-3.29 (m, 2H), 3.91 (s, 3H), 5.43 (dt, J=53.6, 4.0 Hz, 1H), 5.80 (ddd, J=25.6, 9.2, 4.0 Hz, 1H), 6.21 (d, J=9.2 Hz, 1H), 6.54 (d, J=15.6 Hz, 1H), 6.95 (s, 1H), 7.18-7.34 (m, 7H), 7.74 (s, 1H), 7.75 (d, J=15.6 Hz, 1H).

Example 144

Synthesis of (E)-N-[(1R*,2S*)-(2-fluoroindan-1-yl)]-N-(4-methoxybenzyl)-3-[3-methoxy-4-(4-methyl-1H-imidazol-1-yl)phenyl]acrylic acid amide

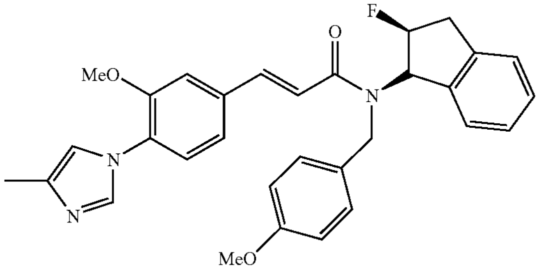

By the same method as in Example 121, the title compound (18.2 mg) was obtained from (E)-3-(4-methyl-1H-imidazol-1-yl-3-methoxyphenyl)acrylic acid (24 mg) and (1R*,2S*)-(2-fluoroindan-1-yl)-(4-methoxybenzyl)amine (15 mg).

ESI-MS; m/z512 [$M^+$+H]. $^1$H-NMR ($CDCl_3$) δ(ppm): 2.28 (s, 3H), 3.24 (d, J=28.4 Hz, 2H), 3.75 (s, 3H), 3.79 (s, 3H), 4.53 (d, J=18.0 Hz, 1H), 4.68 (d, J=18.0 Hz, 1H), 5.59 (d, J=50.0 Hz, 1H), 6.40 (dd, J=25.6, 4.8 Hz, 1H), 6.67 (d, J=15.6 Hz, 1H), 6.82 (s, 1H), 6.87-6.96 (m, 4H), 7.10-7.34 (m, 7H) 7.67 (s, 1H), 7.73 (d, J=15.6 Hz, 1H).

Example 145-1 and Example 145-2

Synthesis of (E)-N-[(1R,2S) and (1S,2R)-(1-fluoroindan-2-yl)]-3-[3-methoxy-4-(4-methyl-1H-imidazol-1-yl)phenyl]-N-methyl acrylic acid amide

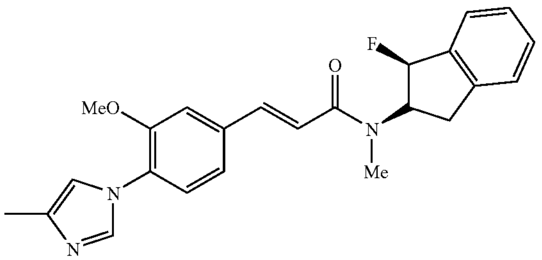

By the same method as in Example 121, the title compound (228 mg) was obtained from (E)-3-(4-methyl-1H-imidazol-1-yl-3-methoxyphenyl)acrylic acid (190 mg) and (1R*,2S*)-(1-fluoroindan-2-yl)methylamine (146 mg).

ESI-MS; m/z406 [$M^+$+H]. $^1$H-NMR ($CDCl_3$) δ(ppm): 2.30 (s, 3H), 3.07-3.14 (m, 1H), 3.27 (s, 3H), 3.36-3.46 (m, 1H), 3.91 (s, 3H), 5.52 (d, J=31.2 Hz, 1H), 5.90 (d, 15 J=57.6

Hz, 1H), 6.94 (s, 1H), 6.98 (d, J=15.6 Hz, 1H), 7.17 (s, 1H), 7.19-7.46 (m, 5H) 7.50-7.55 (m, 1H), 7.73 (s, 1H), 7.74 (d, J=15.6 Hz, 1H).

N-[(1R*,2S*)-(1-fluoroindan-2-yl)]-3-[3-methoxy-4-(4-methyl-1H-imidazol-1-yl)phenyl]-N-methyl acrylic acid amide (270 mg) racemate obtained in the Example 145 was separated by CHIRALPAK AD-H available from Daicel Chemical Industries, Ltd. (2 cm×25 cm mobile phase; ethanol). The title optically-active substance with a retention time of 28 minutes (Example 145-1:105 mg; 99% e.e) and the title optically-active substance with a retention time of 37 minutes (Example 145-2:124 mg; 86% e.e) were obtained.

Example 146

Synthesis of (E)-N-[(1R*,2S*)-(1-fluoroindan-2-yl)]-3-[3-methoxy-4-(4-methyl-1H-imidazol-1-yl)phenyl]acrylic acid amide

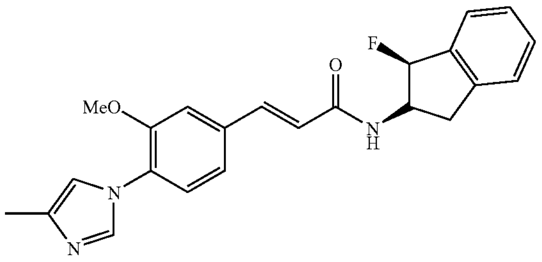

The title compound (9.05 mg) was obtained by the same method as in Example 121 from (E)-3-(4-methyl-1H-imidazol-1-yl-3-methoxyphenyl)acrylic acid (14.3 mg) and (1R*,2S*)-(1-fluoroindan-2-yl)amine (10.1 mg).

ESI-MS; m/z392 $[M^++H]$. $^1$H-NMR ($CDCl_3$) δ: 2.30 (s, 3H), 2.96-2.30 (m, 1H), 3.43 (dd, J=15.2, 8.4 Hz, 1H), 3.91 (s, 3H), 4.90-5.01 (m, 1H), 5.77 (dd, J=58.4, 4.4 Hz, 1H), 6.28 (d, J=8.8 Hz, 1H), 6.51 (d, J=15.6 Hz, 1H), 6.94 (s, 1H), 7.17-7.34 (m, 5H), 7.41-7.44 (m, 1H), 7.52-7.54 (m, 1H), 7.69 (d, J=15.6 Hz, 1H), 7.74 (s, 1H).

Example 147

Synthesis of (E)-N-[(2S)-(2-fluoro-2-phenylethyl)]-3-[3-methoxy-4-(4-methyl-1H-imidazol-1-yl)phenyl] acrylic acid amide

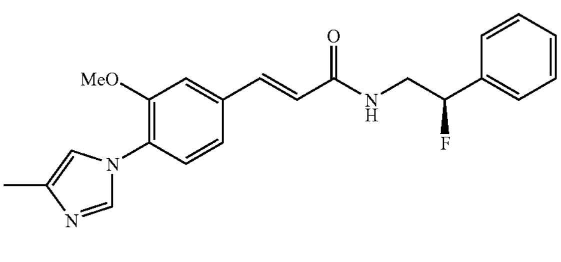

To a methylene chloride (1.0 mL) solution of the N-((2R)-(2-hydroxy-2-phenylethyl))-3-(3-methoxy-4-(4-methyl-1H-imidazol-1-yl)phenyl)acrylic acid amide (36.5 mg) obtained in the Example 195, DAST (23 mg) was added at −78° C, and the reaction solution was agitated for two hours at room temperature. After 2 hrs, the reaction solution was diluted with saturated sodium bicarbonate solution and chloroform, and the organic layer was partitioned. The organic layer was concentrated under reduced pressure after dried over anhydrous magnesium sulfate. The residue was purified by column chromatography (Carrier: Chromatorex™ NH, an elution solvent:heptane-ethyl acetate system), and 5.7 mg of the title compound was obtained.

ESI-MS; m/z380 $[M^++H]$. $^1$H-NMR ($CDCl_3$) δ(ppm): 2.30 (s, 3H), 3.50-3.61 (m, 1H), 3.90 (s, 3H), 4.04-4.19 (m, 1H), 5.63 (ddd, J=48.8, 8.8, 2.8 Hz, 1H), 6.12 (brs, 1H), 6.45 (d, J=15.6 Hz, 1H), 6.94 (s, 1H), 7.14-7.20 (m, 2H), 7.25-7.27 (m, 1H), 7.36-7.46 (m, 5H), 7.65 (d, J=15.6 Hz, 1H), 7.73 (s, 1H).

Example 148-1 and Example 148-2

Synthesis of (E)-N-[(2R) and (2S)-fluoro-2-phenylethyl)-3-[3-methoxy-4-(4-methyl-1H-imidazol-1-yl) phenyl]-N-methylacrylic acid amide

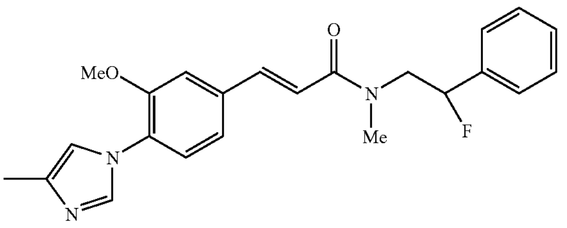

By the same method as in Example 147, 100 mg of the racemate of the title compound was obtained from the N-(2-hydroxy-2-phenylethyl)-3-(3-methoxy-4-(4-methyl-1H-imidazol-1-yl)phenyl)-N-methylacrylic acid amide (310 mg) obtained in the Example 202.

ESI-MS; m/z394 $[M^++H]$. $^1$H-NMR ($CDCl_3$) δ(ppm): 2.31 (s, 3H), 3.11 (s, 0.9H), 3.32 (s, 2.1H), 3.38-3.48 (m, 1H), 3.90 (s, 3H), 4.24 (ddd, J=34.8, 14.4, 2.4 Hz, 1H), 5.81 (ddd, J=49.2, 9.2, 2.4 Hz, 1H), 6.68 (d, J=15.2 Hz, 0.3H), 6.90-6.95 (m, 1.7H), 7.05-7.48 (m, 8H), 7.58 (d, J=15.2 Hz, 0.3H), 7.69-7.74 (m, 1.7H).

(E)-N-(2-fluoro-2-phenylethyl-3-[3-methoxy-4-(4-methyl-1H-imidazol-1-yl)phenyl]-N-methylacrylic acid amide (100 mg) racemate obtained above was separated by CHRALPAK™ AD-H available from Daicel Chemical Industries, Ltd. (cm: 2 cm×25 mobile phase; ethanol). The title optically active substance with a retention time of 15 minutes (Example 148-1: 49 mg; 99% e.e) and the title optically active substance with a retention time of 22 minutes (Example 148-2: 35 mg; 99% e.e) were obtained.

Example 149

Synthesis of N-[(1R, 2R)-(2-fluoroindan-1-yl)]-3-[3-methoxy-4-(4-methyl-1H-imidazol-1-yl)phenyl] acrylic acid amide

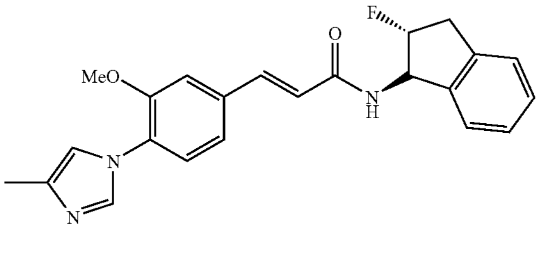

By the same method as in Example 147, 3.20 mg of the title compound was obtained from the N-[(1R,2S)-(2-hydroxyindan-1-yl)]-3-[3-methoxy-4-(4-methyl-1H-imidazol-1-yl)phenyl]acrylic acid amide (50 mg) obtained in the Example 198.

ESI-MS; m/z392 [$M^{+}$+H]. $^{1}$H-NMR ($CDCl_3$) δ(ppm): 2.30 (s, 3H), 3.13-3.24 (m, 1H), 3.36-3.49 (m, 1H), 3.88 (s, 3H), 5.28 (d, J=48.0 Hz, 1H), 5.65 (ddd, J=17.2, 7.2, 2.8 Hz, 1H), 5.77 (d, J=7.2 Hz, 1H), 6.41 (d, J=15.2 Hz, 1H), 6.93 (s, 1H), 7.12-7.20 (m, 2H), 7.24-7.38 (m, 5H), 7.70 (d, J=15.2 Hz, 1H), 7.74 (s, 1H).

The compounds shown in Table 7 were synthesized as in Example 121.

The structural formulae and physicochemical properties are shown in Table 7, respectively.

TABLE 7

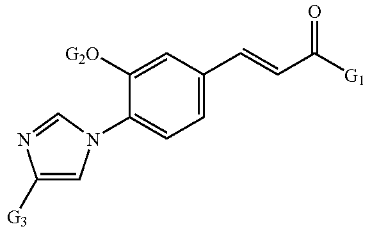

| Example | $G_1$ | $G_2$ | $E_3$ | DATA: MS m/z |
|---|---|---|---|---|
| 150 | 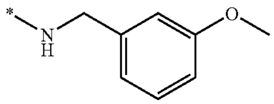 | Me | Me | $M^+$ + H:378 (ESI) |
| 151 | 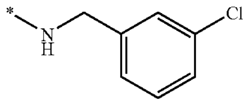 | Me | Me | $M^+$ + H:382 (ESI) |
| 152 | 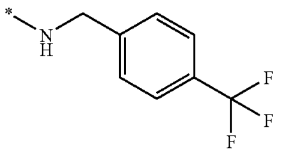 | Me | Me | $M^+$ + H:416 (ESI) |
| 153 | 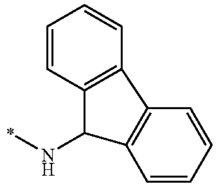 | Me | Me | $M^+$ + H:422 (ESI) |
| 154 | 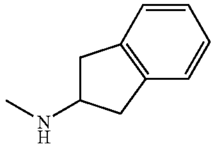 | Me | Me | $M^+$ + H:374 (ESI) |
| 155 | 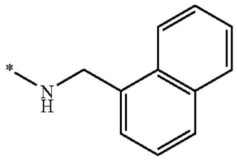 | Me | Me | $M^+$ + H:398 (ESI) |
| 156 | 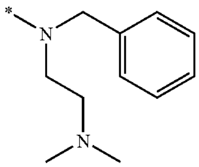 | Me | Me | $M^+$ + H:419 (ESI) |

TABLE 7-continued
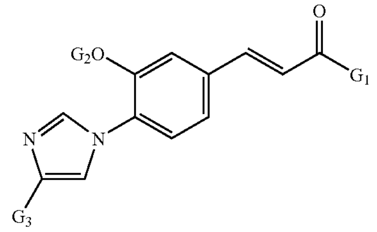
| Example | $G_1$ | $G_2$ | $E_3$ DATA: MS m/z |
|---|---|---|---|
| 157 | 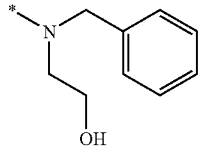 | Me | Me $M^+$ + H:392 (ESI) |
| 158 | 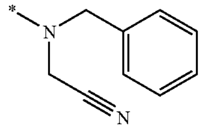 | Me | Me $M^+$ + H:387 (ESI) |
| 159 | 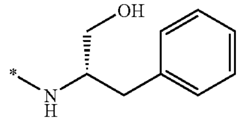 | Me | Me $M^+$ + H:392 (ESI) |
| 160 | 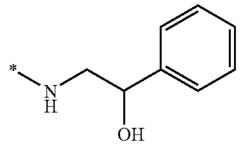 | Me | Me $M^+$ + H:378 (ESI) |
| 161 | 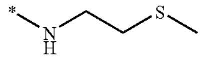 | Me | Me $M^+$ + H:332 (ESI) |
| 162 | 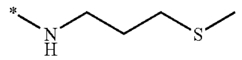 | Me | Me $M^+$ + H:346 (ESI) |
| 163 | 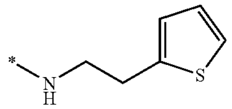 | Me | Me $M^+$ + H:368 (ESI) |
| 164 | 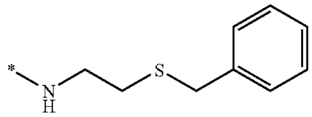 | Me | Me $M^+$ + H:408 (ESI) |
| 165 | 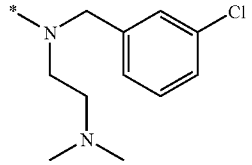 | Me | Me $M^+$ + H:453 (ESI) |

TABLE 7-continued
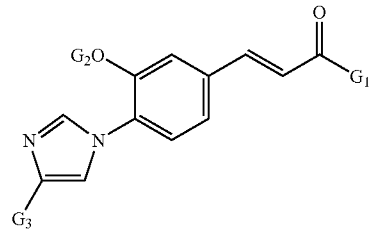
| Example | $G_1$ | $G_2$ | $E_3$ | DATA: MS m/z |
|---|---|---|---|---|
| 166 | 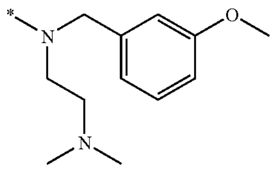 | Me | Me | $M^+$ + H:449 (ESI) |
| 167 | 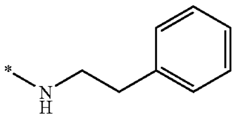 | Me | Me | $M^+$ + H:362 (ESI) |
| 168 | 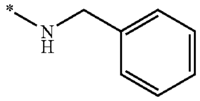 | Me | Me | $M^+$ + H:348 (ESI) |
| 169 | 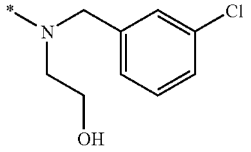 | Me | Me | $M^+$ + H:426 (ESI) |
| 170 | 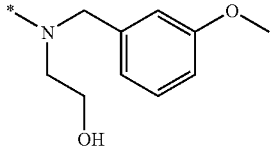 | Me | Me | $M^+$ + H:422 (ESI) |
| 171 | 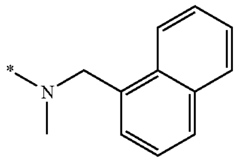 | Me | Me | $M^+$ + H:412 (ESI) |
| 172 | 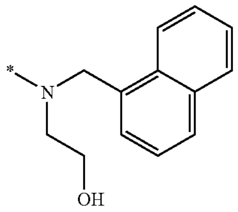 | Me | Me | $M^+$ + H:442 (ESI) |

TABLE 7-continued
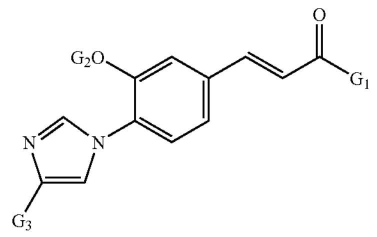
| Example | $G_1$ | $G_2$ | $E_3$ | DATA: MS m/z |
|---|---|---|---|---|
| 173 | 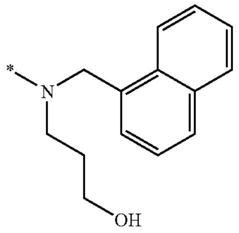 | Me | Me | $M^+$ + H:456 (ESI) |
| 174 | 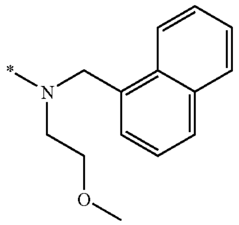 | Me | Me | $M^+$ + H:456 (ESI) |
| 175 | 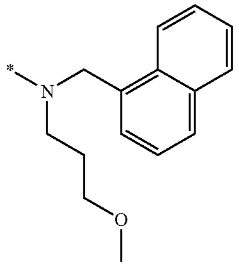 | Me | Me | $M^+$ + H:470 (ESI) |
| 176 | 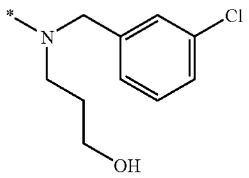 | Me | Me | $M^+$ + H:440 (ESI) |
| 177 | 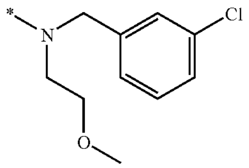 | Me | Me | $M^+$ + H:440 (ESI) |
| 178 | 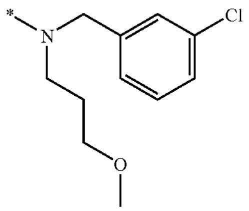 | Me | Me | $M^+$ + H:454 (ESI) |

TABLE 7-continued
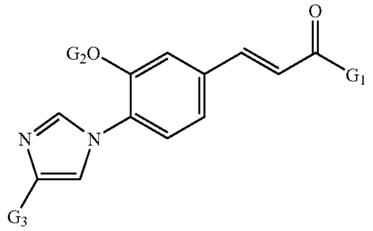
| Example | $G_1$ | $G_2$ | $E_3$ | DATA: MS m/z |
|---|---|---|---|---|
| 179 | 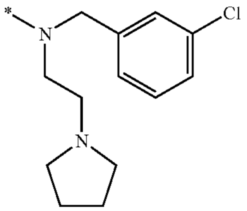 | Me | Me | $M^+$ + H:479 (ESI) |
| 180 | 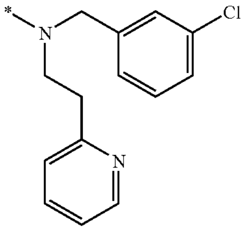 | Me | Me | $M^+$ + H:487 (ESI) |
| 181 | 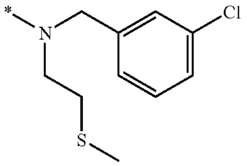 | Me | Me | $M^+$ + H:456 (ESI) |
| 182 | 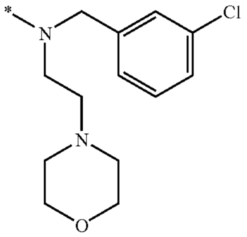 | Me | Me | $M^+$ + H:495 (ESI) |
| 183 | 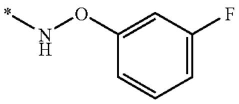 | Me | Me | $M^+$ + H:366 (ESI) |
| 184 | 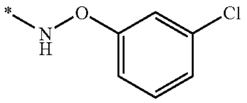 | Me | Me | $M^+$ + H:412 (ESI) |
| 185 | 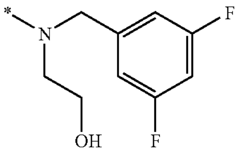 | Me | Me | $M^+$ + H:428 (ESI) |

TABLE 7-continued
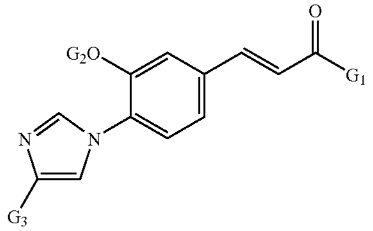
| Example | $G_1$ | $G_2$ | $E_3$ | DATA: MS m/z |
|---|---|---|---|---|
| 186 | 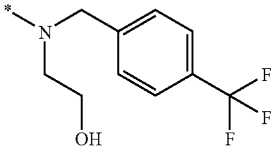 | Me | Me | $M^+$ + H:460 (ESI) |
| 187 | 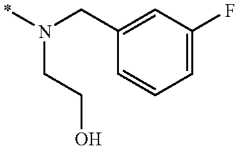 | Me | Me | $M^+$ + H:410 (ESI) |
| 188 | 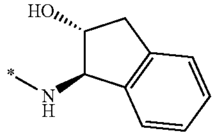 | Me | Me | $M^+$ + H:390 (ESI) |
| 189 | 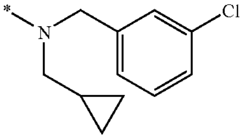 | Me | Me | $M^+$ + H:436 (ESI) |
| 190 | 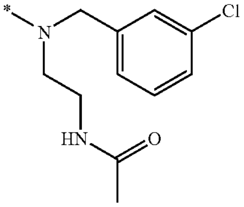 | Me | Me | $M^+$ + H:467 (ESI) |
| 191 | 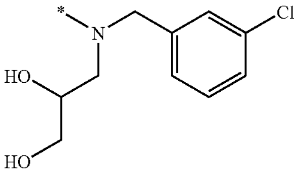 | Me | Me | $M^+$ + H:456 (ESI) |
| 192 | 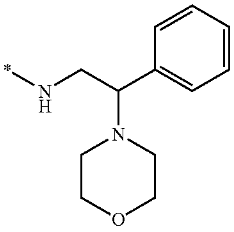 | Me | Me | $M^+$ + H:447 (ESI) |

TABLE 7-continued
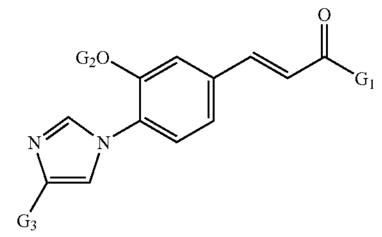
| Example | $G_1$ | $G_2$ | $E_3$ | DATA: MS m/z |
|---|---|---|---|---|
| 193 | 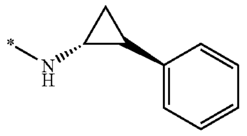 | Me | Me | $M^+$ + H:374 (ESI) |
| 194 | 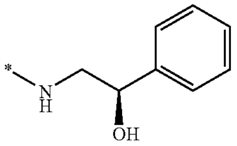 | Me | Me | $M^+$ + H:378 (ESI) |
| 195 | 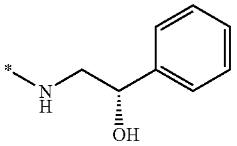 | Me | Me | $M^+$ + H:378 (ESI) |
| 196 | 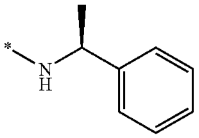 | Me | Me | $M^+$ + H:362 (ESI) |
| 197 | 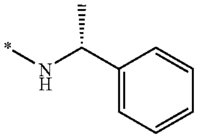 | Me | Me | $M^+$ + H:362 (ESI) |
| 198 | 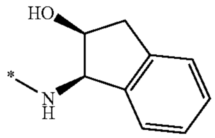 | Me | Me | $M^+$ + H:390 (ESI) |
| 199 | 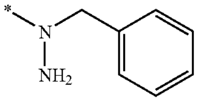 | Me | Me | $M^+$ + H:363 (ESI) |
| 200 | 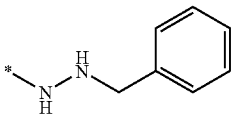 | Me | Me | $M^+$ + H:363 (ESI) |
| 201 | 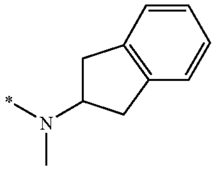 | OMe | Me | $M^+$ + H:388 (ESI) |

TABLE 7-continued
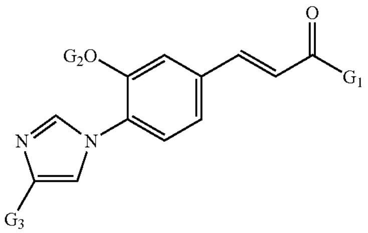
| Example | $G_1$ | $G_2$ | $E_3$ | DATA: MS m/z |
| --- | --- | --- | --- | --- |
| 202 | 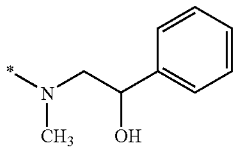 | OMe | Me | $M^+ + H$:392 (ESI) |
| 203 | 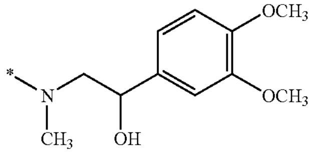 | OMe | Me | $M^+ + H$:452 (ESI) |
| 204 | 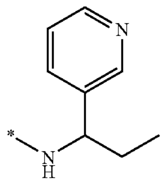 | OMe | Me | $M^+ + H$:377 (ESI) |
| 205 | 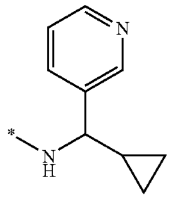 | OMe | Me | $M^+ + H$:389 (ESI) |
| 206 | 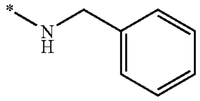 | F | H | $M^+ + H$:322 (ESI) |
| 207 | 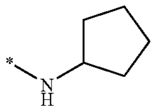 | F | H | $M^+ + H$:300 (ESI) |
| 208 | 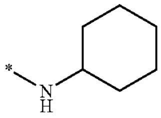 | F | H | $M^+ + H$:314 (ESI) |
| 209 | 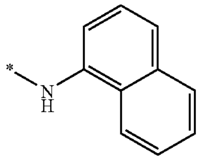 | F | H | $M^+ + H$:358 (ESI) |

TABLE 7-continued
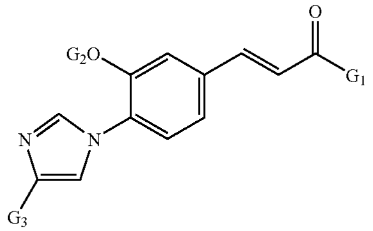
| Example | $G_1$ | $G_2$ | $E_3$ | DATA: MS m/z |
|---|---|---|---|---|
| 210 | 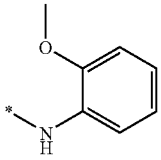 | OMe | H | $M^+$ + H:350 (ESI) |
| 211 | 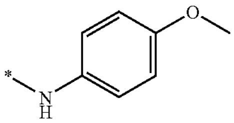 | Me | H | $M^+$ + H:350 (ESI) |
| 212 | 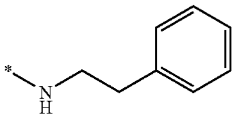 | Me | H | $M^+$ + H:348 (ESI) |
| 213 | 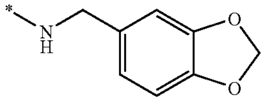 | Me | H | $M^+$ + H:378 (ESI) |
| 214 | 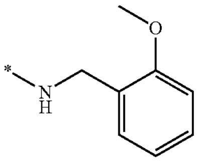 | Me | H | $M^+$ + H:364 (ESI) |
| 215 | 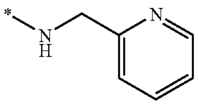 | Me | H | $M^+$ + H:335 (ESI) |
| 216 | 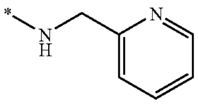 | Me | H | $M^+$ + H:335 (ESI) |
| 217 | 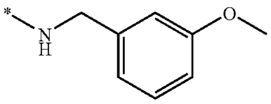 | Me | H | $M^+$ + H:364 (ESI) |
| 218 | 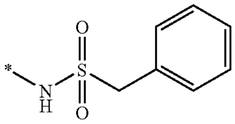 | Me | H | $M^+$ + H:398 (ESI) |

TABLE 7-continued
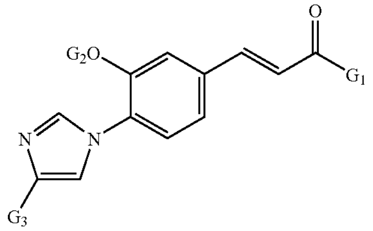
| Example | $G_1$ | $G_2$ | $E_3$ | DATA: MS m/z |
|---|---|---|---|---|
| 219 | 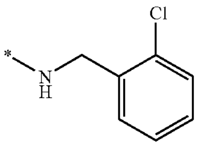 | Me | H | $M^+$ + H:368 (ESI) |
| 220 | 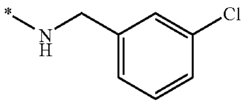 | Me | H | $M^+$ + H:368 (ESI) |
| 221 | 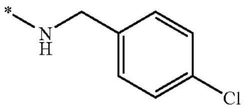 | Me | H | $M^+$ + H:368 (ESI) |
| 222 | 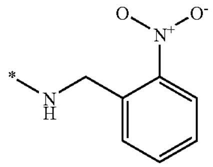 | Me | H | $M^+$ + H:379 (ESI) |
| 223 | 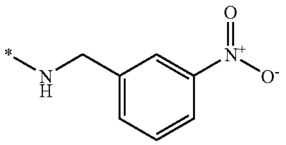 | Me | H | $M^+$ + H:379 (ESI) |
| 224 | 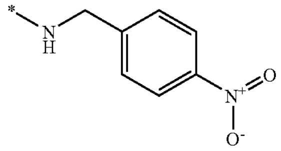 | Me | H | $M^+$ + H:379 (ESI) |
| 225 | 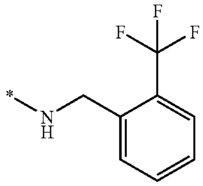 | Me | H | $M^+$ + H:402 (ESI) |
| 226 | 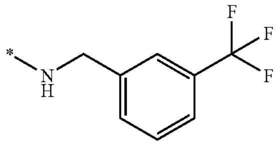 | Me | H | $M^+$ + H:402 (ESI) |

TABLE 7-continued
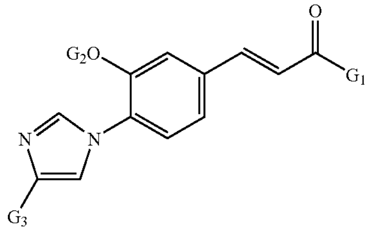
| Example | $G_1$ | $G_2$ | $E_3$ | DATA: MS m/z |
|---|---|---|---|---|
| 227 | 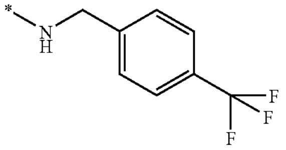 | Me | H | $M^+$ + H:402 (ESI) |
| 228 | 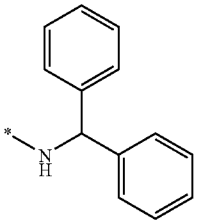 | Me | H | $M^+$ + H:410 (ESI) |
| 229 | 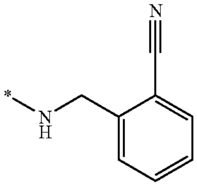 | Me | H | $M^+$ + H:359 (ESI) |
| 230 | 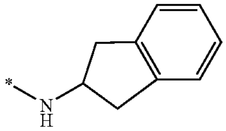 | Me | H | $M^+$ + H:360 (ESI) |
| 231 | 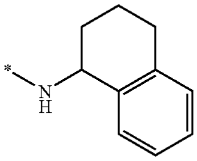 | Me | H | $M^+$ + H:374 (ESI) |
| 232 | 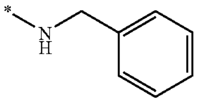 | Me | H | $M^+$ + H:334 (ESI) |
| 233 | 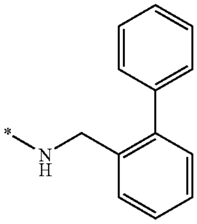 | Me | H | $M^+$ + H:410 (ESI) |

TABLE 7-continued
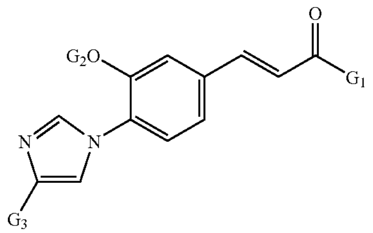
| Example | $G_1$ | $G_2$ | $E_3$ | DATA: MS m/z |
|---|---|---|---|---|
| 234 | 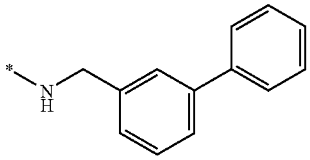 | Me | H | $M^+$ + H:410 (ESI) |
| 235 | 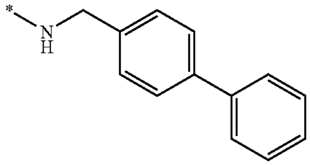 | Me | H | $M^+$ + H:410 (ESI) |
| 236 | 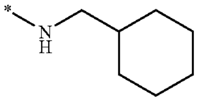 | Me | H | $M^+$ + H:340 (ESI) |
| 237 | 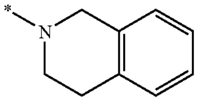 | Me | H | $M^+$ + H:360 (ESI) |
| 238 | 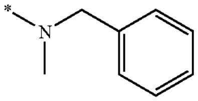 | Me | H | $M^+$ + H:348 (ESI) |
| 239 | 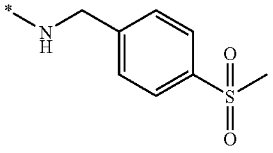 | Me | H | $M^+$ + H:412 (ESI) |
| 240 | 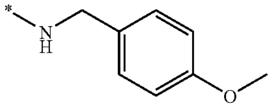 | Me | H | $M^+$ + H:364 (ESI) |
| 241 | 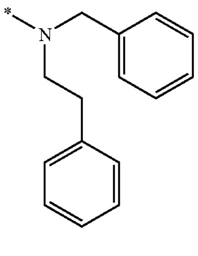 | Me | H | $M^+$ + H:438 (ESI) |

TABLE 7-continued
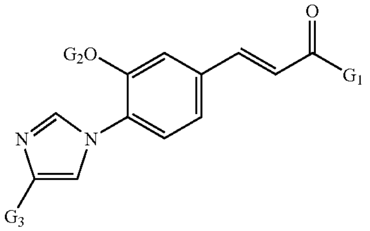
| Example | $G_1$ | $G_2$ | $E_3$ | DATA: MS m/z |
|---|---|---|---|---|
| 242 | 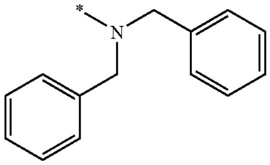 | Me | H | $M^+$ + H:424 (ESI) |
| 243 | 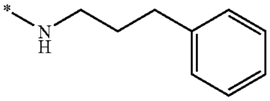 | Me | H | $M^+$ + H:362 (ESI) |
| 244 | 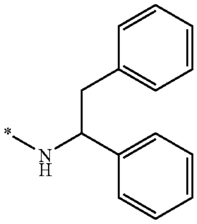 | Me | H | $M^+$ + H:424 (ESI) |
| 245 | 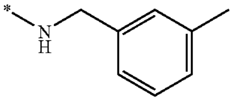 | Me | H | $M^+$ + H:348 (ESI) |
| 246 | 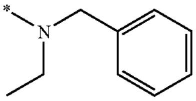 | Me | H | $M^+$ + H:362 (ESI) |
| 247 | 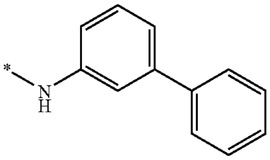 | Me | H | $M^+$ + H:396 (ESI) |
| 248 | 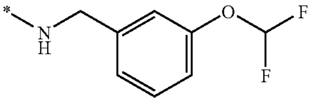 | Me | H | $M^+$ + H:400 (ESI) |
| 249 | 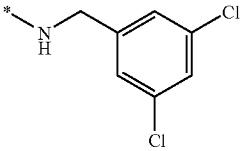 | Me | H | $M^+$ + H:402 (ESI) |

TABLE 7-continued
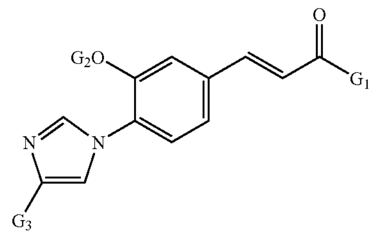
| Example | $G_1$ | $G_2$ | $E_3$ | DATA: MS m/z |
|---|---|---|---|---|
| 250 | 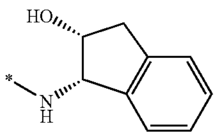 | Me | H | $M^+$ + H:376 (ESI) |
| 251 | 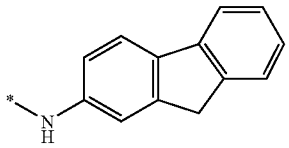 | Me | H | $M^+$ + H:408 (ESI) |
| 252 | 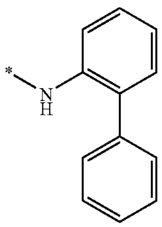 | Me | H | $M^+$ + H:396 (ESI) |
| 253 | 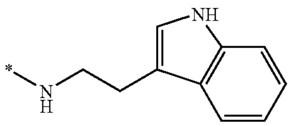 | Me | H | $M^+$ + H:387 (ESI) |
| 254 | 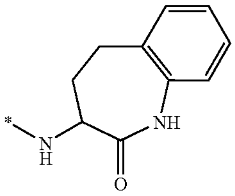 | Me | H | $M^+$ + H:403 (ESI) |
| 255 | 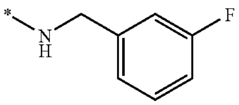 | Me | H | $M^+$ + H:352 (ESI) |
| 256 | 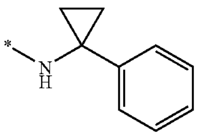 | Me | H | $M^+$ + H:360 (ESI) |
| 257 | 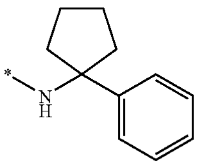 | Me | H | $M^+$ + H:388 (ESI) |

TABLE 7-continued
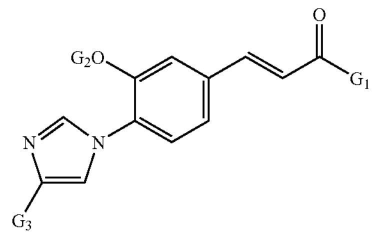
| Example | $G_1$ | $G_2$ | $E_3$ | DATA: MS m/z |
|---|---|---|---|---|
| 258 | 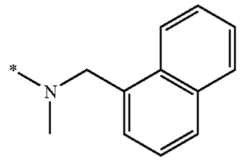 | Me | H | $M^+$ + H:398 (ESI) |
| 259 | 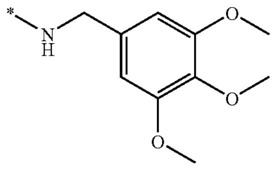 | Me | H | $M^+$ + H:424 (ESI) |
| 260 | 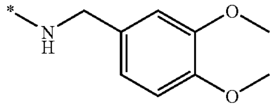 | Me | H | $M^+$ + H:394 (ESI) |
| 261 | 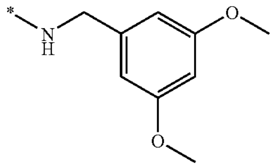 | Me | H | $M^+$ + H:394 (ESI) |
| 262 | 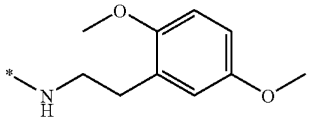 | Me | H | $M^+$ + H:408 (ESI) |
| 263 | 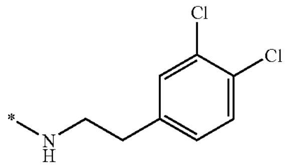 | Me | H | $M^+$ + H:416 (ESI) |
| 264 | 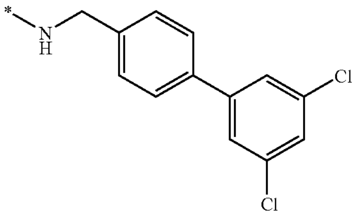 | Me | H | $M^+$ + H:478 (ESI) |
| 265 | 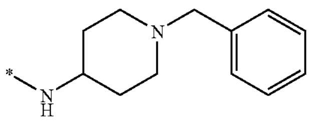 | Me | H | $M^+$ + H:417 (ESI) |

TABLE 7-continued
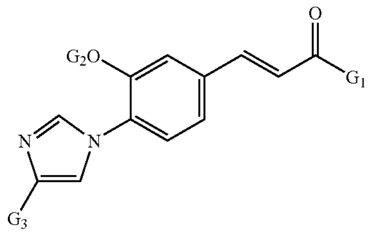
| Example | $G_1$ | $G_2$ | $E_3$ | DATA: MS m/z |
|---|---|---|---|---|
| 266 | 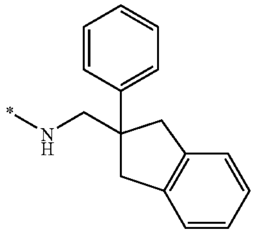 | Me | H | $M^+$ + H:450 (ESI) |
| 267 | 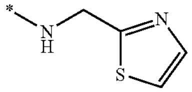 | Me | H | $M^+$ + H:341 (ESI) |
| 268 | 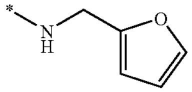 | Me | H | $M^+$ + H:324 (ESI) |
| 269 | 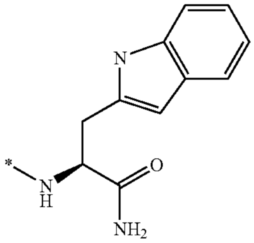 | Me | H | $M^+$ + H:430 (ESI) |
| 270 | 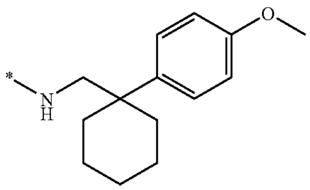 | Me | H | $M^+$ + H:446 (ESI) |
| 271 | 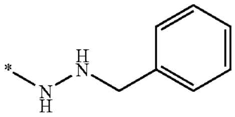 | Me | H | $M^+$ + H:349 (ESI) |
| 272 | 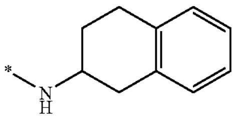 | Me | H | $M^+$ + H:374 (ESI) |

TABLE 7-continued
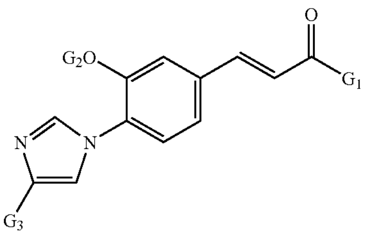
| Example | $G_1$ | $G_2$ | $E_3$ | DATA: MS m/z |
|---|---|---|---|---|
| 273 | 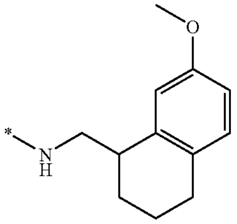 | Me | H | $M^+$ + H:418 (ESI) |
| 274 | 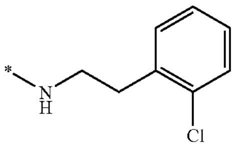 | Me | H | $M^+$ + H:382 (ESI) |
| 275 | 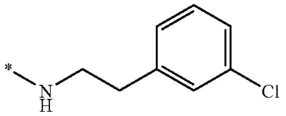 | Me | H | $M^+$ + H:382 (ESI) |
| 276 | 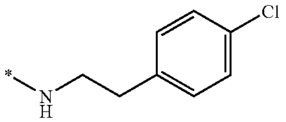 | Me | H | $M^+$ + H:382 (ESI) |
| 277 | 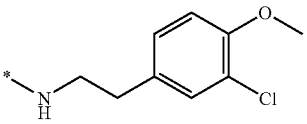 | Me | H | $M^+$ + H:412 (ESI) |
| 278 | 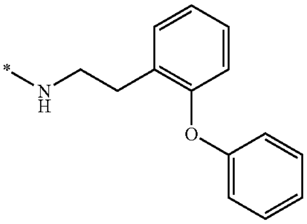 | Me | H | $M^+$ + H:440 (ESI) |
| 279 | 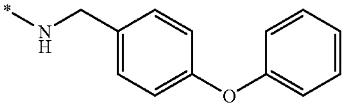 | Me | H | $M^+$ + H:426 (ESI) |
| 280 | 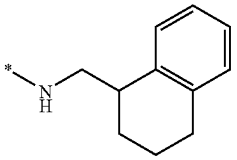 | Me | H | $M^+$ + H:388 (ESI) |

TABLE 7-continued
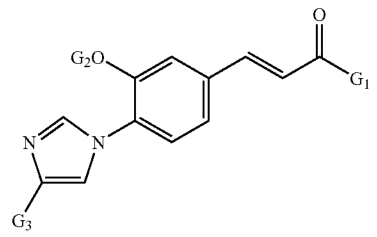
| Example | $G_1$ | $G_2$ | $E_3$ | DATA: MS m/z |
|---|---|---|---|---|
| 281 | 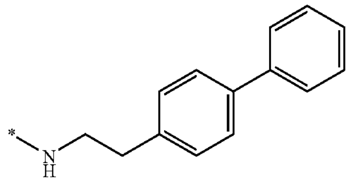 | Me | H | $M^+ + H$:424 (ESI) |
| 282 | 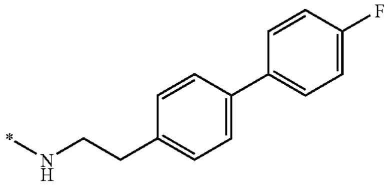 | Me | H | $M^+ + H$:442 (ESI) |
| 283 | 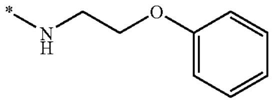 | Me | H | $M^+ + H$:364 (ESI) |
| 284 | 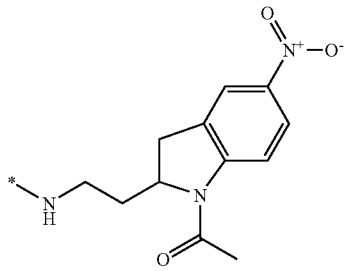 | Me | H | $M^+ + H$:476 (ESI) |
| 285 | 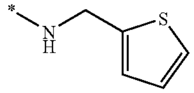 | Me | H | $M^+ + H$:340 (ESI) |
| 286 | 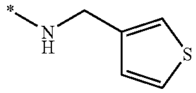 | Me | H | $M^+ + H$:340 (ESI) |
| 287 | 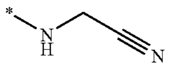 | Me | H | $M^+ + H$:283 (ESI) |
| 288 | 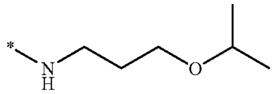 | Me | H | $M^+ + H$:344 (ESI) |
| 289 | 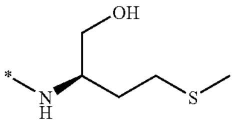 | Me | H | $M^+ + H$:362 (ESI) |

TABLE 7-continued
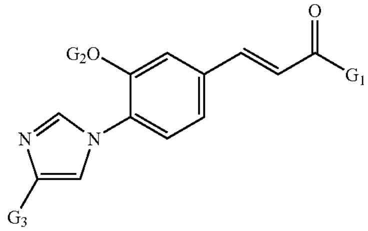
| Example | $G_1$ | $G_2$ | $E_3$ | DATA: MS m/z |
|---|---|---|---|---|
| 290 | 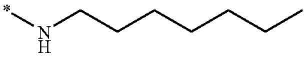 | Me | H | $M^+ + H$:342 (ESI) |
| | 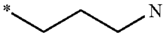 | | | |
| 291 | 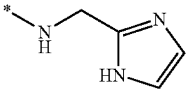 | Me | H | $M^+ + H$:324 (ESI) |
| 292 | 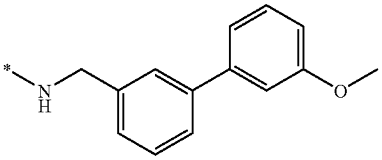 | Me | H | $M^+ + H$:440 (ESI) |
| 293 | 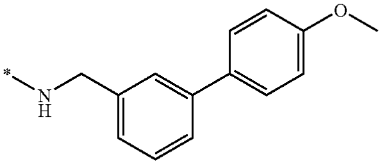 | Me | H | $M^+ + H$:440 (ESI) |
| 294 | 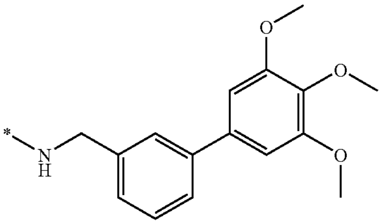 | Me | H | $M^+ + H$:500 (ESI) |
| 295 | 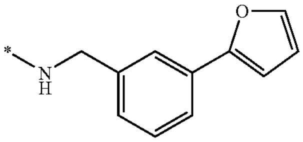 | Me | H | $M^+ + H$:400 (ESI) |
| 296 | 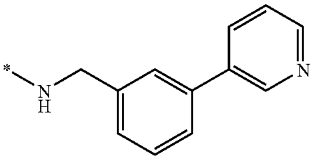 | Me | H | $M^+ + H$:411 (ESI) |
| 297 | 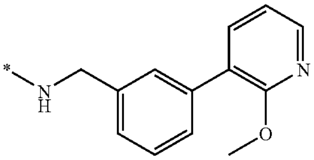 | Me | H | $M^+ + H$:440 (ESI) |

TABLE 7-continued
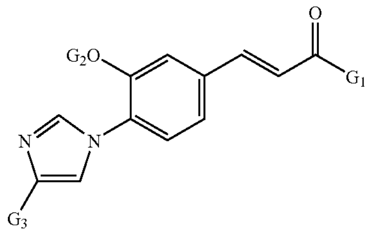
| Example | $G_1$ | $G_2$ | $E_3$ | DATA: MS m/z |
|---|---|---|---|---|
| 298 | 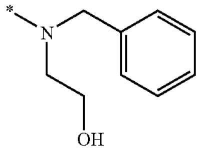 | Me | H | $M^+$ + H:378 (ESI) |
| 299 | 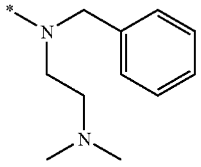 | Me | H | $M^+$ + H:405 (ESI) |
| 300 | 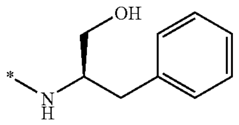 | 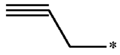 | H | $M^+$ + H:438 (ESI) |
| 301 | 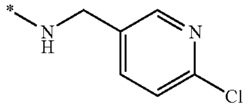 | 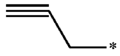 | Me | $M^+$ − H:405 (ESI) |
| 302 | 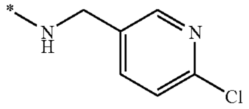 | Me | Me | $M^+$ + H:383 (ESI) |
| 302 | 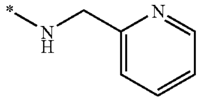 | Me | Me | $M^+$ + H:349 (ESI) |
| 304 | 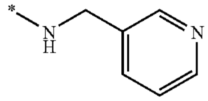 | Me | Me | $M^+$ + H:349 (ESI) |
| 305 | 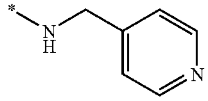 | Me | Me | $M^+$ + H:349 (ESI) |
| 306 | 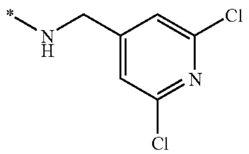 | Me | Me | $M^+$ + H:417 (ESI) |

TABLE 7-continued
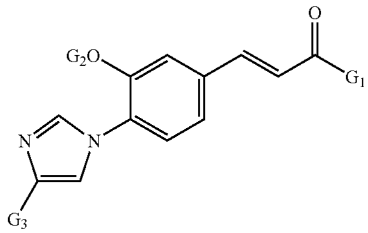
| Example | $G_1$ | $G_2$ | $E_3$ | DATA: MS m/z |
|---|---|---|---|---|
| 307 | 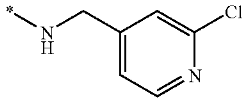 | Me | Me | $M^+$ + H:383 (ESI) |
| 308 | 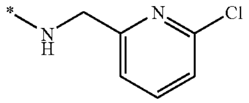 | Me | Me | $M^+$ + H:383 (ESI) |
| 309 | 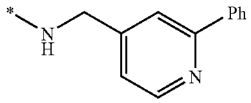 | Me | Me | $M^+$ + H:425 (ESI) |
| 310 | 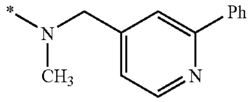 | Me | Me | $M^+$ + H:439 (ESI) |
| 311 | 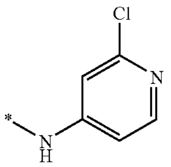 | Me | H | $M^+$ + H:369 (ESI) |
| 312 | 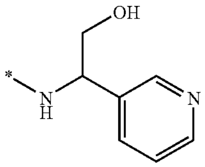 | Me | H | $M^+$ + H:379 (ESI) |
| 313 | 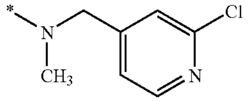 | Me | H | $M^+$ + H:397 (ESI) |
| 314 | 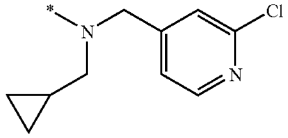 | Me | H | $M^+$ + H:437 (ESI) |
| 315 | 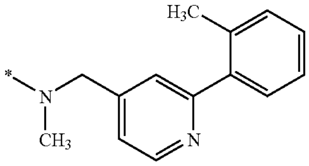 | Me | H | $M^+$ + H:453 (ESI) |

TABLE 7-continued

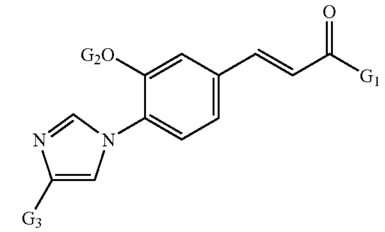

| Example | $G_1$ | $G_2$ | $E_3$ | DATA: MS m/z |
|---|---|---|---|---|
| 316 | 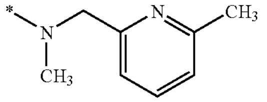 | Me | H | $M^+$ + H:377 (ESI) |
| 317 | 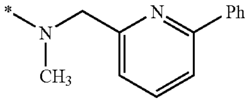 | Me | H | $M^+$ + H:439 (ESI) |
| 318 | 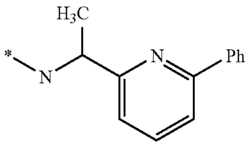 | Me | H | $M^+$ + H:439 (ESI) |
| 319 | 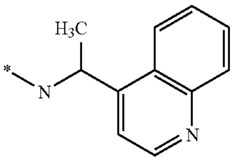 | Me | H | $M^+$ + H:413 (ESI) |

Example 320

Synthesis of (E)-3-[4-(1H-imidazol-1-yl)-3-nitrophenyl]-N-(indan-1-yl)acrylamide

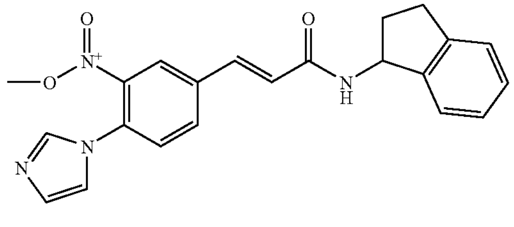

Synthesis of 1-(4-bromo-2-nitro phenyl)-1H-imidazole

Potassium carbonate (1.80 g) and imidazole (667 mg) were added to a DMF (10 mL) solution of 4-bromo-1-fluoro-2-nitro benzene (1.0 mL) one by one, and the reaction solution was agitated at 80° C. for 3 hours and 30 minutes. Water and ethyl acetate were added to the reaction solution, and the organic layer was partitioned. After the obtained organic layer was washed with a saturated saline solution, it was dried over anhydrous magnesium sulfate and 1.04 g of crude bromo compounds was obtained by condensing under reduced pressure. The physical properties of the compound are as follows.

$^1$H-NMR ($CDCl_3$) δ (ppm): 8.15 (d, J=2.0 Hz, 1H), 7.86 (dd, J=2.0, 8.4 Hz, 1H), 7.62 (s, 1H), 7.36 (d, J=8.4 Hz, 1H), 7.22-7.23 (m, 1H), 7.05 (m, 1H).

Synthesis of (E)-3-[4-(1H-imidazol-1-yl)-3-nitrophenyl]-N-(indan-1-yl)acrylamide 21.0 mg of the title compound was obtained from 1-(4-bromo-2-nitrophenyl)-1H-imidazole (40.0 mg) and N-(indan-1-yl)acrylamide (42.0 mg) obtained in the Example 9. The physical properties of the compound are as follows.

$^1$H-NMR ($CDCl_3$) δ (ppm): 8.11 (d, J=2.0 Hz, 1H), 7.79 (dd, J=2.0, 8.0 Hz, 1H), 7.73 (d, J=16 Hz, 1H), 7.63 (s, 1H), 7.47 (d, J=8.0 Hz, 1H), 7.34 (d, J=7.2 Hz, 1H), 7.22-7.29 (m, 4H), 7.07 (s, 1H), 6.56 (d, J=16 Hz, 1H), 6.13 (brd, J=8.0 Hz, 1H), 5.64 (q, J=8.0 Hz, 1H), 3.04 (ddd, J=4.4, 8.8, 16 Hz, 1H), 2.93 (td, J=8.0, 16 Hz, 1H), 2.68 (dtd, J=4.4, 8.0, 12 Hz, 1H), 1.87-1.36 (m, 1H).

Example 321

Synthesis of (E)-3-[3-cyano-4-(1H-imidazol-1-yl)-phenyl]-N-(indan-1-yl)acrylamide

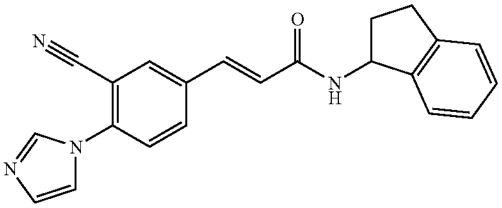

Synthesis of 5-bromo-2-(1H-imidazol-yl)-benzonitrile

Potassium carbonate (1.80 g) and imidazole (667 mg) were added to a DMF (10 mL) solution of 5-bromo-2-fluorobenzonitrile (1.78 g) one by one, and the reaction solution was agitated at 80° C. for 3 hours and 30 minutes. Water and ethyl acetate were added to the reaction solution, and the organic layer was partitioned. After the obtained organic layer was washed with a saturated saline solution, it was dried over anhydrous magnesium sulfate and 1.07 g of crude bromo compounds was obtained by condensing under reduced pressure. The physical properties of the compound are as follows.

$^1$H-NMR ($CDCl_3$) δ (ppm): 7.95 (d, J=2.4 Hz, 1H), 7.84-7.88 (m, 2H), 7.34-7.36 (m, 2H), 7.29 (brs, 1H)

Synthesis of (E)-3-[3-cyano-4-(1H-imidazol-1-yl)-phenyl)-N-indan-1-yl-acrylamide By the same method as in Example 9, 5.20 mg of the title compound was obtained from 5-bromo-2-(1H-imidazol-1-yl)benzonitrile (38.0 mg) and N-indan-1-yl-acrylamide (42.0 mg). The physical properties of the compound are as follows.

$^1$H-NMR ($CDCl_3$) δ (ppm): 7.91 (d, J=1.6 Hz, 1H), 7.85 (s, 1H), 7.81 (dd, J=2.0, 8.4 Hz, 1H), 7.66 (d, J=16 Hz, 1H), 7.45 (d, J=8.4 Hz, 1H), 7.36 (s, 1H), 7.33 (d, J=4.8 Hz, 1H), 7.20-7.28 (m, 4H), 6.54 (d, J=16 Hz, 1H), 6.33 (brs, 1H), 5.63 (q, J=8.4 Hz, 1H), 3.02 (ddd, J=4.8, 8.4, 16 Hz, 1H), 2.88-2.99 (m, 1H), 2.62-2.71 (m, 1H), 1.86-1.96 (m, 1H).

Example 322

Synthesis of (E)-3-[3-amino-4-(1H-imidazol-1-yl)-phenyl]-N-indan-1-yl-acrylamide

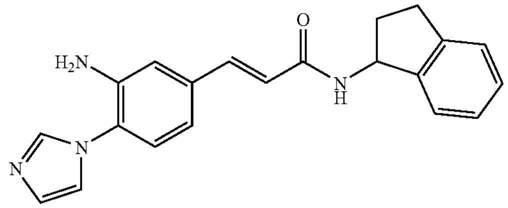

Synthesis of 5-bromo-2-(1H-imidazol-1-yl)-phenylamine

To a solution of 1-(4-bromo-2-nitro phenyl)-1H-imidazole (500 mg) in methylene chloride (10 mL) and methanol (10 mL) at 0° C. nickel hexahydrate (22.0 mg) and sodium borohydride (177 mg) were added one by one, and the reaction solution was agitated for 20 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ m NH; elution solvent:hexane:ethyl acetate=1:1→ethyl acetate), and 431 mg of the title compound was obtained. The physical properties of the compound are as follows.

$^1$H-NMR ($CDCl_3$) δ (ppm): 7.61 (s, 1H), 7.25 (s, 1H), 7.09 (s, 1H), 6.99-6.70 (m, 1H), 6.97 (d, J=8.4 Hz, 1H), 6.94 (m, 1H), 3.78 (brs, 2H).

Synthesis of (E)-3-[3-amino-4-(1H-imidazol-1-yl)-phenyl)-N-indan-1-yl-acrylamide By the same method as in Example 9, 249 mg of the title compound was obtained-from 5-bromo-2-(1H-imidazol-1-yl)-phenylamine (200 mg) and N-indan-1-yl-acrylamide (236 mg). The physical properties of the compound are as follows.

$^1$H-NMR ($CDCl_3$) δ (ppm): 7.64 (s, 1H), 7.62 (d, J=16 Hz, 1H), 7.34 (d, J=6.8 Hz, 1H), 7.22-7.29 (m, 4H), 7.13 (s, 1H), 7.11 (d, J=7.6 Hz, 1H), 6.94-6.98 (m, 2H), 6.39 (d, J=16 Hz, 1H), 5.93 (d, J=8.0 Hz, 1H), 5.64 (q, J=8.0 Hz, 1H), 3.77 (brs, 2H), 3.03 (ddd, J=4.4, 8.8, 16 Hz, 1H), 2.93 (td, J=8.0, 16 Hz, 1H), 2.67 (dtd, J=4.4, 8.0, 13 Hz, 1H), 1.85-1.94 (m, 1H).

Example 323

Synthesis of (Z)-3-[4-(1H-imidazol-1-yl)-3-methoxyphenyl]-N-indan-1-yl-acrylamide

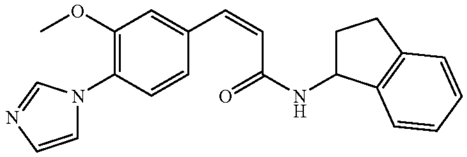

To a THF (7.0 mL) solution of 4-(1H-imidazol-1-yl)-3-methoxy benzaldehyde (300 mg) obtained in Example 328, 18-crown-6 (2.0 g) and potassium bis(trimethylsilyl)amide (0.5M toluene solution, 4.4 mL) and (bis-(2,2,2,-trifluoroethoxy)phosphoryl)ethyl acetate ester (470 μL) were added at −78° C., and the reaction solution was agitated overnight at room temperature. A saturated ammonium chloride solution and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH and elution solvent:hexane:ethyl acetate=1:1→ethyl acetate), and 306 mg of ester product was obtained as an isomer mixture (E:Z=1:5.5). 2N sodium hydroxide solution (5.0 mL) was added to a THF (5.0 mL) solution of the obtained ester product, and the reaction solution was agitated at room temperature overnight. The isomer compound impurities were separated by cooling the reaction solution at 0° C., adding 2N hydrochloric acid to the reaction solution, and filtering off the deposited precipitation by Kiriyama funnel. The obtained filtrate was concentrated under reduced pressure and 253 mg of crude carboxylic acid was obtained. TEA (507 μL), 1-aminoindane (133 μL), and PYBOP (812 mg) were added to a DMF (5.0 mL) solution of the obtained carboxylic acid one by one, and the reaction solution was agitated at room temperature for 1 hour. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane:ethyl acetate=1:1→ethyl acetate), and 9.0 mg of the title compound was obtained. The physical properties of the compound are as follows.

$^1$H-NMR ($CDCl_3$) δ (ppm): 7.81 (s, 1H), 7.41 (s, 1H), 7.21-7.29 (m, 5H), 7.13-7.18 (m, 3H), 6.79 (d, J=12 Hz, 1H), 6.09 (d, J=12 Hz, 1H), 5.83 (brd, J=7.6 Hz, 1H), 5.52 (q, J=7.6 Hz, 1H), 3.87 (s, 3H), 2.82-2.96 (m, 2H), 2.59 (dtd, J=4.8, 7.6, 12 Hz, 1H), 1.70-1.79 (m, 1H).

Example 324

Synthesis of (E)-3-[3-fluoro-4-(1H-imidazol-1-yl)-phenyl]-N-indan-1-yl-acrylamide

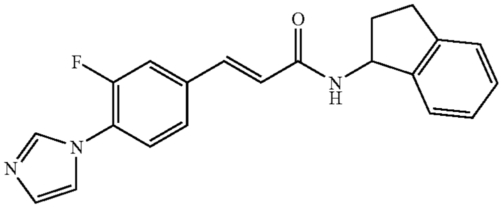

Synthesis of 3-fluoro-4-(1H-imidazol-1-yl)-benzaldehyde

Potassium carbonate (1.71 g) and imidazole (847 mg) were added to a DMF (20 mL) solution of 3,4-difluorobenzaldehyde (2.0 g). The reaction solution was agitated at 100° C. overnight, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane: ethyl acetate=1:1→ethyl acetate), and 1.11 g of the title compound was obtained. The physical properties of the compound are as follows.

The physical properties of the compound are as follows.

$^1$H-NMR ($CDCl_3$) δ (ppm): 10.0 (s, 1H), 7.96 (s, 1H), 7.82 (d, J=7.2 Hz, 2H), 7.61 (t, J=7.2 Hz, 1H), 7.36 (s, 1H), 7.27 (s, 1H).

Synthesis of (E)-3-[3-fluoro-4-(1H-imidazol-1-yl) phenyl)acrylic acid

By the same method as in Example 111, 1.66 g of the title compound was obtained from 3-fluoro-4-(1H-imidazol-1-yl)-benzaldehyde (1.40 g) and dimethylphosphonoacetic acid methyl ester (1.40 mL). The physical properties of the compound are as follows.

$^1$H-NMR (DMSO-d6) δ (ppm): 8.10 (s, 1H), 7.93 (d, J=13 Hz, 1H), 7.70-7.71 (m, 2H), 7.63 (s, 1H), 7.62 (d, J=16 Hz, 1H), 7.15 (s, 1H), 6.69 (d, J=16 Hz, 1H).

Synthesis of (E)-3-[3-fluoro-4-(1H-imidazol-1-yl) phenyl)-N-(indan-1-yl)acrylamide To a DMF (4.0 mL) solution of (E)-3-[3-fluoro-4-(1H-imidazol-1-yl)phenyl]acrylic acid (100 mg), TEA (167 μL), 1-aminoindane (83.0 μL) and PYBOP (448 mg) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane: ethyl acetate=1:1→ethyl acetate), and 95.0 mg of the title compound was obtained. The physical properties of the compound are as follows.

$^1$H-NMR ($CDCl_3$) δ (ppm): 7.82 (s, 1H), 7.64 (d, J=16 Hz, 1H), 7.40 (s, 1H), 7.37-7.38 (m, 2H), 7.32 (d, J=7.2 Hz, 1H), 7.20-7.28 (m, 5H), 6.43 (d, J=16 Hz, 1H), 6.02-6.14 (br, 1H), 5.62 (q, J=7.2 Hz, 1H), 3.02 (ddd, J=4.4, 8.8, 16 Hz, 1H), 2.91 (td, J=8.0, 16 Hz, 1H), 2.62-2.70 (m, 1H), 1.85-1.94 (m, 1H)

Example 325

Synthesis of (E)-3-[3-fluoro-4-(1H-imidazol-1-yl) phenyl)-N-methylacrylamide

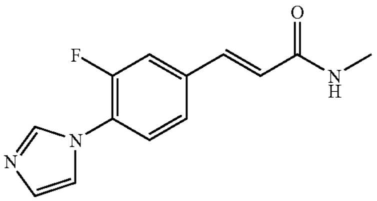

By the same method as in Example 324, 17.5 mg of the title compound was obtained from (E)-3-[3-fluoro-4-(1H-imidazol-1-yl)phenyl]acrylic acid (60.0 mg) and methylamine (650 μL). The physical properties of the compound are as follows.

$^1$H-NMR ($CDCl_3$) δ (ppm): 7.86 (s, 1H), 7.61 (d, J=16 Hz, 1H), 7.42 (d, J=8.4 Hz, 1H), 7.36-7.42 (m, 2H), 7.23-7.29 (m, 2H), 6.40 (d, J=16 Hz, 1H), 5.66 (brs, 1H), 2.97 (d, J=4.8 Hz, 3H)

Example 326

Synthesis of (E)-3-[3-fluoro-4-(1H-imidazol-1-yl) phenyl)-N-phenylacrylamide

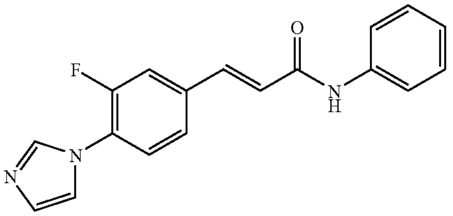

By the same method as in Example 324, 32 mg of the title compound was obtained from (E)-3-[3-fluoro-4-(1H-imidazol-1-yl)phenyl]acrylic acid (50.0 mg) and aniline (29.0 μL). The physical properties of the compound are as follows.

$^1$H-NMR ($CDCl_3$) δ (ppm): 7.94 (brs, 1H), 7.88 (s, 1H), 7.72 (d, J=16 Hz, 1H), 7.67 (d, J=7.6 Hz, 1H), 7.41-7.45 (m, 3H), 7.37 (t, J=8.0 Hz, 1H), 7.30 (d, J=1.2 Hz, 1H), 7.24-7.27 (m, 3H), 7.16 (t, J=8.0 Hz, 1H), 6.64 (d, J=16 Hz, 1H).

Example 327

Synthesis of (E)-3-[3-fluoro-4-(1H-imidazol-1-yl) phenyl)-N-(4-methoxybenzyl)acrylamide

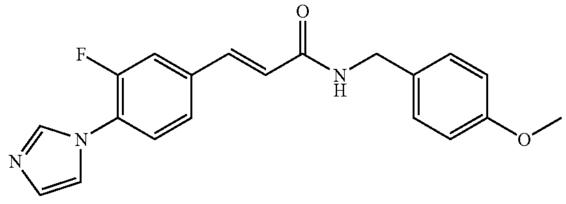

By the same method as in Example 324, 55.0 mg of the title compound was obtained from 3-[3-fluoro-4-(1H-imidazol-1-yl)phenyl]acrylic acid (50.0 mg) and 4-methoxybenzylamine (42.0 μL). The physical properties of the compound are as follows.

$^1$H-NMR ($CDCl_3$) δ (ppm): 7.86 (s, 1H), 7.63 (d, J=16 Hz, 1H), 7.35-7.42 (m, 3H), 7.23-7.28 (m, 4H), 6.88 (td, J=2.0, 8.8 Hz, 2H), 6.43 (d, J=16 Hz, 1H), 6.05 (brs, 1H), 4.52 (d. J=6.0 Hz, 2H), 3.80 (s, 3H).

Example 328

Synthesis of (E)-3-[4-(1H-imidazol-1-yl)-3-methoxyphenyl]-N-indan-1-yl-acrylamide

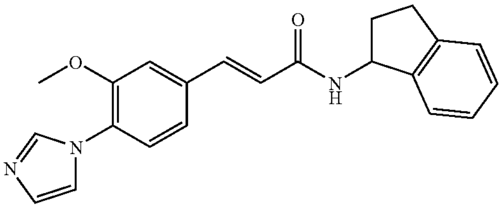

Synthesis of 4-(1H-imidazol-1-yl)-3-methoxybenzaldehyde

Potassium carbonate (2.0 g) and imidazole (662 mg) were added to a DMF (20 mL) solution of 4-fluoro-3-methoxybenzaldehyde (1.50 g). The reaction solution was agitated at 80° C. overnight, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:hexane: ethyl acetate=3:1→ethyl acetate→ethyl acetate:methanol=10:1), and 960 mg of the title compound was obtained. The physical properties of the compound are as follows.

$^1$H-NMR ($CDCl_3$) δ (ppm): 10.0 (s, 1H), 7.92 (s, 1H), 7.56-7.60 (m, 2H), 7.48 (d, J=7.6 Hz, 1H), 7.30 (s, 1H), 7.21 (s, 1H), 3.98 (s, 3H).

Synthesis of (E)-3-[4-(1H-imidazol-1-yl)-3-methoxyphenyl]acrylic acid 11.9 g of the title compound was obtained from 4-(1H-imidazol-1-yl)-3-methoxybenzaldehyde (13.2 g) by the same method as in Example 111. The physical properties of the compound are as follows.

$^1$H-NMR (DMSO-d6) δ (ppm): 7.96 (t, J=1.2 Hz, 1H), 7.63 (d, J=16 Hz, 1H), 7.59 (d, J=1.6 Hz, 1H), 7.48 (t, J=1.2 Hz, 1H), 7.45 (d, J=8.0 Hz, 1H), 7.38 (dd, J=1.6 Hz, 8.0 Hz, 1H), 7.06 (t, J=1.2 Hz, 1H), 6.68 (d, J=16 Hz, 1H), 3.89 (s, 3H).

Synthesis of (E)-3-[4-(1H-imidazol-1-yl)-3-methoxyphenyl]-N-indan-1-yl-acrylamide By the same method as in Example 111, 142 mg of the title compound was obtained from (E)-3-[4-(1H-imidazol-1-yl)-3-methoxyphenyl]acrylic acid (100 mg) and 1-aminoindane (53.0 μL). The physical properties of the compound are as follows.

$^1$H-NMR ($CDCl_3$) δ (ppm): 7.85 (s, 1H), 7.69 (d, J=16 Hz, 1H), 7.35 (d, J=6.8 Hz, 1H), 7.16-7.29 (m, 8H), 6.44 (d, J=16 Hz, 1H), 5.92 (d, J=8.4 Hz, 1H), 5.65 (q, J=8.4 Hz, 1H), 3.88 (s, 3H), 3.04 (ddd, J=4.0, 8.8, 16 Hz, 1H), 2.91-2.96 (m, 1H), 2.64-2.72 (m, 1H), 1.86-1.95 (m, 1H).

Example 329

Synthesis of (E)-N-{3-[1-(4-fluorophenyl)-6-methyl-indan-1-yl]propyl}-3-[3-methoxy-4-(4-methyl-1H-imidazol-1-yl)phenyl]acrylamide and (E)-N-{3-[1-(4-fluorophenyl)-4-methyl-indan-1-yl]propyl}-3-[3-methoxy-4-(4-methyl-1H-imidazol-1-yl)phenyl] acrylamide

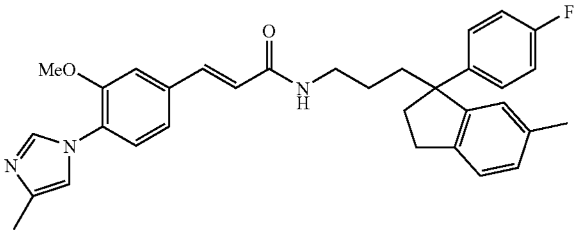

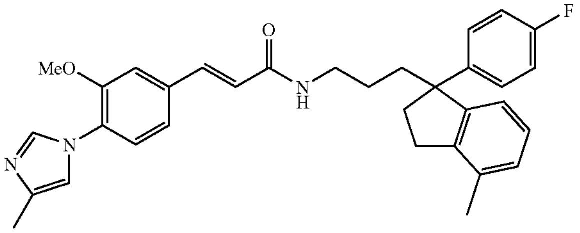

p-Toluenesulfonate monohydrate (95 mg) was added to a toluene (10 mL) solution of 1-[4-(4-fluorophenyl)-4-hydroxyazepan-1-yl]-3-[3-methoxy-4-(4-methyl-1H-imidazol-1-yl)phenyl]propenone (45 mg) obtained in Example 350. Heating refluxing of the reaction solution was carried out for 3 hours. Water was added to the reaction solution after the reaction ended, and the reaction solution extracted with ethyl acetate, and the organic layer was washed with a saturated sodium bicarbonate and also a saturated sodium chloride solution. The partitioned organic layer the solvent was dried over anhydrous magnesium sulfate and evaporated under reduced pressure. The obtained residue was purified by silica gel column chromatography (elution solvent:ethanol:ethyl acetate=1:10), and 10 mg (19%) of the title compound was obtained. The physical properties of the compound are as follows.

$^1$H-NMR ($CDCl_3$) δ(ppm): 1.50 (m, 2H), 2.04 (m, 1H), 2.13 (m, 1H), 2.24 (m, 1H), 2.36 (m, 1H), 2.30 (s, 3H), 2.35 (s, 3H), 2.83 (m, 2H), 3.36 (m, 2H), 3.87 (s, 3H), 5.79 (br.s, 1H), 6.36 (d, J=16.0 Hz, 1H), 6.92 (m, 1H), 6.925 (m, 1H), 6.93 (m, 1H), 7.04 (d, J=8.0 Hz, 1H), 7.11 (br.s, 1H), 7.15 (d, J=8.0 Hz, 1H), 7.16 (d, J=8.0 Hz, 1H), 7.20 (m, 2H) +7.23 (d, J=8.0 Hz, 1H), 7.59 (d, J=16.0 Hz, 1H), 7.71 (s, 1H).

ESI-MS; m/z524 [$M^+$+H]. $^1$H-NMR ($CDCl_3$) δ: 1.50 (m, 2H), 2.04 (m, 1H), 2.13 (m, 1H), 2.24 (m, 1H), 2.36 (m, 1H), 2.26 (s, 3H), 2.30 (s, 3H), 2.78 (m, 1H), 2.82 (m, 1H), 3.36 (m, 2H), 3.87 (s, 3H), 5.79 (br.s, 1H), 6.35 (d, J=16.0 Hz, 1H), 6.925 (m, 1H), 6.93 (m, 2H), 6.98 (m, 1H), 7.03 (d, J=8.0 Hz, 1H), 7.11 (br.s, 1H), 7.15 (d, J=8.0 Hz, 1H), 7.16 (d, J=8.0 Hz, 1H), 7.20 (m, 2H), 7.23 (d, J=8.0 Hz, 1H), 7.59 (d, J=16.0 Hz, 1H), 7.71 (s, 1H).

Example 330

Synthesis of (E)-3-[3-fluoro-4-(1H-imidazol-1-yl) phenyl)-N-indan-1-yl-N-methyl-acrylamide

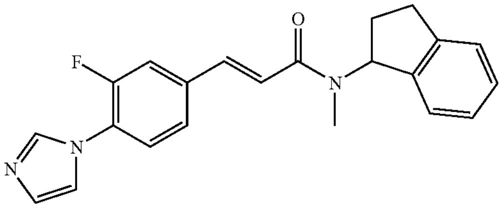

To a DMF (1.0 mL) solution of (E)-3-[3-fluoro-4-(1H-imidazol-1-yl)phenyl]-N-indan-1-yl-acrylamide (30.0 mg) obtained in Example 324, sodium hydride was added at 0° C. (10.0 mg), and the reaction solution was allowed to be warmed to room temperature. Iodomethane (54.0 μL) was added to the reaction solution, the reaction solution was agitated at room temperature for 3 hours, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex NH, elution solvent heptane-ethyl acetate=1:1), and 8.5 mg of the title compound was obtained. The physical properties of the compound are as follows.

$^1$H-NMR ($CDCl_3$) δ (ppm): 7.86 (s, 0.5H), 7.85 (s, 0.5H), 7.74 (d, J=16 Hz, 0.5H), 7.68 (d, J=16 Hz, 0.5H), 7.38-7.47 (m, 3H), 7.13-7.28 (m, 6H), 7.06 (d, J=16 Hz, 0.5H), 6.95 (d, J=16 Hz, 0.5 Hz), 6.41 (t, J=8.0 Hz, 0.5H), 5.67 (t, J=8.0 Hz, 0.5H), 3.00-3.12 (m, 1H), 2.94 (td, J=8.4 Hz, 16 Hz, 1H), 2.80 (s, 1.5H), 2.88 (s, 1.5H), 2.43-2.55 (m, 1H), 2.10-2.20 (m, 0.5H), 1.89-2.00 (m, 0.5H).

Example 331

Synthesis of (E)-N-((1R)-formyl-2-phenylethyl)-3-[3-methoxy-4-(4-methyl-1H-imidazol-1-yl)phenyl] acrylamide

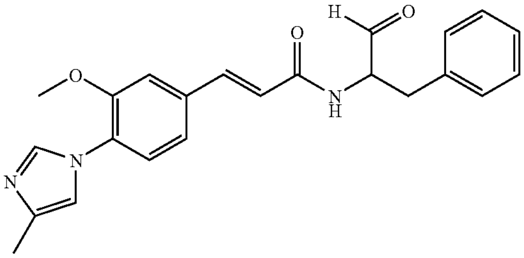

Dimethylsulfoxide (136 μL) was added to a methylene chloride (3 mL) solution of oxalyl chloride (100 μL) at −78° C. and the reaction solution was agitated for 15 minutes. Next, the methylene chloride (2.0 mL) solution of (E)-N-[(1R)-1-hydroxymethyl-2-phenylethyl)-3-(3-methoxy-4-(4-methyl-1H-imidazol-1-yl)phenyl)acrylamide (150 mg) obtained in Example 124 was added to this reaction solution, and the reaction solution was agitated for 15 minutes. then, TEA (534 μL) was added to this reaction solution to warm the reaction solution up to 0° C., it was agitated for 30 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate: ethanol=10:1), and 62.0 mg of the title compound was obtained. The physical properties of the compound are as follows.

$^1$H-NMR ($CDCl_3$) δ (ppm): 9.72 (s, 1H), 7.73 (s, 1H), 7.64 (d, J=16 Hz, 1H), 7.25-7.34 (m, 4H), 7.16-7.20 (m, 3H), 7.14 (s, 1H), 6.93 (s, 1H), 6.45 (d, J=16 Hz, 1H), 6.33 (brs, 1H), 4.92 (dd, J=5.6, 7.2 Hz, 1H), 3.89.(s, 3H), 3.32 (dd, J=5.6, 14 Hz, 1H), 3.25 (dd, J=7.2, 14 Hz, 1H), 2.30 (s, 3H).

Example 332

Synthesis of (E)-3-[3-methoxy-4-(4-(1H-methylimidazol-1-yl)-phenyl]-N-((1R)-morpholin-4-ylmethyl-2-phenylethyl)acrylamide

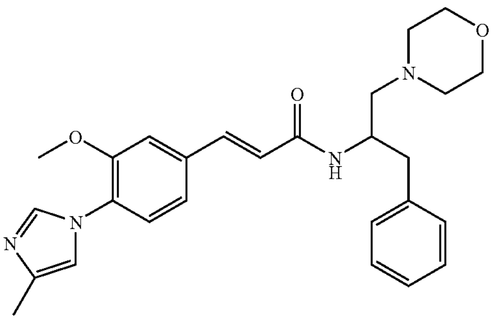

To a methylene chloride (1.0 mL) solution of (E)-N-((1R)-formyl-2-phenylethyl)-3-[3-methoxy-4-(4-methyl-1H-imidazol-1-yl)phenyl]acrylamide (39.0 mg) obtained in Example 331, morpholine (13.0 μL), acetic acid (1.0 mL) and sodium triacetoxy borohydride (64.0 mg) were added one by one. After agitating the reaction solution at room temperature overnight, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, an elution solvent: ethyl acetate→ethyl acetate:ethanol=10:1), and 13.9 mg of the title compound was obtained. The physical properties of the compound are as follows.

$^1$H-NMR (CDCl3) δ (ppm): 7.70 (s, 1H), 7.59 (d, J=16 Hz, 1H), 7.14-7.32 (m, 7H), 7.12 (s, 1H), 6.92 (s, 1H), 6.38 (d, J=16 Hz, 1H), 5.88 (d, J=7.2 Hz, 1H), 4.39-4.47 (m, 1H), 3.88 (s, 3H), 3.64-3.71 (m, 4H), 3.03 (dd, J=4.8, 14 Hz, 1H), 2.97 (dd, J=6.4, 14 Hz, 1H), 2.48-2.55 (m, 2H), 2.31-2.42 (m, 4H), 2.30 (s, 3H).

Example 333

Synthesis of (E)-N-[(1R)-1-(cis-2,6-dimethylmorpholin-4-ylmethyl)-2-phenylethyl]-3-[3-methoxy-4-(4-methyl-1H-imidazol-1-yl)phenyl]acrylamide

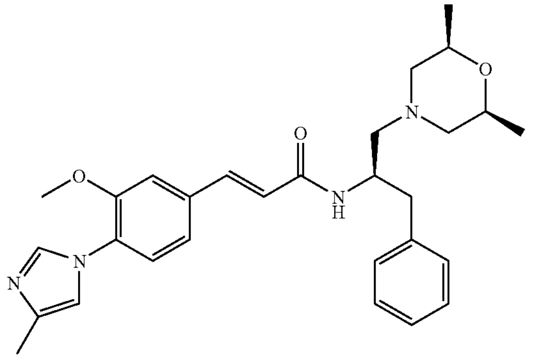

5.2 mg of the title compound was obtained by the same method as in Example 332 from (E)-N-((1R)-formyl-2-phenylethyl)-3-[3-methoxy-4-(4-methyl-1H-imidazol-1-yl)phenyl]acrylamide (25.0 mg) and cis-2 and 6-dimethylmorpholine (23.7 μL) obtained in Example 331. The physical properties of the compound are as follows.

$^1$H-NMR ($CDCl_3$) δ (ppm): 7.72 (d, J=1.2 Hz, 1H), 7.61 (d, J=16 Hz, 1H), 7.29-7.33 (m, 2H), 7.17-7.26 (m, 5H), 7.13 (d, J=1.2 Hz, 1H), 6.93 (t, J=1.2 Hz, 1H), 6.38 (d, J=16 Hz, 1H), 5.82 (d, J=6.8 Hz, 1H), 4.38-4.46 (m, 1H), 3.89 (s, 3H), 3.58-3.69 (m, 2H), 3.05 (dd, J=4.8, 14 Hz, 1H), 2.97 (dd, J=6.4, 14 Hz, 1H), 2.67-2.71 (m, 2H), 2.39 (dd, J=9.2, 13 Hz, 1H), 2.28-2.33 (m, 1H), 2.30 (s, 3H), 1.85 (t, J=12 Hz, 1H), 1.67 (t, J=12 Hz, 1H), 1.13-1.16 (m, 6H).

Example 334

Synthesis of (E)-N-(1-benzyl-2-hydroxy propyl)-3-[3-methoxy-4-(4-methyl-1H-imidazol-1-yl)phenyl] acrylamide

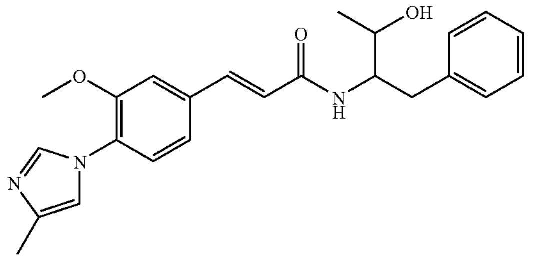

To a THF (3.0 mL) solution of the (E)-N-((1R)1-formyl-2-phenylethyl)-3-[(3-methoxy-4-(4-methyl-1H-imidazol-1-yl)phenyl]acrylamide (100 mg) obtained in Example 331, methyl magnesium chloride (3 MTHF solution, 0.17 mL) was added at −78° C. After warming the reaction solution to room temperature, it was agitated for 3 hours and 30 minutes, and methyl magnesium chloride (3 MTHF solution, 0.51 mL) was added to the reaction solution. The reaction solution was agitated at room temperature overnight, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate: ethanol=10:1), and 33.0 mg of the title compound was obtained as an isomer mixture. The physical properties of the compound are as follows.

$^1$H-NMR ($CDCl_3$) δ (ppm): 7.70 (m, 1H), 7.59 (d, J=16H, 0.5H), 7.53 (d, J=16 Hz, 0.5H), 7.06-7.35 (m, 8H), 6.92-6.93 (m, 1H), 6.42 (d, J=16 Hz, 0.5H), 6.32 (d, J=16 Hz, 0.5H), 5.92-6.30 (br, 1H), 4.30-4.39 (m, 0.5H), 4.19-4.28 (m, 0.5H), 4.00-4.10 (m, 0.5H), 3.90-3.99 (m, 0.5H), 3.86 (s, 1.5H), 3.83 (s, 1.5H), 2.92-3.02 (m, 2H), 2.29 (s, 3H), 1.10-1.30 (m, 3H).

Example 335

Synthesis of (E)-N-(1-benzyl-2-oxopropyl)-3-[3-methoxy-4-(4-methyl-1H-imidazol-1-yl)phenyl] acrylamide

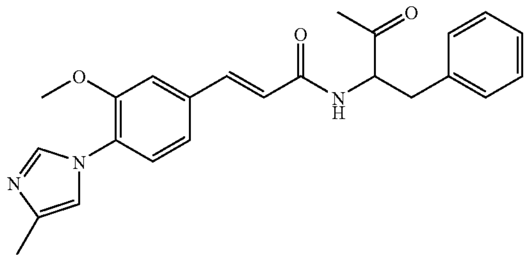

To a methylene chloride (2.0 mL) solution of (E)-N-(1-benzyl-2-hydroxy propyl)-3-[3-methoxy-4-(4-methyl-1H-imidazol-1-yl)phenyl]acrylamide (29.0 mg), Dess-Martin reagent (60.7 mg) was added. After agitating the reaction solution at room temperature for 4 hours and 30 minutes, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate ethanol=10:1), and 15.4 mg of the title compound was obtained. The physical properties of the compound are as follows.

$^1$H-NMR ($CDCl_3$) δ (ppm): 7.73 (s, 1H), 7.60 (d, J=16 Hz, 1H), 7.27-7.33 (m, 3H), 7.25 (s, 1H), 7.14-7.18 (m, 4H), 6.93 (s, 1H), 6.42 (d, J=16 Hz, 1H), 6.34 (d, J=6.8 Hz, 1H), 5.03 (td, J=5.2, 6.8 Hz, 1H), 3.89 (s, 3H), 3.25 (dd, J=6.8, 14 Hz, 1H), 3.16 (dd, J=5.2, 14 Hz, 1H), 2.30 (s, 3H), 2.23 (s, 3H).

Example 336

Synthesis of (E)-N-(1-benzyl-2-hydroxy-2-methyl-propyl)-3-[3-methoxy-4-(4-methyl-1H-imidazol-1-yl)-phenyl]acrylamide

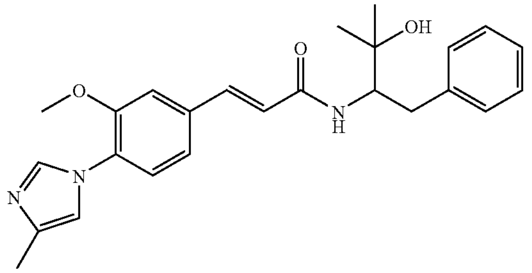

To a THF (1.0 mL) solution of (E)-N-(1-benzyl-2-oxopropyl)-3-[3-methoxy-4-(4-methyl-1H-imidazol-1-yl)phenyl] acrylamide (12.0 mg), methyl magnesium chloride (3 MTHF solution, 198 μL) was added at −78° C., the reaction solution was allowed to be warmed to room temperature and agitated for further 1 hour. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate ethanol=10:1), and 6.8 mg of the title compound was obtained. The physical properties of the compound are as follows.

$^1$H-NMR ($CDCl_3$) δ (ppm): 7.70 (s, 1H), 7.48 (d, J=16 Hz, 1H), 7.18-7.30 (m, 6H), 7.10 (d, J=9.6 Hz, 1H), 7.07 (s, 1H), 6.92 (s, 1H), 6.29 (d, J=16 Hz, 1H), 5.84 (d, J=8.8 Hz, 1H), 4.16-4.23 (m, 1H), 3.86 (s, 3H), 3.20 (dd, J=9.6, 14 Hz, 1H), 2.80 (dd, J=11, 14 Hz, 1H), 2.29 (s, 3H), 1.39 (s, 3H), 1.34 (s, 3H).

Example 337

Synthesis of (E)-3-[3-methoxy-4-(4-methyl-1H-imidazol-1-yl)phenyl]-1-(3-phenylpyrrolidine-1-yl)propenone

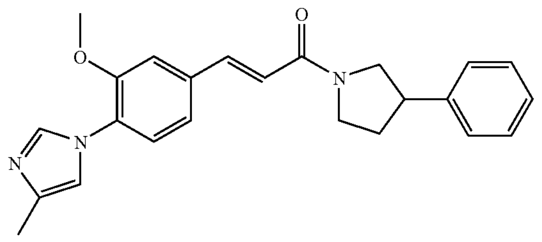

By the same method as in Example 121, 65 mg (62%) of the title compound was obtained from (E)-3-[3-methoxy-4-(4-methyl-1H-imidazol-1-yl)phenyl]acrylic acid (70 mg) and 3-phenylpyrrolidine (40 mg). The physical properties of the compound are as follows.

ESI-MS; m/z388 [M$^+$+H]. $^1$H-NMR (DMSO-$d_6$) δ: 1.99-2.22 (m, 1H), 2.28 (s, 1.5H), 2.29 (s, 1.5H), 2.30-2.51 (m, 1H), 3.38-3.81 (m, 3H), 3.85 (s, 1.5H), 3.87 (s, 1.5H), 3.88-4.20 (m, 2H), 6.73 (d, J=15.6 Hz, 0.5H), 6.77 (d, J=15.6 Hz, 0.5H), 6.91 (brs, 0.5H), 6.93 (brs, 0.5H), 7.12-7.39 (m, 8H), 7.68-7.76 (m, 2H).

Example 338

Synthesis of (E)-1-{4-(1H-indol-2-yl)piperidin-1-yl}-3-[3-methoxy-4-(4-methyl-1H-imidazol-1-yl)phenyl]propenone

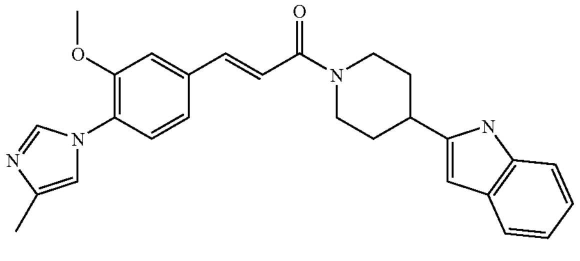

By the same method as in Example 121, 47 mg (43%) of the title compound was obtained from (E)-3-[3-methoxy-4-methyl-1H-imidazol-1-yl)phenyl]acrylic acid (65 mg) and 2-piperidine-4-yl-1H-indol (50 mg). The physical properties of the compound are as follows.

ESI-MS; m/z441 [M$^+$+H]. $^1$H-NMR (DMSO-$d_6$) δ(ppm): 1.70-1.88 (m, 2H), 2.12-2.23 (m, 2H), 2.30 (s, 3H), 2.83-3.11 (m, 2H), 3.27-3.43 (m, 1H), 3.89 (s, 3H), 4.17-4.28 (m, 1H), 4.76-4.87 (m, 1H), 6.27 (s, 1H), 6.93 (brs, 1H), 6.94 (d, J=15.6 Hz, 1H), 7.05-7.28 (m, 5H), 7.33 (d, J=8.0 Hz, 1H), 7.55 (d, J=8.0 Hz, 1H), 7.67 (d, J=15.6H, 1H), 7.74 (s, 1H), 8.25 (brs, 1H).

Example 339

Synthesis of (E)-3-[3-methoxy-4-(4-methyl-1H-imidazol-1-yl)phenyl]-1-(4-pheoxypiperidin-1-yl)propenone

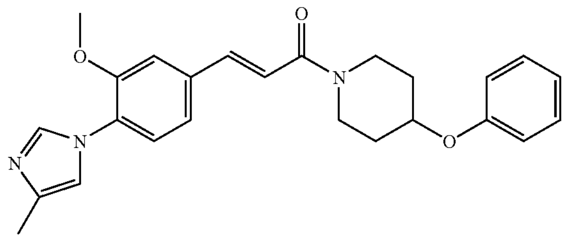

By the same method as in Example 121, 74 mg (91%) of the title compound was obtained from (E)-3-[3-methoxy-4-methyl-1H-imidazol-1-yl)phenyl]acrylic acid (50 mg) and 4-pheoxypiperidine hydrochloride (42 mg). The physical properties of the compound are as follows.

$^1$H-NMR (DMSO-$d_6$) δ(ppm): 1.70-2.10 (m, 4H), 2.30 (s, 3H), 3.62-3.71 (m, 1H), 3.82-3.95 (m, 3H), 3.90 (s, 3H), 4.58-4.65 (m, 1H), 6.88-7.03 (m, 5H), 7.19-7.36 (m, 5H), 7.66 (d, J=15.2 Hz, 1H), 7.73 (s, 1H)

Example 340

Synthesis of (E)-3-[3-methoxy-4-(4-methyl-1H-imidazol-1-yl)phenyl]-1-(6-phenyl-3,4-dihydro-1H-pyrrolo[1,2-a]pyrazine-2-yl)propenone

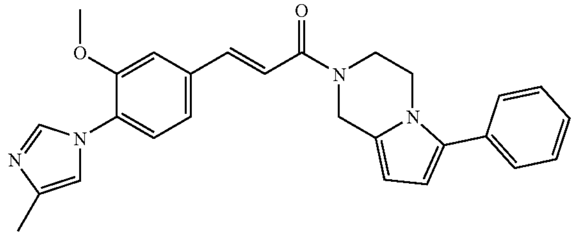

By the same method as in Example 121, 112 mg (94%) of the title compound was obtained from (E)-3-[3-methoxy-4-methyl-1H-imidazol-1-yl)phenyl]acrylic acid (70 mg), 6-phenyl 1, 2, and 3, and 4-tetrahydropyrrolo [1,2-a]pyrazine (54 mg). The physical properties of the compound are as follows.

$^1$H-NMR ($CDCl_3$) δ(ppm): 2.31 (s, 3H), 3.92 (s, 3H), 3.95-4.22 (m, 4H), 4.96-5.03 (m, 2H), 6.11 (d, J=3.2 Hz, 1H), 6.28

(d, J=3.2 Hz, 1H), 6.86-6.97 (m, 2H), 7.17 (brs, 1H), 7.21-7.45 (m, 7H), 7.73 (d, J=15.6 Hz, 1H), 7.74 (brs, 1H).

Example 341

Synthesis of (E)-3-[3-methoxy-4-methyl-1H-imidazol-1-yl)phenyl]-1-(1-phenyl-octahydropyrrolo[3,2c]pyridine-5-yl)propenone

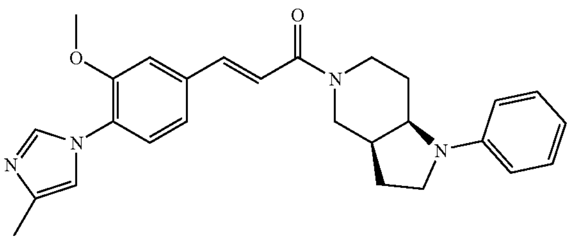

By the same method as in Example 121, 46 mg (90%) of the title compound was obtained from (E)-3-[3-methoxy-4-(4-methyl-1H-imidazol-1-yl)phenyl]acrylic acid (30 mg) and 1-phenyloctahydropyrrolo[3,2-c]pyridine (24 mg). The physical properties of the compound are as follows.

ESI-MS; m/z443 $[M^{+}+H]$. $^{1}$H-NMR ($CDCl_3$) δ(ppm): 1.50-1.91 (m, 1H), 1.91-2.25 (m, 3H), 2.30 (s, 3H), 2.49-2.64 (m, 1H), 3.01-3.12 (m, 0.5H), 3.24-3.55 (m, 3H), 3.65-3.77 (m, 0.5H), 3.89 (s, 3H), 3.90-4.00 (m, 2H), 4.23-4.42 (m, 1H), 6.54-6.63 (m, 2H), 6.68 (t, J=7.2 Hz, 1H), 6.87 (d, J=15.2 Hz, 1H), 6.92 (brs, 1H), 7.12 (s, 1H), 7.17-7.28 (m, 4H), 7.67 (d, J=15.2 Hz, 1H), 7.72 (s, 1H).

Example 342

Synthesis of (E)-1-(4-indol-1-yl)-3-(3-methoxy-4-(4-methyl-1H-imidazol-1-yl)phenylpropenone

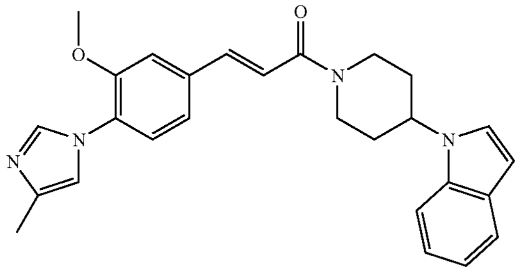

By the same method as in Example 121, 86 mg (82%) of the title compound was obtained from (E)-3-[3-methoxy-4-(4-methyl-1H-imidazol-1-yl)phenyl)acrylic acid (50 mg) and 1-piperidin-4-yl-1H-indol (46 mg). The physical properties of the compound are as follows.

ESI-MS; m/z441 $[M^{+}+H]$. $^{1}$H-NMR ($CDCl_3$) δ(ppm): 1.93-2.10 (m, 2H), 2.19-2.29 (m, 2H), 2.30 (s, 3H), 2.83-2.97 (m, 1H), 3.34-3.46 (m, 1H), 3.91 (s, 3H), 4.26-4.43 (m, 1H), 4.48-4.58 (m, 1H), 4.90-5.10 (m, 1H), 6.55 (d, J=3.2 Hz, 1H), 6.94 (s, 1H), 6.96 (d, J=15.6 Hz, 1H), 7.11-7.19 (m, 3H), 7.21-7.29 (m, 3H), 7.40 (d, J=8.0 Hz, 1H), 7.65 (d, J=8.0 Hz, 1H), 7.71 (d, J=15.6 Hz, 1H), 7.73 (s, 1H).

Example 343

Synthesis of (E)-1-[4-(4-fluorophenyl)piperazin-1-yl]-3-[3-methoxy-4-(4-methyl-1H-imidazol-1-yl)phenyl]propenone 2 trifluoroacetic acid salt

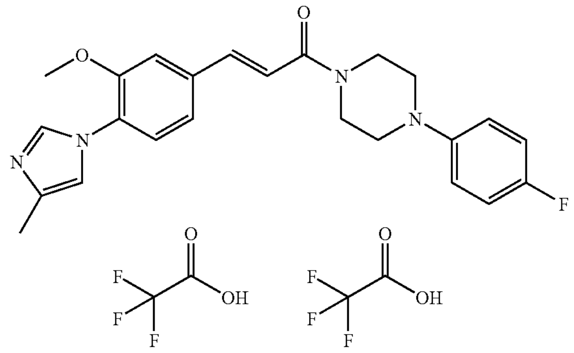

5.30 mg of the title compound was obtained from (E)-3-[3-methoxy-4-(4-methyl-1H-imidazol-1-yl)phenyl]acrylic acid (15.0 mg) and 1-(4-fluorophenyl)piperazine (16.0 mg) by the same method as in Example 94. The physical properties of the compound are as follows.

$^{1}$H-NMR ($CD_3OD$) δ (ppm): 9.16 (d, J=1.6 Hz, 1H), 7.64 (d, J=15.6 Hz, 1H), 7.607.61 (m, 2H), 7.58 (d, J=8.4 Hz, 1H), 7.45 (dd, J=1.6 Hz, 8.4 Hz, 1H), 7.38 (d, J=15.6 Hz, 1H), 6.80-7.03 (m, 4H), 4.00 (s, 3H), 3.95 (brs, 2H), 3.88 (brs, 2H), 3.17 (brs, 4H), 2.43 (s, 3H).

Example 344

Synthesis of (E)-1-[4-(2-fluorophenyl)piperazin-1-yl]-3-[3-methoxy-4-(4-(1H-imidazol-1-yl)phenyl]propenone 2 trifluoroacetic acid salt

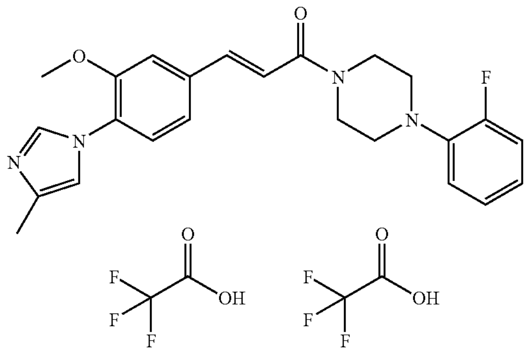

By the same method as in Example 94, 7.5 mg of the title compound was obtained from (E)-3-[3-methoxy-4-(4-methyl-1H-imidazol-1-yl)phenyl]acrylic acid (15.0 mg) and 1-(2-fluorophenyl)piperazine monohydrochloride (19.0 mg). The physical properties of the compound are as follows.

$^{1}$H-NMR ($CD_3OD$) δ (ppm): 9.16 (d, J=1.6 Hz, 1H), 7.64 (d, J=15.6 Hz, 1H), 7.60-7.61 (m, 2H), 7.58 (d, J=8.4 Hz, 1H), 7.45 (dd, J=1.6 Hz, 8.4 Hz, 1H), 7.38 (d, J=15.6 Hz, 1H), 6.80-7.03 (m, 4H), 4.00 (s, 3H), 3.95 (brs, 2H), 3.88 (brs, 2H), 3.17 (brs, 4H), 2.43 (s, 3H).

Example 345

Synthesis of (E)-1-[4-(2,4-difluorobenzyl)piperazin-1-yl]-3-[3-methoxy-4-(4-methyl-1H-imidazol-1-yl)phenyl]propenone 2 trifluoroacetic acid salt

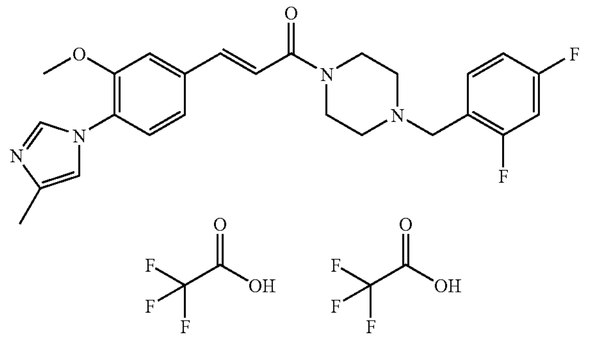

By the same method as in Example 94, 4.00 mg of the title compound was obtained from (E)-3-[3-methoxy-4-(4-methyl-1H-imidazol-1-yl)phenyl]acrylic acid (15.0 mg) and 1-(2,4-difluorobenzyl)piperazine dihydrochloride (25.0 mg). The physical properties of the compound are as follows.

$^1$H-NMR ($CD_3OD$) δ (ppm): 9.16 (d, J=1.6 Hz, 1H), 7.68 (d, J=16 Hz, 1H), 7.59-7.67 (m, 3H), 7.57 (d, J=8.0 Hz, 1H), 7.45 (dd, J=1.6 Hz, 8.4 Hz, 1H), 7.34 (d, J=16 Hz, 1H), 7.12-7.21 (m, 2H), 4.44 (s, 2H), 3.80-4.20 (brs, 4H), 3.99 (s, 3H), 3.40 (brs, 4H), 2.43 (s, 3H).

Example 346

Synthesis of (E)-1-(3,4-dihydro-1H-isoguinoline-2-yl)-3-[3-methoxy-4-(4-methyl-1H-imidazol-1-yl)phenyl]propenone trifluoroacetic acid salt

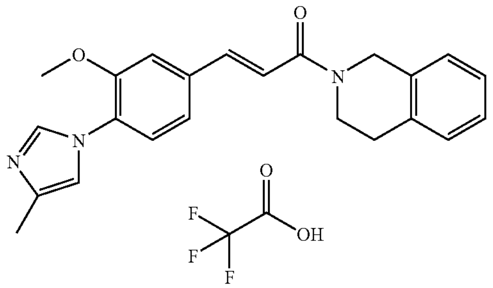

By the same method as in Example 94, 4.90 mg of the title compound was obtained from (E)-3-[3-methoxy-4-(4-methyl-1H-imidazol-1-yl)phenyl]acrylic acid (15.0 mg) and 1,2,3,4-tetrahydroisoquinoline (12.0 mg). The physical properties of the compound are as follows.

$^1$H-NMR ($CD_3OD$) δ (ppm): 9.16 (d, J=1.6 Hz, 1H), 7.65 (d, J=16 Hz, 1H), 7.60-7.63 (m, 2H), 7.57 (d, J=8.0 Hz, 1H), 7.397.48 (m, 2H), 7.20 (brs, 4H), 4.96 (s, 1H), 4.82 (s, 1H), 4.01 (s, 3H), 4.01 (t, J=5.6 Hz, 1H), 3.91 (t, J=5.6 Hz, 1H), 3.00 (t, J=5.6 Hz, 1H), 2.93 (t, J=5.6 Hz, 1H), 2.43 (s, 3H).

Example 347

Synthesis of (E)-1-(3,4-dihydro-1H-isoguinoline-2-yl)-3-[3-fluoro-4-(1H-imidazol-1-yl)-phenyl]propenone

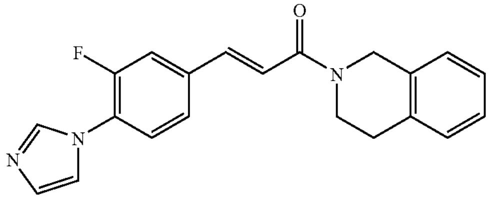

By the same method as in Example 324, 16.0 mg of the title compound was obtained from (E)-3-[3-fluoro-4-(1H-imidazol-1-yl)-phenyl]acrylic acid (20.0 mg) and 1,2,3,4-tetrahydroisoquinoline (22.0 μL). The physical properties of the compound are as follows.

$^1$H-NMR ($CDCl_3$) δ (ppm): 7.91 (s, 1H), 7.63 (d, J=16 Hz, 1H), 7.38-7.45 (m, 3H), 7.27 (s, 1H), 7.14-7.24 (m, 4H), 7.13 (s, 1H), 6.96-7.01 (m, 1H), 4.82 (s, 2H), 3.86-3.92 (m, 2H), 2.92-3.00 (m, 2H).

Example 348, Example 348-1 and Example 348-2

Synthesis of (E)-1-(3-benzyl-3-hydroxymethylpiperidin-1-yl)-3-[3-methoxy-4-(4-methyl-1H-imidazol-1-yl)phenyl]propenone

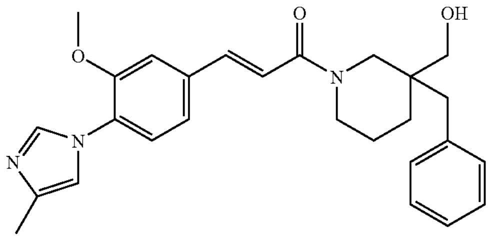

Synthesis of (±)-(E)-1-(3-benzyl-3-hydroxymethyl-piperidin-1-yl)-3-[3-methoxy-4-(4-methyl-1H-imidazol-1-yl)phenyl]propenone To a DMF (5 mL) solution of (E)-3-[4-methyl-1H-imidazol-1-yl]-3-methoxyphenyl)acrylic acid (250 mg) obtained in Example 121 and (3-benzyl-piperidin-3-yl)methanol (200 mg), isopropyl ethylamine (0.34 mL), HOBT (158 mg), and EDC (230 mg) were added, and the reaction solution was agitated at room temperature for 12 hours. Ethyl acetate and a saturated sodium bicarbonate water were added to the reaction solution after the reaction ended, and the organic layer was separated. After drying the obtained organic layer with anhydrous magnesium sulfate, the solvent was evaporated under reduced pressure. The obtained residue was purified by silica gel column chromatography (elution solvent: from ethyl acetate to ethyl acetate:methanol=9:1), and 310 mg (71%) of (±)-(E)-1-(3-benzyl-3-hydroxymethylpiperidin-1-yl)-3-[3-methoxy-4-(4-methyl-1H-imidazol-1-yl)phenyl]propenone was obtained. The physical properties of the compound are as follows.

ESI-MS; m/z446 [$M^+$+H].

Synthesis of (+)-(E)-1-(3-benzyl-3-hydroxymethyl-piperidin-1-yl)-3-[3-methoxy-4-(4-methyl-1H-imidazol-1-yl)phenyl]propenone and (−)-(E)-1-(3-benzyl-3-hydroxymethyl-piperidin-1-yl)-3-[3-methoxy-4-(4-methyl-1H-imidazol-1-yl)phenyl]propenone (±)-(E)-1-(3-benzyl-3-hydroxymethyl-piperidin-1-yl)-3-[3-methoxy-4-(4-methyl-1H-imidazol-1-yl)phenyl]propenone (310 mg) was separated using CHIRALPAK™AD-H (25 cm×2 cm; mobile phase hexane:isopropanol 7:3) available from Daicel Chemical Industries, Ltd. 30 mg of (−)-(E)-1-(3-benzyl-3-hydroxymethylpiperidin-1-yl)-3-[3-methoxy-4-(4-methyl-1H-imidazol-1-yl)phenyl]propenone having a shorter retention time (retention time: 12.9 minutes) was obtained by 99% e.e., and 29 mg of (+)-(E)-1-(3-benzyl-3-hydroxymethylpiperidin-1-yl)-3-[3-methoxy-4-(4-methyl-1H-imidazol-1-yl)phenyl]propenone having a longer retention time (retention time: 13.5 minutes) was obtained by 94% e.e.

Example 349, Example 349-1 and Example 349-2

Synthesis of (±)-(E)-1-[3-(4-fluorophenyl)-3-hydroxypiperidin-1-yl]-3-[3-methoxy-4-(4-methyl-1H-imidazol-1-yl]phenyl]propenone

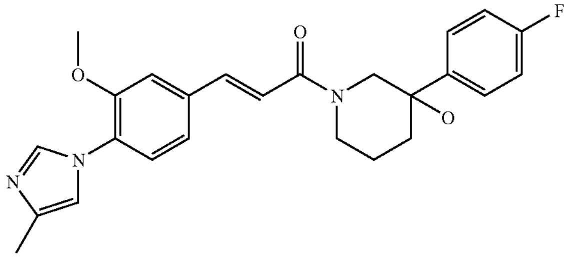

Synthesis of (±)-(E)-1-[3-(4-fluorophenyl)-3-hydroxypiperidin-1-yl]-3-[3-methoxy-4-(4-methyl-1H-imidazol-1-yl)phenyl]propenone Isopropylethylamine (0.07 mL), HOBT (45 mg) and EDC (64 mg) were added to a DMF (3 mL) solution of (E)-3-[4-methyl-1H-imidazol-1-yl-3-methoxyphenyl)acrylic acid (71 mg) obtained in Example 121 and 3-(4-fluorophenyl)piperidin-3-ol (54 mg), and the reaction solution was agitated at room temperature for 12 hours. Ethyl acetate and a saturated sodium bicarbonate water were added to the reaction solution after the reaction ended, and the organic layer was separated. After drying the obtained organic layer with anhydrous magnesium sulfate, the solvent was evaporated under reduced pressure. The obtained residue was purified by silica gel column chromatography (elution solvent: from ethyl acetate to ethyl acetate:methanol 9:1) and 91 mg (75%) of (±)-(E)-1-[3-(4-fluorophenyl)-3-hydroxypiperidin-1-yl]-3-[3-methoxy-4-(4-methyl-1H-imidazol-1-yl)phenyl]propenone was obtained. The physical properties of the compound are as follows.

ESI-MS; m/z436 [$M^+$+H]. $^1$H-NMR ($CDCl_3$) δ(ppm): 1.55-2.20 (m, 3H), 2.32 (s, 3H), 2.68-2.76 (m, 1H), 3.12-3.50 (m, 2H), 3.89 (s, 3H), 4.08-4.22 (m, 1H), 4.55-90) m, 1H), 6.84-7.04 (m, 2H), 7.05-7.33 (m, 5H), 7.50-5.57 (m, 2H), 7.64-7.78 (m, 2H).

Synthesis of (+)-(E)-1-[3-(4-fluorophenyl)-3-hydroxypiperidin-1-yl]-3-[3-methoxy-4-(4-methyl-1H-imidazol-1-yl)phenyl]propenone and (−)-(E)-1-[3-(4-fluorophenyl)-3-hydroxypiperidin-1-yl]-3-[3-methoxy-4-(4-methyl-1H-imidazol-1-yl)phenyl] propenone (±)-(E)-1-(3-(4-fluorophenyl)-3-hydroxypiperidin-1-yl)-3-[3-methoxy-4-(4-methyl-1H-imidazol-1-yl)phenyl]propenone (80 mg) obtained above was separated by CHIRALPAK™AD-H (25 cm×2 cm; mobile phase hexane: isopropanol 7:3) available from Daicel Chemical Industries, Ltd. 14 mg of (−)-(E)-1-[3-(4-fluorophenyl)-3-hydroxypiperidin-1-yl]-3-[3-methoxy-4-(4-methyl-1H-imidazol-1-yl) phenyl]propenone having a short retention time (retention time: 16.3 minutes) was obtained by 99% e.e. and 13 mg of (+)-(E)-1-[3-(4-fluorophenyl)-3-hydroxypiperidin-1-yl]-3-[3-methoxy-4-(4-methyl-1H-imidazol-1-yl)phenyl]propenone having a longer retention time (retention time: 20.4 minutes) of-(E)-1-(3-(4-fluorophenyl)-3-hydroxypiperidin-1-yl)-3-(3-methoxy-4-(4-methyl-1H-imidazol-1-yl)phenyl) propenone was obtained by 89% e.e.

Example 350

Synthesis of (E)-1-[4-(4-fluorophenyl)-4-hydroxyazepan-1-yl]-3-[3-methoxy-4-(4-methyl-1H-imidazol-1-yl)phenyl]propenone

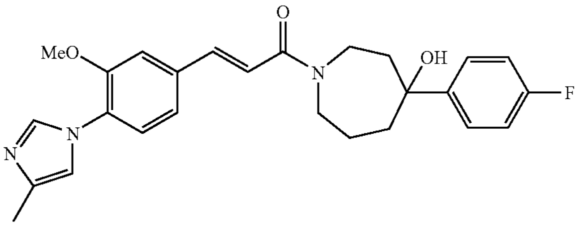

Synthesis of 1-{3-[3-methoxy-4-(4-methyl-1H-imidazol-1-yl)-phenyl]acryloyl}azepan-4-one The method of Example 121 was followed to synthesize 1-{3-[3-methoxy-4-(4-methylimidazol-1-yl)phenyl]acryloyl)azepan-4-one. The physical properties of the compound are as follows.

ESI-MS; m/z354 [$M^+$+H]

Synthesis of (E)-1-[4-(4-fluorophenyl)-4-hydroxyazepan-1-yl]-3-[3-methoxy-4-(4-methyl-1H-imidazol-1-yl)phenyl]propenone Fluorobenzene magnesium bromide (1.0M THF solution, 0.85 mL) was added to a THF (7 mL) solution of-the amide (100 mg) obtained above under ice-cooling. The reaction solution was allowed to be warmed to room temperature and agitated for further 2 hours. An ice-cooled water was added after the reaction ended, extracted with ethyl acetate, and the organic layer was washed with a saturated sodium chloride solution. After the organic layer was dried over anhydrous magnesium sulfate, the solvent was evaporated under reduced pressure. The obtained residue was purified by silica gel column chromatography (elution solvent:ethanol:ethyl acetate=1:4), and 63 mg (50%) of the title compound was obtained. The physical properties of the compound are as follows.

ESI-MS; m/z450 [$M^+$+H]. $^1$H-NMR ($CDCl_3$) δ(ppm): 1.87 (m, 1H), 1.88 (m, 2H), 2.01 (m, 2H), 2.12 (m, 1H), 2.23 (s, 3H), 3.45 (m, 1H), 3.79 (m, 1H), 3.93 (s, 3H), 3.95 (m, 1H), 4.11 (m, 1H), 7.00 (dd, J=9.0, 9.0 Hz, 2H), 7.08 (br.d, J=7.0 Hz, 1H), 7.19 (d, J=15.0 Hz, 1H), 7.32 (m, 1H), 7.36 (m, 1H), 7.44 (m, 1H), 7.47 (m, 2H), 7.61 (d, J=15.0 Hz, 1H), 7.81 (br.d, J=7.0 Hz, 1H).

Example 351

Synthesis of (E)-1-[4-fluoro-4-(4-fluorophenyl) azepan-1-yl]-3-[3-methoxy-4-(4-methyl-1H-imidazol-1-yl)phenyl]propenone

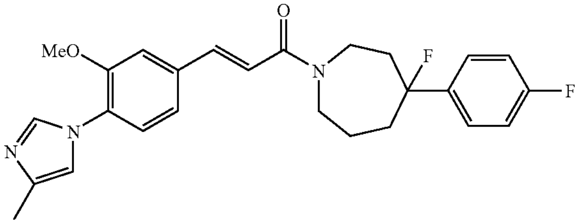

To a methylene chloride (4 mL) solution of (E)-1-[4-(4-fluorophenyl)-4-hydroxyazepan-1-yl]-3-[3-methoxy-4-(4-methyl-1H-imidazol-1-yl)phenyl]propenone (50 mg) obtained in Example 350, DAST (0.022 mL) was added at −78° C., and the reaction solution was allowed to be warmed to room temperature and the reaction solution was agitated for 7 hours. Water was added to the reaction solution after the reaction ended, extracted with ethyl acetate, and the organic layer was washed with a saturated sodium chloride solution. After the organic layer was dried over anhydrous magnesium sulfate, the solvent was evaporated under reduced pressure. The obtained residue was purified by silica gel column chromatography. (elution solvent:ethanol ethyl acetate=1:10), and 43 mg (86%) of the title compound was obtained. The physical properties of the compound are as follows.

ESI-MS; m/z452 [$M^+$+H]. $^1$H-NMR ($CDCl_3$) δ(ppm): 2.03 (m, 2H), 2.16 (m, 2H), 2.22 (s, 3H), 2.72 (m, 1H), 2.85 (m, 1H), 3.46 (br.dd, J=14.0, 14.0 Hz, 1H), 3.55 (ddd, J=7.0, 7.0, 14.0 Hz, 1H), 3.93 (s, 3H), 3.99 (m, 1H), 4.14 (ddd, J=7.0, 7.0, 14.0 Hz, 1H), 7.06 (dd, J=7.0, 9.0 Hz, 2H), 7.09 (d, J=7.0 Hz, 1H), 7.18 (d, J=15.0 Hz, 1H), 7.32 (m, 1H), 7.37 (m, 1H), 7.39 (m, 2H), 7.46 (br.s, 1H), 7.62 (d, J=15.0 Hz, 1H), 7.83 (d, J=7.0 Hz, 1H).

Example 352

Synthesis of (E)-1-[5-(4-fluorophenyl)-2,3,4,7-tetrahydroazepin-1-yl]-3-[3-methoxy-4-(4-methyl-1H-imidazol-1-yl)phenyl]propenone and (E)-1-[4-(4-fluorophenyl)-2,3,6,7-tetrahydroazepin-1-yl]-3-[3-methoxy-4-(4-methyl-1H-imidazol-1-yl)phenyl] propenone

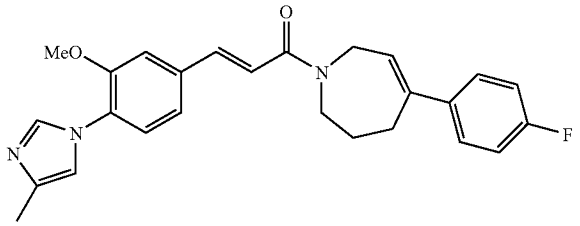

-continued

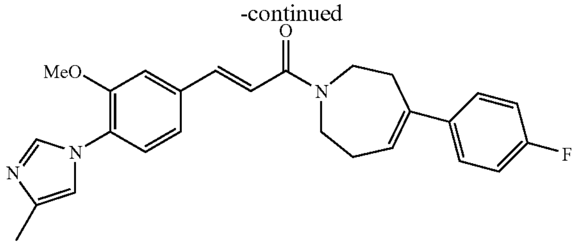

Synthesis of 4-(4-fluorophenyl)-4-hydroxyazepane-1-carboxylic acid tert-butyl ester To a THF (60 mL) solution of tert-butyl ester of 4-oxoazepane-1-carboxylic acid (5 g), fluoro benzene magnesium bromide (1.0M THF solution, 82 mL) was added under ice-cooling, and the reaction solution was allowed to be warmed to room temperature and agitated for 1 hour. Water was added to the reaction solution under ice-cooling after the reaction ended, extracted with ethyl acetate, and the organic layer was washed with a saturated sodium chloride solution. The organic layer separated was dried over anhydrous magnesium sulfate and then the solvent was evaporated under reduced pressure. The obtained residue is purified by silica gel column chromatography (elution solvent:heptane:ethyl acetate=2:1), and 3.73 g (52%) of 4-(4-fluorophenyl)-4-hydroxyazepane-1-carboxylic acid tert-butyl ester was obtained. The physical properties of the compound are as follows.

$^1$H-NMR ($CDCl_3$) δ(ppm): 1.47 (s, 9H), 1.62-2.26 (m, 6H), 3.22-3.44 (m, 2H), 3.37-3.89 (m, 3H) >6.95-7.07 (m, 2H), 7.36-7.48 (m, 2H).

ESI-MS; m/z332 [$M^+$+Na]

Synthesis of 4-(4-fluorophenyl)-2,3,6,7-tetrahydroazepin-1-carboxylic acid tert-butyl ester and 5-(4-fluorophenyl)-2,3,4,7-tetrahydroazepin-1-carboxylic acid 4-(4-fluorophenyl)-4-hydroxy-azepane-1-carboxylic acid tert-butyl ester To a methylene chloride (20 mL) solution of 4-(4-fluorophenyl)-4-hydroxyazepane-1-carboxylic acid tert-butyl ester (500 mg) obtained above, TEA (1.13 mL) and methane sulfonylchloride (0.15 mL) were added under ice-cooling, and the reaction solution was agitated at room temperature for 1 hour. Water is added to the reaction solution under ice-cooling liquid after the reaction ended, extracted with ethyl acetate, and the organic layer was washed with a saturated sodium chloride solution. The organic layer separated was dried over anhydrous magnesium sulfate and the solvent was evaporated under reduced pressure. The obtained residue was purified by silica gel column chromatography (elution solvent:heptane:ethyl acetate 2:1) and 3.73 g (52%) of the olefin compound as an isomer mixture was obtained. The physical properties of the compound are as follows.

$^1$H-NMR ($CDCl_3$) δ(ppm): 1.46 (s, 9H), 1.90 (br.s, 1H), 2.44br.s, 1H), 2.60-2.80 (m, 2H), 3.46-3.70 (m, 3H), 3.92-4.14 (m, 1H), 5.95 (t, J=5.6 Hz, 1H), 6.97 (t, J=8.8 Hz, 2H), 7.20-7.32 (m, 2H).

ESI-MS; m/z314 [$M^+$+Na]. $^1$H-NMR ($CDCl_3$) δ: 1.48 (s, 9H), 1.90 (br.s, 1H), 2.44br.s, 1H), 2.60-2.80 (m, 2H), 3.46-3.70 (m, 3H), 3.92-4.14 (m, 1H), 5.95 (t, J=5.6 Hz, 1H), 6.97 (t, J=8.8 Hz, 2H), 7.20-7.32 (m, 2H).

Synthesis of 4-(4-fluorophenyl)-2,3,6,7-tetrahydro-1H-azepine hydrohloride salt and 5-(4-fluorophenyl)-2,3,4,7-tetrahydro-1H-azepine hydrohloride salt To an ethyl acetate (5 mL) solution of the olefin (250 mg) obtained above, 4N hydrochloric acid was added at room temperature, and the reaction solution was agitated for 2 hours. It was concentrated under reduced pressure after the reaction ended and used for the next reaction as it was without purification.

Synthesis of (E)-1-[5-(4-fluorophenyl)-2,3,4,7-tetrahydroazepin-1-yl]-3-[3-methoxy-4-(4-methyl-1H-imidazol-1-yl)-phenyl]propenone and (E)-1-[4-(4-fluorophenyl)-2,3,6,7-tetrahydroazepin-1-yl]-3-[3-methoxy-4-(4-methyl-1H-imidazol-1-yl)-phenyl]propenone By the same method as in Example 121, 157 mg (55%) of the title compound was obtained from crude amine (150 mg) obtained above and (E)-3-[3-methoxy-4-(4-methyl-1H-imidazol-1-yl)phenyl]acrylic acid. The physical properties of the compound are as follows.

ESI-MS; m/z454 $[M^{+}+Na]$. $^{1}H$-NMR ($CDCl_3$) δ(ppm): 2.00-2.12 (m, 2H), 2.30 (s, 3H), 2.54-2.63 (m, 1.5H), 2.66-2.77 (m, 1H), 2.80-2.90 (m, 1.5H), 3.80-3.98 (m, 3H), 3.90 (s, 3H), 4.33 (d, J=5.6 Hz, 1H), 5.95 (t, J=5.6 Hz, 0.5H), 6.09 (t, J=5.6 Hz, 0.5H), 6.82-7.04 (m, 2H), 7.08-7.18 (m, 1H), 7.19-7.34 (m, 4H), 7.62-7.77 (m, 2H).

$^{1}H$-NMR ($CDCl_3$) δ(ppm): 2.00-2.12 (m, 2H), 2.30 (s, 3H), 2.54-2.63 (m, 1.5H), 2.66-2.77 (m, 1H), 2.80-2.90 (m, 1.5H), 3.80-3.98 (m, 3H), 3.88 (s, 3H), 4.26 (d, J=5.2 Hz, 1H), 5.98-6.06 (m, 1H), 6.82-7.04 (m, 2H), 7.08-7.18 (m, 1H), 7.19-7.34 (m, 4H), 7.62-7.77 (m, 2H).

Example 353

Synthesis of (E)-1-[4-(4-fluorophenyl)azepan-1-yl]-3-[3-methoxy-4-(4-methyl-1H-imidazol-1-yl)phenyl]propenone

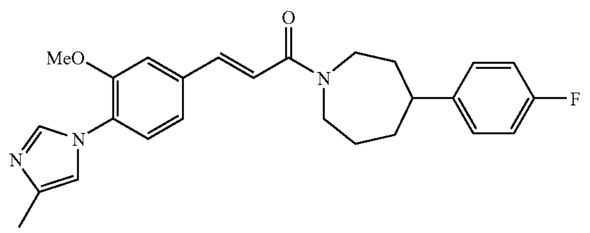

Synthesis of 4-(4-fluorophenyl)azepane-1-carboxylic acid tert-butyl ester

To a methanol (10 mL) solution of 4-(4-fluorophenyl)-4-hydroxyazepane-1-carboxylic acid tert-butyl ester (100 mg) obtained in Example 352, 10% Pd—C (100 mg) was added, and the reaction solution was agitated in hydrogen stream at room temperature for 1 hour. Suction filtration of the reaction solution was carried out using celite after the reaction ended, and the filtrate was concentrated under reduced pressure. The obtained crude product of 4-(4-fluorophenyl)azepane-1-carboxylic acid tert-butyl ester was used for the next reaction, without further purifying.

Synthesis of 4-(4-fluorophenyl)azepane

By the same method as in Example 352, 4-(4-fluorophenyl)azepane was obtained from 4-(4-fluorophenyl)azepane-1-carboxylic acid tert-butyl ester (80 mg) obtained above. The obtained crude product was used for the next reaction without further purifying.

Synthesis of (E)-1-[4-(4-fluorophenyl)azepan-1-yl]-3-[3-methoxy-4-(4-methyl-1H-imidazol-1-yl)phenyl]propenone By the same method as in Example 121, 75 mg (66%) of the title compound was obtained from 4-(4-fluorophenyl)azepane (60 mg) obtained above and (E)-3-[3-methoxy-4-(4-methyl-1H-imidazol-1-yl)phenyl]acrylic acid. The physical properties of the compound are as follows.

ESI-MS; m/z456 $[M^{+}+Na]$. $^{1}H$-NMR ($CDCl_3$) δ(ppm): 1.62-2.03 (m, 4H), 2.04-2.20 (m, 2H), 2.29 (s, 1.5H), 2.30 (s, 1.5H), 2.62-2.76 (m, 1H), 3.44-3.72 (m, 2H), 3.73-3.96 (m, 1.5H), 3.88 (s, 1.5H), 3.90 (s, 1.5H), 3.97-4.07 (m, 0.5H), 6.82-7.00 (m, 4H), 7.06-7.16 (m, 3H), 7.17-7.29 (m, 2H), 7.68-7.76 (m, 2H).

Example 354

Synthesis of (E)-1-[3-(4-fluorophenyl)-4-hydroxyazepan-1-yl]-3-[3-methoxy-4-(4-methyl-1H-imidazol-1-yl)phenyl)propenone

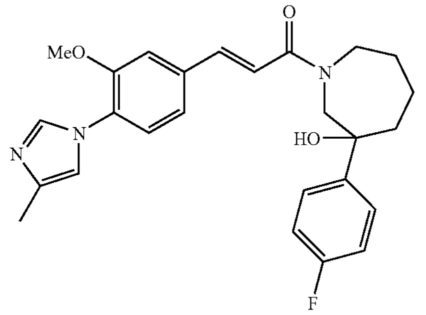

Synthesis of 3-(4-fluorophenyl)-3-hydroxyazepane-1-carboxylic acid tert-butyl ester By the same method as in Example 352, 528 mg (72%) of 3-(4-fluorophenyl)-3-hydroxyazepane-1-carboxylic acid tert-butyl ester was obtained from 3-oxoazepine-1-carboxylic acid tert-butyl ester (507 mg). The physical properties of the compound are as follows.

ESI-MS; m/z332 $[M^{+}+Na]$. $^{1}H$-NMR ($CDCl_3$) δ(ppm): 1.50 (s, 9H), 1.60-1.74 (m, 2H), 1.80-2.10 (m, 4H), 2.90-3.40 (m, 2H), 3.80-4.10 (m, 1H), 4.03 (d, J=15.2 Hz, 1H), 4.66 (s, 1H), 6.94-7.08 (m, 2H), 7.40-7.54 (m, 2H).

Synthesis of 3-(4-fluorophenyl)azepan-3-ol

By the same method as in Example 352, 3-(4-fluorophenyl)azepan-3-ol was obtained from the 3-(4-fluorophenyl)-3-hydroxyazepane-1-carboxylic acid tert-butyl ester (150 mg) obtained above. The obtained crude product was used for the next reaction, without purifying further.

Synthesis of (E)-1-[3-(4-fluorophenyl)-4-hydroxyazepan-1-yl]-3-[3-methoxy-4-(4-methyl-1H-imidazol-1-yl)phenyl]propenone By the same method as in Example 121, 160 mg (74%) of the title compound was obtained from the 3-(4-fluorophenyl) azepan-3-ol (119 mg) obtained above and (E)-3-[3-methoxy-4-(4-methyl-1H-imidazol-1-yl)phenyl]acrylic acid. The physical properties of the compound are as follows.

ESI-MS; m/z472 [$M^+$+Na]. $^1$H-NMR ($CDCl_3$) δ: 1.64-2.26 (m, 6H), 2.24 (s, 3H), 3.50-3.79 (m, 2H), 3.93 (s, 3H), 3.98-4.32 (m, 2H), 7.00-7.15 (m, 3H), 7.20-7.31 (m, 2H), 7.32-7.44 (m, 2H), 7.46-7.73 (m, 3H), 7.87 (dd, J=1.0, 6.8 Hz, 1H)

Example 355

Synthesis of (E)-1-[3-fluoro-3-(4-fluorophenyl) azepan-1-yl]-3-[3-methoxy-4-(4-methyl-1H-imidazol-1-yl)phenyl]propenone

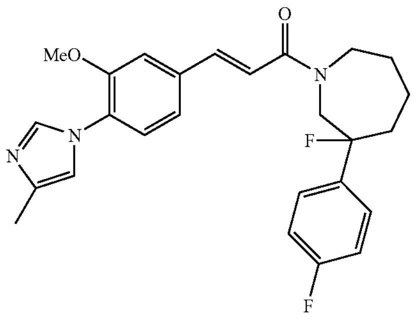

Synthesis of (E)-1-[3-fluoro-3-(4-fluorophenyl) azepan-1-yl]-3-[3-methoxy-4-(4-methyl-1H-imidazol-1-yl)phenyl]propenone To a methylene chloride (5 mL) solution of (E)-1-[3-(4-fluorophenyl)-4-hydroxyazepan-1-yl]-3-[3-methoxy-4-(4-methyl-1H-imidazol-1-yl)phenyl]propenone (50 mg) obtained in Example 354, DAST (0.022 mL) was added at −78° C., and the reaction solution was allowed to be warmed to room temperature and agitated for 13 hours. Water was added to the reaction solution after the reaction ended, extracted with ethyl acetate, and the organic layer was washed with a saturated sodium chloride solution. After the organic layer was dried over anhydrous magnesium sulfate, the solvent was evaporated under reduced pressure. The obtained residue was purified by silica gel column chromatography (elution solvent:ethanol:ethyl acetate=1:5), and 30 mg (60%) of the title compound was obtained. The physical properties of the compound are as follows.

ESI-MS; m/z474 [$M^+$+Na]. $^1$H-NMR ($CDCl_3$) δ(ppm): 1.68-2.40 (m, 5H), 2.30 (s, 3H), 3.15-3.30 (m, 1H), 3.52-3.80 (m, 2H), 3.90 (s, 3H), 4.00-4.45 (m, 2H), 6.82-6.98 (m, 2H), 7.00-7.18 (m, 3H), 7.20-7.34 (m, 2H), 7.36-7.54 (m, 2H), 7.66 (d, J=15.6 Hz, 1H), 7.74 (d, J=7.0 Hz, 1H).

Example 356

Synthesis of (E)-1-[6-(4-fluorophenyl)-2,3,4,5-tetrahydroazepin-1-yl]-3-[3-methoxy-4-(4-methyl-1H-imidazol-1-yl)phenyl]propenone

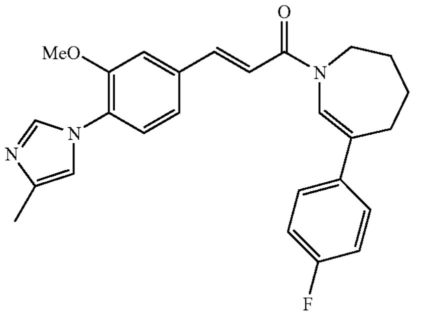

Synthesis of (E)-1-[6-(4-fluorophenyl)-2,3,4,5-tetrahydroazepin-1-yl]-3-[3-methoxy-4-(4-methyl-1H-imidazol-1-yl)phenyl]propenone By the same method as in Example 352, 5 mg (6%) of the title compound was obtained from (E)-1-[3-(4-fluorophenyl)-4-hydroxyazepan-1-yl]-3-[3-methoxy-4-(4-methyl-1H-imidazol-1-yl)phenyl]propenone (52 mg) obtained in Example 354. The physical properties of the compound are as follows.

ESI-MS; m/z432 [$M^+$+H]. $^1$H-NMR ($CDCl_3$) δ: 1.80 (m, 2H), 1.94 (m, 2H), 2.30 (s, 3H), 2.68 (m, 2H), 3.89 (s, 3H), 3.91 (m, 2H), 6.75 (s, 1H), 6.87 (d, J=15.0 Hz, 1H), 6.92 (m, 1H), 7.06 (m, 2H), 7.11 (s, 1H), 7.24 (d, J=6.0 Hz, 1H), 7.27 (d, J=6.0 Hz, 1H), 7.34 (ddd, J=2.0, 5.0, 9.0 Hz, 2H), 7.70 (d, J=15.0 Hz, 1H), 7.76 (m, 1H).

Example 357

Synthesis of (E)-1-(3-hydroxymethyl-4-phenylpyrrolidine-1-yl)-3-[3-methoxy-4-(4-methyl-1H-imidazol-1-yl)phenyl]propenone

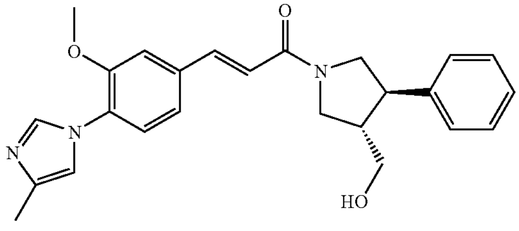

By the same method as in Example 121, 368 mg (76%) of the title compound was obtained from (E)-3-[3-methoxy-4-(4-methyl-1H-imidazol-1-yl)phenyl]acrylic acid (290 mg) and trans-(4-phenylpyrrolidine-3-yl)methanol (200 mg). The physical properties of the compound are as follows.

$^1$H-NMR ($CDCl_3$) δ(ppm): 2.28 (d, J=0.8 Hz, 1.5H), 2.30 (d, J-0.8 Hz, 1.5H), 2.55-2.73 (m, 1H), 3.17 (td, J=10.0, 8.0 Hz, 0.5H), 3.35 (td, J=10.0, 8.0 Hz, 0.5H), 3.50-3.82 (m, 4H), 3.87 (s, 1.5H), 3.91 (s, 1.5H), 4.09-4.22 (m, 2H), 6.68 (d, J=15.2 Hz, 0.5H), 6.78 (d, J=15.2 Hz, 0.5H), 6.91 (brt, 0.5H), 6.93 (brt, 0.5H), 7.11-7.40 (m, 8H), 7.70 (d, J=0.8 Hz, 0.5H), 7.71 (d, J=15.2 Hz, 0.5H), 7.72 (d, J=15.2 Hz, 0.5H), 7.73 (d, J=0.8 Hz, 0.5H).

Example 358

Synthesis of (E)-3-[3-methoxy-4-(4-methyl-1H-imidazol-1-yl)phenyl]-1-(trans-3-phenyl-4-piperidin-1-ylmethylpyrrolidin-1-yl)propenone

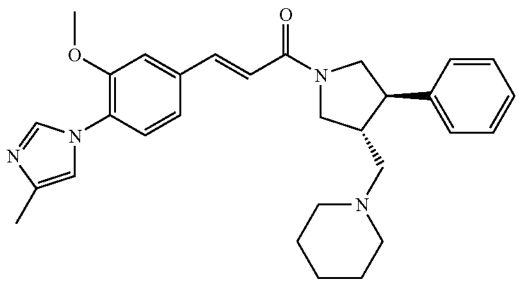

To a methylene chloride (3 mL) solution of (E)-1-(3-hydroxymethyl-4-phenyl-pyrrolidine-1-yl)-3-(3-methoxy-4-(4-methyl-1H-imidazol-1-yl)phenyl)propenone (65 mg) obtained in Example 357, Dess-Martin reagent (128 mg) was added at 0° C., the reaction solution was agitated at the temperature for 1 hour, and then agitated at room temperature for 1 hour. The reaction solution was washed with a saturated sodium bicarbonate water, and after drying the organic layer over anhydrous magnesium sulfate, the solvent was evaporated under reduced pressure. The obtained aldehyde compound was used for the following reaction, without carrying out further purifying. Piperidine (5.9 μL) and acetic acid (4.5 μL) were added to the methylene chloride (2 ml) solution of the above-mentioned aldehyde compound (17 mg). Furthermore, sodium triacetoxy borohydride (17 mg) was added to the solution, and the reaction solution was agitated at room temperature for 12 hours. Ethyl acetate was added to the reaction solution after the reaction ended, and the reaction solution was washed with a saturated sodium bicarbonate water. After drying the separated organic layer with anhydrous magnesium sulfate, the solvent was evaporated under reduced pressure. The obtained residue was purified by silica gel column chromatography (Carrier: Chromatorex™ NH, an elution solvent: from ethyl acetate to ethyl acetate:methanol 9:1), and 19.7 mg (76%) of the title compound was obtained. The physical properties of the compound are as follows.

ESI-MS; m/z507 [M+Na$^+$]. $^1$H-NMR ($CDCl_3$) δ(ppm): 1.35-1.60 (m, 6H), 2.15-2.48 (m, 9H), 2.55-2.72 (m, 1H), 3.01 (q, J=9.6 Hz, 0.5H), 3.15 (q, J=9.6 Hz, 0.5H), 3.38 (dd, J=12.8, 9.2 Hz, 0.5H), 3.52 (t, J=10.0 Hz, 0.5H), 3.61 (dd, J=12.8, 9.2 Hz, 0.5H), 3.67 (t, J=10.0 Hz, 0.5H), 3.87 (s, 1.5H), 3.93 (s, 1.5H), 4.06-4.21 (m, 2H), 6.70 (d, J=15.6 Hz, 0.5H), 6.80 (d, J=15.6 Hz, 0.5H), 6.92 (brt, 0.5H), 6.95 (brt, 0.5H), 7.11 (d, J=1.6 Hz, 0.5H), 7.15-7.40 (m, 7.5H), 7.70 (d, J=15.6 Hz, 0.5H), 7.72 (d, J=1.6 Hz, 0.5H), 7.73 (d, J=15.6 Hz, 0.5H), 7.74 (d, J=1.6 Hz, 0.5H).

Example 359

Synthesis of (E)-1-{3-[3-methoxy-4-(4-methyl-1H-imidazol-1-yl]phenyl}acryloyl)-4-phenylpyrrolidine-3-carbaldehyde oxime

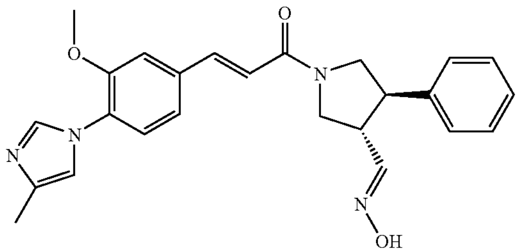

To an ethanol (2 ml) solution of (E)-1-{3-[3-methoxy-4-(4-methyl-1H-imidazol-1-yl)phenyl)acryloyl}-4-phenylpyrrolidine-3-carbaldehyde (34 mg) obtained in Example 358, hydroxylamine hydrochloride and sodium acetate were added, and the reaction solution was agitated at room temperature for 12 hours. After condensing reaction solution under reduced pressure, ethyl acetate and saturated sodium bicarbonate water were added, and the organic layer was partitioned. The obtained organic layer was dried over anhydrous magnesium sulfate, and the solvent was evaporated under reduced pressure. The obtained residue was purified by silica gel column chromatography (Carrier: Chromatorex™ NH, an elution solvent:ethyl acetate:methanol=10:1), and 16.2 mg (46%) of the title compound was obtained as a mixture of oxime moiety Z:E=1:2. The physical properties of the compound are as follows.

$^1$H-NMR ($CDCl_3$) δ(ppm): 2.28 (s, 1.5H), 2.29 (s, 1.5H), 3.19-3.77 (m, 4H), 3.87 (s, 1.5H), 3.90 (s, 1.5H), 4.08-4.37 (m, 2H), 6.67-6.79 (m, 1.3H), 6.92 (brs, 0.5H), 6.94 (brs, 0.5H), 7.11-7.42 (m, 8.7H), 7.71 (brs, 0.5H), 7.72 (brs, 0.5H), 7.75 (brs, 1H), 8.70 (brs, 0.35H), 9.01 (brs, 0.15H), 9.20 (brs, 0.35H), 9.64 (brs, 0.15H).

Example 360

Synthesis of (E)-1-{3-[3-methoxy-4-(4-methyl-1H-imidazol-1-yl)phenyl]acryloyl}-4-phenylpyrrolidine-3-carbonitrile

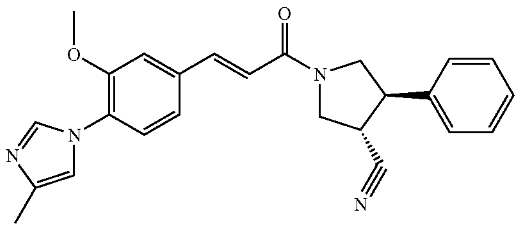

To a THF (3 ml) solution of (E)-1-{3-[3-methoxy-4-(4-methyl-1H-imidazol-1-yl)phenyl]acryloyl}-4-phenylpyrrolidine-3-carbaldehyde oxime (17.8 mg) obtained in Example 359, CDI (32.4 mg) was added at room temperature, and heat-refluxing was carried out for 3 hours. After the reaction solution was allowed to be cooled to room temperature, ethyl acetate and saturated sodium bicarbonate solution were added to the reaction solution, and the organic layer was partitioned. After drying the obtained organic layer with anhydrous magnesium sulfate, the solvent was evaporated under reduced pressure. The obtained residue was purified by silica gel column chromatography (elution solvent:ethyl acetate methanol 10:1), and the 14.6 mg (86%) title compound was obtained. The physical properties of the compound are as follows.

ESI-MS; m/z413 [$M^+$+H]. $^1$H-NMR ($CDCl_3$) δ(ppm): 2.30 (s, 1.8H), 2.31 (s, 1.2H), 3.18-3.34 (m, 1H), 3.65-3.87 (m, 2.6H), 3.89 (s, 1.8H), 3.92 (s, 1.2H), 4.03 (t, J=9.2 Hz, 0.4H), 4.24-4.35 (m, 2H), 6.67 (d, J=15.6 Hz, 0.6H), 6.68 (d, J=15.6 Hz, 0.4H), 6.93 (brs, 0.6H), 6.95 (brs, 0.4H), 7.13-7.46 (m, 8H), 7.73 (brs, 0.6H), 7.74 (brs, 0.4H), 7.75 (d.J=15.6 Hz, 0.6H), 7.76 (d, J=15.6 Hz, 0.4H).

Example 361

Synthesis of-(E) trans-1-[4-(4-fluoropheoxy)-2-hydroxymethyl-piperidin-1-yl]-3-[3-methoxy-4-(4-methyl-1H-imidazol-1-yl)phenyl]propenone

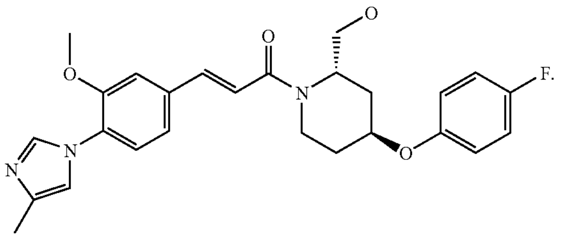

By the same method as in Example 121, 78 mg (68%) of the title compound was obtained from (E)-3-[3-methoxy-4-(4-methyl-1H-imidazol-1-yl)phenyl]acrylic acid (63 mg) and trans-(4-(4-fluoropheoxy)piperidine-2-yl)methanol (55 mg). The physical properties of the compound are as follows.

ESI-MS; m/z466 [$M^+$+H]. $^1$H-NMR ($CDCl_3$) δ(ppm): 1.76-1.86 (m, 1H), 2.16-2.35 (m, 5H), 2.82-2.99 (m, 1H), 3.41-3.58 (m, 1H), 3.76-4.13 (m, 5H), 4:75-5.06 (m, 3H), 6.85 (dd, J=9.2, 4.4 Hz, 2H), 6.93 (brs, 1H), 6.98 (t, J=9.2 Hz, 2H), 7.11 (brs, 1H), 7.14-7.28 (m, 3H), 7.64 (d, J=15.2 Hz, 1H), 7.72 (brs, 1H).

The racemates or racemic compounds shown in Table 8 were synthesized as in Example 358, 359 and 360.

The structural formulae and physicochemical properties are shown in Table 8, respectively.

TABLE 8

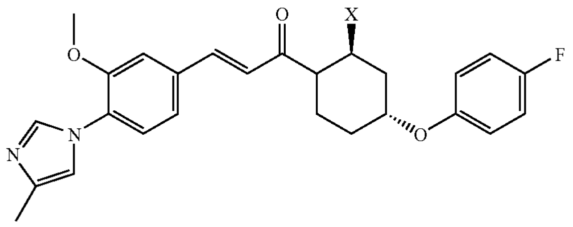

| Example | X | DATA: MS m/z |
|---|---|---|
| 362 |  | $M^+$ + H: 461 (ESI) |
| 363 | 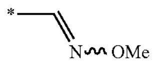 | $M^+$ + H: 493 (ESI) |

TABLE 8-continued

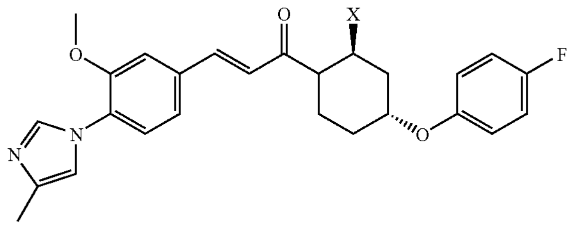

| Example | X | DATA: MS m/z |
|---|---|---|
| 364 | 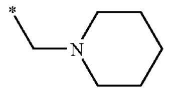 | $M^+$ + H: 533 (ESI) |

Example 365

Synthesis of (E)-3-[3-methoxy-4-(4-methyl-1H-imidazol-1-yl)phenyl]-1-[4-(1-methyl-1H-indol-2-yl)piperidin-1-yl]propenone

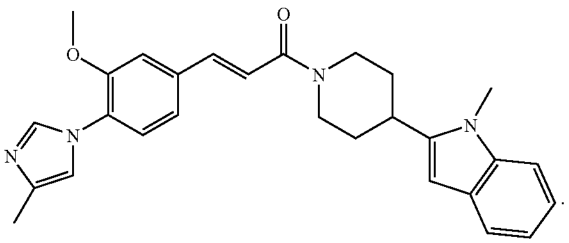

To a THF (1 mL) solution of (E)-1-{4-(1H-indol-2-yl)piperidin-1-yl}-3-[3-methoxy-4-(4-methyl-1H-imidaxol-1-yl)phenyl]propenone (20 mg) obtained in Example 338 and iodomethane (0.04 mL), sodium hydride (2.2 mg) was added at room temperature. The reaction solution was agitated at room temperature for 7 hours. Ethyl acetate and a saturated ammonium chloride solution were added to the reaction solution after the reaction ended, and the organic layer was partitioned. After drying the obtained organic layer with anhydrous magnesium sulfate, the solvent was evaporated under reduced pressure. The obtained residue was purified by silica gel column chromatography (Carrier: Chromatorex™ NH, an elution solvent:ethyl acetate), and 10 mg (49%) of the title compound was obtained. The physical properties of the compound are as follows.

$^1$H-NMR ($CDCl_3$) δ(ppm): 1.72-1.85 (m, 2H), 2.09-2.18 (m, 2H), 2.30 (s, 3H), 2.80-2.96 (m, 1H), 2.99-3.07 (m, 1H), 3.28-3.44 (m, 1H), 3.75 (s, 3H), 3.91 (s, 3H), 4.22-4.35 (m, 1H), 4.86-4.95 (m, 1H), 6.23 (s, 1H), 6.94 (s, 1H), 6.95 (d, J=15.6 Hz, 1H), 7.07-7.32 (m, 6H), 7.55 (d, J=7.6 Hz, 1H), 7.68 (d, J=15.6 Hz, 1H), 7.73 (brs, 1H).

Example 366

Synthesis of (E)-1-{4-[1-(2-hydroxy ethyl)-1H-indol-2-yl]piperidin-1-yl}-3-[3-methoxy-4-(4-methyl-1H-imidazol-1-yl)phenyl]propenone

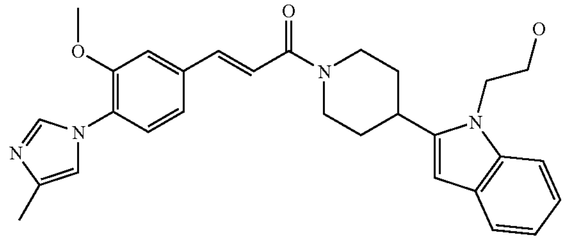

By the same method as in Example 365, (E)-1-{4-(1H-indol-2-yl)piperidine-1-yl}-3-[3-methoxy-4-(4-methyl-1H-imidazol-1-yl)phenyl]propenone (6 mg) a obtained in Example 338 and (2-bromoethoxy)tert-butyldimethylsilane (0.04 mL), (E)-1-{4-[1-(2-tert-butyldimethylsiloxyethyl)-1H-indol-2-yl]piperidin-1-yl}-3-[3-methoxy-4-(4-methyl- 1H-imidazol-1-yl)phenyl]propenone was obtained. TBAF (1M THF solution, 0.02 mL) was added to a THF (1 mL) solution of the obtained silyl protected compound, and the reaction solution was agitated at room temperature for 3 hours. Ethyl acetate and a saturated ammonium chloride solution were added to the reaction solution after the reaction ended, and the organic layer was separated. After drying the obtained organic layer with anhydrous magnesium sulfate, the solvent was evaporated under reduced pressure. The obtained residue was purified by silica gel column chromatography (elution solvent:ethyl acetate methanol=9:1), and 0.9 mg (14%) of the title compound was obtained. The physical properties of the compound are as follows.

ESI-MS; m/z485 [$M^+$+H]. $^1$H-NMR ($CDCl_3$) δ(ppm): 1.75-1.83 (m, 2H), 2.09-2.18 (m, 2H), 2.280 (s, 3H), 2.79-2.94 (m, 1H), 3.10-3.20 (m, 1H), 3.23-3.40 (m, 1H), 3.91 (s, 3H), 4.00 (t, J=5.6 Hz, 2H), 4.22-4.33 (m, 1H), 4.34 (t, J=5.2 Hz, 2H), 4.84-4.95 (m, 1H), 6.30 (s, 1H), 6.94 (t, J=1.2 Hz, 1H), 6.95 (d, J=15.6 Hz, 1H), 7.08-7.34 (m, 6H), 7.56 (d, J=7.6 Hz, 1H), 7.68 (d, J=15.6 Hz, 1H), 7.72 (d, J=1.2 Hz, 1H).

The compounds shown in Table 9 were synthesized as in Example 121. The structural formulae and physicochemical properties are shown in Table 9, respectively.

TABLE 9

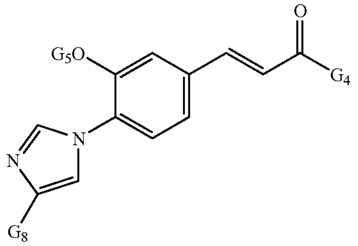

| Example | $G_4$ | $G_5$ | $G_6$ | DATA: MS m/z |
|---|---|---|---|---|
| 367 | 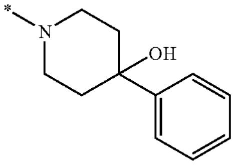 | Me | Me | $M^+$ + H: 418 (ESI) |
| 368 | 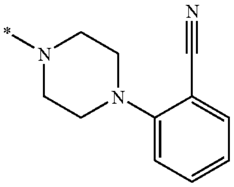 | Me | Me | $M^+$ + H: 428 (ESI) |
| 369 | 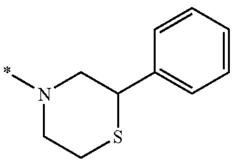 | Me | Me | $M^+$ + H: 420 (ESI) |

TABLE 9-continued
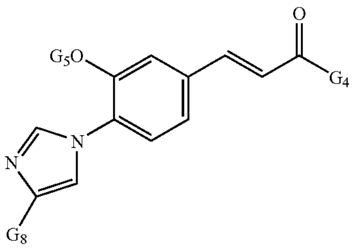
| Example | G4 | G5 | G6 | DATA: MS m/z |
|---|---|---|---|---|
| 370 | 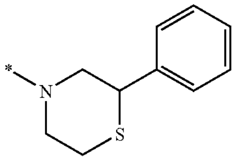 | Me | Me | $M^{+}$ + H: 404 (ESI) |
| 371 | 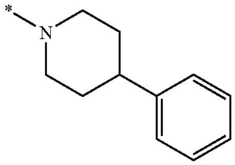 | Me | Me | $M^{+}$ + H: 402 (ESI) |
| 372 | 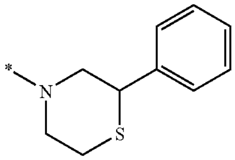 | Me | Me | $M^{+}$ + H: 402 (ESI) |
| 373 | 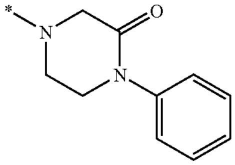 | Me | Me | $M^{+}$ + H: 417 (ESI) |
| 374 | 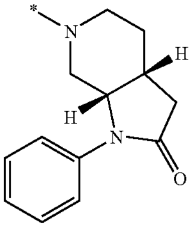 | Me | Me | $M^{+}$ + H: 457 (ESI) |
| 375 | 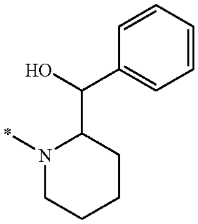 | Me | Me | $M^{+}$ + H: 432 (ESI) |

TABLE 9-continued
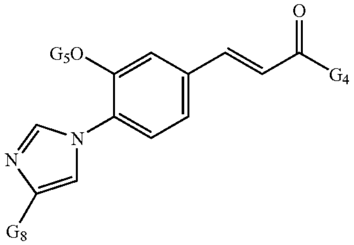
| Example | $G_4$ | $G_5$ | $G_6$ | DATA: MS m/z |
|---|---|---|---|---|
| 376 | 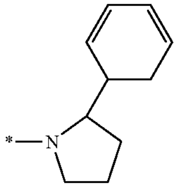 | Me | Me | $M^+ + H$: 388 (ESI) |
| 377 | 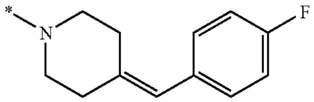 | Me | Me | $M^+ + H$: 432 (ESI) |
| 378 | 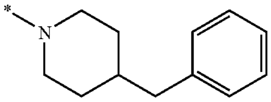 | Me | Me | $M^+ + H$: 416 (ESI) |
| 379 | 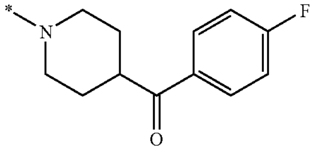 | Me | Me | $M^+ + H$: 448 (ESI) |
| 380 | 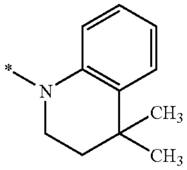 | Me | Me | $M^+ + H$: 402 (ESI) |
| 381 | 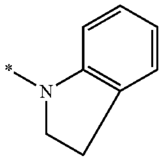 | Me | Me | $M^+ + H$: 360 (ESI) |
| 383 | 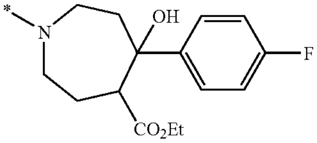 | Me | Me | $M^+ - H$: 450 (ESI) |
| 384 | 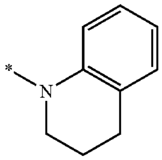 | Me | Me | $M^+ + H$: 360 (ESI) |

TABLE 9-continued
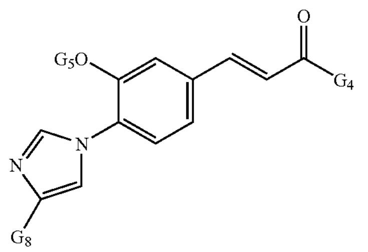
| Example | $G_4$ | $G_5$ | $G_6$ | DATA: MS m/z |
|---|---|---|---|---|
| 385 | 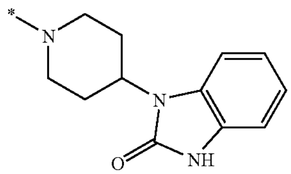 | Me | H | $M^+ + H$: 444 (ESI) |
| 386 | 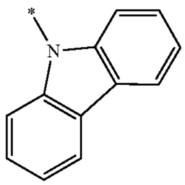 | Me | H | $M^+ + H$: 394 (ESI) |
| 387 | 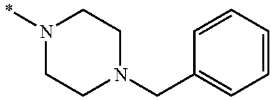 | Me | H | $M^+ + H$: 403 (ESI) |
| 388 | 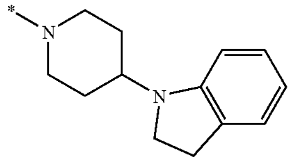 | Me | H | $M^+ + H$: 427 (ESI) |
| 389 | 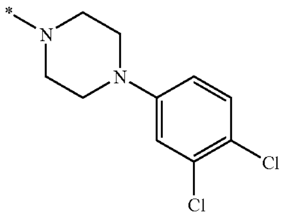 | Me | H | $M^+ + H$: 457 (ESI) |
| 390 | 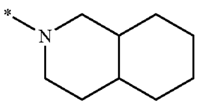 | Me | H | $M^+ + H$: 366 (ESI) |
| 391 | 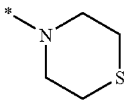 | Me | H | $M^+ + H$: 330 (ESI) |

TABLE 9-continued

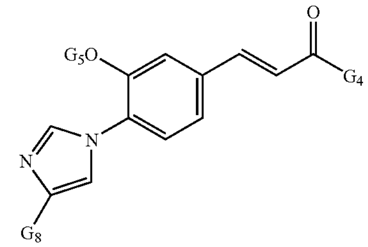

| Example | $G_4$ | $G_5$ | $G_6$ | DATA: MS m/z |
|---|---|---|---|---|
| 392 | 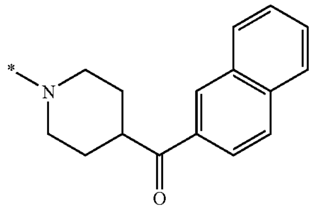 | Me | H | $M^+ + H$: 480 (ESI) |
| 393 | 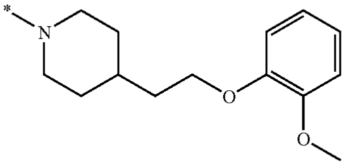 | Me | H | $M^+ + H$: 462 (ESI) |
| 394 | 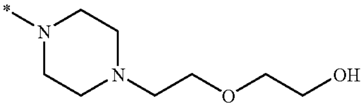 | Me | H | $M^+ + H$: 401 (ESI) |
| 395 | 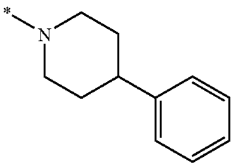 | 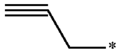 | Me | $M^+ + H$: 448 (ESI) |
| 396 | 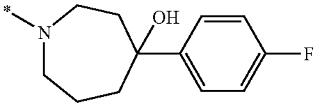 | 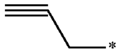 | Me | $M^+ + H$: 496 (ESI) |

Example 397

Synthesis of (E)-1-(3-fluorobenzyl)-3-[3-methoxy-4-(4-methyl-1H-imidazol-1-yl)benzylidene]pyrrolidin-2-one

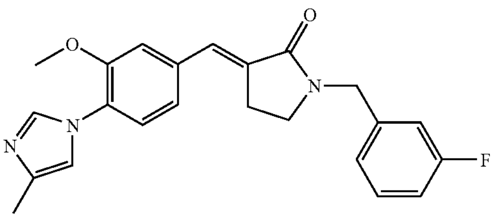

Synthesis of 4-(tert-butyldimethylsilanyloxy)-2-(diethoxyphosphoryl)butyric acid tert-butyl ester To a DMF (4.0 mL) solution of dimethylphosphonoacetic acid tert-butyl ester (1.0 mL), sodium hydride (256 mg) was added at 0° C., and the reaction solution was allowed to be warmed to 60° C., and agitated for 2 hours. (2-bromoethoxy) tert-butyldimethylsilane (1.37 mL) was added to the reaction solution, and the reaction solution was agitated at 80° C. overnight. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (heptane-ethyl acetate=1:1→ethyl acetate), and 510 mg of the title compound was obtained. The physical properties of the compound are as follows.

$^1$H-NMR ($CDCl_3$) δ (ppm): 4.09-4.18 (m, 4H), 3.66-3.72 (m, 1H), 3.54 (dt, J=5.2, 9.2 Hz, 1H), 3.15 (ddd, J=3.6, 11, 22 Hz, 1H), 1.97-2.17 (m, 2H), 1.47 (s, 9H), 1.31-1.36 (m, 6H), 0.89 (s, 9H), 0.04 (s, 6H).

Synthesis of (E)-4-(tert-butyldimethylsilanyloxy)-2-[3-methoxy-4-(4-methyl-1H-imidazol-1-yl)-benzylidene]butyric acid tert-butyl ester To a solution of 3-methoxy-4-(4-methyl-1H-imidazol-1-yl)benzaldehyde (295 mg) obtained in Example 1 in THF (5.0 mL) and ethanol (5.0 mL), 4-(tert-butyldimethylsilanyloxy)-2-(diethoxyphosphoryl)butyric acid tert-butyl ester (509 mg) and lithium hydroxide monohydrate (104 mg) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (heptane-ethyl acetate=2:1→1:1), and 395 mg of the title compound was obtained. The physical properties of the compound are as follows.

$^1$H-NMR ($CDCl_3$) δ (ppm): 7.73 (s, 1H), 7.69 (s, 1H), 7.22-7.30 (m, 2H), 7.24 (s, 1H), 6.94 (s, 1H), 3.91 (t, J=6.4 Hz, 2H), 3.87 (s, 3H), 2.77 (t, J=6.4 Hz, 2H), 2.30 (s, 3H), 1.56 (s, 9H), 0.87 (s, 9H), 0.03 (s, 6H).

Synthesis of (E)-4-hydroxy-2-[3-methoxy-4-(4-methyl-1H-imidazol-1-yl)benzylidene]butyric acid tert-butyl ester To a THF (10 mL) solution of (E)-4-(tert-butyldimethylsilanyloxy)-2-(3-methoxy-4-(4-methyl-1H-imidazol-1-yl)benzylidene)butyric acid tert-butyl ester (122 mg), TBAF (1M THF solution, 318 μL) was added, and the reaction solution was agitated at room temperature for 1 hour. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate:ethanol=10:1), and 49.7 mg of the title compound was obtained. The physical properties of the compound are as follows.

$^1$H-NMR ($CDCl_3$) δ (ppm): 7.72 (s, 1H), 7.69 (s, 1H), 7.20-7.25 (m, 3H), 7.07 (d, J=8.0 Hz, 1H), 6.93 (s, 1H), 3.88-3.94 (m, 2H), 3.86 (s, 3H), 2.76-2.84 (s, 2H), 2.30 (s, 3H), 1.56 (s, 9H)

Synthesis of (E)-4-(1,3-dioxo-1,3-dihydro-isoindol-2-yl)-2-[3-methoxy-4-(4-methyl-1H-imidazol-1-yl)benzylidene]butyric acid tert-butyl ester To an anhydrous THF (3.0 mL) solution of (E)-4-hydroxy-2-[3-methoxy-4-(4-methyl-1H-imidazol-1-yl)benzylidene]butyric acid tert-butyl ester (100 mg), triphenylphosphine (87.8 mg), phthalimide (49.3 mg) and diisopropyl azodicarboxylate (77.0 μL) were added one by one. After agitating reaction solution at room temperature for 1.5 hours, reaction solution was concentrated under reduced pressure as it was, the residue was purified by silica gel chromatography (elution solvent:ethyl acetate), and 119 mg of the title compound was obtained. The physical properties of the compound are as follows.

$^1$H-NMR ($CDCl_3$) δ (ppm): 7.72-7.76 (m, 2H), 7.63-7.68 (m, 4H), 7.13 (d, J=8.0 Hz, 1H), 6.99 (d, J=7.2 Hz, 1H), 6.90 (s, 1H), 6.86 (s, 1H), 3.91 (t, J=6.8 Hz, 2H), 3.77 (s, 3H), 2.95 (t, J=6.8 Hz, 2H), 2.30 (s, 3H), 1.60 (s, 9H).

Synthesis of (E)-4-amino-2-[3-methoxy-4-(4-methyl-1H-imidazol-1-yl)benzylidene]butyric acid tert-butyl ester To an ethanol (2.0 mL) solution of (E)-4-(1,3-dioxo-1,3-dihydroisoindol-2-yl)-2-[3-methoxy-4-(4-methyl-1H-imidazol-1-yl)benzylidene]butyric acid tert-butyl ester (119 mg), hydrazine monohydrate (48.9 mg) was added. The white precipitation was filtered off, after refluxing the reaction solution for 30 minutes and confirming disappearance of the starting materials. The obtained filtrate was concentrated under reduced pressure and 86 mg of crude amino compounds was obtained. The physical properties of the compound are as follows.

$^1$H-NMR ($CDCl_3$) δ (ppm): 7.71 (d, J=1.2 Hz, 1H), 7.63 (s, 1H), 7.24 (d, J=8.0 Hz, 1H), 7.10 (d, J=1.2 Hz, 1H), 7.04 (dd, J=1.2, 8.0 Hz, 1H), 6.92 (t, J=1.2 Hz, 1H), 3.86 (s, 3H), 2.92 (t, J=7.6 Hz, 2H), 2.68 (t, J=7.6 Hz, 2H), 2.30 (s, 3H), 1.56 (s, 9H).

Synthesis of (E)-4-(3-fluorobenzylamino)-2-[3-methoxy-4-(4-methyl-1H-imidazol-1-yl)benzylidene]butyric acid tert-butyl ester To a methylene chloride (2.0 mL) solution of (E)-4-amino-2-[3-methoxy-4-(4-methyl-1H-imidazol-1-yl)benzylidene] butyric acid tert-butyl ester (71 mg), 3-fluorobenzaldehyde (21.1 μL), acetic acid (0.1 mL) and sodium triacetoxy borohydride (63.3 mg) were added one by one. After agitating reaction solution at room temperature for 5.5 hours, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by NH silica gel chromatography (elution solvent:ethyl acetate→ethyl acetate:ethanol=20:1), and 47.5 mg of the title compound was obtained. The physical properties of the compound are as follows.

$^1$H-NMR ($CDCl_3$) δ (ppm): 7.72 (s, 1H), 7.62 (s, 1H), 7.22-7.28 (m, 2H), 7.10 (s, 1H), 7.00-7.06 (m, 3H), 6.90-6.96 (m, 2H), 3.82 (s, 3H), 3.78 (s, 2H), 2.84 (t, J=6.8 Hz, 2H), 2.74 (t, J=6.8 Hz, 2H), 2.30 (s, 3H), 1.53 (s, 9H).

Synthesis of (E)-1-(3-fluorobenzyl)-3-[3-methoxy-4-(4-methyl-1H-imidazol-1-yl)benzylidene]pyrrolidin-2-one To a methylene chloride (0.5 mL) solution of (E)-4-(3-fluorobenzylamino)-2-(3-methoxy-4-(4-methyl-1H-imidazol-1-yl)benzylidene]butyric acid tert-butyl ester (4.50 mg), trifluoroacetic acid (500 μL) was added. After agitating reaction solution at room temperature for 1.5 hours and agitating that materials disappeared, reaction solution was concentrated under reduced pressure as it was. The residue was dissolved in DMF (0.5 mL), IPEA (17.0 μL), EDC (5.58 mg), and HOBT (3.93 mg) were added to the reaction solution one by one, and the reaction solution was agitated at room temperature for 1.5 hours. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate:ethanol=20:1), and 2.30 mg of the title compound was obtained. The physical properties of the compound are as follows.

$^1$H-NMR ($CDCl_3$) δ (ppm): 7.74 (s, 1H), 7.42 (t, J=2.8 Hz, 1H), 7.28-7.35 (m, 1H), 7.28 (d, J=8.0 Hz, 1H), 7.15 (d, J=8.0 Hz, 1H), 7.13 (s, 1H), 7.07 (d, J=8.0 Hz, 1H), 6.70-7.30 (m, 2H), 6.94 (s, 1H), 4.69 (s, 2H), 3.88 (s, 3H), 3.44 (t, J=6.8 Hz, 2H), 3.09 (dt, J=2.8, 6.8 Hz, 2H), 2.30 (s, 3H).

Example 398

Synthesis of (E)-1-(3-fluorobenzyl)-3-[3-methoxy-4-(4-methyl-1H-imidazol-1-yl)benzylidene]piperidin-2-one

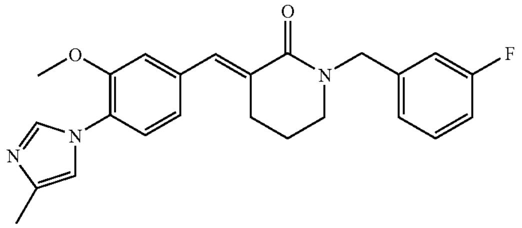

Synthesis of 2-(diethoxyphosphoryl)-4-[1,3]dioxolan-2-yl-butyric acid ethyl ester To a DMF (25 mL) solution of diethylphosphono ethyl acetate ester (10.0 mL), sodium hydride (3.02 g) was added at 0° C., and the reaction solution was heated to 70° C. and was agitated for 70 minutes. Next, after adding 2-(2-bromo ethyl)-1,3-dioxolane (14.8 mL) to the reaction solution and the reaction solution was agitated at 80° C. for 15 hours, and sodium hydride (1.40 g) and 2-(2-bromo ethyl)-1,3-dioxolane (7.70 mL) were further added to the reaction solution, and the reaction solution was agitated for 4 hours. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent; heptane-ethyl acetate=1:1→1:2→ethyl acetate), and 3.58 g of the title compound was obtained. The physical properties of the compound are as follows.

$^1$H-NMR ($CDCl_3$) δ (ppm): 4.87 (t, J=4.4 Hz, 1H), 4.10-4.25 (m, 6H), 3.93-3.99 (m, 2H), 3.81-3.88 (m, 2H), 3.03 (ddd, J=4.4, 11, 23 Hz, 1H), 1.94-2.16 (m, 2H), 1.64-1.84 (m, 2H), 1.30-1.36 (m, 9H)

Synthesis of (E)-4-[1,3]dioxolan-2-yl-2-[3-methoxy-4-(4-methyl-1H-imidazol-1-yl)benzylidene]butyric acid ethyl ester To a THF (20 mL) solution of (1.75 g) of the 3-methoxy-4-(4-methyl-1H-imidazol-1-yl)benzaldehyde obtained in Example 1, 2-(diethoxyphosphoryl)-4-[1,3]dioxolan-2-yl-butyric acid ethyl ester (2.50 g) and lithium hydroxide monohydrate (388 mg) were added one by one, and the reaction solution was agitated at room temperature overnight. Water and ethyl acetate were added to the reaction solution after confirming disappearance of the starting materials, and the organic layer was partitioned. After the obtained organic layer was washed with a saturated saline solution, it was dried over anhydrous magnesium sulfate and concentrated under reduced pressure. The residue was purified by silica gel chromatography (elution solvent; heptane-ethyl acetate=1:2→ethyl acetate), and 1.05 g of the title compound as an isomer mixture (E:Z=4:1) was obtained. The physical properties of the compound are as follows.

$^1$H-NMR ($CDCl_3$) δ (ppm): 7.74 (s, 1H), 7.66 (s, 1H), 7.27 (d, J=8.4 Hz, 1H), 7.13 (5, 1H), 7.09 (d, J=8.4 Hz, 1H), 6.95 (s, 1H), 4.95 (t, J=4.4, 1H), 4.29 (q, J=7.2 Hz, 2H), 3.92-4.00 (m, 2H), 3.90 (s, 3H), 3.82-3.88 (m, 2H), 2.71-2.75 (m, 2H), 2.31 (s, 3H), 1.96-2.10 (m, 2H), 1.37 (t, J=7.2 Hz, 3H).

Synthesis of (E)-2-[3-methoxy-4-(4-methyl-1H-imidazol-1-yl)benzylidene]-5-oxovaleric acid ethyl ester To an aqueous solution of (243 mg) of (E)-4-[1,3]dioxolan-2-yl-2-[3-methoxy-4-(4-methyl-1H-imidazol-1-yl)benzylidene]butyric acid ethyl ester, acetic acid (2 mL) and trifluoroacetic acid (2.0 mL) were added one by one, and the reaction solution was agitated at room temperature for 4 hours. After confirming disappearance of the starting materials, a saturated sodium bicarbonate water and ethyl acetate were added to the reaction solution, and the organic layer was partitioned. After the obtained organic layer was washed with a saturated saline solution, it was dried over anhydrous magnesium sulfate and 110 mg of the title compound was obtained by condensing under reduced pressure. The physical properties of the compound are as follows.

$^1$H-NMR ($CDCl_3$) δ (ppm): 9.81 (s, 1H), 7.72-7.74 (m, 2H), 7.27 (d, J=8.0 Hz, 1H), 6.94-7.01 (m, 3H), 4.30 (q, J=7.2 Hz, 2H), 3.87 (s, 3H), 2.89 (t, J=8.0 Hz, 2H), 2.74 (t, J=8.0 Hz, 2H), 2.30 (s, 3H), 1.37 (t, J=7.2 Hz, 3H).

Synthesis of (E)-5-(3-fluorobenzylamino)-2-[3-methoxy-4-(4-methyl-1H-imidazol-1-yl)benzylidene]valeric acid ethyl ester To a methylene chloride (2.0 mL) solution of (E)-2-(3-methoxy-4-(4-methyl-1H-imidazol-1-yl)benzylidene)-5-oxo-valeric acid ethyl ester (142 mg), 3-fluorobenzylamine (141 μL), acetic acid (1.0 mL) and sodium triacetoxy borohydride (105 mg) were added one by one. After agitating reaction solution at room temperature overnight, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, an elution solvent:ethyl acetate→ethyl acetate:ethanol=10:1), and 81 mg of the title compound was obtained. The physical properties of the compound are as follows.

$^1$H-NMR ($CDCl_3$) δ (ppm): 7.72 (s, 1H), 7.66 (s, 1H), 7.23 (d, J=8.4 Hz, 1H), 6.89-7.07 (m, 7H), 4.29 (q, J=7.2 Hz, 2H), 3.83 (s, 3H), 3.78 (s, 2H), 2.69 (t, J=6.8 Hz, 2H), 2.62 (t, J=8.0 Hz, 2H), 2.30 (s, 3H), 1.74-1.83 (m, 2H), 1.36 (t, J=7.2 Hz, 3H).

Synthesis of (E)-1-(3-fluorobenzyl)-3-[3-methoxy-4-(4-methyl-1H-imidazol-1-yl)benzylidene]piperidin-2-one An acetic acid (3 mL) solution of (E)-5-(3-fluorobenzylamino)-2-(3-methoxy-4-(4-methyl-1H-imidazol-1-yl)benzylidene)valeric acid ethyl ester (81 mg) was heated to reflux overnight. After cooling the reaction solution to 0° C., it was neutralized with 1N sodium hydroxide solution, and then a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, elution solvent:heptane-ethyl acetate=1:5→ethyl acetate), and 21 mg of the title compound was obtained. The physical properties of the compound are as follows.

$^1$H-NMR ($CDCl_3$) δ (ppm): 7.88 (s, 1H), 7.73 (s, 1H), 7.25-7.34 (m, 3H), 7.09 (d, J=7.2 Hz, 1H), 6.94-7.05 (m, 4H), 4.73 (s, 2H), 3.87 (s, 3H), 3.39 (t, J=6.0 Hz, 2H), 2.84 (dt, J=2.0, 6.4 Hz, 2H), 2.30 (s, 3H), 1.89 (m, 2H).

Example 399

Synthesis of (E)-3-[3-methoxy-4-(4-methyl-1H-imidazol-1-yl)benzylidene]-1-[(1S)-1-phenylethyl]piperidin-2-one

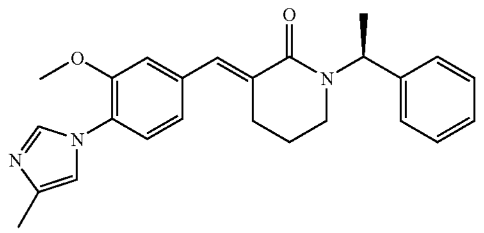

To a methylene chloride (2 mL) solution of (E)-2-[3-methoxy-4-(4-methyl-1H-imidazol-1-yl)benzylidene]-5-oxovaleric acid ethyl ester (162 mg), (S)-(−)-alpha-methylbenzylamine (183 μL), acetic acid (1.0 mL) and sodium triacetoxy borohydride (120 mg) were added one by one. After agitating reaction solution at room temperature overnight, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The obtained residue was dissolved in acetic acid (2 mL), and heat-refluxing of the reaction solution was carried out overnight. After cooling reaction solution to 0° C., neutralized with a saturated sodium bicarbonate water, ethyl acetate was added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, elution solvent:heptane-ethyl acetate=1:1→ethyl acetate ethanol=10:1), and 13.7 mg of the title compound was obtained. The physical properties of the compound are as follows.

$^1$H-NMR ($CDCl_3$) δ (ppm): 7.90 (s, 1H), 7.72 (d, J=1.2 Hz, 1H), 7.24-7.29 (m, 6H), 7.04-7.06 (m, 2H), 6.94 (t, J=1.2 Hz, 1H), 6.26 (q, J=7.2 Hz, 1H), 3.85 (s, 3H), 3.25 (ddd, J=3.6, 8.4, 12 Hz, 1H), 2.96 (ddd, J=4.4, 6.8, 11 Hz, 1H), 2.72-2.85 (m, 2H), 2.30 (s, 3H), 1.79-1.83 (m, 1H), 1.68-1.74 (m, 1H), 1.58 (d, J=7.2 Hz, 3H).

Example 400

Synthesis of (E)-3-[3-methoxy-4-(4-methyl-1H-imidazol-1-yl)benzylidene]-1-[1-(3-morpholin-4-ylphenyl)ethyl]piperidin-2-one

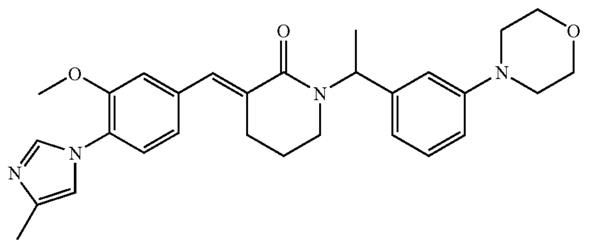

Synthesis of (E)-2-[3-methoxy-4-(4-methyl-1H-imidazol-1-yl)-benzylidene]-5-[1-(3-morpholin-4-ylphenyl)ethylamino]valeric acid ethyl ester To a methylene chloride (10 mL) solution of (E)-2-[3-methoxy-4-(4-methyl-1H-imidazol-1-yl)-benzylidene]-5-oxovaleric acid ethyl ester (173 mg) obtained in Example 398, 1-(3-morpholin-4-yl-phenyl)ethyl amine (157 mg) and acetic acid (0.1 mL) and sodium triacetoxy borohydride (214 mg) were added one by one. The reaction solution was agitated at room temperature for 1 hour, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex NH, elution solvent:heptane-ethyl acetate=1:2), and 205 mg of the title compound was obtained. The physical properties of the compound are as follows.

$^1$H-NMR ($CDCl_3$) δ (ppm): 7.72 (s, 1H), 7.62 (s, 1H), 7.19-7.23 (m, 2H), 7.02 (d, J=8.4 Hz, 1H), 6.98 (s, 1H), 6.93 (s, 1H), 6.87 (s, 1H), 6.78-6.81 (m, 2H), 4.27 (q, J=7.2 Hz, 2H), 3.82-3.86 (m, 4H), 3.81 (s, 3H), 3.70 (q, J=6.8 Hz, 1H), 3.14 (t, J=4.8 Hz, 4H), 2.43-2.61 (m, 4H), 2.30 (s, 3H), 1.62-1.80 (m, 2H), 1.35 (t, J=7.2 Hz, 3H), 1.31 (d, J=6.8 Hz, 3H).

Synthesis of (E)-3-[3-methoxy-4-(4-methyl-1H-imidazol-1-yl)benzylidene]-1-[1-(3-morpholin-4-ylphenyl)ethyl]piperidin-2-one To a solution of (E)-2-[3-methoxy-4-(4-methyl-1H-imidazol-1-yl)benzylidene]-5-[1-(3-morpholin-4-ylphenyl)ethylamino]valeric acid ethyl ester (55.0 mg) in THF (1.0 mL) and ethanol (1.0 mL), 2N sodium hydroxide solution (1.0 m) was added. The reaction solution was agitated at room temperature overnight, 2N hydrochloric acid and ethyl acetate were added, and the organic layer was partitioned. After the obtained organic layer was washed with a saturated saline solution, it was dried over anhydrous magnesium sulfate and 50.0 mg of crude carboxylic acid compound was obtained by condensing under reduced pressure. To a DMF (2.0 mL) solution of the obtained carboxylic acid compound, IPEA (51.8 μL), EDC (38.0 mg) and HOBT (26.8 mg) were added one by one, and the reaction solution was agitated at room temperature for 1 hour. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex NH, elution solvent:ethyl acetate=1:1→heptane-ethyl acetate), and 6.00 mg of the title compound was obtained. The physical properties of the compound are as follows.

$^1$H-NMR ($CDCl_3$) δ (ppm): 7.89 (s, 1H), 7.72 (d, J=1.6 Hz, 1H), 7.22-7.28 (m, 2H), 7.05-7.07 (m, 2H), 6.93 (s, 1H), 6.83-6.90 (m, 3H), 6.21 (q, J=7.2 Hz, 1H), 3.85-3.87 (m, 7H), 3.24 (dd, J=4.0, 8.4, 12 Hz, 1H), 3.16 (t, J=4.8 Hz, 4H), 2.95-3.01 (m, 1H), 2.76-2.82 (m, 2H), 2.30 (s, 3H), 1.76-1.84 (m, 1H), 1.67-1.73 (m, 1H), 1.55 (d, J=7.2 Hz, 3H).

Example 401

Synthesis of (E)-1-[(1R,2S)-2-hydroxyindan-1-yl]-3-[3-methoxy-4-(4-methyl-1H-imidazol-1-yl)benzylidene]piperidin-2-one

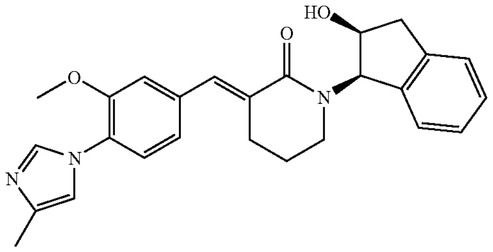

Synthesis of (E)-5-[(1R,2S)-2-hydroxyindan-1-ylamino]-2-[3-methoxy-4-(4-methyl-1H-imidazol-1-yl)benzylidene]valeric acid ethyl ester To a methylene chloride (2.0 mL) solution of (E)-2-[3-methoxy-4-(4-methyl-1H-imidazol-1-yl)benzylidene]-5-oxovaleric acid ethyl ester (110 mg), (1R,2S)-amino-2-indanol (63.2 mg), acetic acid (0.1 mL) and sodium triacetoxy borohydride (81.7 mg) were added one by one. After agitating reaction solution at room temperature overnight, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, elution solvent:ethyl acetate=1:1→heptane-ethyl acetate), and 120 mg of the title compound was obtained. The physical properties of the compound are as follows.

$^1$H-NMR ($CDCl_3$) δ (ppm): 7.71 (d, J=1.6 Hz, 1H), 7.68 (s, 1H), 7.17-7.27 (m, 5H), 7.05 (dd, J=1.6 Hz, 1H), 7.01 (d, J=1.6 Hz, 1H), 6.93 (t, J=1.6 Hz, 1H), 4.39 (dt, J=2.8, 5.2 Hz, 1H), 4.30 (q, J=7.2 Hz, 2H), 4.03 (d, J=5.2 Hz, 1H), 3.85 (s, 3H), 3.04 (dd, J=5.2 Hz, 1H), 2.92-2.99 (m, 2H), 2.75-2.83 (m, 1H), 2.61-2.73 (m, 2H), 2.30 (s, 3H), 1.84 (qu, 7.2 Hz, 2H), 1.37 (t, J=7.2 Hz, 3H).

Synthesis of (E)-1-[(1R,2S)-2-hydroxyindan-1-yl]-3-[3-methoxy-4-(4-methyl-1H-imidazol-1-yl)benzylidene]piperidin-2-one To an ethanol (2.0 mL) solution of (E)-5-[(1R,2S)-2-hydroxyindan-1-ylamino]-2-[3-methoxy-4-(4-methyl-1H-imidazol-1-yl)benzylidene]valeric acid ethyl ester (120 mg), 2N sodium hydroxide solution (1.0 mL) was added. After carrying out heat-refluxing of the reaction solution for 30 minutes and confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH, elution solvent: heptane-ethyl acetate=1:1→ethyl acetate→ethyl acetate: ethanol=10:1), and 78.9 mg of the title compound was obtained. The physical properties of the compound are as follows.

$^1$H-NMR ($CDCl_3$) δ (ppm): 7.82 (s, 1H), 7.71 (d, J=1.2 Hz, 1H), 7.22-7.30 (m, 5H), 7.02 (d, J=7.2 Hz, 1H), 7.01 (s, 1H), 6.92 (s, 1H), 6.01 (d, J=7.2 Hz, 1H), 4.91 (q, J=7.2 Hz, 1H), 3.84 (s, 3H), 3.30 (dd, J=7.2, 16 Hz, 1H), 3.11-3.22 (m, 2H), 2.96 (dd, J=7.2, 16 Hz, 1H), 2.75-2.86 (m, 2H), 2.30 (s, 3H), 1.70-1.90 (m, 2H).

Example 402

Synthesis of (E)-1-(3-iodobenzyl)-3-[3-methoxy-4-(4-methyl-1H-imidazol-1-yl)benzylidene]piperidin-2-one monotrifluoroacetic acid salt

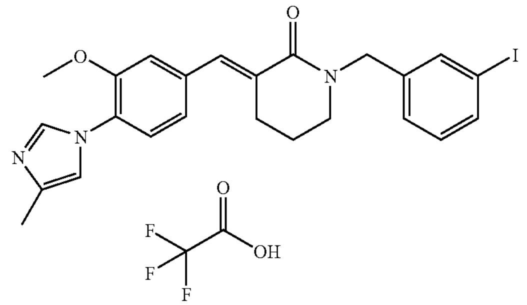

By the same method as in Example 398, (E)-2-[3-methoxy-4-(4-methyl-1H-imidazol-1-yl)benzylidene]-5-oxovaleric acid ethyl ester (197 mg) and 3-iodobenzylamine (310 μL) were reacted. 7.8 mg of the title compound was obtained by purifying the obtained crude product by LC-MS. The physical properties of the compound are as follows.

$^1$H-NMR ($CDCl_3$) δ (ppm): 8.72 (s, 1H), 7.88 (s, 1H), 7.63-7.66 (m, 2H), 7.34 (d, J=8.0 Hz, 1H), 7.29 (d, J=88.0 Hz, 1H), 7.07-7.12 (m, 4H), 4.68 (s, 2H), 3.91 (s, 3H), 3.39 (t, J=5.6 Hz, 2H), 2.80-2.83 (m, 2H), 2.48 (s, 3H), 1.86-1.92 (m, 2H).

Example 403

Synthesis of (E)-1-(2,6-dichloropyridine-4-ylmethyl)-3-[3-methoxy-4-(4-methyl-1H-imidazol-1-yl)benzylidene]piperidin-2-one

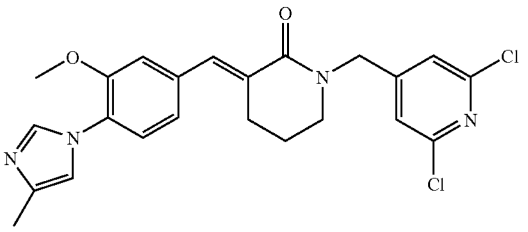

By the same method as in Example 398, 7.4 mg of the title compound was obtained from (E)-2-[3-methoxy-4-(4-methyl-1H-imidazol-1-yl)-benzylidene]-5-oxovaleric acid ethyl ester (130 mg) and C-(2,6-dichloro-pyridin-4-yl)methylamine (101 mg). The physical properties of the compound are as follows.

$^1$H-NMR ($CDCl_3$) δ (ppm): 7.87 (s, 1H), 7.73 (s, 1H), 7.27 (d, J=8.4 Hz, 1H), 7.20 (s, 2H), 7.05 (d, J=8.4 Hz, 1H), 7.04 (s, 1H), 6.95 (s, 1H), 4.69 (s, 2H), 3.87 (s, 3H), 3.44 (t, J=5.6 Hz, 2H), 2.89 (t, J=5.6 Hz, 2H), 2.05 (s, 3H), 1.92-1.98 (m, 2H).

Example 404

Synthesis of (E)-1-(3-fluorobenzyl)-3-[3-methoxy-4-(4-methyl-1H-imidazol-1-yl)benzylidene]azepan-2-one

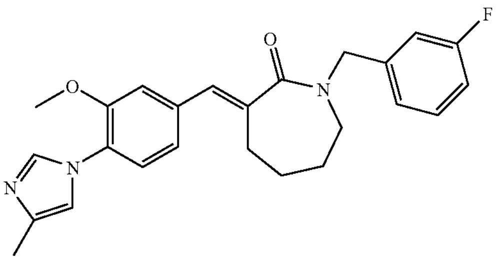

Synthesis of 2-(diethoxyphosphoryl)-5-[1,3]dioxolan-2-yl valeric acid ethyl ester To a DMF (50 mL) solution of diethylphosphono ethyl acetate ester (2.65 mL), sodium hydride (643 mg) and 2-(3-chloropropyl)-1,3-dioxolane (2.6 g) were added at 0° C. one by one, and the reaction solution was allowed to be warmed to 60° C. and agitated overnight. Water and ethyl acetate were added to the reaction solution, and the organic layer was partitioned. After the obtained organic layer was washed with a saturated saline solution, it was dried over anhydrous magnesium sulfate and the organic layer was concentrated under reduced pressure. The obtained residue was purified by silica gel chromatography (heptane-ethyl acetate=from 1:2 to 1:5 to ethyl acetate), and 1.62 g of the title compound was obtained. The physical properties of the compound are as follows.

$^1$H-NMR ($CDCl_3$) δ (ppm): 4.84 (t, J=4.8 Hz, 1H), 4.10-4.25 (m, 6H), 3.93-3.97 (m, 2H), 3.80-3.85 (m, 2H), 2.88-2.90 (m, 1H), 1.97-2.10 (m, 1H), 1.82-1.94 (m, 1H), 1.64-1.71 (m, 2H), 1.40-1.57 (m, 2H), 1.21-1.35 (m, 9H).

Synthesis of (E)-5-[1,3]dioxolan-2-yl-2-[3-methoxy-4-(4-methyl-1H-imidazol-1-yl)benzylidene]valeric acid ethyl ester To a solution of 3-methoxy-4-(4-methyl-1H-imidazol-1-yl)-benzaldehyde (580 mg) obtained in Example 1 in THF (10 mL) and ethanol (10 mL), 2-(diethoxyphosphoryl)-5-[1,3]dioxolan-2-yl valeric acid ethyl ester (826 mg) and lithium hydroxide monohydrate (205 mg) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate:ethanol=20:1), and it was obtained 485 mg, the title compound was obtained as an isomer mixture (E:Z=4:1). The physical properties of the compound are as follows.

$^1$H-NMR ($CDCl_3$) δ (ppm): 7.72 (s, 1H), 7.64 (s, 1H), 7.24-7.26 (m, 1H), 7.01-7.04 (m, 2H), 6.93 (s, 1H), 4.89 (t, J=4.0 Hz, 1H), 4.28 (q, J=7.2 Hz, 2H), 3.92-3.95 (m, 2H), 3.87 (s, 3H), 3.81-3.85 (m, 2H), 2.57-2.61 (m, 2H), 2.30 (s, 3H), 1.66-1.78 (m, 4H), 1.36 (t, J=7.2 Hz, 3H).

Synthesis of (E)-2-[3-methoxy-4-(4-methyl-1H-imidazol-1-yl)benzylidene]-6-oxohexanoic acid ethyl ester To an aqueous solution (2.0 mL) of (E)-5-[1,3]dioxolan-2-yl-2-[3-methoxy-4-(4-methyl-1H-imidazol-1-yl)benzylidene]valeric acid ethyl ester (480 mg), acetic acid (1.0 mL) and trifluoroacetic acid (1.0 mL) were added one by one, and the reaction solution was agitated at room temperature for 2.5 hours. A saturated sodium bicarbonate water and ethyl acetate were added to the reaction solution after confirming disappearance of the starting materials, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate→ethyl acetate:ethanol=10:1), and 400 mg of the title compound was obtained. The physical properties of the compound are as follows.

$^1$H-NMR ($CDCl_3$) δ (ppm): 9.78 (s, 1H), 7.50-7.80 (brs, 1H), 7.69 (s, 1H), 7.28-7.31 (m, 1H), 7.08 (d, J=8.0 Hz, 1H), 7.03 (s, 1H), 6.90-6.96 (m, 1H), 4.30 (q, J=7.2 Hz, 2H), 3.89 (s, 3H), 2.47-2.61 (m, 4H), 2.31 (s, 3H), 1.86-1.93 (s, 2H), 1.37 (t, J=7.2 Hz, 3H).

Synthesis of (E)-6-(3-fluorobenzylamino)-2-[3-methoxy-4-(4-methyl-1H-imidazol-1-yl)benzylidene]hexanoic acid ethyl ester To a methylene chloride (6 mL) solution of (E)-2-(3-methoxy-4-(4-methyl-1H-imidazol-1-yl)benzylidene)-6-oxohexanoic acid ethyl ester (231 mg), 3-fluorobenzylamine (88.7 μL), acetic acid (0.5 mL) and sodium triacetoxy borohydride (165 mg) were added one by one. After agitating the reaction solution at room temperature overnight, a saturated sodium bicarbonate water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex NH, elution solvent; heptane-ethyl acetate=1:1→ethyl acetate→ethyl acetate:ethanol=10:1), and 173 mg of the title compound was obtained. The physical properties of the compound are as follows.

$^1$H-NMR ($CDCl_3$) δ (ppm): 7.71 (s, 1H), 7.62 (s, 1H), 7.20-7.25 (m, 2H), 6.98-7.08 (m, 4H), 6.86-6.93 (m, 2H), 4.27 (q, J=7.2 Hz, 2H), 3.84 (s, 3H), 3.77 (s, 2H), 2.60-2.70 (m, 2H), 2.52-2.60 (m, 2H), 2.30 (s, 3H), 1.76-1.87 (m, 4H), 1.35 (t, J=7.2 Hz, 3H).

Synthesis of (E)-1-(3-fluorobenzyl)-3-[3-methoxy-4-(4-methyl-1H-imidazol-1-yl)benzylidene]azepan-2-one To a to ethanol (2.0 mL) solution of (E)-6-(3-fluorobenzylamino)-2-(3-methoxy-4-(4-methyl-1H-imidazol-1-yl)benzylidene)hexanoic acid ethyl ester (173 mg), 2N sodium hydroxide solution (2.0 mL) was added. After refluxing the reaction solution for 1 hour and confirming disappearance of the starting materials, 2N hydrochloric acid and ethyl acetate were added to the reaction solution, and the organic layer was partitioned. After the obtained organic layer was washed with a saturated saline solution, it was dried over anhydrous magnesium sulfate and concentrated under reduced pressure. IPEA (134 μL), EDC (98.2 mg), and HOBT (69.2 mg) were added to a DMF (5.0 mL) solution of the obtained carboxylic acid compound (112 mg) one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:ethyl acetate), and 70.3 mg of the title compound was obtained. The physical properties of the compound are as follows.

$^1$H-NMR ($CDCl_3$) δ (ppm): 7.72 (d, J=1.2 Hz, 1H), 7.28-7.34 (m, 1H), 7.23 (d, J=26 Hz, 1H), 6.95-7.15 (m, 6H), 6.94 (t, J=1.2 Hz, 1H), 4.67 (s, 2H), 3.86 (s, 3H), 3.36 (t, J=5.2 Hz, 2H), 2.62 (t, J=5.2 Hz, 2H), 2.30 (s, 3H), 1.82-1.88 (m, 2H), 1.61-1.68 (m, 2H).

Example 405

Synthesis of 3-[4-(1H-imidazol-1-yl)-3-methoxybenzylidene]-1-naphthalen-1-ylmethyl-piperidin-2-one trifluoroacetic acid salt

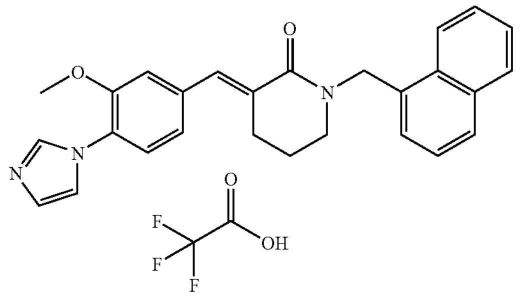

Synthesis of 1-naphthalen-1-ylmethyl-piperidin-2-one

To a DMF (20 mL) solution of 6-valerolactam (1.0 g), sodium hydride (404 mg), 1-(chloromethyl)naphthalene (1.78 g) and sodium iodide (151 mg) were added one by one at 0° C., and the reaction solution was allowed to be warmed to 60° C., and was agitated for 6 hours. 2N hydrochloric acid and THF were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (heptane:elution solvent; ethyl acetate=1:2→ethyl acetate), and 2.42 g of the title compound was obtained. The physical properties of the compound are as follows.

$^1$H-NMR ($CDCl_3$) δ (ppm): 8.08-8.11 (m, 1H), 7.83-7.85 (m, 1H), 7.78 (d, J=8.4 Hz, 1H), 7.45-7.53 (m, 2H), 7.40 (dd, J=6.8, 8.0 Hz, 1H), 7.31 (d, J=6.8 Hz, 1H), 5.08 (s, 2H), 3.09 (t, J=6.0 Hz, 2H), 2.50 (t, J=6.0 Hz, 2H), 1.67-1.79 (m, 4H).

Synthesis of 3-[4-(1H-imidazol-1-yl)-3-methoxybenzylidene]-1-naphthalen-1-ylmethylpiperidin-2-one trifluoroacetic acid salt To a THF (7.0 mL) solution of 1-naphthalen-1-ylmethylpiperidin-2-one (800 mg), lithium bis(trimethylsilyl)amide (1.5M THF capacity, 6.68 mL) was added at 0° C., and the reaction solution was agitated for 20 minutes. A THF (2 mL) solution of 4-(1H-imidazol-1-yl)-3-methoxy benzaldehyde (676 mg) obtained in Example 1 was added dropwise to the reaction solution, and the reaction solution was agitated at room temperature overnight. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (hexane: elution solvent:ethyl acetate=one→ethyl acetate→ethyl acetate:ethanol 10:1), and 330 mg of alcoholic compounds was obtained. Next, methane sulfonyl chloride (31 μL) and TEA were added to a methylene chloride (1.0 mL) solution of the obtained alcoholic compound at 0° C. (113 μL), and the reaction solution was agitated for 3 hours and 30 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. DBU (24.7 mg) was added to the methylene chloride (1.0 mL) solution of the obtained residue, and the reaction solution was agitated at room temperature overnight. The reaction solution was purified in LC-MS as it was, and 3.1 mg of the title compound was obtained. The physical properties of the compound are as follows.

$^1$H-NMR ($CD_3OD$) δ (ppm): 9.24 (s, 1H), 8.10-8.12 (m, 1H), 7.89-7.92 (m, 1H), 7.83-7.85 (m, 2H), 7.72 (s, 1H), 7.51-7.55 (m, 2H), 7.44-7.47 (m, 2H), 7.36 (d, J=6.4 Hz, 1H), 7.25 (s, 1H), 7.08 (d, J=8.0 Hz, 1H), 5.19 (d, J=15 Hz, 1H), 5.07 (d, J=15 Hz, 1H), 3.89 (s, 3H), 3; 41 (dd, J=4.0, 13 Hz, 1H), 3.14-3.24 (m, 2H), 2.95 (dd, J=9.2, 14 Hz, 1H), 2.78-2.84 (m, 1H), 1.78-1.88 (m, 2H), 1.66-1.76 (m, 1H), 1.51-1.60 (m, 1H).

Example 406

Synthesis of 3-[3-methoxy-4-(4-methyl-1H-imidazol-1-yl)benzylidene]-1-naphthalen-1-ylmethylpyrrolidin-2-one trifluoroacetic acid salt

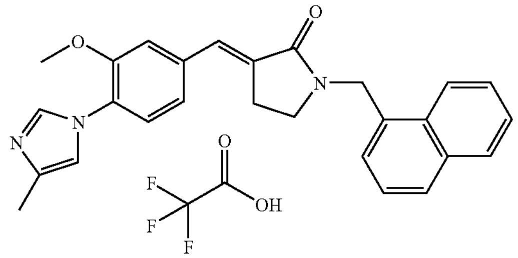

Synthesis of 1-naphthalen-1-ylmethy-pyrrolidin-2-one

By the same way as Example 405, 2.32 g of the title compound was obtained from 2-pyrrolidone (767 μL) and 1-(chloromethyl)naphthalene (1.78 g). The physical properties of the compound are as follows.

$^1$H-NMR ($CDCl_3$) δ (ppm): 9.41 (s, 1H), 8.15-8.17 (m, 1H), 8.00 (s, 1H), 7.94-7.97 (m, 1H), 7.87 (d, J=8.0 Hz, 1H), 7.85 (s, 1H), 7.78 (s, 1H), 7.64 (d, J=8.0 Hz, 1H), 7.47-7.57 (m, 3H), 7.40-7.42 (m, 2H), 7.23 (d, J=8.4 Hz, 1H), 5.14 (s, 2H), 3.89 (s, 3H), 3.32 (t, J=5.6 Hz, 2H), 2.81 (t, J=5.6 Hz, 2H), 1.78 (t, J=5.6 Hz, 2H).

Synthesis of 3-[3-methoxy-4-(4-methyl-1H-imidazol-1-yl)benzylidene]-1-naphthalen-1-ylmethyl-pyrrolidin-2-one mono(trifluoroacetic-acid) salt By the same method as in Example 405, 1-naphthalen-1-ylmethylpyrrolidin-2-one (300 mg) obtained in Example 1, 3.4 mg of the title compound was obtained from the 3-methoxy-4-(4-methyl-1H-imidazol-1-yl)benzaldehyde (431 mg). The physical properties of the compound are as follows.

$^1$H-NMR ($CD_3OD$) δ (ppm): 9.14 (t, J=1.2 Hz, 1H), 8.16-8.18 (m, 1H), 7.88-7.93 (m, 2H), 7.46-7.58 (m, 7H), 7.38-7.41 (m, 1H), 7.32 (d, J=7.6 Hz, 1H), 5.11 (s, 2H), 3.95 (s, 3H), 3.37 (t, J=6.8 Hz, 2H), 3.05-3.10 (m, 2H), 2.42 (s, 3H)

Example 407

Synthesis of 3-[3-methoxy-4-(4-methyl-1H-imidazol-1-yl)benzylidene]-1-naphthalen-1-ylmethylazepan-2-one trifluoroacetic acid salt

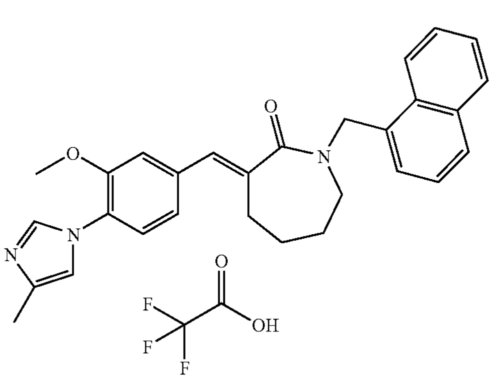

Synthesis of 1-naphthalen-1-ylmethylazepan-2-one

By the same method as in Example 405, 2.53 g of the title compound was obtained from ϵ-caprolactam (1.14 g) and 1-(chloromethyl)naphthalene (1.78 g). The physical properties of the compound are as follows.

$^1$H-NMR ($CDCl_3$) δ (ppm): 8.12 (d, J=8.4 Hz, 1H), 7.85-7.87 (m, 1H), 7.80 (d, J=8.4 Hz, 1H), 7.48-7.56 (m, 2H), 7.42 (t, J=8.4 Hz, 1H), 7.35 (d, J=6.4 Hz, 1H), 5.06 (s, 2H), 3.26-3.29 (m, 2H), 2.62-2.65 (m, 2H), 1.58-1.70 (m, 4H), 1.21-1.26 (m, 2H).

Synthesis of 3-[3-methoxy-4-(4-methyl-1H-imidazol-1-yl)benzylidene]-1-naphthalen-1-ylmethylazepan-2-one the trifluoroacetic acid salt By the same method as in Example 405, 1.0 mg of the title compound was obtained from the 3-methoxy-4-(4-methyl-1H-imidazol-1-yl)benzaldehyde (383 mg) obtained in Example 1 and 1-naphthalen-1-ylmethyl-azepin-2-one (300 mg). The physical properties of the compound are as follows.

1H-NMR ($CD_3OD$) δ (ppm): 9.08 (d, J=1.2 Hz, 1H), 8.18 (d, J=9.2 Hz, 1H), 7.92 (dd, J=2.0, 7.6 Hz, 1H), 7.88 (d, J=7.6 Hz, 1H), 7.44-7.57 (m, 6H), 7.31 (d, J=1.2 Hz, 1H), 7.23 (dd, J=1.6, 8.4 Hz, 1H), 7.04 (s, 1H), 5.16 (s, 2H), 3.94 (s, 3H), 3.44 (t, J=5.6 Hz, 2H), 2.59 (t, J=5.6 Hz, 2H), 2.43 (s, 3H), 1.63-1.69 (m, 2H), 1.22-1.25 (m, 2H).

Example 408

Synthesis of (Z)-3-benzyl-5-[3-methoxy-4-(4-methyl-1H-imidazol-1-yl)benzylidene]imidazolidine-2,4-dione

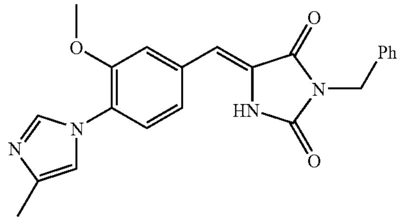

Synthesis of (Z)-2-benzyloxycarbonylamino-3-[3-methoxy-4-(4-methyl-1H-imidazol-1-yl)phenyl] acrylic acid methyl ester To a methylene chloride (10 mL) suspension of potassium tert-butoxide (290 mg), a methylene chloride (3 mL) solution of benzyloxycarbonylamino(diethoxyphosphono)acetic acid methyl ester (850 mg) was added dropwise at −70° C. After agitating the reaction solution at −70° C. for 2 hours, a methylene chloride (7 mL) solution of 3-methoxy-4-(4-methyl-1H-imidazol-1-yl)benzaldehyde (500 mg) obtained in Example 1 was added dropwise. The reaction solution was agitated at −70° C. for 1 hour, and then agitated at room temperature for 4 hours. Ethyl acetate and a saturated ammonium chloride solution were added to the reaction solution after the reaction ended, and the organic layer was separated. After drying the obtained organic layer with anhydrous magnesium sulfate, the solvent was evaporated under reduced pressure. The obtained residue was purified by silica gel column chromatography (ethyl acetate 4:1→elution solvent: hexane:ethyl acetate), and 433 mg (45%) of (Z)-2-benzyloxycarbonylamino-3-[3-methoxy-4-(4-methyl-1H-imidazol-1- yl)phenyl]acrylic acid methyl ester was obtained. The physical properties of the compound are as follows.

$^1$H-NMR ($CDCl_3$) δ (ppm): 2.37 (s, 3H), 3.68 (s, 3H), 3.86 (s, 3H), 5.11 (s, 2H), 6.50 (brs, 1H), 6.91 (s, 1H), 7.11-7.35 (m, 9H), 7.70 (s, 1H).

Synthesis of (Z)-(1-benzylcarbamoyl-2-[3-methoxy-4-(4-methyl-1H-imidazol-1-yl)phenyl]vinyl)carbamic acid benzyl ester To a solution of (Z)-2-benzyloxycarbonylamino-3-[3-methoxy-4-(4-methyl-1H-imidazol-1-yl)phenyl]acrylic acid methyl ester (433 mg) obtained at the above step in THF (1 mL) and methanol (2 mL), 2N sodium hydroxide solution (1.5 mL) was added, and the reaction solution was agitated at room temperature for 12 hours. After the reaction ended, 2N hydrochloric acid (1.5 mL) was added to the reaction solution to neutralize it, and the reaction solution was extracted with ethyl acetate. After the organic layer was washed with a saturated saline solution and dried with anhydrous magnesium sulfate, the solvent was evaporated under reduced pressure. By adding ether to the obtained residue, 363 mg (87%) of carboxylic acid compound was obtained as a solid. Diethyliso propylamine (0.05 mL), HOBT (30 mg), and EDC (40 mg) were added to a DMF (3 mL) solution of the obtained carboxylic acid (66 mg) and benzylamine (0.018 mL), and the reaction solution was agitated at room temperature for 12 hours. Ethyl acetate and saturated sodium bicarbonate water were added to the reaction solution after the reaction ended, and after separating the organic layer and drying the obtained organic layer with anhydrous magnesium sulfate, the solvent was evaporated under reduced pressure. The obtained residue was purified by silica gel column chromatography (elution solvent:hexane:ethyl acetate=4:1→ethyl acetate), and 448 mg (60%) of (Z)-(1-benzylcarbamoyl-2-[3-methoxy-4-(4-methyl-1H-imidazol-1-yl)phenyl]vinyl)carbamic acid benzyl ester was obtained. The physical properties of the compound are as follows.

$^1$H-NMR ($CDCl_3$) δ(ppm): 2.30 (s, 3H), 3.68 (s, 3H), 4.55 (d, J=7.2 Hz, 2H), 5.15 (s, 2H), 6.22-6.38 (m, 1H), 6.55 (brt, J=7.2 Hz, 1H), 6.91 (s, 1H), 7.03-7.39 (m, 14H), 7.68 (s, 1H).

Synthesis of (Z)-3-benzyl-5-[3-methoxy-4-(4-methyl-1H-imidazol-1-yl)benzylidene]imidazolidine-2,4-dione To a THF (3 mL) solution of (Z)-{1-benzylcarbamoyl-2-[3-methoxy-4-(4-methyl-1H-imidazol-1-yl)phenyl]vinyl}carbamic acid benzyl ester (48 mg) obtained above, TBAF (1M THF solution, 0.01 mL) was added and heat-refluxing of the reaction solution was carried out for 3 hours. After the reaction solution was allowed to be cooled to room temperature, ethyl acetate was added and washed with a saturated ammonium chloride solution. After drying the organic layer over anhydrous magnesium sulfate, the solvent was evaporated under reduced pressure. The obtained residue was purified by silica gel column chromatography (elution solvent:from hexane:ethyl acetate 1:1 to ethyl acetate), and 28 mg (75%) of (Z)-3-benzyl-5-[3-methoxy-4-(4-methyl-1H-imidazol-1-yl)benzylidene]imidazolidine-2,4-dione was obtained. The physical properties of the compound are as follows.

$^1$H-NMR ($CDCl_3$) δ(ppm): 2.31 (s, 3H), 3.78 (s, 3H), 4.79 (s, 2H), 6.72 (s, 1H), 6.88 (brs, 1H), 7.03-7.45 (m, 9H), 9.95 (s, 1H), 12.7 (brs, 1H).

Example 409

Synthesis of (Z)-5-[3-methoxy-4-(4-methyl-1H-imidazol-1-yl)benzylidene]-3-(4-methoxyphenyl)-2-thioxsoimidazolidine-4-one

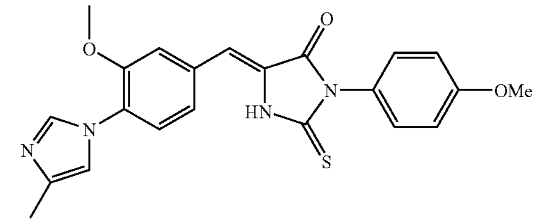

Synthesis of (Z)-5-[3-methoxy-4-(4-methyl-1H-imidazol-1-yl)benzylidene]-3-(4-methoxyphenyl)-2-thioxoimidazolidine-4-one Piperidine (0.019 mL) was added to an ethanol (2 mL) solution of 3-methoxy-4-(4-methyl-1H-imidazol-1-yl)benzaldehyde (20 mg) obtained in Example 1 and 3-(4-methoxyphenyl)-2-thioxoimidazolidine-4-one (21 mg), and heat-refluxing of the reaction solution was carried out for 12 hours. The reaction solution was allowed to be cooled to room temperature and the solid deposited was separated by filtering, and 18 mg (47%) of the title compound was obtained by washing with ethanol and ether. The physical properties of the compound are as follows.

$^1$H-NMR (DMSO-d6) δ(ppm): 2.15 (s, 3H), 3.81 (s, 3H), 3.93 (s, 3H), 6.69 (s, 1H), 7.22 (d, J=9.2 Hz, 2H), 7.20 (s, 1H), 7.38 (d, J=9.2 Hz, 2H), 7.44 (d, J=8.0 Hz, 1H), 7.54 (brs, 1H), 7.56 (brd, J=8.0 Hz, 1H), 7.85 (brs, 1H).

The compounds shown in Table 9 were synthesized as in Example 409. The structural formulae and physicochemical properties are shown in Table 9, respectively.

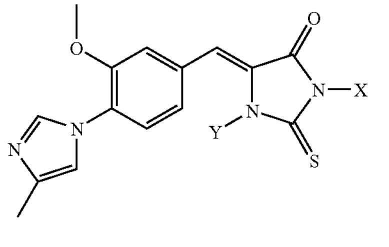

TABLE 9

| Example | X | Y | DATA: MS m/z |
|---|---|---|---|
| 410 | 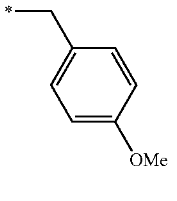 | H | $M^+$ + H: 435 (ESI) |

TABLE 9-continued

| Example | X | Y | DATA: MS m/z |
|---|---|---|---|
| 411 | 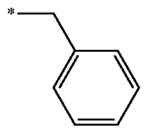 | H | M$^+$ + H: 405 (ESI) |
| 412 | 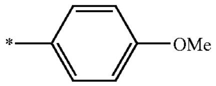 | Me | M$^+$ + H: 435 (ESI) |

Example 413 and Example 414

Synthesis of (E)-N-[(4R) and (4S)-chroman-4-yl]-3-[3-methoxy-4-(4-methyl-1H-imidazol-1-yl)phenyl] acrylamide

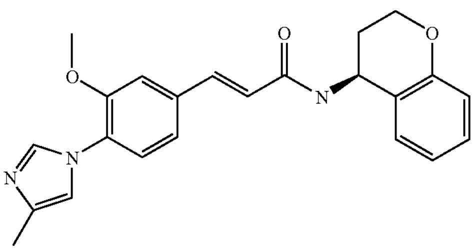

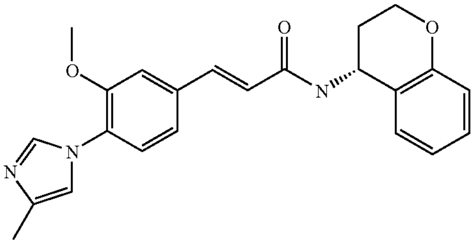

To a DMF (4 mL) solution of (E)-3-[3-methoxy-4-(4-methyl-1H-imidazol-1-yl)phenyl]acrylic acid (70 mg) obtained in Example 121, chroman-4-ylamine (CAS#53981-38-7) (49 mg), EDC (62 mg) and HOBT (44 mg) were added at room temperature under nitrogen atmosphere, and the reaction solution was agitated at room temperature for 17 hours. Water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The obtained residue was purified by silica gel chromatography (elution solvent:methanol-ethyl acetate system), and (E)-N-(chroman-4-yl)-3-[3-methoxy-4-(4-methyl-1H-imidazol-1-yl)phenyl]acrylamide racemate (90 mg) was obtained. This compound (50 mg) was separated by CHIRALPAK™ AD-H (2 cm×25 cm: mobile phase; hexane-ethanol 20%) available from Daicel Chemical Industries, Ltd., and the title optically-active substance with a retention time of 22 minutes (16 mg;>99% ee) and the title optically-active substance with a retention time of 28 minutes (19 mg;>98% ee) were obtained. The physical properties of the title optically-active substance with a retention time of 22 minutes (Example 413) are as follows.

$^1$H-NMR ($CDCl_3$) δ (ppm): 2.11-2.21 (m, 1H), 2.26-2.36 (m, 1H), 2.29 (s, 3H), 3.88 (s, 3H), 4.15-4.23 (m, 1H), 4.27-4.35 (m, 1H), 5.25-5.32 (m, 1H), 5.88 (d, J=7.2 Hz, 1H), 6.39 (d, J=15.6 Hz, 1H), 6.83-6.95 (m, 3H), 7.11-7.28 (m, 5H), 7.67 (d, J=15.2 Hz, 1H), 7.71 (d, J=1.2 Hz, 1H).

The physical properties of the title optically-active substance with a retention time of 22 minutes (Example 414) are as follows.

$^1$H-NMR ($CDCl_3$) δ (ppm): 2.11-2.21 (m, 1H), 2.26-2.36 (m, 1H), 2.29 (s, 3H), 3.88 (s, 3H), 4.15-4.23 (m, 1H), 4.27-4.35 (m, 1H), 5.25-5.32 (m, 1H), 5.88 (d, J=7.2 Hz, 1H), 6.39 (d, J=15.6 Hz, 1H), 6.83-6.95 (m, 3H), 7.11-7.28 (m, 5H), 7.67 (d, J=15.2 Hz, 1H), 7.71 (d, J=1.2 Hz, 1H).

Example 415

Synthesis of (E)-N-[1-(4-fluorophenyl)-1-methyl ethyl]-3-[3-methoxy-4-(4-methyl-1H-imidazol-1-yl) phenyl]acrylamide

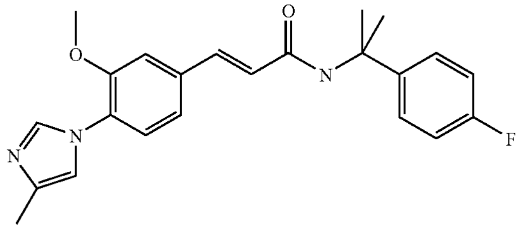

To a DMF (5 mL) solution of (E)-3-(3-methoxy-4-(4-methyl-1H-imidazol-1-yl)phenyl)acrylic acid (60 mg) obtained in Example 121, 1-(4-fluorophenyl)-1-methylethylamine (CAS#17797-10-3) (43 mg), EDC (53 mg) and HOBT (38 mg) were added at room temperature under nitrogen atmosphere, and the reaction solution was agitated at room temperature for 12 hours. Water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The obtained residue was purified by silica gel chromatography (elution solvent:methanol-ethyl acetate system), and the title compound (60 mg) was obtained.

$^1$H-NMR ($CDCl_3$) δ (ppm): 1.77 (s, 6H), 2.29 (d, J=0.8 Hz, 3H), 3.87 (s, 3H), 5.90 (brs, 1H), 6.41 (d, J=15.2 Hz, 1H), 6.90-6.94 (m, 1H), 6.97-7.05 (m, 2H), 7.09 (d, J=2.0 Hz, 1H), 7.14 (dd, J=2.0, 8.0 Hz, 1H), 7.20-7.28 (m, 1H), 7.35-7.43 (m, 2H), 7.54 (d, J=15.2 Hz, 1H), 7.71 (d, J=1.2 Hz, 1H).

Example 416

Synthesis of (E)-1-(3,4-difluorobenzyl)-3-[3-methoxy-4-(4-methyl-1H-imidazol-1-yl)benzylidene] piperidin-2-one

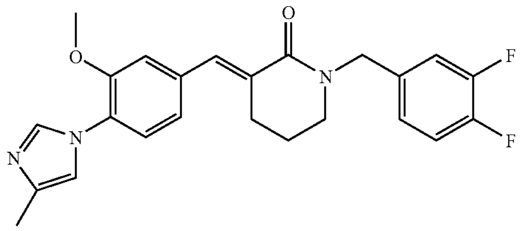

Synthesis of (E)-3-[3-methoxy-4-(4-methyl-1H-imidazol-1-yl)benzylidene]piperidin-2-one To a sodium hydride suspension (40% mineral oil content, 2.77 g) in THF (50 mL) and DMF (200 mL), a solution of 3-methoxy-4-(4-methyl-1H-imidazol-1-yl)benzaldehyde (10 g) obtained in Example 1 and 1-acetylpiperidin-2-one (7.17 g) in THF (50 mL) and DMF (200 mL) were added dropwise over 20 minutes at 5° C. This reaction solution was agitated at 0° C. for 2 hours. The reaction solution was added to iced water and the reaction solution was extracted with ethyl acetate. The obtained organic layer was washed with a saturated sodium chloride solution, and concentrated under reduced pressure after dried over anhydrous magnesium sulfate. The deposited solids were separated by filtering and 5.0 g of the title compound was obtained by washing with diethyl ether. The physical properties of the compound are as follows.

$^1$H-NMR ($CDCl_3$) δ (ppm): 1.86-1.96 (m, 2H), 2.30 (s, 3H), 2.81-2.87 (m, 2H), 3.42-3.50 (m, 2H), 3.86 (s, 3H), 5.97 (brs, 1H), 6.93 (s, 1H), 7.00-7.08 (m, 2H), 7.22-7.28 (m, 1H), 7.71 (d, J=1.2 Hz, 1H), 7.79 (s, 1H).

Synthesis of (E)-1-(3,4-difluorobenzyl)-3-[3-methoxy-4-(4-methyl-1H-imidazol-1-yl)benzylidene]piperidin-2-one To a DMF (6.0 mL) solution of (E)-3-(3-methoxy-4-(4-methyl-1H-imidazol-1-yl)benzylidene)piperidin-2-one (100 mg) obtained above, lithium bis(trimethylsilyl)amide (1M hexane solution, 0.60 mL) was added dropwise at 0° C., and the reaction solution was agitated at 0° C. for 30 minutes. 3,4-difluorobenzylbromide (0.06 mL) was added to this solution at 0° C., and the reaction solution was agitated at room temperature for 1 hour. The reaction solution was added to iced water and the reaction solution was extracted with ethyl acetate. The obtained organic layer was washed with a saturated sodium chloride solution, and concentrated under reduced pressure after dried over anhydrous magnesium sulfate. The obtained residue was purified by silica gel column chromatography (elution solvent:heptane-ethyl acetate system), and 110 mg of the title compound was obtained. The physical properties of the compound are as follows.

$^1$H-NMR ($CDCl_3$) δ (ppm): 1.83-1.92 (m, 2H), 2.30 (s, 3H), 2.80-2.87 (m, 2H), 3.34-3.41 (m, 2H), 3.86 (s, 3H), 4.66 (s, 2H), 6.91-6.95 (m, 1H), 7.00-7.07 (m, 3H), 7.07-7.18 (m, 2H), 7.22-7.28 (m, 1H), 7.71 (d, J=1.6 Hz, 1H), 7.86 (s, 1H).

Example 417

Synthesis of (E)-1-[1-(3,4-difluorobenzyl)-(3S)-pyrrolidin-3-yl]-3-[3-methoxy-4-(4-methyl-1H-imidazol-1-yl)benzylidene]piperidin-2-one

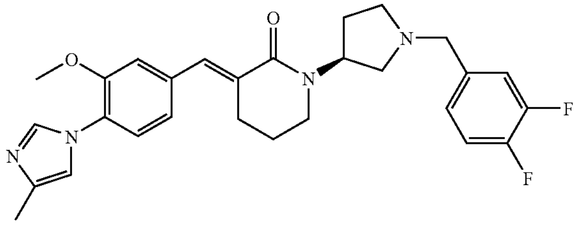

Synthesis of 5-chloro-2-(diethoxyphosphoryl)valeric acid ethyl ester

Sodium hydride (40% mineral oil content, 9.8 g) was washed with hexane (50 mL) 3 times to remove oily substances. A THF (100 mL) solution of phosphonoacetic acid triethyl (50 g) was added dropwise to a THF (400 mL) suspension of this sodium hydride at 0° C. for 30 minutes. Then, the reaction solution was allowed to be warmed to room temperature and agitated for further 1 hour. 1-bromo-3-chloropropane (70.2 g) was added dropwise to this reaction solution for 30 minutes. Heating refluxing of the reaction solution was carried out after the dropping end for 15 hours. This reaction solution was allowed to be cooled to room temperature, ethyl acetate (1 L) and saturated ammonium chloride water (1 L) were added, and the organic layer was partitioned. 61.2 g of the title compound was obtained by drying with anhydrous magnesium sulfate and condensing the obtained organic layer under reduced pressure. The physical properties of the compound are as follows.

$^1$H-NMR ($CDCl_3$) δ (ppm): 1.26-1.38 (m, 9H), 1.55-2.36 (m, 4H), 2.89-3.01 (m, 1H), 3.54 (t, J=6.4 Hz, 2H), 4.23-4.58 (m, 6H).

Synthesis of (E)-5-chloro-2-[3-methoxy-4-(4-methyl-1H-imidazol-1-yl)benzylidene]valeric acid ethyl ester To a solution of 3-methoxy-4-(4-methyl-1H-imidazol-1-yl)benzaldehyde (5 g) obtained in Example 1 in THF (60 mL) and ethanol (20 mL), 5-chloro-2-(diethoxyphosphoryl)valeric acid ethyl ester (7.6 g) and lithium hydroxide monohydrate (2.9 g) were added one by one, and the reaction solution was agitated at room temperature overnight. Water and ethyl acetate were added to the reaction solution after confirming disappearance of the starting materials, and the organic layer was partitioned. After the obtained organic layer was washed with a saturated saline solution, it was dried over anhydrous magnesium sulfate and concentrated under reduced pressure. 3.76 g of the title compound was obtained by purifying the residue by silica gel chromatography (heptane:elution solvent:ethyl acetate=1:1), and re-crystallizing the obtained solid from a mixed solvent of ethyl acetate and hexane. The physical properties of the compound are as follows.

$^1$H-NMR ($CDCl_3$) δ (ppm): 1.37 (t, J=7.6 Hz, 3H), 2.02-2.09 (m, 2H), 2.30 (s, 3H), 2.70-2.76 (m, 2H), 3.60 (t, J=6.4 Hz, 2H), 3.88 (s, 3H), 4.29 (q, J=7.6 Hz, 2H), 6.94 (m, 1H), 7.02 (d, J=1.2 Hz, 1H), 7.06 (dd, J=8.4, 1.2 Hz, 1H), 7.26 (d, J=8.4 Hz, 1H), 7.68 (s, 1H), 7.72 (d, J=1.2 Hz, 1H).

Synthesis of [(3S)-1-(3,4-difluorobenzyl)pyrrolidine-3-yl]carbamic acid tert-butyl ester To a methylene chloride (10 mL) solution of (3S)-3-(tert-butoxycarbonylamino) pyrrolidine (916 mg), 3,4-difluorobenzylbromide (0.7 mL) and IPEA (2.2 mL) were added one by one, and the reaction solution was agitated at room temperature for 20 hours. A saturated sodium bicarbonate water was added to the reaction solution after the reaction ended, and the organic layer was partitioned. It was dried over anhydrous magnesium sulfate and the obtained organic layer was concentrated under reduced pressure. 1.55 g of the title compound was obtained by purifying the residue by silica gel chromatography (elution solvent:heptane:ethyl acetate=1:1). The physical properties of the compound are as follows.

$^1$H-NMR ($CDCl_3$) δ (ppm): 1.44 (s, 9H), 1.55-1.64 (m, 1H), 2.18-2.22 (m, 2H), 2.46-2.81 (m, 3H), 3.52 (d, J=13.6 Hz, 1H), 3.55 (d, J=13.6 Hz, 1H), 4.11-4.23 (m, 1H), 4.82 (brs, 1H), 6.97-7.19 (m, 3H).

Synthesis of [(3S)-1-(3,4-difluorobenzyl)pyrrolidine-3-yl]amine dihydrochloride

To an ethyl acetate solution (5 mL) of (3S)-(1-(3,4-difluorobenzyl)pyrrolidin-3-yl)carbamic acid tert-butyl ester (1.55 g), an ethyl acetate (5 mL) solution of 4N hydrochloric acid was added, and the reaction solution was agitated at room temperature. Deposited substances in the reaction solution was separated by filtering after 10 hours, and 904 mg of the title compound was obtained by further washing with ether. The physical properties of the compound are as follows.

ESI-MS; m/z213 [$M^+$+H].

Synthesis of (E)-1-[1-(3,4-difluorobenzyl)-(3S)-pyrrolidin-3-yl]-3-[3-methoxy-4-(4-methyl-1H-imidazol-1-yl)benzylidene]piperidin-2-one To a solution of (E)-5-chloro-2-(3-methoxy-4-(4-methyl-1H-imidazol-1-yl)benzylidene)valeric acid ethyl ester (200 mg) and ((3S)-1-(3,4-difluorobenzyl)pyrrolidine-3-yl)amine dihydrochloride (315 mg) in acetonitrile (8 mL) and water (2 mL), potassium carbonate (228 mg) and sodium iodide (831 mg) were added. After carrying out heat-refluxing of the reaction solution for 12 hours, the reaction solution allowed to be cooled to room temperature and concentrated under reduced pressure. A 2N sodium hydroxide solution (1 mL) in ethanol (5 mL) was added to the obtained residue. After agitating the reaction mixture at room temperature for 12 hours, it was neutralized with a 5N hydrochloric acid solution, and the reaction solution was extracted with ethyl acetate. After the obtained organic layer was washed with a saturated saline solution, it was dried over anhydrous magnesium sulfate and concentrated under reduced pressure. 200 mg of the title compound was obtained by purifying the residue by silica gel chromatography (Carrier: Chromatorex™ NH; elution solvent:ethyl acetate). The physical properties of the compound are as follows.

$^1$H-NMR ($CDCl_3$) δ (ppm): 1.75-1.93 (m, 3H), 2.22-2.33 (m, 2H), 2.29 (s, 3H), 2.50 (dd, J=10.4, 8.4 Hz, 1H), 2.70 (dd, J=10.4, 3.6 Hz, 1H), 2.77-2.95 (m, 3H), 3.45-3.62 (m, 4H), 3.84 (s, 3H), 5.17-5.45 (m, 1H), 6.92 (s, 1H), 6.98-7.27 (m, 6H), 7.70 (d, J=1.2 Hz, 1H), 7.78 (s, 1H).

Example 418

Synthesis of (E)-1-indan-2-yl-3-[3-methoxy-4-(4-methyl-1H-imidazol-1-yl)benzylidene]piperidin-2-one

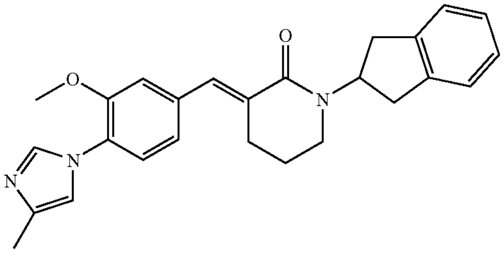

Synthesis of 5-chloro-2-(diethoxyphosphoryl)valeric acid tert-butyl ester

Sodium hydride (40% mineral oil content, 17.4 g) was washed with hexane (100 mL) 3 times to remove oily substances. A THF (100 mL) solution of diethylphosphonoacetic acid tert-butyl ester (100 g) was added dropwise to a THF (500 mL) suspension of this sodium hydride at 0° C. for 30 minutes. Then, the reaction solution was allowed to be warmed to room temperature and agitated for further 1 hour. A THF (100 mL) solution of 1-bromo-3-chloropropane (125 g) was added dropwise to this reaction solution for 30 minutes. Heating refluxing of the reaction solution was carried out after the dropping end for 15 hours. This reaction solution was allowed to be cooled to room temperature, ethyl acetate (1 L) and saturated ammonium chloride water (1 L) were added, and the organic layer was partitioned. 113.4 g of the title compound was obtained by drying with anhydrous magnesium sulfate and condensing the obtained organic layer under reduced pressure. The physical properties of the compound are as follows.

$^1$H-NMR ($CDCl_3$) δ (ppm): 1.31-1.48 (m, 6H), 1.48 (s, 9H), 1.79-2.14 (m, 4H), 2.73-2.91 (m, 1H), 3.55 (t, J=6.4 Hz, 2H), 4.10-4.19 (m, 4H).

Synthesis of (E)-5-chloro-2-[3-methoxy-4-(4-methyl-1H-imidazol-1-yl)benzylidene]valeric acid tert-butyl ester To a solution of 3-methoxy-4-(4-methyl-1H-imidazol-1-yl)benzaldehyde (50 g) in THF (600 mL) and ethanol (200 mL), 5-chloro-2-(diethoxyphosphoryl)valeric acid tert-butyl ester (83.5 g) and lithium hydroxide monohydrate (29.1 g) were added to the one by one, and the reaction solution was agitated at room temperature overnight. Water and ethyl acetate were added to the reaction solution after confirming disappearance of the starting materials, and the organic layer was partitioned. After the obtained organic layer was washed with a saturated saline solution, it was dried over anhydrous magnesium sulfate and concentrated under reduced pressure. 54.9 g of the title compound was obtained by purifying the residue by silica gel chromatography (elution solvent:heptane:ethyl acetate=1:1), and re-crystallizing the obtained solid from the mixed-solution of ethyl acetate and hexane. The physical properties of the compound are as follows.

$^1$H-NMR ($CDCl_3$) δ (ppm): 1.55 (s, 9H), 1.99-2.08 (m, 2H), 2.30 (s, 3H), 2.63-2.71 (m, 2H), 3.59 (t, J=6.4 Hz, 2H), 3.87 (s, 3H), 6.93 (m, 1H), 7.00 (d, J=1.2 Hz, 1H), 7.09 (dd, J=8.4, 1.2 Hz, 1H), 7.27 (d, J=8.4 Hz, 1H), 7.58 (s, 1H), 7.72 (m, 1H).

Synthesis of (E)-5-chloro-2-[3-methoxy-4-(4-methyl-1H-imidazol-1-yl)benzylidene]valeric acid trifluoroacetic acid salt To a methylene chloride (20 mL) solution of (E)-5-chloro-2-(3-methoxy-4-(4-methyl-1H-imidazol-1-yl)benzylidene) valeric acid tert-butyl ester (5 g), trifluoroacetic acid (10 mL) was added and the reaction solution was agitated at room temperature for 2 hours. After confirming disappearance of the starting materials, the reaction solution was concentrated under reduced pressure. The resulted solids were separated by filtering and 5.7 g of the title compound was obtained by washing with ethyl acetate further. The physical properties of the compound are as follows.

$^1$H-NMR (DMSO-$d_6$) δ (ppm): 1.93-2.03 (m, 2H), 2.35 (s, 3H), 2.58-2.66 (m, 2H), 3.70 (t, J=6.4 Hz, 2H), 3.91 (s, 3H), 7.24 (dd, J=8.4, 1.2 Hz, 1H), 7.37 (d, J=1.2 Hz, 1H), 7.64 (d, J=8.4, 1H), 7.66 (m, 1H), 7.76 (s, 1H), 9.36 (m, 1H).

Synthesis of (E)-5-chloro-2-[3-methoxy-4-(4-methyl-1H-imidazol-1-yl)benzylidene]valeric acid indan-2-ylamide To a DMF solution (200 mL) of (E)-5-chloro-2-(3-methoxy-4-(4-methyl-1H-imidazol-1-yl)benzylidene)valeric acid trifluoroacetic acid salt (13 g) and 2-amino indan hydrochloride (7.8 g), IPEA (24.1 mL), HOBT (9.4 g) and EDC (13.3 g) were added one by one, and the reaction solution was agitated at room temperature. Ethyl acetate and saturated sodium bicarbonate water were added to the reaction solution after 15 hours, and the organic layer was partitioned. After the obtained organic layer was washed with a saturated sodium chloride solution, it was dried over anhydrous magnesium sulfate and concentrated under reduced pressure. 6.93 g of the title compound was obtained by purifying the residue by silica gel chromatography (elution solvent:ethyl acetate). The physical properties of the compound are as follows.

$^1$H-NMR ($CDCl_3$) δ (ppm): 1.93-2.04 (m, 2H), 2.28 (s, 3H), 2.67-2.73 (m, 2H), 2.90 (dd, J=16.0, 4.4 Hz, 2H), 3.40 (dd, J=16.0, 7.2 Hz, 2H), 3.56 (t, J=5.6 Hz, 2H), 3.84 (s, 3H), 4.81-4.95 (m, 1H), 6.29 (d, J=7.2 Hz, 1H), 6.90-6.94 (m, 3H), 7.10 (s, 1H), 7.18-7.27 (m, 5H), 7.68 (d, J=1.6 Hz, 1H).

Synthesis of (E)-1-indan-2-yl-3-[3-methoxy-4-(4-methyl-1H-imidazol-1-yl)benzylidene]piperidin-2-one To a DMF (50 mL) solution of (E)-5-chloro-2-(3-methoxy-4-(4-methyl-1H-imidazol-1-yl)benzylidene)valeric acid indan-2-ylamide (6.9 g), sodium hydride (40% mineral oil content, 740 mg) was added at room temperature, and the reaction solution was agitated at room temperature for 1 hour and 30 minutes. The reaction solution was poured into iced water after the reaction ended, and the deposited solids were separated by filtering. 4.9 g of the title compound was obtained by recrystallizing the obtained solid from a mixed solvent of ethyl acetate, ethanol, and hexane. The physical properties of the compound are as follows.

$^1$H-NMR ($CDCl_3$) δ (ppm): 1.81-1.88 (m, 2H), 2.30 (s, 3H), 2.77-2.84 (m, 2H), 3.00 (dd, J=16.4, 6.0 Hz, 2H), 3.24-3.32 (m, 4H), 3.86 (s, 3H), 5.75-5.83 (m, 1H), 6.93 (d, J=1.2 Hz, 1H), 7.02-7.07 (m, 2H), 7.17-7.28 (m, 5H), 7.71 (d, J=1.2 Hz, 1H), 7.85 (s, 1H).

Example 419 and Example 420

Synthesis of (E)-1-[(4R) and (4S)-chroman-4-yl]-3-[3-methoxy-4-(4-methyl-1H-imidazol-1-yl)benzylidene]piperidin-2-one

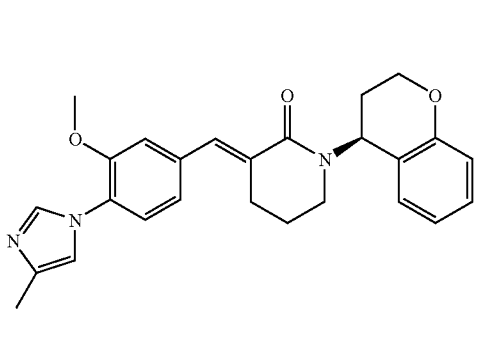

-continued

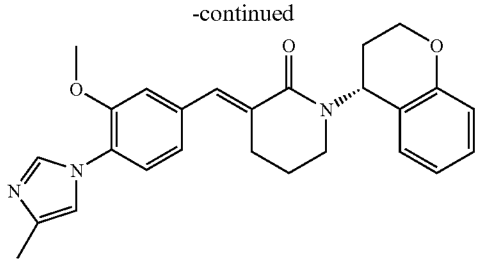

To a solution of (E)-5-chloro-2-(3-methoxy-4-(4-methyl-1H-imidazol-1-yl)benzylidene)valeric acid ethyl ester (50.mg) obtained in Example 417 in acetonitrile (2 mL) and water (0.2 mL), chroman-4-ylamine (CAS#53981-38-7) (31 mg) and cesium carbonate (90 mg) were added at room temperature, and the mixture was reacted in a microwave synthesizing equipment (80 W;150° C.) for 1 hour. The reaction solution was allowed to be cooled to room temperature, water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The obtained residue was purified by silica gel chromatography (Carrier: Chromatorex™ NH, an elution solvent:heptane-ethyl acetate system), and (E)-5-(chroman-4-ylamino)-2-[3-methoxy-4-(4-methyl-1H-imidazol-1-yl)benzylidene]valeric acid ethyl ester (25 mg) was obtained. 2N sodium hydroxide solution (1 mL) was added to an ethanol (3 mL) solution of the (E)-5-(chroman-4-ylamino)-2-[3-methoxy-4-(4-methyl-1H-imidazol-1-yl)benzylidene]valeric acid ethyl ester (59 mg) obtained by repeating the above-mentioned operation at room temperature, the reaction solution was agitated at room temperature for 12 hours, and heat-refluxing was carried out for further 1 hour. The reaction solution was allowed to be cooled to room temperature, 2N hydrochloric acid (1 mL) was added to the reaction solution under ice-cooling, and the reaction solution was concentrated under reduced pressure. EDC (50 mg) and HOBT (36 mg) were added to a DMF (3 mL) suspension of the obtained residue, and the reaction solution was agitated at room temperature for 16 hours. Water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The obtained residue was purified by silica gel chromatography (Carrier: Chromatorex™ NH, an elution solvent:heptane-ethyl acetate system), and (E)-1-(chroman-4-yl)-3-[3-methoxy-4-(4-methyl-1H-imidazol-1-yl)benzylidene]piperidin-2-one racemate (21 mg) was obtained. This compound (21 mg) was separated in CHIRALPAK™ AD-H available from Daicel Chemical Industries, Ltd. (2 cm×25 cm: mobile phase; ethanol), and the title optically-active substance with a retention time of 45 minutes (7 mg;>99% ee) and the title optically-active substance with a retention time of 61 minutes (6 mg;>99% ee) were obtained. The physical properties of the title optically-active substance with a retention time of 45 minutes (Example 419) is as follows.

$^1$H-NMR ($CDCl_3$) δ (ppm): 1.70-1.95 (m, 2H), 2.00-2.28 (m, 2H), 2.30 (s, 3H), 2.74-2.85 (m, 1H), 2.87-2.98 (m, 1H), 3.05-3.14 (m, 1H), 3.15-3.26 (m, 1H), 3.87 (s, 3H), 4.20-4.30 (m, 1H), 4.31-4.40 (m, 1H), 6.23 (dd, J=6.4, 9.6 Hz, 1H), 6.84 (d, J=8.0 Hz, 1H), 6.89 (dd, J=7.2, 7.6 Hz, 1H), 6.94 (s, 1H), 7.02-7.10 (m, 3H), 7.12-7.18 (m, 1H), 7.23-7.29 (m, 1H), 7.72 (s, 1H), 7.91 (s, 1H)

The physical properties of the title optically-active substance with a retention time of 61 minutes (Example 420) are as follows.

$^1$H-NMR ($CDCl_3$) δ (ppm): 1.70-1.95 (m, 2H), 2.00-2.28 (m, 2H), 2.30 (s, 3H), 2.74-2.85 (m, 1H), 2.87-2.98 (m, 1H), 3.05-3.14 (m, 1H), 3.15-3.26 (m, 1H), 3.87 (s, 3H), 4.20-4.30 (m, 1H), 4.31-4.40 (m, 1H), 6.23 (dd, J=6.4, 9.6 Hz, 1H), 6.84 (d, J=8.0 Hz, 1H), 6.89 (dd, J=7.2, 7.6 Hz, 1H), 6.94 (s, 1H), 7.02-7.10 (m, 3H), 7.12-7.18 (m, 1H), 7.23-7.29 (m, 1H), 7.72 (s, 1H), 7.91 (s, 1H).

Example 421 and Example 422

Synthesis of (E)-1-[(R) and (S)-6-methoxyindan-1-yl]-3-[3-methoxy-4-(4-methyl-1H-imidazol-1-yl)benzylidene]piperidin-2-one

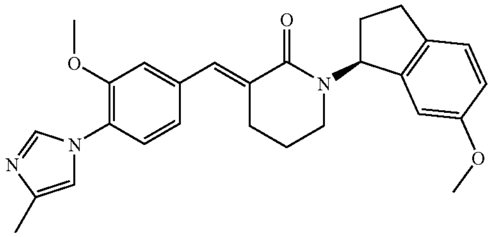

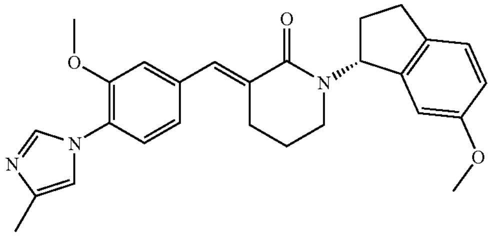

To a DMF (2 mL) suspension of (E)-5-chloro-2-[3-methoxy-4-(4-methyl-1H-imidazol-1-yl)benzylidene]valeric acid trifluoroacetic acid salt (50 mg) obtained in Example 418 and 6-methoxyindan-1-ylamine (CAS#103028-81-5) (27 mg), IPEA (0.06 mL), EDC (64 mg) and HOBT (45 mg) were added at room temperature, and the reaction solution was agitated at room temperature for 12 hours. Saturated sodium bicarbonate solution and ethyl acetate were added to the reaction solution, and the organic layer was partitioned. The organic layer was washed one by one with a saturated ammonium chloride solution and water, and also saturated sodium chloride solution, and the organic layer was concentrated under reduced pressure after dried over anhydrous magnesium sulfate. The obtained residue was purified by silica gel chromatography (elution solvent:methanol-ethyl acetate system) and (E)-5-chloro-2-[3-methoxy-4-(4-methyl-1H-imidazol-1-yl)benzylidene]valeric acid (6-methoxyindan-1-yl) amide (29 mg) was obtained. To a DMF (2 mL) solution of (E)-5-chloro-2-(3-methoxy-4-(4-methyl-1H-imidazol-1-yl) benzylidene)valeric acid (6-methoxyindan-1-yl)amide (29 mg) obtained, sodium hydride (40% mineral oil content, 20 mg) was added at room temperature, and the reaction solution was agitated for 10 minutes at room temperature. Saturated sodium bicarbonate solution and ethyl acetate were added to the reaction solution, and the organic layer was partitioned. The organic layer was washed one by one in a saturated ammonium chloride solution and water, and also saturated sodium chloride solution, and the organic layer was concentrated under reduced pressure after dried over anhydrous magnesium sulfate. The obtained residue was purified by silica gel chromatography (elution solvent:methanol-ethyl acetate system), and (E)-1-(6-methoxyindan-1-yl)-3-[3-methoxy-4-(4-methyl-1H-imidazol-1-yl)benzylidene]piperidin-2-one racemate (17 mg) was obtained. This compound (17 mg) was separated by CHIRALCEL™ AD-H available from Daicel Chemical Industries, Ltd. (2 cm×25 cm: mobile phase; ethanol), and the title optically-active substance with a retention time of 36 minutes (6 mg;>99% ee) and the title optically-active substance with a retention time of 43 minutes (6 mg;>95% ee) were obtained. The physical properties of the title optically-active substance with a retention time of 36 minutes (Example 421) is as follows.

$^1$H-NMR ($CDCl_3$) δ (ppm): 1.73-1.90 (m, 2H), 1.94-2.03 (m, 1H), 2.30 (s, 3H), 2.45-2.56 (m, 1H), 2.74-3.02 (m, 4H), 3.04-3.21 (m, 2H), 3.77 (s, 3H), 3.86 (s, 3H), 6.47 (dd, J=7.6, 8.4 Hz, 1H), 6.70 (d, J=2.4 Hz, 1H), 6.80 (dd, J=2.4, 8.4 Hz, 1H), 6.94 (s, 1H), 7.03-7.10 (m, 2H), 7.15 (d, J=8.4 Hz, 1H), 7.22-7.28 (m, 1H), 7.72 (s, 1H), 7.90 (s, 1H).

The physical properties of the title optically-active substance with a retention time of 43 minutes (Example 422) are as follows.

$^1$H-NMR ($CDCl_3$) δ (ppm): 1.73-1.90 (m, 2H), 1.94-2.03 (m, 1H), 2.30 (s, 3H), 2.45-2.56 (m, 1H), 2.74-3.02 (m, 4H), 3.04-3.21 (m, 2H), 3.77 (s, 3H), 3.86 (s, 3H), 6.47 (dd, J=7.6, 8.4 Hz, 1H), 6.70 (d, J=2.4 Hz, 1H), 6.80 (dd, J=2.4, 8.4 Hz, 1H), 6.94 (s, 1H), 7.03-7.10 (m, 2H), 7.15 (d, J=8.4 Hz, 1H), 7.22-7.28 (m, 1H), 7.72 (s, 1H), 7.90 (s, 1H).

Example 423 and Example 424

Synthesis of (E)-3-[3-methoxy-4-(4-methyl-1H-imidazol-1-yl)benzylidene]-1-[(R) and (S)-7-methoxy-1,2,3,4-tetrahydronaphthalen-1-yl]piperidin-2-one

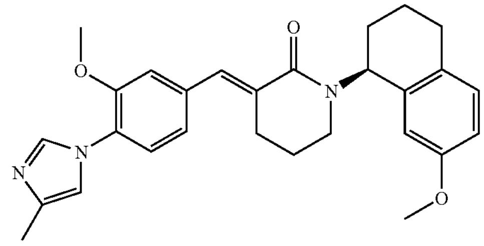

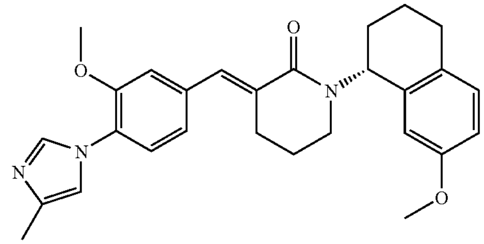

To a solution of (E)-5-chloro-2-[3-methoxy-4-(4-methyl-1H-imidazol-1-yl)benzylidene]valeric acid ethyl ester (50 mg) obtained in Example 417 in acetonitrile (3 mL) and water (0.3 mL), 7-methoxy-1,2,3, 4-tetrahydronaphthalen-1-ylamine (CAS#50399-51-4) (25 mg), potassium carbonate (57 mg) and sodium iodide (21 mg) were added at room temperature, and heat-refluxing of the reaction solution was carried out for two days. The reaction solution was allowed to be cooled to room temperature, water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The residue was purified by silica gel chromatography (Carrier: Chromatorex™ NH, an elution solvent:heptane-ethyl acetate system), and (E)-2-[3-methoxy-4-(4-methyl-1H-imidazol-1-yl)benzylidene]-5-(7-methoxy-1,2,3,4-tetrahydronaphthalen-1-ylamino)valeric acid ethyl ester (24 mg) was obtained. 2N sodium hydroxide solution (0.3 mL) was added to an ethanol (1 mL) solution of obtained (E)-2-[3-methoxy-4-(4-methyl-1H-imidazol-1-yl)benzylidene]-5-(7-methoxy-1,2,3,4-tetrahydronaphthalen-1-ylamino)valeric acid ethyl ester (24 mg) at room temperature, and the reaction solution was agitated at room temperature for 16 hours. 2N hydrochloric acid (0.3 mL) was added to the reaction solution under ice-cooling, and the reaction solution was concentrated under reduced pressure. EDC (25 mg) and HOBT (18 mg) were added to a DMF (2 mL) suspension of the obtained residue, and the reaction solution was agitated at room temperature for 24 hours. Water and ethyl acetate were added to the reaction solution, and the organic layer was partitioned. The organic layer was washed with a saturated sodium chloride solution, and the organic layer was concentrated under reduced pressure after dried over anhydrous magnesium sulfate. The residue was purified by silica gel chromatography (Carrier: Chromatorex™ NH, an elution solvent:heptane-ethyl acetate system), and (E)-3-[3-methoxy-4-(4-methyl-1H-imidazol-1-yl)benzylidene]-1-(7-methoxy-1,2,3,4-tetrahydronaphthalen-1-yl)piperidin-2-one racemate (19 mg) was obtained. This compound (19 mg) was separated in CHIRALCEL™ AD-H available from Daicel Chemical Industries, Ltd. (2 cm×25 cm: mobile phase; ethanol), and the title optically-active substance with a retention time of 17 minutes (7 mg;>99% ee) and the title optically-active substance with a retention time of 25 minutes (6 mg;>99% ee) were obtained. The physical properties of the title optically-active substance with a retention time of 17 minutes (Example 423) are as follows.

$^1$H-NMR ($CDCl_3$) δ (ppm): 1.72-1.82 (m, 4H), 1.96-2.14 (m, 2H), 2.31 (s, 3H), 2.68-2.84 (m, 3H), 2.88-2.98 (m, 1H), 3.05-3.13 (m, 1H), 3.18-3.26 (m, 1H), 3.75 (s, 3H), 3.87 (s, 3H), 6.07-6.15 (m, 1H), 6.66 (d, J=2.8 Hz, 1H), 6.75 (dd, J=2.8, 8.4 Hz, 1H), 6.95 (s, 1H), 7.02-7.11 (m, 3H), 7.24-7.30 (m, 1H), 7.73 (d, J=1.2 Hz, 1H), 7.92 (s, 1H).

The physical properties of the title optically-active substance (Example 424) for retention time 25 minutes are as follows.

$^1$H-NMR ($CDCl_3$) δ (ppm): 1.72-1.82 (m, 4H), 1.96-2.14 (m, 2H), 2.31 (s, 3H), 2.68-2.84 (m, 3H), 2.88-2.98 (m, 1H), 3.05-3.13 (m, 1H), 3.18-3.26 (m, 1H), 3.75 (s, 3H), 3.87 (s, 3H), 6.07-6.15 (m, 1H), 6.66 (d, J=2.8 Hz, 1H), 6.75 (dd, J=2.8, 8.4 Hz, 1H), 6.95 (s, 1H), 7.02-7.11 (m, 3H), 7.24-7.30 (m, 1H), 7.73 (d, J=1.2 Hz, 1H), 7.92 (s, 1H).

Example 425

Synthesis of (E)-1-[(1S)-1-(4-fluorophenyl)ethyl]-3-[3-methoxy-4-(4-methyl-1H-imidazol-1-yl)benzylidene]piperidin-2-one

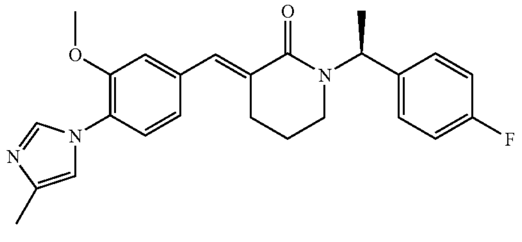

Synthesis of (E)-5-chloro-2-[3-methoxy-4-(4-methyl-1H-imidazol-1-yl)benzylidene]valeric acid ((1S)-1-(4-fluorophenyl)ethyl)amide To a DMF (50 mL) solution of 5-chloro-2-(3-methoxy-4-(4-methyl-1H-imidazol-1-yl)benzylidene)valeric acid trifluoroacetic acid salt (8.00 g) and (S)-1-(4-fluorophenyl)ethylamine (2.60 g), IPEA (12.4 mL), EDC (6.82 g) and HOBT (4.81 g) were added one by one, and the reaction solution was agitated at room temperature overnight. After confirming disappearance of the starting materials, the solvent was concentrated under reduced pressure, water and ethyl acetate were added to the residue, and the organic layer was partitioned. After the organic layer was washed with a saturated saline solution, it was dried over anhydrous magnesium sulfate and concentrated under reduced pressure. The obtained residue was purified by silica gel chromatography (elution solvent: heptane-ethyl acetate=2:3→1:1→ethyl acetate), and 3.90 g of the title compound was obtained. The physical properties of the compound are as follows.

$^1$H-NMR ($CDCl_3$) δ (ppm): 1.56 (d, J=6.8 Hz, 3H), 1.95-2.02 (m, 2H), 2.30 (s, 3H), 2.70-2.74 (m, 2H), 3.58 (t, J=6.0 Hz, 2H), 3.85 (s, 3H), 5.17-5.24 (m, 1H), 6.15 (d, J=6.8 Hz, 1H), 6.92-6.96 (m, 3H), 7.02-7.07 (m, 2H), 7.17 (s, 1H), 7.23-7.25 (m, 1H), 7.32-7.36 (m, 2H), 7.70-7.71 (s, 1H).

Synthesis of (E)-1-[(1S)-1-(4-fluorophenyl)ethyl]-3-[3-methoxy-4-(4-methyl-1H-imidazol-1-yl)benzylidene]piperidin-2-one To a DMF (30 mL) solution of (E)-5-chloro-2-[3-methoxy-4-(4-methyl-1H-imidazol-1-yl]benzylidene valeric acid ((S)-1-(4-fluorophenyl)ethyl)amide (3.90 g), sodium hydride (40% mineral oil content, 410 mg) was added at 0° C., the reaction solution was allowed to be warmed to room temperature and agitated overnight. The reaction solution was cooled to 0° C. after confirming disappearance of the starting materials, and water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent; ethyl acetate→ethyl acetate:ethanol 10:1). The obtained solid was washed with diethyl ether and 2.60 g of the title compound was obtained by further performing recrystallization with ethyl acetate. The physical properties of the compound are as follows.

$^1$H-NMR ($CDCl_3$) δ (ppm): 1.50 (d, J=7.2 Hz, 3H), 1.65-1.74 (m, 1H), 1.78-1.87 (m, 1H), 2.30 (s, 3H), 2.71-2.85 (m, 2H), 2.91-2.97 (m, 1H), 3.24 (ddd, J=3.6, 8.8, 12.0 Hz, 1H), 3.86 (s, 3H), 6.23 (q, J=7.2 Hz, 1H), 6.93 (t, J=1.2 Hz, 1H), 7.00-7.06 (m, 4H), 7.24-7.26 (m, 1H), 7.31-7.34 (m, 2H), 7.72 (d, J=1.2 Hz, 1H), 7.89 (s, 1H).

Example 426

Synthesis of (E)-1-[3-fluoro-4-(morpholin-4-yl)benzyl]-3-[3-methoxy-4-(4-methyl-1H-imidazol-1-yl)benzylidene]piperidin-2-one

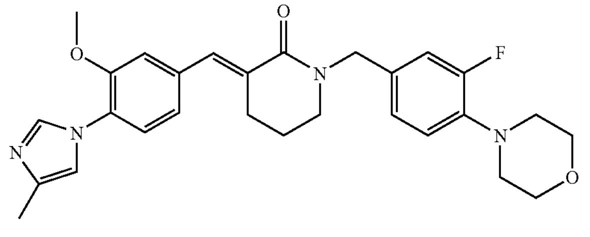

Synthesis of 3-fluoro-4-(morpholin-4-yl)benzonitrile

To a DMF (20 mL) solution of 3,4-difluorobenzonitrile (3.00 g), morpholine (2.82 g) and potassium carbonate (5.97 g) were added, and the reaction solution was allowed to be warmed to 100° C. and agitated for 5.5 hours. Water and ethyl acetate were added to the reaction solution after confirming disappearance of the starting materials, and the organic layer was partitioned. After the obtained organic layer was washed with a saturated saline solution, it was dried over anhydrous magnesium sulfate and 4.41 g of the title compound was obtained by condensing under reduced pressure. The physical properties of the compound are as follows.

$^1$H-NMR ($CDCl_3$) δ (ppm): 3.19-3.22 (m, 4H), 3.86-3.88 (m, 4H), 6.92 (t, J=8.4 Hz, 1H), 7.29 (dd, J=2.0, 13.0 Hz, 1H), 7.37-7.40 (m, 1H).

Synthesis of 3-fluoro-4-(morpholin-4-yl)benzylamine

To a THF (30 mL) suspension of lithium aluminum hydride (975 mg), a THF (10 mL) solution of 3-fluoro-4-(morpholin-4-yl)benzonitrile (4.41 g) was added dropwise at −78° C. Then, the reaction solution was allowed to be warmed to room temperature and agitated overnight. The reaction solution was cooled to 0° C. after confirming disappearance of the starting materials, water and 5N sodium hydroxide solution, and also ethyl acetate were added to the reaction solution one by one, and the organic layer was partitioned. After the obtained organic layer was washed with a saturated saline solution, it was dried over anhydrous magnesium sulfate and concentrated under reduced pressure. The obtained residue was purified by silica gel chromatography (Carrier: Chromatorex™ NH, elution solvent:ethyl acetate=1:1→heptane-ethyl acetate), and 3.60 g of the title compound was obtained. The physical properties of the compound are as follows.

$^1$H-NMR ($CDCl_3$) δ (ppm): 3.06-3.08 (m, 4H), 3.81 (s, 2H), 3.87-3.89 (m, 4H), 6.91 (t, J=8.8 Hz, 1H), 7.01-7.05 (m, 2H).

Synthesis of (E)-5-chloro-2-[3-methoxy-4-(4-methyl-1H-imidazol-1-yl)benzylidene]valeric acid[3-fluoro-4-(morpholin-4-yl)benzyl]amide To a DMF (4.0 mL) solution of 5-chloro-2-[3-methoxy-4-(4-methyl-1H-imidazol-1-yl)benzylidene]-valeric acid trifluoroacetic acid salt (200 mg) obtained in Example 418 and 3-fluoro-4-(morpholin-4-yl)benzylamine (112 mg), IPEA (231 mg), EDC (171 mg) and HOBT (120 mg) were added one by one, and the reaction solution was agitated at room temperature overnight. After confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. 135 mg of the title compound was obtained by purifying the obtained residue by silica gel chromatography (elution solvent:ethyl acetate→ethyl acetate:methanol=90:10). The physical properties of the compound are as follows.

$^1$H-NMR ($CDCl_3$) δ (ppm): 1.99-2.06 (m, 2H), 2.29 (s, 3H), 2.72-2.76 (m, 2H), 3.06-3.09 (m, 4H), 3.58 (t, J=6.0 Hz, 2H), 3.85 (s, 3H), 3.84-3.88 (m, 4H), 4.49 (d, J=5.6 Hz, 2H), 6.28-6.38 (m, 1H), 6.88-6.98 (m, 4H), 7.01-7.06 (m, 2H), 7.17 (s, 1H), 7.22-7.25 (m, 1H), 7.70 (s, 1H).

Synthesis of (E)-1-[3-fluoro-4-(morpholin-4-yl)benzyl]-3-[3-methoxy-4-(4-methyl-1H-imidazol-1-yl)benzylidene]piperidin-2-one To a DMF (4 mL) solution of (E)-5-chloro-2-[3-methoxy-4-(4-methyl-1H-imidazol-1-yl]benzylidene)valeric acid [3-fluoro-4-(morpholin-4-yl)benzyl]amide (135 mg), sodium hydride was added at 0° C. (40% mineral oil content, 35.6 mg) was added, and the reaction solution was allowed to be warmed to room temperature and agitated for 45 minutes. The reaction solution was cooled to 0° C. after confirming disappearance of the starting materials, water and ethyl acetate were added to the reaction solution, and the organic layer was partitioned. After washed with a saturated saline solution the organic layer, it was dried over anhydrous magnesium sulfate and concentrated under reduced pressure. 113 mg of the title compound was obtained by purifying the obtained residue by silica gel chromatography (elution solvent; ethyl acetate→ethyl acetate:ethanol 90:10). The physical properties of the compound are as follows.

$^1$H-NMR ($CDCl_3$) δ (ppm): 1.82-1.90 (m, 2H), 2.30 (s, 3H), 2.83 (t, J=5.6 Hz, 2H), 3.07-3.09 (m, 4H), 3.37 (t, J=5.6 Hz, 2H), 3.86 (s, 3H), 3.86-3.88 (m, 4H), 4.66 (s, 2H), 6.90 (t, J=8.0 Hz, 1H), 6.94 (s, 1H), 7.02-7.05 (m, 4H), 7.25-7.27 (m, 1H), 7.72 (S, 1H), 7.82 (S, 1H).

Example 427

Synthesis of (E)-1-[(6-chloropyridin-2-yl)methyl]-3-[3-methoxy-4-(4-methyl-1H-imidazol-1-yl)benzylidene]piperidin-2-one

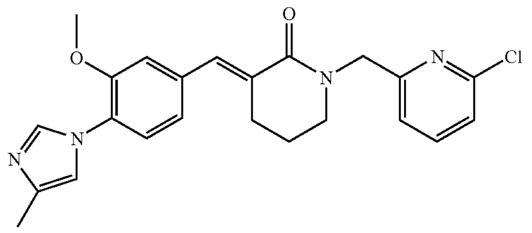

To a suspension of (E)-5-chloro-2-[3-methoxy-4-(4-methyl-1H-imidazol-1-yl]benzylidene)valeric acid ethyl ester (200 mg) obtained in Example 417 and 2-(aminomethyl)-6-chloropyridine (CA 188637-75-4) hydrochloride (100 mg) in ethanol (3 mL) and DMF (3 mL), anhydrous potassium carbonate (100 mg) was added and the reaction mixture was agitated at 100° C. for 8 hours. After the reaction mixture was allowed to be cooled to room temperature, the reaction mixture was poured into iced water and the reaction solution was extracted with ethyl acetate. The obtained organic layer was washed with a saturated sodium chloride solution, and concentrated under reduced pressure after dried over anhydrous magnesium sulfate. Ethanol (10 mL) and sodium hydroxide (1.0 g) aqueous solution (5 mL) were added to the residue, and the reaction solution was agitated at room temperature for 1 hour. The reaction solution was added to iced water and the reaction solution was extracted with ethyl acetate. The obtained organic layer was washed with a saturated sodium chloride solution, and it concentrated under reduced pressure after dried over anhydrous magnesium sulfate. 23 mg of the title compound was obtained by the residue was purified by silica gel chromatography (elution solvent:heptane-ethyl acetate system).

$^1$H-NMR ($CDCl_3$) δ (ppm): 1.88-1.96 (m, 2H), 2.30 (s, 3H), 2.82-2.89 (m, 2H), 3.54-3.62 (m, 2H), 3.85 (s, 3H), 4.78 (s, 2H), 6.92 (s, 1H), 6.99-7.05 (m, 2H), 7.20-7.28 (m, 2H), 7.31 (d, J=7.6 Hz, 1H), 7.63 (t, J=7.6 Hz, 1H), 7.70 (d, J=1.2 Hz, 1H), 7.83 (s, 1H).

Example 428

Synthesis of (E)-3-[3-methoxy-4-(4-methyl-1H-imidazol-1-yl)benzylidene]-1-[(6-(morpholin-4-yl)pyridine-3-yl)methyl]piperidin-2-one

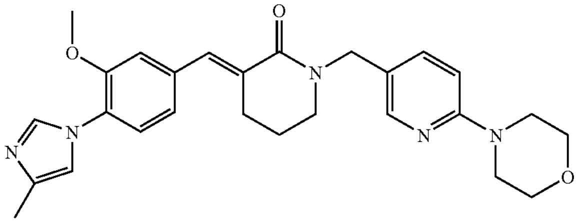

Synthesis of 2-[6-(morpholin-4-yl)pyridin-3-yl]methylisoindol-1,3-dione

To a THF (200 mL) solution of (6-(morpholin-4-yl)pyridine-3-yl)methanol (CA 388088-73-1) (3.2 g), phthalimide (3.64 g) and triphenylphosphine (6.49 g), diisopropylazodicarboxylate (5.43 mL) was added at 0° C. for 5 minutes. The reaction solution was concentrated under reduced pressure after 12-hour stirring at room temperature. 3.8 g of the title compound was obtained by the residue was purified by silica gel chromatography (heptane-ethyl acetate system).

$^1$H-NMR ($CDCl_3$) δ (ppm): 3.42-3.50 (m, 4H), 3.74-3.82 (m, 4H), 4.73 (s, 2H), 6.56 (d, J=8.4 Hz, 1H), 7.42-7.72 (m, 1H), 7.64-7.72 (m, 2H), 7.78-7.84 (m, 2H), 8.29 (d, J=2.0 Hz, 1H).

Synthesis of (E)-3-[3-methoxy-4-(4-methyl-1H-imidazol-1-yl]benzylidene)-1-[(6-(morpholin-4-yl)pyridine-3-yl]methyl) piperidin-2-one To an ethanol (50 mL) solution of 2-[6-(morpholin-4-yl) pyridine-3-yl]methylisoindoindol-1,3-dione (3.8 g) obtained above, hydrazine monohydrate (2.95 mL) was added, and heat-refluxing of the reaction solution was carried out for 2 hours. The reaction solution was allowed to be cooled to room temperature, diethyl ether (100 mL) was added to the reaction solution, and the reaction solution was agitated for 30 minutes at room temperature. C-[6-(morpholin-4-yl)pyridine-3-yl] methylamine (3.0 g) was obtained by filtering off insoluble solids in the reaction solution and condensing the obtained filtrate under reduced pressure. To a DMF (30 mL) solution of (E)-5-chloro-2-(3-methoxy-4-(4-methyl-1H-imidazol-1-yl) benzylidene)valeric acid trifluoroacetic acid salt (0.20 g) obtained in Example 418 and C-[6-(morpholin-4-yl)pyridine-3-yl]methylamine (0.30 g), HOBT (0.181 g), IPEA (0.388 mL) and EDC (0.257 g) were added at room temperature, and the reaction solution was agitated at room temperature for 12 hours. The reaction solution was added to water and the reaction solution was extracted with ethyl acetate. The obtained organic layer was washed with a saturated salt solution, and concentrated under reduced pressure after dried over anhydrous magnesium sulfate. The residue was purified by silica gel column chromatography (elution solvent:from heptane-ethyl acetate system to methanol-ethyl acetate system) and 0.21 g of (E)-5-chloro-2-[3-methoxy-4-(4-methyl-1H-imidazol-1-yl)benzylidene]valeric acid [6-(morpholin-4-yl) pyridine-3-yl]methyl amide was obtained.

To a DMF (30 mL) solution of (E)-5-chloro-2-[3-methoxy-4-(4-methyl-1H-imidazol-1-yl)benzylidene]valeric acid [6-(morpholin-4-yl)pyridine-3-yl]methyl amide (0.21 g) obtained above, sodium hydrite (40% mineral oil content, 29.7 mg) was added at room temperature, and the reaction solution was agitated for 30 minutes at the temperature. The reaction solution was added to water and the reaction solution was extracted with ethyl acetate. The obtained organic layer was washed with a saturated salt solution, and concentrated under reduced pressure after dried over anhydrous magnesium sulfate. 0.125 g of the title compound was obtained by the residue was purified by silica gel chromatography (elution solvent: from heptane-ethyl acetate system to methanol-ethyl acetate system).

$^1$H-NMR ($CDCl_3$) δ (ppm): 1.78-1.88 (m, 2H), 2.30 (s, 3H), 2.75-2.83 (m, 2H), 3.32-3.39 (m, 2H), 3.44-3.54 (m, 4H), 3.76-3.88 (m, 4H), 3.85 (s, 3H), 4.59 (s, 2H), 6.62 (d, J=8.8 Hz, 1H), 6.92 (s, 1H), 6.98-7.04 (m, 2H), 7.20-7.28 (m, 1H), 7.57 (dd, J=2.0, 8.8 Hz, 1H), 7.70 (s, 1H), 7.84 (s, 1H), 8.12 (d, J=2.0 Hz, 1H).

Example 429

Synthesis of (E)-1-[(5-chloro-2-methylpyridin-3-yl) methyl]-3-[3-methoxy-4-(4-methyl-1H-imidazol-1-yl)benzylidene]piperidin-2-one

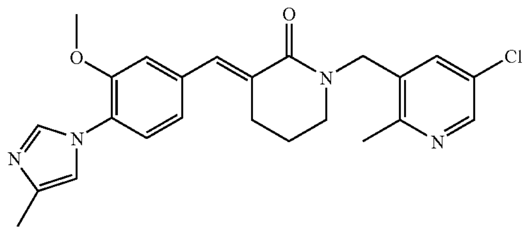

Synthesis of (5-chloro-2-methylpyridin-3-yl)methanol

To a THF (30 mL) solution of 5-chrolo-2-methyl nicotinic acid methyl ester (CAS# 350597-49-8) (1.0 g), boron lithium hydride (0.153 g) was added at 0° C. The reaction solution was agitated at room temperature for 2 hours. The reaction solution was added to iced water and the reaction solution was extracted with ethyl acetate. The obtained organic layer was washed with a saturated salt solution, and it concentrated under reduced pressure after dried over anhydrous magnesium sulfate. 0.26 g of the title compound was obtained by the residue was purified by silica gel chromatography (elution solvent:heptane-ethyl acetate system).

$^1$H-NMR ($CDCl_3$) δ (ppm): 2.47 (s, 3H), 4.70 (s, 2H), 7.74 (d, J=2.4 Hz, 1H), 8.33 (d, J=2.4 Hz, 1H).

Synthesis of 2-[(5-chloro-2-methylpyridin-3-yl]methyl)isoindole-1,3-dione

To a THF (10 mL) solution of (5-chloro-2-methylpyridin-3-yl)methanol (0.26 g) obtained above, phthalimide (0.364 g) and triphenylphosphine (0.649 g), diisopropylazodicarboxylate (0.585 mL) were added at 0° C. for 5 minutes. The reaction solution was agitated for three days at room temperature and concentrated under reduced pressure. 0.20 g of the title compound was obtained by the residue was purified by silica gel chromatography (elution solvent:heptane-ethyl acetate system).

$^1$H-NMR ($CDCl_3$) δ (ppm): 2.68 (s, 3H), 4.83 (s, 2H), 7.55 (s, 1H), 7.70-7.80 (m, 2H), 7.80-7.95 (m, 2H), 8.35 (s, 1H).

Synthesis of (E)-1-[(5-chloro-2-methylpyridin-3-yl) methyl]-3-[3-methoxy-4-(4-methyl-1H-imidazol-1-yl)benzylidene]piperidin-2-one To an ethanol (10 mL) solution of 2-((5-chloro-2-methyl-pyridine-3-yl)methyl)isoindole-1,3-dione (0.20 g), hydrazine monohydrate (0.50 mL) was added, and heat-refluxing of the reaction solution was carried out for 2 hours. The reaction solution was allowed to be cooled to room temperature, diethyl ether (50 mL) was added to the reaction solution, and the reaction solution was agitated for 30 minutes at room temperature. C-(5-chloro-2-methylpyridin-3-yl)methylamine (0.13 g) was obtained by filtering off insoluble matters in the reaction solution and condensing the obtained filtrate under reduced pressure.

To a DMF (20 mL) solution of (E)-5-chloro-2-[3-methoxy-4-(4-methyl-1H-imidazol-1-yl)benzylidene]valeric acid trifluoroacetic acid salt (0.20 g) obtained according to Example 418 and C-(5-chloro-2-methylpyridin-3-yl)methylamine (0.13 g), HOBT (0.301 g), IPEA (0.397 mL), and EDC (0.428 g) were added, and the reaction solution was agitated under room temperature for 12 hours. The reaction solution was added to water and the reaction solution was extracted with ethyl acetate. The obtained organic layer was washed with a saturated salt solution, and concentrated under reduced pressure after dried over anhydrous magnesium sulfate. The residue was purified by silica gel column chromatography (elution solvent: heptane-ethyl acetate system) and 0.14 g of (E)-5-chloro-2-[3-methoxy-4-(4-methyl-1H-imidazol-1-yl) benzylidene]valeric acid (5-chloro-2-methylpyridin-3-yl) methyl amide was obtained.

To a DMF (10 mL) solution of (E)-5-chloro-2-(3-methoxy-4-(4-methyl-1H-imidazol-1-yl)benzylidene)valeric acid (5-chloro-2-methylpyridin-3-yl)methyl amide (0.14 g) obtained above, sodium hydride (40% mineral oil content, 47.4 mg) was added at room temperature, and the reaction solution was agitated at that temperature for 1 hour. The reaction solution was added to water and the reaction solution was extracted with ethyl acetate. The obtained organic layer was washed with a saturated sodium chloride solution, and concentrated under reduced pressure after dried over anhydrous magnesium sulfate. 0.027 g of the title compound was obtained by the residue was purified by silica gel chromatography (elution solvent:heptane-ethyl acetate system).

1H-NMR ($CDCl_3$) δ (ppm): 1.90-2.00 (m, 2H), 2.30 (s, 3H), 2.54 (s, 3H), 2.85-2.92 (m, 2H), 3.34-3.41 (m, 2H), 3.87 (s, 3H), 4.72 (s, 2H), 6.92-6.95 (m, 1H), 7.02-7.08 (m, 2H), 7.24-7.30 (m, 1H), 7.41 (d, J=2.4 Hz, 1H), 7.72 (d, J=1.2 Hz, 1H), 7.87 (s, 1H), 8.37 (d, J=2.4 Hz, 1H).

Example 430

Synthesis of (E)-1-(4-tert-butylbenzyl)-3-[3-methoxy-4-(4-methyl-1H-imidazol-1-yl)benzylidene] piperidin-2-one

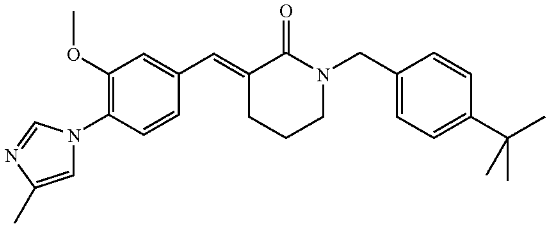

To a DMF (2 mL) solution of (E)-3-[3-methoxy-4-(4-methyl-1H-imidazol-1-yl)benzylidene]piperidin-2-one (70 mg) obtained in Example 416, lithium bis(trimethylsilyl)amide (1M THF solution, 0.47 mL) was added dropwise under ice-cooling, and the reaction solution was agitated for 30 minutes under ice-cooling. Subsequently, 1-tert-butyl-4-chloromethylbenzene (0.073 mL) was added to the reaction solution, and the reaction solution was agitated for 30 minutes under ice-cooling. Water and ethyl acetate were added to the reaction solution, and the organic layer was partitioned. The obtained organic layer was dried with magnesium sulfate and was concentrated under reduced pressure. The residue was purified by silica gel column chromatography (elution solvent:heptane-ethyl acetate system), and 37.8 mg of the title compound was obtained. The physical properties are as follows.

$^1$H-NMR ($CDCl_3$) δ (ppm): 1.31 (s, 9H), 1.86 (m, 2H), 2.30 (s, 3H), 2.82 (m, 2H), 3.38 (m, 2H), 3.85 (s, 3H), 4.70 (s, 2H), 6.92 (t, J=1.2 Hz, 1H), 7.01 (s, 1H), 7.02 (d, J=8.4 Hz, 1H), 7.22-7.26 (m, 3H), 7.34 (d, J=8.4 Hz, 2H), 7.70 (d, J=1.2 Hz, 1H), 7.86 (s, 1H).

Example 431

Synthesis of (E)-3-[4-(4-fluoromethyl-1H-imidazol-1-yl)-3-methoxyphenyl]-N-indan-1-ylacrylamide

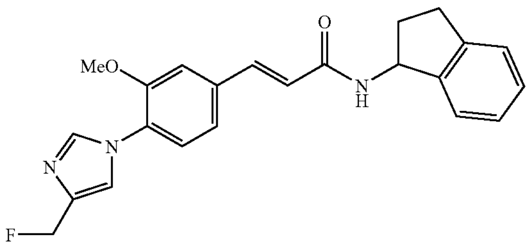

By the same as in Example 147, 11 mg of the title compound was obtained from (E)-3-[4-(4-hydroxymethyl-1H-imidazol-1-yl)-3-methoxyphenyl]-N-indan-1-ylacrylamide (20 mg) obtained in Example 45.

$^1$H-NMR ($CDCl_3$) δ (ppm): 1.87-1.96 (m, 1H), 2.65-2.73 (m, 1H), 2.90-2.98 (m, 1H), 3.01-3.08 (m, 1H), 3.90 (s, 3H), 5.40 (d, J=49.2 Hz, 2H), 5.66 (q, J=7.6 Hz, 1H), 5.99 (d, J=8 Hz, 1H), 6.46 (d, J=15.6 Hz, 1H), 7.17-7.37 (m, 8H), 7.70 (d, J=15.6 Hz, 1H), 7.79 (s, 1H).

Example 432

Synthesis of (E)-3-[4-(4-formyl-1H-imidazol-1-yl)3-methoxyphenyl]-N-indan-1-ylacrylamide

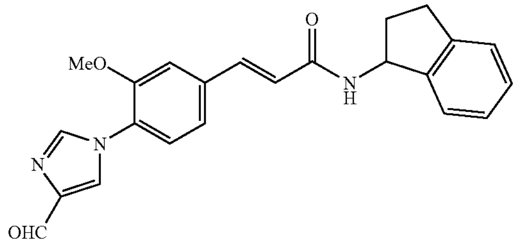

To a chloroform (5 mL) solution of (E)-3-(4-(4-hydroxymethyl-1H-imidazol-1-yl)-3-methoxyphenyl)-N-indan-1-ylacrylamide (15 mg) obtained in Example 45, activated manganese dioxide (280 mg) was added, and the reaction mixture was agitated at room temperature overnight. The reaction solution was filtered through a filter paper and the filtrate was concentrated under reduced pressure. The residue was purified by silica gel column chromatography (elution solvent: ethyl acetate), and 30 mg of the title compound was obtained.

$^1$H-NMR ($CDCl_3$) δ (ppm): 1.86-1.96 (m, 1H), 2.63-2.73 (m, 1H), 2.89-2.97 (m, 1H), 3.00-3.07 (m, 1H), 3.91 (s, 3H), 5.65 (q, J=7.6 Hz, 1H), 5.94 (d, J=8.8 Hz, 1H), 6.47 (d, J=15.6 Hz, 1H), 7.19-7.36 (m, 6H), 7.70 (d, J=15.6 Hz, 1H), 7.84 (d, J=1 Hz, 1H), 7.92 (d, J=1 Hz, 1H), 9.96 (s, 1H).

Example 433

Synthesis of (E)-3-[4-(4-difluoromethyl-1H-imidazol-1-yl)-3-methoxyphenyl]-N-indan-1-ylacrylamide

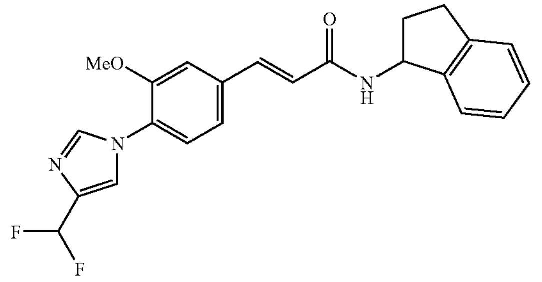

6 mg of the title compound was obtained from the above (E)-3-(4-(4-formyl-1H-imidazol-1-yl)3-methoxyphenyl)-N-indan-1-ylacrylamide (9 mg) and DAST (0.012 mL) in a similar way as in the synthesis in Example 147.

$^1$H-NMR ($CDCl_3$) δ (ppm): 1.86-1.96 (m, 1H), 2.65-2.73 (m, 1H), 2.89-2.97 (m, 1H), 3.01-3.08 (m, 1H), 3.90 (s, 3H), 5.65 (q, J=7.6 Hz, 1H), 5.85 (d, J=8.8 Hz, 1H), 6.44 (d, J=15.6 Hz, 1H), 6.74 (t, J=56 Hz, 1H), 7.17-7.36 (m, 6H), 7.46 (s, 1H), 7.70 (d, J=15.6 Hz, 1H), 7.80 (s, 1H).

Example 434

Synthesis of (E)-N-indan-1-yl-3-[3-methoxy-4-(4-methoxymethyl-1H-imidazol-1-yl]phenyl)acrylamide

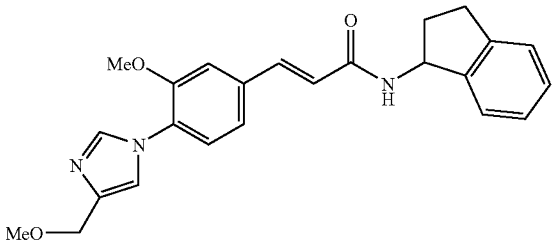

A thionyl chloride (0.4 mL) solution of (E)-3-[4-(4-hydroxymethyl-1H-imidazole-1-yl)-3-methoxyphenyl]-N-indan-1-ylacrylamide (15 mg) obtained in Example 45 was agitated for 40 minutes at 50° C., and then the reaction solution was concentrated under reduced pressure. A solution of sodium methoxide (40% methanol solution, 2 mL) was added to the obtained residue, and the reaction solution was agitated for 90 minutes at room temperature. After the reaction solution was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (Carrier: Chromatorex™ NH, elution solvent:hexane-ethyl acetate system), and 4 mg of the title compound was obtained.

$^1$H-NMR ($CDCl_3$) δ (ppm): 1.86-1.95 (m, 1H), 2.64-2.73 (m, 1H), 2.89-2.97 (m, 1H), 3.00-3.07 (m, 1H), 3.47 (s, 3H), 3.88 (s, 3H), 4.48 (s, 2H), 5.65 (q, J=7.6 Hz, 1H), 5.85 (d, J=8.4 Hz, 1H), 6.42 (d, J=15.6 Hz, 1H), 7.15-7.29 (m, 7H), 7.35 (d, J=7.6 Hz, 1H), 7.69 (d, J=15.6 Hz, 1H), 7.78 (s, 1H).

Example 435

Synthesis of (E)-5-hydroxy-2-[3-methoxy-4-(4-methyl-1H-imidazol-1-yl)benzylidene]valeric acid (biphenyl-3-ylmethyl)amide

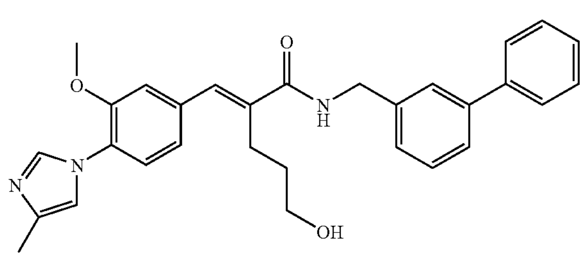

Synthesis of (E)-2-[3-methoxy-4-(4-methyl-1H-imidazol-1-yl)benzylidene]5-(tetrahydropyran-2-yloxy) valeric acid ethyl ester To a DMF (30 mL) suspension of sodium hydride (40% mineral oil content, 1.25 g), triethylphosphonoacetic acid (4.89 mL) was added dropwise at room temperature. After agitating the reaction solution at room temperature for 3 hours, a DMF (10 mL) solution of 2-(3-bromopropoxy)tetrahydro-2H-pyran was added dropwise to the solution. The reaction solution was agitated at 60° C. for 6 hours. The reaction solution was allowed to be cooled to room temperature and concentrated under reduced pressure. Ethyl acetate and a saturated ammonium chloride solution were added to the residue, and the organic layer was partitioned. After the obtained organic layer was washed with a saturated saline solution, it was dried over anhydrous magnesium sulfate and concentrated under reduced pressure. The residue is purified by silica gel chromatography (elution solvent:hexane:ethyl acetate=2:1→ethyl acetate), and 2.9 g of 2-(diethoxyphosphoryl)-5-(tetrahydropyran-2-yloxy) valeric acid ethyl ester was obtained.

To a THF (5 mL) solution of 3-methoxy-4-(4-methyl-1H-imidazol-1-yl)benzaldehyde (283 mg) obtained in Example 1 and 2-(diethoxyphosphoryl)-5-(tetrahydropyran-2-yloxy)valeric acid ethyl ester (480 mg), lithium hydroxide monohydrate (110 mg) was added, and the reaction solution was agitated at room temperature for 19 hours. Ethyl acetate and a saturated ammonium chloride solution were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (Carrier: Chromatorex™ NH and elution solvent:hexane:ethyl acetate=1:1→ethyl acetate), and 186 mg of the title compound was obtained. The physical properties of the compound are as follows.

$^1$H-NMR ($CDCl_3$) δ (ppm): 1.36 (t, J=7.2 Hz, 3H), 1.47-1.93 (m, 10H), 2.31 (s, 3H), 2.62-2.76 (m, 2H), 3.39-3.53 (m, 2H), 3.76-3.87 (m, 2H), 3.88 (s, 3H), 4.29 (q, J=7.2 Hz, 2H), 4.54 (brs, 1H), 6.94 (brs, 1H), 7.05 (brs, 1H), 7.13 (brd, J=7.6 Hz, 1H), 7.25 (d, J=7.6 Hz, 1H), 7.66 (brs, 1H), 7.72 (brs, 1H).

Synthesis of (E)-2-[3-methoxy-4-(4-methyl-1H-imidazol-1-yl)benzylidene]-5-(tetrahydropyran-2-yloxy) valeric acid (biphenyl-3-ylmethyl)amide To a methanol (3 mL) solution of (E)-2-(3-methoxy-4-(4-methyl-1H-imidazol-1-yl)benzylidene)5-(tetrahydropyran-2-yloxy)valeric acid ethyl ester (186 mg), 2N sodium hydroxide aqueous solution (0.5 mL) was added and the reaction solution was agitated at room temperature for 19 hours. 2N hydrochloric acid (0.5 mL) was added to the reaction solution, and the solution was concentrated under reduced pressure. 3-phenylbenzylamine (87 mg), HOBT (86 mg), EDC (108 mg), and IPEA (0.15 mL) were added to a DMF (5 mL) solution of the residue one by one, and the reaction solution was agitated at room temperature for 12 hours. Ethyl acetate and a saturated ammonium chloride solution were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent: ethyl acetate→ethyl acetate:methanol=9:1), and 168 mg of the title compound was obtained. The physical properties of the compound are as follows.

$^1$H-NMR ($CDCl_3$) δ (ppm): 1.32-1.71 (m, 6H), 1.84-1.95 (m, 2H), 2.30 (s, 3H), 2.64-2.77 (m, 2H), 3.40-3.47 (m, 2H), 3.70-3.84 (m, 2H), 3.85 (s, 3H), 4.48 (brs, 1H), 4.63 (dd, J=10.4, 5.6 Hz, 1H), 4.70 (dd, J=10.4, 4.5 Hz, 1H), 6.71 (t, J=5.6 Hz, 1H), 6.92 (brs, 1H), 6.98 (brs, 1H), 7.02 (brd, J=8.0 Hz, 1H), 7.23 (d, J=8.0 Hz, 1H), 7.33-7.62 (m, 10H), 7.71 (brs, 1H).

Synthesis of (E)-5-hydroxy-2-[3-methoxy-4-(4-methyl-1H-imidazol-1-yl)benzylidene]valeric acid (biphenyl-3-ylmethyl)amide To the methanol (5 mL) solution of (E)-2-(3-methoxy-4-(4-methyl-1H-imidazol-1-yl)benzylidene)-5-(tetrahydropyran-2-yloxy) valeric acid (biphenyl-3-ylmethyl)amide (168 mg), Dow-X™50W X-8 (300 mg) was added, and the reaction solution was agitated at 45° C. for 5 hours. The resin was filtered off, the ammonia water (1 mL) was added to the filtrate, and the solution was concentrated under reduced pressure. The residue was purified by silica gel chromatography (elution solvent:ethyl acetate→ethyl acetate:methanol=9:1), and 120 mg of the title compound was obtained. The physical properties of the compound are as follows.

ESI-MS; m/z482 [M$^+$+H]. $^1$H-NMR ($CDCl_3$) δ (ppm): 1.81 (quintet, J=6.8 Hz, 2H), 2.30 (s, 3H), 2.73 (t, J=6.8 Hz, 2H), 3.67 (t, J=6.8 Hz, 2H), 3.85 (s, 3H), 4.65 (d, J=5.6 Hz, 2H), 6.63 (t, J=5.6 Hz, 1H), 6.92 (brs, 1H), 6.98-7.02 (m, 2H), 7.25 (d, J=8.8 Hz, 1H), 7.33-7.62 (m, 10H), 7.71 (brs, 1H).

Example 436

Synthesis of (E)-3-[4-(4-ethyl-1H-imidazol-1-yl)-3-methoxyphenyl]-N-((1S)-1-hydroxymethyl-2-phenylethyl)acrylamide

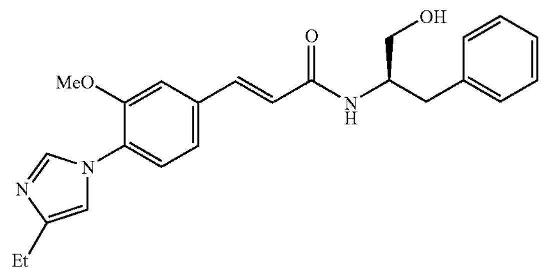

Synthesis of (E)-3-[4-(4-ethyl-1H-imidazol-1-yl)-3-methoxyphenyl]acrylic acid

By the same method as in Example 121, 3.05 g of the title compound was obtained from 4-(4-ethyl-1H-imidazol-1-yl)-3-methoxybenzaldehyde (2.72 g) obtained in Example 637 and diethylphosphono ethyl acetate ester (3.17 g). The physical properties of the compound are as follows.

$^1$H-NMR (DMSO-$d_6$) δ (ppm): 0.46 (t, J=7.6 Hz, 3H), 1.83 (q, J=7.6 Hz, 2H), 3.13 (s, 3H), 5.76 (d, J=16 Hz, 1H), 6.35 (s, 1H), 6.50 (dd, J=2 Hz, 8.4 Hz, 1H), 6.61 (d, J=8.4 Hz, 1H), 6.62 (d, J=1.6 Hz, 1H), 6.61 (d, J=8.4 Hz, 1H), 6.86 (d, J=16 Hz, 1H), 7.18 (s, 1H).

Synthesis of (E)-3-[4-(4-ethyl-1H-imidazol-1-yl)-3-methoxyphenyl]-N-((1S)-1-hydroxymethyl-2-phenylethyl)acrylamide By the same method as in Example 121, 58 mg of the title compound was obtained from (E)-3-(4-(4-ethyl-1H-imidazol-1-yl)-3-methoxyphenyl)acrylic acid (116 mg) and D-phenylalaninol (78 mg). The physical properties of the compound are as follows.

$^1$H-NMR ($CDCl_3$) δ (ppm): 1.28 (t, J=7.6 Hz, 3H), 2.66 (q, J=7.6 Hz, 2H), 3.68 (dd, J=4.4 Hz, 11.2 Hz, 1H), 3.79 (dd, J=3.6 Hz, 11.2 Hz, 1H), 3.83 (s, 3H), 4.33-4.37 (m, 2H), 6.31 (d, J=7.6 Hz, 1H), 6.38 (d, J=16 Hz, 1H), 6.92 (s, 1H), 7.06 (s, 1H), 7.08 (dd, J=1.6 Hz, 8 Hz, 1H), 7.18-7.33 (m, 6H), 7.57 (d, J=16 Hz, 1H), 7.72 (d, J=1.2 Hz, 1H).

Example 437

Synthesis of (E)-3-[3-formyl-4-(1H-imidazol-1-yl) phenyl]-N-indan-1-ylacrylamide

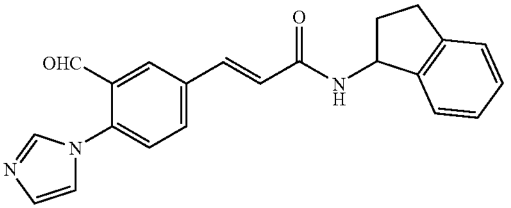

Synthesis of 5-bromo-2-(1H-imidazol-1-yl)benzaldehyde

By the same method as in Example 11, 2.8 g of the title compound was obtained from 5-bromo-2-fluorobenzaldehyde (5 g) and imidazole(2 g).

$^1$H-NMR ($CDCl_3$) δ (ppm): 7.21 (t, J=1.2 Hz, 1H), 7.28-7.29 (m, 1H), 7.34 (d, J=8.4 Hz, 1H), 7.71 (t, J=1.2 Hz, 1H), 7.86 (dd, J=2.8 Hz, 8.4 Hz, 1H), 8.17 (d, J=2.8 Hz, 1H), 9.75 (s, 1H).

Synthesis of (E)-3-[3-formyl-4-(1H-imidazol-1-yl)phenyl]-N-indan-1-ylacrylamide

By the same method as in Example 9, 44 mg of the title compound was obtained from 5-bromo-2-(1H-imidazol-1-yl)benzaldehyde (50 mg) and N-indan-1-yl-acrylamide (45 mg).

$^1$H-NMR ($CDCl_3$) δ (ppm): 1.87-1.96 (m, 1H), 2.64-2.72 (m, 1H), 2.90-3.07 (m, 2H), 5.64 (q, J=7.6 Hz, 1H), 6.19 (d, J=8.4 Hz, 1H), 6.60 (d, J=15.6 Hz, 1H), 7.21-7.35 (m, 5H), 7.44 (d, J=8.4 Hz, 1H), 7.72 (s, 1H), 7.75 (d, J=15.6 Hz, 1H), 7.81 (dd, J=2 Hz, 15.6 Hz, 1H), 8.18 (d, J=2 Hz, 1H), 9.82 (s, 1H).

Example 438

Synthesis of (E)-3-[5-bromo-2-(1H-imidazol-1-yl)phenyl]-N-indan-1-ylacrylamide

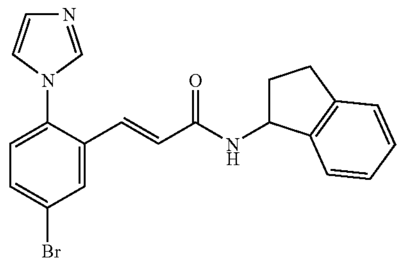

By the same method as in Example 1, 49 mg of the title compound was obtained from 5-bromo-2-(1H-imidazol-1-yl)benzaldehyde (30 mg) and indan-1-ylcarbamoyl methylphosphonic acid diethyl ester (37 mg).

$^1$H-NMR ($CDCl_3$) δ (ppm): 1.80-1.89 (m, 1H), 2.58-2.66 (m, 1H), 2.85-2.93 (m, 1H), 2.96-3.03 (m, 1H), 5.55 (q, J=7.6 Hz, 1H), 5.99 (d, J=8.4 Hz, 1H), 6.20 (d, J=15.6 Hz, 1H), 7.06 (t, J=1.2 Hz, 1H), 7.16-7.28 (m, 5H), 7.38 (d, J=15.6 Hz, 1H), 7.55-7.58 (m, 2H), 7.79 (d, J=2 Hz, 1H).

Example 439

Synthesis of (E)-3-[3-hydroxymethyl-4-(1H-imidazol-1-yl)phenyl]-N-indan-1-ylacrylamide

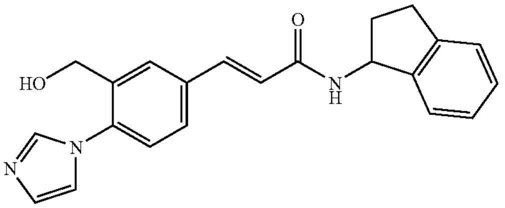

Sodium borohydride (2 mg) is added to an ethanol (1 mL) solution of (E)-3-(3-formyl-4-(1H-imidazol-1-yl)phenyl)-N-indan-1-ylacrylamide (17 mg) obtained in Example 437 and the reaction mixture was agitated for 30 minutes at room temperature. After the reaction solution was concentrated under reduced pressure, water and ethyl acetate were added to the residue, and the organic layer was partitioned. The organic layer was washed with a saturated saline solution, dried over anhydrous magnesium sulfate, and concentrated under reduced pressure. The residue was purified by silica gel column chromatography (Carrier: Chromatorex™ NH, elution solvent:methanol-ethyl acetate system), and 1.8 mg of the title compound was obtained.

$^1$H-NMR ($CDCl_3$) δ (ppm): 1.86-1.95 (m, 1H), 2.63-2.72 (m, 1H), 2.89-2.97 (m, 1H), 3.00-3.07 (m, 1H), 4.55 (s, 2H), 5.65 (q, J=7.6 Hz, 1H), 5.89 (d, J=8.4 Hz, 1H), 6.48 (d, J=15.6 Hz, 1H), 7.18-7.35 (m, 7H), 7.54 (dd, J=2.4 Hz, 8 Hz, 1H), 7.71 (d, J=1.2 Hz, 1H), 7.79 (d, J=2 Hz, 1H).

Example 440

Synthesis of (E)-3-[3-(1-hydroxy ethyl)-4-(1H-imidazol-1-yl)phenyl]-N-indan-1-ylacrylamide

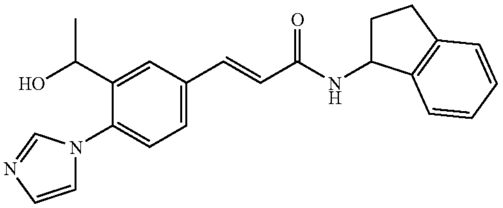

To a THF (0.5 mL) solution of (E)-3-(3-formyl-4-(1H-imidazol-1-yl)phenyl)-N-indan-1-ylacrylamide (23 mg) obtained in Example 437, methyl magnesium bromide (3M ether solution, 0.04 mL) was added under nitrogen atmosphere under ice-cooling and the reaction mixture was agitated for 1 hour. A saturated ammonium chloride water and ethyl acetate were added to the reaction solution, and the organic layer was partitioned. The organic layer was washed with a saturated saline solution, dried over anhydrous magnesium sulfate, and concentrated under reduced pressure. The residue was purified by silica gel column chromatography (Carrier: Chromatorex™ NH, elution solvent:methanol-ethyl acetate system), and 10 mg of the title compound was obtained.

$^1$H-NMR ($CDCl_3$) δ (ppm): 1.40 (d, J=6.4 Hz, 3H), 1.86-1.95 (m, 1H), 2.66-2.73 (m, 1H), 2.89-2.97 (m, 1H), 3.00-3.07 (m, 1H), 4.79 (q, J=6.4 Hz, 1H), 5.65 (q, J=7.6 Hz, 1H), 5.90 (d, J=8.4 Hz, 1H), 6.50 (d, J=15.6 Hz, 1H), 7.09 (t, J=1.2 Hz, 1H), 7.20-7.35 (m, 5H), 7.49 (dd, J=1.6 Hz, 8 Hz, 1H), 7.61 (s, 1H), 7.73 (d, J=15.6 Hz, 1H), 7.89 (d, J=2 Hz, 1H).

Example 441

Synthesis of (E)-3-[3-acetyl-4-(1H-imidazol-1-yl)phenyl]-N-indan-1-ylacrylamide

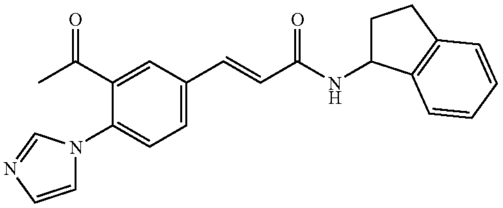

To a chloroform (0.5 mL) solution of (E)-3-(3-(1-hydroxyethyl)-4-(1H-imidazol-1-yl)phenyl)-N-indan-1-ylacrylamide (3 mg) obtained in Example 440, activated manganese dioxide (14 mg) was added and the reaction mixture was agitated at room temperature overnight. The reaction solution was filtered through a filter paper and the filtrate was concentrated under reduced pressure. The residue was purified by silica gel column chromatography (elution solvent:ethyl acetate), and 3.8 mg of the title compound was obtained.

$^1$H-NMR ($CDCl_3$) δ (ppm): 1.86-1.96 (m, 1H), 2.02 (s, 3H), 2.65-2.73 (m, 1H), 2.89-2.97 (m, 1H), 3.00-3.08 (m, 1H), 5.64 (q, J=7.6 Hz, 1H), 5.88 (d, J=8.4 Hz, 1H), 6.49 (d, J=15.6 Hz, 1H), 7.12 (t, J=1.2 Hz, 1H), 7.22-7.39 (m, 6H), 7.64 (t, J=1.2 Hz, 1H), 7.70 (dd, J=1.6 Hz, 8 Hz, 1H), 7.78 (d, J=1.6 Hz, 1H).

Example 442

Synthesis of (E)-3-[4-(1H-imidazol-1-yl)-3-methoxymethylphenyl]-N-indan-1-ylacrylamide

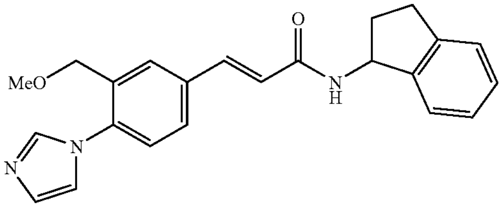

Sodium borohydride (127 mg) was added to an ethanol (10 mL) solution of the 5-bromo-2-(1H-imidazol-1-yl)benzaldehyde (420 mg) obtained in Example 437, and the reaction mixture was agitated at room temperature for 1 hour. After the reaction solution was concentrated under reduced pressure, water and ethyl acetate was added to the residue and the organic layer was partitioned. The organic layer was washed with a saturated saline solution, dried over anhydrous magnesium sulfate, and concentrated under reduced pressure. Sodium methoxide (40% methanol solution, 10 mL) was added to a methanol (2 mL) solution of the obtained crude alcohol compound, and the reaction mixture was agitated at room temperature overnight. After the reaction solution was concentrated under reduced pressure, water and ethyl acetate were added to the residue, and the organic layer was partitioned. The organic layer was washed with a saturated saline solution, dried over anhydrous magnesium sulfate, concentrated under reduced pressure, and a crude methoxymethyl compound (211 mg) was obtained. By the same method as in Example 9, 15 mg of the title compound was obtained from this crude methoxymethyl compound (23 mg) and N-indan-1-yl-acrylamide (16 mg).

$^1$H-NMR ($CDCl_3$) δ (ppm): 1.86-1.97 (m, 1H), 2.63-2.72 (m, 1H), 2.90-2.96 (m, 1H), 3.00-3.07 (m, 1H), 3.39 (s, 3H), 4.23 (s, 2H), 5.65 (q, J=7.6 Hz, 1H), 5.89 (d, J=8.4 Hz, 1H), 6.47 (d, J=15.6 Hz, 1H), 7.17 (t, J=1.2 Hz, 1H), 7.22-7.35 (m, 7H), 7.54 (dd, J=2 Hz, 8.4 Hz, 1H), 7.70-7.75 (m, 2H).

Example 443

Synthesis of (E)-3-[3-fluoro-5-methoxy-4-(4-methyl-1H-imidazol-1-yl)phenyl]-N-indan-1-ylacrylamide

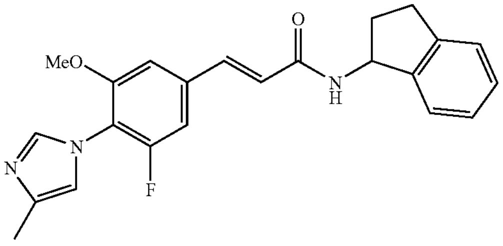

By the same method as in Example 9, 32 mg of the title compound was obtained from 1-(4-bromo-2-fluoro-6-methoxyphenyl)-4-methyl-1H-imidazole (30 mg) and N-indan-1-yl-acrylamide (24 mg) synthesized by the same method as in Example 16. The physical properties of the compound are as follows.

$^1$H-NMR ($CDCl_3$) δ (ppm): 1.85-1.94 (m, 1H), 2.29 (s, 3H), 2.62-2.70 (m, 1H), 2.87-2.95 (m, 1H), 2.98-3.06 (m, 1H), 3.96 (s, 3H), 5.62 (q, J=7.6 Hz, 1H), 6.02 (d, J=8.4 Hz, 1H), 6.39 (d, J=15.6 Hz, 1H), 6.96 (d, J=0.8 Hz, 1H), 7.04-7.08 (m, 2H), 7.20-7.34 (m, 4H), 7.61 (d, J=15.6 Hz, 1H), 7.70 (t, J=1.6 Hz, 1H).

Example 444

Synthesis of (E)-3-[2,5-dimethoxy-4-(4-methyl-1H-imidazol-1-yl)phenyl]-N-indan-1-ylacrylamide

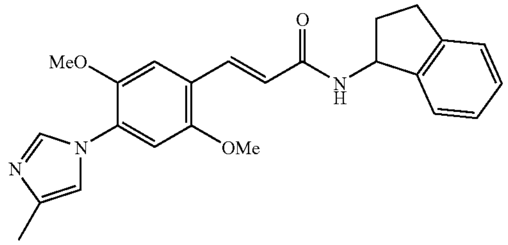

35 mg of the title compound was obtained from 1-(4-bromo-2,5-dimethoxyphenyl)-4-methyl-1H-imidazole (58 mg) prepared by a similar method as in Example 18 and N-indan-1-yl-acrylamide (44 mg) by the same method as in Example 9. The physical properties of the compound are as follows.

$^1$H-NMR ($CDCl_3$) δ (ppm): 1.86-1.95 (m, 1H), 2.30 (s, 3H), 2.63-2.72 (m, 1H), 2.88-2.96 (m, 1H), 2.99-3.05 (m, 1H), 3.81 (s, 3H), 3.86 (s, 3H), 5.65 (q, J=7.6 Hz, 1H), 5.92 (d, J=8.4 Hz, 1H), 6.59 (d, J=15.6 Hz, 1H), 6.81 (s, 1H), 6.94-6.95 (m, 1H), 7.13 (s, 1H), 7.21-7.29 (m, 3H), 7.36 (d, J=6.8 Hz, 1H), 7.74 (d, J=1.2 Hz, 1H), 7.86 (d, J=15.6 Hz, 1H).

Example 445

Synthesis of (E)-3-[2-chloro-5-methoxy-4-(4-methyl-1H-imidazol-1-yl)phenyl]-N-indan-1-ylacrylamide

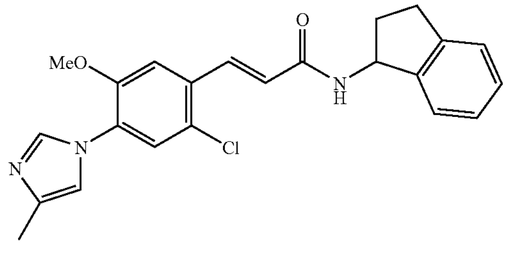

19 mg of the title compound was obtained by the same method as in Example 9 from 1-(4-bromo-5-chloro-2-methoxyphenyl)-4-methyl-1H-imidazole (72 mg) prepared by a similar method as in Example 18 and N-indan-1-yl-acrylamide (49 mg).

The physical properties of the compound are as follows.

$^1$H-NMR ($CDCl_3$) δ (ppm): 1.87-1.96 (m, 1H), 2.29 (s, 3H), 2.64-2.73 (m, 1H), 2.89-2.97 (m, 1H), 3.00-3.07 (m, 1H), 3.88 (s, 3H), 5.65 (q, J=7.6 Hz, 1H), 5.96 (d, J=8.4 Hz, 1H), 6.45 (d, J=15.6 Hz, 1H), 6.92 (t, J=1.2 Hz, 1H), 7.17 (s, 1H), 7.22-7.29 (m, 3H), 7.33 (s, 1H), 7.36 (d, J=6.8 Hz, 1H), 7.73 (d, J=1.6 Hz, 1H), 7.98 (d, J=15.6 Hz, 1H).

Example 446

Synthesis of (E)-3-[3-cyano-4-(5-methyl-1H-imidazol-1-yl)phenyl]-N-indan-1-ylacrylamide

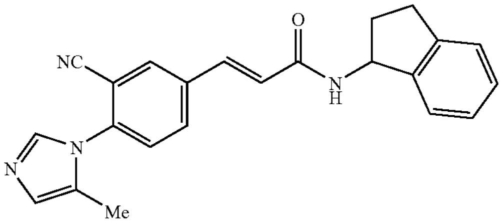

By the same method as in Example 9, 9 mg of the title compound was obtained from 5-bromo-2-(5-methyl-1H-imidazol-1-yl)benzonitrile (30 mg)

$^1$H-NMR ($CDCl_3$) δ (ppm): 1.87-1.97 (m, 1H), 2.18 (s, 3H), 2.65-2.74 (m, 1H), 2.90-2.98 (m, 1H), 3.01-3.08 (m, 1H), 5.65 (q, J=7.6 Hz, 1H), 5.91 (d, J=8.4 Hz, 1H), 6.50 (d, J=16 Hz, 1H), 6.98 (t, J=1.2 Hz, 1H), 7.22-7.30 (m, 3H), 7.34 (d, J=7.6 Hz, 1H), 7.41 (d, J=8.4 Hz, 1H), 7.58 (d, J=1.2 Hz, 1H) 7.73 (d, J=16 Hz, 1H), 7.83 (dd, J=2.4 Hz, 8.4 Hz, 1H), 7.94 (d, J=2 Hz, 1H).

Compounds shown in Table 10 were synthesized in which Example 447 to Example 450 followed the method of Example 434, Example 451 to Example 455 followed the method of Example 20 and Example 456 and Example 457 followed the method of Example 1 changing the substitutent groups on the imidazolering ring and the benzene ring. The structural formulae and physical properties are shown in Table 10, respectively.

TABLE 10

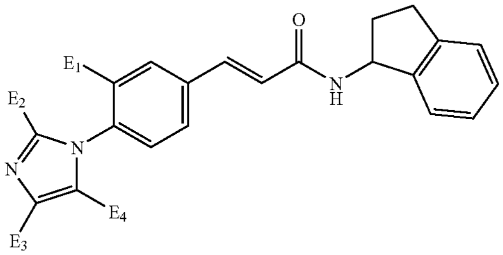

| Example | $E_1$ | $E_2$ | $E_3$ | $E_4$ | DATA: MS m/z |
|---|---|---|---|---|---|
| 447 | F | H | 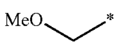 | H | $M^+$ + H: 344 (ESI) |
| 448 | MeO | H | 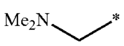 | H | $M^+$ + H: 362 (ESI) |

TABLE 10-continued

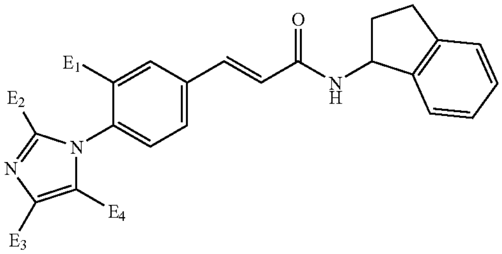

| Example | $E_1$ | $E_2$ | $E_3$ | $E_4$ | DATA: MS m/z |
|---|---|---|---|---|---|
| 449 | MeO | H | 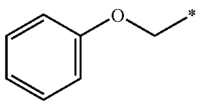 | H | $M^+$ + H: 362 (ESI) |
| 450 | MeO | H | 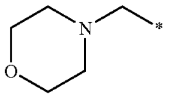 | H | $M^+$ + H: 424 (ESI) |
| 451 | F | H | H | Cl | $M^+$ + H: 382 (ESI) |
| 452 | MeO | Cl | Cl | Cl | $M^+$ + H: 462 (ESI) |
| 453 | MeO | H | Cl | Cl | $M^+$ + H: 428 (ESI) |
| 454 | MeO | H | Me | Cl | $M^+$ + H: 408 (ESI) |
| 455 | MeO | H | H | Br | $M^+$ + H: 439 (ESI) |
| 456 | EtO | H | H | H | $M^+$ + H: 374 (ESI) |
| 457 | 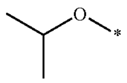 | H | H | H | $M^+$ + H: 388 (ESI) |

The compounds shown in Table 11 were synthesized as in Example 85. The structural formulae and physical properties are shown in Table 11, respectively.

TABLE 11

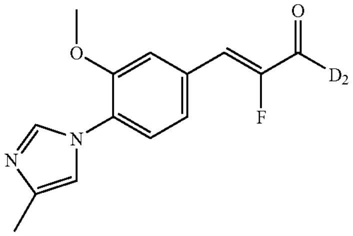

| Example | $D_2$ | DATA: MS m/z |
|---|---|---|
| 458 | 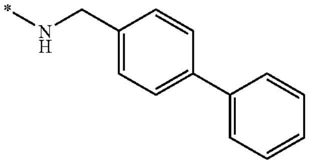 | $M^+$ + H: 442 (ESI) |

TABLE 11-continued
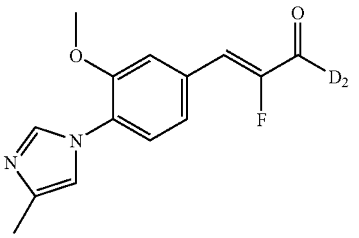
| Example | $D_2$ | DATA: MS m/z |
|---|---|---|
| 459 | 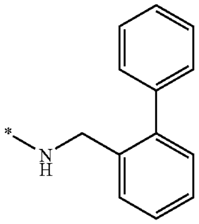 | $M^+$ + H: 442 (ESI) |
| 460 | 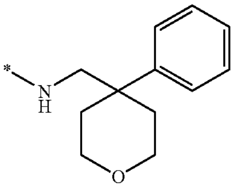 | $M^+$ + H: 450 (ESI) |
| 461 | 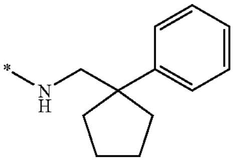 | $M^+$ + H: 434 (ESI) |
| 462 | 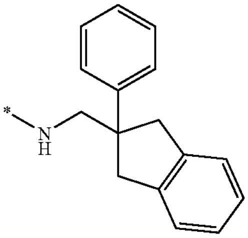 | $M^+$ + H: 482 (ESI) |
| 463 | 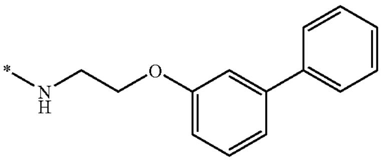 | $M^+$ + H: 472 (ESI) |
| 464 | 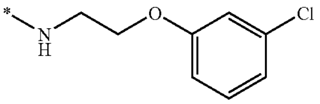 | $M^+$ + H: 430 (ESI) |
TABLE 11-continued
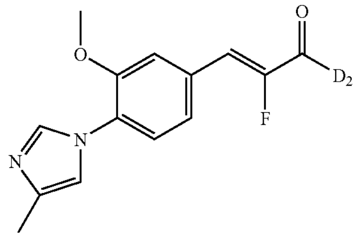
| Example | $D_2$ | DATA: MS m/z |
|---|---|---|
| 465 | 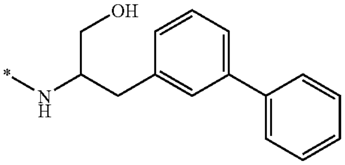 | $M^+$ + H: 486 (ESI) |
| 466 | 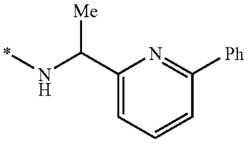 | $M^+$ + H: 457 (ESI) |
| 467 | 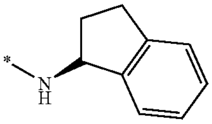 | $M^+$ + H: 392 (ESI) |
| 468 | 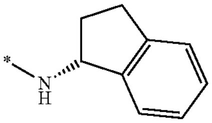 | $M^+$ + H: 392 (ESI) |
| 469 | 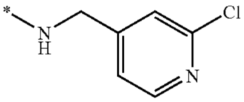 | $M^+$ + H: 401 (ESI) |
| 470 | 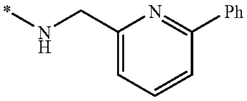 | $M^+$ + H: 443 (ESI) |
| 471 | 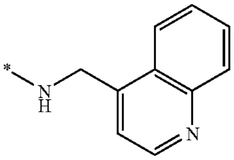 | $M^+$ + H: 417 (ESI) |
| 472 | 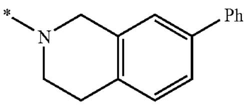 | $M^+$ + H: 468 (ESI) |
| 473 | 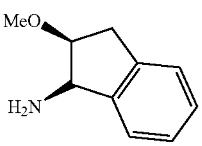 | $M^+$ + H: 422 (ESI) |

Example 474

Synthesis of (Z)-2-fluoro-3-[3-methoxy-4-(4-methyl-1H-imidazol-1-yl)phenyl]-N-(6-phenylpyridin-2-ylmethyl)acrylic acid amide

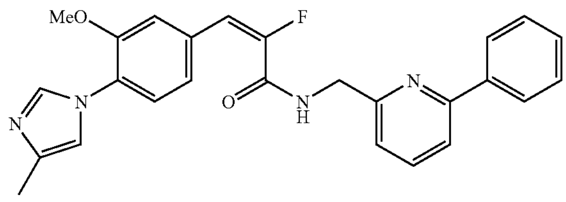

Synthesis of (Z)-2-fluoro-3-[3-methoxy-4-(4-methyl-1H-imidazol-1-yl)phenyl]acrylic acid By the same method as in Example 111, 4.52 g of the title compound was obtained from 3-methoxy-4-(4-methyl-1H-imidazol-1-yl)benzaldehyde (4.0 g) synthesized in Example 1, 2-fluoro-2-phosphonoacetic acid triethyl ester (5.82 g) and lithium hydroxide monohydrate (0.664 g). The physical properties of the compound are as follows.

$^1$H-NMR (DMSO-$d_6$) δ (ppm): 2.16 (s, 3H), 3.82 (s, 3H), 7.02 (d, J=24 Hz, 1H), 7.20 (s, 1H), 7.25 (d, J=8.0 Hz, 1H), 7.36 (d, J=8.0 Hz, 1H), 7.59 (s, 1H), 7.93 (s, 1H).

Synthesis of (Z)-2-fluoro-3-[3-methoxy-4-(4-methyl-1H-imidazol-1-yl)phenyl]-N-(6-phenylpyridin-2-ylmethyl)acrylic acid amide By the same method as in Example 111, 12.1 mg of the title compound was obtained from (Z)-2-fluoro-3-(3-methoxy-4-(4-methyl-1H-imidazol-1-yl)phenyl)acrylic acid (10 mg) and (6-phenylpyridin-2-yl)methylamine (10 mg). The physical properties of the compound are as follows.

ESI-MS; m/z443 [$M^+$+H].

The following compounds in Table 12 were synthesized as in Example 474. The structural formulae and physicochemical properties are shown in Table 12, respectively.

TABLE 12

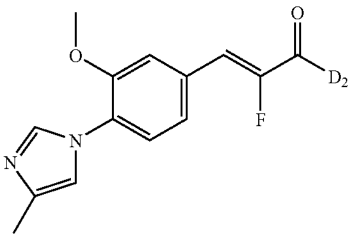

| Example | $D_3$ | DATA: MS m/z |
|---|---|---|
| 475 | 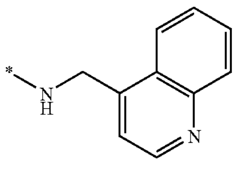 | $M^+$ + H: 417 (ESI) |

TABLE 12-continued

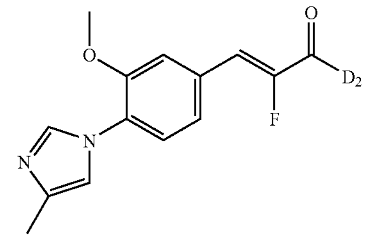

| Example | $D_3$ | DATA: MS m/z |
|---|---|---|
| 476 | 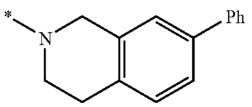 | $M^+$ + H: 467 (ESI) |
| 478 | 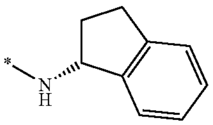 | $M^+$ + H: 392 (ESI) |
| 479 | 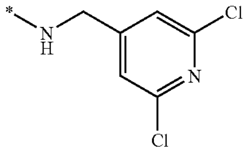 | $M^+$ + H: 435 (ESI) |
| 480 | 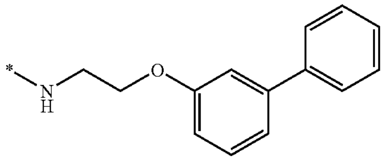 | $M^+$ + H: 472 (ESI) |
| 481 | 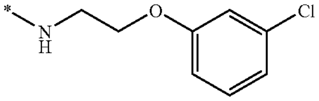 | $M^+$ + H: 430 (ESI) |
| 482 | 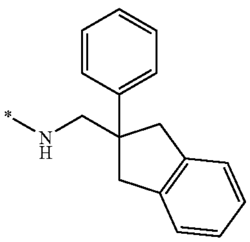 | $M^+$ + H: 482 (ESI) |
| 483 | 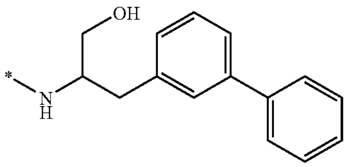 | $M^+$ + H: 486 (ESI) |

The following compounds in Table 13 were synthesized as in Example 23. The structural formulae and physicochemical properties are shown in Table 13, respectively.

TABLE 13
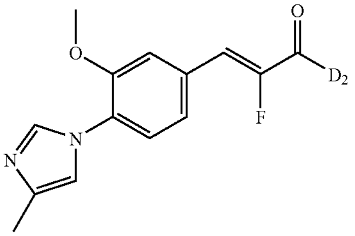
| Example | $G_7$ | DATA: MS m/z |
|---|---|---|
| 484 | 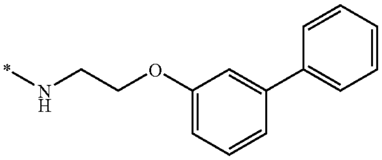 | $M^+ + H$: 455 (ESI) |
| 485 | 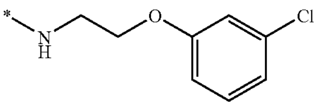 | $M^+ + H$: 413 (ESI) |
| 486 | 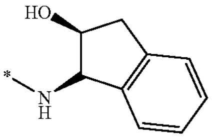 | $M^+ + H$: 391 (ESI) |
TABLE 13-continued
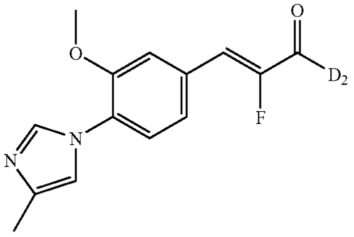
| Example | $G_7$ | DATA: MS m/z |
|---|---|---|
| 487 | 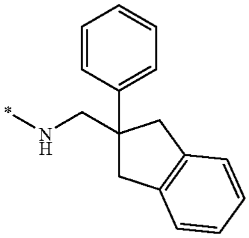 | $M^+ + H$: 465 (ESI) |
| 488 | 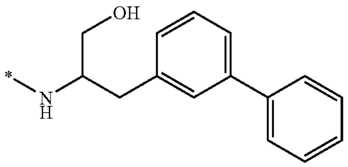 | $M^+ + H$: 469 (ESI) |
The following compounds in Table 14 were synthesized as in Example 121. The structural formulae and physicochemical properties are shown in Table 14, respectively.
TABLE 14
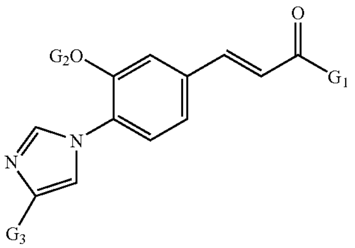
| Example | $G_1$ | $G_2$ | $G_3$ | DATA: MS m/z |
|---|---|---|---|---|
| 489 | 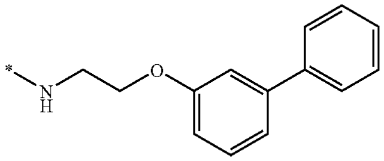 | Me | Me | $M^+ + H$: 454 (ESI) |
| 490 | 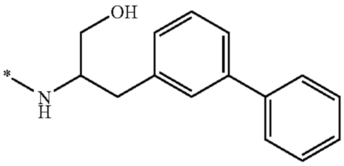 | Me | Me | $M^+ + H$: 468 (ESI) |

TABLE 14-continued
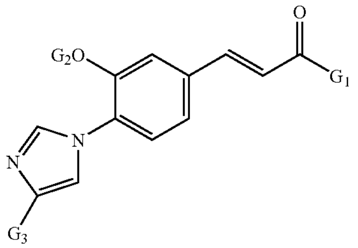
| Example | $G_1$ | $G_2$ | $G_3$ | DATA: MS m/z |
|---|---|---|---|---|
| 491 | 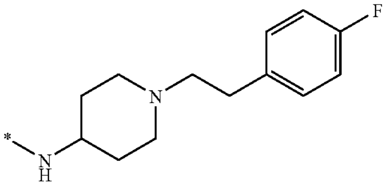 | Me | Me | $M^+ + H$: 463 (ESI) |
| 492 | 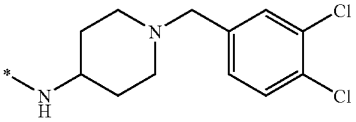 | Me | Me | $M^+ + H$: 499 (ESI) |
| 493 | 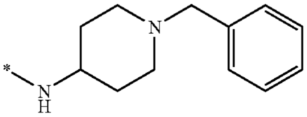 | Me | Me | $M^+ + H$: 431 (ESI) |
| 494 | 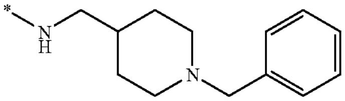 | Me | Me | $M^+ + H$: 445 (ESI) |
| 495 | 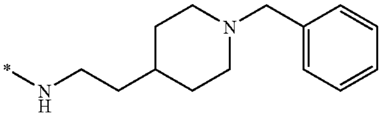 | Me | Me | $M^+ + H$: 459 (ESI) |
| 496 | 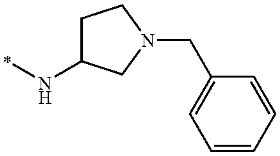 | Me | Me | $M^+ + H$: 417 (ESI) |
| 497 | 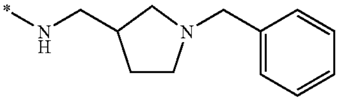 | Me | Me | $M^+ + H$: 431 (ESI) |
| 498 | 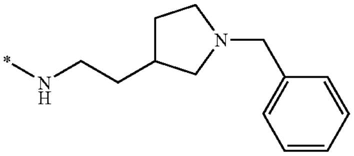 | Me | Me | $M^+ + H$: 445 (ESI) |
| 499 | 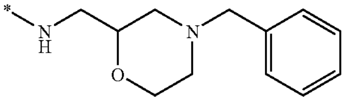 | Me | Me | $M^+ + H$: 447 (ESI) |

TABLE 14-continued
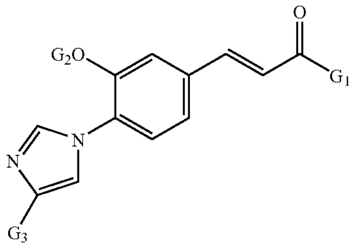
| Example | $G_1$ | $G_2$ | $G_3$ | DATA: MS m/z |
|---|---|---|---|---|
| 500 | 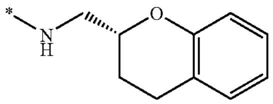 | Me | Me | $M^+ + H$: 404 (ESI) |
| 501 | 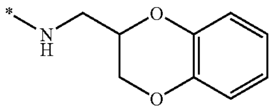 | Me | Me | $M^+ + H$: 406 (ESI) |
| 502 | 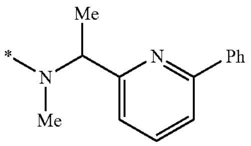 | Me | Me | $M^+ + H$: 453 (ESI) |
| 503 | 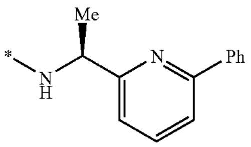 | Me | Me | $M^+ + H$: 439 (ESI) |
| 504 | 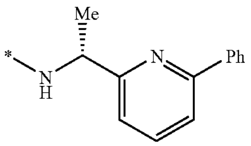 | Me | Me | $M^+ + H$: 439 (ESI) |
| 505 | 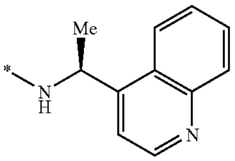 | Me | Me | $M^+ + H$: 413 (ESI) |
| 506 | 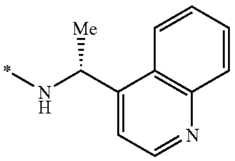 | Me | Me | $M^+ + H$: 413 (ESI) |
| 507 | 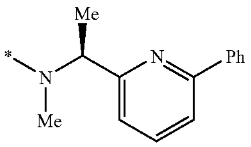 | Me | Me | $M^+ + H$: 453 (ESI) |

TABLE 14-continued
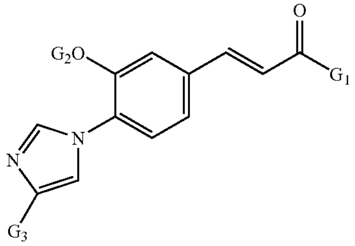
| Example | $G_1$ | $G_2$ | $G_3$ | DATA: MS m/z |
|---|---|---|---|---|
| 508 | 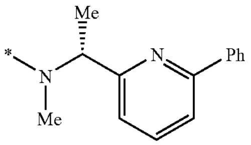 | Me | Me | $M^+ + H$: 453 (ESI) |
| 509 | 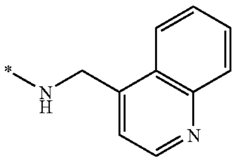 | Me | Me | $M^+ + H$: 399 (ESI) |
| 510 | 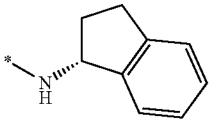 | Me | Me | $M^+ + H$: 374 (ESI) |
| 511 | 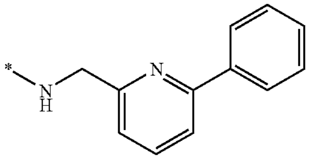 | Me | Et | $M^+ + H$: 439 (ESI) |
| 512 | 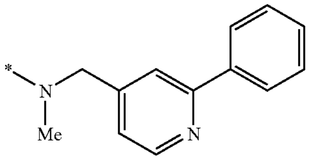 | Me | Et | $M^+ + H$: 453 (ESI) |
| 513 | 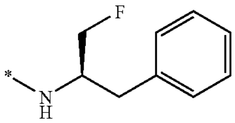 | Me | Et | $M^+ + H$: 408 (ESI) |
| 514 | 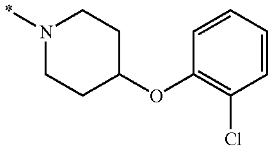 | Me | Me | $M^+ + H$: 452 (ESI) |
| 515 | 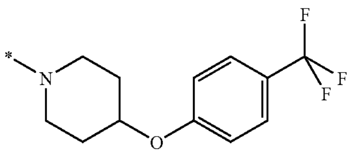 | Me | Me | $M^+ + H$: 486 (ESI) |

TABLE 14-continued
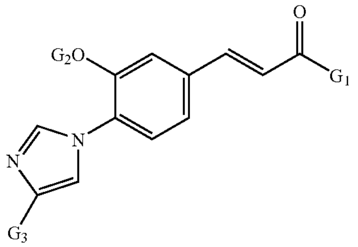
| Example | $G_1$ | $G_2$ | $G_3$ | DATA: MS m/z |
|---|---|---|---|---|
| 516 | 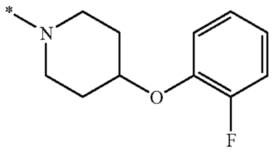 | Me | Me | $M^+ + H$: 436 (ESI) |
| 517 | 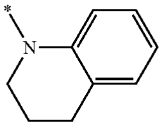 | Me | Me | $M^+ + H$: 374 (ESI) |
| 518 | 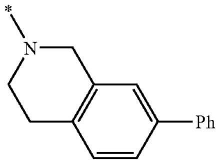 | Me | Me | $M^+ + H$: 450 (ESI) |
| 519 | 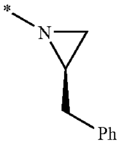 | Me | Me | $M^+ + H$: 374 (ESI) |
| 520 | 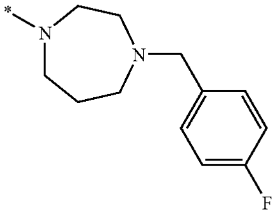 | Me | Me | $M^+ + H$: 449 (ESI) |
| 521 | 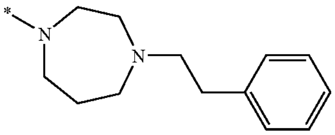 | Me | Me | $M^+ + H$: 445 (ESI) |
| 522 | 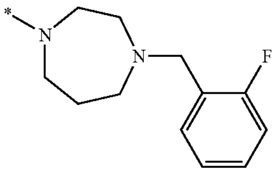 | Me | Me | $M^+ + H$: 449 (ESI) |

TABLE 14-continued
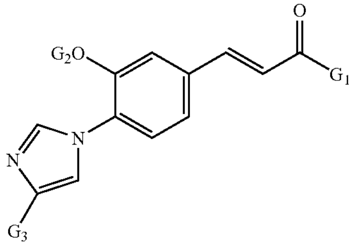
| Example | $G_1$ | $G_2$ | $G_3$ | DATA: MS m/z |
|---|---|---|---|---|
| 523 | 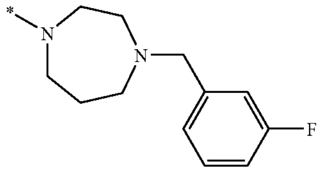 | Me | Me | $M^+ + H$: 449 (ESI) |
| 524 | 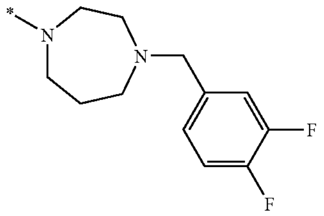 | Me | Me | $M^+ + H$: 467 (ESI) |
| 525 | 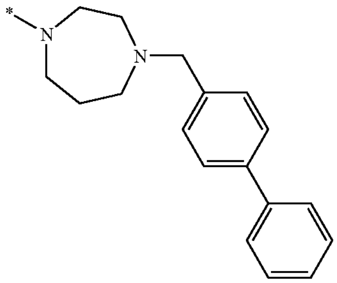 | Me | Me | $M^+ + H$: 507 (ESI) |
| 526 | 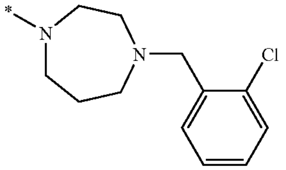 | Me | Me | $M^+$: 465 (ESI) |
| 527 | 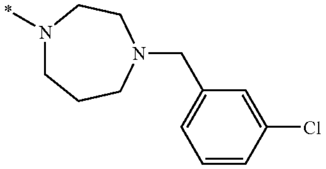 | Me | Me | $M^+$: 465 (ESI) |
| 528 | 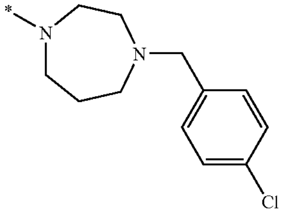 | Me | Me | $M^+$: 465 (ESI) |

TABLE 14-continued
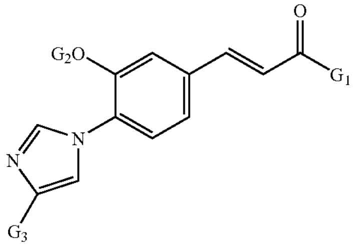
| Example | $G_1$ | $G_2$ | $G_3$ | DATA: MS m/z |
|---|---|---|---|---|
| 529 | 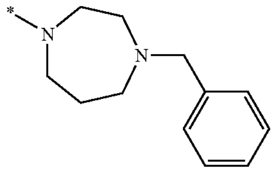 | Me | Me | $M^+ + H$: 431 (ESI) |
| 530 | 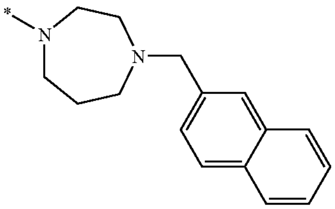 | Me | Me | $M^+ + H$: 481 (ESI) |
| 531 | 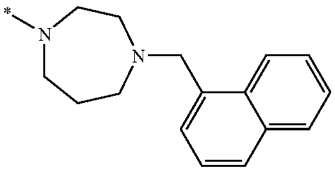 | Me | Me | $M^+ + H$: 481 (ESI) |
| 532 | 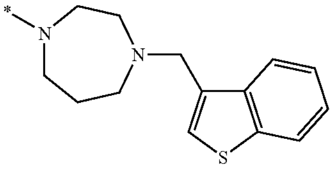 | Me | Me | $M^+ + H$: 487 (ESI) |
| 533 | 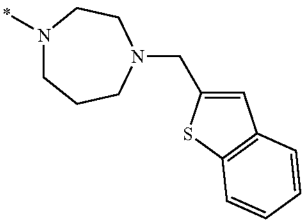 | Me | Me | $M^+ + H$: 487 (ESI) |
| 534 | 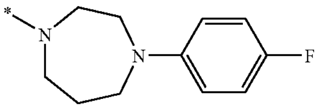 | Me | Me | $M^+ + H$: 435 (ESI) |
| 535 | 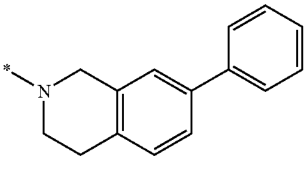 | Me | Et | $M^+ + H$: 464 (ESI) |

TABLE 14-continued

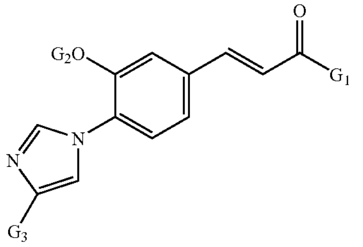

| Example | $G_1$ | $G_2$ | $G_3$ | DATA: MS m/z |
|---|---|---|---|---|
| 536 | 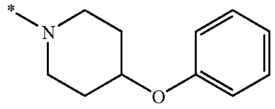 | Me | Et | $M^+ + H$: 432 (ESI) |
| 537 | 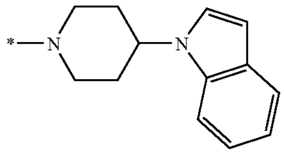 | Me | Et | $M^+ + H$: 432 (ESI) |

Example 538

Synthesis of (E)-1-(3,4-difluorobenzyl)-3-[3-methoxy-4-(4-methyl-1H-imidazol-1-yl)benzylidene]pyrrolidin-2-one

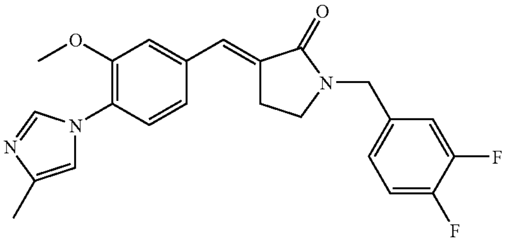

Synthesis of (E)-1-acetyl-3-[3-methoxy-4-(4-methyl-1H-imidazol-1-yl)benzylidene]pyrrolidin-2-one Triethylamine (45 mL) was added to an ethanol (80 mL) solution of 3-methoxy-4-(4-methyl-1H-imidazol-1-yl)benzaldehyde (3.0 g) and (1-acetyl-2-oxopyrrolidin-3-yl)triphenylphosphonyl bromide (8.4 g) synthesized by the method described in Journal of Medicinal Chemistry, vol. 30, No. 11, p. 1995, 1987. The reaction solution was made to react at 60° C. for 2 hours. The reaction solution was cooled to room temperature and was added to a mixed-solution of ethyl acetate and iced water. The deposited solids were dried under reduced pressure after separated by filtration, and 3.3 g of the title compound was obtained. The physical properties of the compound are as follows.

$^1$H-NMR (DMSO-$d_6$) δ (ppm): 2.15 (s, 3H), 2.46-3.54 (m, 3H), 3.08-3.16 (m, 2H), 3.74-3.80 (m, 2H), 3.89 (s, 3H), 7.18 (t, J=1.2 Hz, 1H), 7.28-7.34 (m, 1H), 7.42-7.50 (m, 3H), 7.84 (d, J=1.2 Hz, 1H).

Synthesis of (E)-3-[3-methoxy-4-(4-methyl-1H-imidazol-1-yl)benzylidene]pyrrolidin-2-one A mixed solution of ethanol (100 mL) and methanol (100 mL) of (E)-1-acetyl-3-[3-methoxy-4-(4-methyl-1H-imidazol-1-yl)benzylidene]pyrrolidin-2-one (7.5 g) and potassium carbonate (1.6 g) was agitated at room temperature for 2 hours. After condensing reaction solution to ⅓, added to iced water and ethyl acetate and deposited solids were separated by filtration to obtain 4.7 g of the title compound. Furthermore, the filtrate was extracted with ethyl acetate and the organic layer was dried over anhydrous magnesium sulfate after washed with a saturated saline solution. This solution was concentrated and the deposited solids was obtained by filtration to yield 2.7 g of the title compound. The physical properties of the compound are as follows.

$^1$H-NMR ($CDCl_3$) δ (ppm): 2.30 (s, 3H), 3.15-3.25 (m, 2H), 3.55-3.63 (m, 2H), 3.88 (s, 3H), 5.97 (brs, 1H), 6.94 (d, J=1.2 Hz, 1H), 7.11 (d, J=1.6 Hz, 1H), 7.15 (dd, J=1.6, 8.0 Hz, 1H), 7.28 (d, J=8.0 Hz, 1H), 7.35 (t, J=2.8 Hz, 1H), 7.72 (d, J=1.6 Hz, 1H).

Synthesis of (E)-1-(3,4-difluorobenzyl)-3-[3-methoxy-4-(4-methyl-1H-imidazol-1-yl)benzylidene]pyrrolidin-2-one To a DMF (6.0 mL) solution of (E)-3-(3-methoxy-4-(4-methyl-1H-imidazol-1-yl)benzylidene)pyrrolidin-2-one (100 mg), lithium bis(trimethylsilyl)amide (1M hexane solution, 0.53 mL) was added at 0° C., and the reaction solution was agitated for 30 minutes at 0° C. 3,4-difluorobenzylbromide (0.060 mL) was added to this solution at 0° C., and that reaction solution was agitated at room temperature for 1 hour. The reaction solution was added to iced water and ethyl acetate, and the organic layer was partitioned. The obtained organic layer was washed with a saturated salt solution, and it concentrated under reduced pressure after dried over anhydrous magnesium sulfate. The residue was purified by silica gel column chromatography (elution solvent:heptane-ethyl acetate system), and 80 mg of the title compound was obtained. The physical properties of the compound are as follows.

$^1$H-NMR ($CDCl_3$) δ (ppm): 2.30 (s, 3H), 3.05-3.13 (m, 2H), 3.38-3.45 (m, 2H), 3.88 (s, 3H), 4.58 (s, 2H), 6.91-6.95 (m, 1H), 6.99-7.05 (m, 1H), 7.08-7.17 (m, 4H), 7.27 (d, J=8.0 Hz, 1H), 7.40 (t, J=2.8 Hz, 1H), 7.72 (d, J=1.2 Hz, 1H).

The following compounds in Table 15 were synthesized as in Example 538. The structural formulae and physicochemical properties are shown in Table 15, respectively.

TABLE 15

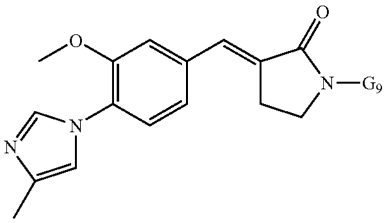

| Example | $G_9$ | DATA: MS m/z |
|---|---|---|
| 539 | 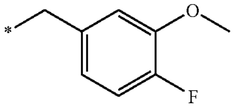 | $M^+$ + H: 422 (ESI) |
| 540 | 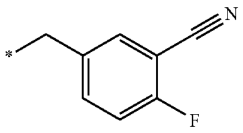 | $M^+$ + H: 417 (ESI) |
| 541 | 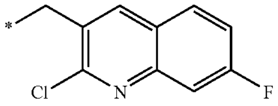 | $M^+$ + H: 477 (ESI) |
| 542 | 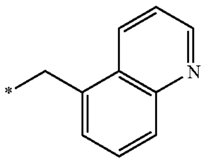 | $M^+$ + H: 425 (ESI) |
| 543 | 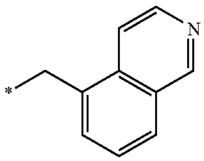 | $M^+$ + H: 425 (ESI) |
| 544 | 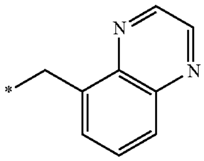 | $M^+$ + H: 426 (ESI) |
| 545 | 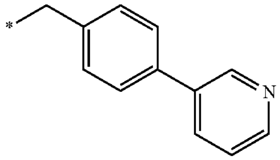 | $M^+$ + H: 451 (ESI) |

TABLE 15-continued

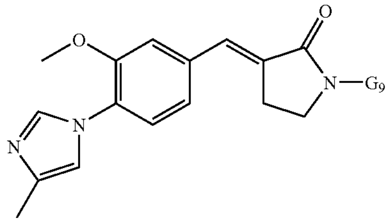

| Example | $G_9$ | DATA: MS m/z |
|---|---|---|
| 546 | 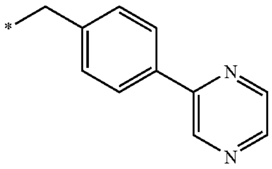 | $M^+$ + H: 452 (ESI) |
| 547 | 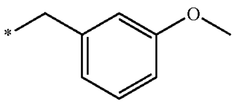 | $M^+$ + H: 404 (ESI) |
| 548 | 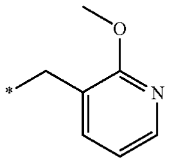 | $M^+$ + H: 405 (ESI) |
| 549 | 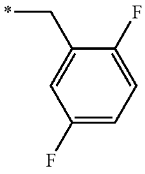 | $M^+$ + H: 410 (ESI) |
| 550 | 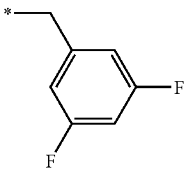 | $M^+$ + H: 410 (ESI) |
| 551 | 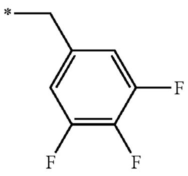 | $M^+$ + H: 428 (ESI) |
| 552 | 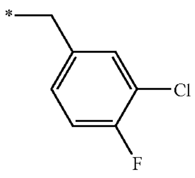 | $M^+$ + H: 426 (ESI) |

TABLE 15-continued

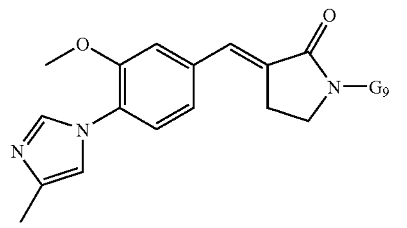

| Example | $G_9$ | DATA: MS m/z |
| --- | --- | --- |
| 553 | 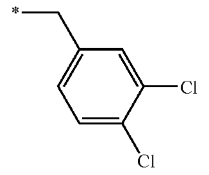 | $M^+$ + H: 442 (ESI) |

Example 554, Example 555 and Example 556

Synthesis of (E)-1-[1-(3,4-difluorobenzyl)-(4R)-hydroxy-(3R)-pyrrolidin-3-yl]-3-[3-methoxy-4-(4-methyl-1H-imidazol-1-yl)benzylidene]piperidin-2-one and (E)-1-[1-(3,4-difluorobenzyl)-(4S)-hydroxy-(3S)-pyrrolidine-3-yl)-3-(3-methoxy-4-(4-methyl-1H-imidazol-1-yl)benzylidene]piperidin-2-one

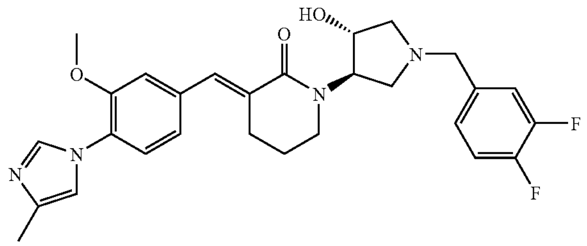

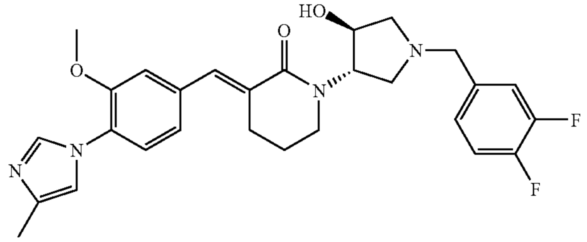

Synthesis of (E)-trans-3-hydroxy-4-(3-[3-methoxy-4-(4-methyl-1H-imidazol-1-yl)benzylidene]-2-oxopiperidin-1-yl)pyrrolidine-1-carboxylic acid tert-butyl ester By the same method as in Example 418, 2.61 g of the title compound was obtained from (E)-5-chloro-2-(3-methoxy-4-(4-methyl-1H-imidazol-1-yl)benzylidene)valeric acid trifluoroacetic acid salt (3.66 g) and trans-3-amino-4-hydroxy-pyrrolidin-1-carbamic acid tert-butyl ester (1.5 g) synthesized according to the method described in The Journal of Organic Chemistry, vol. 62, No. 12, p. 4197, 1997. The physical properties of the compound are as follows.

$^1$H-NMR ($CDCl_3$) δ (ppm): 1.47 (s, 9H), 1.83-2.02 (m, 2H), 2.30 (s, 3H), 2.70-2.88 (m, 2H), 3.25-3.63 (m, 4H), 3.79-3.83 (m, 2H), 3.85 (s, 3H), 4.33-4.43 (m, 1H), 4.87-4.95 (m, 1H), 6.92 (brs, 1H), 7.00 (brs, 1H), 7.01 (dd, J=9.6, 1.2 Hz, 1H), 7.24 (d, J=9.6 Hz, 1H), 7.71 (d, J=1.2 Hz, 1H), 7.80 (brs, 1H).

Synthesis of (E)-1-[1-(3,4-difluorobenzyl)-trans-4-hydroxy-3-pyrrolidin-3-yl]-3-[3-methoxy-4-(4-methyl-1H-imidazol-1-yl)benzylidene]piperidin-2-one Tri-fluoroacetic acid (1 mL) was added to a methylene chloride (1 mL) solution of tert-butyl ester (100 mg) of (E)-trans-3-hydroxy-4(3-(3-methoxy-4-(4-methyl-1H-imidazol-1-yl)benzylidene)-2-oxopiperidin-1-yl)pyrrolidine-1-carboxylic acid and the reaction solution was agitated at room temperature for 2 hours. The reaction solution was concentrated under reduced pressure, the residue was dissolved with methylene chloride (3 mL), and 3,4-difluorobenzaldehyde (0.046 mL) and sodium triacetoxyborohydride (132 mg) were added to the solution. After agitating the reaction solution at room temperature for 6 hours, ethyl acetate and a saturated sodium bicarbonate water were added to the reaction solution, and the organic layer was partitioned. After the obtained organic layer was washed with a saturated saline solution, it was dried over anhydrous magnesium sulfate and concentrated under reduced pressure. 100 mg of the title compound was obtained by purifying the residue by silica gel chromatography (Carrier: Chromatorex™ NH and elution solvent:heptane:ethyl acetate=1:1→ethyl acetate). The physical properties of the compound are as follows.

$^1$H-NMR ($CDCl_3$) δ (ppm): 1.79-1.89 (m, 1H), 1.93-2.02 (m, 1H), 2.30 (s, 3H), 2.39-2.45 (m, 1H), 2.63-2.97 (m, 4H), 3.08-3.13 (m, 1H), 3.34-3.42 (m, 1H), 3.49 (d, J=13.2 Hz, 1H), 3.50-3.58 (m, 1H), 3.63 (d, J=13.2 Hz, 1H), 3.72 (brs, 1H), 3.85 (s, 3H), 4.18-4.24 (m, 1H), 4.55-4.61 (m, 1H), 6.92 (brs, 1H), 7.00 (brs, 1H), 7.01 (brd, J=8.0 Hz, 1H), 7.05-7.19 (m, 3H), 7.24 (d, J=8.0 Hz, 1H), 7.71 (d, J=0.8 Hz, 1H), 7.77 (brs, 1H).

Synthesis of (E)-1-[1-(3,4-difluorobenzyl)-(4R)-hydroxy-(3R)-pyrrolidin-3-yl]-3-[3-methoxy-4-(4-methyl-1H-imidazol-1-yl)benzylidene]piperidin-2-one and (E)-1-[1-(3,4-difluorobenzyl)-(4S)-hydroxy-(3S)-pyrrolidin-3-yl]-3-[3-methoxy-4-(4-methyl-1H-imidazol-1-yl)benzylidene]piperidin-2-one The above-mentioned racemate (10 mg) was separated by CHIRALPAK™ AD-H available from Daicel Chemical Industries, Ltd. (2 cm×25 cm: mobile phase; hexane:iso propanol=30:70). The title optically active substance with a retention time of 13 minutes (4 mg;>99% ee) and the title optically active substance with a retention time of 16 minutes (4 mg;>99% ee) were obtained. The physical properties of the title optically active substance with a retention time of 13 minutes (Example 555) are as follows.

$^1$H-NMR ($CDCl_3$) δ (ppm): 1.79-1.89 (m, 1H), 1.93-2.02 (m, 1H), 2.30 (s, 3H), 2.39-2.45 (m, 1H), 2.63-2.97 (m, 4H), 3.08-3.13 (m, 1H), 3.34-3.42 (m, 1H), 3.49 (d, J=13.2 Hz, 1H), 3.50-3.58 (m, 1H), 3.63 (d, J=13.2 Hz, 1H), 3.72 (brs, 1H), 3.85 (s, 3H), 4.18-4.24 (m, 1H), 4.55-4.61 (m, 1H), 6.92 (brs, 1H), 7.00 (brs, 1H), 7.01 (brd, J=8.0 Hz, 1H), 7.05-7.19 (m, 3H), 7.24 (d, J=8.0 Hz, 1H), 7.71 (d, J=0.8 Hz, 1H), 7.77 (brs, 1H).

The physical properties of the title optically active substance with a retention time of 16 minutes (Example 556) are as follows.

$^1$H-NMR ($CDCl_3$) δ (ppm): 1.79-1.89 (m, 1H), 1.93-2.02 (m, 1H), 2.30 (s, 3H), 2.39-2.45 (m, 1H), 2.63-2.97 (m, 4H), 3.08-3.13 (m, 1H), 3.34-3.42 (m, 1H), 3.49 (d, J=13.2 Hz, 1H), 3.50-3.58 (m, 1H), 3.63 (d, J=13.2 Hz, 1H), 3.72 (brs, 1H), 3.85 (s, 3H), 4.18-4.24 (m, 1H), 4.55-4.61 (m, 1H), 6.92 (brs, 1H), 7.00 (brs, 1H), 7.01 (brd, J=8.0 Hz, 1H), 7.05-7.19 (m, 3H), 7.24 (d, J=8.0 Hz, 1H), 7.71 (d, J=0.8 Hz, 1H), 7.77 (brs, 1H).

The following compounds in Table 16 were synthesized as in Example 554, Example 555 and Example 556. The structural formulae and physicochemical properties are shown in Table 16, respectively.

TABLE 16

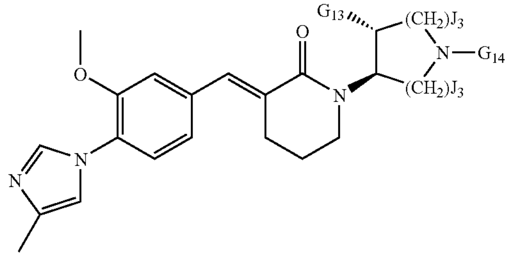

| Example | $J_2$ | $J_3$ | $G_{13}$ | $G_{14}$ | DATA: MS m/z |
|---|---|---|---|---|---|
| 557 | 1 | 1 | OH | 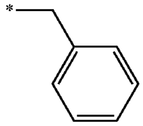 | $M^+$ + H: 473 (ESI) |
| 558 | 1 | 1 | OH | 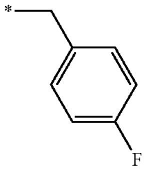 | $M^+$ + H: 491 (ESI) |
| 559 | 1 | 1 | OH | 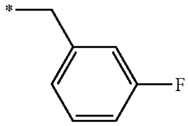 | $M^+$ + H: 491 (ESI) |
| 560 | 1 | 1 | OH | 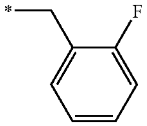 | $M^+$ + H: 491 (ESI) |
| 561 | 1 | 1 | OH | 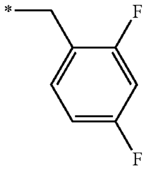 | $M^+$ + H: 509 (ESI) |
| 562 | 1 | 2 | H | 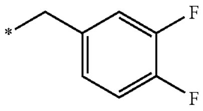 | $M^+$ + H: 507 (ESI) |

TABLE 16-continued

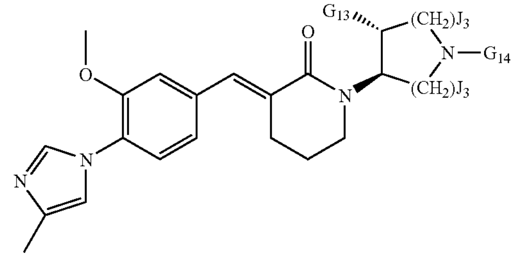

| Example | $J_2$ | $J_3$ | $G_{13}$ | $G_{14}$ | DATA: MS m/z |
|---|---|---|---|---|---|
| 563 | 1 | 2 | H | 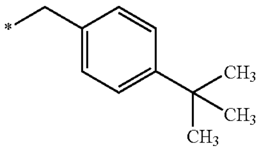 | $M^+$ + H: 527 (ESI) |
| 564 | 1 | 2 | H | 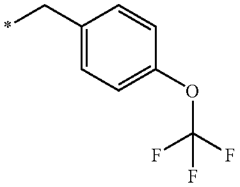 | $M^+$ + H: 555 (ESI) |
| 565 | 2 | 1 | H | 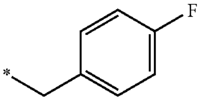 | $M^+$ + H: 489 (ESI) |
| 566 | 2 | 1 | H | 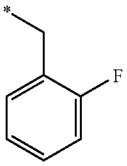 | $M^+$ + H: 489 (ESI) |
| 567 | 2 | 1 | H | 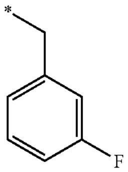 | $M^+$ + H: 489 (ESI) |
| 568 | 2 | 1 | H | 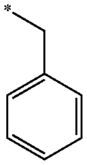 | $M^+$ + H: 471 (ESI) |
| 569 | 2 | 1 | H | 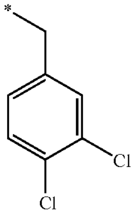 | $M^+$ + H: 539 (ESI) |

TABLE 16-continued

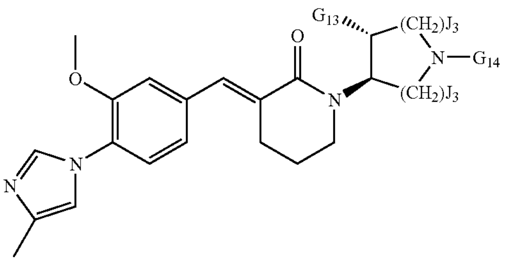

| Example | $J_2$ | $J_3$ | $G_{13}$ | $G_{14}$ | DATA: MS m/z |
|---|---|---|---|---|---|
| 570 | 2 | 1 | H | 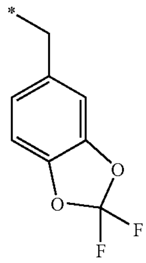 | $M^+ + H$: 551 (ESI) |
| 571 | 2 | 1 | H | 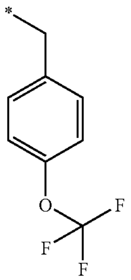 | $M^+ + H$: 555 (ESI) |
| 572 | 2 | 1 | H | 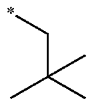 | $M^+ + H$: 451 (ESI) |
| 573 | 2 | 1 | H | 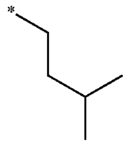 | $M^+ + H$: 451 (ESI) |
| 574 | 2 | 1 | H | 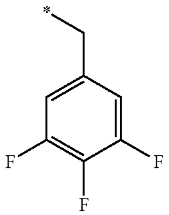 | $M^+ + H$: 525 (ESI) |
| 575 | 2 | 1 | H | 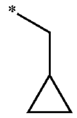 | $M^+ + H$: 435 (ESI) |

Example 576

Synthesis of (E)-cis-3-hydroxy-4-{3-(3-methoxy-4-(4-methyl-1H-imidazol-1-yl)benzylidene]-2-oxopiperidin-1-yl}pyrrolidine-1-carboxylic acid tert-butyl ester

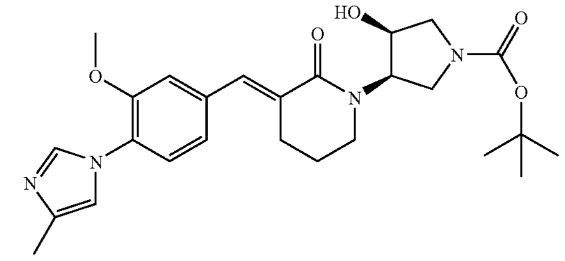

To a THF (5 mL) solution of (E)-trans-3-hydroxy-4-(3-(3-methoxy-4-(4-methyl-1H-imidazol-1-yl)benzylidene)-2-oxopiperidin-1-yl)pyrrolidine-1-carboxylic acid tert-butyl ester (30 mg) obtained in Example 554, diisopropylazodicarboxylate (0.024 mL), triphenylphosphine (33 mg) and acetic acid (0.007 mL) were added, and the reaction solution was agitated at room temperature for 3 hours. Ethyl acetate and a saturated sodium bicarbonate water were added to the reaction solution, and the organic layer was partitioned. After the obtained organic layer was washed with a saturated saline solution, it was dried over anhydrous magnesium sulfate and concentrated under reduced pressure. 10 mg of the title compound was obtained by purifying the residue by silica gel chromatography (Carrier: Chromatorex™ NH, elution solvent:ethyl acetate). The physical properties of the compound are as follows.

$^1H$-NMR ($CDCl_3$) δ (ppm): 1.49 (s, 9H), 1.91-1.99 (m, 2H), 2.31 (s, 3H), 2.75-2.90 (m, 2H), 3.20-3.84 (m, 6H), 3.86 (s, 3H), 4.61-4.71 (m, 1H), 4.73-4.80 (m, 1H), 6.93 (brs, 1H), 7.01 (brs, 1H), 7.03 (dd, J=10.0, 1.2 Hz, 1H), 7.25 (d, J=10.0 Hz, 1H), 7.72 (d, J=1.6 Hz, 1H), 7.80 (brs, 1H).

Example 577

Synthesis of (E)-1-benzoyl-3-[3-methoxy-4-(4-methyl-1H-imidazol-1-yl)benzylidene]-[1,4']bipiperidinyl-2-one trifluoroacetic acid salt

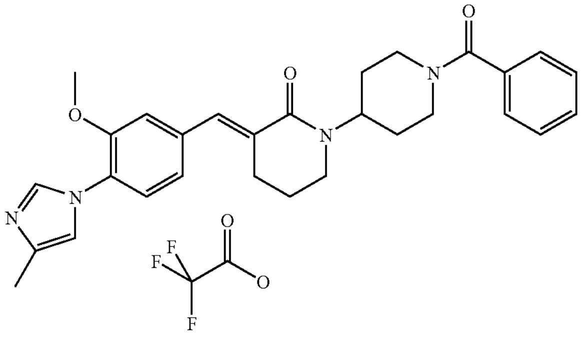

To methylene chloride (1 mL) solution of (E)-3-(3-methoxy-4-(4-methyl-1H-imidazol-1-yl)benzylidene)-2-oxo-[1,4']bipiperidinyl-1'-carboxylic acid tert-butyl ester (20 mg)

obtained in Example 716, trifluoroacetic acid (1 mL) was added, and the reaction solution was agitated at room temperature for 2 hours. The reaction solution was concentrated under reduced pressure and IPEA (0.022 mL) and benzoyl chloride (0.01 mL) were added to the methylene chloride (2 mL) solution of the residue. The reaction solution was agitated at room temperature for 12 hours, a saturated sodium bicarbonate water was added to the reaction solution, and the organic layer was partitioned. 9.4 mg of the title compound was obtained by condensing the obtained organic layer and purifying by LC-MS. The physical properties of the compound are as follows.

ESI-MS; m/z485 [$M^{+}$+H].

Example 578

Synthesis of (E)-1-trifluoroacetyl-3-[3-methoxy-4-(4-methyl-1H-imidazol-1-yl)benzylidene]-[1,4']bipiperidinyl-2-one trifluoroacetic acid salt

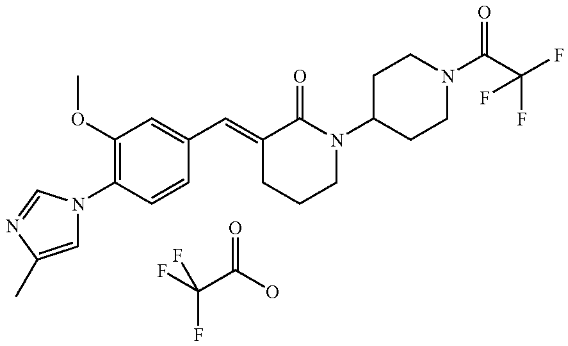

By the same method as in Example 577, 11 mg of the title compound was obtained from (E)-3-(3-methoxy-4-(4-methyl-1H-imidazol-1-yl)benzylidene)-2-oxo-[1,4']bipiperidinyl-1'-carboxylic acid tert-butyl ester (20 mg) and a trifluoroacetic acid anhydride (0.02 mL). The physical properties of the compound are as follows.

ESI-MS;m/z477 [$M^{+}$+H].

Example 579

Synthesis of (E)-3-[4-(4-ethyl-1H-imidazol-1-yl)-3-methoxybenzylidene]-1-(7-methoxy-1,2,3,4-tetrahydronaphthalen-1-yl)piperidin-2-one

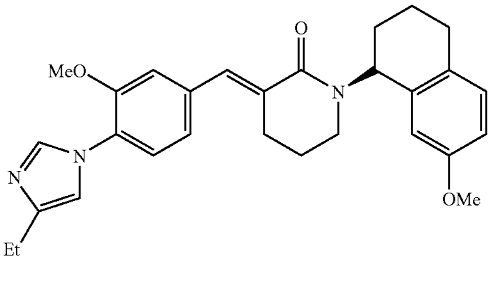

Synthesis of 4-(4-ethyl-1H-imidazol-1-yl)-3-methoxy benzaldehyde 7.3 g of the title compound was obtained via series of steps starting from 4-formylamino-3-methoxybenzoic acid methyl ester (24.8 g) in a similar method from 4-formylamino-3-methoxybenzoic acid methyl ester to 3-methoxy-4-(4-methyl-1H-imidazol-1-yl)benzaldehyde as in Example 1 except that chloroacetone was changed to 1-bromo-2-butanone.

$^{1}$H-NMR ($CDCl_3$) δ: 1.30 (t, J=7.6 Hz, 3H), 2.69 (q, J=7.6 Hz, 2H), 3.97 (s, 3H), 7.00 (q, J=1.2 Hz, 1H), 7.46 (d, J=7.6 Hz, 1H), 7.55 (dd, J=1.6 Hz, 7.6 Hz, 1H), 7.58 (d, J=1.6 Hz, 1H), 7.86 (d, J=1.6 Hz, 1H), 10.01 (s, 1H).

Synthesis of (E)-5-chloro-2-[4-(4-ethyl-1H-imidazol-1-yl)-3-methoxybenzylidene]valeric acid tert-butyl ester By the same method as in Example 418, 3.2 g of the title compound was obtained from 4-(4-ethyl-1H-imidazol-1-yl)-3-methoxybenzaldehyde (7.3 g) and 5-chloro-2-(diethoxyphosphoryl)valeric acid tert-butyl ester (12.5 g). The physical properties of the compound are as follows.

$^{1}$H-NMR ($CDCl_3$) δ (ppm): 1.29 (t, J=7.6 Hz, 3H), 1.60 (s, 9H), 2.00-2.07 (m, 2H), 2.65-2.71 (m, 4H), 3.60 (t, J=6.4 Hz, 2H), 3.88 (s, 3H), 6.94 (s, 1H), 7.01 (s, 1H), 7.03 (d, J=8 Hz, 1H), 7.28 (d, J=8 Hz, 1H), 7.60 (s, 1H), 7.76 (d, J=0.8 Hz, 1H).

Synthesis of (E)-5-chloro-2-[4-(4-ethyl-1H-imidazol-1-yl)-3-methoxybenzylidene]valeric acid trifluoroacetic acid salt By the same method as in Example 418 and following the synthesis method of (E)-5-chloro-2-(3-methoxy-4-(4-methyl-1H-imidazol-1-yl)benzylidene)valeric acid trifluoroacetic acid salt, 3.5 g of the title compound was obtained from (E)-5-chloro-2-(4-(4-ethyl-1H-imidazol-1-yl)-3-methoxybenzylidene)valeric acid tert-butyl ester (3.2 g). The physical properties of the compound are as follows.

$^{1}$H-NMR (DMSO-d6) δ (ppm): 1.25 (t, J=7.6 Hz, 3H), 1.94-2.01 (m, 2H), 2.60-2.64 (m, 2H), 2.71 (q, J=7.6 Hz, 2H), 3.70 (t, J=6 Hz, 2H), 3.91 (s, 3H), 7.24 (dd, J=8, 1.6 Hz, 1H), 7.37 (d, J=1.6 Hz, 1H), 7.64 (d, J=8 Hz, 1H), 7.69 (s, 1H), 7.75 (d, J=1.2 Hz, 1H), 9.27 (s, 1H).

Synthesis of (E)-3-[4-(4-ethyl-1H-imidazol-1-yl)-3-methoxybenzylidene]-1-(7-methoxy-1,2,3,4-tetrahydronaphthalen-1-yl)piperidin-2-one By the same method as in Example 418, 159 mg of the title compound was obtained from (E)-5-chloro-2-(4-(4-ethyl-1H-imidazol-1-yl)-3-methoxybenzylidene)valeric acid trifluoroacetic acid salt (200 mg) and (S)-7-methoxy-1,2,3,4-tetrahydronaphthalen-1-ylamine (144 mg). The physical properties of the compound are as follows.

$^{1}$H-NMR ($CDCl_3$) δ (ppm): 1.30 (t, J=7.0 Hz, 3H), 1.58-1.89 (m, 4H), 1.98-2.05 (m, 1H), 2.08-2.12 (m, 1H), 2.66-2.82 (m, 5H), 2.90-2.96 (m, 1H), 3.07-3.12 (m, 1H), 3.18-3.25 (m, 1H), 3.75 (s, 3H), 3.88 (s, 3H), 6.08-6.12 (m, 1H), 6.65 (s, 1H), 6.75 (d, J=4.4 Hz, 1H), 6.94 (s, 1H), 7.03-7.10 (m, 3H), 7.26-7.29 (m, 1H), 7.75 (s, 1H), 7.92 (s, 1H).

The following compounds in Table 17 were synthesized as in Example 579. The structural formulae and physicochemical properties are shown in Table 17, respectively.

TABLE 17
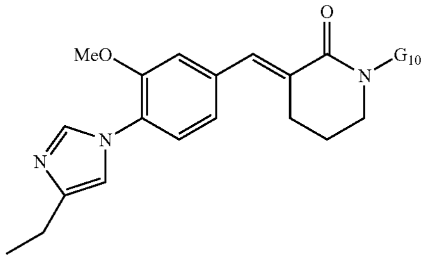
| Example | $G_{10}$ | DATA:MS m/z |
|---|---|---|
| 580 | 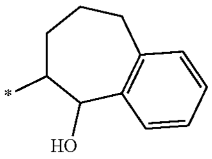 | $M^+ + H$:472 (ESI) |
| 581 | 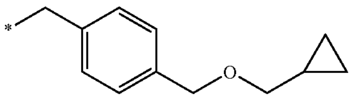 | $M^+ + H$:486 (ESI) |
| 582 | 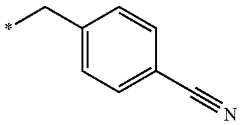 | $M^+ + H$:472 (ESI) |
| 583 | 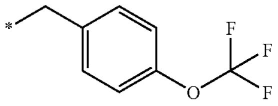 | $M^+ + H$:486 (ESI) |
| 584 | 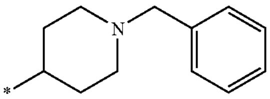 | $M^+ + H$:485 (ESI) |
| 585 | 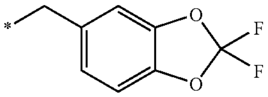 | $M^+ + H$:482 (ESI) |
| 586 | 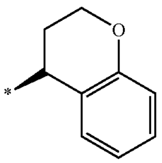 | $M^+ + H$:444 (ESI) |
| 587 | 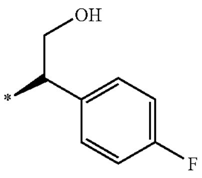 | $M^+ + H$:450 (ESI) |
| 588 | 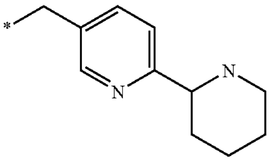 | $M^+ + H$:486 (ESI) |
TABLE 17-continued
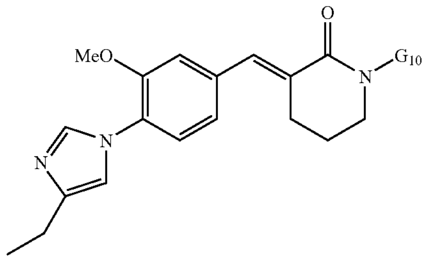
| Example | $G_{10}$ | DATA:MS m/z |
|---|---|---|
| 589 | 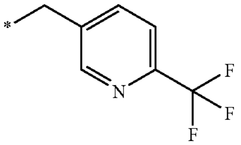 | $M^+ + H$:471 (ESI) |
| 590 | 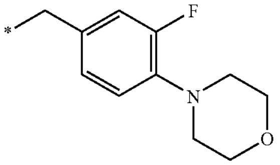 | $M^+ + H$:505 (ESI) |
| 591 | 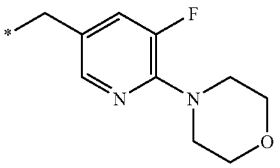 | $M^+ + H$:506 (ESI) |
| 592 | 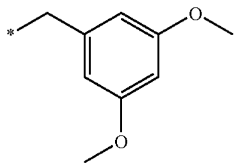 | $M^+ + H$:462 (ESI) |
| 593 | 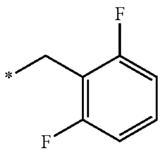 | $M^+ + H$:438 (ESI) |
| 594 | 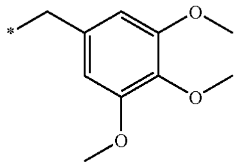 | $M^+ + H$:492 (ESI) |
| 595 | 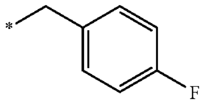 | $M^+ + H$:420 (ESI) |

Example 596

Synthesis of (E)-3-[4-(2-chloro-1H-imidazol-1-yl)-3-methoxybenzylidene]-1-(indan-2-yl)piperidin-2-one

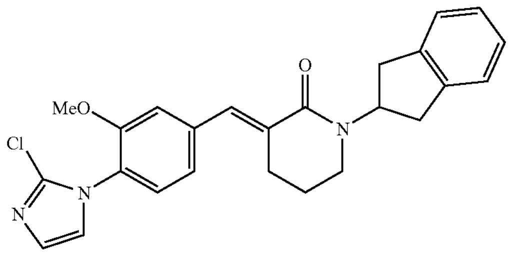

Synthesis of 1-(4-[1,3]dioxolan-2-yl-2-methoxyphenyl)-1H-imidazole

To a toluene (70 mL) solution of 4-(1H-imidazol-1-yl-3-methoxybenzaldehyde (4.3 g) and ethylene glycol (6.5 g), para-toluenesulfonic acid monohydrate (4.8 g) was added, Dean-Stark equipment was attached and heat-refluxing was carried out for 4 hours. After allowing cool the reaction mixture to room temperature, a saturated sodium bicarbonate water and ethyl acetate were added, and the organic layer was partitioned. The organic layer was washed with a saturated salt solution and concentrated under reduced pressure after dried over anhydrous magnesium sulfate. The residue was purified by silica gel column chromatography (elution solvent:hexane-ethyl acetate system), and 3.15 g of the title compound was obtained. The physical properties of the compound are as follows.

$^1$H-NMR ($CDCl_3$) δ (ppm): 3.88 (s, 3H), 4.06-4.18 (m, 4H), 5.85 (s, 1H), 7.15-7.17 (m, 2H), 7.19-7.20 (m, 2H), 7.29 (d, J=7.6 Hz, 1H), 7.78 (t, J=1 Hz, 1H).

Synthesis of 2-chloro-1-(4-[1,3]dioxolan-2-yl-2-methoxyphenyl)-1H-imidazole

To a THF (50 mL) solution of 1-(4-[1,3]dioxolan-2-yl-2-methoxyphenyl)-1H-imidazole (3.85 g), n-butyllithium (1.6M hexane solution, 12 mL) was added dropwise under nitrogen atmosphere at −78° C., and the reaction solution was agitated for 30 minutes. THF (10 mL) solution of hexachloroethane (6.1 g) was added to the reaction solution and the reaction solution was agitated at room temperature for 1 hour after agitating for 30 minutes at −78° C. Water and ethyl acetate were added to the reaction mixture, and the organic layer was partitioned. The organic layer was washed with a saturated saline solution, dried over anhydrous magnesium sulfate, and concentrated under reduced pressure. The residue was purified by silica gel column chromatography (elution solvent:hexane-ethyl acetate system), and 3.19 g of the title compound was obtained. The physical properties of the compound are as follows.

$^1$H-NMR ($CDCl_3$) δ (ppm): 3.84 (s, 3H), 4.07-4.19 (m, 4H), 5.85 (s, 1H), 6.98 (d, J=1.6 Hz, 1H), 7.06 (d, J=1.6 Hz, 1H), 7.17 (dd, J=1.6 Hz, 8.0 Hz, 1H), 7.19 (d, J=1.6 Hz, 1H), 7.27 (d, J=8 Hz, 1H).

Synthesis of 4-(2-chloro-1H-imidazol-1-yl)-3-methoxybenzaldehyde

To a THF (40 mL) solution of 2-chloro-1-(4-[1,3]dioxolan-2-yl -2-methoxyphenyl)-1H-imidazole (3.19 g), 5N hydrochloric acid (15 mL) was added and the reaction solution was agitated for 2 hours. The reaction mixture was made basic with 5N sodium hydroxide aqueous solution, ethyl acetate was added and the organic layer was partitioned. The organic layer obtained was washed with a saturated saline solution, dried with anhydrous magnesium sulfate and concentrated under reduced pressure to yield 2.69 g of the title compound. The physical properties of the compound are as follows.

$^1$H-NMR ($CDCl_3$) δ (ppm): 3.91 (s, 3H), 7.04 (d, J=1.6 Hz, 1H), 7.10 (d, J=1.6 Hz, 1H), 7.48 (d, J=8.0 Hz, 1H), 7.57-7.59 (m, 2H), 10.06 (s, 1H).

Synthesis of (E)-5-chloro-2-[4-(2-chloro-1H-imidazol-1-yl)-3-methoxybenzylidene]valeric acid tert-butyl ester 4.55 g of the title compound was obtained from 4-(2-chloro-1H-imidazol-1-yl)-3-methoxy benzaldehyde (3.19 g) and 5-chloro-2-(diethoxyphosphoryl)valeric acid tert-butyl ester (5.32 g) in a similar way as in the synthesis of (E)-5-chloro-2-[3-methoxy-4-(4-methyl-1H-imidazol-1-yl)benzylidene]valeric acid tert-butyl ester in Example 418. The physical properties of the compound are as follows.

$^1$H-NMR ($CDCl_3$) δ (ppm): 1.60 (s, 9H), 2.00-2.07 (m, 2H), 2.67-2.71 (m, 2H), 3.60 (t, J=6.4 Hz, 2H), 3.84 (s, 3H), 6.70-7.08 (m, 4H), 7.26-7.29 (m, 1H), 7.27 (s, 1H).

Synthesis of (E)-5-chloro-2-[4-(2-chloro-1H-imidazol-1-yl)-3-methoxybenzylidene]valeric acid A trifluoroacetic acid (15 mL) solution of 5-chloro-2-(4-(2-chloro-1H-imidazol-1-yl)-3-methoxybenzylidene)valeric acid tert-butyl ester (1.35 g) was agitated under ice-cooling. The reaction solution was concentrated under reduced pressure after 2 hours. When the residue was purified in LC-MS, 0.99 g of the title compound was obtained. The physical properties of the compound are as follows.

$^1$H-NMR (DMSO-$d_6$) δ (ppm): 1.96-2.00 (m, 2H), 2.60-2.64 (m, 2H), 3.70 (t, J=6.4 Hz, 2H), 3.83 (s, 3H), 7.04 (s, 1H), 7.17 (d, J=8.0 Hz, 1H), 7.28 (s, 1H), 7.40 (s, 1H), 7.43 (d, J=8.0 Hz, 1H), 7.68 (s, 1H).

Synthesis of (E)-5-chloro-2-[4-(2-chloro-1H-imidazol-1-yl)-3-methoxybenzylidene]valeric acid indan-2-ylamide By the same method as in Example 418, 11 mg of the title compound was obtained from (E)-5-chloro-2-(4-(2-chloro-1H-imidazol-1-yl)-3-methoxybenzylidene)valeric acid (50 mg) and 2-aminoindan hydrochloride salt (36 mg). The physical properties of the compound are as follows.

$^1$H-NMR ($CDCl_3$) δ: 1.83-1.87 (m, 2H), 2.79-2.83 (m, 2H), 2.98-3.04 (m, 2H), 3.25-3.32 (m, 4H), 3.82 (s, 3H), 5.76-5.81 (m, 1H), 7.01-7.02 (m, 2H), 7.04-7.07 (m, 2H), 7.16-7.26 (m, 5H), 7.87 (s, 1H).

The compounds shown in Table 18 were synthesized as in Example 596. The structural formulae and physicochemical properties are shown in Table 18, respectively.

TABLE 18

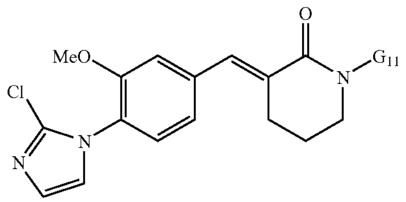

| Example | $G_{11}$ | DATA:MS m/z | Note |
|---|---|---|---|
| 597 | 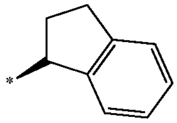 | $M^+$ + Na:456(ESI) | optically active substance |
| 598 | 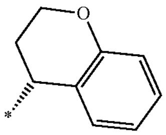 | $M^+$ + H:450(ESI) | optically active substance (separation condition A: retention time: 22 minutes; absolute configuration: unknown) |
| 599 | 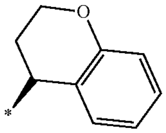 | $M^+$ + H:450(ESI) | optically active substance (separation condition A: retention time: 22 minutes; absolute configuration: unknown) |
| 600 | 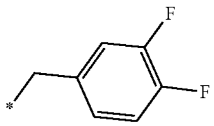 | $M^+$ + H:450(ESI) | |
| 601 | 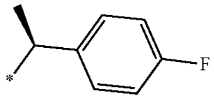 | $M^+$ + H:440(ESI) | optically active substance |
| 602 | 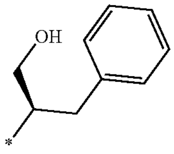 | $M^+$ + H:452(ESI) | optically active substance |
| 603 | 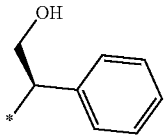 | $M^+$ + H:438(ESI) | optically active substance |
| 604 | 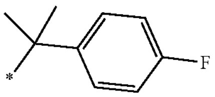 | $M^+$ + H:454(ESI) | |
| 605 | 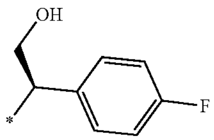 | $M^+$ + Na:478(ESI) | optically active substance |

TABLE 18-continued

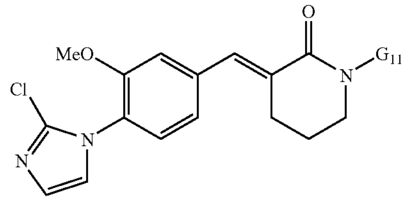

| Example | $G_{11}$ | DATA:MS m/z | Note |
| --- | --- | --- | --- |
| 606 | 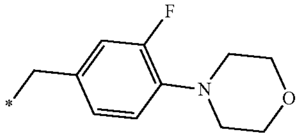 | $M^+$ + H:511(ESI) | |
| 607 | 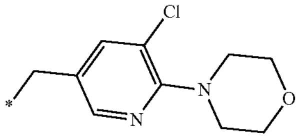 | $M^+$ + H:528(ESI) | |
| 608 | 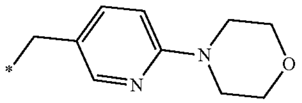 | $M^+$ + H:494(ESI) | |
| 609 | 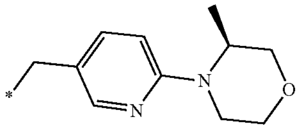 | $M^+$ + H:508(ESI) | optically active substance |
| 610 | 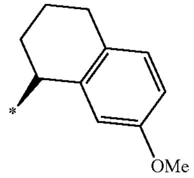 | $M^+$ + H:478(ESI) | optically active substance |

Example 611

Synthesis of (E)-1-(3,4-difluorobenzyl)-3-{[5-methoxy-6-(4-methyl-1H-imidazol-1-yl)pyridin-3-yl]methylene}piperidin-2-one

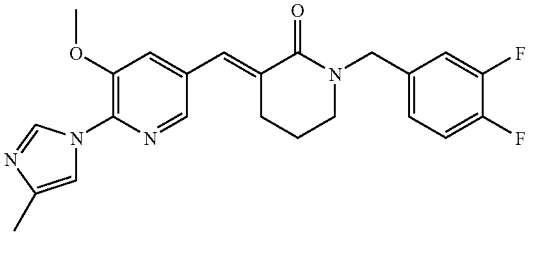

Synthesis of 5-methoxy-6-(4-methyl-1H-imidazol-1-yl)pyridin-3-carbaldehyde

Ozone was boubled into a methanol (5 mL) solution of (E)-3-(6-chloro-5-methoxypyridin-3-yl)acrylic acid ethyl ester (123 mg) synthesized by the method of Example 22 under agitation at −78° C. After 10 minutes, introduction of ozone was stopped, dimethylsulfide (1 mL) was added to the reaction solution and the reaction mixture was allowed to be warmed to room temperature for 1 hour and 30 minutes under agitation. The reaction solution was concentrated under reduced pressure and 4-methylimidazole(125 mg) was added to a DMF (1 mL) solution of the residue. The reaction solution was agitated at 120° C. for 3 hours. After the reaction solution was allowed to be cooled to room temperature, ethyl acetate and saturated sodium bicarbonate water were added to the reaction solution, and the organic layer was partitioned. After the obtained organic layer was washed with a saturated sodium bicarbonate water, it was dried over anhydrous magnesium sulfate and concentrated under reduced pressure. 50 mg of the title compound was obtained by purifying the residue by silica gel chromatography (elution solvent heptane:ethyl acetate=9:1 to ethyl acetate). The physical properties of the compound are as follows.

$^1$H-NMR ($CDCl_3$) δ (ppm): 2.31 (s, 3H), 4.05 (s, 3H), 7.65 (s, 1H), 7.78 (s, 1H), 8.52 (s, 2H), 10.07 (s, 1H).

Synthesis of (E)-5-chloro-2-[5-methoxy-6-(4-methyl-1H-imidazol-1-yl)pyridin-3-ylmethylene]valeric acid tert-butyl ester By the same method as in Example 418, 35 mg of the title compound was obtained from 5-methoxy-6-(4-methyl-1H-imidazol-1-yl)pyridine-3-carbaldehyde (50 mg) and 5-chloro-2-(diethoxyphosphoryl)valeric acid tert-butyl ester (83 mg). The physical properties of the compound are as follows.

$^1$H-NMR ($CDCl_3$) δ (ppm): 1.56 (s, 9H), 1.78-1.90 (m, 2H), 2.30 (s, 3H), 2.66-2.73 (m, 2H), 3.58-3.64 (m, 2H), 3.98 (s, 3H), 7.35 (s, 1H), 7.54 (s, 2H), 8.06 (s, 1H), 8.37 (S, 1H).

Synthesis of (E)-1-(3,4-difluorobenzyl)-3-[5-methoxy-6-(4-methyl-1H-imidazol-1-yl)pyridin-3-ylmethylene]piperidin-2-one By the same method as in Example 418, 15 mg of the title compound was obtained from (E)-5-chloro-2-[5-methoxy-6-(4-methyl-1H-imidazol-1-yl)pyridin-3-ylmethylene]valeric acid tert-butyl ester (35 mg) and 3,4-difluorobenzylamine (0.02 mL). The physical properties of the compound are as follows.

$^1$H-NMR ($CDCl_3$) δ (ppm): 1.76-1.83 (m, 2H), 2.30 (s, 3H), 2.81-2.87 (m, 2H), 3.36-3.41 (m, 2H), 3.97 (s, 3H), 4.66 (s, 2H), 7.02-7.18 (m, 3H), 7.31 (d, J=1.2 Hz, 1H), 7.54 (brs, 1H), 7.82 (brs, 1H), 8.09 (d, J=1.2 Hz, 1H), 8.36 (d, J=1.2 Hz, 1H).

The compounds shown in Table 19 were synthesized as in Example 611. The structural formulae and physicochemical properties are shown in Table 19, respectively.

TABLE 19

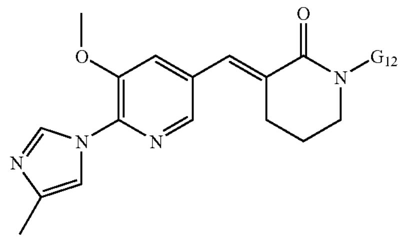

| Example | $G_{12}$ | DATA: MS m/z | Note |
|---|---|---|---|
| 612 | 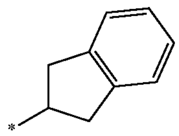 | $M^+$ + 415 (ESI) | |
| 613 | 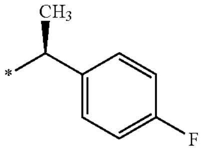 | $M^+$ + 421 (ESI) | optically active substance |
| 614 | 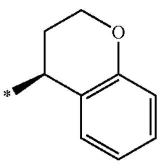 | $M^+$ + 431 (ESI) | optically active substance |

TABLE 19-continued

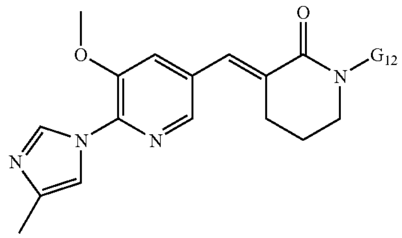

| Example | $G_{12}$ | DATA: MS m/z | Note |
|---|---|---|---|
| 615 | 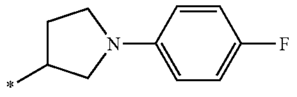 | $M^+$ + 462 (ESI) | racemate |

Example 616 and Example 617

Synthesis of (E)-3-[3-methoxy-4-(4-methyl-1H-imidazol-1-yl)benzylidene]-one-[(R)and(S)-(5-morpholin-4-yl-indan-1-yl))piperidin-2-one

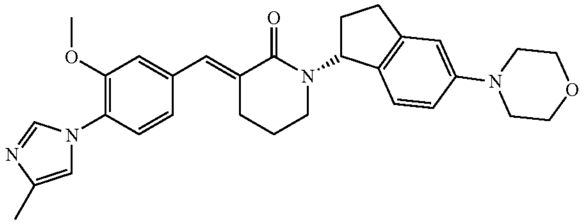

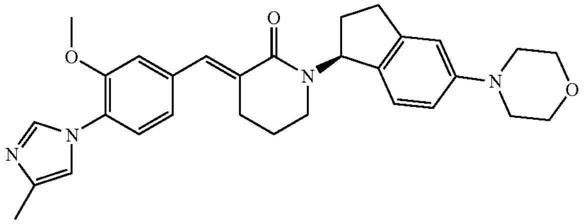

Synthesis of 5-morpholin-4-yl-indan-1-one

A 1-methyl-2-pyrrolidone (10 mL) solution of 5-fluoroindanone (1.97 g) and morpholine (1.71 g) was agitated at 100° C. for 26 hours and 30 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:heptane-ethyl acetate system), and 2.20 g of the title compound was obtained. The physical properties of the compound are as follows.

$^1$H-NMR ($CDCl_3$) δ (ppm): 2.64-2.67 (m, 2H), 3.03-3.07 (m, 2H), 3.34 (t, J=4.8 Hz, 4H), 3.86 (t, J=4.8 Hz, 4H), 6.82 (s, 1H), 6.88 (dd, J=2.0, 8.8 Hz, 1H), 7.65 (d, J=8.8 Hz, 1H).

Synthesis of 5-morpholin-4-yl-indan-1-on-oxime

An ethanol (5.0 mL) solution of 5-morpholin-4-yl-indan-1-one(2.20 g), hydroxyl ammonium chloride (1.05 g) and the triethylamine (4.22 mL) was refluxed for 3 hours. Water and ethyl acetate were added to the reaction solution, and the organic layer was partitioned. The obtained organic layer was washed with a saturated sodium chloride solution, and 2.28 g of the title compound was obtained by condensing under reduce pressure after drying over anhydrous magnesium sulfate. The physical properties of the compound are as follows.

$^1$H-NMR ($CDCl_3$) δ (ppm): 2.92-2.96 (m, 2H), 2.98-3.04 (m, 2H), 3.20-3.26 (m, 4H), 3.85 (t, J=4.8 Hz, 4H), 6.78-6.85 (m, 2H), 7.53 (d, J=8.8 Hz, 1H).

Synthesis of 5-morpholin-4-yl-indan-1-ylamine

An ethanol (20 mL) suspension of 5-morpholin-4-yl-indan-1-on-oxime (2.76 g) and 10% palladium carbon (48% water content, 1.0 g) was agitated at room temperature under 0.4 MPa hydrogen atmosphere for 6 hours. After filtering the reaction solution and condensing the filtrate under reduced pressure, 1.64 g of the title compound was obtained by purifying the obtained residue by silica gel chromatography (Carrier: Chromatorex™ NH, elution solvent:heptane-ethyl acetate system→ethyl acetate-methanol system). The physical properties of the compound are as follows.

$^1$H-NMR ($CDCl_3$) δ (ppm): 1.65-1.70 (m, 1H), 2.47-2.53 (m, 1H), 2.78 (td, J=8.4, 16 Hz, 1H), 2.92 (ddd, J=3.6, 8.8, 16 Hz, 1H), 3.13 (t, J=4.8 Hz, 4H), 3.85 (t, J=4.8 Hz, 4H), 4.31 (t, J=7.2 Hz, 1H), 6.79-6.81 (m, 2H), 7.21 (d, J=8.8 Hz, 1H).

Synthesis of (E)-5-chloro-2-[3-methoxy-4-(4-methyl-1H-imidazol-1-yl)benzylidene]valeric acid (5-morpholin-4-yl-indan-1-yl)amide To a DMF (5.0 mL) solution of (E)-5-chloro-2-(3-methoxy-4-(4-methyl-1H-imidazol-1-yl)benzylidene)valeric acid trifluoroacetic acid salt (3.0 g) obtained in Example 418 and 5-morpholin-4-yl-indan-1-ylamine (1.80 g), IPEA (5.18 mg), EDC (3.84 g) and HOBT (2.71 g) were added one by one, and the reaction solution was agitated at room temperature for 1 hour. After confirming disappearance of the starting materials, the solvent was concentrated under reduced pressure, water and ethyl acetate were added to the residue, and the organic layer was partitioned. After washed with a saturated saline solution the organic layer, it was dried over anhydrous magnesium sulfate and concentrated under reduced pressure. 2.80 g of the title compound was obtained by purifying the obtained residue by silica gel chromatography (elution solvent:heptane-ethyl acetate system). The physical properties of the compound are as follows.

$^1$H-NMR ($CDCl_3$) δ (ppm): 1.88-1.97 (m, 1H), 2.00-2.08 (m, 2H), 2.30 (s, 3H), 2.63-2.72 (m, 1H), 2.74 (t, J=7.2 Hz, 2H), 2.82-2.94 (m, 1H), 2.87-3.05 (m, 1H), 3.10-3.18 (m, 4H), 3.59 (t, J=6.0 Hz, 2H), 3.82-3.84 (m, 4H), 3.85 (s, 3H), 5.52 (q, J=7.6 Hz, 1H), 6.10 (d, J=7.6 Hz, 1H), 6.80-6.83 (m, 2H), 6.92-6.96 (m, 3H), 7.14 (s, 1H), 7.23-7.25 (m, 2H), 7.70 (s, 1H).

Synthesis of (E)-3-[3-methoxy-4-(4-methyl-1H-imidazol-1-yl)benzylidene]-1-[(R) and (S)-(5-morpholin-4-yl-indan-1-yl)]-piperidin-2-one To a DMF (5.0 mL) solution of ((E)-5-chloro-2-(3-methoxy-4-(4-methyl-1H-imidazol-1-yl)benzylidene)valeric acid (5-morpholin-4-yl-indan-1-yl)amide (2.80 g), sodium hydride (40% mineral oil content, 267 mg) was added at 0° C., and the reaction solution was agitated for 15 minutes. Water and ethyl acetate were added to the reaction solution after confirming disappearance of the starting materials, and the organic layer was partitioned. After the organic layer was washed with a saturated saline solution, it was dried over anhydrous magnesium sulfate and concentrated under reduced pressure. By purifying the obtained residue by silica gel chromatography (elution solvent:a heptane-ethyl acetate system, ethyl acetate-ethanol system), 2.12 g of (E)-3-(3-methoxy-4-(4-methyl-1H-imidazol-1-yl)benzylidene)-1-(5-morpholin-4-yl-indan-1-yl)piperidin-2-one racemate was obtained. Next, this compound (140 mg) was separated in CHRIALPAK™ AD-H available from Daicel Chemical Industries, Ltd. (2 cm×25 cm mobile phase; ethanol), and the title optically active substance with a retention time of 14 minutes (64 mg; >99% ee) and the title optically active substance with a retention time of 16 minutes (58 mg; >97% ee) were obtained. The physical properties of the title optically active substance with a retention time of 14 minutes are as follows.

$^1$H-NMR ($CDCl_3$) δ (ppm): 1.72-1.86 (m, 2H), 1.90-2.00 (m, 1H), 2.30 (s, 3H), 2.44-2.56 (m, 1H), 2.78-2.86 (m, 2H), 2.86-3.00 (m, 2H), 3.02-3.14 (m, 2H), 3.14-3.17 (m, 4H), 3.85-3.86 (m, 4H), 3.86 (s, 3H), 6.41 (t, J=6.8 Hz, 1H), 6.78-6.80 (m, 2H), 6.93 (s, 1H), 7.04-7.08 (m, 3H), 7.24-7.25 (m, 1H), 7.71 (s, 1H), 7.88 (s, 1H).

The physical properties of the title optically active substance with a retention time of 16 minutes are as follows.

$^1$H-NMR ($CDCl_3$) δ (ppm): 1.72-1.86 (m, 2H), 1.90-2.00 (m, 1H), 2.30 (s, 3H), 2.44-2.56 (m, 1H), 2.78-2.86 (m, 2H), 2.86-3.00 (m, 2H), 3.02-3.14 (m, 2H), 3.14-3.17 (m, 4H), 3.85-3.86 (m, 4H), 3.86 (s, 3H), 6.41 (t, J=6.8 Hz, 1H), 6.78-6.80 (m, 2H), 6.93 (s, 1H), 7.04-7.08 (m, 3H), 7.24-7.25 (m, 1H), 7.71 (s, 1H), 7.88 (s, 1H).

Example 618 and Example 619

Synthesis of (E)-1-[(R) and (S)-1-(4-fluoro -2-morpholin-4-ylphenyl)ethyl]-3-[3-methoxy-4-(4-methyl-1H-imidazol-1-yl)benzylidene]piperidin-2-one

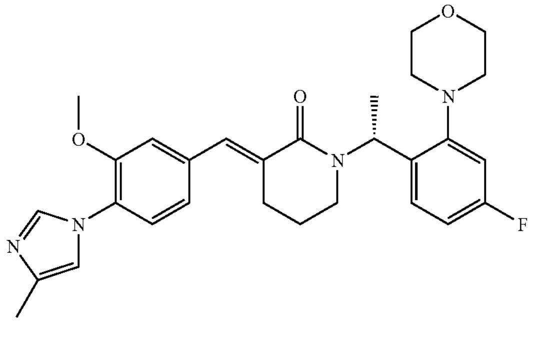

-continued

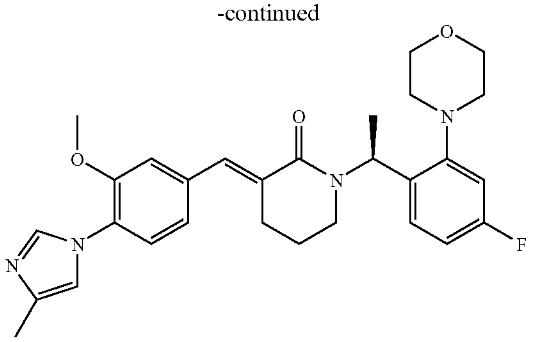

Synthesis of 1-(4-fluoro-2-morpholin-4-ylphenyl)-ethanone

A DMF (5.0 mL) solution of 2,4-difluoroacetophenone (1.0 g) and morpholine (558 mg) was agitated at 110° C. for 6 hours and 30 minutes. Water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent: heptane-ethyl acetate system), and 642 mg of the title compound was obtained. The physical properties of the compound are as follows.

$^1$H-NMR ($CDCl_3$) δ (ppm): 2.64 (s, 3H), 2.98-3.00 (m, 4H), 3.84-3.87 (m, 4H), 6.71-6.77 (m, 2H), 7.44-7.48 (m, 1H).

Synthesis of 1-(4-fluoro-2-morpholin-4-ylphenyl)ethane oxime

An ethanol (5.0 mL) solution of 1-(4-fluoro-2-morpholin-4-ylphenyl)ehanone (630 mg), hydroxylammonium chloride (294 mg) and the triethylamine (1.18 mL) was refluxed for 5 hours. Water was added to the reaction solution and precipitation generated was filtered and air-dried to yield 642 mg of the title compound. The physical properties of the compound are as follows.

$^1$H-NMR ($CDCl_3$) δ (ppm): 2.24 (s, 0.75H), 2.27 (s, 2.25H), 2.96-2.99 (t, J=4.8 Hz, 4H), 3.81 (t, J=4.8 Hz, 4H), 6.70-6.79 (m, 2H), 7.14 (t, J=6.8 Hz, 0.25H), 7.22 (t, J=6.8 Hz, 0.75H), 7.97 (brs, 0.25H), 8.24 (brs, 0.75H).

Synthesis of 1-(4-fluoro-2-morpholin-4-ylphenyl)ethylamine

An ethanol (5.0 mL) suspension of 1-(4-fluoro-2-morpholin-4-ylphenyl)ethane oxime (548 mg) and 10% palladium carbon (48% water content, 548 mg) was agitated for 32 hours and 30 minutes at room temperature under 0.4 MPa hydrogen atmosphere. After filtering the reaction solution and condensing the filtrate under reduced pressure, 155 mg of the title compound was obtained by purifying the obtained residue by silica gel chromatography (Carrier: Chromatorex™]NH, elution solvent:heptane-ethyl acetate system→ethyl acetate-methanol system). The physical properties of the compound are as follows.

$^1$H-NMR ($CDCl_3$) δ (ppm): 1.38 (d, J=6.4 Hz, 3H), 1.68 (brs, 2H), 2.88 (t, J=4.4 Hz, 4H), 3.85 (t, J=4.4 Hz, 4H), 4.54 (q, J=6.4 Hz, 1H), 6.81-6.85 (m, 2H), 7.35-7.39 (m, 1H).

Synthesis of (E)-5-chloro-2-[3-methoxy-4-(4-methyl-1H-imidazol-1-yl)benzylidene]valeric acid [1-(4-fluoro-2-morpholin-4-ylphenyl]ethyl)amide To a DMF (3.0 mL) solution (E)-5-chloro-2-(3-methoxy-4-(4-methyl-1H-imidazol-1-yl)benzylidene)valeric acid trifluoroacetic acid salt (280 mg) obtained in the Example 418 and 1-(4-fluoro-2-morpholin-4-ylphenyl)ethylamine (155 mg), IPEA (484 mg) and EDC (359 mg) and HOBT (253 mg) were added one by one, and the reaction solution was agitated at room temperature for 1 hour and 20 minutes. After confirming disappearance of the starting materials, the solvent was concentrated under reduced pressure, water and ethyl acetate were added to the residue, and the organic layer was partitioned. After the organic layer was washed with a saturated saline solution, it was dried over anhydrous magnesium sulfate and concentrated under reduced pressure. The obtained residue was purified by silica gel chromatography (elution solvent: from heptane:ethyl acetate system to ethyl acetate-methanol system), and 270 mg of the title compound was obtained. The physical properties of the compound are as follows.

$^1$H-NMR ($CDCl_3$) δ (ppm): 1.49 (d, J=6.8 Hz, 3H), 1.95-2.01 (m, 2H), 2.29 (s, 3H), 2.70-2.74 (m, 2H), 2.78-2.82 (m, 2H), 3.13-3.17 (m, 2H), 3.58 (t, J=6.0 Hz, 2H), 3.85 (s, 3H), 3.82-3.93 (m, 4H), 5.53-5.60 (m, 1H), 6.68-6.74 (m, 1H), 6.83-6.95 (m, 4H), 7.15 (s, 1H), 7.23-7.30 (m, 3H), 7.70 (s, 1H).

Synthesis of (E)-1-[(R) and (S)-1-(4-fluoro-2-morpholin-4-ylphenyl)ethyl]-3-[3-methoxy-4-(4-methyl-1H-imidazol-1-yl)benzylidene]piperidin-2-one To a DMF (3.0 mL) solution of (E)-5-chloro-2-(3-methoxy-4-(4-methyl-1H-imidazol-1-yl)benzylidene)valeric acid (1-(4-fluoro -2-morpholin-4-ylphenyl)-ethyl)amide (270 mg), sodium hydride (40% mineral oil content, 50 mg) was added at 0° C., the reaction solution was allowed to be warmed to room temperature and agitated for 5 hours and 20 minutes. The reaction solution was cooled to 0° C. after confirming disappearance of the starting materials, water and ethyl acetate were added to the reaction solution, and the organic layer was partitioned. After the obtained organic layer was washed with a saturated saline solution, it was dried over anhydrous magnesium sulfate and concentrated under reduced pressure. The residue was purified by silica gel chromatography (elution solvent:heptane-ethyl acetate system→ethyl acetate-methanol system) 223 mg of (E)-1-(1-(4-fluoro-2-morpholin-4-ylphenyl)ethyl)-3-(3-methoxy-4-(4-methyl-1H-imidazol-1-yl)benzylidene)piperidin-2-one racemate was obtained. Next, this compound (150 mg) was separated in CHIRALPAK™ AD-H available from Daicel Chemical Industries, Ltd. (2 cm×25 cm: mobile phase; ethanol), and the title optically active substance with a retention time of 6 minutes (63.6 mg; >99% ee) and the title optically active substance with a retention time of 7 minutes (54.0 mg; >98% ee) were obtained. The physical properties of the title optically active substance with a retention time of 6 minutes is as follows.

$^1$H-NMR ($CDCl_3$) δ (ppm): 1.52 (d, J=7.2 Hz, 3H), 1.74-1.82 (m, 2H), 2.30 (s, 3H), 2.59-2.72 (m, 1H), 2.79-2.94 (m, 6H), 3.21 (td, J=5.6, 12 Hz, 1H), 3.77-3.88 (m, 4H), 3.86 (s, 3H), 6.27 (q, J=7.2 Hz, 1H), 6.83-6.93 (m, 3H), 7.01-7.03 (m, 2H), 7.22-7.25 (m, 1H), 7.31 (t, J=7.6 Hz, 1H), 7.70 (s, 1H), 7.84 (s, 1H).

The physical properties of the title optically active substance with a retention time of 7 minutes is as follows.

$^1$H-NMR ($CDCl_3$) δ (ppm): 1.52 (d, J=7.2 Hz, 3H), 1.74-1.82 (m, 2H), 2.30 (s, 3H), 2.59-2.72 (m, 1H), 2.79-2.94 (m, 6H), 3.21 (td, J=5.6, 12 Hz, 1H), 3.77-3.88 (m, 4H), 3.86 (s, 3H), 6.27 (q, J=7.2 Hz, 1H), 6.83-6.93 (m, 3H), 7.01-7.03 (m, 2H), 7.22-7.25 (m, 1H), 7.31 (t, J=7.6 Hz, 1H), 7.70 (s, 1H), 7.84 (s, 1H).

Example 620 and Example 621

Synthesis of (E)-1-[(1R) and (1S)-1-(2,4-difluorophenyl)ethyl]-3-[3-methoxy-4-(4-methyl-1H-imidazol-1-yl)benzylidene]piperidin-2-one

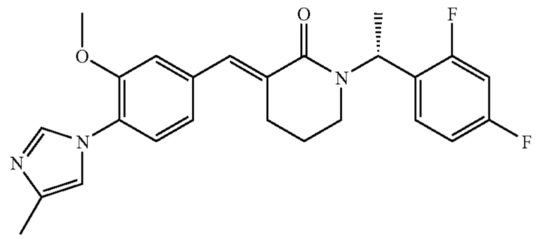

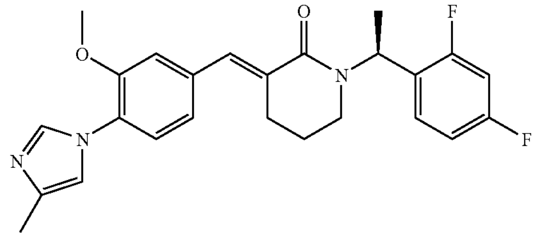

To a DMF (5 mL) solution of (E)-5-chloro-2-(3-methoxy-4-(4-methyl-1H-imidazol-1-yl)benzylidene)valeric acid trifluoroacetic acid salt (250 mg) obtained in Example 418 and 1-(2,4-difluorophenyl)ethylamine (CAS#603951-43-5,141 mg), IPEA (0.5 mL), EDC (430 mg) and HOBT (303 mg) were added one by one, and the reaction solution was agitated at room temperature for 1 hour. Water and ethyl acetate were added to the reaction solution, and the organic layer was partitioned. The obtained organic layer was dried with anhydrous magnesium sulfate, the solvent was evaporated under reduced pressure, and the residue was purified by silica gel column chromatography (elution solvent:heptane-ethyl acetate system). (E)-5-chloro-2-[3-methoxy-4-(4-methyl-1H-imidazol-1-yl)benzylidene]valeric acid [1-(2,4-difluorophenyl)ethyl]amide was obtained. Sodium hydride (40% mineral oil content, 20 mg) was added to a DMF (5 mL) solution of this compound, and that reaction solution was agitated at room temperature for 5 minutes. Water and ethyl acetate were added to the reaction solution, and the organic layer was partitioned. The obtained organic layer was dried with anhydrous magnesium sulfate, the solvent was evaporated under reduced pressure, and the residue was purified by silica gel chromatography (elution solvent:heptane-ethyl acetate system) 151 mg of (E)-1-(1-(2,4-difluorophenyl) ethyl)-3-(3-methoxy-4-(methyl-1H-imidazol-1-yl)benzylidene)piperidin-2-one racemate was obtained. This compound (25 mg) was separated in CHIRALPAK™ AD-H available from Daicel Chemical Industries, Ltd. (2 cm×25 cm: mobile phase; hexane:ethanol=7:3), and the title optically active substance with a retention time of 25 minutes (11.8 mg; >99% ee) and the title optically active substance with a retention time of 45 minutes (11.2 mg; >99% ee) were obtained. The physical properties of the title optically active compound with a retention time of 25 minutes are as follows.

Example 620

$^1$H-NMR ($CDCl_3$) δ (ppm): 1.59 (d, J=7.2 Hz, 3H), 1.77-1.84 (m, 2H), 2.30 (s, 3H), 2.71-2.83 (m, 2H), 2.99-3.05 (m, 1H), 3.27-3.33 (m, 1H), 3.85 (s, 3H), 6.18 (q, J=7.2 Hz, 1H), 6.79-6.85 (m, 1H), 6.86-6.92 (m, 1H), 6.93 (t, J=1.6 Hz, 1H), 7.02 (s, 1H), 7.02 (d, J=8.0 Hz, 1H), 7.24 (d, J=8.0 Hz, 1H), 7.33-7.39 (m, 1H), 7.71 (d, J=1.2 Hz, 1H), 7.86 (s, 1H).

The physical properties of the title optically active compound with a retention time of 45 minutes are as follows.

Example 621

$^1$H-NMR ($CDCl_3$) δ (ppm): 1.59 (d, J=7.2 Hz, 3H), 1.77-1.84 (m, 2H), 2.30 (s, 3H), 2.71-2.83 (m, 2H), 2.99-3.05 (m, 1H), 3.27-3.33 (m, 1H), 3.85 (s, 3H), 6.18 (q, J=7.2 Hz, 1H), 6.79-6.85 (m, 1H), 6.86-6.92 (m, 1H), 6.93 (t, J=1.6 Hz, 1H), 7.02 (s, 1H), 7.02 (d, J=8.0 Hz, 1H), 7.24 (d, J=8.0 Hz, 1H), 7.33-7.39 (m, 1H), 7.71 (d, J=1.2 Hz, 1H), 7.86 (s, 1H).

Example 622

Synthesis of (E)-1-[1-(4-fluorophenyl)-trans-4-hydroxypyrrolidin-3-yl]-3-[3-methoxy-4-(4-methyl-1H-imidazol-1-yl)benzylidene]piperidin-2-one

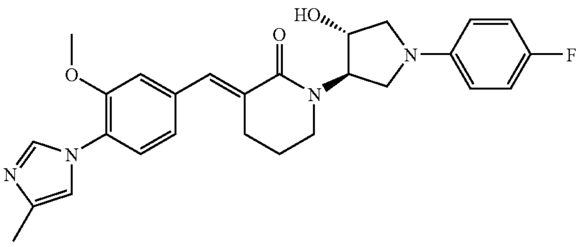

Synthesis of 3-(4-fluorophenyl)-6-oxa-3-azabicyclo[3.1.0]hexane

To a methanol (5 mL) solution of 1-(4-fluorophenyl)-2,5-dihydro-1H-pyrrole (300 mg) synthesized according to the method described in The Journal of Organic Chemistry vol. 25, p. 2230, 1960, acetonitrile (0.8 mL), potassium hydrogen carbonate (221 mg) and 20% hydrogen peroxide (0.8 mL) were added one by one, and the reaction solution was agitated at room temperature for 10 hours. Ethyl acetate and saturated sodium thiosulfate solution were added to the reaction solution, and the organic layer was partitioned. After the obtained organic layer was washed with a saturated sodium bicarbonate water, it was dried over anhydrous magnesium sulfate and concentrated under reduced pressure. 75 mg of the title compound was obtained by purifying the residue by silica gel chromatography (heptane:elution solvent;ethyl acetate=3:1). The physical properties of the compound are as follows.

$^1$H-NMR ($CDCl_3$) δ (ppm): 3.25 (d, J=8.1 Hz, 2H), 3.69 (d, J=8.1 Hz, 2H), 3.87 (brs, 2H), 6.37-6.43 (m, 2H), 6.88-6.96 (m, 2H).

Synthesis of trans-4-amino-1-(4-fluorophenyl)pyrrolidine-3-ol

To a 1,4-dioxane (3 mL) solution of 3-(4-fluorophenyl)-6-oxa-3-azabicyclo[3.1.0]hexane (75 mg), an aqueous (1 mL)

solution of sodium azide (82 mg) was added, and the reaction solution was agitated at 100° C. for 7 hours. After the reaction solution was allowed to be cooled to room temperature, ethyl acetate and a saturated sodium chloride solution were added to the reaction solution, and the organic layer was partitioned. The obtained organic layer was dried over anhydrous magnesium sulfate and concentrated under reduced pressure. 10% Palladium carbon (48% water content, 10 mg) was added to an ethanol (5 mL) solution of the residue, and the reaction solution was agitated at room temperature under a hydrogen current for 3 hours. 61 mg of the title compound was obtained by carrying out celite filtration of the reaction solution, and condensing the filtrate under reduced pressure. The physical properties of the compound are as follows.

$^1$H-NMR ($CD_3OD_3$) δ (ppm): 3.05-3.17 (m, 2H), 3.38-3.44 (m, 1H), 3.57-3.67 (m, 2H), 4.10-4.14 (m, 1H), 6.44-6.49 (m, 2H), 6.87-6.94 (m, 2H).

Synthesis of (E)-1-[1-(4-fluorophenyl)-trans-4-hydroxypyrrolidin-3-yl]-3-[3-methoxy-4-(4-methyl-1H-imidazol-1-yl)benzylidene]piperidin-2-one By the same method as in Example 418, 70 mg of the title compound was obtained from (E)-5-chloro-2-(3-methoxy-4-(4-methyl-1H-imidazol-1-yl)benzylidene)valeric acid trifluoroacetic acid salt (175 mg) and trans-4-amino-1-(4-fluorophenyl)pyrrolidine-3-ol (61 mg). The physical properties of the compound are as follows.

$^1$H-NMR ($CDCl_3$) δ (ppm): 1.83-2.00 (m, 2H), 2.30 (s, 3H), 2.72-2.96 (m, 2H), 3.22 (dd, J=10.0, 5.6 Hz, 1H), 3.41-3.48 (m, 3H), 3.62 (dd, J=10.0, 8.0 Hz, 1H), 3.70 (dd, J=10.0, 6.8 Hz, 1H), 3.86 (s, 3H), 4.50-4.56 (m, 1H), 5.03-5.10 (m, 1H), 6.50-6.55 (m, 2H), 6.92-7.05 (m, 5H), 7.25 (d, J=8.6 Hz, 1H), 7.71 (d, J=1.2 Hz, 1H), 7.82 (brs, 1H).

Example 623, Example 624 and Example 625

Synthesis of (E)-1-[1-(4-fluorophenyl)-(3S) and (3R)-pyrrolidin-3-yl]-3-[3-methoxy-4-(4-methyl-1H-imidazol-1-yl)benzylidene]piperidin-2-one

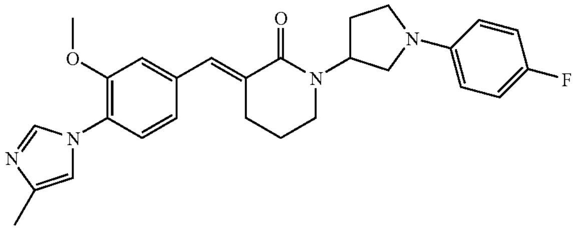

Synthesis of 1-(4-fluorophenyl)-3-pyrrolidinol of 1-(4-fluorophenyl)pyrrolidin-3-ylamine Sodium azide (722 mg) was added to a DMSO (10 mL) solution of methane sulphonate (CAS#618068-72-7, 289 mg). The reaction solution was agitated at 50° C. for 15 hours. The reaction solution was allowed to be cooled to room temperature, ether and saturated sodium bicarbonate water were added to the reaction solution, and the organic layer was partitioned. After the obtained organic layer was washed with a saturated sodium bicarbonate water, it was dried over anhydrous magnesium sulfate and concentrated under reduced pressure. 10% Palladium carbon (48% water, 10 mg) was added to the ethanol (5 mL) solution of the obtained residue, and the reaction solution was agitated at room temperature under a hydrogen stream for 20 hours. 187 mg of the title compound was obtained by carrying out celite filtration of the reaction solution, and condensing filtrate under reduced pressure. The physical properties of the compound are as follows.

$^1$H-NMR ($CDCl_3$) δ (ppm): 1.75-1.85 (m, 1H), 2.18-2.28 (m, 1H), 2.96-3.01 (m, 1H), 3.25-3.32 (m, 1H), 3.38-3.50 (m, 2H), 3.68-3.75 (m, 1H), 6.43-6.49 (m, 2H), 6.90-6.97 (m, 2H).

Synthesis of (E)-1-(1-(4-fluorophenyl)-pyrrolidin-3-yl)-3-[3-methoxy-4-(4-methyl-1H-imidazol-1-yl)benzylidene]piperidin-2-one (Example 623)

By the same method as in Example 418, 82 mg of the title compound was obtained from (E)-5-chloro-2-(3-methoxy-4-(4-methyl-1H-imidazol-1-yl)benzylidene)valeric acid trifluoroacetic acid salt (278 mg) and 1-(4-fluorophenyl)pyrrolidin-3-ylamine (142 mg). The physical properties of the compound are as follows.

$^1$H-NMR ($CDCl_3$) δ (ppm): 1.83-1.97 (m, 2H), 2.11-2.21 (m, 1H), 2.30 (s, 3H), 2.31-2.39 (m, 1H), 2.75-2.90 (m, 2H), 3.23-3.30 (m, 2H), 3.39-3.55 (m, 4H), 3.86 (s, 3H), 5.53-5.61 (m, 1H), 6.48-6.54 (m, 2H), 6.91-7.05 (m, 5H), 7.24 (dd, J=8.0, 2.0 Hz, 1H), 7.71 (s, 1H), 7.83 (brs, 1H).

Synthesis of (E)-1-[1-(4-fluorophenyl)-(3S) and (3R)-pyrrolidin-3-yl]-3-[3-methoxy-4-(4-methyl-1H-imidazol-1-yl)benzylidene]piperidin-2-one The above-mentioned racemate (14 mg) was separated in CHIRALPAK™ AD-H available from Daicel Chemical Industries, Ltd. (2 cm×25 cm: mobile phase; hexane:ethanol=70:30). The title optically active substance with a retention time of 36 minutes (4.6 mg; >99% ee) and the title optically active substance with a retention time of 39 minutes (4.3 mg; >88% ee) were obtained. The physical properties of the title optically active substance with a retention time of 36 minutes (Example 624) are as follows.

$^1$H-NMR ($CDCl_3$) δ (ppm): 1.83-1.97 (m, 2H), 2.11-2.21 (m, 1H), 2.30 (s, 3H), 2.31-2.39 (m, 1H), 2.75-2.90 (m, 2H), 3.23-3.30 (m, 2H), 3.39-3.55 (m, 4H), 3.86 (s, 3H), 5.53-5.61 (m, 1H), 6.48-6.54 (m, 2H), 6.91-7.05 (m, 5H), 7.24 (dd, J=8.0, 2.0 Hz, 1H), 7.71 (s, 1H), 7.83 (brs, 1H).

The physical properties of the title optically active substance with a retention time of 39 minutes (Example 625) are as follows.

$^1$H-NMR ($CDCl_3$) δ (ppm): 1.83-1.97 (m, 2H), 2.11-2.21 (m, 1H), 2.30 (s, 3H), 2.31-2.39 (m, 1H), 2.75-2.90 (m, 2H), 3.23-3.30 (m, 2H), 3.39-3.55 (m, 4H), 3.86 (s, 3H), 5.53-5.61 (m, 1H), 6.48-6.54 (m, 2H), 6.91-7.05 (m, 5H), 7.24 (dd, J=8.0, 2.0 Hz, 1H), 7.71 (s, 1H), 7.83 (brs, 1H).

Example 626 and Example 627

Synthesis of (E)-1-[(R) and (S)-cyclopropyl-(4-fluorophenyl)methyl]-3-[3-methoxy-4-(4-methyl-1H-imidazol-1-yl)benzylidene]piperidin-2-one

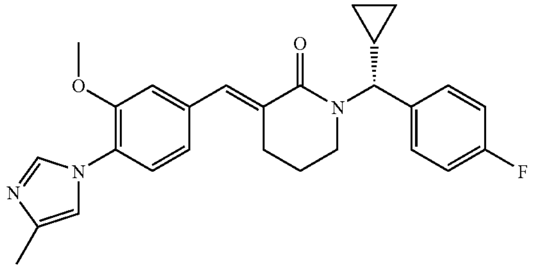

-continued

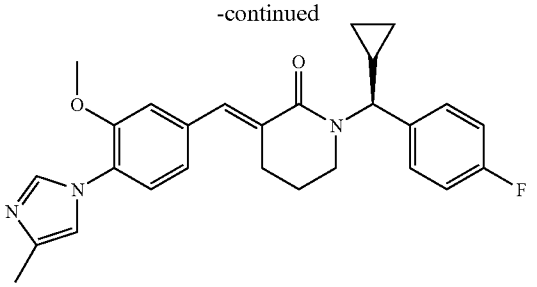

By the same method as in Example 418, 133 mg of (E)-1-cyclopropyl-(4-fluorophenyl)methyl)-3-(3-methoxy-4-(4-methyl-1H-imidazol-1-yl)benzylidene)piperidin-2-one racenate was obtained from (E)-5-chloro-2-(3-methoxy-4-(4-methyl-1H-imidazol-1-yl)benzylidene)valeric acid trifluoroacetic acid salt (250 mg) and cyclopropyl-(4-fluorophenyl)methylamine (CAS#705-14-6, 187 mg). Next, this compound (8.0 mg) was separated by CHIRALCEL™ OJ available from Daicel Chemical Industries, Ltd. (2 cm×25 cm: mobile phase; hexane:ethanol=80:20), the title optically active substance with a retention time of 9 minutes (0.9 mg; >87% ee) and the title optically active substance with a retention time of 12 minutes (0.8 mg; >88% ee) were obtained.

The physical properties of the title optically active substance with a retention time of 9 minutes are as follows.

$^1$H-NMR ($CDCl_3$) δ (ppm): 0.50-0.68 (m, 3H), 0.86-0.92 (m, 1H), 1.29-1.38 (m, 1H), 1.68-1.78 (m, 1H), 1.86-1.94 (m, 1H), 2.30 (s, 3H), 2.75-2.82 (m, 1H), 2.91 (td, J=4.8, 16 Hz, 1H), 3.10-3.16 (m, 1H), 3.51 (ddd, J=3.6, 10, 12 Hz, 1H), 3.86 (s, 3H), 5.22 (d, J=10 Hz, 1H), 6.94 (s, 1H), 7.00-7.07 (m, 4H), 7.25-7.27 (m, 1H), 7.44 (dd, J=5.6, 6.8 Hz, 2H), 7.73 (s, 1H), 7.89 (s, 1H).

The physical properties of the title optically active substance with a retention time of 12 minutes are as follows.

$^1$H-NMR ($CDCl_3$) δ (ppm): 0.50-0.68 (m, 3H), 0.86-0.92 (m, 1H), 1.29-1.38 (m, 1H), 1.68-1.78 (m, 1H), 1.86-1.94 (m, 1H), 2.30 (s, 3H), 2.75-2.82 (m, 1H), 2.91 (td, J=4.8, 16 Hz, 1H), 3.10-3.16 (m, 1H), 3.51 (ddd, J=3.6, 10, 12 Hz, 1H), 3.86 (s, 3H), 5.22 (d, J=10 Hz, 1H), 6.94 (s, 1H), 7.00-7.07 (m, 4H), 7.25-7.27 (m, 1H), 7.44 (dd, J=5.6, 6.8 Hz, 2H), 7.73 (s, 1H), 7.89 (s, 1H).

Example 628

Synthesis of (E)-1-[2-fluoro-4-morpholin-4-ylbenzyl]-3-[3-methoxy-4-(4-methyl-1H-imidazol-1-yl)benzylidene]piperidin-2-one

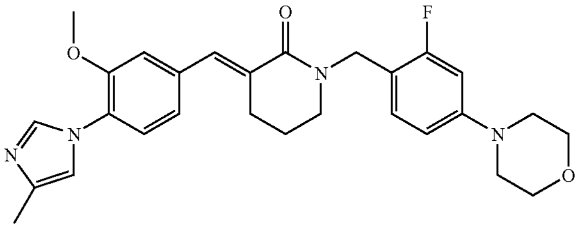

Synthesis of 2-fluoro-4-morpholin-4-ylbenzylamine

By the same method as in Example 426, 740 mg of the title compound was obtained using 2-fluoro-4-morpholin-4-ylbenzonitrile (CAS#554448-62-3, 1.0 g). The physical properties of the compound are as follows.

$^1$H-NMR ($CDCl_3$) δ (ppm): 1.55 (brs, 2H), 3.13 (t, J=4.8 Hz, 4H), 3.80 (s, 2H), 3.84 (t, J=4.8 Hz, 4H), 6.56 (dd, J=2.4, 13 Hz, 1H), 6.63 (dd, J=2.4, 8.4 Hz, 1H), 7.17 (t, J=8.8 Hz, 1H).

Synthesis of (E)-1-[2-fluoro-4-morpholin-4-ylbenzyl]-3-[3-methoxy-4-(4-methyl-1H-imidazol-1-yl)benzylidene]piperidin-2-one By the same method as in Example 418, 126 mg of the title compound was obtained from (E)-5-chloro-2-(3-methoxy-4-(4-methyl-1H-imidazol-1-yl)benzylidene)valeric acid trifluoroacetic acid salt (200 mg) and 2-fluoro -4-morpholin-4-ylbenzylamine (141 mg). The physical properties of the compound are as follows.

$^1$H-NMR ($CDCl_3$) δ (ppm): 1.82-1.88 (m, 2H), 2.30 (s, 3H), 2.78-2.81 (m, 2H), 3.15 (t, J=3.6 Hz, 4H), 3.41 (t, J=5.6 Hz, 2H), 3.83-3.86 (m, 4H), 3.84 (s, 3H), 4.69 (s, 2H), 6.56 (dd, J=2.4, 13 Hz, 1H), 6.64 (dd, J=2.4, 8.8 Hz, 1H), 6.92 (s, 1H), 7.00-7.02 (m, 2H), 7.23 (d, J=8.4, 1H), 7.32 (t, J=8.8 Hz, 1H), 7.70 (s, 1H), 7.83 (s, 1H).

Example 629

Synthesis of (E)-1-[(1R)-(4-fluorophenyl)-2-hydroxy ethyl]-3-[3-methoxy-4-(4-methyl-1H-imidazol-1-yl) benzylidene]piperidin-2-one

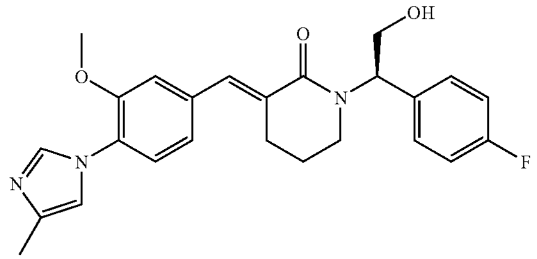

Synthesis of (2R)-amino-2-(4-fluorophenyl)ethanol

A THF (5.0 mL) solution of D-(−)-4-fluorophenylglycine (500 mg) was cooled to 0° C. Sodium borohydride (246 mg) and iodine (751 mg) were added to the reaction solution. After refluxing the reaction solution overnight, methanol was added to the reaction solution and the reaction solution was concentrated under reduced pressure. Next, 5N sodium hydroxide solution and ethyl acetate were added to the reaction solution, and the organic layer was partitioned. 389 mg of the title compound was obtained by drying with anhydrous magnesium sulfate and condensing under reduced pressure, after the obtained organic layer was washed with a saturated sodium chloride solution. The physical properties of the compound are as follows.

$^1$H-NMR ($CDCl_3$) δ (ppm): 2.24 (brs, 3H), 3.52 (dd, J=8.0, 11 Hz, 1H), 3.70 (dd, J=4.0, 11 Hz, 1H), 4.04 (dd, J=4.0, 8.0 Hz, 1H), 7.00-7.04 (m, 2H), 7.27-7.31 (m, 2H).

Synthesis of (E)-1-[(1R)-(4-fluorophenyl)-2-hydroxyethyl]-3-[3-methoxy-4-(4-methyl-1H-imidazol-1-yl)benzylidene]piperidin-2-one By the same method as in Example 418, 25 mg of the title compound was obtained from (E)-5-chloro-2-(3-methoxy-4-

(4-methyl-1H-imidazol-1-yl)benzylidene)valeric acid trifluoroacetic acid salt (250 mg) and (2R)-amino-2-(4-fluorophenyl)ethanol (104 mg). The physical properties of the compound are as follows.

$^1$H-NMR ($CDCl_3$) δ (ppm): 1.72-1.90 (m, 2H), 2.30 (s, 3H), 2.79-2.84 (m, 2H), 3.09 (ddd, J=4.4, 7.6, 12 Hz, 1H), 3.33 (ddd, J=4.4, 8.0, 12 Hz, 1H), 3.85 (s, 3H), 4.17-4.25 (m, 2H), 5.86 (dd, J=6.0, 8.0 Hz, 1H), 6.92-6.93 (m, 1H), 7.02-7.08 (m, 4H), 7.20-7.32 (m, 3H), 7.71 (d, J=1.2 Hz, 1H), 7.87 (s, 1H).

Example 630 and Example 631

Synthesis of (E)-1-[(1R) and (1S)-(3,4-difluorophenyl)ethyl]-3-[3-methoxy-4-(4-methyl-1H-imidazol-1-yl)benzylidene]piperidin-2-one

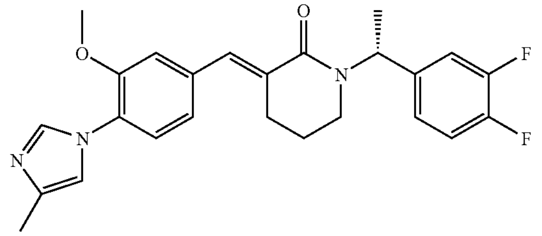

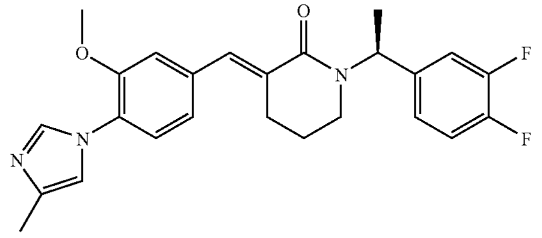

Synthesis of (E)-1-((1R) and (1S)-(3,4-difluorophenyl)-ethyl)-3-(3-methoxy-4-(4-methyl-1H-imidazol-1-yl)benzylidene)piperidin-2-one By the same method as in Example 418, 150 mg of (E)-1-(1-(3,4-difluorophenyl)-ethyl-3-(3-methoxy-4-(4-methyl-1H-imidazol-1-yl)benzylidene)piperidin-2-one racemate was obtained from (E)-5-chloro-2-(3-methoxy-4-(4-methyl-1H-imidazol-1-yl)benzylidene)valeric acid trifluoroacetic acid salt (250 mg) and 1-(3,4-difluorophenyl)ethylamine (CAS#276875-21-9, 140 mg). Next, this compound (150 mg) was separated by CHIRALPAK™ AD-H available from Daicel Chemical Industries, Ltd. (2 cm×25 cm: mobile phase: ethanol), and the title optically active substance with a retention time of 6 minutes (68.0 mg; >99% ee) and the title optically active substance with a retention time of 7 minutes (66.2 mg; >91% ee) were obtained. The physical properties of the title optically active substance with a retention time of 6 minutes is as follows.

$^1$H-NMR ($CDCl_3$) δ (ppm): 1.54 (d, J=7.2 Hz, 3H), 1.62-1.76 (m, 1H), 1.80-1.90 (m, 1H), 2.30 (s, 3H), 2.72-2.80 (m, 1H), 2.83-2.90 (m, 1H), 2.92-2.98 (m, 1H), 3.26 (ddd, J=3.6, 8.8, 12 Hz, 1H), 3.86 (s, 3H), 6.19 (q, J=7.2 Hz, 1H), 6.92 (s, 1H), 7.03-7.18 (m, 5H), 7.24-7.25 (m, 1H), 7.71 (s, 1H), 7.88 (s, 1H).

The physical properties of the title optically active substance with a retention time of 7 minutes is as follows.

$^1$H-NMR ($CDCl_3$) δ (ppm): 1.54 (d, J=7.2 Hz, 3H), 1.62-1.76 (m, 1H), 1.80-1.90 (m, 1H), 2.30 (s, 3H), 2.72-2.80 (m, 1H), 2.83-2.90 (m, 1H), 2.92-2.98 (m, 1H), 3.26 (ddd, J=3.6, 8.8, 12 Hz, 1H), 3.86 (s, 3H), 6.19 (q, J=7.2 Hz, 1H), 6.92 (s, 1H), 7.03-7.18 (m, 5H), 7.24-7.25 (m, 1H), 7.71 (s, 1H), 7.88 (s, 1H)

Example 632 and Example 633

Synthesis of (E)-1-[(1R) and (1S)-(4-fluorophenyl)propyl]-3-[3-methoxy-4-(4-methyl-1H-imidazol-1-yl)benzylidene]piperidin-2-one

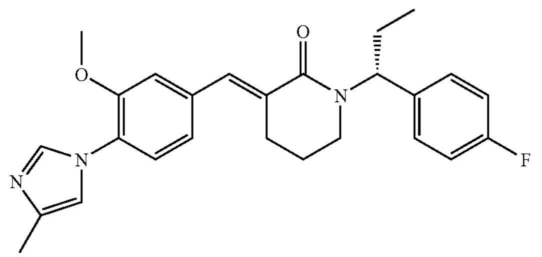

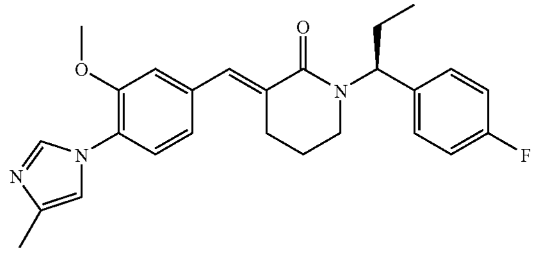

Synthesis of (E)-1-[(1R) and (1S)-(4-fluorophenyl)propyl]-3-[3-methoxy-4-(4-methyl-1H-imidazol-1-yl)benzylidene]piperidin-2-one By the same method as in Example 418, 21.9 mg of (E)-1-(1-(4-fluorophenyl)propyl)-3-(3-methoxy-4-(4-methyl-1H-imidazol-1-yl)benzylidene)piperidin-2-one racemate was obtained from (E)-5-chloro-2-(3-methoxy-4-(4-methyl-1H-imidazol-1-yl)benzylidene)valeric acid trifluoroacetic acid salt (150 mg) and 1-(4-fluorophenyl)propylamine (CAS#74877-10-4, 76.8 mg). Next, this compound (20.0 mg) was separated by CHIRALPAK™ AD-H available from Daicel Chemical Industries, Ltd. (2 cm×25 cm: mobile phase: ethanol), and the title optically active substance with a retention time of 6 minutes (6.10 mg; >99% ee) and the title optically active substance with a retention time of 7 minutes (5.10 mg; >92% ee) were obtained. The physical properties of the title optically active substance with a retention time of 6 minutes is as follows.

$^1$H-NMR ($CDCl_3$) δ (ppm): 1.02 (t, J=7.2 Hz, 3H), 1.57-1.70 (m, 1H), 1.76-1.88 (m, 1H), 1.89-1.97 (m, 1H), 1.99-2.07 (m, 1H), 2.30 (s, 3H), 2.71-2.84 (m, 2H), 2.92-2.97 (m, 1H), 3.21 (ddd, J=3.6, 8.4, 12 Hz, 1H), 3.85 (s, 3H), 6.01 (dd, J=6.0, 10 Hz, 1H), 6.92 (s, 1H), 6.99-7.04 (m, 4H), 7.23-7.25 (m, 1H), 7.31-7.35 (m, 2H), 7.71 (s, 1H), 7.87 (s, 1H).

The physical properties of the title optically active substance with a retention time of 7 minutes is as follows.

$^1$H-NMR ($CDCl_3$) δ (ppm): 1.02 (t, J=7.2 Hz, 3H), 1.57-1.70 (m, 1H), 1.76-1.88 (m, 1H), 1.89-1.97 (m, 1H), 1.99-2.07 (m, 1H), 2.30 (s, 3H), 2.71-2.84 (m, 2H), 2.92-2.97 (m, 1H), 3.21 (ddd, J=3.6, 8.4, 12 Hz, 1H), 3.85 (s, 3H), 6.01 (dd, J=6.0, 10 Hz, 1H), 6.92 (s, 1H), 6.99-7.04 (m, 4H), 7.23-7.25 (m, 1H), 7.31-7.35 (m, 2H), 7.71 (s, 1H), 7.87 (s, 1H).

Example 634

Synthesis of (E)-3-[3-methoxy-4-(4-methyl-1H-imidazol-1-yl)benzylidene]-1-(2-piperidin-1-ylbenzyl) piperidin-2-one

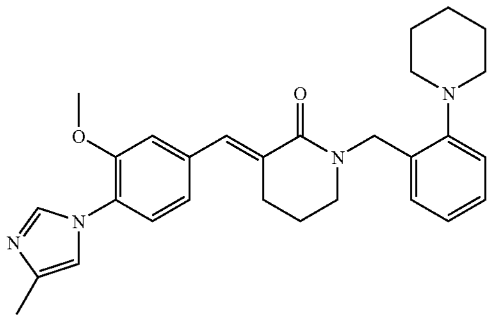

By the same method as in Example 641, 8.40 mg of the title compound was obtained from (E)-5-chloro-2-(3-methoxy-4-(4-methyl-1H-imidazol-1-yl)benzylidene)valeric acid tert-butyl ester (50 mg) and 2-piperidin-1-ylbenzylamine (1M DMF solution, 256 μL). The physical properties of the compound are as follows.

$^1$H-NMR ($CDCl_3$) δ (ppm): 1.52-1.74 (m, 6H), 1.82-1.88 (m, 2H), 2.30 (d, J=1.2 Hz, 3H), 2.82-2.86 (m, 6H), 3.28-3.31 (m, 2H), 3.86 (S, 3H), 4.86 (s, 2H), 6.93 (m, 1H), 7.02-7.06 (m, 3H), 7.09 (dd, J=1.2, 8.4 Hz, 1H), 7.20-7.26 (m, 3H), 7.79 (d, J=1.2 Hz, 1H), 7.88 (S, 1H).

Example 635

Synthesis of (E)-1-[(1S)-(4-chlorophenyl)ethyl]-3-[3-methoxy-4-(4-methylimidazole-2-yl)benzylidene] piperidin-2-one

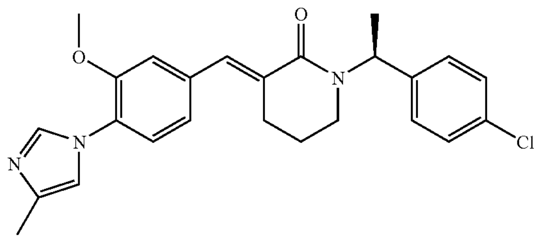

By the same method as in Example 641, 10.5 mg of the title compound was obtained from (E)-5-chloro-2-(3-methoxy-4-(4-methyl-1H-imidazol-1-yl)benzylidene)valeric acid tert-butyl ester (50 mg) and (S)-1-(4-chlorophenyl)ethylamine (32.0 mg). The physical properties of the compound are as follows.

$^1$H-NMR ($CDCl_3$) δ (ppm): 1.55 (d, J=6.8 Hz, 3H), 1.64-1.73 (m, 1H), 1.76-1.88 (m, 1H), 2.30 (s, 3H), 2.71-2.85 (m, 2H), 2.91-2.96 (m, 1H), 3.24 (dtd, J=4.0, 8.8, 12 Hz, 1H), 3.85 (s, 3H), 6.21 (q, J=6.8 Hz, 1H), 6.92-6.93 (m, 1H), 7.03-7.05 (m, 2H), 7.22-7.32 (m, 5H), 7.70 (d, J=1.6 Hz, 1H), 7.88 (s, 1H).

Example 636

Synthesis of (E)-3-[3-methoxy-4-(4-methyl-1H-imidazol-1-yl)benzylidene]-1-(4-trifluoromethylbenzyl) piperidin-2-one trifluoroacetic acid salt

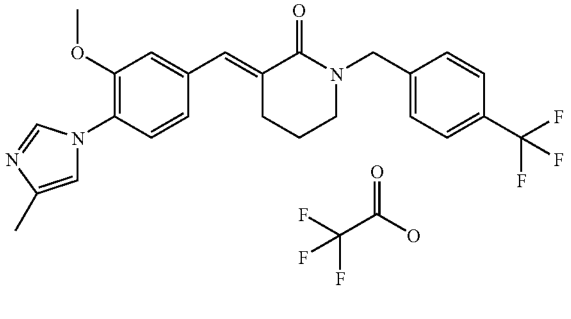

By the same method as in Example 416, 12.5 mg of the title compound was obtained from (E)-5-chloro-2-(3-methoxy-4-(4-methyl-1H-imidazol-1-yl)benzylidene)valeric acid tert-butyl ester (50 mg) and 4-(trifluoromethyl)benzylamine (36.0 mg). The physical properties of the compound are as follows.

$^1$H-NMR ($CDCl_3$) δ (ppm): 1.87-1.93 (m, 2H), 2.48 (S, 3H), 2.82 (t, J=5.6 Hz, 2H), 3.41 (t, J=6.0 Hz, 2H), 3.90 (s, 3H), 4.78 (s, 2H), 7.06 (d, J=6.4 Hz, 2H), 7.09 (d, J=8.0 Hz, 1H), 7.33 (d, J=8.0 Hz, 1H), 7.42 (d, J=8.0 Hz, 1H), 7.60 (d, J=8.0 Hz, 2H), 7.87 (s, 2H), 8.71 (d, J=1.2 Hz, 1H).

Example 637

Synthesis of (E)-3-[4-(4-ethyl-1H-imidazol-1-yl)-3-methoxybenzylidene]-1-(7-methoxy-1,2,3,4-tetrahydronaphthalen-1-yl)piperidin-2-one

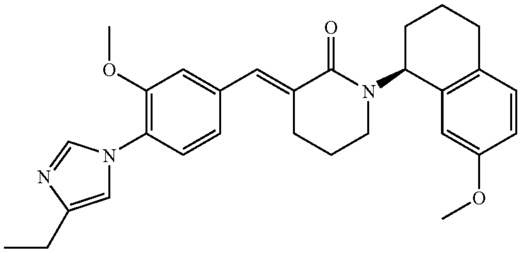

Synthesis of (E)-5-chloro-2-[4-(4-ethyl-1H-imidazol-1-yl)-3-methoxybenzylidene]valeric acid trifluoroacetic acid salt By the same method as in Example 418, 3.5 g of the title compound was obtained from (E)-5-chloro-2-(4-(4-ethyl-1H-imidazol-1-yl)-3-methoxybenzylidene)valeric acid tert-butyl ester (3.2 g) obtained above. The physical properties of the compound are as follows.

$^1$H-NMR (DMSO-$d_6$) δ (ppm): 1.25 (t, J=7.6 Hz, 3H), 1.94-2.01 (m, 2H), 2.60-2.64 (m, 2H), 2.71 (q, J=7.6 Hz, 2H), 3.70 (t, J=6 Hz, 2H), 3.91 (s, 3H), 7.24 (dd, J=1.6 Hz, 8 Hz, 1H), 7.37 (d, J=1.6 Hz, 1H), 7.64 (d, J=8 Hz, 1H), 7.69 (s, 1H), 7.75 (d, J=1.2 Hz, 1H), 9.27 (s, 1H).

Synthesis of (E)-3-[4-(4-ethyl-1H-imidazol-1-yl)-3-methoxybenzylidene]-1-(7-methoxy-1,2,3,4-tetrahydronaphthalen-1-yl)piperidin-2-one By the same method as in Example 641, 159 mg of the title compound was obtained from (E)-5-chloro-2-(4-(4-ethyl-1H-imidazol-1-yl)-3-methoxybenzylidene)valeric acid trifluoroacetic acid salt (200 mg) and (S)-7-methoxy-1,2,3,4-tetrahydronaphthalen-1ylamine (144 mg). The physical properties of the compound are as follows.

$^1$H-NMR ($CDCl_3$) δ (ppm): 1.30 (t, J=7.0 Hz, 3H), 1.58-1.89 (m, 4H), 1.98-2.05 (m, 1H), 2.08-2.12 (m, 1H), 2.66-2.82 (m, 5H), 2.90-2.96 (m, 1H), 3.07-3.12 (m, 1H), 3.18-3.25 (m, 1H), 3.75 (s, 3H), 3.88 (s, 3H), 6.08-6.12 (m, 1H), 6.65 (s, 1H), 6.75 (d, J=4.4 Hz, 1H), 6.94 (s, 1H), 7.03-7.10 (m, 3H), 7.26-7.29 (m, 1H), 7.75 (s, 1H), 7.92 (s, 1H).

Example 638

Synthesis of (E)-1-[(1R)-(4-fluorophenyl)ethyl]-3-[3-methoxy-4-(4-methyl-1H-imidazol-1-yl)benzylidene]piperidin-2-one

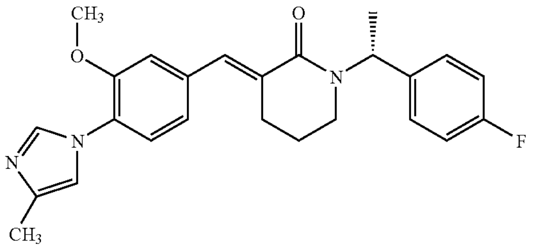

By the same method as Example 418, 1.0 g of the title compound was obtained from (E)-5-chloro-2-(3-methoxy-4-(4-methyl-1H-imidazol-1-yl)benzylidene)valeric acid trifluoroacetic acid salt (1.6 g) and (R)-1-(4-fluorophenyl)ethylamine (495 mg). The physical properties of the compound are as follows.

$^1$H-NMR ($CDCl_3$) δ (ppm): 1.50 (d, J=7.2 Hz, 3H), 1.65-1.74 (m, 1H), 1.78-1.87 (m, 1H), 2.30 (s, 3H), 2.71-2.85 (m, 2H), 2.91-2.97 (m, 1H), 3.24 (ddd, J=3.6, 8.8, 12.0 Hz, 1H), 3.86 (s, 3H), 6.23 (q, J=7.2 Hz, 1H), 6.93 (t, J=1.2 Hz, 1H), 7.00-7.06 (m, 4H), 7.24-7.26 (m, 1H), 7.31-7.34 (m, 2H), 7.72 (d, J=1.2 Hz, 1H), 7.89 (s, 1H).

Example 639

Synthesis of (E)-1-[4-(4-fluorophenyl)tetrahydropyran-4-yl)-3-(3-methoxy-4-(4-methyl-1H-imidazol-1-yl)benzylidene]piperidin-2-one

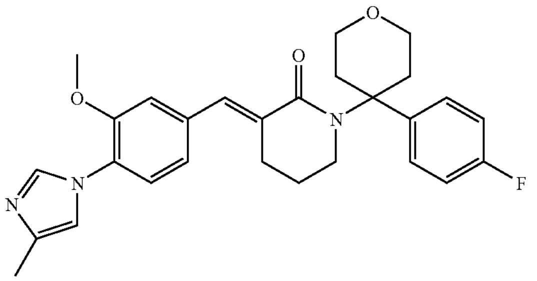

By the same method as in Example 418, 1.15 g of the title compound was obtained from (E)-5-chloro-2-(3-methoxy-4-(4-methyl-1H-imidazol-1-yl)benzylidene)valeric acid trifluoroacetic acid salt (2.1 g) and 4-(4-fluorophenyl)tetrahydropyran-4-ylamine (833 mg) synthesized according to the method described in Journal of Medicinal Chemistry, vol. 10, No. 1 p. 128 1967. The physical properties of the compound are as follows.

$^1$H-NMR ($CDCl_3$) δ (ppm): 1.75-1.84 (m, 2H), 2.30 (s, 3H), 2.32-2.38 (m, 2H), 2.74-2.88 (m, 4H), 3.34-3.39 (m, 2H), 3.71-3.78 (m, 2H), 3.80-3.88 (m, 5H), 6.92 (brs, 1H), 6.99-7.07 (m, 4H), 7.23 (d, J=8.0 Hz, 1H), 7.44-7.50 (m, 2H), 7.68 (brs, 1H), 7.72 (s, 1H)

Example 640

Synthesis of (E)-1-[1-(3,4-difluorobenzyl)-(3R)-pyrrolidin-3-yl]-3-[3-methoxy-4-(4-methyl-1H-imidazol-1-yl)benzylidene]piperidin-2-one

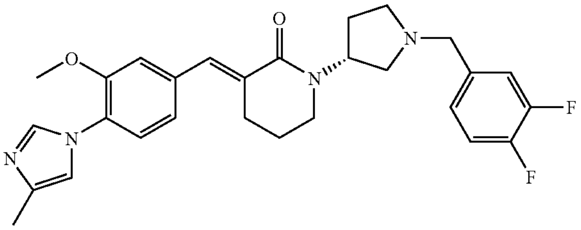

By the same method as in Example 417, 12 mg of the title compound was obtained from (E)-5-chloro-2-(3-methoxy-4-(4-methyl-1H-imidazol-1-yl)benzylidene)valeric acid ethyl ester (50 mg) and (3R)-1-(3,4-difluorobenzyl)pyrrolidin-3-ylamine dihydrochloride (40 mg)

The physical properties of the compound are as follows.

$^1$H-NMR ($CDCl_3$) δ (ppm): 1.75-1.93 (m, 3H), 2.22-2.33 (m, 2H), 2.29 (s, 3H), 2.50 (dd, J=10.4, 8.4 Hz, 1H), 2.70 (dd, J=10.4, 3.6 Hz, 1H), 2.77-2.95 (m, 3H), 3.45-3.62 (m, 4H), 3.84 (s, 3H), 5.17-5.45 (m, 1H), 6.92 (s, 1H), 6.98-7.27 (m, 6H), 7.70 (d, J=1.2 Hz, 1H), 7.78 (s, 1H).

Example 641

Synthesis of (E)-4-{(3S)-(3-[3-methoxy-4-(4-methyl-1H-imidazol-1-yl)benzylidene]-2-oxopiperidin-1-yl)pyrrolidine-1-yl}benzonitrile

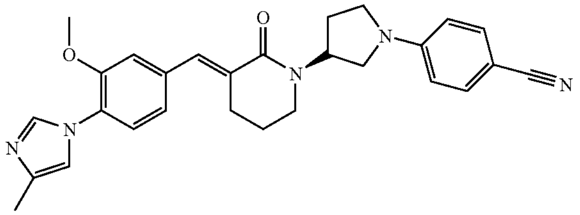

Synthesis of [(1S)-(4-silanophenyl)pyrrolidin-3-yl]carbamic acid tert-butyl ester DMF (10 mL) suspension of (3S)-3-(tertbutoxycarbonylamino)pyrrolidine (837 mg) and 4-fluorobenzonitrile (544 mg) and potassium carbonate (1.24 g) was agitated at 120° C. for 22 hours. After the reaction solution was allowed to be cooled to room temperature, ethyl acetate and saturated sodium bicarbonate water were added to the reaction solution, and the organic layer was partitioned. The obtained organic layer was dried over anhydrous magnesium sulfate and was concentrated under reduced pressure. 320 mg of the title compound was obtained by re-crystallizing the residue from the mixed-solution of ethyl acetate and hexane. The physical properties of the compound are as follows.

$^1$H-NMR ($CDCl_3$) δ (ppm): 1.45 (s, 9H), 1.94-2.05 (m, 1H), 2.25-2.37 (m, 1H), 3.16-3.67 (m, 4H), 4.36 (brs, 1H), 4.67 (brs, 1H), 6.49 (d, J=6.8 Hz, 2H), 7.45 (d, J=6.8 Hz, 2H).

Synthesis of 4-[(3S)-aminopyrrolidin-1-yl]benzonitrile 2 trifluoroacetic-acid salt Trifluoroacetic acid (1 mL) was added to a methylene chloride (3 mL) solution of ((1S)-(4-silanophenyl)pyrrolidin-3-yl)carbamic acid tert-butyl ester (100 mg), and the reaction solution was agitated at room temperature for 15 hours. 144 mg of the title compound was obtained by condensing reaction solution under reduced pressure. The physical properties of the compound are as follows.

$^1$H-NMR ($CD_3OD$) δ (ppm): 2.18-2.28 (m, 1H), 2.45-2.56 (m, 1H), 3.43-3.75 (m, 4H), 3.99-4.07 (m, 1H), 6.67 (d, J=6.8 Hz, 2H), 7.53 (d, J=6.8 Hz, 2H).

Synthesis of (E)-4-{(3S)-{(3-[3-methoxy-4-(4-methyl-1H-imidazol-1-yl)benzylidene]-2-oxopiperidin-1-yl}pyrrolidin-1-yl}benzonitrile To a mixed solution of 4-((3S)-aminopyrrolidin-1-yl)benzonitrile 2 trifluoroacetic-acid salt (144 mg) and (E)-5-chloro-2-(3-methoxy-4-(4-methyl-1H-imidazol-1-yl)benzylidene)valeric acid tert-butyl ester (136 mg) in acetonitrile (5 mL) and water (0.5 mL), potassium carbonate (239 mg) and sodium iodide (52 mg) were added, and heat-refluxing of the reaction mixture was carried out for 34 hours. After the reaction solution was allowed to be cooled to room temperature, ethyl acetate and water were added to the reaction solution, and the organic layer was partitioned. The obtained organic layer was dried over anhydrous magnesium sulfate and was concentrated under reduced pressure. Trifluoroacetic acid (1 mL) was added to a methylene chloride (3 mL) solution of the residue, and the reaction solution was agitated at room temperature for 12 hours. The reaction solution was concentrated under reduced pressure and HOBT (188 mg), EDC (266 mg), and IPEA (0.36 mL) were added to a DMF (3 mL) solution of the obtained residue. The reaction mixture was agitated at room temperature for 6 hours. Ethyl acetate and saturated sodium bicarbonate water were added to the reaction solution, and the organic layer was partitioned. The obtained organic layer was dried over anhydrous magnesium sulfate and concentrated under reduced pressure. 47 mg of the title compound was obtained by purifying the residue by silica gel chromatography (Carrier: Chromatorex™ NH and elution solvent:heptane:ethyl acetate=1:1→ethyl acetate). The physical properties of the compound are as follows.

$^1$H-NMR ($CDCl_3$) δ (ppm): 1.86-2.00 (m, 2H), 2.19-2.38 (m, 5H), 2.75-2.92 (m, 2H), 3.29-3.4 (m, 4H), 3.53-3.67 (m, 2H), 3.86 (s, 3H), 5.48-5.57 (m, 1H), 6.53 (d, J=6.8 Hz, 2H), 6.93 (brs, 1H), 7.01 (brs, 1H), 7.04 (brd, J=7.0 Hz, 1H), 7.25 (d, J=7.0 Hz, 1H), 7.47 (d, J=6.8 Hz, 2H), 7.70 (s, 1H), 7.83 (brs, 1H).

Example 642

Synthesis of (E)-4-{3-[3-methoxy-4-(4-methyl-1H-imidazol-1-yl)benzylidene]-2-oxopiperidin-1-yl}piperidin-1-yl)benzonitrile

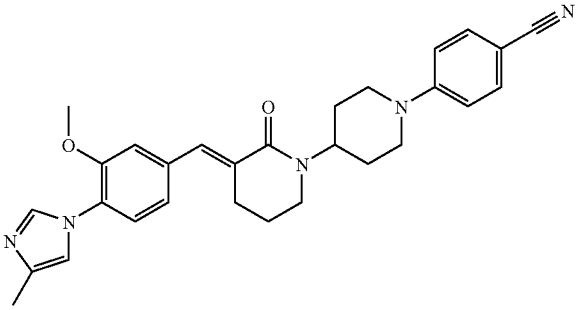

By the same method as in Example 641, 72 mg of the title compound was obtained from 4-(4-aminopiperidin-1-yl)benzonitrile (142 mg) and (E)-5-chloro-2-(3-methoxy-4-(4-methyl-1H-imidazol-1-yl)benzylidene)valeric acid tert-butyl ester (129 mg). The physical properties of the compound are as follows.

$^1$H-NMR (DMSO-$d_6$) δ (ppm): 1.60-1.81 (m, 6H), 2.14 (s, 3H), 2.73-2.78 (m, 2H), 2.92-3.02 (m, 2H), 3.24-3.30 (m, 2H), 3.84 (s, 3H), 4.01-4.10 (m, 2H), 4.60-4.71 (m, 1H), 7.04 (d, J=9.2 Hz, 2H), 7.08 (dd, J=9.2, 1.6 Hz, 1H), 7.14 (s, 1H), 7.23 (d, J=1.6 Hz, 1H), 7.38 (d, J=9.2 Hz, 1H), 7.55 (d, J=9.2 Hz, 2H), 7.62 (brs, 1H), 7.77 (dd, J=1.2 Hz, 1H).

Example 643

Synthesis of (E)-1-[4-(1-methoxy-1-methylethyl)benzyl]-3-[3-methoxy-4-(4-methyl-1H-imidazol-1-yl)benzylidene]piperidin-2-one

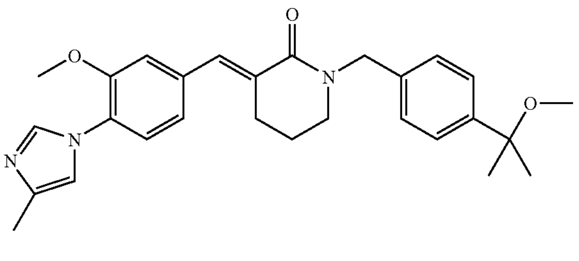

By the same method as in Example 418, 100 mg of the title compound was obtained from (E)-chloro-2-(3-methoxy-4-(4-methyl-1H-imidazol-1-yl)benzylidene)valeric acid trifluoroacetic acid salt (250 mg) and 4-(1-methoxy-1-methylethyl)benzylamine (174 mg). The physical properties of the compound are as follows.

$^1$H-NMR ($CDCl_3$) δ (ppm): 1.52 (s, 6H), 1.84-1.91 (m, 2H), 2.30 (s, 3H), 2.82-2.85 (m, 2H), 3.07 (s, 3H), 3.38-3.41 (m, 2H), 3.86 (s, 3H), 4.73 (s, 2H), 6.94 (t, J=1.2 Hz, 1H), 7.03 (s, 1H), 7.03-7.05 (m, 1H), 7.25-7.30 (m, 3H), 7.38 (d, J=8.0 Hz, 2H), 7.72 (d, J=1.2 Hz, 1H), 7.89 (s, 1H)

Example 644

Synthesis of (E)-1-[3-fluoro-4-(1-methoxy-1-methyl-ethyl)benzyl]-3-[3-methoxy-4-(4-methyl-1H-imidazol-1-yl)benzylidene]piperidin-2-one

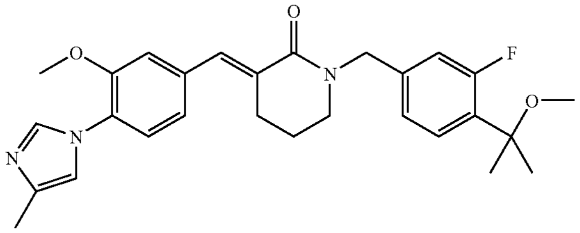

By the same method as in Example 418, 57 mg of the title compound was obtained from (E)-chloro-2-(3-methoxy-4-(4-methyl-1H-imidazol-1-yl)benzylidene)valeric acid trifluoroacetic acid (250 mg) and 3-fluoro 4-(1-methoxy-1-methyl-ethyl)benzylamine (132 mg). The physical properties of the compound are as follows.

$^1$H-NMR ($CDCl_3$) δ (ppm): 1.59 (s, 6H), 1.86-1.92 (m, 2H), 2.30 (s, 3H), 2.81-2.86 (m, 2H), 3.18 (s, 3H), 3.38-3.42 (m, 2H), 3.86 (s, 3H), 4.70 (s, 2H), 6.92 (s, 1H), 6.97 (d, J=12 Hz, 1H), 7.02 (s, 1H), 7.03 (d, J=8.0 Hz, 1H), 7.04 (t, J=8.0 Hz, 1H), 7.24 (m, 1H), 7.37 (t, J=8.0 Hz, 1H), 7.71 (1H, s, 1H), 7.86 (1H, s, 1H).

Example 645

Synthesis of (E)-1-[2-fluoro-4-(1-methoxy-1-methyl-ethyl)benzyl]-3-[3-methoxy-4-(4-methyl-1H-imidazol-1-yl)benzylidene]piperidin-2-one

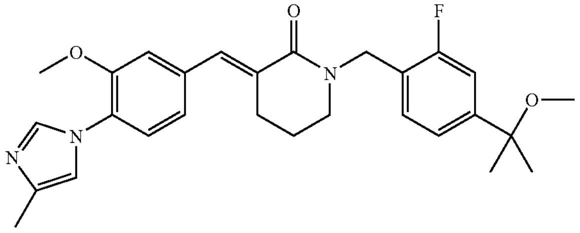

By the same method as Example 418, 110 mg of the title compound was obtained from (E)-chloro-2-(3-methoxy-4-(4-methyl-1H-imidazol-1-yl)benzylidene)valeric acid trifluoroacetic acid salt (250 mg) and 3-fluoro 4-(1-methoxy-1-methyl-ethyl)benzylamine (154 mg). The physical properties of the compound are as follows.

$^1$H-NMR ($CDCl_3$) δ (ppm): 1.50 (s, 6H), 1.86-1.92 (m, 2H), 2.30 (s, 3H), 2.81-2.85 (m, 2H), 3.08 (s, 3H), 3.45-3.48 (m, 2H), 3.85 (s, 3H), 4.76 (s, 2H), 6.92 (t, J=1.2 Hz, 1H), 7.00 (s, 1H), 7.00-7.03 (m, 1H), 7.09-7.15 (m, 2H), 7.22-7.24 (m, 1H), 7.36 (t, J=8.0 Hz, 1H), 7.70 (d, J=1.2 Hz, 1H), 7.85 (s, 1H).

Example 646

Synthesis of (E)-1-(4-chloro-3-fluorobenzyl)-3-[3-methoxy-4-(4-methyl-1H-imidazol-1-yl)benzylidene]piperidin-2-one

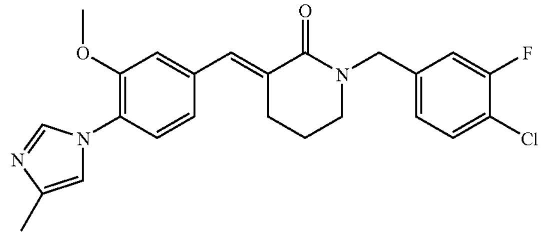

By the same method as in Example 416, 100 mg of the title compound was obtained from (E)-3-(3-methoxy-4-(4-methyl-1H-imidazol-1-yl)benzylidene)piperidin-2-one (80 mg) and 4-chloro-3-fluorobenzylbromide (0.070 mL). The physical properties of the compound are as follows.

$^1$H-NMR ($CDCl_3$) δ (ppm): 1.84-1.92 (m, 2H), 2.30 (s, 3H), 2.80-2.88 (m, 2H), 3.34-3.42 (m, 2H), 3.86 (s, 3H), 4.68 (s, 2H), 6.93 (s, 1H), 7.00-7.08 (m, 3H), 7.11 (d, J=8.8 Hz, 1H), 7.22-7.30 (m, 1H), 7.35 (t, J=8.4 Hz, 1H), 7.71 (s, 1H), 7.86 (s, 1H).

Example 647

Synthesis of (E)-1-[4-methyl-2-(4-trifluoromethylphenyl)-1,3-thioazol-5-ylmethyl]-3-[3-methoxy-4-(4-methyl-1H-imidazol-1-yl)benzylidene]piperidin-2-one

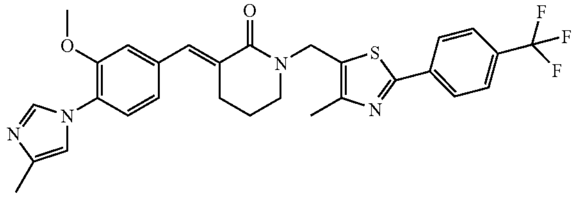

By the same method as in Example 416, 24 mg of the title compound was obtained from (E)-3-(3-methoxy-4-(4-methyl-1H-imidazol-1-yl)benzylidene)piperidin-2-one (80 mg) and 5-(chloromethyl)-4-methyl-2-(4-trifluoromethylphenyl)-1,3-thiazole (94.2 mg). The physical properties of the compound are as follows.

$^1$H-NMR ($CDCl_3$) δ (ppm): 1.85-1.95 (m, 2H), 2.30 (s, 3H), 2.55 (s, 3H), 2.80-2.85 (m, 2H), 3.45-3.54 (m, 2H), 3.85 (s, 3H), 4.83 (s, 2H), 6.91-6.93 (m, 1H), 6.98-7.05 (m, 2H), 7.22-7.27 (m, 1H), 7.65 (d, J=8.4 Hz, 2H), 7.70 (d, J=1.2 Hz, 1H), 7.86 (s, 1H), 8.00 (d, J=8.4 Hz, 2H).

Example 648

Synthesis of (E)-1-(3,4,5-trifluorobenzyl)-3-[3-methoxy-4-(4-methyl-1H-imidazol-1-yl)benzylidene]piperidin-2-one

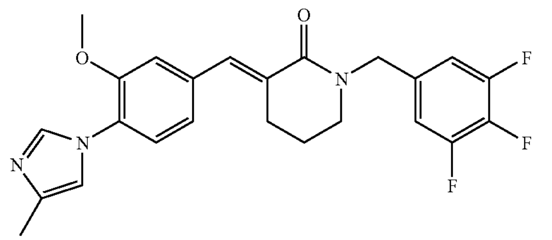

By the same method as in Example 416, 55 mg of the title compound was obtained from (E)-3-[3-methoxy-4-(4-methyl-1H-imidazol-1-yl)benzylidene]piperidin-2-one (50 mg) and 3, 4,5-trifluorobenzylchloride (0.027 mL). The physical properties of the compound are as follows.

$^1$H-NMR ($CDCl_3$) δ (ppm): 1.86-1.94 (m, 2H), 2.30 (s, 3H), 2.80-2.88 (m, 2H), 3.35-3.42 (m, 2H), 3.86 (s, 3H), 4.64 (s, 2H), 6.90-6.98 (m, 3H), 7.00-7.05 (m, 2H), 7.22-7.28 (m, 1H), 7.69-7.73 (m, 1H), 7.85 (s, 1H).

Example 649

Synthesis of (E)-1-(3,4-dichlorobenzyl)-3-[3-methoxy-4-(4-methyl-1H-imidazol-1-yl)benzylidene]piperidin-2-one

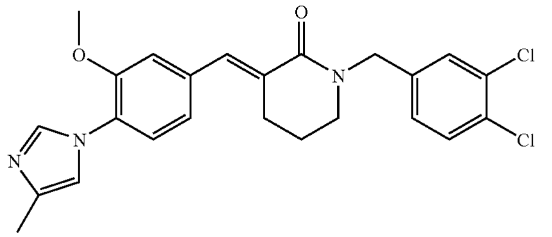

By the same method as in Example 416, 30 mg of the title compound was obtained from (E)-3-[3-methoxy-4-(4-methyl-1H-imidazol-1-yl)benzylidene]piperidin-2-one (30 mg) and 3,4-dichlorobenzylchloride (0.020 mL). The physical properties of the compound are as follows.

$^1$H-NMR ($CDCl_3$) δ (ppm): 1.84-1.92 (m, 2H), 2.30 (s, 3H), 2.80-2.88 (m, 2H), 3.34-3.41 (m, 2H), 3.86 (s, 3H), 4.67 (s, 2H), 6.90-6.95 (m, 1H), 7.00-7.06 (m, 2H), 7.17 (dd, J=2.0, 8.4 Hz, 1H), 7.23-7.27 (m, 1H), 7.40 (d, J=2.0 Hz, 1H), 7.40 (d, J=8.4 Hz, 1H), 7.71 (d, J=1.2 Hz, 1H), 7.86 (s, 1H).

Example 650

Synthesis of (E)-1-[6-chloro-2-(morpholin-4-yl)pyridin-3-ylmethyl]-3-[3-methoxy-4-(4-methyl-1H-imidazol-1-yl)benzylidene]piperidin-2-one

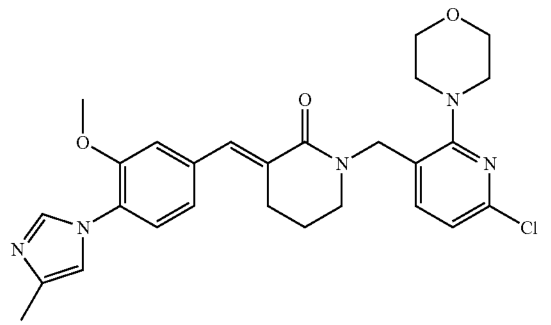

By the same method as in Example 418, 27 mg of the title compound was obtained from (E)-5-chloro-2-[3-methoxy-4-(4-methyl-1H-imidazol-1-yl)benzylidene]valeric acid trifluoroacetic acid salt (200 mg) and (6-chloro-2-(morpholin-4-yl)-pyridin-3-yl)methylamine (250 mg). The physical properties of the compound are as follows.

$^1$H-NMR ($CDCl_3$) δ (ppm): 1.82-1.92 (m, 2H), 2.31 (s, 3H), 2.82-2.90 (m, 2H), 3.12-3.20 (m, 4H), 3.22-3.30 (m, 2H), 3.80-3.90 (m, 4H), 3.87 (s, 3H), 4.71 (s, 2H), 6.90-7.00 (m, 1H), 6.97 (d, J=8.0 Hz, 1H), 7.04 (s, 1H), 7.05 (d, J=8.4 Hz, 1H), 7.20-7.30 (m, 1H), 7.43 (d, J=8.0 Hz, 1H), 7.74 (brs, 1H), 7.88 (s, 1H).

Example 651

Synthesis of (E)-(2,2-difluorobenzo[1,3]dioxol-5-ylmethyl)-3-[3-methoxy-4-(4-methyl-1H-imidazol-1-yl)benzylidene]piperidin-2-one

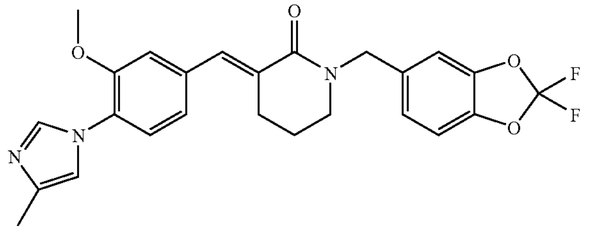

By the same method as in Example 427, 44 mg of the title compound was obtained from (E)-5-chloro-2-[3-methoxy-4-(4-methyl-1H-imidazol-1-yl)benzylidene]valeric acid ethyl (100 mg) and methylamine (2,2-difluorobenzo [1,3]dioxol-5-ylmethyl) (77.5 mg). The physical properties of the compound are as follows.

$^1$H-NMR ($CDCl_3$) δ (ppm): 1.83-1.92 (m, 2H), 2.30 (s, 3H), 2.80-2.86 (m, 2H), 3.35-3.41 (m, 2H), 3.86 (s, 3H), 4.68 (s, 2H), 6.91-6.94 (m, 1H), 6.98-7.05 (m, 4H), 7.07-7.10 (m, 1H), 7.22-7.27 (m, 1H), 7.71 (d, J=1.2 Hz, 1H), 7.86 (s, 1H).

Example 652

Synthesis of (E)-1-(3-chloro-4-fluorobenzyl)-3-[3-methoxy-4-(4-methyl-1H-imidazol-1-yl)benzylidene]piperidin-2-one

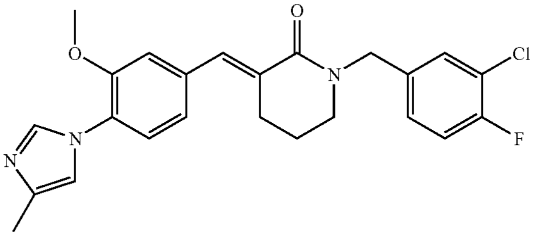

By the same method as in Example 427, 27 mg of the title compound was obtained from (E)-5-chloro-2-[3-methoxy-4-(4-methyl-1H-imidazol-1-yl)benzylidene]valeric acid ethyl (100 mg) and 3-chloro-4-fluorobenzylamine (100 mg). The physical properties of the compound ate as follows.

$^1$H-NMR ($CDCl_3$) δ (ppm): 1.84-1.92 (m, 2H), 2.30 (s, 3H), 2.80-2.87 (m, 2H), 3.34-3.41 (m, 2H), 3.88 (s, 3H), 4.66 (s, 2H), 6.91-6.94 (m, 1H), 7.00-7.05 (m, 2H), 7.10 (t, J=8.8 Hz, 1H), 7.17-7.23 (m, 1H), 7.23-7.28 (m, 1H), 7.36 (dd, J=2.0, 6.8 Hz, 1H), 7.71 (d, J=1.6 Hz, 1H), 7.86 (s, 1H).

The compounds shown in Table 20 were synthesized as in Example 85.

The structural formulae and physical properties are shown in Table 20, respectively.

The separation conditions in the notes to Table 20 are as follows: Separation Condition A: CHIRALPAK™ AD-H (2 cm×25 cm: mobile phase: hexane-ethanol system) Separation Condition B: CHIRALPAK™ OJ-H (2 cm×25 cm: mobile phase: hexane-ethanol system)

TABLE 20

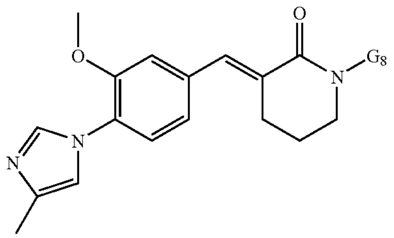

| Example | $G_8$ | DATA:MS m/z | Note |
|---|---|---|---|
| 653 | 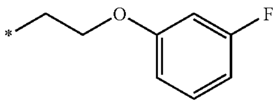 | $M^+$ + H:436 (ESI) | |
| 654 | 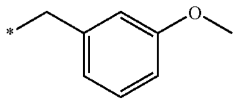 | $M^+$ + H:418 (ESI) | |
| 655 | 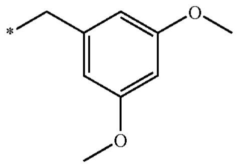 | $M^+$ + H:448 (ESI) | |
| 656 | 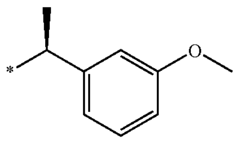 | $M^+$ + H:432 (ESI) | optically active substance |
| 657 | 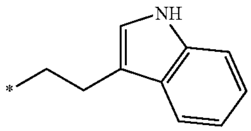 | $M^+$ + H:441 (ESI) | |

TABLE 20-continued

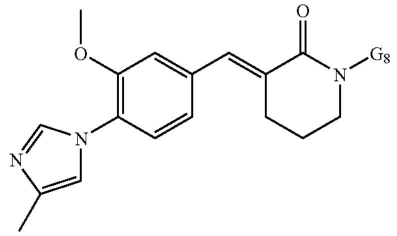

| Example | $G_8$ | DATA:MS m/z | Note |
|---|---|---|---|
| 658 | 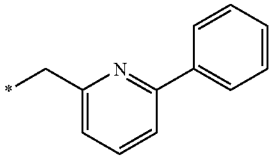 | $M^+$ + H:465 (ESI) | |
| 659 | 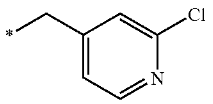 | $M^+$ + H:423 (ESI) | |
| 660 | 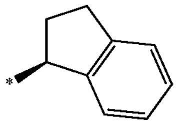 | $M^+$ + H:414 (ESI) | optically active substance |
| 681 | 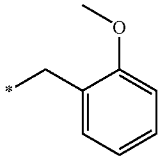 | $M^+$ + H:418 (ESI) | |
| 662 | 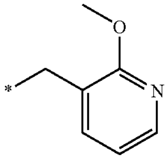 | $M^+$ + H:419 (ESI) | |
| 663 | 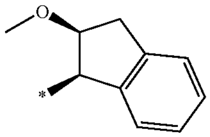 | $M^+$ + H:444 (ESI) | optically active substance |
| 664 | 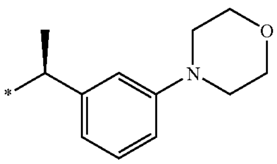 | $M^+$ + H:487 (ESI) | optically active substance (separation condition A; retention time: 9 minutes; absolute configuration: unknown) |
| 665 | 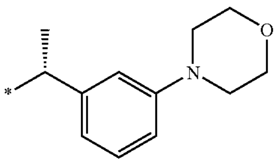 | $M^+$ + H:487 (ESI) | optically active substance (separation condition A; retention time: 11 minutes; absolute configuration: unknown) |

TABLE 20-continued
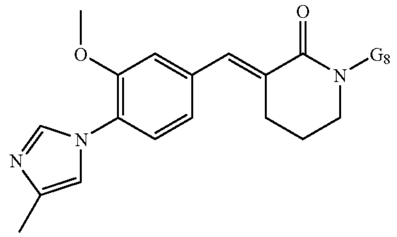
| Example | $G_8$ | DATA:MS m/z | Note |
|---|---|---|---|
| 666 | 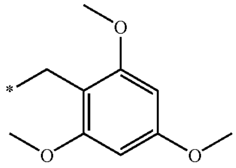 | $M^+$ + H:478 (ESI) | |
| 667 | 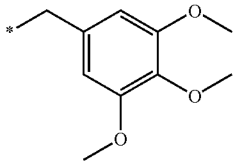 | $M^+$ + H:478 (ESI) | |
| 668 | 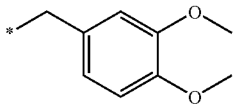 | $M^+$ + H:448 (ESI) | |
| 669 | 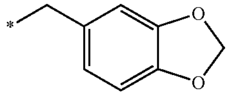 | $M^+$ + H:432 (ESI) | |
| 670 | 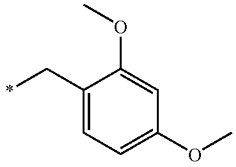 | $M^+$ + H:448 (ESI) | |
| 671 | 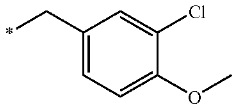 | $M^+$ + H:452 (ESI) | |
| 672 | 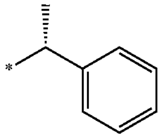 | $M^+$ + H:402 (ESI) | optically active substance |
| 673 | 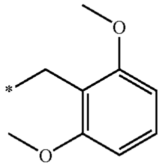 | $M^+$ + H:448 (ESI) | |

TABLE 20-continued
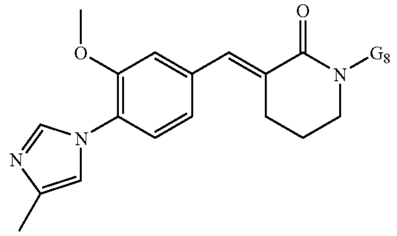
| Example | $G_8$ | DATA:MS m/z | Note |
|---|---|---|---|
| 674 | 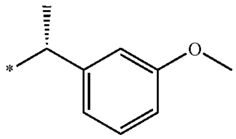 | $M^+$ + H:432 (ESI) | optically active substance |
| 675 | 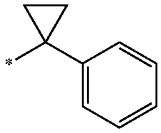 | $M^+$ + H:414 (ESI) | |
| 676 | 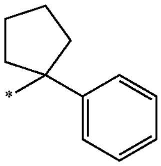 | $M^+$ + H:442 (ESI) | |
| 677 | 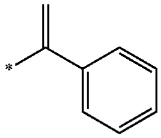 | $M^+$ + H:400 (ESI) | |
| 678 | 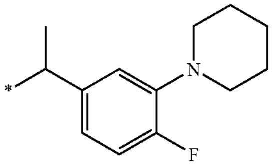 | $M^+$ + H:503 (ESI) | racemate |
| 679 | 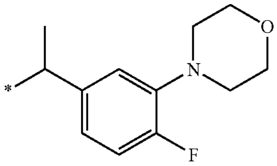 | $M^+$ + H:505 (ESI) | racemate |
| 680 | 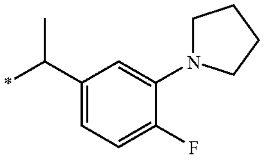 | $M^+$ + H:489 (ESI) | racemate |
| 681 | 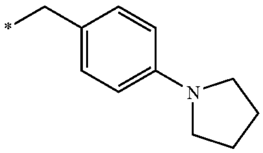 | $M^+$ + H:457 (ESI) | |

TABLE 20-continued
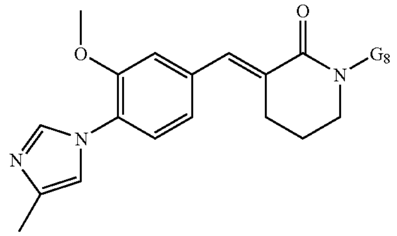
| Example | $G_8$ | DATA:MS m/z | Note |
|---|---|---|---|
| 682 | 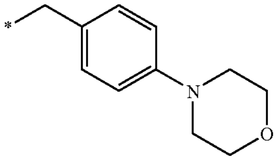 | $M^+ + H$:473 (ESI) | |
| 683 | 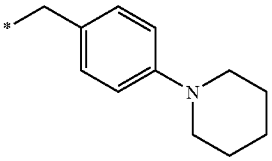 | $M^+ + H$:471 (ESI) | |
| 684 | 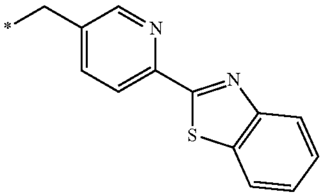 | $M^+ + H$:522 (ESI) | |
| 685 | 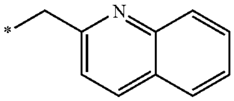 | $M^+ + H$:439 (ESI) | |
| 686 | 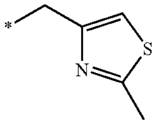 | $M^+ + H$:409 (ESI) | |
| 687 | 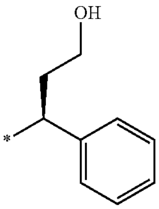 | $M^+ + H$:432 (ESI) | optically active substance |
| 688 | 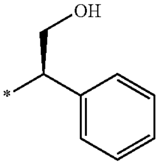 | $M^+ + H$:418 (ESI) | optically active substance |

TABLE 20-continued
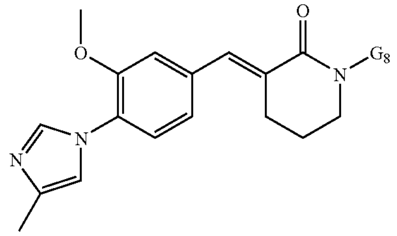
| Example | $G_8$ | DATA:MS m/z | Note |
|---|---|---|---|
| 689 | 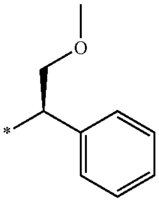 | $M^+ + H$:432 (ESI) | optically active substance |
| 690 | 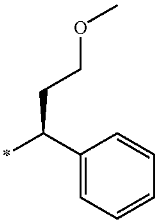 | $M^+ + H$:446 (ESI) | optically active substance |
| 691 | 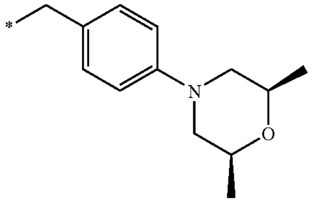 | $M^+ + H$:501 (ESI) | |
| 692 | 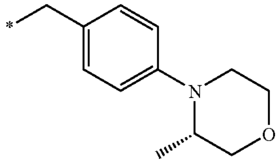 | $M^+ + H$:487 (ESI) | optically active substance |
| 693 | 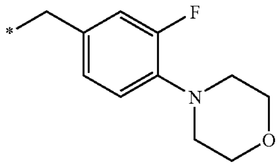 | $M^+ + H$:491 (ESI) | |
| 694 | 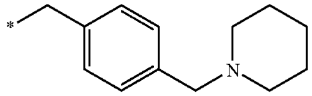 | $M^+ + H$:485 (ESI) | |
| 695 | 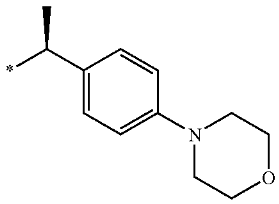 | $M^+ + H$:487 (ESI) | optically active substance (separation condition A: retention time: 16 minutes; absolute configuration: unknown) |

TABLE 20-continued

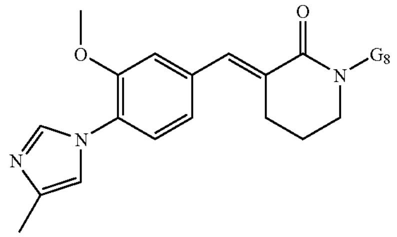

| Example | $G_8$ | DATA:MS m/z | Note |
|---|---|---|---|
| 696 | 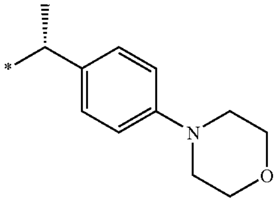 | $M^+$ + H:487 (ESI) | optically active substance (separation condition A: retention time: 20 minutes; absolute configuration: unknown) |
| 697 | 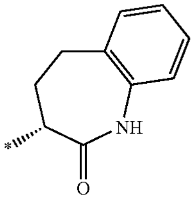 | $M^+$ + H:457 (ESI) | optically active substance (separation condition B: retention time: 12 minutes; absolute configuration: unknown) |
| 698 | 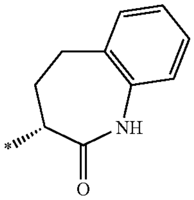 | $M^+$ + H:457 (ESI) | optically active substance (separation condition B: retention time: 15 minutes; absolute configuration: unknown) |
| 699 | 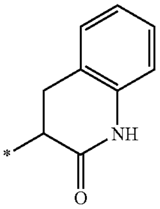 | $M^+$ + H:443 (ESI) | racemate |
| 700 | 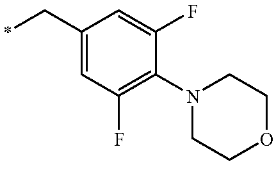 | $M^+$ + H:509 (ESI) | |
| 701 | 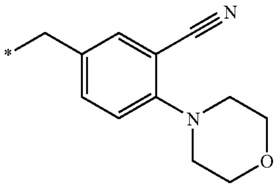 | $M^+$ + H:498 (ESI) | |

TABLE 20-continued

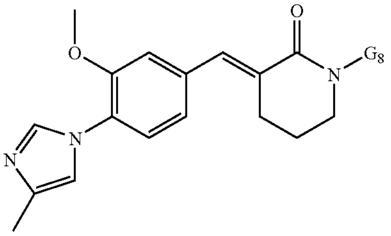

| Example | $G_8$ | DATA:MS m/z | Note |
|---|---|---|---|
| 702 | 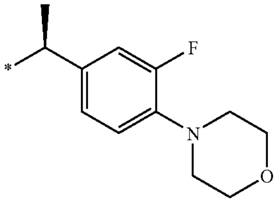 | $M^+$ + H:505 (ESI) | optically active substance (separation condition A: retention time: 13 minutes; absolute configuration: unknown) |
| 703 | 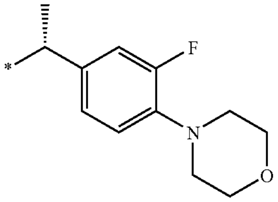 | $M^+$ + H:504 (ESI) | optically active substance (separation condition A: retention time: 16 minutes; absolute configuration: unknown) |
| 704 | 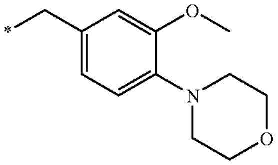 | $M^+$ + H:503 (ESI) | |
| 705 | 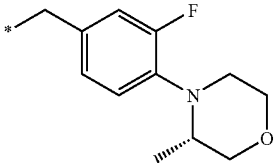 | $M^+$ + H:504 (ESI) | optically active substance |
| 706 | 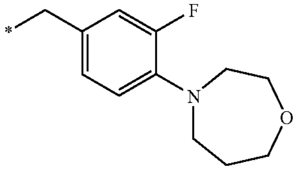 | $M^+$ + H:505 (ESI) | |
| 707 | 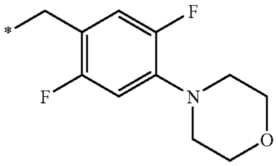 | $M^+$ + H:509 (ESI) | |
| 708 | 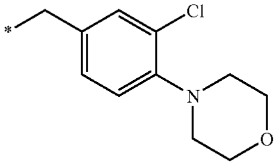 | $M^+$ + H:507 (ESI) | |

TABLE 20-continued

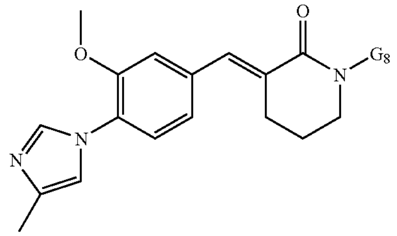

| Example | $G_8$ | DATA:MS m/z | Note |
|---|---|---|---|
| 709 | 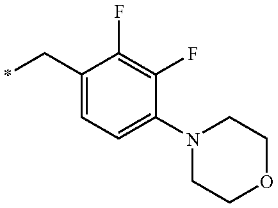 | $M^+$ + H:509 (ESI) | |
| 710 | 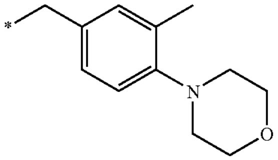 | $M^+$ + H:487 (ESI) | |
| 711 | 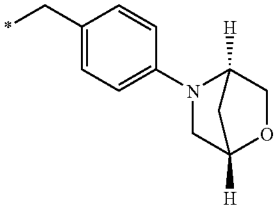 | $M^+$ + H:485 (ESI) | optically active substance |
| 712 | 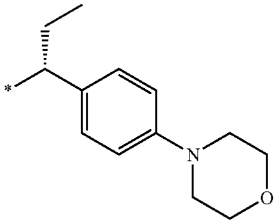 | $M^+$ + H:501 (ESI) | optically active substance (separation condition A: retention time: 13 minutes; absolute configuration: unknown) |
| 713 | 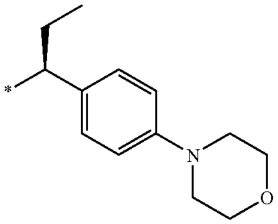 | $M^+$ + H:501 (ESI) | optically active substance (separation condition A: retention time: 15 minutes; absolute configuration: unknown) |
| 714 | 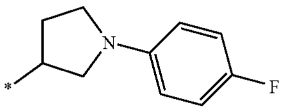 | $M^+$ + H:461 (ESI) | racemate |

TABLE 20-continued
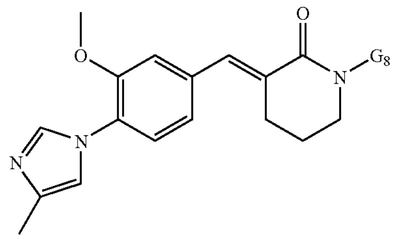
| Example | $G_8$ | DATA:MS m/z | Note |
|---|---|---|---|
| 715 | 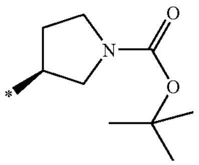 | $M^+ + H$:467 (ESI) | optically active substance |
| 716 | 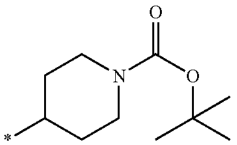 | $M^+ + H$:481 (ESI) | |
| 717 | 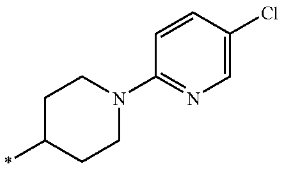 | $M^+ + H$:492 (ESI) | |
| 718 | 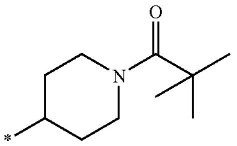 | $M^+ + H$:465 (ESI) | |
| 719 | 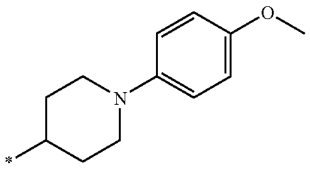 | $M^+ + H$:487 (ESI) | |
| 720 | 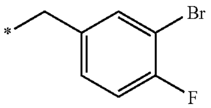 | $M^+ + H$:485 (ESI) | |
| 721 | 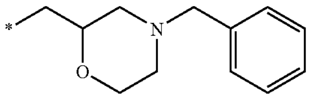 | $M^+ + H$:487 (ESI) | |
| 722 | 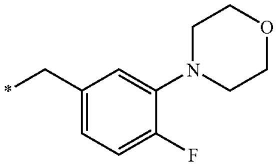 | $M^+ + H$:491 (ESI) | |

TABLE 20-continued

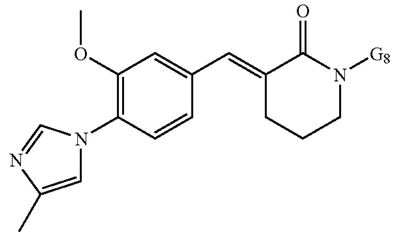

| Example | $G_8$ | DATA:MS m/z | Note |
|---|---|---|---|
| 723 | 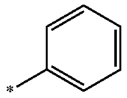 | $M^+$ + H:374 (ESI) | |
| 724 | 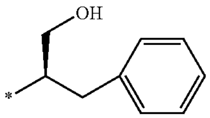 | $M^+$ + H:432 (ESI) | optically active substance |
| 725 | 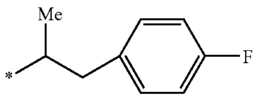 | $M^+$ + H:434 (ESI) | racemate |
| 726 | 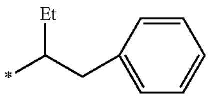 | $M^+$ + H:430 (ESI) | racemate |
| 727 | 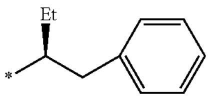 | $M^+$ + H:430 (ESI) | optically active substance (separation conditionA: retention time: 11 minutes; absolute configuration unknown) |
| 728 | 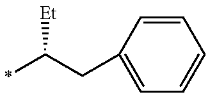 | $M^+$ + H:430 (ESI) | optically active substance (separation conditionA: retention time: 14 minutes; absolute configuration unkonwn) |
| 729 | 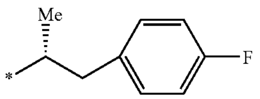 | $M^+$ + H:434 (ESI) | optically active substance (separation conditionB: retention time: 24 minutes; absolute configuration unknown) |
| 730 | 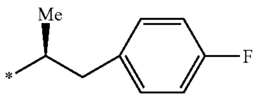 | $M^+$ + H:434 (ESI) | optically active substance (separation conditionB: retention time: 30 minutes; absolute configuration unknown) |
| 731 | 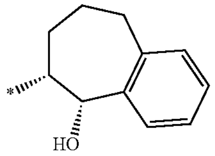 | $M^+$ + H:458 (ESI) | optically active substance (separation conditionA: retention time: 10 minutes; aboslute configuration unknown) |

TABLE 20-continued
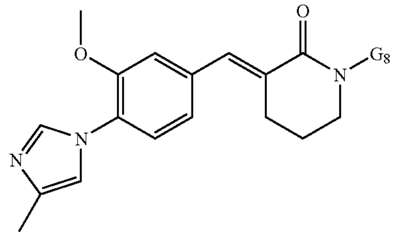
| Example | $G_8$ | DATA:MS m/z | Note |
|---|---|---|---|
| 732 | 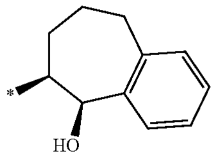 | $M^+$ + H:458 (ESI) | optically active substance (separation conditionA: retention time: 16 minutes; absolute configuration unknwon) |
| 733 | 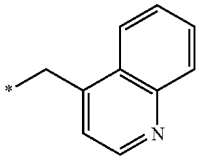 | $M^+$ + H:439 (ESI) | |
| 734 | 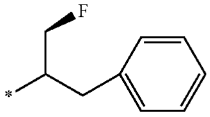 | $M^+$ + H:434 (ESI) | optically active substance |
| 735 | 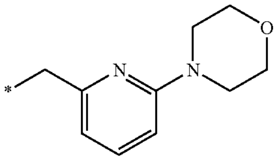 | $M^+$ + H:474 (ESI) | |
| 736 | 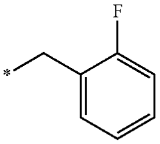 | $M^+$ + H:406 (ESI) | |
| 737 | 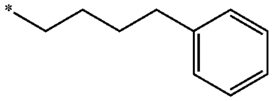 | $M^+$ + H:430 (ESI) | |
| 738 | 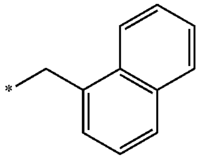 | $M^+$ + H:438 (ESI) | |
| 739 | 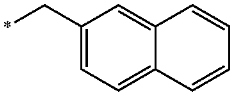 | $M^+$ + H:438 (ESI) | |

TABLE 20-continued
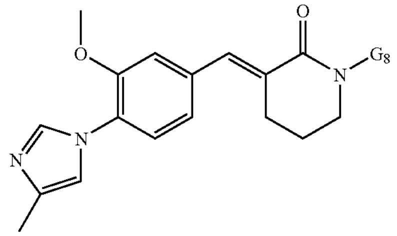
| Example | $G_8$ | DATA:MS m/z | Note |
|---|---|---|---|
| 740 | 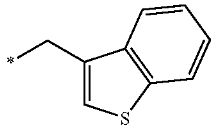 | $M^+ + H$:444 (ESI) | - Continued - |
| 741 | 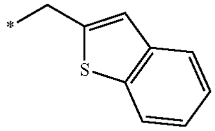 | $M^+ + H$:444 (ESI) | |
| 742 | 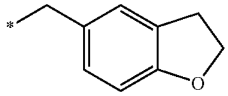 | $M^+ + H$:430 (ESI) | |
| 743 | 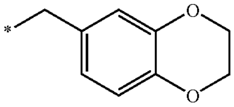 | $M^+ + H$:446 (ESI) | |
| 744 | 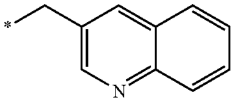 | $M^+ + H$:439 (ESI) | |
| 745 | 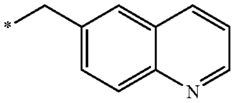 | $M^+ + H$:439 (ESI) | |
| 746 | 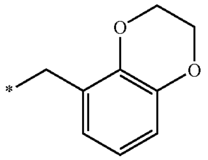 | $M^+ + H$:446 (ESI) | |
| 747 | 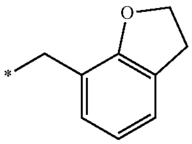 | $M^+ + H$:430 (ESI) | |
| 748 | 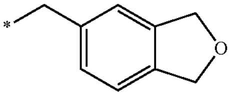 | $M^+ + H$:430 (ESI) | |

TABLE 20-continued
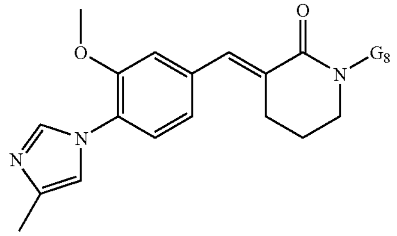
| Example | $G_8$ | DATA:MS m/z | Note |
| --- | --- | --- | --- |
| 749 | 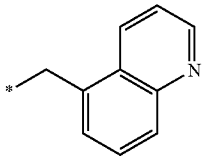 | $M^+$ + H:439 (ESI) | |
| 750 | 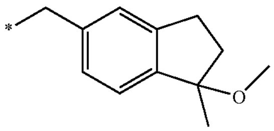 | $M^+$ + H:472 (ESI) | racemate |
| 751 | 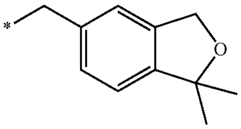 | $M^+$ + H:458 (ESI) | |
| 752 | 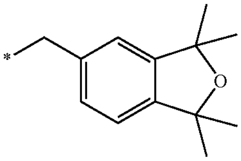 | $M^+$ + H:485 (ESI) | |
| 753 | 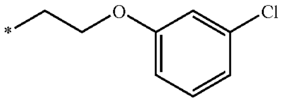 | $M^+$ + H:452 (ESI) | |
| 754 | 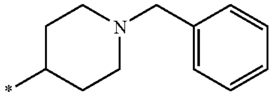 | $M^+$ + H:471 (ESI) | |
| 755 | 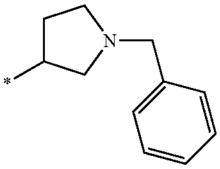 | $M^+$ + H:457 (ESI) | racemate |
| 756 | 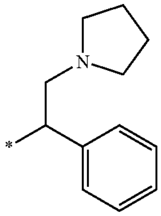 | $M^+$ + H:471 (ESI) | racemate |

TABLE 20-continued
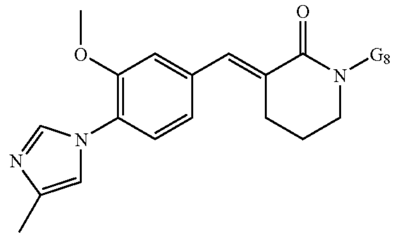
| Example | $G_8$ | DATA:MS m/z | Note |
|---|---|---|---|
| 757 | 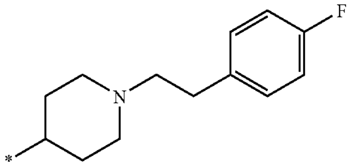 | $M^+$ + H:503 (ESI) | |
| 758 | 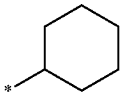 | $M^+$ + H:380 (ESI) | |
| 759 | 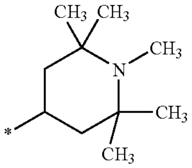 | $M^+$ + H:451 (ESI) | |
| 760 | 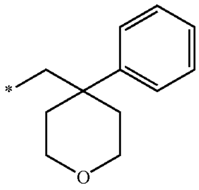 | $M^+$ + H:472 (ESI) | |
| 761 | 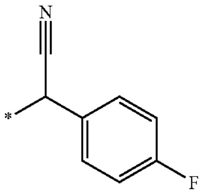 | $M^+$ + H:431 (ESI) | racemate |
| 762 | 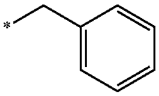 | $M^+$ + H:388 (ESI) | |
| 763 | 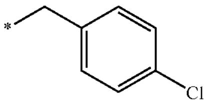 | $M^+$ + H:422 (ESI) | |
| 764 | 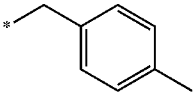 | $M^+$ + H:402 (ESI) | |

TABLE 20-continued
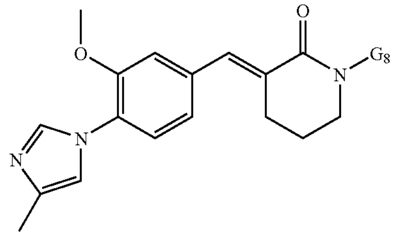
| Example | $G_8$ | DATA:MS m/z | Note |
| --- | --- | --- | --- |
| 765 | 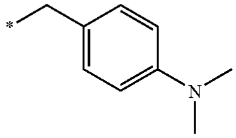 | $M^+$ + H:431 (ESI) | |
| 766 | 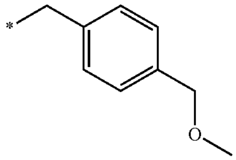 | $M^+$ + H:432 (ESI) | |
| 767 | 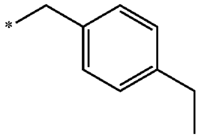 | $M^+$ + H:416 (ESI) | |
| 768 | 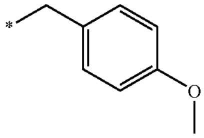 | $M^+$ + H:418 (ESI) | |
| 769 | 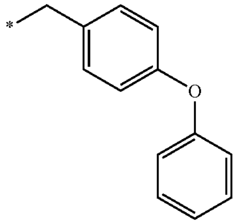 | $M^+$ + H:480 (ESI) | |
| 770 | 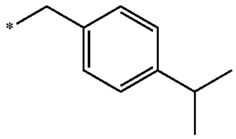 | $M^+$ + H:430 (ESI) | |
| 771 | 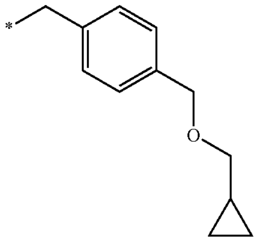 | $M^+$ + H:472 (ESI) | |

TABLE 20-continued
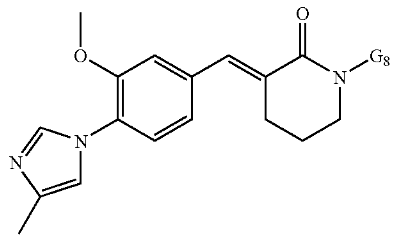
| Example | $G_8$ | DATA:MS m/z | Note |
| --- | --- | --- | --- |
| 772 | 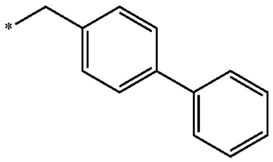 | $M^+$ + H:464 (ESI) | |
| 773 | 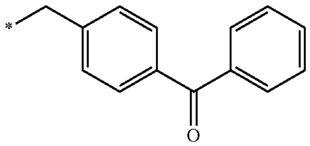 | $M^+$ + H:492 (ESI) | |
| 774 | 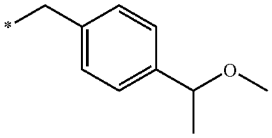 | $M^+$ + H:446 (ESI) | racemate |
| 775 | 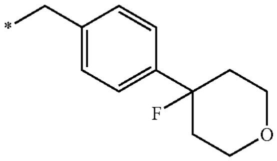 | $M^+$ + H:490 (ESI) | |
| 776 | 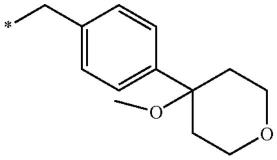 | $M^+$ + H:502 (ESI) | |
| 777 | 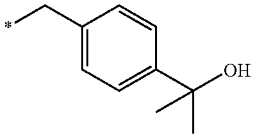 | $M^+$ + H:446 (ESI) | |
| 778 | 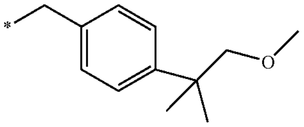 | $M^+$ + H:474 (ESI) | |
| 779 | 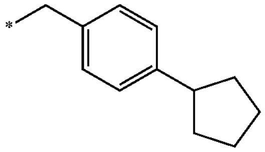 | $M^+$ + H:458 (ESI) | |

TABLE 20-continued
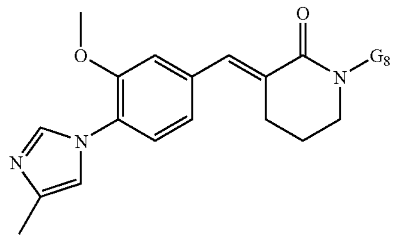
| Example | $G_8$ | DATA:MS m/z | Note |
|---|---|---|---|
| 780 | 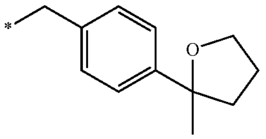 | $M^+$ + H:472 (ESI) | racemate |
| 781 | 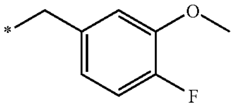 | $M^+$ + H:436 (ESI) | |
| 782 | 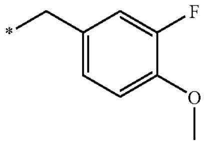 | $M^+$ + H:436 (ESI) | |
| 783 | 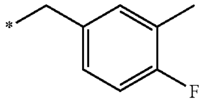 | $M^+$ + H:420 (ESI) | |
| 784 | 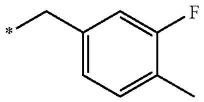 | $M^+$ + H:420 (ESI) | |
| 785 | 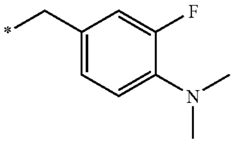 | $M^+$ + H:449 (ESI) | |
| 786 | 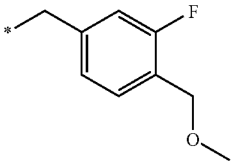 | $M^+$ + H:450 (ESI) | |
| 787 | 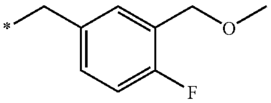 | $M^+$ + H:450 (ESI) | |
| 788 | 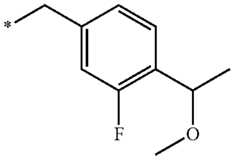 | $M^+$ + H:464 (ESI) | racemate |

TABLE 20-continued
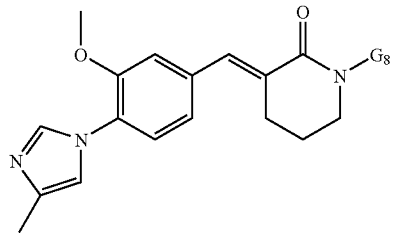
| Example | $G_8$ | DATA:MS m/z | Note |
|---|---|---|---|
| 789 | 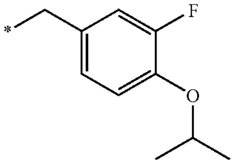 | $M^+$ + H:464 (ESI) | |
| 790 | 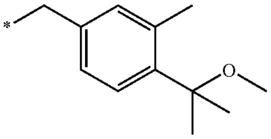 | $M^+$ + H:474 (ESI) | |
| 791 | 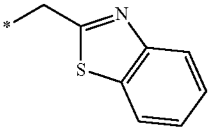 | $M^+$ + H:445 (ESI) | |
| 792 | 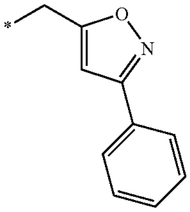 | $M^+$ + H:455 (ESI) | |
| 793 | 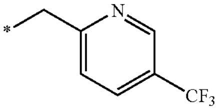 | $M^+$ + H:457 (ESI) | |
| 794 | 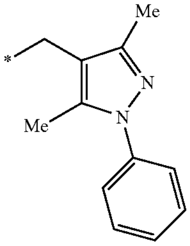 | $M^+$ + H:482 (ESI) | |
| 795 | 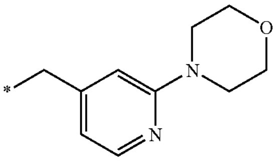 | $M^+$ + H:474 (ESI) | |

TABLE 20-continued
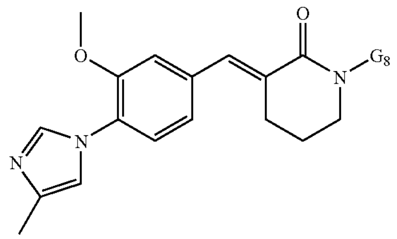
| Example | $G_8$ | DATA:MS m/z | Note |
|---|---|---|---|
| 796 | 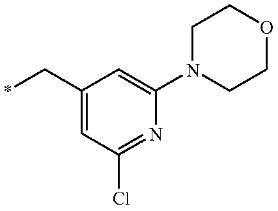 | $M^+$ + H:508 (ESI) | |
| 797 | 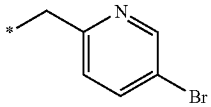 | $M^+$ + H:467 (ESI) | |
| 798 | 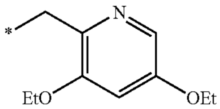 | $M^+$ + H:477 (ESI) | |
| 799 | 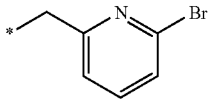 | $M^+$ + H:467 (ESI) | |
| 800 | 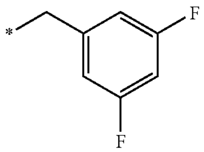 | $M^+$ + H:424 (ESI) | |
| 801 | 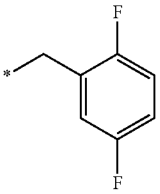 | $M^+$ + H:424 (ESI) | |
| 802 | 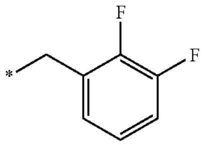 | $M^+$ + H:424 (ESI) | |
| 803 | 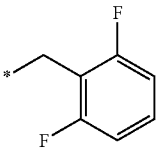 | $M^+$ + H:424 (ESI) | |

TABLE 20-continued
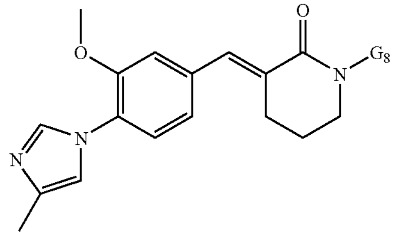
| Example | $G_8$ | DATA:MS m/z | Note |
|---|---|---|---|
| 804 | 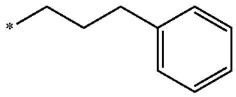 | $M^+$ + H:416 (ESI) | |
| 805 | 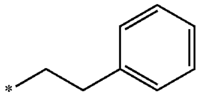 | $M^+$ + H:402 (ESI) | |
| 806 | 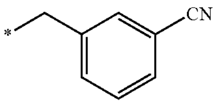 | $M^+$ + H:413 (ESI) | |
| 807 | 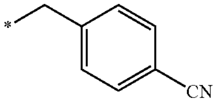 | $M^+$ + H:413 (ESI) | |
| 808 | 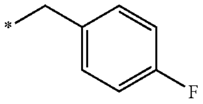 | $M^+$ + H:406 (ESI) | |
| 809 | 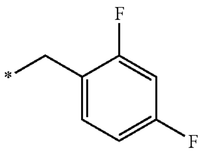 | $M^+$ + H:424 (ESI) | |
| 810 | 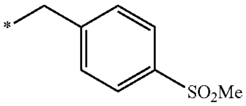 | $M^+$ + H:466 (ESI) | |
| 811 | 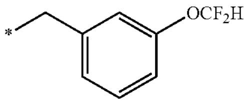 | $M^+$ + H:454 (ESI) | |
| 812 | 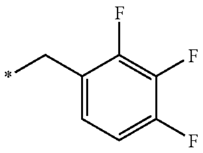 | $M^+$ + H:442 (ESI) | |
| 813 | 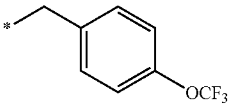 | $M^+$ + H:472 (ESI) | |

TABLE 20-continued
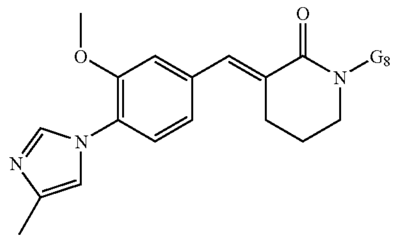
| Example | $G_8$ | DATA:MS m/z | Note |
| --- | --- | --- | --- |
| 814 | 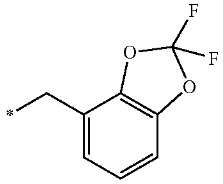 | $M^+$ + H:468 (ESI) | |
| 815 | 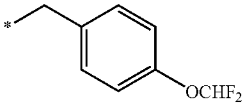 | $M^+$ + H:454 (ESI) | |
| 816 | 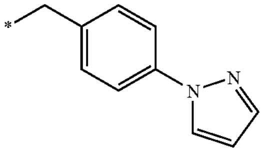 | $M^+$ + H:454 (ESI) | |
| 817 | 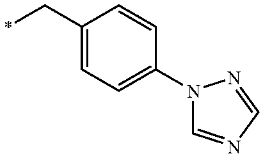 | $M^+$ + H:455 (ESI) | |
| 818 | 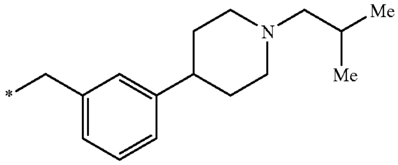 | $M^+$ + H:527 (ESI) | |
| 819 | 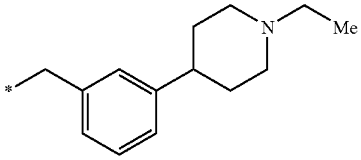 | $M^+$ + H:499 (ESI) | |
| 820 | 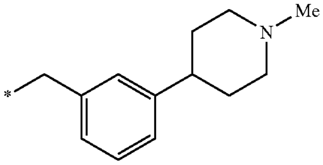 | $M^+$ + H:485 (ESI) | |

TABLE 20-continued
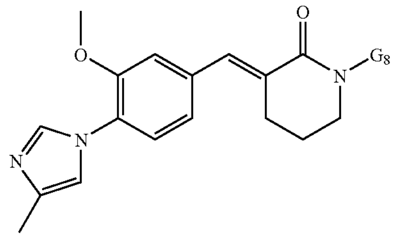
| Example | $G_8$ | DATA:MS m/z | Note |
|---|---|---|---|
| 821 | 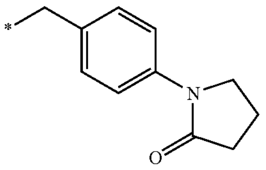 | $M^+$ + H:471 (ESI) | |
| 822 | 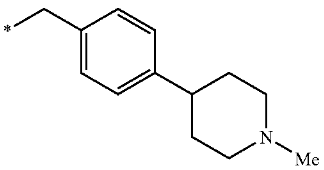 | $M^+$ + H:485 (ESI) | |
| 823 | 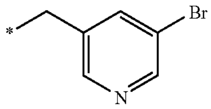 | $M^+$ + H:467 (ESI) | |
| 824 | 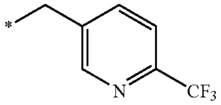 | $M^+$ + H:457 (ESI) | |
| 825 | 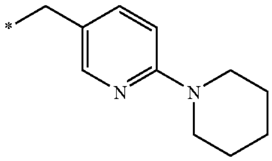 | $M^+$ + H:472 (ESI) | |
| 826 | 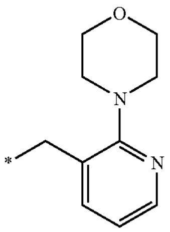 | $M^+$ + H:474 (ESI) | |
| 827 | 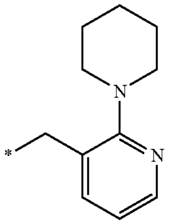 | $M^+$ + H:472 (ESI) | |

TABLE 20-continued
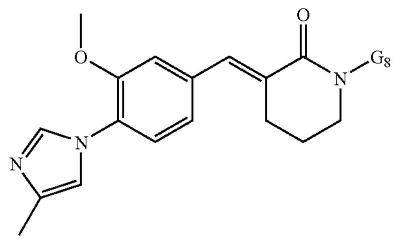
| Example | $G_8$ | DATA:MS m/z | Note |
|---|---|---|---|
| 828 | 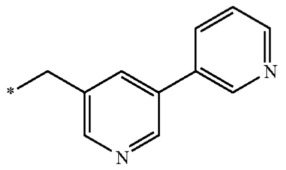 | $M^+$ + H:466 (ESI) | |
| 829 | 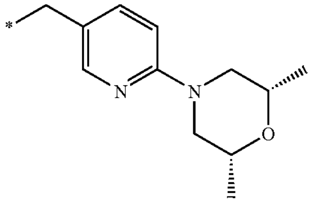 | $M^+$ + H:502 (ESI) | |
| 830 | 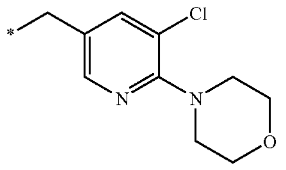 | $M^+$ + H:508 (ESI) | |
| 831 | 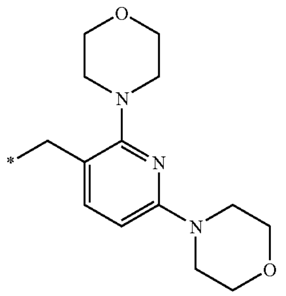 | $M^+$ + H:559 (ESI) | |

TABLE 20-continued

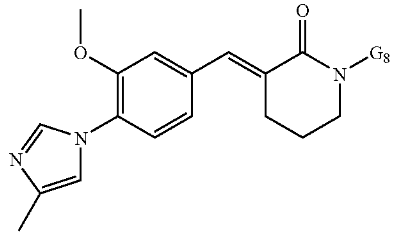

| Example | $G_8$ | DATA:MS m/z | Note |
|---|---|---|---|
| 832 | 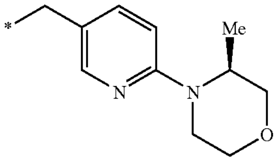 | $M^+$ + H:488 (ESI) | optically active substance |
| 833 | 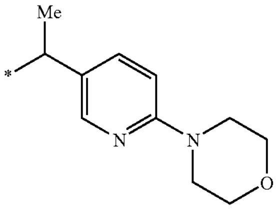 | $M^+$ + H:488 (ESI) | |
| 834 | 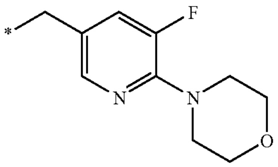 | $M^+$ + H:492 (ESI) | |
| 835 | 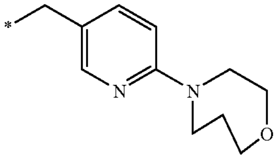 | $M^+$ + H:488 (ESI) | |
| 836 | 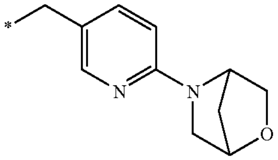 | $M^+$ + H:486 (ESI) | optically active substance |
| 837 | 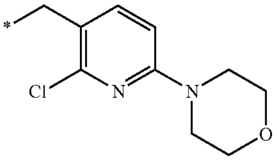 | $M^+$ + H:508 (ESI) | |
| 838 | 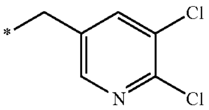 | $M^+$ + H:457 (ESI) | |

The compounds shown in Table 21 were synthesized as in Example 85. The structural formulae and physical properties are shown in Table 21, respectively. The separation conditions in the notes to the table are as follows: Separation Condition E: CHIRALCELK™ OD available from Daicel Chemical Industries, Ltd. (2 cm×25 cm: mobile phase: hexane-ethanol)

TABLE 21

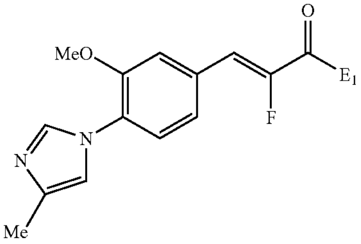

| Example | $E_1$ | DATA:MS m/z | Note |
|---|---|---|---|
| 839 | 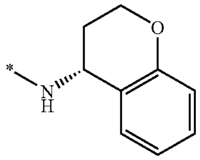 | $M^+$ + H:408 (ESI) | optically active substance (separation condition E: retention time: 8.7 minutes; absolute configuration: unknown) |
| 840 | 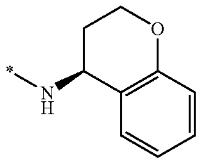 | $M^+$ + H:408 (ESI) | optically active substance (separation condition E: retention time: 13.6 minutes; absolute configuration: unknown) |

The compounds shown in Table 22 were synthesized as in the Example 121. The structural formulae and physical properties are shown in Table 22, respectively.

TABLE 22

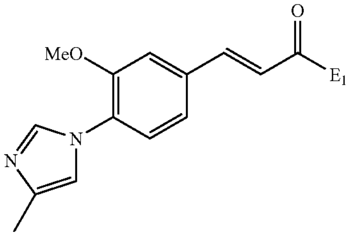

| Example | $E_1$ | DATA: MS m/z |
|---|---|---|
| 841 | 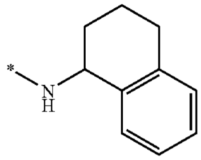 | $M^+$ + H:388 (ESI) |
| 842 | 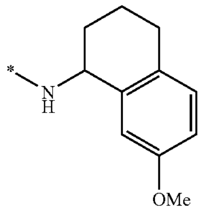 | $M^+$ + H:418 (ESI) |

TABLE 22-continued

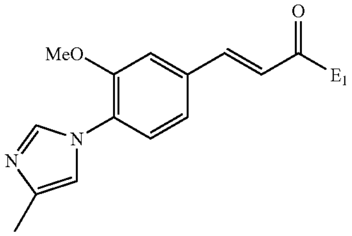

| Example | $E_1$ | DATA: MS m/z |
|---|---|---|
| 843 | 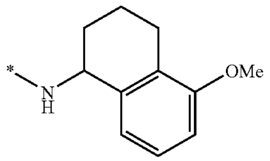 | $M^+$ + H:418 (ESI) |
| 844 | 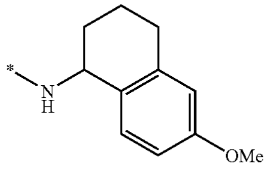 | $M^+$ + H:458 (ESI) |
| 845 | 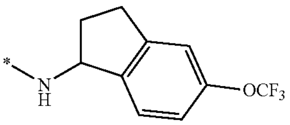 | $M^+$ + H:408 (ESI) |

TABLE 22-continued

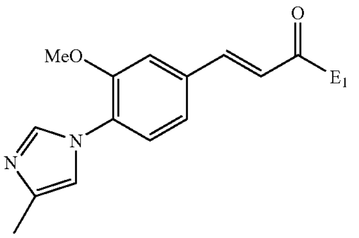

| Example | $E_1$ | DATA: MS m/z |
|---|---|---|
| 846 | 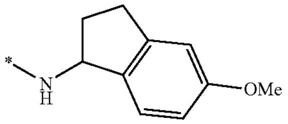 | $M^+$ + H:40 4 (ESI) |
| 847 | 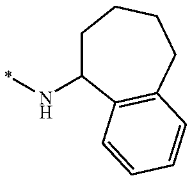 | $M^+$ + H:40 2 (ESI) |
| 848 | 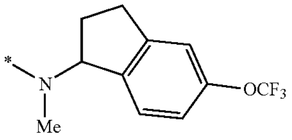 | $M^+$ + H:47 2 (ESI) |
| 849 | 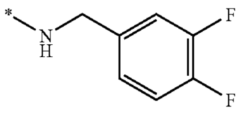 | $M^+$ + H:38 4 (ESI) |
| 850 | 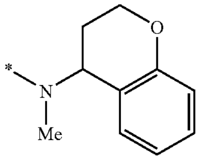 | $M^+$ + H:40 4 (ESI) |

The compound shown in Table 23 was synthesized as in Example 1. The structural formulae and physical properties are shown in Table 23, respectively.

TABLE 23

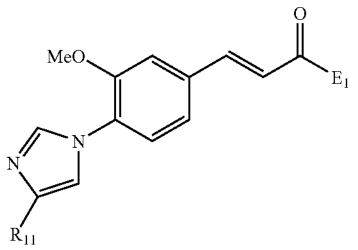

| Example | R11 | $E_1$ | DATA: MS m/z | Note |
|---|---|---|---|---|
| 851 | Me | 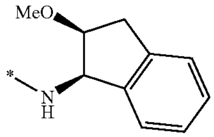 | $M^+$ + H:40 4 (ESI) | optically active substance |
| 852 | Et | 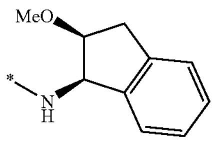 | $M^+$ + H:41 8 (ESI) | optically active substance |

The compounds shown in Table 24 were synthesized as in Example 121. The structural formulae and physical properties are shown in Table 24, respectively.

TABLE 24

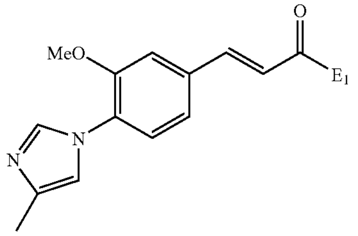

| Example | $E_1$ | DATA: MS m/z |
|---|---|---|
| 853 | 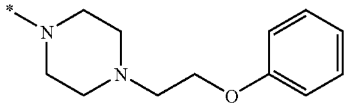 | $M^+$ + H:44 7 (ESI) |
| 854 | 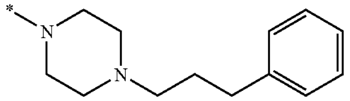 | $M^+$ + H:44 5 (ESI) |
| 855 | 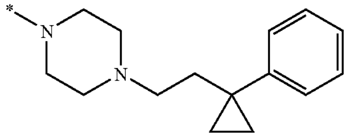 | $M^+$ + H:47 1 (ESI) |

TABLE 24-continued

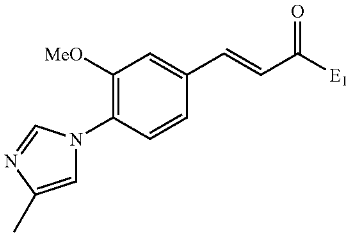

| Example | $E_1$ | DATA: MS m/z |
|---|---|---|
| 856 | 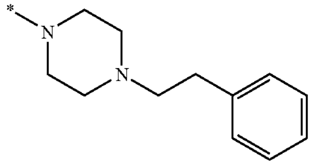 | $M^+$ + H:431 (ESI) |
| 857 | 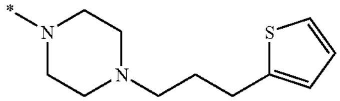 | $M^+$ + H:431 (ESI) |
| 858 | 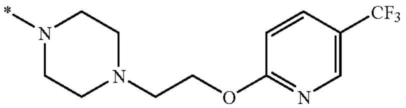 | $M^+$ + H:516 (ESI) |
| 859 | 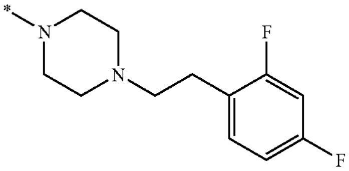 | $M^+$ + H:467 (ESI) |
| 860 | 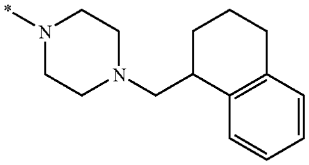 | $M^+$ + H:471 (ESI) |
| 861 | 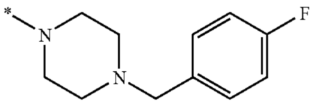 | $M^+$ + H:435 (ESI) |

TABLE 24-continued

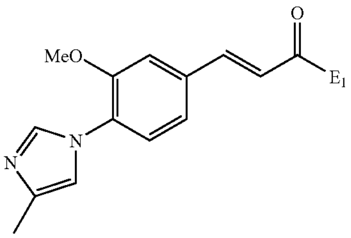

| Example | $E_1$ | DATA: MS m/z |
|---|---|---|
| 862 | 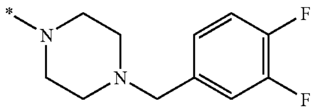 | $M^+$ + H:453 (ESI) |
| 863 | 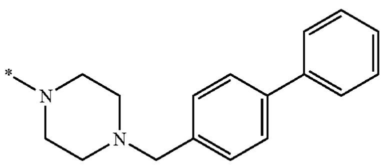 | $M^+$ + H:493 (ESI) |
| 864 | 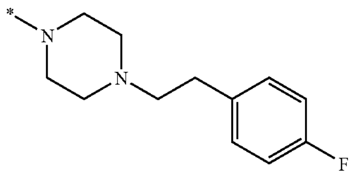 | $M^+$ + H:449 (ESI) |
| 865 | 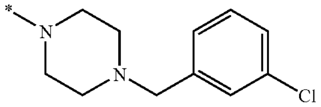 | $M^+$ + H:451 (ESI) |
| 866 | 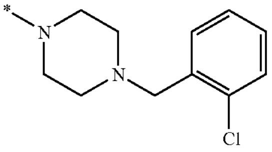 | $M^+$ + H:451 (ESI) |
| 867 | 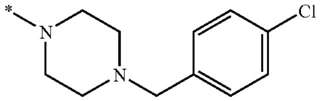 | $M^+$ + H:451 (ESI) |

The compounds shown in Table 24 were synthesized as in Example 418. The structural formulae and physical properties are shown in Table 25, respectively. The separation conditions in the notes to the table are as follows: Separation Condition A: CHIRALPAK™ AD-H available from Daicel Chemical Industries, Ltd. (2 cm×25 cm: mobile phase: hexane-ethanol system)

TABLE 25

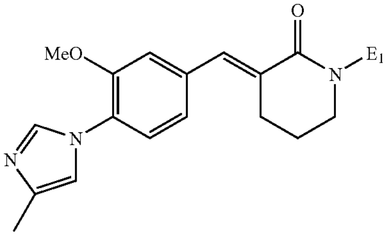

| Example | $E_1$ | DATA; MS m/z | Note |
|---|---|---|---|
| 868 | 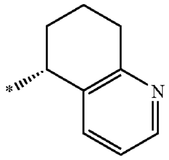 | $M^+$ + H:429 (ESI) | optically active substance (separation condition A: retention time: 71.1 minutes; absolute configuration: unknown) |
| 869 | 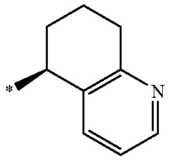 | $M^+$ + H:429 (ESI) | optically active substance (separation condition A: retention time: 77.9 minutes; absolute configuration: unknown) |
| 870 | 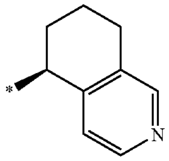 | $M^+$ + H:429 (ESI) | optically active substance (separation condition A: retention time: 8.7 minutes; absolute configuration: unknown) |
| 871 | 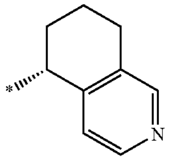 | $M^+$ + H:429 (ESI) | optically active substance (separation condition A: retention time: 10.6 minutes; absolute configuration: unknown) |
| 872 | 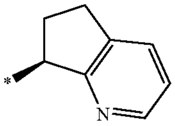 | $M^+$ + H:415 (ESI) | optically active substance (separation condition A: retention time: 9.5 minutes; absolute configuration: unknown) |
| 873 | 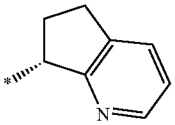 | $M^+$ + H:415 (ESI) | optically active substance (separation condition A: retention time: 11.0 minutes; absolute configuration: unknown) |
| 874 | 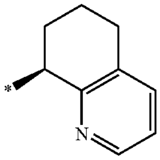 | $M^+$ + H:429 (ESI) | optically active substance (separation condition A: retention time: 8.7 minutes; absolute configuration: unknown) |
| 875 | 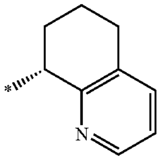 | $M^+$ + H:429 (ESI) | optically active substance (separation condition A: retention time: 9.7 minutes; absolute configuration: unknown) |

TABLE 25-continued

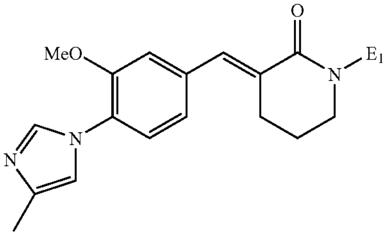

| Example | $E_1$ | DATA; MS m/z | Note |
|---|---|---|---|
| 876 | 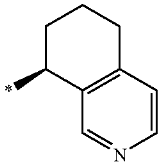 | $M^+$ + H:429 (ESI) | optically active substance (separation condition A: retention time: 12.8 minutes; absolute configuration: unknown) |
| 877 | 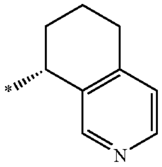 | $M^+$ + H:429 (ESI) | optically active substance (separation condition A: retention time: 15.9 minutes; absolute configuration: unknown) |
| 878 | 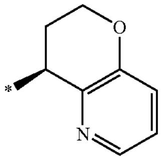 | $M^+$ + H:431 (ESI) | optically active substance (separation condition A: retention time: 10.4 minutes; absolute configuration: unknown) |
| 879 | 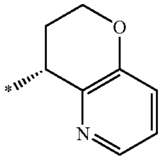 | $M^+$ + H:431 (ESI) | optically active substance (separation condition A: retention time: 13.5 minutes; absolute configuration: unknown) |
| 880 | 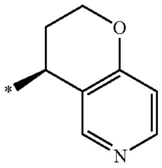 | $M^+$ + H:431 (ESI) | optically active substance (separation condition A: retention time: 5.1 minutes; absolute configuration: unknown) |
| 881 | 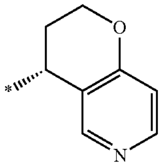 | $M^+$ + H:431 (ESI) | optically active substance (separation condition A: retention time: 6.3 minutes; absolute configuration: unknown) |

The compounds shown in Table 26 were synthesized as in Example 418. The structural formulae and physical properties are shown in Table 26, respectively. The separation conditions in the notes to the table are as follows: Separation Condition A: CHIRALPAK™ AD-H available from Daicel Chemical Industries, Ltd. (2 cm×25 cm: mobile phase: hexane-ethanol system) Separation Condition B: CHIRALPAK™ OJ-H available from Daicel Chemical Industries, Ltd. (2 cm×25 cm: mobile phase: hexane-ethanol system)

TABLE 26

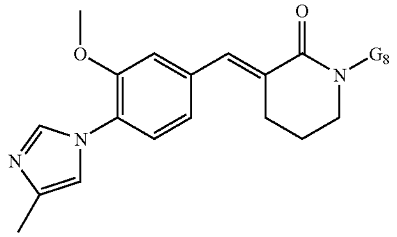

| Example | $G_8$ | DATA: MS m/z | Note |
|---|---|---|---|
| 883 | 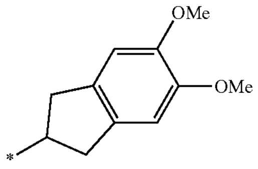 | $M^+$ + H:474 (ESI) | |
| 884 | 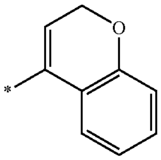 | $M^+$ + H:428 (ESI) | |
| 885 | 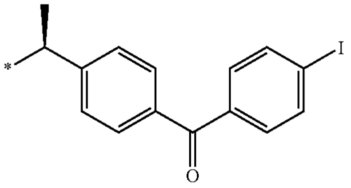 | $M^+$ + H:634 (ESI) | optically active substance (separation condition B: retention time: 7 minutes; absolute configuration: unknown) |
| 886 | 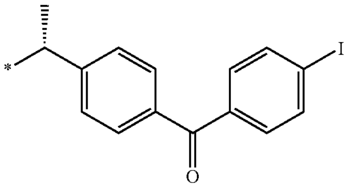 | $M^+$ + H:634 (ESI) | optically active substance (separation condition B: retention time: 19 minutes; absolute configuration: unknown) |
| 887 | 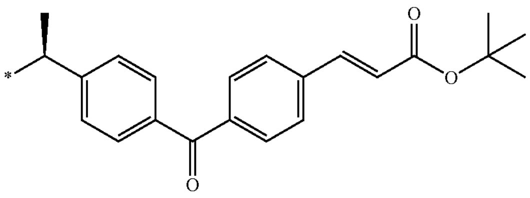 | $M^+$ + H:632 (ESI) | optically active substance |
| 888 | 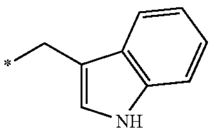 | $M^+$ + H:427 (ESI) | |
| 889 | 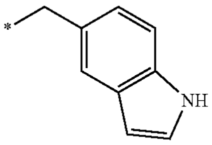 | $M^+$ + H:427 (ESI) | |

TABLE 26-continued
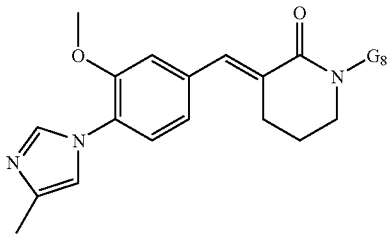
| Example | $G_8$ | DATA: MS m/z | Note |
|---|---|---|---|
| 890 | 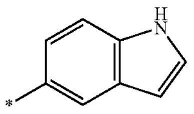 | $M^+$ + H:413 (ESI) | |
| 891 | 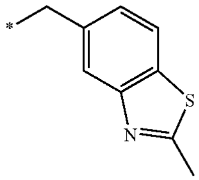 | $M^+$ + H:459 (ESI) | |
| 892 | 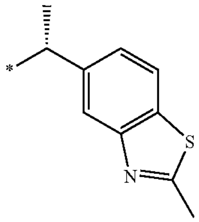 | $M^+$ + H:473 (ESI) | optically active substance (separation condition A: retention time: 12 minutes; absolute configuration: unknown) |
| 893 | 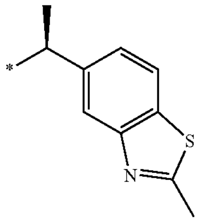 | $M^+$ + H:473 (ESI) | optically active substance (separation condition A: retention time: 17 minutes; absolute configuration: unknown) |
| 894 | 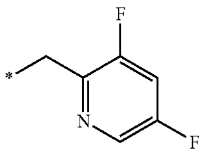 | $M^+$ + H:425 (ESI) | |
| 895 | 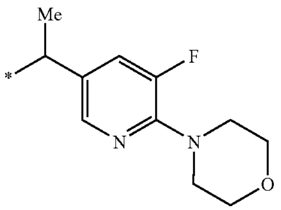 | $M^+$ + H:506 (ESI) | racemate |

TABLE 26-continued
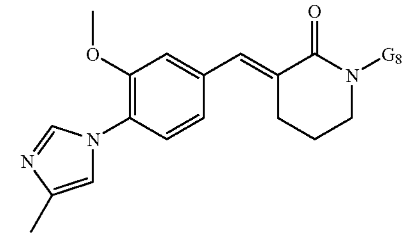
| Example | $G_8$ | DATA: MS m/z | Note |
|---|---|---|---|
| 896 | 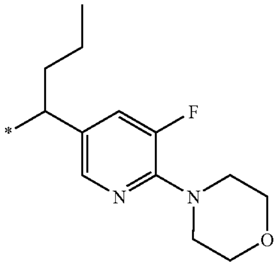 | $M^+ + H$:534 (ESI) | racemate |
| 897 | 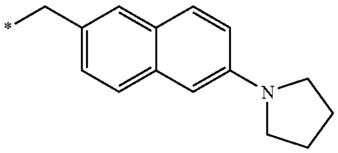 | $M^+ + H$:507 (ESI) | |
| 898 | 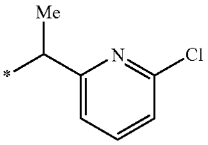 | $M^+ + H$:437 (ESI) | racemate |
| 899 | 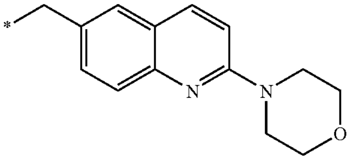 | $M^+ + H$:524 (ESI) | |
| 900 | 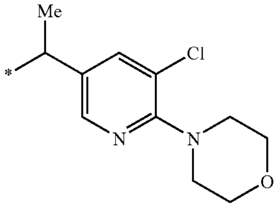 | $M^+ + H$:522 (ESI) | racernate |
| 901 | 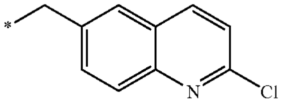 | $M^+ + H$:473 (ESI) | |
| 902 | 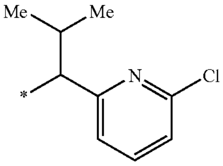 | $M^+ + H$:465 (ESI) | racemate |

TABLE 26-continued

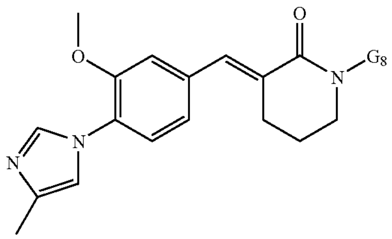

| Example | $G_8$ | DATA: MS m/z | Note |
|---|---|---|---|
| 903 | 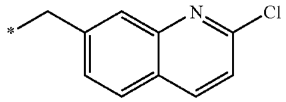 | $M^+$ + H:473 (ESI) | |
| 904 | 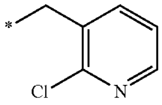 | $M^+$ + H:423 (ESI) | |
| 905 | 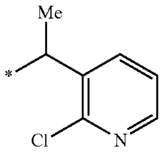 | $M^+$ + H:437 (ESI) | racemate |
| 906 | 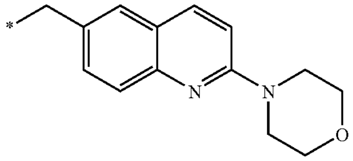 | $M^+$ + H:524 (ESI) | |
| 907 | 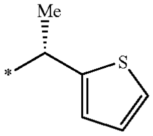 | $M^+$ + H:408 (ESI) | optically active substance (separation condition A: retention time: 22 minutes; absolute configuration: unknown) |
| 908 | 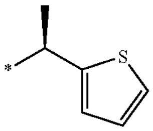 | $M^+$ + H:408 (ESI) | optically acitve substance (separation condition A: retention time: 30 minutes; absolute configuration: unknown) |
| 909 | 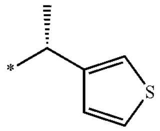 | $M^+$ + H:408 (ESI) | optically active substance (separation condition A: retention time: 26 minutes; absolute configuration: unknown) |
| 910 | 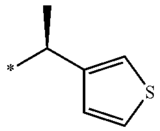 | $M^+$ + H:408 (ESI) | optically active substance (separation condition A: retention time: 33 minutes; absolute configuration: unknown) |
| 911 | 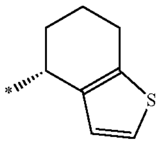 | $M^+$ + H:434 (ESI) | optically active substance (separation condition A: retention time: 33 minutes; absolute configuration: unknown) |

TABLE 26-continued

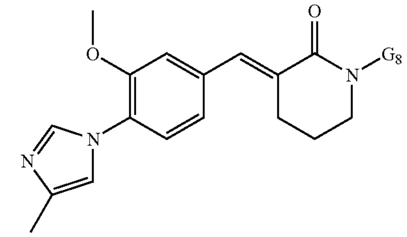

| Example | $G_8$ | DATA: MS m/z | Note |
|---|---|---|---|
| 912 | 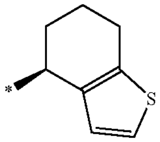 | $M^+$ + H:434 (ESI) | optically active substance (separation condition A: retention time: 54 minutes; absolute configuration: unknown) |
| 913 | 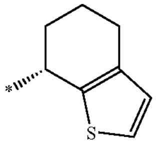 | $M^+$ + H:434 (ESI) | optically active substance (separation condition A: retention time: 32 minutes: absolute configuration: unknown) |
| 914 | 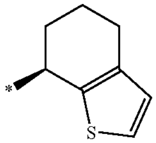 | $M^+$ + H:434 (ESI) | optically active substance (sepatation condition A: retention time: 39 minutes; absolute configuration: unknown) |
| 915 | 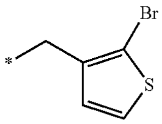 | $M^+$ + H:473 (ESI) | |
| 916 | 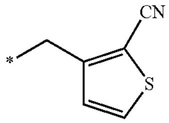 | $M^+$ + H:419 (ESI) | |
| 917 | 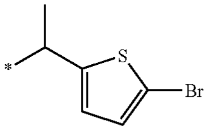 | $M^+$ + H:487 (ESI) | racemate |
| 918 | 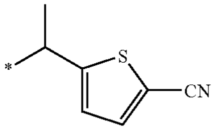 | $M^+$ + H:433 (ESI) | racemate |
| 919 | 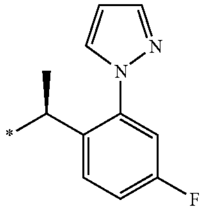 | $M^+$ + H:500 (ESI) | optically active substance (separation condition C: retention time: 10 minutes; absolute configuration: unknown) |

TABLE 26-continued

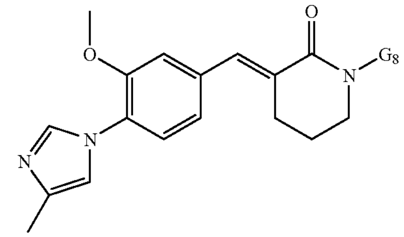

| Example | $G_8$ | DATA: MS m/z | Note |
|---|---|---|---|
| 920 | 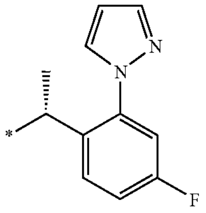 | $M^+$ + H:464 (ESI) | optically active substance (separation condition C: retention time: 12 minutes; absolute configuration: unknown) |
| 921 | 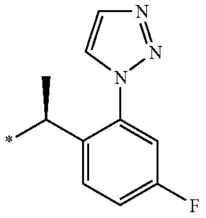 | $M^+$ + H:420 (ESI) | optically active substance (separation condition A: retention time: 9 minutes; absolute configuration: unknown) |
| 922 | 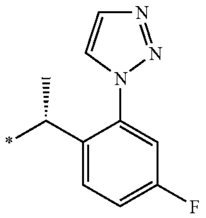 | $M^+$ + H:464 (ESI) | optically active substance (speatation condition A: retention time: 14 minutes; absolute configuration: unknown) |
| 923 | 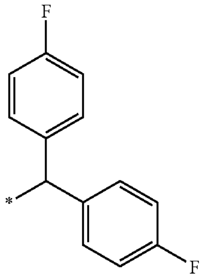 | $M^+$ + H:500 (ESI) | |
| 924 | 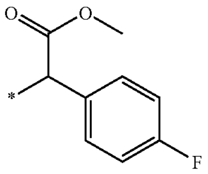 | $M^+$ + H:464 (ESI) | racemate |
| 925 | 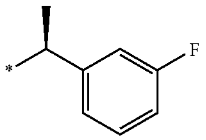 | $M^+$ + H:420 (ESI) | optically active substance |

TABLE 26-continued

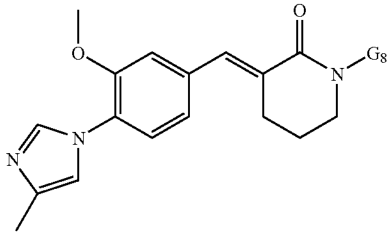

| Example | $G_8$ | DATA: MS m/z | Note |
|---|---|---|---|
| 926 | 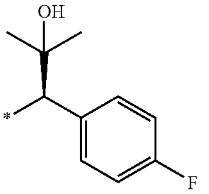 | $M^+$ + H:464 (ESI) | optically active substance |

Example 927 and Example 928

Synthesis of (E)-1-{(R)-(4-fluorophenyl)-[(S)-tetrahydrofuran-2-yl]methyl]-3-[3-methoxy-4-(4-methyl-1H-imidazol-1-yl)benzylidene]piperidin-2-one and (E)-1-{(S)-(4-fluorophenyl)-[(R)-tetrahydrofuran-2-yl}methyl}-3-[3-methoxy-4-(4-methyl-1H-imidazol-1-yl) benxylidene]piperidin-2-one

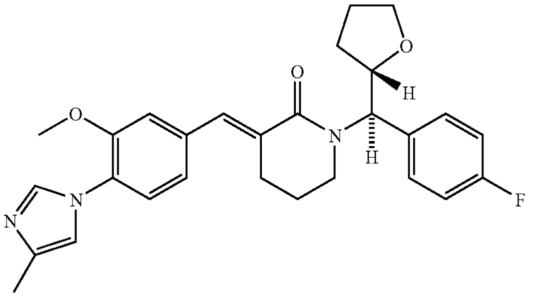

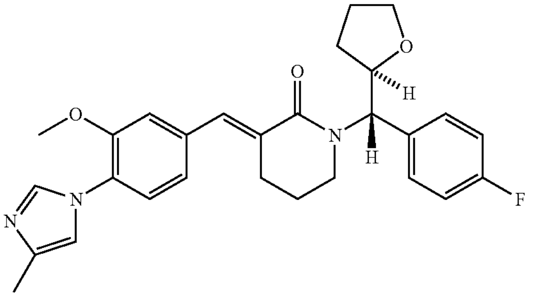

Synthesis of erythro-(4-fluorophenyl)-(tetrahydrofuran-2-yl)methyl azide

Diethyl azodicarboxylate (120 mg), threo-(4-fluorophenyl)-(tetrahydrofuran-2-yl)methanol (90 mg) synthesized in accordance with a method described in Chem. Comm., 1999, p. 1745, and diphenylphosphoryl azide (0.099 mL) were sequentially added to a solution of triphenylphosphine (180 mg) in THF (5 mL) at 0° C., and the reaction solution was stirred for 1 hour. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent:heptane→heptane:ethyl acetate=4:1) to obtain 28 mg of the title compound. The physical properties of the compound are as follows.

$^1$H-NMR ($CDCl_3$) δ (ppm): 1.79-1.94 (m, 4H), 3.76-3.82 (m, 1H), 3.85-3.93 (m, 1H), 4.08-4.14 (m, 1H), 4.63 (d, J=4.8 Hz, 1H), 7.01-7.08 (m, 2H), 7.26-7.33 (m, 2H).

Synthesis of erythro-(4-fluorophenyl)-(tetrahydrofuran-2-yl)methylamine

10% palladium-carbon (water content: 50%, 5 mg) was added to a solution of erythro-(4-fluorophenyl)-(tetrahydrofuran-2-yl)methylazide (28 mg) in ethanol, and the reaction solution was stirred in a hydrogen stream at room temperature for 10 hours. The reaction solution was filtered on a celite, and the filtrate was concentrated under reduced pressure to obtain 25 mg of the title compound. The physical properties of the compound are as follows.

$^1$H-NMR ($CDCl_3$) δ (ppm): 1.55-1.99 (m, 4H), 3.66-3.83 (m, 2H), 4.25-4.40 (m, 2H), 6.97-7.06 (m, 2H), 7.44-7.55 (m, 2H), 8.78-9.02 (brs, 2H).

Synthesis of (E)-1-{(R)-(4-fluorophenyl)-[(S)-tetrahydrofuran-2-yl]methyl}-3-[3-methoxy-4-(4-methyl-1H-imidazol-1-yl)benzylidene]piperidin-2-one and (E)-1-{(S)-(4-fluorophenyl)-[(R)-tetrahydrofuran-2-yl]methyl}-3-[3-methoxy-4-(4-methyl-1H-imidazol-1-yl)benzylidene]piperidin-2-one 41 mg of a racemate was obtained from (E)-5-chloro-2-(3-methoxy-4-(4-methyl-1H-imidazol-1-yl)benzylidene)valeric acid trifluoroacetate (63 mg) and erythro-(4-fluorophenyl)-(tetrahydrofuran-2-yl)methylamine (25 mg) in the same manner as in Example 418.

The racemate (41 mg) was fractionated using CHIRALPAK™ AD-H manufactured by Daicel Chemical Industries, Ltd. (2 cm×25 cm: mobile phase: hexane:ethanol=3:7) to obtain the title optically active substance with a retention time of 43 minutes (13.5 mg; >99% ee) and the title optically active substance with a retention time of 64 minutes (10.5 mg; >99% ee).

The physical properties of the optically active substance with a retention time of 43 minutes (Example 927) are as follows.

$^1$H-NMR ($CDCl_3$) δ (ppm): 1.61-1.72 (m, 1H), 1.77-2.12 (m, 5H), 2.30 (s, 3H), 2.74-2.80 (m, 2H), 3.06-3.14 (m, 1H), 3.27-3.35 (m, 1H), 3.82-3.96 (m, 5H), 4.52-4.59 (m, 1H), 5.92 (d, J=8.8 Hz, 1H), 6.93 (brs, 1H), 6.99-7.05 (m, 4H), 7.24 (d, J=8.0 Hz, 1H), 7.46-7.50 (m, 2H), 7.72 (d, J=1.2 Hz, 1H), 7.87 (brs, 1H).

The physical properties of the optically active substance with a retention time of 64 minutes (Example 928) are as follows.

$^1$H-NMR ($CDCl_3$) δ (ppm): 1.61-1.72 (m, 1H), 1.77-2.12 (m, 5H), 2.30 (s, 3H), 2.74-2.80 (m, 2H), 3.06-3.14 (m, 1H), 3.27-3.35 (m, 1H), 3.82-3.96 (m, 5H), 4.52-4.59 (m, 1H), 5.92 (d, J=8.8 Hz, 1H), 6.93 (brs, 1H), 6.99-7.05 (m, 4H), 7.24 (d, J=8.0 Hz, 1H), 7.46-7.50 (m, 2H), 7.72 (d, J=1.2 Hz, 1H), 7.87 (brs, 1H).

Example 929 and Example 930

Synthesis of (E)-1-{(R)-(4-fluorophenyl)-[(R)-tetrahydrofuran-2-yl]methyl}-3-[3-methoxy-4-(4-methyl-1H-imidazol-1-yl)benzylidene]piperidin-2-one and (E)-1-{(S)-(4-fluorophenyl)-[(S)-tetrahydrofuran-2-yl]methyl}-3-[3-methoxy-4-(4-methyl-1H-imidazol-1-yl)benzylidene]piperidin-2-one

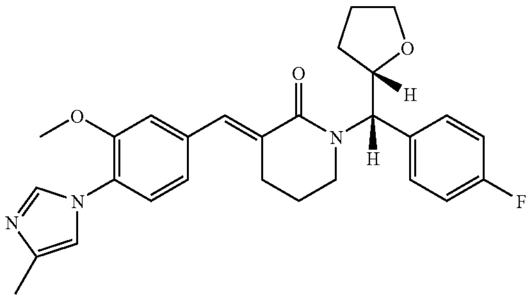

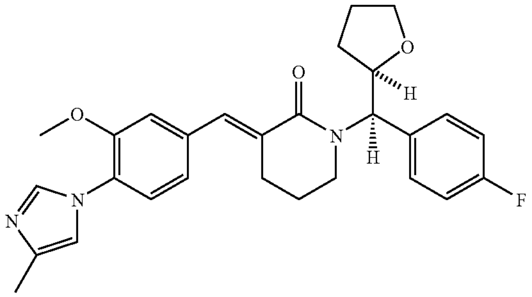

Synthesis of erythro-(4-fluorophenyl)-(tetrahydrofuran-2-yl)methanol

Diethyl azodicarboxylate (491 mg), threo-(4-fluorophenyl)-(tetrahydrofuran-2-yl)methanol (368 mg), and benzoic acid (251 mg) were sequentially added to a solution of triphenylphosphine (736 mg) in THF (20 mL) at 0° C. The reaction solution was stirred at 0° C. for 1 hour, and was further stirred at room temperature for 12 hours. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (elution solvent: heptane→heptane:ethyl acetate=3:1) to obtain 187 mg of (4-fluorophenyl)-(tetrahydrofuran-2-yl)methyl benzoate. A 1 N aqueous solution of sodium hydroxide (3 mL) was added to a solution of the resulting (4-fluorophenyl)-(tetrahydrofuran-2-yl)methyl benzoate (187 mg) in methanol (5 mL), and the reaction solution was stirred at room temperature for 4 hours. Brine and ethyl acetate were added to the reaction solution and the organic layer was partitioned. The resulting organic layer was dried over magnesium sulfate, and concentrated under reduced pressure to obtain 120 mg of the title compound.

The physical properties of the compound are as follows.

$^1$H-NMR ($CDCl_3$) δ (ppm): 1.54-1.90 (m, 4H), 3.77-3.85 (m, 1H), 3.89-3.96 (m, 1H), 4.02-4.08 (m, 1H), 4.90 (d, J=4.0 Hz, 1H), 6.99-7.05 (m, 2H), 7.31-7.36 (m, 2H).

Synthesis of threo-(4-fluorophenyl)-(tetrahydrofuran-2-yl)methylamine 81 mg of threo-(4-fluorophenyl)-(tetrahydrofuran-2-yl)methylamine was obtained from erythro-(4-fluorophenyl)-(tetrahydrofuran-2-yl)methanol (120 mg) in the same manner as in Example 927.

The physical properties of the compound are as follows.

$^1$H-NMR ($CDCl_3$) δ (ppm): 1.49-1.69 (m, 2H), 1.80-1.90 (m, 2H), 3.79-3.92 (m, 4H), 6.97-7.03 (m, 2H), 7.30-7.36 (m, 2H).

Synthesis of (E)-1-{(R)-(4-fluorophenyl)-[(R)-tetrahydrofuran-2-yl]methyl}-3-[3-methoxy-4-(4-methyl-1H-imidazol-1-yl)benzylidene]piperidin-2-one and (E)-1-{(S)-(4-fluorophenyl)-[(S)-tetrahydrofuran-2-yl]methyl}-3-[3-methoxy-4-(4-methyl-1H-imidazol-1-yl)benzylidene]piperidin-2-one A racemate obtained from (E)-5-chloro-2-(3-methoxy-4-(4-methyl-1H-imidazol-1-yl)benzylidene)valeric acid trifluoroacetate (205 mg) and threo-(4-fluorophenyl)-(tetrahydrofuran-2-yl)methylamine (81 mg) in the same manner as in Example 418 was fractionated using CHIRALCEL™ AD-H manufactured by Daicel Chemical Industries, Ltd. (2 cm×25 cm: mobile phase: hexane:ethanol=1:1) to obtain the title optically active substance with a retention time of 18 minutes (653 mg; >99% ee) and the title optically active substance with a retention time of 27 minutes (59 mg; >99% ee).

The physical properties of the optically active substance with a retention time of 18 minutes (Example 929) are as follows.

$^1$H-NMR ($CDCl_3$) δ (ppm): 1.56-1.73 (m, 2H), 1.82-2.12 (m, 4H), 2.31 (s, 3H), 2.74-2.82 (m, 2H), 3.10-3.18 (m, 1H), 3.50-3.58 (m, 1H), 3.81-3.98 (m, 5H), 4.58 (q, J=7.6 Hz, 1H), 5.97 (d, J=7.6 Hz, 1H), 6.92 (s, 1H), 6.99-7.06 (m, 4H), 7.23 (d, J=8.8 Hz, 1H), 7.40-7.46 (m, 2H), 7.73 (s, 1H), 7.86 (brs, 1H).

The physical properties of the optically active substance with a retention time of 27 minutes (Example 930) are as follows.

$^1$H-NMR ($CDCl_3$) δ (ppm): 1.56-1.73 (m, 2H), 1.82-2.12 (m, 4H), 2.31 (s, 3H), 2.74-2.82 (m, 2H), 3.10-3.18 (m, 1H), 3.50-3.58 (m, 1H), 3.81-3.98 (m, 5H), 4.58 (q, J=7.6 Hz, 1H), 5.97 (d, J=7.6 Hz, 1H), 6.92 (s, 1H), 6.99-7.06 (m, 4H), 7.23 (d, J=8.8 Hz, 1H), 7.40-7.46 (m, 2H), 7.73 (s, 1H), 7.86 (brs, 1H).

Example 931

Synthesis of (E)-3-[3-methoxy-4-(4-methyl-1H-imidazol-1-yl)benzylidene]-1-[phenyl(tetrahydrofuran-2-yl)methyl]piperidin-2-one

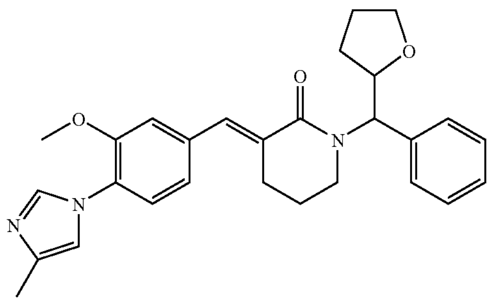

125 mg of the title compound was obtained in the same manner as in Example 418 from (E)-5-chloro-2-(3-methoxy-4-(4-methyl-1H-imidazol-1-yl)benzylidene)valeric acid trifluoroacetate (232 mg) and phenyl(tetrahydrofuran-2-yl)methylamine (92 mg) obtained in the same manner as in Example 927. The physical properties of the compound are as follows.

$^1$H-NMR ($CDCl_3$) δ (ppm): 1.58-2.14 (m, 6H), 2.30 (s, 3H), 2.73-2.80 (m, 2H), 3.07-3.21 (m, 1H), 3.27-3.35 (m, 0.3H), 3.50-3.58 (m, 0.7H), 3.82-3.97 (m, 5H), 4.58-4.67 (m, 1H), 5.97 (d, J=8.8 Hz, 0.3H), 6.00 (d, J=8.0 Hz, 0.7H), 6.92 (s, 1H), 7.01-7.05 (m, 2H), 7.22-7.53 (m, 6H), 7.71 (s, 1H), 7.87 (brs, 1H).

Example 932

Synthesis of (E)-1-[(1R)-1-(4-fluorophenyl)-2-methoxyethyl]-3-[3-methoxy-4-(4-methyl-1H-imidazol-1-yl)benzylidene]piperidin-2-one

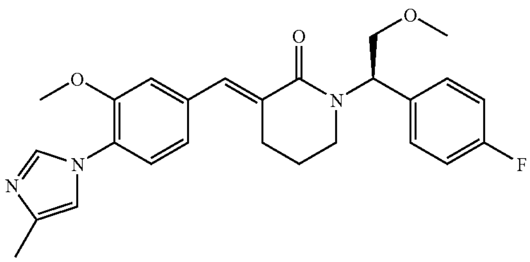

Sodium hydride (containing mineral oil at 40%, 24 mg) was added to a solution of (E)-1-(1-(4-fluorophenyl)-2-hydroxyethyl)-3-(3-methoxy-4-(4-methyl-1H-imidazol-1-yl)benzylidene)piperidin-2-one synthesized by the method described in Example 629 (216 mg) in THF (5 mL), and the reaction solution was stirred at room temperature for 50 minutes. Then, methyl iodide (85 mg) was added to the reaction solution, and the reaction solution was stirred at room temperature for 14 hours. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent:heptane:ethyl acetate=1:1→ethyl acetate) to obtain 185 mg of the title compound. The physical properties of the compound are as follows.

$^1$H-NMR ($CDCl_3$) δ (ppm): 1.64-1.76 (m, 1H), 1.81-1.92 (m, 1H), 2,31 (s, 3H), 2.73-2.85 (m, 2H), 3.07-3.15 (m, 1H), 3.34-3.42 (m, 1H), 3.45 (s, 3H), 3.85 (s, 3H), 3.86-4.01 (m, 2H), 6.17 (brt, J=6.4 Hz, 1H), 6.94 (brs, 1H), 7.00-7.09 (m, 4H), 7.25 (d, J=8.0 Hz, 1H), 7.31-7.39 (m, 2H), 7.73 (brs, 1H), 7.88 (brs, 1H).

Example 933

Synthesis of (E)-1-{(1,3]dioxolan-2-yl-(4-fluorophenyl)methyl}-3-[3-methoxy-4-(4-methyl-1H-imidazol-1-yl)benzylidene]piperidin-2-one

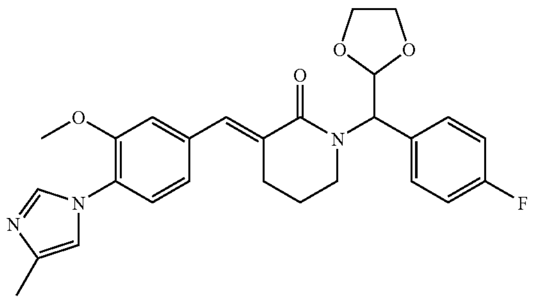

A solution of dimethyl sulfoxide (0.19 mL) in methylene chloride (1 mL) was added dropwise to a solution of oxalyl chloride (167 mg) in methylene chloride (2 mL) at −78° C. The reaction solution was stirred at −78° C. for 5 minutes, and then a solution of (E)-1-(1-(4-fluorophenyl)-2-hydroxyethyl)-3-(3-methoxy-4-(4-methyl-1H-imidazol-1-yl)benzylidene)piperidin-2-one synthesized by the method described in Example 629 (260 mg) in methylene chloride (3 mL) was added dropwise to the reaction solution. The reaction solution was stirred at −78° C. for 1 hour, and then triethylamine (0.42 mL) was added to the reaction solution. The reaction solution was stirred at −78° C. for 15 minutes, and further stirred at room temperature for 45 minutes. Saturated sodium bicarbonate water and ethyl acetate were added to the reaction solution and the organic layer was partitioned. The resulting organic layer was dried over magnesium sulfate, and concentrated under reduced pressure to obtain 250 mg of crude (E)-(4-fluorophenyl)-(3-(3-methoxy-4-(4-methyl-1H-imidazol-1-yl)benzylidene)-2-oxopiperidin-1-yl) acetaldehyde. p-Toluenesulfonic acid (107 mg) and ethylene glycol (0.29 mL) were added to a solution of the resulting crude (E)-(4-fluorophenyl)-(3-(3-methoxy-4-(4-methyl-1H) benzylidene)-2-oxopiperidin-1-yl)acetaldehyde (225 mg) in toluene (5 mL), and the reaction solution was heated to reflux for 1 hour and 20 minutes. After allowing the reaction solution to be cooled to room temperature, saturated sodium bicarbonate water and ethyl acetate were added to the reaction solution and the organic layer was partitioned. The resulting organic layer was dried-over magnesium sulfate, and concentrated under reduced pressure. The residue was purified by silica gel column chromatography (Carrier: Chromatorex™

NH, elution solvent:heptane:ethyl acetate=1:1→ethyl acetate) to obtain 7 mg of the title compound. The physical properties of the compound are as follows.

ESI-MS; m/z478 [M$^+$+H]. $^1$H-NMR ($CDCl_3$) δ (ppm): 1.63-1.75 (m, 1H), 1.82-1.93 (m, 1H), 2,33 (s, 3H), 2.77-2.84 (m, 2H), 3.16-3.24 (m, 1H), 3.47-3.55 (m, 1H), 3.86 (s, 3H), 3.92-4.10 (m, 4H), 5.52 (d, J=5.6 Hz, 1H), 6.07 (d, J=5.6 Hz, 1H), 6.94 (brs, 1H), 7.01-7.07 (m, 4H), 7.24 (d, J=8.0 Hz, 1H), 7.44-7.49 (m, 2H), 7.79 (brs, 1H), 7.89 (brs, 1H)

Example 934

Synthesis of (E)-2-(4-fluorophenyl)-2-{3-[3-methoxy-4-(4-methyl-1H-imidazol-1-yl)benzylidene]-2-oxopiperidin-1-yl}-N-methylacetamide

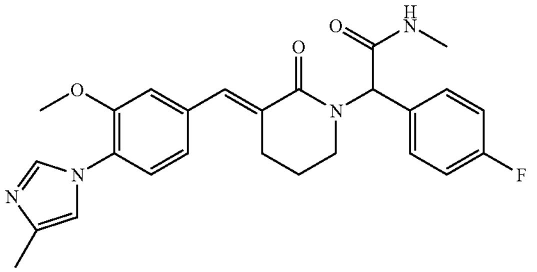

A 1 N aqueous solution of sodium hydroxide (0.8 mL) was added to a solution of a solution of methyl (E)-(4-fluorophenyl)-(3-(3-methoxy-4-(4-methyl-1H-imidazol-1-yl)benzylidene)-2-oxopiperidin-1-yl)acetate synthesized by the method described in Example 924 (74 mg) in methanol (3 mL), and the reaction solution was stirred at room temperature for 13 hours. 2 N hydrochloric acid (0.4 mL) was added to the reaction solution, and the reaction solution was concentrated under reduced pressure to obtain 72 mg of crude (E)-(4-fluorophenyl)-(3-(3-methoxy-4-(4-methyl-1H-imidazol-1-yl)benzylidene)-2-oxopiperidin-1-yl)acetic acid. HOBT (16 mg) and EDC (23 mg) were added to a solution of the resulting crude (E)-(4-fluorophenyl)-(3-(3-methoxy-4-(4-methyl-1H-imidazol-1-yl)benzylidene)-2-oxopiperidin-1-yl)acetic acid (36 mg) and methylamine (2M THF solution, 0.4 mL) in DMF (3 mL), and the reaction solution was stirred at room temperature for 5 hours. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent:ethyl acetate→ethyl acetate:methanol=9:1) to obtain 32 mg of the title compound. The physical properties of the compound are as follows.

$^1$H-NMR ($CDCl_3$) δ (ppm): 1.72-1.96 (m, 2H), 2,31 (s, 3H), 2.68-2.78 (m, 1H), 2.82-2.93 (m, 4H), 3.03-3.11 (m, 1H), 3.57-3.66 (m, 1H), 3.85 (s, 3H), 5.99 (brd, J=4.8 Hz, 1H), 6.35 (s, 1H), 6.93 (s, 1H), 6.99-7.09 (m, 4H), 7.25 (d, J=8.0 Hz, 1H), 7.37-7.45 (m, 2H), 7.74 (s, 1H), 7.83 (brs, 1H)

Example 935

Synthesis of (E)-2-(4-fluorophenyl)-2-{3-[3-methoxy-4-(4-methyl-1H-imidazol-1-yl)benzylidene]-2-oxopiperidin-1-yl}-N,N-dimethylacetamide

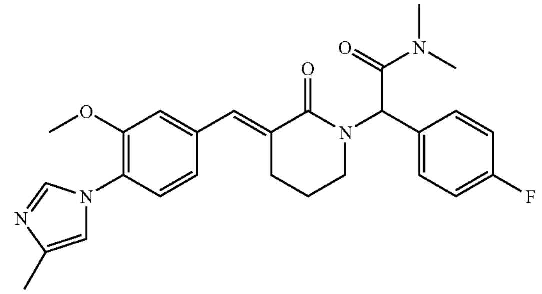

17 mg of the title compound was obtained from crude (E)-(4-fluorophenyl)-(3-(3-methoxy-4-(4-methyl-1H-imidazol-1-yl)benzylidene)-2-oxopiperidin-1-yl)acetic acid (36 mg) and dimethylamine (2M THF solution, 0.4 mL) in the same manner as in Example 934. The physical properties of the compound are as follows.

$^1$H-NMR ($CDCl_3$) δ (ppm): 1.66-1.76 (m, 1H), 1.89-1.99 (m, 1H), 2,31 (s, 3H), 2.67-2.75 (m, 1H), 2.81-2.91 (m, 2H), 2.95 (s, 3H), 3.04 (s, 3H), 3.63-3.70 (m, 1H), 3.85 (s, 3H), 6.79(s, 1H), 6.92(brs, 1H), 7.00-7.12 (m, 4H), 7.26 (d, J=8.0 Hz, 1H), 7.28-7.32 (m, 2H), 7.72 (s, 1H), 7.82 (brs, 1H).

Example 936 and Example 937

Synthesis of (E)-1-[5-fluoro-(2R)-hydroxyindan-(1S)-yl]-3-[3-methoxy-4-(4-methyl-1H-imidazol-1-yl)benzylidene]piperidin-2-one and (E)-1-[5-fluoro-(2S)-hydroxyindan-(1R)-yl]-3-[3-methoxy-4-(4-methyl-1H-imidazol-1-yl)benzylidene]piperidin-2-one

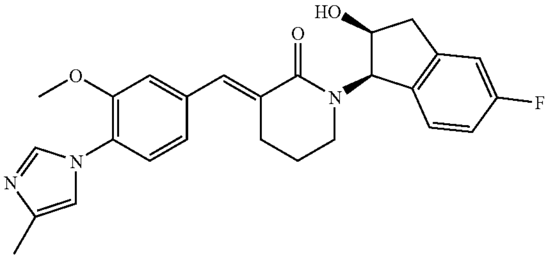

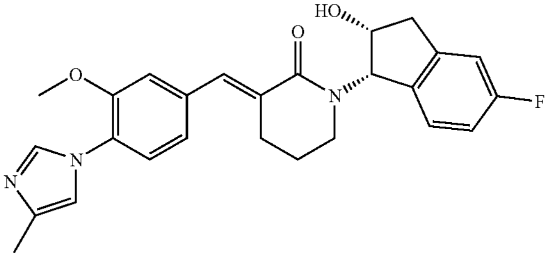

Synthesis of 2-bromo-5-fluoroindan-1-one

Bromine (1.98 mL) was added to a solution of 5-fluoroindanone (5.53 g) in acetic acid (100 mL), and the reaction solution was stirred at 60° C. for 10 minutes. After allowing the reaction solution to be cooled to room temperature, the solvent was evaporated under reduced pressure. Ethyl acetate and a saturated aqueous solution of sodium bicarbonate were added to the residue and the organic layer was partitioned. The resulting organic layer was dried over magnesium sulfate, and the solvent was evaporated under reduced pressure. The residue was purified by silica gel chromatography (elution solvent:heptane-ethyl acetate system) to obtain 8.43 g of the title compound. The physical properties of the compound are as follows.

$^1$H-NMR ($CDCl_3$) δ (ppm): 3.41 (dd, J=18.6, 2.8 Hz, 1H), 3.83 (dd, J=18.6, 7.6 Hz, 1H), 4.66 (dd, J=7.6, 2.8 Hz, 1H), 7.10-7.16 (m, 2H), 7.85 (dd, J=8.4, 5.2 Hz, 1H).

Synthesis of cis-2-bromo-5-fluoroindan-1-ol

Sodium borohydride (2.09 g) was added to a solution of 2-bromo-5-fluoroindan-1-one (8.43 g) in a mixture of tetrahydrofuran (120 mL) with methanol (30 mL) while cooling with ice, and the reaction solution was stirred for 20 minutes. Water and ethyl acetate were added to the reaction solution while cooling with ice and the organic layer was partitioned. The resulting organic layer was dried over magnesium sulfate, and the solvent was evaporated under reduced pressure. The resulting solid was washed with heptane to obtain 7.54 g of the title compound. The physical properties of the compound are as follows.

$^1$H-NMR ($CDCl_3$) δ (ppm): 2.42 (d, J=9.2 Hz, 1H), 3.32-3.44 (m, 2H), 4.88-4.95 (m, 2H), 6.93-7.00 (m, 2H), 7.38 (dd, J=8.0, 5.2Hz, 1H).

Synthesis of 2-bromo-5-fluoroindan-1-yl trans-4-nitrobenzoate

Diisopropyl azodicarboxylate (13.3 mL) was added dropwise to a solution of cis-2-bromo-5-fluoroindan-1-ol (7.74 g), 4-nitrobenzoic acid (10.9 g) and triphenylphosphine (17.1 g) in THF (250 mL), and the reaction solution was stirred at room temperature for 3 hours. Water and ethyl acetate were added to the reaction solution and the organic layer was partitioned. The resulting organic layer was dried over magnesium sulfate, and the solvent was evaporated under reduced pressure. The residue was purified by silica gel chromatography (elution solvent:heptane-ethyl acetate system) to obtain 7.19 g of the title compound. The physical properties of the compound are as follows.

$^1$H-NMR ($CDCl_3$) δ (ppm): 3.34 (dd, J=17.2, 3.6 Hz, 1H), 3.82 (dd, J=17.2, 6.8 Hz, 1H), 4.67-4.70 (m, 1H), 6.51 (d, J=3.2 Hz, 1H), 6.70-7.03 (m, 2H), 7.46 (dd, J=8.0, 4.8 Hz, 1H), 8.17 (d, J=9.2 Hz, 2H), 8.26 (d, J=9.2 Hz, 2H).

Synthesis of 4-fluoro-6,6a-dihydro-1aH-oxacycloprop[a]indene

Sodium methoxide (25 wt % methanol solution, 3.52 mL) was added to a solution of (2-bromo-5-fluoro-indan-1-yl) trans-4-nitrobenzoate (4.18 g) in dichloromethane (120 mL), and the reaction solution was stirred for 5 minutes while cooling with ice. Water and dichloromethane were added to the reaction solution and the organic layer was partitioned. The resulting organic layer was dried over magnesium sulfate, and the solvent was evaporated under reduced pressure. The residue was purified by silica gel chromatography (elution solvent:heptane-ethyl acetate system) to obtain 2.07 g of a crude purified product containing the title compound at Ca 30%. The physical properties of the compound are as follows.

$^1$H-NMR ($CDCl_3$) δ (ppm): 2.99 (dd, J=18.0 Hz, 2.4 Hz, 1H), 3.20 (d, J=18.0 Hz, 1H), 4.14 (dd, J=2.4, 2.4 Hz, 1H), 4.23 (d, J=2.4Hz, 1H), 6.83-6.93 (m, 2H), 7.42 (dd, J=8.0, 5.2Hz, 1H).

Synthesis of (E)-5-chloro-2-[3-methoxy-4-(4-methyl-1H-imidazol-1-yl)-benzylidene]valeric acid (5-fluoro-2-hydroxyindan-1-yl)amide Concentrated sulfuric acid (0.7 mL) was added to a solution of 4-fluoro-6,6a-dihydro-1aH-oxa-cycloprop[a]indene (purity: about 30 wt %, 2.07 g) in acetonitrile (30 mL), and the reaction solution was stirred at room temperature for 1 hour. Then, concentrated sulfuric acid (1 mL) and water (10 mL) were added to the reaction solution, and the reaction solution was heated to reflux for 4 hours. The reaction solution was returned to room temperature, made basic by the addition of 5 N sodium hydroxide, and then extracted with chloroform. The resulting organic layer was dried over magnesium sulfate, and the solvent was evaporated under reduced pressure. 5-chloro-2-(3-methoxy-4-(4-methyl-1H-imidazol-1-yl)benzylidene)valeric acid trifluoroacetate (1.86 g), IPEA (2 mL), EDC (2.38 g) and HOBT (1.68 g) were added to a solution of the resulting residue in DMF (20 mL), and the reaction solution was stirred at room temperature for 1 hour. Water and ethyl acetate were added to the reaction solution and the organic layer was partitioned. The resulting organic layer was dried over magnesium sulfate, and the solvent was evaporated under reduced pressure. The residue was purified by silica gel chromatography (Carrier: Chromatorex™ NH, elution solvent:heptane-ethyl acetate system→ethyl acetate-methanol system) to obtain 916 mg of the title compound. The physical properties of the compound are as follows.

$^1$H-NMR ($CDCl_3$) δ (ppm): 2.05 (m, 2H), 2.28 (d, J=1.2 Hz, 3H), 2.76 (m, 2H), 3.01 (dd, J=16.8 Hz, 2.0 Hz, 1H), 3.24 (dd, J=16.8 Hz, 5.2 Hz, 1H), 3.60 (t, J=6.0 Hz, 2H), 3.84 (s, 3H), 4.78 (td, J=5.2 Hz, J=2.0 Hz, 1H), 5.48 (m, 1H), 6.74 (d, J=8.0 Hz, 1H), 6.92-6.98 (m, 4H), 7.17 (d, J=8.0 Hz, 1H), 7.20 (s, 1H), 7.27 (dd, J=8.0 Hz, 4.8 Hz, 1H), 7.70 (d, J=1.2 Hz, 1H).

Synthesis of (E)-1-[5-fluoro-(2R)-hydroxyindan-(1S)-yl]-3-[3-methoxy-4-(4-methyl-1H-imidazol-1-yl)benzylidene]piperidin-2-one and (E)-1-[5-fluoro-(2S)-hydroxyindan-(1R)-yl]-3-[3-methoxy-4-(4-methyl-1H-imidazol-1-yl)benzylidene]piperidin-2-one Sodium hydride (containing mineral oil at 40%, 136 mg) was added to a solution of (E)-5-chloro-2-(3-methoxy-4-(4-methyl-1H-imidazol-1-yl)benzylidene)valeric acid (5-fluoro-2-hydroxyindan-1-yl)amide (915 mg) in DMF (10 mL), and the reaction solution was stirred at room temperature for 20 minutes. Water and ethyl acetate were added to the reaction solution and the organic layer was partitioned. The resulting organic layer was dried over magnesium sulfate, and the solvent was evaporated under reduced pressure. The residue was purified by silica gel chromatography (Carrier: Chromatorex™ NH, elution solvent:heptane-ethyl acetate system→ethyl acetate-methanol system) to obtain 535 mg of the title compound as a racemate. The compound (16 mg) was fractionated using CHIRALPAK™ AD-H manufactured by Daicel Chemical Industries, Ltd. (2 cm×25 cm: mobile phase:

hexane:ethanol=1:1) to obtain the title optically active substance with a retention time of 40 minutes (5.0 mg; >99% ee) and the title optically active substance with a retention time of 48 minutes (4.1 mg; >99% ee). The physical properties of the compounds are as follows.

$^1$H-NMR ($CDCl_3$) δ (ppm): 1.77-1.88 (m, 2H), 2.31 (d, J=1.2 Hz, 3H), 2.75-2.88 (m, 2H), 2.91-2.97 (m, 1H), 3.10-3.13 (m, 2H), 3.27 (dd, J=16.8, 7.6 Hz, 1H), 3.86 (s, 3H), 4.90 (dd, J=7.6, 7.3 Hz, 1H), 5.91 (d, J=7.2 Hz, 1H), 6.92-6.98 (m, 3H), 7.03 (s, 1H), 7.03-7.06 (m, 1H), 7.19 (dd, J=8.0, 5.2 Hz, 1H), 7.24-7.26 (m, 1H), 7.75 (d, J=1.2 Hz, 1H), 7.84 (s, 1H).

Example 938 and Example 939

Synthesis of (E)-1-[(1S) and (1R)-(2,3-difluorophenyl)ethyl]-3-[3-methoxy-4-(4-methyl-1H-imidazol-1-yl)benzylidene]piperidin-2-one

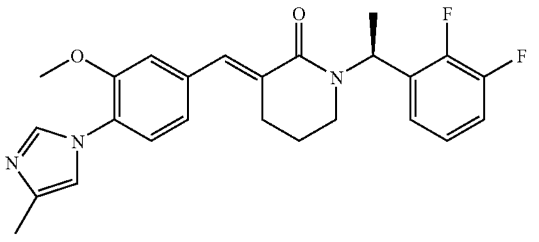

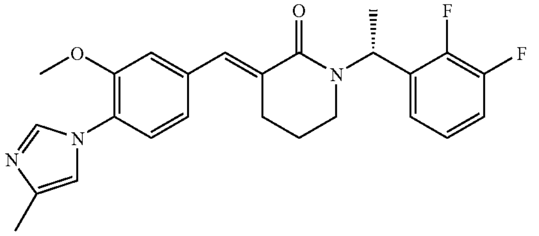

Synthesis of 1-(2,3-difluorophenyl)ethylamine

Triethylamine (2.66 mL) and hydroxylamine hydrochloride (712 mg) were added to a solution of 2,3-difluoroacetophenone (1 g) in ethanol (35 mL), and the reaction solution was heated to reflux for 3 hours. The reaction solution was returned to room temperature, and the solvent was evaporated under reduced pressure. Zinc (2.29 g) was added to a solution of the resulting residue in trifluoroacetic acid (30 mL), and the reaction solution was stirred at room temperature for 2 hours. The reaction solution was made basic with a 5 N aqueous solution of sodium hydroxide, and then extracted with chloroform. The resulting organic layer was dried over magnesium sulfate, and the solvent was evaporated under reduced pressure to obtain 1.4 g of a crude purified product containing the title compound (purity: 72 wt %). The physical properties of the compound are as follows.

$^1$H-NMR ($CDCl_3$) δ (ppm): 1.40 (d, J=6.8 Hz, 3H), 4.43 (q, J=6.8 Hz, 1H), 7.01-7.07 (m, 2H), 7.15-7.19 (m, 1H).

Synthesis of (E)-1-[(1R) and (1S)-(2,3-difluorophenyl)ethyl]-3-[3-methoxy-4-(4-methyl-1H-imidazol-1-yl)benzylidene]piperidin-2-one 1-(2,3-difluorophenyl)ethylamine (purity: 72 wt %, 195 mg), IPEA (1 mL), EDC (257 mg) and HOBT (181 mg) were added to a solution of 5-chloro-2-(3-methoxy-4-(4-methyl-1H-imidazol-1-yl)benzylidene)valeric acid trifluoroacetate (200 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid (1-(2,3-difluorophenyl)ethyl)amide. Sodium hydride (containing mineral oil at 40%, 30 mg) was added to a solution of the resulting 5-chloro-2-(3-methoxy-4-(4-methyl-1H-imidazol-1-yl)benzylidene)valeric acid (1-(2,3-difluorophenyl)ethyl) amide in DMF (5 mL), and the reaction solution was stirred at room temperature for 5 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 95 mg of the title compound as a racemate. The compound (18 mg) was fractionated using CHIRALPAK™ AD-H manufactured by Daicel Chemical Industries, Ltd. (2 cm×25 cm: mobile phase: hexane:ethanol=5:5) to obtain the title optically active substance with a retention time of 28 minutes (7.5 mg; >99% ee) and the title optically active substance with a retention time of 37 minutes (7.5 mg; >90% ee). The physical properties of the compounds are as follows.

$^1$H-NMR ($CDCl_3$) δ (ppm): 1.61 (d, J=7.2 Hz, 3H), 1.79-1.86 (m, 2H), 2.33 (s, 3H), 2.75-2.80 (m, 2H), 3.03-3.10 (m, 1H), 3.30-3.36 (m, 1H), 3.85 (s, 3H), 6.19 (q, J=7.2 Hz, 1H), 6.93 (t, J=1.2 Hz, 1H), 7.01 (s, 1H), 7.01-7.04 (m, 1H), 7.07-7.15 (m, 3H), 7.24-7.25 (m, 1H), 7.82 (s, 1H), 7.85 (s, 1H).

Example 940 and Example 941

Synthesis of (E)-1-[(1S) and (1R)-(3,5-difluorophenyl)ethyl]-3-[3-methoxy-4-(4-methyl-1H-imidazol-1-yl)benzylidene]piperidin-2-one

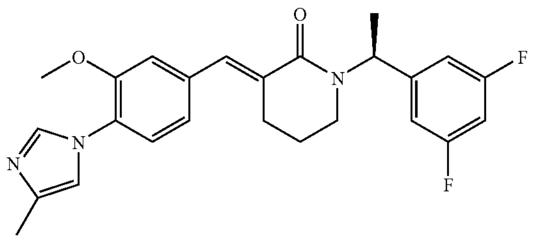

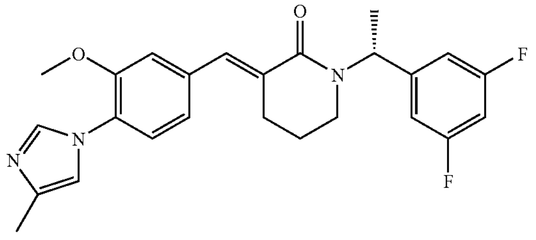

Synthesis of 1-(3,5-difluorophenyl)ethylamine

A crude purified product containing the title compound (purity: 83 wt %, 738 mg) was obtained from 3,5-difluoroacetophenone (611 mg) in the same manner as in Example 938. The physical properties of the compound are as follows.

$^1$H-NMR ($CDCl_3$) δ (ppm): 1.48 (d, J=6.8 Hz, 3H), 4.19 (q, J=6.8 Hz, 1H), 6.72 (tt, J=8.4, 2.4 Hz, 1H), 6.90 (dd, J=8.4 Hz, 2.4 Hz, 2H).

Synthesis of (E)-1-[(1S) and (1R)-(3,5-difluorophenyl)ethyl]-3-[3-methoxy-4-(4-methyl-1H-imidazol-1-yl)benzylidene]piperidin-2-one 1-(2,3-difluorophenyl)ethylamine (purity: 83 wt %, 253 mg), IPEA (1 mL), EDC (320 mg) and HOBT (226 mg) were added to a solution of 5-chloro-2-(3-methoxy-4-(4-methyl-1H-imidazol-1-yl)benzylidene)valeric acid trifluoroacetate (250 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid (1-(3,5-difluorophenyl)ethyl)amide. Sodium hydride (containing mineral oil at 40%, 40 mg) was added to a solution of the resulting 5-chloro-2-(3-methoxy-4-(4-methyl-1H-imidazol-1-yl)benzylidene)valeric acid (1-(3,5-difluorophenyl)ethyl) amide in DMF (5 mL), and the reaction solution was stirred at room temperature for 5 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system), and the resulting oil was solidified with diethyl ether to obtain 80 mg of the title compound as a racemate. The compound (20 mg) was fractionated using CHIRALPAK™ AD-H manufactured by Daicel Chemical Industries, Ltd. (2 cm×25 cm: mobile phase: ethanol) to obtain the title optically active substance with a retention time of 23 minutes (8.7 mg; >99% ee) and the title optically active substance with a retention time of 25 minutes (7.0 mg; >90% ee). The physical properties of the compounds are as follows.

$^1$H-NMR ($CDCl_3$) δ (ppm): 1.55 (d, J=7.2 Hz, 3H) 1.70-1.79 (m, 1H), 1.82-1.89 (m, 1H), 2.32 (d, J=1.2 Hz, 3H), 2.71-2.79 (m, 1H), 2.84-2.90 (m, 1H), 2.95-3.00 (m, 1H), 3.25-3.31 (m, 1H), 3.86 (s, 3H), 6.18 (q, J=7.2 Hz, 1H), 6.72 (tt, J=8.8, 2.0 Hz, 1H), 6.83-6.89 (m, 2H), 6.93 (t, J=1.2 Hz, 1H), 7.03 (s, 1H), 7.03-7.06 (m, 1H), 7.23-7.27 (m, 1H), 7.77 (d, J=1.2 Hz, 1H), 7.88 (s, 1H).

Example 942 and Example 943

Synthesis of (E)-1-[(1S) and (1R)-(2,5-difluorophenyl)ethyl]-3-[3-methoxy-4-(4-methyl-1H-imidazol-1-yl)benzylidene]piperidin-2-one

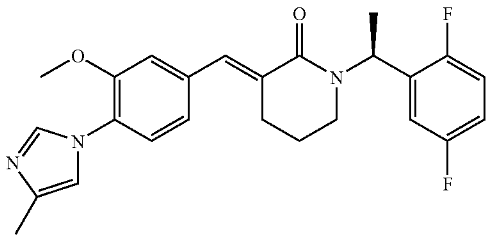

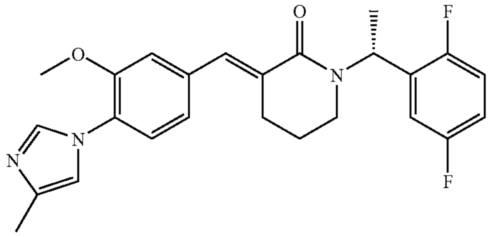

Synthesis of 1-(2,5-difluorophenyl)ethylamine 884 mg of the title compound was obtained from 2,5-difluoroacetophenone (1 g) in the same manner as in Example 938. The physical properties of the compound are as follows.

$^1$H-NMR ($CDCl_3$) δ (ppm): 1.42 (d, J=6.4 Hz, 3H), 4.40 (q, J=6.4 Hz, 1H), 6.85-6.91 (m, 1H), 6.94-6.99 (m, 1H), 7.12-7.16 (m, 1H).

Synthesis of (E)-1-[(1S) and (1R)-(2,5-difluorophenyl)ethyl]-3-[3-methoxy-4-(4-methyl-1H-imidazol-1-yl)benzylidene]piperidin-2-one IPEA (1 mL), EDC (320 mg) and HOBT (226 mg) were added to a solution of 5-chloro-2-(3-methoxy-4-(4-methyl-1H-imidazol-1-yl)benzylidene)valeric acid trifluoroacetate (250 mg) and 1-(2,5-difluorophenyl)ethylamine (175 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent: heptane-ethyl acetate system→ethyl acetate-methanol system) to obtain 5-chloro-2-(3-methoxy-4-(4-methyl-1H-imidazol-1-yl)benzylidene)valeric acid (1-(2,5-difluorophenyl)ethyl)amide. Sodium hydride (containing mineral oil at 40%, 30 mg) was added to a solution of the resulting 5-chloro-2-(3-methoxy-4-(4-methyl-1H-imidazol-1-yl)benzylidene)valeric acid (1-(2,5-difluorophenyl)ethyl) amide in DMF (5 mL), and the reaction solution was stirred at room temperature for 5 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 140 mg of the title compound as a racemate. The compound (15 mg) was fractionated using CHIRALPAK™ AD-H manufactured by Daicel Chemical Industries, Ltd. (2 cm×25 cm: mobile phase: hexane:ethanol=3:7) to obtain the title optically active substance with a retention time of 25 minutes (6.2 mg; >99% ee) and the title optically active substance with a retention time of 39 minutes (5.8 mg; >99% ee). The physical properties of the compounds are as follows.

$^1$H-NMR ($CDCl_3$) δ (ppm): 1.57 (d, J=7.2 Hz, 3H), 1.79-1.86 (m, 2H), 2.30 (d, J=1.2 Hz, 3H), 2.75-2.81 (m, 2H), 3.02-3.09 (m, 1H), 3.28-3.35 (m, 1H), 3.85 (s, 3H), 6.15 (q, J=7.2Hz, 1H), 6.92-7.09 (m, 6H), 7.22-7.25 (m, 1H), 7.73 (d, J=1.2 Hz, 1H), 7.85 (s, 1H).

Example 944 and Example 945

Synthesis of (E)-1-[(1S) and (1R)-(2,6-difluorophenyl)ethyl]-3-[3-methoxy-4-(4-methyl-1H-imidazol-1-yl)benzylidene]piperidin-2-one

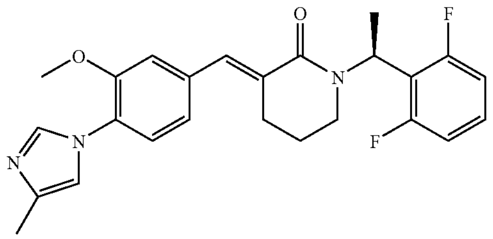

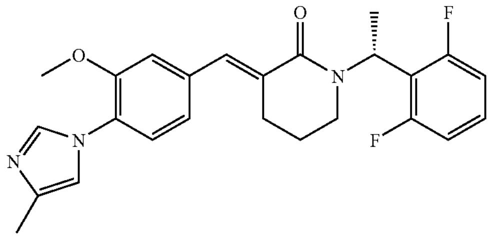

Synthesis of 1-(2,6-difluorophenyl)ethylamine

Triethylamine (2.37 mL) and hydroxylamine hydrochloride (634 mg) were added to a solution of 2,6-difluoroacetophenone (890 mg) in ethanol (30 mL), and the reaction solution was heated to reflux for 4 hours. The reaction solution was returned to room temperature, and the solvent was evaporated under reduced pressure. Zinc (1.86 g) was added to a solution of the resulting residue in trifluoroacetic acid (10 mL), and the reaction solution was stirred at room temperature overnight. The reaction solution was filtered on a celite, made basic with a 5 N aqueous solution of sodium hydroxide, and then extracted with chloroform. The resulting organic layer was dried over magnesium sulfate, and the solvent was evaporated under reduced pressure to obtain 210 mg of a crude purified product containing the title compound (purity: 50 wt %). The physical properties of the compound are as follows.

$^1$H-NMR ($CDCl_3$) δ (ppm): 1.57 (d, J=6.8 Hz, 3H), 4.57 (q, J=6.8z, 1H), 6.72-6.77 (m, 1H), 7.07-7.31 (m, 2H).

Synthesis of (E)-1-[(1S) and (1R)-(2,6-difluorophenyl)ethyl]-3-[3-methoxy-4-(4-methyl-1H-imidazol-1-yl)benzylidene]piperidin-2-one IPEA (1 mL), EDC (257 mg) and HOBT (181 mg) were added to a solution of 5-chloro-2-(3-methoxy-4-(4-methyl-1H-imidazol-1-yl)benzylidene)valeric acid trifluoroacetate (200 mg) and 1-(2,6-difluorophenyl)ethylamine (purity: 50 wt %, 210 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid (1-(2,6-difluorophenyl)ethyl)amide. Sodium hydride (containing mineral oil at 40%, 30 mg) was added to a solution of the resulting 5-chloro-2-(3-methoxy-4-(4-methyl-1H-imidazol-1-yl)benzylidene)valeric acid (1-(2,6-difluorophenyl)ethyl)amide in DMF (5 mL), and the reaction solution was stirred at room temperature for 5 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 105 mg of the title-compound as a racemate. The compound (15 mg) was fractionated using CHIRALPAK™ AD-H manufactured by Daicel Chemical Industries, Ltd. (2 cm×25 cm: mobile phase: hexane:ethanol=1:1) to obtain the title optically active substance with a retention time of 29 minutes (6.9 mg; >99% ee) and the title optically active substance with a retention time of 34 minutes (6.2 mg; >93% ee). The physical properties of the compounds are as follows.

$^1$H-NMR ($CDCl_3$) δ (ppm): 1.65 (dt, J=7.2, 1.6 Hz, 3H), 1.83-1.90 (m, 2H), 2.33 (s, 3H), 2.72-2.82 (m, 2H), 3.33-3.39 (m, 1H), 3.51-3.57 (m, 1H), 3.84 (s, 3H), 6.24 (q, J=7.2Hz, 1H), 6.87-6.94 (m, 3H), 7.01 (s, 1H), 7.01-7.04 (m, 1H), 7.19-7.27 (m, 2H), 7.81 (s, 1H), 7.83 (s, 1H).

Example 946 and Example 947

Synthesis of (E)-3-[3-methoxy-4-(4-methyl-1H-imidazol-1-yl)benzylidene]-1-[(1S) and (1R)-o-tolylethyl]piperidin-2-one

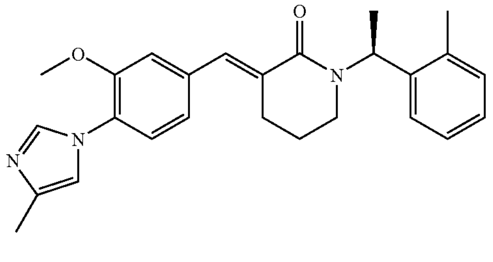

-continued

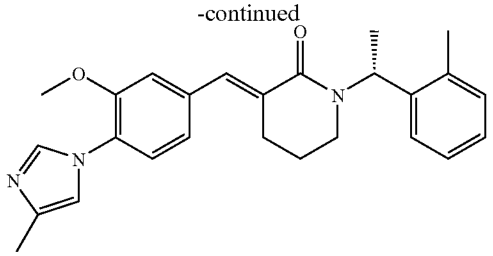

Synthesis of 1-o-tolyl-ethanol

Sodium borohydride (564 mg) was added to a solution of 2-methylacetophenone (1 g) in a mixture of THF (8 mL) with methanol (32 mL), and the reaction solution was stirred at room temperature for 20 minutes. Water and ethyl acetate were added to the reaction solution and the organic layer was partitioned. The resulting organic layer was dried over magnesium sulfate, and the solvent was evaporated under reduced pressure. The residue was purified by silica gel column chromatography (heptane-ethyl acetate system) to obtain 911 mg of the title compound. The physical properties of the compound are as follows.

$^1$H-NMR ($CDCl_3$) δ (ppm): 1.47 (d, J=6.4 Hz, 3H), 1.68 (brs, 1H), 2.35 (s, 3H), 5.14 (q, J=6.4 Hz, 1H) 7.14 (t, J=6.8 Hz, 1H), 7.18(t, J=6.8 Hz, 1H), 7.23 (d, J=6.8 Hz, 1H), 7.52 (d, J=6.8 Hz, 1H).

Synthesis of 1-(1-azidoethyl)-2-methylbenzene

Triethylamine (2.78 mL) and methanesulfonyl chloride (777 μL) were added to a solution of 1-o-tolylethanol (911 mg) in dichloromethane (30 mL), and the reaction solution was stirred at room temperature for 5 hours. Water and dichloromethane were added to the reaction solution and the organic layer was partitioned. The resulting organic layer was dried over magnesium sulfate, and the solvent was evaporated under reduced pressure. Sodium azide (0.87 g) was added to a solution of the residue in DMF (20 mL), and the reaction solution was stirred at room temperature overnight. Water and ethyl acetate were added to the reaction solution and the organic layer was partitioned. The resulting organic layer was dried over magnesium sulfate, and the solvent was evaporated under reduced pressure. The residue was purified by silica gel chromatography (heptane-ethyl acetate system) to obtain 744 mg of the title compound. The physical properties of the compound are as follows.

$^1$H-NMR ($CDCl_3$) δ (ppm): 1.52 (d, J=6.8 Hz, 3H), 2.37 (s, 3H), 4.83 (q, J=6.8 Hz, 1H), 7.15-7.25 (m, 3H), 7.35-7.38 (m, 1H).

Synthesis of 1-o-tolylethylamine

10% palladium-carbon (water content: 50%, 50 mg) was added to a solution of 1-(1-azidoethyl)-2-methylbenzene (744 mg) in methanol (5 mL), and the reaction solution was stirred in a hydrogen atmosphere at room temperature for 1 hour. The reaction solution was filtered on a celite, and the filtrate was concentrated under reduced pressure to obtain 482 mg of the title compound. The physical properties of the compound are as follows.

$^1$H-NMR ($CDCl_3$) δ (ppm): 1.35 (d, J=6.8 Hz, 3H), 2.36 (s, 3H), 4.36 (q, J=6.8 Hz, 1H), 7.11-7.13 (m, 2H), 7.19-7.23 (m, 1H), 7.45 (d, J=7.6 Hz, 1H).

Synthesis of (E)-3-[3-methoxy-4-(4-methyl-1H-imidazol-1-yl)benzylidene]-1-((1S) and (1R)-o-tolylethyl)piperidin-2-one IPEA (0.5 mL), EDC (128 mg) and HOBT (90.4 mg) were added to a solution of 5-chloro-2-(3-methoxy-4-(4-methyl-1H-imidazol-1-yl)benzylidene)valeric acid trifluoroacetate (100 mg) and 1-o-tolylethylamine (60 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid (1-o-tolylethyl)amide. Sodium hydride (containing mineral oil at 40%, 50 mg) was added to a solution of the resulting 5-chloro-2-(3-methoxy-4-(4-methyl-1H-imidazol-1-yl)benzylidene)valeric acid (1-o-tolylethyl) amide in DMF (4 mL), and the reaction solution was stirred at room temperature for 10 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 60 mg of the title compound as a racemate. The compound (10 mg) was fractionated using CHIRALPAK™ AD-H manufactured by Daicel Chemical Industries, Ltd. (2 cm×25 cm: mobile phase: hexane:ethanol=7:3) to obtain the title optically active substance with a retention time of 39 minutes (4.4 mg; >99% ee) and the title optically active substance with a retention time of 48 minutes (4.4 mg; >99% ee). The physical properties of the compounds are as follows.

$^1$H-NMR ($CDCl_3$) δ (ppm): 1.57 (d, J=6.8 Hz, 3H), 1.66-1.75 (m, 2H), 2.78 (s, 3H), 2.32 (s, 3H), 2.61-2.71 (m, 2H), 2.79-2.86 (m, 1H), 3.08-3.15 (m, 1H), 3.85 (s, 3H), 6.15 (q, J=6.8 Hz, 1H), 6.93 (s, 1H), 7.03 (s, 1H), 7.03-7.04 (m, 1H), 7.17-7.24 (m, 4H), 7.35-7.38 (m, 1H), 7.76 (s, 1H), 7.87 (s, 1H)

Example 948

Synthesis of 1-[1-(2-fluorophenyl)-1-methylethyl]-3-[3-methoxy-4-(4-methyl-1H-imidazol-1-yl)benzylidene]piperidin-2-one

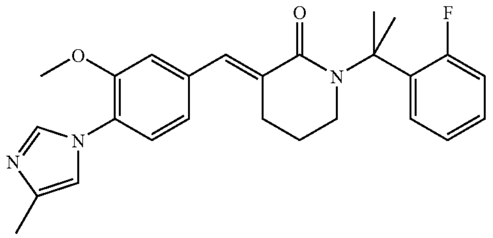

Synthesis of methyl (2-fluorophenyl)acetate

Trimethylsilyl chloride (4.12 mL) was added to a solution of 2-fluorophenylacetic acid (2 g) in methanol (40 mL) in a nitrogen atmosphere, and the reaction solution was stirred at room temperature for 2 days. The reaction solution was concentrated under reduced pressure, and the residue was purified by silica gel column chromatography (elution solvent: heptane-ethyl acetate system) to obtain 1.978 g of the title compound. The physical properties of the compound are as follows.

$^1$H-NMR ($CDCl_3$) δ (ppm): 3.68 (s, 2H), 3.72 (s, 3H), 7.04-7.13 (m, 2H), 7.24-7.29 (m, 2H).

Synthesis of methyl 2-(2-fluorophenyl)-2-methylpropionate

A solution of methyl (2-fluorophenyl)acetate (1.98 g) in THF (30 mL) was added dropwise to a suspension of sodium hydride (containing mineral oil at 40%, 1.7 g) in THF (70 mL) in a nitrogen atmosphere. Then, methyl iodide (1.76 mL) was added to the reaction solution, and the reaction solution was stirred at room temperature overnight. A saturated aqueous solution of ammonium chloride and ethyl acetate were added to the reaction solution and the organic layer was partitioned. The resulting organic layer was dried over magnesium sulfate, and the solvent was evaporated under reduced pressure. The residue was purified by silica gel chromatography (elution solvent:heptane-ethyl acetate system) to obtain 1.36 g of the title compound. The physical properties of the compound are as follows.

$^1$H-NMR ($CDCl_3$) δ (ppm): 1.57 (s, 6H), 3.67 (s, 3H), 7.00 (ddd, J=11.6; 8.0, 1.2 Hz, 1H), 7.12 (td, J=7.6, 1.2 Hz, 1H), 7.21-7.26 (m, 1H), 7.31 (td, J=7.6, 1.6 Hz, 1H).

Synthesis of 2-(2-fluorophenyl)-2-methylpropionic acid

A 5 N aqueous solution of sodium hydroxide (10 mL) was added to a solution of methyl 2-(2-fluorophenyl)-2-methylpropionate (1.357 g) in methanol (10 mL), and the reaction solution was stirred at 80° C. for 3 hours. The reaction solution was returned to room temperature, made acidic with 5 N hydrochloric acid, and then extracted with ethyl acetate. The resulting organic layer was dried over magnesium sulfate, and the solvent was evaporated under reduced pressure to obtain 1.15 g of the title compound. The physical properties of the compound are as follows.

$^1$H-NMR ($CDCl_3$) δ (ppm): 1.61 (s, 6H), 7.03 (dd, J=11.2, 8.4 Hz, 1H), 7.13 (t, J=7.6 Hz, 1H), 7.22-7.28 (m, 1H), 7.33 (td, J=7.6, 1.6 Hz, 1H).

Synthesis of 1-(2-fluorophenyl)-1-methylethylamine t-Butyl alcohol (30 mL), diphenylphosphoryl azide (1.63 mL) and triethylamine (1.05 mL) were added to a solution of 2-(2-fluorophenyl)-2-methylpropionic acid (1.15 g) in toluene (60 mL), and the reaction solution was heated to reflux overnight. The reaction solution was returned to room temperature, and water and ethyl acetate were added thereto and the organic layer was partitioned. The resulting organic layer was dried over magnesium sulfate, and the solvent was evaporated under reduced pressure. 10 mL of 5 N hydrochloric acid was added to a solution of the residue in THF (5 mL), and the reaction solution was heated to reflux for 3 hours. The reaction solution was returned to room temperature, made basic with 5 N sodium hydroxide, and then extracted with ethyl acetate. The resulting organic layer was dried over magnesium sulfate, and the solvent was evaporated under reduced pressure to obtain 735 mg of the title compound. The physical properties of the compound are as follows.

$^1$H-NMR ($CDCl_3$) δ (ppm): 1.56 (s, 6H). 6.99-7.07 (m, 1H), 7.10 (dd, J=7.6, 1.2 Hz, 1H), 7.18-7.24 (m, 1H), 7.41-7.45 (m, 1H).

Synthesis of 1-[1-(2-fluorophenyl)-1-methylethyl]-3-[3-methoxy-4-(4-methyl-1H-imidazol-1-yl)benzylidene]piperidin-2-one IPEA (0.5 mL), EDC (192 mg) and HOBT (135 mg) were added to a solution of 5-chloro-2-(3-methoxy-4-(4-methyl-1H-imidazol-1-yl)benzylidene)valeric acid trifluoroacetate (150 mg) and 1-(2-fluorophenyl)-1-methylethylamine (102 mg) in DMF (5 mL), and the reaction solution was stirred at room temperature for 3 hours. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid (1-(2-fluorophenyl)-1-methylethyl)amide. Sodium hydride (containing mineral oil at 40%, 40 mg) was added to a solution of the resulting 5-chloro-2-(3-methoxy-4-(4-methyl-1H-imidazol-1-yl)benzylidene)valeric acid (1-(2-fluorophenyl)-1-methylethyl)amide in DMF (5 mL), and the reaction solution was stirred at room temperature for 20 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 70 mg of the title compound. The physical properties of the compound are as follows.

ESI-MS; m/z434 [$M^+$+H]. $^1$H-NMR ($CDCl_3$) δ (ppm): 1.79 (s, 6H), 1.90-1.97 (m, 2H), 2.29 (d, J=1.2 Hz, 3H), 2.73-2.77 (m, 2H), 3.64-3.67 (m, 2H), 3.80 (s, 3H), 6.89-6.99 (m, 4H), 7.10-7.21 (m, 3H), 7.40-7.45 (m, 1H), 7.58 (s, 1H), 7.69 (d, J=1.2 Hz, 1H).

Example 949

Synthesis of 1-[1-(3,4-difluorophenyl)-1-methylethyl]-3-[3-methoxy-4-(4-methyl-1H-imidazol-1-yl)benzylidene]piperidin-2-one

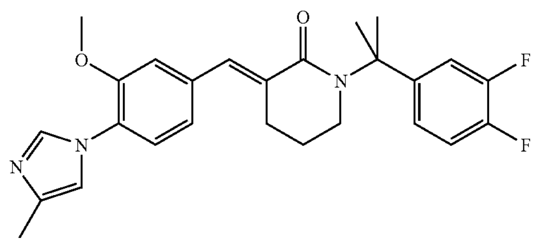

Synthesis of 1-(3,4-difluorophenyl)-1-methylethylamine 928 mg of the title compound was obtained from 3,4-difluorophenylacetic acid (2 g) in the same manner as in Example 948. The physical properties of the compound are as follows.

$^1$H-NMR ($CDCl_3$) δ (ppm): 1.47 (s, 6H), 7.04-7.11 (m, 1H), 7.17-7.21 (m, 1H), 7.30-7.35 (m, 1H).

Synthesis of 1-[1-(3,4-difluorophenyl)-1-methylethyl]-3-[3-methoxy-4-(4-methyl-1H-imidazol-1-yl)benzylidene]piperidin-2-one IPEA (0.5 mL), EDC (192 mg) and HOBT (135 mg) were added to a solution of 5-chloro-2-(3-methoxy-4-(4-methyl-1H-imidazol-1-yl)benzylidene)valeric acid trifluoroacetate (150 mg) and 1-(3,4-difluorophenyl)-1-methylethylamine (114 mg) in DMF (5 mL), and the reaction solution was stirred at room temperature for 3 hours. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene) valeric acid (1-(3,4-difluorophenyl)-1-methylethyl)amide. Sodium hydride (containing mineral oil at 40%, 40 mg) was added to a solution of the resulting 5-chloro-2-(3-methoxy-4-(4-methyl-1H-imidazol-1-yl)benzylidene)valeric acid (1-(3,4-fluorophenyl)-1-methylethyl)-amide in DMF (5 mL), and the reaction solution was stirred at room temperature for 20 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 85 mg of the title compound. The physical properties of the compound are as follows.

$^1$H-NMR ($CDCl_3$) δ (ppm): 1.71 (s, 6H), 1.95-2.01 (m, 2H), 2.30 (d, J=1.2 Hz, 3H), 2.78-2.82 (m, 2H), 3.62-3.65 (m, 2H), 3.82 (s, 3H), 6.92 (t, J=1.2 Hz, 1H), 6.97-7.13 (m, 5H), 7.22-7.24 (m, 1H), 7.61 (s, 1H), 7.71 (d, J=1.2 Hz, 1H).

Example 950

Synthesis of 1-[1-(3,5-difluorophenyl)-1-methylethyl]-3-[3-methoxy-4-(4-methyl-1H-imidazol-1-yl)benzylidene]piperidin-2-one

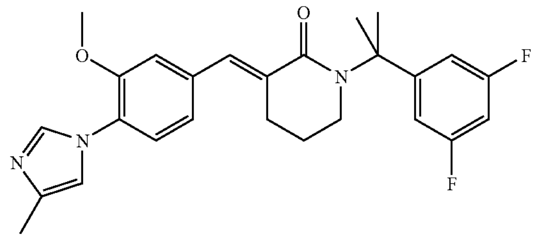

Synthesis of 1-(3,5-difluorophenyl)-1-methylethylamine 780 mg of the title compound was obtained from 3,5-difluorophenylacetic acid (1.56 g) in the same manner as in Example 948. The physical properties of the compound are as follows.

$^1$H-NMR ($CDCl_3$) δ (ppm): 1.47 (s, 6H), 6.65 (tt, J=8.8, 2.4 Hz, 1H), 7.00-7.05 (m, 2H).

Synthesis of 1-[1-(3,5-difluorophenyl)-1-methylethyl]-3-[3-methoxy-4-(4-methyl-1H-imidazol-1-yl)benzylidene]piperidin-2-one IPEA (0.5 mL), EDC (192 mg) and HOBT (135 mg) were added to a solution of 5-chloro-2-(3-methoxy-4-(4-methyl-1H-imidazol-1-yl)benzylidene)valeric acid trifluoroacetate (150 mg) and 1-(3,4-difluorophenyl)-1-methylethylamine (114 mg) in DMF (5 mL), and the reaction solution was stirred at room temperature for 3 hours. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene) valeric acid (1-(3,5-difluorophenyl)-1-methylethyl)amide. Sodium hydride (containing mineral oil at 40%, 40 mg) was added to a solution of the resulting 5-chloro-2-(3-methoxy-4-(4-methyl-1H-imidazol-1-yl)benzylidene)valeric acid (1-(3,5-fluorophenyl)-1-methylethyl)amide in DMF (5 mL), and the reaction solution was stirred at room temperature for 20 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 84 mg of the title compound. The physical properties of the compound are as follows.

$^1$H-NMR ($CDCl_3$) δ (ppm): 1.69 (s, 6H), 1.96-2.04 (m, 2H), 2.31 (d, J=1.2 Hz, 3H), 2.78-2.82 (m, 2H), 3.63-3.65 (m, 2H), 3.82 (s, 3H), 6.61 (tt, J=8.8, 2.4 Hz, 1H), 6.78-6.83 (m, 2H), 6.92 (t, J=1.2 Hz, 1H), 6.96 (d, J=1.2 Hz, 1H), 6.99 (dd, J=8.0,1.2 Hz, 1H), 7.22 (d, J=8.0 Hz, 1H), 7.60 (s, 1H), 7.74 (d, J=1.2 Hz, 1H).

Example 951

Synthesis of (E)-1-[(1S)-(4-fluoro-3-methoxyphenyl)ethyl]-3-[3-methoxy-4-(4-methyl-1H-imidazol-1-yl)benzylidene]piperidin-2-one

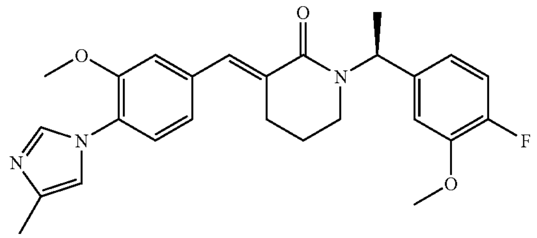

Synthesis of 1-(4-fluoro-3-methoxyphenyl)ethanol

Methyl magnesium chloride (3 M tetrahydrofuran solution, 7.8 mL) was added to a solution of 4-fluoro-3-methoxybenzaldehyde (3 g) in THF (200 mL) while cooling with ice, and the reaction solution was stirred for 2 hours while cooling with ice. A saturated aqueous solution of ammonium chloride and ethyl acetate were added to the reaction solution and the organic layer was partitioned. The resulting organic layer was dried over magnesium sulfate, and the solvent was evaporated under reduced pressure. The residue was purified by silica gel column chromatography (Carrier: Chromatorex™ NH, elution solvent:heptane-ethyl acetate system) to obtain 2.65 g of the title compound. The physical properties of the compound are as follows.

$^1$H-NMR ($CDCl_3$) δ (ppm): 1.48 (d, J=6.4 Hz, 3H), 1.82 (brs, 1H), 3.90 (s, 3H), 4.86 (q, J=6.4 Hz, 1H), 6.83-6.87 (m, 1H), 6.99-7.04 (m, 2H).

Synthesis of 4-fluoro-3-methoxyacetophenone

A solution of dimethyl sulfoxide (1.33 mL) in dichloromethane (5 mL) was added dropwise to a solution of oxalyl chloride (1.63 mL) in dichloromethane (80 mL) in a nitrogen atmosphere at −78° C. After stirring the reaction solution at −78° C. for 3 minutes, a solution of 1-(4-fluoro-3-methoxyphenyl)ethanol (2.6 g) in dichloromethane (15 mL) was added dropwises to the reaction solution. Further, the reaction solution was stirred at −78° C. for 20 minutes, and triethylamine (10.8 mL) was added dropwise to the reaction solution. Then, the reaction solution was stirred at −78° C. for 10 minutes, and further stirred at room temperature for 30 minutes. Water and dichloromethane were added to the reaction solution and the organic layer was partitioned. The resulting organic layer was dried over magnesium sulfate, and the solvent was evaporated under reduced pressure. The residue was purified by silica gel column chromatography (elution solvent:heptane-ethyl acetate system) to obtain 2.54 g of the title compound. The physical properties of the compound are as follows.

$^1$H-NMR ($CDCl_3$) δ (ppm): 2.59 (s, 3H), 3.94 (s, 3H), 7.13 (dd, J=10.8, 8.4 Hz, 1H), 7.49-7.53 (m, 1H), 7.60 (dd, J=8.4, 2.0 Hz, 1H).

Synthesis of (1R)-(4-fluoro-3-methoxyphenyl)ethanol

A solution of 4-fluoro-3-methoxyacetophenone (1 g) in THF (10 mL) was added dropwise to a solution of (+)-DIPCl™ (2.29 g) in THF (30 mL) in a nitrogen atmosphere at −20° C., and the reaction solution was stirred at −20° C. for 5 hours. The reaction solution was heated to room temperature, and the solvent was evaporated under reduced pressure. The residue was diluted with an ether, diethanolamine (1.25 mL) was added to the diluent, and the reaction solution was stirred at room temperature overnight. The reaction solution was filtered on a celite, and the filtrate was concentrated under reduced pressure. The residue was purified by silica gel column chromatography (elution solvent:heptane-ethyl acetate system) to obtain 918 mg of the title compound. The physical properties of the compound are as follows.

$^1$H-NMR ($CDCl_3$) δ (ppm): 1.48 (d, J=6.4 Hz, 3H), 1.82 (brs, 1H), 3.90 (s, 3H), 4.86 (q, J=6.4 Hz, 1H), 6.83-6.87 (m, 1H), 6.99-7.04 (m, 2H).

Synthesis of 4-[(1S)-azidoethyl]-1-fluoro-2-methoxybenzene 1,8-diazabicyclo[5.4.0]undec-7-ene (1 mL) was added dropwise to a solution of (1R)-(4-fluoro-3-methoxyphenyl) ethanol (910 mg) and diphenylphosphoryl azide (1.44 mL) in toluene (12.5 mL) in a nitrogen atmosphere while cooling with ice. The reaction solution was stirred at that temperature for 2 hours, and further stirred at room temperature overnight. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (elution solvent:heptane-ethyl acetate system) to obtain 789 mg of the title compound.

$^1$H-NMR ($CDCl_3$) δ (ppm): 1.52 (d, J=6.8 Hz, 3H), 3.92 (s, 3H), 4.59 (q, J=6.8 Hz, 1H), 6.82-6.86 (m, 1H), 6.93 (dd, J=8.0, 2.4 Hz, 1H), 7.60 (dd, J=11.2, 8.0 Hz, 1H).

Synthesis of (1S)-(4-fluoro-3-methoxyphenyl)ethylamine

10% palladium-carbon (water content: 50%, 80 mg) was added to a solution of 4-((1S)-azido-ethyl)-1-fluoro-2-methoxybenzene (789 mg) in methanol (8 mL), and the reaction solution was stirred in a hydrogen atmosphere at room temperature for 1 hour. The reaction solution was filtered on a celite, and the filtrate was concentrated under reduced pressure to obtain 352 mg of the title compound. The physical properties of the compound are as follows.

$^1$H-NMR ($CDCl_3$) δ (ppm): 1.37 (d, J=6.4 Hz, 3H), 3.91 (s, 3H), 4.11 (q, J=6.4 Hz, 1H), 6.83-6.87 (m, 1H), 6.99-7.04 (m, 2H).

Synthesis of 1-[(1S)-(4-fluoro-3-methoxyphenyl) ethyl]-3-[3-methoxy-4-(4-methyl-1H-imidazol-1-yl) benzylidene]piperidin-2-one IPEA (0.5 mL), EDC (192 mg) and HOBT (135 mg) were added to a solution of 5-chloro-2-(3-methoxy-4-(4-methyl-1H-imidazol-1-yl)benzylidene)valeric acid trifluoroacetate (150 mg) and (1S)-(4-fluoro-3-methoxy phenyl)ethylamine (114 mg) in DMF (5 mL), and the reaction solution was stirred at room temperature for 1 hour. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 5-chloro-2-(3-methoxy-4-(4-methyl-1H-imidazol-1-yl)benzylidene)valeric acid ((1S)-(4-fluoro-3-methoxyphenyl)ethyl)amide. Sodium hydride (containing mineral oil at 40%, 40 mg) was added to a solution of the resulting 5-chloro-2-(3-methoxy-4-(4-methyl-1H-imidazol-1-yl)benzylidene)valeric acid ((1S)-(4-fluoro-3-methoxyphenyl)ethyl)amide in DMF (5 mL), and the reaction solution was stirred at room temperature for 20 minutes. Water and ethyl acetate were added to the reaction solution and the organic layer was partitioned. The resulting organic layer was dried over anhydrous magnesium sulfate, and the solvent was evaporated under reduced pressure. The residue was purified by silica gel column chromatography (Carrier: Chromatorex™ NH, elution solvent:heptane-ethyl acetate system→ethyl acetate-methanol system) to obtain 60 mg of the title compound. The physical properties of the compound are as follows.

$^1$H-NMR ($CDCl_3$) δ (ppm): 1.54 (d, J=6.8 Hz, 3H), 1.60-1.73 (m, 1H), 1.80-1.86 (m, 1H), 2.32 (s, 3H), 2.75-2.84 (m, 2H), 2.92-2.98 (m, 1H), 3.21-3.27 (m, 1H), 3.86 (s, 3H), 3.88 (s, 3H), 6.20 (q, J=6.8 Hz, 1H), 6.85-6.89 (m, 1H), 6.19-6.95 (m, 2H), 7.01-7.06 (m, 3H), 7.24-7.27 (m, 1H), 7.78 (s, 1H), 7.88 (s, 1H).

Example 952

Synthesis of (E)-3-[3-methoxy-4-(4-methyl-1H-imidazol-1-yl)benzylidene]-1-((1S)-p-tolylethyl)piperidin-2-one

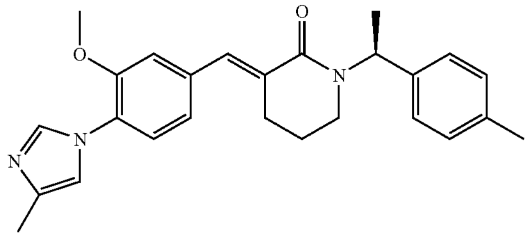

80 mg of the title compound was obtained from (E)-chloro-2-(3-methoxy-4-(4-methyl-1H-imidazol-1-yl)benzylidene) valeric acid trifluoroacetate (100 mg) and (1S)-(p-tolyl)ethylamine (60 mg) in the same manner as in Example 418. The physical properties of the compound are as follows.

$^1$H-NMR ($CDCl_3$) δ (ppm): 1.55 (d, J=6.8 Hz, 3H), 1.66-1.73 (m, 1H), 1.75-1.83 (m, 1H), 2.30 (d, J=0.8 Hz, 3H), 2.34 (s, 3H), 2.71-2.83 (m, 2H), 2.92-2.97 (m, 1H), 3.19-3.25 (m, 1H), 3.85 (s, 3H), 6.21 (q, J=6.8 Hz, 1H), 6.93 (t, J=1.2 Hz, 1H), 7.03 (s, 1H), 7.04 (dd, J=6.4, 1.2 Hz, 1H) 7.14 (d, J=8.0 Hz, 2H), 7.21-7.7.24 (m, 3H), 7.73 (d, J=0.8 Hz, 1H), 7.88 (s, 1H).

Examples 953 and 954

Synthesis of (E)-3-[3-methoxy-4-(4-methyl-1H-imidazol-1-yl)benzylidene]-1-[(1S) and (1R)-m-tolylethyl]piperidin-2-one

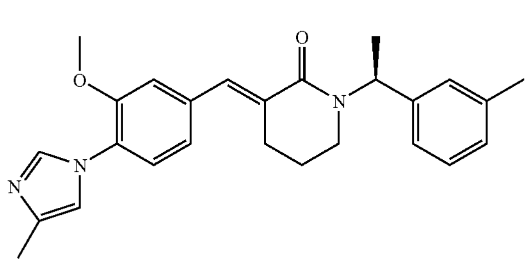

67 mg of the title compound as a racemate was obtained from (E)-chloro-2-(3-methoxy-4-(4-methyl-1H-imidazol-1-yl)benzylidene)valeric acid trifluoroacetate (150 mg) and 1-(m-tolyl)ethylamine (90.3 mg) in the same manner as in Example 418. The compound (16 mg) was fractionated using CHIRALPAK™ AD-H manufactured by Daicel Chemical Industries, Ltd. (2 cm×25 cm: mobile phase: hexane:ethanol=7:3) to obtain the title optically active substance with a retention time of 108 minutes (2.8 mg; >99% ee) and the title optically active substance with a retention time of 112 minutes (1.8 mg; >83% ee). The physical properties of the compounds are as follows.

$^1$H-NMR ($CDCl_3$) δ (ppm): 1.56 (d, J=6.8 Hz, 3H), 1.57-1.74 (m, 1H), 1.76-1.84 (m, 1H), 2.31 (s, 3H), 2.36 (s, 3H), 2.75-2.82 (m, 2H), 2.93-2.99(m, 1H), 3.21-3.27(m, 1H), 3.86 (s, 3H), 6.22 (q, J=6.8 Hz, 1H), 6.94 (s, 1H), 7.05 (s, 1H), 7.05-7.10 (m, 2H), 7.14-7.16 (m, 2H), 7.22-7.27 (m, 2H), 7.76 (s, 1H), 7.90 (s, 1H).

Example 955

Synthesis of (E)-1-[(1S)-(3-fluoro-4-methoxyphenyl)ethyl]-3-[3-methoxy-4-(4-methyl-1H-imidazol-1-yl)benzylidene]piperidin-2-one

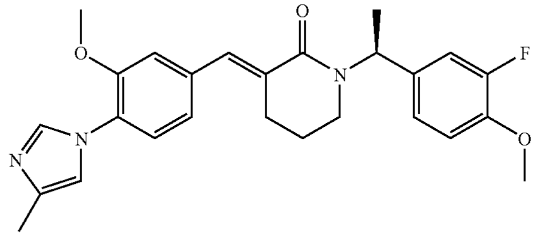

67 mg of the title compound was obtained from (E)-chloro-2-(3-methoxy-4-(4-methyl-1H-imidazol-1-yl)benzylidene) valeric acid trifluoroacetate (150 m) and (1S)-(3-fluoro-4-methoxyphenyl)ethylamine (114 mg) in the same manner as in Example 418. The physical properties of the compound are as follows.

$^1$H-NMR ($CDCl_3$) δ (ppm): 1.53 (d, J=7.2 Hz, 3H), 1.57-1.84 (m, 2H), 2.31 (d, J=1.2 Hz, 3H), 2.71-2.85 (m, 2H), 2.92-2.98 (m, 1H), 3.19-3.26 (m, 1H), 3.86 (s, 3H), 3.88 (s, 3H), 6.17 (q, J=7.2 Hz, 1H), 6.91-6.94 (m, 2H), 7.03-7.08 (m, 3H), 7.23-7.27 (m, 2H), 7.74 (d, J=1.2 Hz, 1H), 7.88 (s, 1H).

Example 956

Synthesis of (E)-1-[(1S)-(2-fluoro-6-methoxyphenyl)ethyl]-3-[3-methoxy-4-(4-methyl-1H-imidazol-1-yl)benzylidene]piperidin-2-one

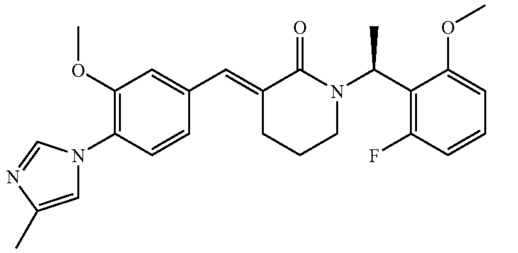

70 mg of the title compound was obtained from (E)-chloro-2-(3-methoxy-4-(4-methyl-1H-imidazol-1-yl)benzylidene) valeric acid trifluoroacetate (150 mg) and (1S)-(2-fluoro-6- methoxyphenyl)ethylamine (114 mg) in the same manner as in Example 418. The physical properties of the compound are as follows.

$^1$H-NMR ($CDCl_3$) δ (ppm): 1.60 (dd, J=7.2, 2.4 Hz, 3H), 1.81-1.88 (m, 2H), 2.31 (d, J=0.8 Hz, 3H), 2.69-2.83 (m, 2H), 3.32-3.38 (m, 1H), 3.47-3.54 (m, 1H), 3.84 (s, 3H), 3.87 (s, 3H), 6.23 (q, J=7.2 Hz, 1H), 6.68 (t, J=8.0 Hz, 2H), 6.93 (t, J=1.2 Hz, 1H), 7.01-7.03 (m, 2H), 7.17-7.24 (m, 2H), 7.73 (d, J=0.8 Hz, 1H), 7.82(s, 1H).

Example 957

(E)-2-fluoro-5-[(1S)-{3-[methoxy-4-(4-methyl-1H-imidazol-1-yl)benzylidene]-2-oxopiperidin-1-yl}ethyl)benzonitrile

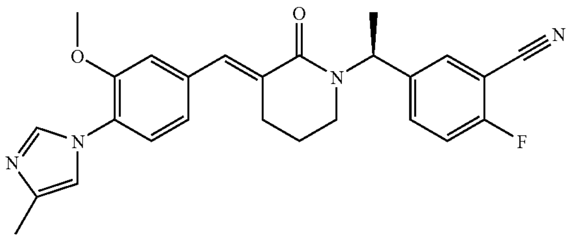

38 mg of the title compound was obtained from (E)-chloro-2-(3-methoxy-4-(4-methyl-1H-imidazol-1-yl)benzylidene) valeric acid trifluoroacetate (250 mg) and 5-((1S)-aminoethyl)-2-fluorobenzonitrile (220 mg) in the same manner as in Example 418. The physical properties of the compound are as follows.

$^1$H-NMR ($CDCl_3$) δ (ppm): 1.59 (d, J=6.8 Hz, 3H), 1.60-1.88 (m, 2H), 2.34 (s, 3H), 2.71-2.78 (m, 1H), 2.85-2.95 (m, 2H), 3.28-3.34 (m, 1H), 3.87 (s, 3H), 6.20 (q, J=6.8 Hz, 1H), 6.94 (s, 1H), 7.04-7.06 (m, 2H), 7.19 (t, J=8.0 Hz, 1H), 7.25-7.27 (m, 1H), 7.58-7.62 (m, 2H), 7.82 (s, 1H), 7.88 (s, 1H).

Example 958 and Example 959

Synthesis of (E)-1-[(1S) and (1R)-(5-fluorothiophen-2-yl)ethyl]-3-[3-methoxy-4-(4-methyl-1H-imidazol-1-yl)benzylidene]-1-piperidin-2-one

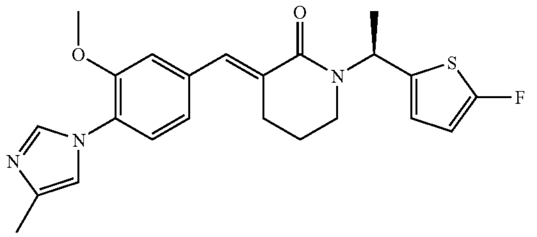

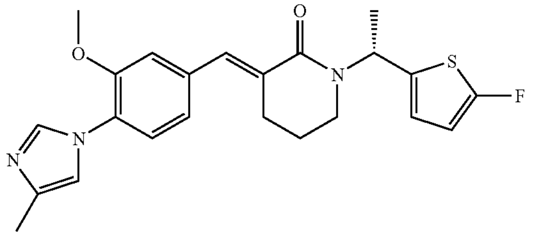

Synthesis of 2-(1-azidoethyl)-5-fluorothiophene

Methyl magnesium bromide (0.84 M, tetrahydrofuran solution, 20 mL) was added to a solution of 5-fluorothiophene-2-carboxyaldehyde (977 mg) in THF (10 mL) while cooling with ice, and the reaction solution was stirred for 30 minutes. A saturated aqueous solution of ammonium chloride and ethyl acetate were added to the reaction solution and the organic layer was partitioned. The organic layer was washed with brine, dried over anhydrous magnesium sulfate, and concentrated under reduced pressure. 1,8-diazabicyclo [5.4.0]undec-7-ene (1.1 mL) was added to a solution of the resulting crude oil (952 mg) and diphenylphosphoryl azide (2.06 g) in toluene (5 mL) while cooling with ice. The reaction solution was stirred for 2 hours, and further stirred at room temperature overnight. Water and ethyl acetate were added to the reaction mixture and the organic layer was partitioned. The organic layer was washed with brine, dried over anhydrous magnesium sulfate, and concentrated under reduced pressure. The residue was purified by silica gel column chromatography (elution solvent:heptane-ethyl acetate system) to obtain 518 mg of the title compound. The physical properties of the compound are as follows.

$^1$H-NMR ($CDCl_3$) δ (ppm): 1.56 (d, J=6.8 Hz, 3H), 4.63-4.69 (m, 1H), 6.34-6.35 (m, 1H), 6.62-6.64 (m, 1H).

Synthesis of 1-(5-fluorothiophen-2-yl)ethylamine

Triphenylphosphine (873 mg) was added to a solution of 2-(1-azidoethyl)-5-fluorothiophene (518 mg) in THF (10 mL), and the reaction solution was stirred at room temperature for 1 hour. Water (2 mL) was added to the reaction mixture, and the mixture was heated to reflux for 3 hours. After allowing the reaction mixture to be cooled, a 5 N aqueous solution of hydrochloric acid and ethyl acetate were added thereto to separate the aqueous layer. A 5 N aqueous solution of sodium hydroxide was added to the aqueous layer to make the layer basic, and the aqueous layer was extracted with ethyl acetate. The organic layer was washed with brine, dried over anhydrous magnesium sulfate, and concentrated under reduced pressure to obtain 324 mg of the title compound. The physical properties of the compound are as follows.

$^1$H-NMR ($CDCl_3$) δ (ppm): 1.44 (d, J=6.8 Hz, 3H), 4.20-4.25 (m, 1H), 6.27 (dd, J=1.6, 4 Hz, 1H), 6.48 (t, J=3.6 Hz, 1H).

Synthesis of (E)-1-[(1S)-(5-fluorothiophen-2-yl) ethyl]-3-[3-methoxy-4-(4-methyl-1H-)benzylidene]-1-piperidin-2-one and (E)-1-[(1R)-(5-fluorothiophen-2-yl)ethyl]-3-[3-methoxy-4-(4-methyl-1H-imidazol-1-yl)benzylidene]-1-piperidin-2-one 72 mg of a racemate was obtained from (E)-5-chloro-2-(3-methoxy-4-(4-methyl-1H-imidazol-1-yl)benzylidene)valeric acid trifluoroacetate (112 mg) and 1-(5-fluorothiophen-2-yl)ethylamine (67 mg) in the same manner as in Example 418.

The racemate (58 mg) was fractionated using CHIRALCEL™ OD-H manufactured by Daicel Chemical Industries, Ltd. (2 cm×25 cm: mobile phase: hexane:ethanol=8:2; flow rate: 5 mL/min) to obtain the title optically active substance with a retention time of 43 minutes (19 mg; >99% ee) and the title optically active substance with a retention time of 49 minutes (16 mg; >99% ee).

The physical properties of the optically active substance with a retention time of 43 minutes (Example 958) are as follows.

$^1$H-NMR ($CDCl_3$) δ: 1.55 (d, J=7.2 Hz, 3H), 1.73-1.91 (m, 2H), 2.30 (s, 3H), 2.69-2.77 (m, 1H), 2.83-2.90 (m, 1H), 3.16-3.22 (m, 1H), 3.26-3.32 (m, 1H), 3.86 (s, 3H), 6.16-6.23 (m, 1H), 6.30 (dd, J=1.6, 4.0 Hz, 1H), 6.57-6.59 (m, 1H), 6.93 (t, J=1.2 Hz, 1H), 7.03-7.05 (m, 2H), 7.25 (dd, J=1.6, 6.8 Hz, 1H), 7.72 (d, J=1.2 Hz, 1H), 7.86 (s, 1H).

The physical properties of the optically active substance with a retention time of 49 minutes (Example 959) are as follows.

$^1$H-NMR ($CDCl_3$) δ: 1.55 (d, J=7.2 Hz, 3H), 1.73-1.91 (m, 2H), 2.30 (s, 3H), 2.69-2.77 (m, 1H), 2.83-2.90 (m, 1H), 3.16-3.22 (m, 1H), 3.26-3.32 (m, 1H), 3.86 (s, 3H), 6.16-6.23 (m, 1H), 6.30 (dd, J=1.6, 4.0 Hz, 1H), 6.57-6.59 (m, 1H), 6.93 (t, J=1.2 Hz, 1H), 7.03-7.05 (m, 2H), 7.25 (dd, J=1.6, 6.8 Hz, 1H), 7.72 (d, J=1.2 Hz, 1H), 7.86 (s, 1H).

Example 960 and Example 961

Synthesis of (E)-1-[(1S) and (1R)-(5-chlorothiophen-2-yl)ethyl]-3-[3-methoxy-4-(4-methyl-1H-imidazol-1-yl)benzylidene]-1-piperidin-2-one

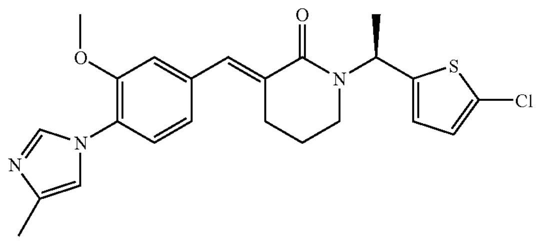

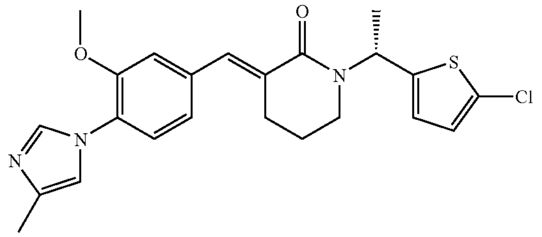

65 mg of a racemate was obtained from (E)-5-chloro-2-(3-methoxy-4-(4-methyl-1H-imidazol-1-yl)benzylidene)valeric acid trifluoroacetate (112 mg) and 1-(5-chlorothiophen-2-yl)ethylamine (48 mg) in the same manner as in Example 418.

The racemate (11 mg) was fractionated using CHIRALCEL™ OD-H manufactured by Daicel Chemical Industries, Ltd. (2 cm×25 cm: mobile phase: hexane:ethanol=8:2; flow rate: 5 mL/min) to obtain the title optically active substance with a retention time of 54 minutes (4.0 mg; >99% ee) and the title optically active substance with a retention time of 60 minutes (4.6 mg; >99% ee).

The physical properties of the optically active substance with a retention time of 54 minutes (Example 960) are as follows.

$^1$H-NMR ($CDCl_3$) δ: 1.57 (d, J=7.6 Hz, 3H), 1.72-1.80 (m, 1H), 1.84-1.92 (m, 1H), 2.30 (s, 3H), 2.69-2.77 (m, 1H), 2.84-2.91 (m, 1H), 3.16-3.22 (m, 1H), 3.27-3.33 (m, 1H), 3.86 (s, 3H), 6.25 (q, J=7.2 Hz, 1H), 6.75-6.78 (m, 2H), 6.94 (s, 1H), 7.04-7.06 (m, 2H), 7.26 (d, J=8.8 Hz, 1H), 7.72 (d, J=1.6 Hz, 1H), 7.88 (s, 1H).

The physical properties of the optically active substance with a retention time of 60 minutes (Example 961) are as follows.

$^1$H-NMR ($CDCl_3$) δ: 1.57 (d, J=7.6 Hz, 3H), 1.72-1.80 (m, 1H), 1.84-1.92 (m, 1H), 2.30 (s, 3H), 2.69-2.77 (m, 1H), 2.84-2.91 (m, 1H), 3.16-3.22 (m, 1H), 3.27-3.33 (m, 1H), 3.86 (s, 3H), 6.25 (q, J=7.2 Hz, 1H), 6.75-6.78 (m, 2H), 6.94 (s, 1H), 7.04-7.06 (m, 2H), 7.26 (d, J=8.8 Hz, 1H), 7.72 (d, J=1.6 Hz, 1H), 7.88 (s, 1H).

Example 962 and Example 963

Synthesis of (E)-1-[(1S) and (1R)-(4-bromothiophen-2-yl)ethyl]-3-[3-methoxy-4-(4-methyl-1H-imidazol-1-yl)benzylidene]-1-piperidin-2-one

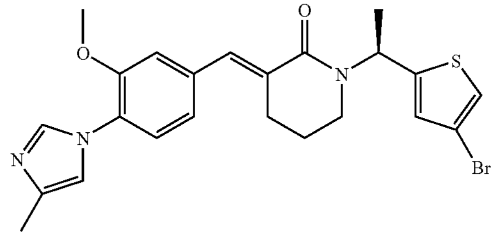

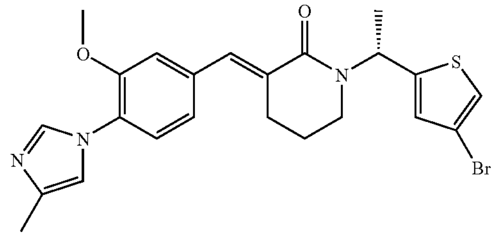

85 mg of a racemate was obtained from (E)-5-chloro-2-(3-methoxy-4-(4-methyl-1H-imidazol-1-yl)benzylidene)valeric acid trifluoroacetate (112 mg) and 1-(4-bromothiophen-2-yl)ethylamine (62 mg) in the same manner as in Example 418.

The racemate (10 mg) was fractionated using CHIRALPAK™ AD-H manufactured by Daicel Chemical Industries, Ltd. (2 cm×25 cm: mobile phase: ethanol; flow rate: 5 mL/min) to obtain the title optically active substance with a retention time of 44 minutes (3.3 mg; >99% ee) and the title optically active substance with a retention time of 53 minutes (2.6 mg; >99% ee).

The physical properties of the optically active-substance with a retention time of 44 minutes (Example 962) are as follows.

$^1$H-NMR ($CDCl_3$) δ: 1.60 (d, J=7.2 Hz, 3H), 1.72-1.92 (m, 2H), 2.30 (s, 3H), 2.70-2.78 (m, 1H), 2.85-2.92 (m, 1H), 3.14-3.20 (m, 1H), 3.28-3.35 (m, 1H), 3.86 (s, 3H), 6.33 (q, J=7.2 Hz, 1H), 6.90 (d, J=1.2 Hz, 1H), 6.95 (s, 1H), 7.04-7.06 (m, 2H), 7.16 (d, J=1.2 Hz, 1H), 7.26 (d, J=8 Hz, 1H), 7.72 (d, J=1.2 Hz, 1H), 7.89 (s, 1H).

The physical properties of the optically active substance with a retention time of 53 minutes (Example 963) are as follows.

$^1$H-NMR ($CDCl_3$) δ: 1.60 (d, J=7.2 Hz, 3H), 1.72-1.92 (m, 2H), 2.30 (s, 3H), 2.70-2.78 (m, 1H), 2.85-2.92 (m, 1H), 3.14-3.20 (m, 1H), 3.28-3.35 (m, 1H), 3.86 (s, 3H), 6.33 (q,

J=7.2 Hz, 1H), 6.90 (d, J=1.2 Hz, 1H), 6.95 (s, 1H), 7.04-7.06 (m, 2H), 7.16 (d, J=1.2 Hz, 1H), 7.26 (d, J=8 Hz, 1H), 7.72 (d, J=1.2 Hz, 1H), 7.89 (s, 1H).

Example 964 and Example 965

Synthesis of (E)-1-[(1R) and (1S)-(1H-indol-3-yl) ethyl]-3-[3-methoxy-4-(4-methyl-1H-imidazol-1-yl) benzylidene]piperidin-2-one

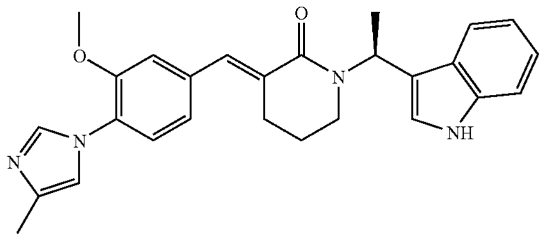

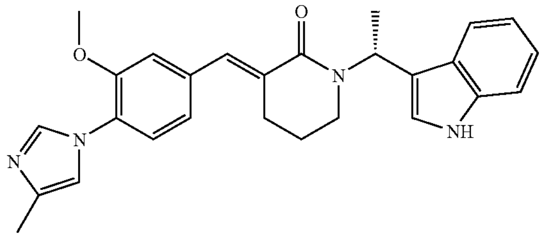

Synthesis of 1-(1H-indol-3-yl)ethanone oxime

Triethylamine (3.93 mL) was added to a solution of 3-acetylindole (500 mg) and hydroxylamine hydrochloride (981 mg) in ethanol (20 mL), and the reaction solution was heated to reflux at 90° C. for 14 hours. The reaction solution was allowed to be cooled to room temperature, the solvent was concentrated under reduced pressure, and ethyl acetate and water were added to the resulting residue and the organic layer was partitioned. The resulting organic layer was washed with brine, and then dried over anhydrous sodium sulfate and concentrated under reduced pressure. The residue was purified by silica gel chromatography (elution solvent:ethyl acetate) to obtain 0.53 g of the title compound. The physical properties of the compound are as follows.

$^1$H-NMR (DMSO-$d_6$) δ (ppm): 2.17 (s, 3H), 7.05 (dd, J=7.2, 14.4 Hz, 1H), 7.13 (dd, J=7.2, 14.4 Hz, 1H), 7.38 (d, J=8.0 Hz, 1H), 7.67 (s, 1H), 8.13 (d, J=8.0 Hz, 1H), 10.49 (s, 1H), 11.29 (s, 1H)

Synthesis of 1-(1H-indol-3-yl)ethylamine

10% palladium-carbon (water content: 50%, 12.2 mg) was added to a solution of 1-(1H-indol-3-yl)ethanone oxime (0.20 g) obtained as above and acetic acid (0.7 mL) in ethanol (7 mL) at room temperature. The reaction mixture was stirred in a hydrogen stream at room temperature for 10 hours, and then filtered on a celite. The filtrate was concentrated under reduced pressure. The residue was extracted with chloroform. The organic layer was washed sequentially with a 1 N aqueous solution of sodium hydroxide and brine, dried over anhydrous magnesium sulfate, and concentrated under reduced pressure. The residue was purified by silica gel column chromatography (Carrier: Chromatorex™ NH, elution solvent: chloroform-methanol system) to obtain 0.137 g of the title compound.

$^1$H-NMR ($CDCl_3$) δ (ppm): 1.55 (d, J=6.4 Hz, 3H), 1.68 (s, 2H), 4.48 (q, J=6.4 Hz, 1H), 7.11-7.23 (m, 3H), 7.37 (d, J=8.0 Hz, 1H), 7.71 (d, J=8.0 Hz, 1H), 8.02 (s, 1H).

Synthesis of (E)-1-[(1R) and (1S)-1-(1H-indol-3-yl) ethyl]-3-[3-methoxy-4-(4-methyl-1H-imidazol-1-yl) benzylidene]piperidin-2-one EDC (384 mg), HOBT (271 mg) and IPEA (0.582 mL) were sequentially added to a solution of (E)-5-chloro-2-(3-methoxy-4-(4-methyl-1H-imidazol-1-yl)benzylidene)valeric acid trifluoroacetate (300 mg) and 1-(1H-indol-3-yl) ethylamine (130 mg) in DMF (5 mL), and the reaction solution was stirred at room temperature for 12 hours. After confirming that the raw materials disappeared, ethyl acetate and water were added to the reaction solution and the organic layer was partitioned. The resulting organic layer was sequentially washed with a saturated aqueous solution of ammonium chloride and brine, and then dried over anhydrous sodium sulfate and concentrated under reduced pressure. The residue was purified by silica gel chromatography (Carrier: Chromatorex™ NH, elution solvent:chloroform:methanol system) to obtain (E)-5-chloro-2-(3-methoxy-4-(4-methyl-1H-imidazol-1-yl)benzylidene)valeric acid (1-(1H-indol-3-yl)ethyl) amide (332 mg). Sodium hydride (containing mineral oil at 40%, 19.3 mg) was added to a solution of the resulting (E)-5-chloro-2-(3-methoxy-4-(4-methyl-1H-imidazol-1-yl)benzylidene)valeric acid (1-(1H-indol-3-yl)ethyl)amide (92 mg) in THF (3 mL) at 0° C., and the reaction solution was stirred at room temperature for 90 minutes. The reaction solution was cooled to 0° C., water and ethyl acetate were added to the reaction solution, and the organic layer was partitioned. The organic layer was washed sequentially with water and a saturated aqueous solution of sodium chloride. The organic layer was dried over anhydrous sodium sulfate, and then concentrated under reduced pressure. The residue was purified by silica gel chromatography (Carrier: Chromatorex™ NH, elution solvent:chloroform:methanol system) to obtain (E)-1-[1-(1H-indol-3-yl)ethyl]-3-(3-methoxy-4-(4-methyl-1H-imidazol-1-yl)benzylidene)piperidin-2-one as a racemate (37.3 mg). The compound (37 mg) was fractionated using CHIRALPAK™ AD-H manufactured by Daicel Chemical Industries, Ltd. (2 cm×25 cm: mobile phase: ethanol) to obtain the title optically active substance with a retention time of 10 minutes (15 mg; >99% ee) and the title optically active substance with a retention time of 14 minutes (14.2 mg; >99% ee).

The physical properties of the optically active substance with a retention time of 10 minutes (Example 964) are as follows.

$^1$H-NMR ($CDCl_3$) δ (ppm): 1.58-1.64 (m, 1H), 1.63 (d, J=6.8 Hz, 3H), 1.69-1.74 (m, 1H), 2.31 (s, 3H), 2.71-2.78 (m, 2H), 2.92-2.99 (m, 1H), 3.18-3.25 (m, 1H), 3.86 (s, 3H), 6.51 (q, J=6.8 Hz, 1H), 6.94 (s, 1H), 7.06-7.26 (m, 6H), 7.38 (d, J=8.0 Hz, 1H), 7.63 (d, J=8.0 Hz, 1H), 7.74 (s, 1H), 7.96 (s, 1H), 8.39 (s, 1H).

The physical properties of the optically active substance with a retention time of 14 minutes (Example 965) are as follows.

$^1$H-NMR ($CDCl_3$) δ (ppm): 1.58-1.64 (m, 1H), 1.63 (d, J=6.8 Hz, 3H), 1.69-1.74 (m, 1H), 2.31 (s, 3H), 2.71-2.78 (m, 2H), 2.92-2.99 (m, 1H), 3.18-3.25 (m, 1H), 3.86 (s, 3H), 6.51

(q, J=6.8 Hz, 1H), 6.94 (s, 1H), 7.06-7.26 (m, 6H), 7.38 (d, J=8.0 Hz, 1H), 7.63 (d, J=8.0 Hz, 1H), 7.74 (s, 1H), 7.96 (s, 1H), 8.37 (s, 1H).

Example 966

Synthesis of (E)-1-(2-chloroquinolin-4-ylmethyl)-3-[3-methoxy-4-(4-methyl-1H-imidazol-1-yl)benzylidene]piperidin-2-one

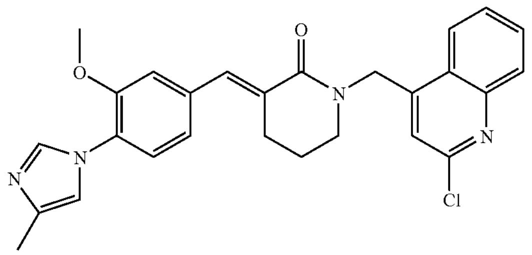

28 mg of the title compound was obtained from (E)-5-chloro-2-(3-methoxy-4-(4-methyl-1H-imidazol-1-yl)benzylidene)valeric acid trifluoroacetate (263 mg) and (2-chloroquinolin-4-yl)methylamine (200 mg) in the same manner as in Example 418. The physical properties of the compound are as follows.

$^1$H-NMR ($CDCl_3$) δ (ppm): 1.90-2.00 (m, 2H), 2.30 (s, 3H), 2.85-2.94 (m, 2H), 3.38-3.45 (m, 2H), 3.87 (s, 3H), 5.20 (s, 2H), 6.92-6.95 (m, 1H), 7.03-7.08 (m, 2H), 7.21-7.29 (m, 2H), 7.58-7.65 (m, 1H), 7.70-7.79 (m, 2H), 7.91 (s, 1H), 8.04-8.09 (m, 2H).

Example 967

Synthesis of (E)-1-(2-morpholin-4-yl-guinolin-4-ylmethyl)-3-[3-methoxy-4-(4-methyl-1H-imidazol-1-yl)benzylidene]piperidin-2-one

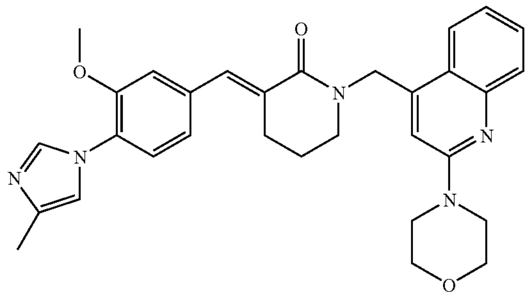

100 mg of the title compound was obtained from ethyl (E)-5-chloro-2-(3-methoxy-4-(4-methyl-1H-imidazol-1-yl)benzylidene)valerate (230 mg) and (2-morpholin-4-yl-quinolin-4-yl)methylamine (230 mg) in the same manner as in Example 418. The physical properties of the compound are as follows.

$^1$H-NMR ($CDCl_3$) δ (ppm): 1.82-1.90 (m, 2H), 2.34 (s, 3H), 2.81-2.88 (m, 2H), 3.30-3.38 (m, 2H), 3.67-3.75 (m, 4H), 3.80-3.90 (m, 4H), 3.88 (s, 3H), 5.14 (s, 2H), 6.88 (s, 1H), 6.96 (s, 1H), 7.02-7.10 (m, 2H), 7.24-7.34 (m, 2H), 7.56-7.62 (m, 1H), 7.74-7.84 (m, 1H), 7.83 (s, 1H), 7.86-7.92 (m, 1H), 7.93 (s, 1H).

Example 968

Synthesis of (E)-1-(6-morpholin-4-yl-quinolin-2-ylmethyl)-3-[3-methoxy-4-(4-methyl-1H-imidazol-1-yl)benzylidene]piperidin-2-one

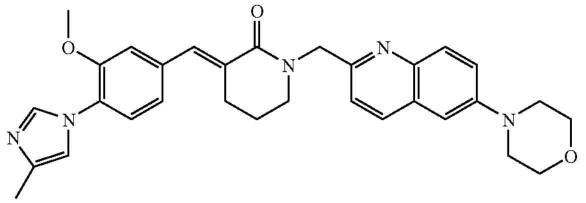

14 mg of the title compound was obtained from ethyl (E)-5-chloro-2-(3-methoxy-4-(4-methyl-1H-imidazol-1-yl)benzylidene)valerate (300 mg) and (6-morpholin-4-yl-quinolin-2-yl)methylamine (200 mg) in the same manner as in Example 418. The physical properties of the compound are as follows.

$^1$H-NMR ($CDCl_3$) δ (ppm): 1.83-1.93 (m, 2H), 2.36 (s, 3H), 2.80-2.90 (m, 2H), 3.25-3.33 (m, 4H), 3.50-3.57 (m, 2H), 3.87 (s, 3H), 3.85-3.97 (m, 4H), 5.00 (s, 2H), 6.96 (s, 1H), 7.02-7.10 (m, 3H), 7.24-7.30 (m, 1H), 7.43-7.52 (m, 2H), 7.84-7.92 (m, 2H), 7.92-8.04 (m, 2H).

Example 969

Synthesis of (E)-1-(6-morpholin-4-yl-naphthalen-2-ylmethyl)-3-[3-methoxy-4-(4-methyl-1H-imidazol-1-yl)benzylidene]piperidin-2-one

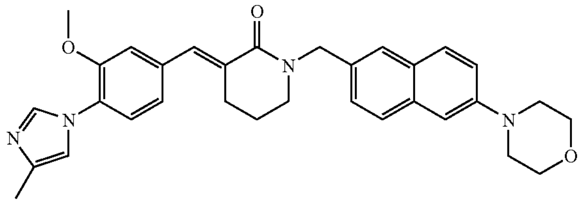

173 mg of the title compound was obtained from ethyl (E)-5-chloro-2-(3-methoxy-4-(4-methyl-1H-imidazol-1-yl)benzylidene)valerate (350 mg) and (6-morpholin-4-yl-naphthalen-2-yl)methylamine (259 mg) in the same manner as in Example 418. The physical properties of the compound are as follows.

$^1$H-NMR ($CDCl_3$) δ (ppm): 1.78-1.88 (m, 2H), 2.32 (s, 3H), 2.78-2.85 (m, 2H), 3.22-3.30 (m, 4H), 3.35-3.42 (m, 2H), 3.86 (s, 3H), 3.87-3.95 (m, 4H), 4.85 (s, 2H), 6.93 (s, 1H), 7.02-7.07 (m, 2H), 7.10 (d, J=2.0 Hz, 1H), 7.22-7.28 (m, 2H), 7.39 (dd, J=2.0, 8.4 Hz, 1H), 7.62 (s, 1H), 7.67 (d, J=8.4 Hz, 1H), 7.71 (d, J=8.8 Hz, 1H), 7.76 (s, 1H), 7.90 (s, 1H)

Example 970

Synthesis of (E)-1-[(1S)-(2-fluorophenyl)ethyl]-3-[3-methoxy-4-(4-methyl-1H-imidazol-1-yl)benzylidene]piperidin-2-one

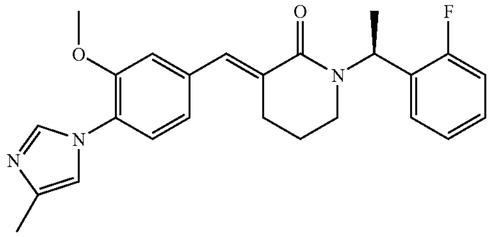

Synthesis of (E)-5-chloro-2-[3-methoxy-4-(4-methyl-1H-imidazol-1-yl)benzylidene]valeric acid ((1S)-(2-fluorophenyl)ethyl)amide IPEA (300 μL), EDC (165 mg) and HOBT (116 mg) were sequentially added to a solution of (E)-5-chloro-2-(3-methoxy-4-(4-methyl-1H-imidazol-1-yl)benzylidene)valeric acid trifluoroacetate (193 mg) and (S)-1-(2-fluorophenyl)ethylamine (60.0 mg) in DMF (3.0 mL) at room temperature, and the reaction solution was stirred at room temperature for 1 hour. After confirming that the raw materials disappeared, water and ethyl acetate were added to the residue and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system→ethyl acetate-methanol system) to obtain 258 mg of the title compound. The physical properties of the compound are as follows.

$^1$H-NMR ($CDCl_3$) δ (ppm): 1.60 (d, J=7.2 Hz, 3H), 1.95-2.02 (m, 2H), 2.32 (s, 3H), 2.69-2.73 (m, 2H), 3.57 (t, J=6.4 Hz, 2H), 3.86 (s, 3H), 5.35 (quint, J=7.2 Hz, 1H), 6.43 (d, J=7.2 Hz, 1H), 6.93-6.97 (m, 3H), 7.05-7.16 (m, 2H), 7.16 (s, 1H), 7.23-7.28 (m, 2H), 7.34 (t, J=7.2 Hz, 1H), 7.78 (s, 1H).

Synthesis of (E)-1-[(1S)-(2-fluorophenyl)ethyl]-3-[3-methoxy-4-(4-methyl-1H-imidazol-1-yl)benzylidene]piperidin-2-one Sodium hydride (containing mineral oil at 40%, 34.5 mg) was added to a solution of (E)-5-chloro-2-(3-methoxy-4-(4-methyl-1H-imidazol-1-yl)benzylidene)valeric acid ((1S)-(2-fluorophenyl)ethyl)amide (258 mg) in DMF (3.0 mL) at 0° C., and the reaction solution was stirred at room temperature for 20 minutes. After confirming that the raw materials disappeared, water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system→ethyl acetate-methanol system) to obtain 180 mg of the title compound. The physical properties of the compound are as follows.

$^1$H-NMR ($CDCl_3$) δ (ppm): 1.60 (d, J=7.2 Hz, 3H), 1.77-1.82 (m, 2H), 2.26 (s, 3H), 2.68-2.86 (m, 2H), 2.96-3.02 (m, 1H), 3.29 (td, J=5.6, 12 Hz, 1H), 3.84 (s, 3H), 6.23 (q, J=7.2 Hz, 1H), 6.92 (t, J=1.2 Hz, 1H), 7.01-7.07 (m, 3H), 7.14 (dt, J=1.2, 7.6 Hz, 1H), 7.23 (d, J=8.4 Hz, 1H), 7.24-7.31 (m, 1H), 7.38 (dt, J=1.2, 7.6 Hz, 1H), 7.72 (d, J=1.2 Hz, 1H), 7.86 (brs, 1H).

Example 971 and Example 972

Synthesis of (E)-3-[3-methoxy-4-(4-methyl-1H-imidazol-1-yl)benzylidene]-1-[(1R) and (1S)-7-morpholin-4-yl-1,2,3,4-tetrahydronaphthalen-1-yl]piperidin-2-one

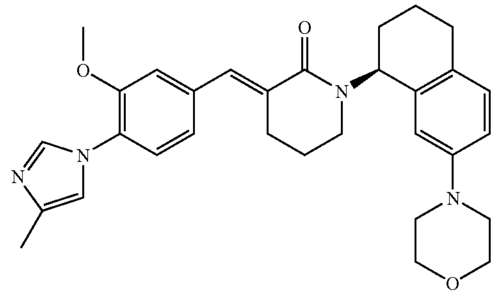

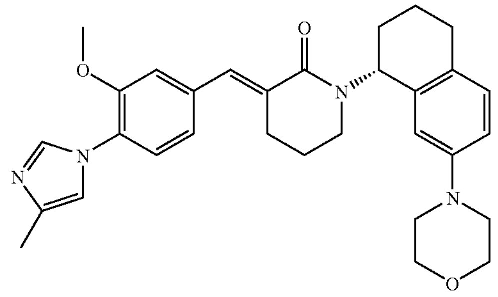

Synthesis of 7-morpholin-4-yl-3,4-dihydro-2H-naphthalen-1-one

A solution of 7-bromo-3,4-dihydro-2H-naphthalen-1-one (600 mg), morpholine (1.16 g), tripotassium phosphate (850 mg), tris(dibenzylideneacetone)dipalladium (0) (24.4 mg) and 2-(di-tert-butylphosphino)biphenyl (15.9 mg) in toluene (5.0 mL) was stirred in a nitrogen atmosphere at 100° C. overnight. Water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain 360 mg of the title compound. The physical properties of the compound are as follows.

$^1$H-NMR ($CDCl_3$) δ (ppm): 2.11 (quint, J=6.0 Hz, 2H), 2.63 (t, J=6.0 Hz, 2H), 2.89 (t, J=6.0 Hz, 2H), 3.16-3.18 (m, 4H), 3.85-3.87 (m, 4H), 7.07 (dd, J=2.8, 8.4 Hz, 1H), 7.16 (d, J=8.4 Hz, 1H), 7.53 (d, J=2.8 Hz, 1H)

Synthesis of 7-morpholin-4-yl-3,4-dihydro-2H-naphthalen-1-one oxime

A solution of 7-morpholin-4-yl-3,4-dihydro-2H-naphthalen-1-one (360 mg), hydroxylammonium chloride (163 mg) and sodium acetate (384 mg) in ethanol (5.0 mL) was heated to reflux for 1 hour and 50 minutes. Water and ethyl acetate were added to the reaction solution and the organic layer was partitioned. The resulting organic layer was washed with brine, and then dried over anhydrous magnesium sulfate and concentrated under reduced pressure to obtain 384 mg of the title compound as a crude product. The physical properties of the compound are as follows.

$^1$H-NMR ($CDCl_3$) δ (ppm): 1.80-1.89 (m, 2H), 2.69 (t, J=6.8 Hz, 2H), 2.78 (t, J=6.8 Hz, 2H), 3.14-3.16 (m, 4H), 3.85-3.87 (m, 4H), 6.90 (dd, J=2.0, 8.4 Hz, 1H), 7.06 (d, J=8.4 Hz, 1H), 7.43 (s, 1H)

Synthesis of 7-morpholin-4-yl-1,2,3,4-tetrahydronaphthalen-1-ylamine

A solution of crude 7-morpholin-4-yl-3,4-dihydro-2H-naphthalen-1-one oxime (384 mg) and 10% palladium-carbon (water content: 48%, 350 mg) in ethanol (10 mL) was stirred in a hydrogen atmosphere (0.4 Mpa) at room temperature for 8 hours. The reaction solution was filtered on a celite, and the filtrate was concentrated under reduced pressure. The resulting residue was purified by silica gel chromatography (Carrier: Chromatorex™ NH, elution solvent:heptane-ethyl acetate system→ethyl acetate-methanol system) to obtain 110 mg of the title compound. The physical properties of the compound are as follows.

$^1$H-NMR ($CDCl_3$) δ (ppm): 1.62-1.79 (m, 2H), 1.86-1.95 (m, 1H), 1.98-2.04 (m, 1H), 2.62-2.77 (m, 2H), 3.12-3.14 (m, 4H), 3.84-3.86 (m, 4H), 3.93 (t, J=5.6 Hz, 1H), 6.75 (dd, J=2.8, 8.4 Hz, 1H), 6.98-7.00 (m, 2H).

Synthesis of (E)-5-chloro-2-[3-methoxy-4-(4-methyl-1H-imidazol-1-yl)-benzylidene]valeric acid (7-morpholin-4-yl-1,2,3,4-tetrahydronaphthalen-1-yl)amide IPEA (330 μL), EDC (181 mg) and HOBT (128 mg) were sequentially added to a solution of (E)-5-chloro-2-(3-methoxy-4-(4-methyl-1H-imidazol-1-yl)benzylidene)valeric acid trifluoroacetate (276 mg) and 7-morpholin-4-yl-1,2,3,4-tetrahydronaphthalen-1-ylamine (110 mg) in DMF (3.0 mL) at room temperature, and the reaction solution was stirred at room temperature for 30 minutes. After confirming that the raw materials disappeared, water and ethyl acetate were added to the residue and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system→ethyl acetate-methanol system) to obtain 213 mg of the title compound. The physical properties of the compound are as follows.

$^1$H-NMR ($CDCl_3$) δ (ppm): 1.80-1.96 (m, 3H), 2.00-2.11 (m, 3H), 2.30 (s, 3H), 2.68-2.80 (m, 4H), 3.10-3.12 (m, 4H), 3.57 (t, J=6.4 Hz, 2H), 3.83-3.86 (m, 4H), 3.86 (s, 3H), 5.24-5.29 (m, 1H), 6.19 (d, J=8.8 Hz, 1H), 6.81-6.84 (m, 2H), 6.92-6.95 (m, 3H), 7.04 (d, J=8.4 Hz, 1H), 7.11 (s, 1H), 7.24 (d, J=8.8 Hz, 1H), 7.72 (s, 1H).

Synthesis of (E)-3-[3-methoxy-4-(4-methyl-1H-imidazol-1-yl)benzylidene]-1-[(1R) and (1S)-7-morpholin-4-yl-1,2,3,4-tetrahydronaphthalen-1-yl]piperidin-2-one Sodium hydride (containing mineral oil at 40%, 37.8 mg) was added to a solution of (E)-5-chloro-2-(3-methoxy-4-(4-methyl-1H-imidazol-1-yl)-benzylidene)valeric acid (7-morpholin-4-yl-1,2,3,4-tetrahydronaphthalen-1-yl)amide (213 mg) in DMF (5.0 mL) at 0° C., and the reaction solution was stirred for 30 minutes. After confirming that the raw materials disappeared, water and ethyl acetate were added to the reaction solution and the organic layer was partitioned. The organic layer was washed with brine, and then dried over anhydrous magnesium sulfate and concentrated under reduced pressure. The residue was purified by silica gel chromatography (elution solvent:heptane-ethyl acetate system→ethyl acetate-methanol system) to obtain 195 mg of (E)-3-(3-methoxy-4-(4-methyl-1H-imidazol-1-yl)benzylidene)-1-(7-morpholin-4-yl-1,2,3,4-tetrahydronaphthalen-1-yl)piperidin-2-one as a racemate.

Next, the compound (8.00 mg) was fractionated using CHIRALPAK™ AD-H manufactured by Daicel Chemical Industries, Ltd. (2 cm×25 cm: mobile phase: ethanol) to obtain the title optically active substance with a retention time of 7.6 minutes (Example 971, 3.60 mg; >99% ee) and the title optically active substance with a retention time of 12 minutes (Example 972, 1.40 mg; >99% ee). Properties data of the optically active substances are as follows.

$^1$H-NMR ($CDCl_3$) δ (ppm): 1.68-1.90 (m, 3H), 1.90-2.24 (m, 2H), 2.07-2.14 (m, 1H), 2.31 (s, 3H), 2.68-2.74 (m, 2H), 2.74-2.85 (m, 1H), 2.85-2.98 (m, 1H), 3.04-3.08 (m, 4H), 3.05-3.12 (m, 1H), 3.17-3.25 (m, 1H), 3.81-3.84 (m, 4H), 3.87 (s, 3H), 6.07-6.11 (m, 1H), 6.63 (d, J=2.4 Hz, 1H), 6.77 (dd, J=2.4, 8.4 Hz, 1H), 6.94 (s, 1H), 7.03 (d, J=8.4 Hz, 1H), 7.08-7.10 (m, 2H), 7.26 (d, J=8.4 Hz, 1H), 7.74 (brs, 1H), 7.91 (brs, 1H).

Example 973 and Example 974

Synthesis of (E)-1-[(1R) and (1S)-6-fluoro-5-morpholin-4-ylindan-1-yl]-3-[3-methoxy-4-(4-methyl-1H-imidazol-1-yl)benzylidene]piperidin-2-one

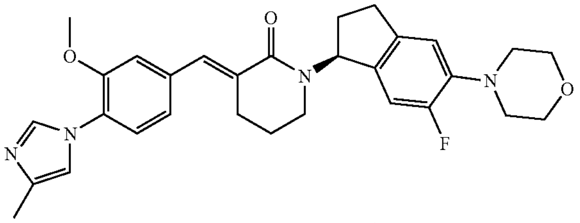

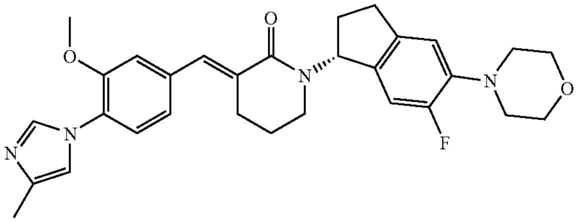

Synthesis of 5,6-difluoro-1-indanone

Oxalyl chloride (1.12 mL) and DMF (78.2 mg) were added to a solution of 3,4-difluorohydrocinnamic acid (2.00 g) in dichloromethane (3.0 mL) at 0° C., and the reaction solution was stirred at room temperature overnight. After confirming that the raw materials disappeared, the reaction solution was concentrated under reduced pressure. Next, a solution of the resulting residue in dichloromethane (10 mL) was added to a solution of aluminum chloride (2.13 g) in dichloromethane (20 mL) at −30° C. The reaction solution was stirred at room temperature for 1.5 hours. After confirming that the raw materials disappeared, the reaction solution was poured into ice water. The solution was extracted with ethyl acetate. The organic layer was washed with brine, and then dried over anhydrous magnesium sulfate and concentrated under reduced pressure. The resulting residue was purified by silica gel chromatography (elution solvent:heptane-ethyl acetate system) to obtain 535 mg of the title compound. The physical properties of the compound are as follows.

$^1$H-NMR ($CDCl_3$) δ (ppm): 2.72-2.75 (m, 2H), 3.11-3.14 (m, 2H), 7.27 (t, J=8.0 Hz, 1H), 7.53 (t, J=8.0 Hz, 1H).

Synthesis of 6-fluoro-5-morpholin-4-ylindan-1-one

A solution of 5,6-difluoro-1-indanone (535 mg) and morpholine (554 mg) in 1-methyl-2-pyrrolidinone (6.0 mL) was stirred at 100° C. for 7 hours. After confirming that the raw materials disappeared, water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain 635 mg of the title compound. The physical properties of the compound are as follows.

$^1$H-NMR ($CDCl_3$) δ (ppm): 2.67-2.69 (m, 2H), 3.03-3.06 (m, 2H), 3.20-3.22 (m, 4H), 3.87-3.89 (m, 4H), 6.89 (d, J=7.2 Hz, 1H), 7.35 (d, J=12 Hz, 1H).

Synthesis of 6-fluoro-5-morpholin-4-ylindan-1-ylamine

A solution of 6-fluoro-5-morpholin-4-ylindan-1-one (200 mg), hydroxylammonium chloride (102 mg) and sodium acetate (241 mg) in ethanol (5.0 mL) was heated to reflux for 1 hour. After confirming that the raw materials disappeared, water and ethyl acetate were added to the reaction solution and the organic layer was partitioned. The resulting organic layer was washed with brine, dried over anhydrous magnesium sulfate, and then concentrated under reduced pressure to obtain 218 mg of 6-fluoro-5-morpholin-4-ylindan-1-one oxime. Next, 10% palladium-carbon (water content: 48%, 200 mg) was added to a solution of the resulting 6-fluoro-5-morpholin-4-ylindan-1-one oxime (218 mg) in ethanol (5.0 mL), and the reaction solution was stirred in a hydrogen atmosphere (0.4 MPa) at room temperature for 9 hours. The reaction solution was filtered on a celite, and the filtrate was concentrated under reduced pressure. The resulting residue was purified by silica gel chromatography (Carrier: Chromatorex™ NH, elution solvent:heptane-ethyl acetate system→ethyl acetate-methanol system) to obtain 56.0 mg of the title compound. The physical properties of the compound are as follows.

$^1$H-NMR ($CDCl_3$) δ (ppm): 1.60-1.72 (m, 1H), 2.50 (dtd, J=3.6, 7.2, 16 Hz, 1H), 2.74 (td, J=7.2, 16 Hz, 1H), 2.89 (ddd, J=3.6, 8.8, 16 Hz, 1H), 3.03-3.05 (m, 4H), 3.85-3.88 (m, 4H), 4.30 (t, J=7.2 Hz, 1H), 6.79 (d, J=7.6 Hz, 1H), 6.98 (d, J=12 Hz, 1H).

Synthesis of (E)-5-chloro-2-[3-methoxy-4-(4-methyl-1H-imidazol-1-yl)benzylidene]valeric acid (6-fluoro-5-morpholin-4-ylindan-1-yl)amide IPEA (165 μL), EDC (90.9 mg) and HOBT (64.0 mg) were sequentially added to a solution of (E)-5-chloro-2-(3-methoxy-4-(4-methyl-1H-imidazol-1-yl)benzylidene)valeric acid trifluoroacetate (138 mg) and 6-fluoro-5-morpholin-4-ylindan-1-ylamine (56.0 mg) in DMF (3.0 mL), and the reaction solution was stirred at room temperature for 1 hour. After confirming that the raw materials disappeared, the solvent was concentrated under reduced pressure, and water and ethyl acetate were added to the residue and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system, ethyl acetate-methanol system) to obtain 123 mg of the title compound. The physical properties of the compound are as follows.

$^1$H-NMR ($CDCl_3$) δ (ppm): 1.88-1.98 (m, 1H), 2.00-2.08 (m, 2H), 2.30 (s, 3H), 2.62-2.78 (m, 3H), 2.82-3.20 (m, 2H), 3.05-3.08 (m, 4H), 3.61 (t, J=6.0 Hz, 2H), 3.87 (s, 3H), 3.87-3.89 (m, 4H), 5.55 (q, J=7.6 Hz, 1H), 6.16-6.22 (m, 1H), 6.84 (d, J=7.2 Hz, 1H), 6.94-6.99 (m, 3H), 7.03 (d, J=12 Hz, 1H), 7.19 (s, 1H), 7.25-7.27 (m, 1H), 7.74 (s, 1H).

Synthesis of (E)-1-[(1R) and (1S)-6-fluoro-5-morpholin-4-ylindan-1-yl]-3-[3-methoxy-4-(4-methyl-1H-imidazol-1-yl)benzylidene]piperidin-2-one Sodium hydride (containing mineral oil at 40%, 19.0 mg) was added to a solution of (E)-5-chloro-2-(3-methoxy-4-(4-methyl-1H-imidazol-1-yl)benzylidene)valeric acid (6-fluoro-5-morpholin-4-ylindan-1-yl)amide (123 mg) in DMF (3.0 mL) at 0° C., and the reaction solution was stirred for 15 minutes. After confirming that the raw materials disappeared, water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system, ethyl acetate-methanol system) to obtain 85 mg of (E)-1-(6-fluoro-5-morpholin-4-ylindan-1-yl)-3-(3-methoxy-4-(4-methyl-1H-imidazol-1-yl)benzylidene)piperidin-2-one as a racemate. Next, the compound (12.0 mg) was fractionated using CHIRALCEL™ OD-H manufactured by Daicel Chemical Industries, Ltd. (2 cm×25 cm: mobile phase: hexane:ethanol=70:30) to obtain the title optically active substance with a retention time of 13 minutes (Example 973, 4.60 mg; >99% ee) and the title optically active substance with a retention time of 15 minutes (Example 974, 4.70 mg; >99% ee). The physical properties of the optically active substances are as follows.

$^1$H-NMR ($CDCl_3$) δ (ppm): 1.76-2.04 (m, 3H), 2.31 (s, 3H) 2.46-2.58 (m, 1H), 2.74-3.00 (m, 5H), 3.04-3.10 (m, 4H), 3.08-3.18 (m, 1H), 3.87 (s, 3H), 3.87-3.89 (m, 4H), 6.43 (t, J=7.6 Hz, 1H), 6.82-6.88 (m, 2H), 6.95 (s, 1H), 7.06 (d, J=0.8 Hz, 1H), 7.26-7.27 (m, 2H), 7.74 (s, 1H), 7.89 (s, 1H).

Example 975 and Example 976

Synthesis of (E)-1-[(1S) and (1R)-1-(4-fluorophenyl)-2-methylpropyl]-3-[3-methoxy-4-(4-methyl-1H-imidazol-1-yl)benzylidene]piperidin-2-one

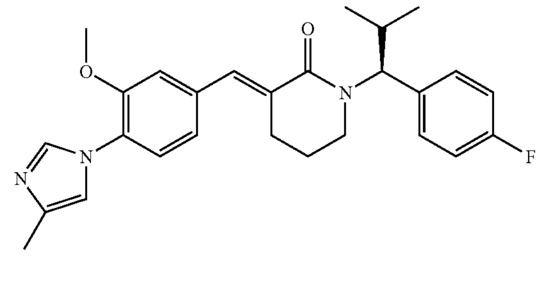

-continued

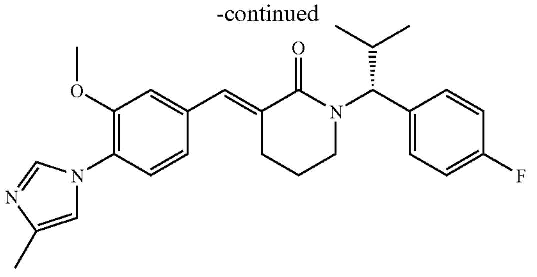

Synthesis of 1-(4-fluorophenyl)-2-methylpropan-1-one oxime 1.06 g of the title compound was obtained from 1-(4-fluorophenyl)-2-methylpropan-1-one (1.00 g) in the same manner as in Example 971. The physical properties of the compound are as follows.

$^1$H-NMR ($CDCl_3$) δ (ppm): 1.11 (d, J=6.8 Hz, 3H), 1.19 (d, J=7.2 Hz, 3H), 2.78-2.85 (m, ½H), 3.55-3.62 (m, ½H), 7.02 (t, J=8.8 Hz, 1H), 7.09 (t, J=8.8 Hz, 1H), 7.28 (dd, J=5.6, 8.8 Hz, 1H), 7.34 (dd, J=5.6, 8.8 Hz, 1H).

Synthesis of 1-(4-fluorophenyl)-2-methylpropylamine 364 mg of the title compound was obtained from 1-(4-fluorophenyl)-2-methylpropan-1-one oxime (500 mg) in the same manner as in Example 971. The physical properties of the compound are as follows.

$^1$H-NMR ($CDCl_3$) δ (ppm): 0.75 (d, J=6.8 Hz, 3H), 0.96 (d, J=6.4 Hz, 3H), 1.75-1.85 (m, 1H), 3.60 (d, J=7.6 Hz, 1H), 6.99 (t, J=8.8 Hz, 2H), 7.24 (dd, J=5.6, 8.8 Hz, 2H).

Synthesis of (E)-5-chloro-2-[3-methoxy-4-(4-methyl-1H-imidazol-1-yl)benzylidene]valeric acid (1-(4-fluorophenyl)-2-methylpropyl)amide 219 mg of the title compound was obtained from (E)-5-chloro-2-(3-methoxy-4-(4-methyl-1H-imidazol-1-yl)benzylidene)valeric acid trifluoroacetate (300 mg) and 1-(4-fluorophenyl)-2-methylpropylamine (168 mg) in the same manner as in Example 418. The physical properties of the compound are as follows.

$^1$H-NMR ($CDCl_3$) δ (ppm): 0.94 (d, J=6.4 Hz, 3H), 1.04 (d, J=6.0 Hz, 3H), 1.91-2.01 (m, 2H), 2.01-2.19 (m, 1H), 2.30 (s, 3H), 2.70-2.75 (m, 2H), 3.58 (s, 2H), 3.85 (s, 3H), 4.81 (t, J=8.4 Hz, 1H), 6.24 (d, J=8.4 Hz, 1H), 6.92-6.96 (m, 3H), 7.03 (t, J=8.4 Hz, 2H), 7.18 (s, 1H), 7.23-7.28 (m, 3H), 7.71 (s, 1H).

Synthesis of (E)-1-[(1R) and (1S)-1-(4-fluorophenyl)-2-methylpropyl]-3-[3-methoxy-4-(4-methyl-1H-imidazol-1-yl)benzylidene]piperidin-2-one 177 mg of (E)-1-(1-(4-fluorophenyl)-2-methylpropyl)-3-(3-methoxy-4-(4-methyl-1H-imidazol-1-yl)benzylidene)piperidin-2-one as a racemate was obtained from (E)-5-chloro-2-(3-methoxy-4-(4-methyl-1H-imidazol-1-yl)benzylidene) valeric acid (1-(4-fluorophenyl)-2-methylpropyl)amide (219 mg) in the same manner as in Example 418. Next, the compound (10.0 mg) was fractionated using CHIRALPAK™ AD-H manufactured by Daicel Chemical Industries, Ltd. (2 cm×25 cm: mobile phase: ethanol) to obtain the title optically active substance with a retention time of 5.0 minutes (Example 975, 2.4 mg; >99% ee) and the title optically active substance with a retention time of 5.9 minutes (Example 976, 2.2 mg; >98% ee). The physical properties of the optically active substances are as follows.

$^1$H-NMR ($CDCl_3$) δ (ppm): 0.93 (d, J=6.4 Hz, 3H), 1.05 (d, J=6.0 Hz, 3H), 1.60-1.72 (m, 1H), 1.76-1.86 (m, 1H), 2.29 (s, 3H), 2.36-2.46 (m, 1H), 2.62-2.72 (m, 1H), 2.72-2.82 (m, 1H), 3.00-3.08 (m, 1H), 3.24-3.32 (m, 1H), 3.84 (s, 3H), 5.68 (d, J=12 Hz, 1H), 6.91 (s, 1H), 7.00-7.04 (m, 4H), 7.21-7.28 (m, 1H), 7.37 (t, J=6.4 Hz, 2H), 7.69 (s, 1H), 7.84 (s, 1H).

Example 977 and Example 978

Synthesis of (E)-3-[3-methoxy-4-(4-methyl-1H-imidazol-1-yl)benzylidene]-1-[(1S) and (1R)-2-methyl-1-(4-morpholin-4-ylphenyl)propyl]piperidin-2-one

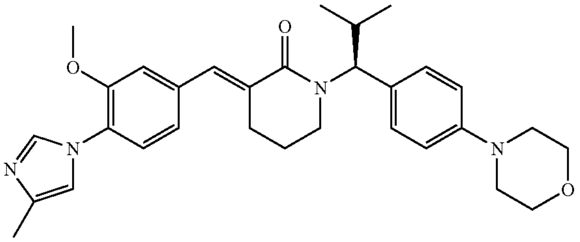

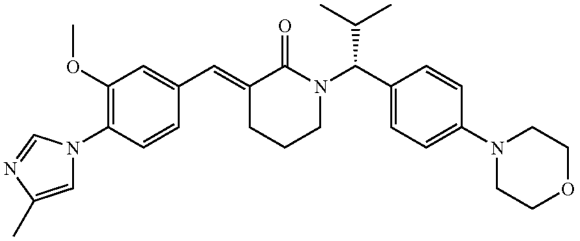

Synthesis of 2-methyl-1-(4-morpholin-4-ylphenyl)propan-1-one 491 mg of the title compound was obtained from 1-(4-fluorophenyl)-2-methylpropan-1-one (500 mg) in the same manner as in Example 973. The physical properties of the compound are as follows.

$^1$H-NMR ($CDCl_3$) δ (ppm): 1.20 (d, J=6.8 Hz, 6H), 3.31 (t, J=4.8 Hz, 4H), 3.46-3.56 (m, 1H), 3.86 (t, J=4.8 Hz, 4H), 6.88 (d, J=9.2 Hz, 2H), 7.92 (d, J=9.2 Hz, 2H).

Synthesis of 2-methyl-1-(4-morpholin-4-ylphenyl)propan-1-one oxime 424 mg of the title compound was obtained from 1-(4-fluorophenyl)-2-methylpropan-1-one (491 mg) in the same manner as in Example 971. The physical properties of the compound are as follows.

$^1$H-NMR ($CDCl_3$) δ (ppm): 1.12 (d, J=6.8 Hz, 3H), 1.22 (d, J=6.8 Hz, 3H), 2.80-2.87 (m, ½H), 3.17-3.22 (m, 4H), 3.53-3.60 (m, ½H), 3.86 (t, J=4.8 Hz, 4H), 6.86 (d, J=8.4 Hz, 1H), 6.93 (d, J=8.4 Hz, 1H), 7.27 (d, J=8.8 Hz, 1H), 7.33 (d, J=8.8 Hz, 1H).

Synthesis of 2-methyl-1-(4-morpholin-4-ylphenyl)propylamine 300 mg of the title compound was obtained from 2-methyl-1-(4-morpholin-4-ylphenyl)propan-1-one oxime (424 mg) in the same manner as in Example 971. The physical properties of the compound are as follows.

$^1$H-NMR ($CDCl_3$) δ (ppm): 0.75 (d, J=6.4 Hz, 3H), 0.97 (d, J=6.8 Hz, 3H), 1.64 (brs, 2H), 1.77-1.86 (m, 1H), 3.14 (t, J=4.8 Hz, 4H), 3.53 (d, J=7.2 Hz, 1H), 3.85 (t, J=4.8 Hz, 4H), 6.86 (d, J=8.4 Hz, 2H), 7.18 (d, J=8.8 Hz, 2H).

Synthesis of (E)-5-chloro-2-[3-methoxy-4-(4-methyl-1H-imidazol-1-yl)benzylidene]valeric acid (2-methyl-1-(4-morpholin-4-ylphenyl)propyl)amide 290 mg of the title compound was obtained from (E)-5-chloro-2-(3-methoxy-4-(4-methyl-1H-imidazol-1-yl)benzylidene)valeric acid trifluoroacetate (300 mg) and 2-methyl-1-(4-morpholin-4-ylphenyl)propylamine (235 mg) in the same manner as in Example 418. The physical properties of the compound are as follows.

$^1$H-NMR ($CDCl_3$) δ (ppm): 0.88 (d, J=6.4 Hz, 3H), 1.04 (d, J=6.8 Hz, 3H), 1.94-2.01 (m, 2H), 2.06-2.14 (m, 1H), 2.30 (s, 3H), 2.69-2.73 (m, 2H), 3.15 (t, J=4.8 Hz, 4H), 3.57 (dt, J=2.4, 6.0 Hz, 2H), 3.85 (t, J=4.8 Hz, 4H), 3.85 (s, 3H), 4.78 (t, J=8.4 Hz , 1H), 6.26 (d, J=8.4 Hz, 1H), 6.88 (d, J=8.4 Hz, 2H), 6.92-6.95 (m, 3H), 7.14 (s, 1H), 7.19 (d, J=8.8 Hz, 2H), 7.23 (d, J=8.4 Hz, 1H), 7.70 (s, 1H).

Synthesis of (E)-3-[3-methoxy-4-(4-methyl-1H-imidazol-1-yl)benzylidene]-1-[(1R) and (1S)-2-methyl-1-(4-morpholin-4-ylphenyl)propyl]piperidin-2-one 210 mg of (E)-3-(3-methoxy-4-(4-methyl-1H-imidazol-1-yl)benzylidene)-1-(2-methyl-1-(4-morpholin-4-ylphenyl) propyl)piperidin-2-one as a racemate was obtained from (E)-5-chloro-2-(3-methoxy-4-(4-methyl-1H-imidazol-1-yl) benzylidene)valeric acid (2-methyl-1-(4-morpholin-4-ylphenyl)propyl)amide (290 mg) in the same manner as in Example 418. Next, the compound (100 mg) was fractionated using CHIRALPAK™ AD-H manufactured by Daicel Chemical Industries, Ltd. (2 cm×25 cm: mobile phase: ethanol) to obtain the title optically active substance with a retention time of 11 minutes (Example 977, 50.0 mg; >99% ee) and the title optically active substance with a retention time of 26 minutes (Example 978, 46.0 mg; >99% ee). The physical properties of the optically active substances are as follows.

$^1$H-NMR ($CDCl_3$) δ (ppm): 0.93 (d, J=6.4 Hz, 3H), 1.04 (d, J=6.8 Hz, 3H), 1.56-1.72 (m, 1H), 1.74-1.84 (m, 1H), 2.29 (s, 3H), 2.36-2.45 (m, 1H), 2.60-2.70 (m, 1H), 2.72-2.80 (m, 1H), 3.06 (ddd, J=3.6, 7.6, 12 Hz, 1H), 3.15-3.18 (m, 4H), 3.25 (ddd, J=2.0, 7.2, 12 Hz, 1H), 3.83 (s, 3H), 3.84-3.87 (m, 4H), 5.65 (d, J=12 Hz, 1H), 6.86 (d, J=8.8 Hz , 2H), 6.91 (s, 1H), 6.99-7.00 (m, 2H), 7.21 (d, J=8.4 Hz, 1H), 7.29 (d, J=8.8 Hz, 2H), 7.69 (s, 1H), 7.84 (s, 1H).

Examples 979 and 980

Synthesis of (E)-1-[(S) and (R)-cyclopropyl-(4-morpholin-4-ylphenyl)methyl]-3-[3-methoxy-4-(4-methyl-1H-imidazol-1-yl)benzylidene]piperidin-2-one

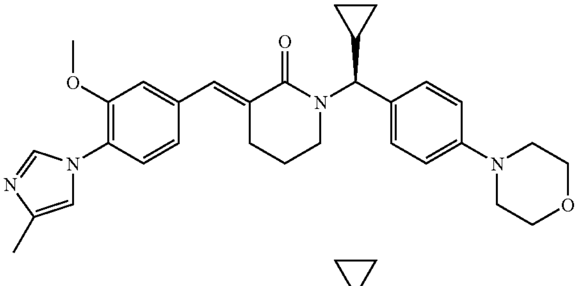

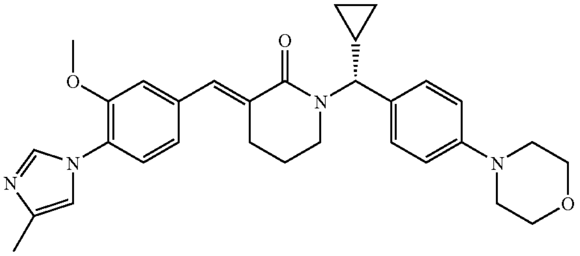

Synthesis of cyclopropyl-(4-morpholin-4-ylphenyl)methanone 680 mg of the title compound was obtained from cyclopropyl 4-fluorophenyl ketone (750 mg) in the same manner as in Example 973. The physical properties of the compound are as follows.

$^1$H-NMR ($CDCl_3$) δ (ppm): 0.95-0.99 (m, 2H), 1.17-1.21 (m, 2H), 2.59-2.65 (m, 1H), 3.30 (t, J=4.8 Hz, 4H), 3.85 (t, J=4.8 Hz, 4H), 6.88 (d, J=9.2 Hz, 2H), 7.96 (d, J=9.2 Hz, 2H).

Synthesis of cyclopropyl-(4-morpholin-4-ylphenyl)methanone oxime 267 mg of the title compound was obtained from cyclopropyl-(4-morpholin-4-ylphenyl)methanone (680 mg) in the same manner as in Example 971. The physical properties of the compound are as follows.

$^1$H-NMR ($CDCl_3$) δ (ppm): 0.64-0.68 (m, 2H), 0.92-0.97 (m, 2H), 2.18-2.25 (m, 1H), 3.18 (t, J=4.8 Hz, 4H), 3.86 (t, J=4.8 Hz, 4H), 6.85 (d, J=8.8 Hz, 2H), 7.33 (d, J=8.4 Hz, 2H).

Synthesis of cyclopropyl-(4-morpholin-4-ylphenyl)methylamine 131 mg of the title compound was obtained from cyclopropyl-(4-morpholin-4-ylphenyl)methanone oxime (267 mg) in the same manner as in Example 971. The physical properties of the compound are as follows.

$^1$H-NMR ($CDCl_3$) δ (ppm): 0.22-0.33 (m, 2H), 0.43-0.50 (m, 1H), 0.56-0.62 (m, 1H), 1.04-1.13 (m, 1H), 3.14-3.17 (m, 5H), 3.85-3.88 (m, 4H), 6.90 (d, J=8.8 Hz, 2H), 7.32 (d, J=8.4 Hz, 2H).

Synthesis of (E)-5-chloro-2-[3-methoxy-4-(4-methyl-1H-imidazol-1-yl)benzylidene]valeric acid (cyclopropyl-(4-morpholin-4-ylphenyl)methyl)amide The title compound was obtained from (E)-5-chloro-2-(3-methoxy-4-(4-methyl-1H-imidazol-1-yl)benzylidene)valeric acid trifluoroacetate (300 mg) and cyclopropyl-(4-morpholin-4-ylphenyl)methylamine (131 mg) in the same manner as in Example 418. The physical properties of the compound are as follows.

$^1$H-NMR ($CDCl_3$) δ (ppm): 0.37-0.43 (m, 1H), 0.49-0.54 (m, 1H), 0.60-0.66 (m, 2H), 1.20-1.28 (m, 1H), 1.97-2.02 (m, 2H), 2.04 (s, 3H), 2.66-2.76 (m, 2H), 3.14-3.17 (m, 4H), 3.54-3.66 (m, 2H), 3.82-3.88 (m, 4H), 3.84 (s, 3H), 4.50 (t, J=8.4 Hz, 1H), 6.39 (brd, J=8.4 Hz, 1H), 6.89-6.96 (m, 5H), 7.16 (s, 1H), 7.22 (d, J=8.8 Hz, 1H), 7.32 (d, J=8.4 Hz, 2H), 7.79 (d, J=1.2 Hz, 1H).

Synthesis of (E)-1-[(R) and (S)-cyclopropyl-(4-morpholin-4-ylphenyl)methyl]-3-[3-methoxy-4-(4-methyl-1H-imidazol-1-yl)benzylidene]piperidin-2-one 270 mg of (E)-1-(cyclopropyl-(4-morpholin-4-ylphenyl)methyl)-3-(3-methoxy-4-(4-methyl-1H-imidazol-1-yl)benzylidene)piperidin-2-one as a racemate was obtained from (E)-5-chloro-2-(3-methoxy-4-(4-methyl-1H-imidazol-1-yl)benzylidene)valeric acid (cyclopropyl-(4-morpholin-4-ylphenyl)methyl)amide in the same manner as in Example 418. Next, the compound (20 mg) was fractionated using CHIRALPAK™ AD-H manufactured by Daicel Chemical Industries, Ltd. (2 cm×25 cm: mobile phase: ethanol) to obtain the title optically active substance with a retention time of 13 minutes (Example 979, 7.9 mg; >99% ee) and the title optically active substance with a retention time of 17 minutes (Example 980, 4.6 mg; >99% ee). The physical properties of the optically active substances are as follows.

$^1$H-NMR ($CDCl_3$) δ (ppm): 0.48-0.64 (m, 3H), 0.82-0.90 (m, 1H), 1.28-1.39 (m, 1H), 1.66-1.76 (m, 1H), 1.84-1.92 (m, 1H), 2.30 (s, 3H), 2.72-2.82 (m, 1H), 2.82-2.94 (m, 1H), 3.10-3.20 (m, 1H), 3.15-3.17 (m, 4H), 3.44-3.50 (m, 1H), 3.85-3.87 (m, 4H), 3.86 (s, 3H), 5.20 (d, J=10 Hz, 1H), 6.88 (d, J=8.4 Hz, 2H), 6.93 (s, 1H), 7.04 (s, 1H), 7.04 (d, J=7.2 Hz, 1H), 7.24 (d, J=7.2 Hz, 1H), 7.36 (d, J=8.4 Hz, 2H), 7.71 (s, 1H), 7.87 (s, 1H).

Example 981 and Example 982

Synthesis of (E)-[(1S) and (1R)-(2-fluoro-4-morpholin-4-ylphenyl)ethyl]-3-[3-methoxy-4-(4-methyl-1H-imidazol-1-yl)benzylidene]piperidin-2-one

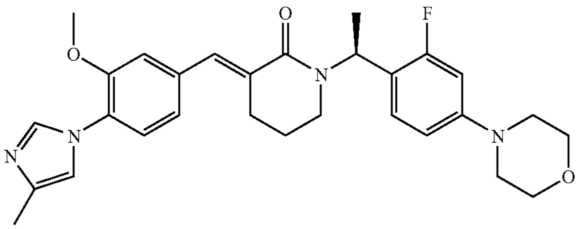

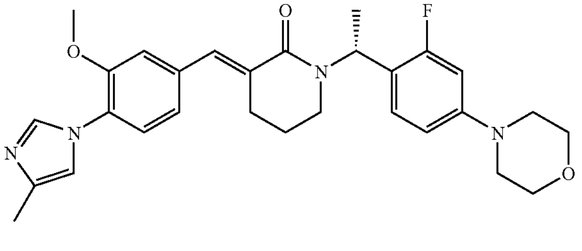

1-(2-fluoro-4-morpholin-4-yl-phenyl)ethanone 350 mg of the title compound was obtained from 2,4-difluoroacetophenone (1.0 g) in the same manner as in Example 793. The physical properties of the compound are as follows.

$^1$H-NMR ($CDCl_3$) δ (ppm): 2.56 (d, J=5.6 Hz, 3H), 3.30 (t, J=4.8 Hz, 4H), 3.84 (t, J=4.8 Hz, 4H), 6.46 (dd, J=2.8, 15 Hz, 1H), 6.64 (dd, J=2.8, 9.2 Hz, 1H), 7.83 (t, J=8.8 Hz, 1H).

Synthesis of 1-(2-fluoro-4-morpholin-4-yl-phenyl)ethanone oxime 364 mg of the title compound was obtained from 1-(2-fluoro-4-morpholin-4-yl-phenyl)ethanone (350 mg) in the same manner as in Example 971. The physical properties of the compound are as follows.

$^1$H-NMR ($CDCl_3$) δ (ppm): 2.27 (d, J=2.4 Hz, 3H), 3.18-3.20 (m, 4H), 3.83-3.86 (m, 4H), 6.56 (dd, J=2.4, 12 Hz, 1H), 6.65 (dd, J=2.4, 8.8 Hz, 1H), 7.37 (t, J=8.8 Hz, 1H).

Synthesis of 1-(2-fluoro-4-morpholin-4-yl-phenyl)ethylamine 140 mg of the title compound was obtained from 1-(2-fluoro-4-morpholin-4-ylphenyl)ethanone oxime (364 mg) in the same manner as in Example 971. The physical properties of the compound are as follows.

$^1$H-NMR ($CDCl_3$) δ (ppm): 1.38 (d, J=6.4 Hz, 3H), 3.11-3.14 (m, 4H), 3.83-3.85 (m, 4H), 4.24 (q, J=6.4 Hz, 1H), 6.54 (dd, J=2.4, 14 Hz, 1H), 6.64 (dd, J=2.4, 8.4 Hz, 1H), 7.25 (t, J=8.4 Hz, 1H).

Synthesis of (E)-5-chloro-2-[3-methoxy-4-(4-methyl-1H-imidazol-1-yl)benzylidene]valeric acid [1-(2-fluoro-4-morpholin-4-ylphenyl)ethyl]amide 406 mg of the title compound was obtained from (E)-5-chloro-2-(3-methoxy-4-(4-methyl-1H-imidazol-1-yl)benzylidene)valeric acid trifluoroacetate (300 mg) and 1-(2-fluoro-4-morpholin-4-yl-phenyl)ethylamine (140 mg) in the same manner as in Example 418. The physical properties of the compound are as follows.

$^1$H-NMR ($CDCl_3$) δ (ppm): 1.56 (d, J=6.8 Hz, 3H), 1.94-2.04 (m, 2H), 2.31 (s, 3H), 2.70 (t, J=7.2 Hz, 2H), 3.13-3.15 (m, 4H), 3.56 (t, J=6.0 Hz, 2H), 3.83-3.85 (m, 4H), 3.85 (s, 3H), 5.22-5.30 (m, 1H), 6.36 (brd, J=6.8 Hz, 1H), 6.58 (d, J=15 Hz, 1H), 6.64 (d, J=8.8 Hz, 1H), 6.93-6.99 (m, 3H), 7.14 (s, 1H), 7.16-7.23 (m, 2H), 7.76 (s, 1H).

Synthesis of (E)-1-[(1R) and (1S)-(2-fluoro-4-morpholin-4-ylphenyl)ethyl]-3-[3-methoxy-4-(4-methyl-1H-imidazol-1-yl)benzylidene]piperidin-2-one 267 mg of (E)-1-(1-(2-fluoro-4-morpholin-4-ylphenyl)ethyl)-3-(3-methoxy-4-(4-methylimidazol-1-yl)benzylidene)piperidin-2-one as a racemate was obtained from (E)-5-chloro-2-(3-methoxy-4-(4-methyl-1H-imidazol-1-yl)benzylidene)valeric acid (1-(2-fluoro-4-morpholin-4-ylphenyl)ethyl)amide (406 mg) in the same manner as in Example 418. Next, the compound (160 mg) was fractionated using CHIRALPAK™ AD-H manufactured by Daicel Chemical Industries, Ltd. (2 cm×25 cm: mobile phase: ethanol) to obtain the title optically active substance with a retention time of 12 minutes (Example 981, 61 mg; >99% ee) and the title optically active substance with a retention time of 14 minutes (Example 982, 31 mg; >92% ee). The physical properties of the optically active substances are as follows.

$^1$H-NMR ($CDCl_3$) δ (ppm): 1.55 (d, J=7.2 Hz, 3H), 1.72-1.80 (m, 2H), 2.31 (s, 3H), 2.66-2.84 (m, 2H), 2.97-3.03 (m, 1H), 3.15-3.18 (m, 4H), 3.24-3.29 (m, 1H), 3.80-3.88 (m, 4H), 3.85 (s, 3H), 6.18 (q, J=7.2 Hz, 1H), 6.58 (dd, J=2.0, 9.6 Hz, 1H), 6.65 (dd, J=2.0, 8.4 Hz, 1H), 6.93 (s, 1H), 7.02-7.04 (m, 2H), 7.23-7.28 (m, 2H), 7.74 (s, 1H), 7.87 (s, 1H).

Example 983 and Example 984

Synthesis of (E)-3-[3-methoxy-4-(4-methyl-1H-imidazol-1-yl)benzylidene]-1-[(2R) and (2S)-5-morpholin-4-ylindan-2-yl]piperidin-2-one

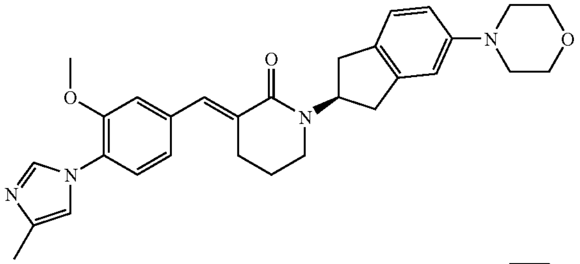

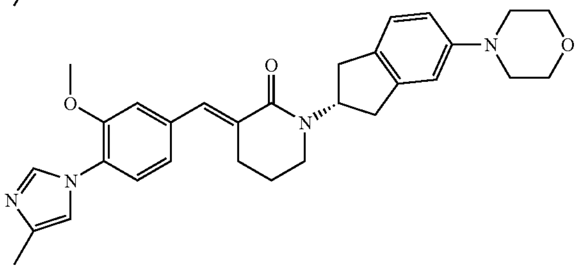

Synthesis of 5-morpholin-4-ylindan-1,2-dinone 2-oxime 1.30 g of the title compound was obtained from 5-morpholin-4-ylindan-1-one (1.50 g) synthesized in accordance with the method described in The Journal of Medicinal Chemistry, 1991, vol. 34, no. 5, p. 1662. Properties data of the compound are as follows.

$^1$H-NMR ($CDCl_3$) δ (ppm): 2.64-2.66 (m, 4H), 2.91 (s, 2H), 3.00-3.03 (m, 4H), 6.18 (d, J=2.0 Hz, 1H), 6.21 (dd, J=2.0, 8.8 Hz, 1H), 6.87 (d, J=8.8 Hz, 1H).

Synthesis of 5-morpholin-4-ylindan-2-ylamine 258 mg of the title compound was obtained from 5-morpholin-4-ylindan-1,2-dinone 2-oxime (300 mg) synthesized in accordance with the method described in The Journal of Medicinal Chemistry, 1982, vol. 25, no. 12, p. 1442. Properties data of the compound are as follows.

$^1$H-NMR ($CDCl_3$) δ (ppm): 2.78-2.88 (m, 2H), 3.09-3.12 (m, 4H), 3.16-3.25 (m, 2H), 3.78-3.98 (m, 1H), 3.84-3.87 (m, 4H), 4.90-5.44 (brs, 2H), 6.75 (dd, J=2.4, 8.4 Hz, 1H), 6.80 (s, 1H), 7.11 (d, J=8.4 Hz, 1H).

Synthesis of (E)-5-chloro-2-[3-methoxy-4-(4-methyl-1H-imidazol-1-yl)-benzylidene]valeric acid (5-morpholin-4-ylindan-2-yl)amide 258 mg of the title compound was obtained from (E)-5-chloro-2-(3-methoxy-4-(4-methyl-1H-imidazol-1-yl)benzylidene)valeric acid trifluoroacetate (288 mg) and 5-morpholin-4-ylindan-2-ylamine (100 mg) in the same manner as in Example 418. Properties data of the compound are as follows.

$^1$H-NMR ($CDCl_3$) δ (ppm): 1.95-2.02 (m, 2H), 2.30 (s, 3H) 2.67-2.95 (m, 4H), 3.12-3.14 (m, 4H), 3.33 (dd, J=6.8, 13 Hz, 1H), 3.37 (dd, J=6.8, 13 Hz, 1H), 3.57 (t, J=6.4 Hz, 2H), 3.85 (s, 3H), 3.86-3.88 (m, 4H), 4.80-4.88 (m, 1H), 6.25 (brd, J=6.0 Hz, 1H), 6.74-6.80 (m, 1H), 6.84 (s, 1H), 6.92-6.94 (m, 3H), 7.10 (s, 1H), 7.15 (d, J=8.0, 1H), 7.23 (d, J=8.4 Hz, 1H), 7.77 (s, 1H).

Synthesis of (E)-3-[3-methoxy-4-(4-methyl-1H-imidazol-1-yl)benzylidene]-1-[(2R) and (2S)-5-morpholin-4-ylindan-2-yl]piperidin-2-one 149 mg of (E)-3-(3-methoxy-4-(4-methylimidazol-1-yl)benzylidene)-1-(5-morpholin-4-ylindan-2-yl)piperidin-2-one as a racemate was obtained from (E)-5-chloro-2-(3-methoxy-4-(4-methyl-1H-imidazol-1-yl)benzylidene)valeric acid (5-morpholin-4-ylindan-2-yl)amide in the same manner as in Example 418. Next, the compound (149 mg) was fractionated using CHIRALCEL™ OJ manufactured by Daicel Chemical Industries, Ltd. (2 cm×25 cm: mobile phase: ethanol) to obtain the title optically active substance with a retention time of 14 minutes (Example 983, 30.0 mg; >99% ee) and the title optically active substance with a retention time of 26 minutes (Example 984, 31.0 mg; >99% ee). The physical properties of the optically active substances are as follows.

$^1$H-NMR ($CDCl_3$) δ (ppm): 1.81-1.87 (m, 2H), 2.30 (s, 3H), 2.78-2.81 (m, 2H), 2.90-2.98 (m, 2H), 3.10-3.14 (m, 4H), 3.17-3.27 (m, 4H), 3.84-3.88 (m, 4H), 3.85 (s, 3H), 5.73-5.81 (m, 1H), 6.76 (dd, J=2.4, 8.4 Hz, 1H), 6.81 (s, 1H), 6.92 (s, 1H), 7.02 (s, 1H), 7.03 (d, J=8.0 Hz, 1H), 7.12 (d, J=8.4 Hz, 1H), 7.24 (d, J=8.0 Hz, 1H), 7.71 (s, 1H), 7.83 (s, 1H)

Example 985 and Example 986

Synthesis of (E)-3-[3-methoxy-4-(4-methyl-1H-imidazol-1-yl)benzylidene]-1-[(1R) and (1S)-(6-morpholin-4-yl-1,2,3,4-tetrahydronaphthalen-1-yl)]piperidin-2-one

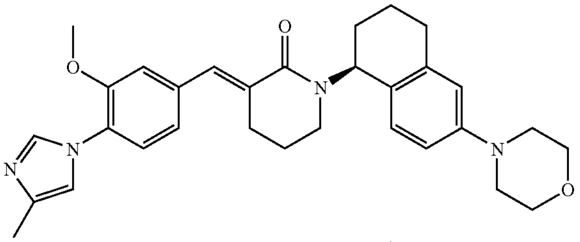

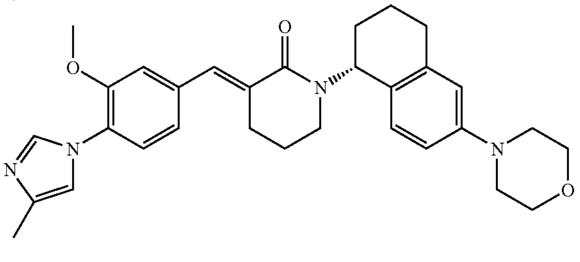

Synthesis of 5-oxo-5,6,7,8-tetrahydronaphthalen-2-yl trifluoromethanesulfonate Trifluoromethanesulfonic anhydride (2.51 mL) was added to a solution of 6-hydroxy-3,4-dihydro-2H-naphthalen-1-one (2.00 g) and triethylamine (4.11 mL) in dichloromethane (20 mL) at −20° C., and the reaction solution was stirred at that temperature for 20 minutes. After confirming that the raw materials disappeared, the reaction solution was concentrated under reduced pressure, and water and chloroform were added to the residue and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain 3.30 g of the title compound. Properties data of the compound are as follows.

$^1$H-NMR ($CDCl_3$) δ (ppm): 2.15-2.21 (m, 2H), 2.69 (t, J=6.0 Hz, 2H), 3.02 (t, J=6.4 Hz, 2H), 7.17-7.21 (m, 2H), 8.12 (d, J=8.4 Hz, 1H).

Synthesis of 6-morpholin-4-yl-3,4-dihydro-2H-naphthalen-1-one

A solution of 5-oxo-5,6,7,8-tetrahydronaphthalen-2-yl trifluoromethanesulfonate (3.40 g), morpholine (5.18 g), tripotassium phosphate (3.79 g), tris(dibenzylideneacetone) dipalladium (0) (109 mg) and 2-(di-tert-butylphosphino)biphenyl (71 mg) in 1,2-dimethoxyethane (24 mL) was stirred in a nitrogen atmosphere at 80° C. for one and a half hours. The reaction solution was returned to room temperature, and water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain 2.56 g of the title compound. Properties data of the compound are as follows.

$^1$H-NMR ($CDCl_3$) δ (ppm): 2.07-2.13 (m, 2H), 2.59 (t, J=6.4 Hz, 2H), 2.89 (t, J=6.4 Hz, 2H), 3.31 (t, J=4.8 Hz, 4H), 3.85 (t, J=4.8 Hz, 4H), 6.61 (d, J=2.4 Hz, 1H), 6.79 (dd, J=2.4, 9.2 Hz, 1H), 7.96 (d, J=8.8 Hz, 1H).

Synthesis of 6-morpholin-4-yl-3,4-dihydro-2H-naphthalen-1-one oxime 630 mg of the title compound was obtained from 6-morpholin-4-yl-3,4-dihydro-2H-naphthalen-1-one (700 mg) in the same manner as in Example 971. Properties data of the compound are as follows.

$^1$H-NMR ($CDCl_3$) δ (ppm): 1.82-1.89 (m, 2H), 2.71 (t, J=6.4 Hz, 2H), 2.78 (t, J=6.4 Hz, 2H), 3.20 (t, J=4.8 Hz, 4H), 3.85 (t, J=4.8 Hz, 4H), 6.62 (d, J=2.4, 8.8 Hz, 1H), 6.77 (dd, J=2.4, 8.8 Hz, 1H), 7.78 (d, J=8.8 Hz, 1H).

Synthesis of 6-morpholin-4-yl-1,2,3,4-tetrahydronaphthalen-1-ylamine 429 mg of the title compound was obtained from 6-morpholin-4-yl-3,4-dihydro-2H-naphthalen-1-one oxime (547 mg) in the same manner as in Example 971. Properties data of the compound are as follows.

$^1$H-NMR ($CDCl_3$) δ (ppm): 1.52-1.68 (m, 1H), 1.70-1.78 (m, 1H), 1.86-2.04 (m, 2H), 2.65-2.81 (m, 2H), 3.12 (t, J=4.8 Hz, 4H), 3.84 (t, J=4.8 Hz, 4H), 3.92 (t, J=5.6 Hz, 1H), 6.60 (d, J=2.4 Hz, 1H), 6.77 (dd, J=2.4, 8.4 Hz, 1H), 7.29 (d, J=8.4 Hz, 1H).

Synthesis of (E)-5-chloro-2-[3-methoxy-4-(4-methyl-1H-imidazol-1-yl)-benzylidene]valeric acid (6-morpholin-4-yl-1,2,3,4-tetrahydronaphthalen-1-yl)amide 300 mg of the title compound was obtained from (E)-5-chloro-2-(3-methoxy-4-(4-methyl-1H-imidazol-1-yl)benzylidene)valeric acid trifluoroacetate (377 mg) and 6-morpholin-4-yl-1,2,3,4-tetrahydronaphthalen-1-ylamine (150 mg) in the same manner as in Example 418. Properties data of the compound are as follows.

$^1$H-NMR ($CDCl_3$) δ (ppm): 1.82-1.95 (m, 3H), 2.00-2.11 (m, 3H), 2.30 (s, 3H), 2.72-2.81 (m, 4H), 3.13-3.16 (m, 4H), 3.58 (t, J=6.4 Hz, 2H), 3.84-3.86 (m, 4H), 3.85 (s, 3H), 5.20-5.25 (m, 1H), 6.11 (d, J=8.4 Hz, 1H), 6.63 (d, J=2.4, 1H), 6.79 (dd, J=2.4, 8.4 Hz, 1H), 6.92-6.95 (m, 2H). 6.93 (s, 1H), 7.09 (s, 1H), 7.20-7.24 (m, 2H), 7.71 (s, 1H).

Synthesis of (E)-3-[3-methoxy-4-(4-methyl-1H-imidazol-1-yl)benzylidene]-1-[(1R) and (1S)-(6-morpholin-4-yl-1,2,3,4-tetrahydronaphthalen-1-yl]piperidin-2-one 259 mg of (E)-3-(3-methoxy-4-(4-methyl-1H-imidazol-1-yl)benzylidene)-1-(6-morpholin-4-yl-1,2,3,4-tetrahydronaphthalen-1-yl)piperidin-2-one as a racemate was obtained from (E)-5-chloro-2-(3-methoxy-4-(4-methyl-1H-imidazol-1-yl)benzylidene)valeric acid (6-morpholin-4-yl-1,2,3,4-tetrahydronaphthalen-1-yl)amide (300 mg) in the same manner as in Example 418. Next, the compound (70.0 mg) was fractionated using CHIRALPAK™ AD-H manufactured by Daicel Chemical Industries, Ltd. (2 cm×25 cm: mobile phase: hexane:ethanol=30:70) to obtain the title optically active substance with a retention time of 10 minutes (Example 985, 27.0 mg; >98% ee) and the title optically active substance with a retention time of 14 minutes (Example 986, 28.0 mg; >97% ee). The physical properties of the optically active substances are as follows.

$^1$H-NMR ($CDCl_3$) δ (ppm): 1.71-1.88 (m, 4H), 1.95-2.02 (m, 1H), 2.06-2.12 (m, 1H), 2.30 (s, 3H), 2.72-2.82 (m, 4H), 3.03-3.12 (m, 1H), 3.12-3.16 (m, 4H), 3.14-3.22 (m, 1H), 3.83-3.86 (m, 4H), 3.86 (s, 3H), 6.60 (dd, J=6.4, 10 Hz, 1H), 6.62 (d, J=2.4 Hz, 1H), 6.73 (dd, J=2.4, 8.4 Hz, 1H), 6.93 (s, 1H), 7.01 (d, J=8.8 Hz, 1H), 7.06 (s, 1H), 7.07 (d, J=8.8 Hz, 1H), 7.25 (d, J=8.4 Hz, 1H), 7.72 (s, 1H), 7.90 (s, 1H).

Example 987 and Example 988

Synthesis of (E)-3-[3-methoxy-4-(4-methyl-1H-imidazol-1-yl)benzylidene]-1-[(1R) and [(1S)-4-morpholin-4-ylindan-1-yl]piperidin-2-one

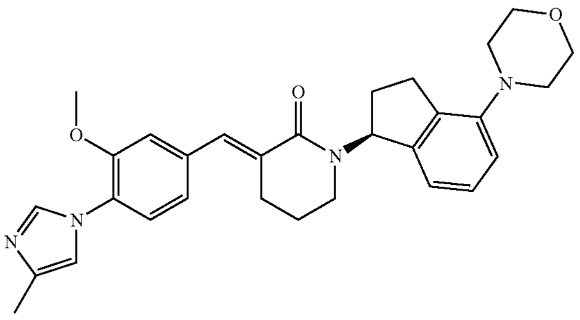

-continued

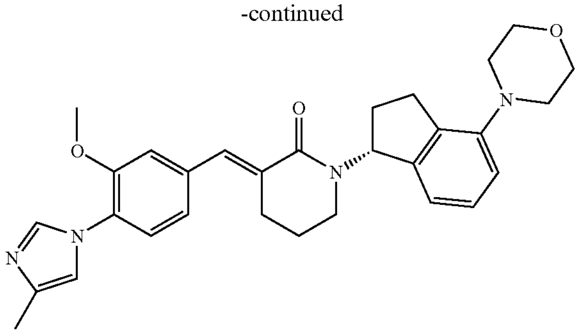

Synthesis of 1-oxo-indan-4-yl trifluoromethanesulfonate 1.30 g of the title compound was obtained from 4-hydroxy-indanone (2.00 g) in the same manner as in Example 985. Properties data of the compound are as follows.

$^1$H-NMR ($CDCl_3$) δ (ppm): 2.77-2.80 (m, 2H), 3.24-3.27 (m, 2H), 7.47-7.52 (m, 2H), 7.79 (dd, J=2.0, 6.0 Hz, 1H)

Synthesis of 4-morpholin-4-ylindan-1-one 627 mg of the title compound was obtained from 1-oxo-indan-4-yl trifluoromethansulfonate (3.28 g) in the same manner as in Example 985. Properties data of the compound are as follows.

$^1$H-NMR ($CDCl_3$) δ (ppm): 2.69-2.72 (m, 2H), 3.06-3.10 (m, 6H), 3.87-3.89 (m, 4H), 7.14 (d, J=8.0 Hz, 1H), 7.35 (t, J=8.0 Hz, 1H), 7.44 (d, J=8.0 Hz, 1H).

Synthesis of 4-morpholin-4-ylindan-1-one oxime 178 mg of the title compound was obtained from 4-morpholin-4-ylindan-1-one (250 mg) in the same manner as in Example 971. Properties data of the compound are as follows.

$^1$H-NMR ($CDCl_3$) δ (ppm): 2.80-3.01 (m, 4H), 3.01-3.04 (m, 4H), 3.85-3.87 (m, 4H), 6.77 (dd, J=0.8, 8.0 Hz, ⅓H), 6.93 (dd, J=0.8, 8.0 Hz, ⅔H), 7.14 (t, J=8.0, ⅓H), 7.22-7.26 (m, 1H), 7.35 (dd, J=0.8, 8.0 Hz, ⅔H).

Synthesis of 4-morpholin-4-ylindan-1-ylamine 140 mg of the title compound was obtained from 4-morpholin-4-ylindan-1-one oxime (178 mg) in the same manner as in Example 971. Properties data of the compound are as follows.

$^1$H-NMR ($CDCl_3$) δ (ppm): 1.71-1.79 (m, 1H), 2.45-2.53 (m, 1H), 2.71 (td, J=8.0, 16 Hz, 1H), 2.92-3.01 (m, 3H), 3.03-3.09 (m, 2H), 3.80-3.88 (m, 4H), 4.39 (t, J=7.6 Hz, 1H), 6.78 (d, J=7.6 Hz, 1H), 7.04 (d, J=7.6 Hz, 1H), 7.21 (t, J=7.6 Hz, 1H).

Synthesis of (E)-5-chloro-2-[3-methoxy-4-(4-methyl-1H-imidazol-1-yl)-benzylidene]valeric acid (4-morpholin-4-ylindan-1-yl)amide 203 mg of the title compound was obtained from (E)-5-chloro-2-(3-methoxy-4-(4-methyl-1H-imidazol-1-yl)benzylidene)valeric acid trifluoroacetate (432 mg) and 4-morpholin-4-ylindan-1-ylamine (140 mg) in the same manner as in Example 418. Properties data of the compound are as follows.

$^1$H-NMR ($CDCl_3$) δ (ppm): 1.82-1.94 (m, 2H), 2.02-2.09 (m, 1H), 2.29 (s, 3H), 2.65-2.73 (m, 1H), 2.72-2.79 (m, 2H), 2.79-2.88 (m, 1H), 2.93-2.99 (m, 2H), 2.97-3.05 (m, 1H), 3.07-3.12 (m, 2H), 3.60 (t, J=6.0 Hz, 2H), 3.84-3.87 (m, 4H), 3.86 (s, 3H), 5.59 (q, J=8.0 Hz, 1H), 6.21 (d, J=8.0 Hz, 1H), 6.84 (d, J=8.0 Hz, 1H), 6.92 (t, J=0.8 Hz, 1H), 6.95-6.97 (m, 2H), 7.00 (d, J=8.0 Hz, 1H), 7.18 (s, 1H), 7.21-7.26 (m, 2H), 7.70 (s, 1H).

Synthesis of (E)-3-[3-methoxy-4-(4-methyl-1H-imidazol-1-yl)benzylidene]-1-[(1R) and (1S)-4-morpholin-4-ylindan-1-yl]piperidin-2-one 118 mg of (E)-3-(3-methoxy-4-(4-methyl-1H-imidazol-1-yl)benzylidene)-1-(4-morpholin-4-ylindan-1-yl)piperidin-2-one as a racemate was obtained from (E)-5-chloro-2-(3-methoxy-4-(4-methyl-1H-imidazol-1-yl)benzylidene)valeric acid (4-morpholin-4-ylindan-1-yl)amide (203 mg) in the same manner as in Example 418. Next, the compound (5.00 mg) was fractionated using CHIRALPAK™ AD-H manufactured by Daicel Chemical Industries, Ltd. (2 cm×25 cm: mobile phase: hexane:ethanol=70:30) to obtain the title optically active substance with a retention time of 45 minutes (Example 987, 0.80 mg; >99% ee) and the title optically active substance with a retention time of 47 minutes (Example 988, 0.90 mg; >87% ee). The physical properties of the optically active substances are as follows.

$^1$H-NMR ($CDCl_3$) δ (ppm): 1.74-1.90 (m, 2H), 1.92-2.04 (m, 1H), 2.30 (s, 3H), 2.44-2.53 (m, 1H), 2.74-3.04 (m, 6H), 3.06-3.18 (m, 4H), 3.81-3.90 (m, 4H), 3.86 (s, 3H), 6.50 (t, J=8.0 Hz, 1H), 6.81 (d, J=7.6 Hz, 1H), 6.83 (d, J=7.6 Hz, 1H), 6.93 (s, 1H), 7.05 (s, 1H), 7.06 (d, J=7.6 Hz, 1H), 7.19 (t, J=7.6 Hz, 1H), 7.25 (d, J=7.6 Hz, 1H), 7.72 (s, 1H), 7.90 (s, 1H).

Example 989 and Example 990

Synthesis of (E)-1-[(1R) and (1S)-(2-fluoro-4-[1,2,4]triazol-1-ylphenyl)ethyl]-3-[3-methoxy-4-(4-methyl-1H-imidazol-1-yl)benzylidene]piperidin-2-one

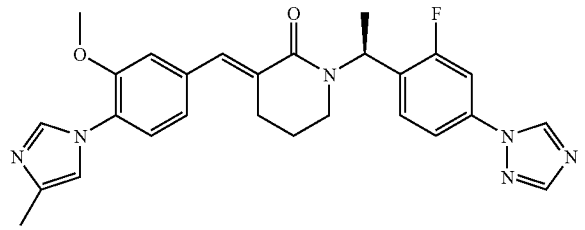

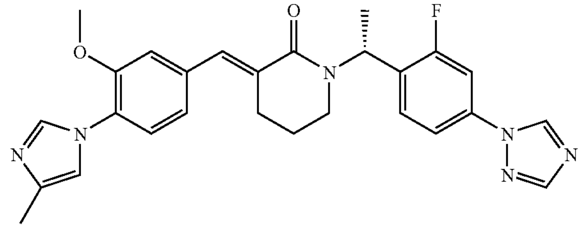

Synthesis of 1-(2-fluoro-4-[1,2,4]triazol-1-ylphenyl)ethanone

A solution of 2,4-difluoroacetophenone (2.43 mL), 1,2,4-triazole (1.59 g) and potassium carbonate (5.32 g) in toluene (10 mL) was stirred at 100° C. overnight. The reaction solution was returned to room temperature, and then water and ethyl acetate were added to the reaction solution and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain 187 mg of the title compound. Properties data of the compound are as follows.

$^1$H-NMR ($CDCl_3$) δ (ppm): 2.68 (d, J=4.8 Hz, 3H), 7.56 (dd, J=2.5, 8.0 Hz, 1H), 7.60 (dd, J=2.5, 12 Hz, 1H), 8.05 (t, J=8.4 Hz, 1H), 8.13 (s, 1H), 8.65 (s, 1H).

Synthesis of 1-(2-fluoro-4-[1,2,4]triazol-1-ylphenyl)ethylamine 80 mg of the title compound was obtained from 1-(2-fluoro-4-[1,2,4]triazol-1-yl-phenyl)ethanone (187 mg) via a crude oxime in the same manner as in Example 971. Properties data of the compound are as follows.

$^1$H-NMR ($CDCl_3$) δ (ppm): 1.44 (d, J=6.8 Hz, 3H), 4.45 (q, J=6.8 Hz, 1H), 7.41-7.47 (m, 2H), 7.58-7.63 (m, 1H), 8.10 (s, 1H), 8.55 (s, 1H).

Synthesis of (E)-5-chloro-2-[3-methoxy-4-(4-methyl-1H-imidazol-1-yl)-benzylidene]valeric acid [1-(2-fluoro-4-[1,2,4]-triazol-1-ylphenyl)ethyl]amide 171 mg of the title compound was obtained from (E)-5-chloro-2-(3-methoxy-4-(4-methyl-1H-imidazol-1-yl)benzylidene)valeric acid trifluoroacetate (226 mg) and 1-(2-fluoro-4-[1,2,4]triazol-1-ylphenyl)ethylamine (80 mg) in the same manner as in Example 418. Properties data of the compound are as follows.

$^1$H-NMR ($CDCl_3$) δ (ppm): 1.64 (d, J=7.2 Hz, 3H), 1.95-2.03 (m, 2H), 2.30 (s, 3H), 2.70-2.74 (m, 2H), 3.57-3.60 (m, 2H), 3.86 (s, 3H), 5.36 (quint, 7.2 Hz, 1H), 6.44-6.50 (brs, 1H), 6.93-6.97 (m, 3H), 7.21 (s, 1H), 7.25 (d, J=7.6 Hz, 1H), 7.45 (dd, J=2.0, 8.4 Hz, 1H) 7.48-7.51 (m, 2H), 7.72 (s, 1H), 8.09 (s, 1H), 8.54 (s, 1H).

Synthesis of (E)-1-[(1R) and (1S)-(2-fluoro-4-[1,2,4]triazol-1-ylphenyl)ethyl]-3-[3-methoxy-4-(4-methyl-1H-imidazol-1-yl)benzylidene]piperidin-2-one 121 mg of (E)-1-(1-(2-fluoro-4-[1,2,4]triazol-1-ylphenyl)ethyl)-3-(3-methoxy-4-(4-methyl-1H-imidazol-1-yl)benzylidene)piperidin-2-one as a racemate was obtained from (E)-5-chloro-2-(3-methoxy-4-(4-methyl-1H-imidazol-1-yl)benzylidene)valeric acid (1-(2-fluoro-4-[1,2,4]-triazol-1-ylphenyl)ethyl)amide (171 mg) in the same manner as in Example 418. Next, the compound (10.0 mg) was fractionated using CHIRALPAK™ AD-H manufactured by Daicel Chemical Industries, Ltd. (2 cm×25 cm: mobile phase: ethanol) to obtain the title optically active substance with a retention time of 13 minutes (Example 989, 2.6 mg; >99% ee) and the title optically active substance with a retention time of 15 minutes (Example 990, 3.9 mg; >94% ee). Properties data of the compounds are as follows.

$^1$H-NMR ($CDCl_3$) δ (ppm): 1.65 (d, J=7.2 Hz, 3H), 1.80-1.88 (m, 2H), 2.30 (s, 3H), 2.75-2.84 (m, 2H), 3.09-3.15 (m, 1H), 3.35-3.41 (m, 1H), 3.85 (s, 3H), 6.17 (q, J=7.2 Hz, 1H), 6.93 (s, 1H), 7.02-7.04 (m, 2H), 7.25 (d, J=8.4 Hz, 1H), 7.47-7.57 (m, 3H), 7.72 (s, 1H), 7.86 (s, 1H), 8.11 (s, 1H), 8.57 (s, 1H).

Example 991 and Example 992

Synthesis of (E)-1-[(2S) and (2R)-5-fluoroindan-2-yl]-3-[3-methoxy-4-(4-methyl-1H-imidazol-1-yl)benzylidene]piperidin-2-one

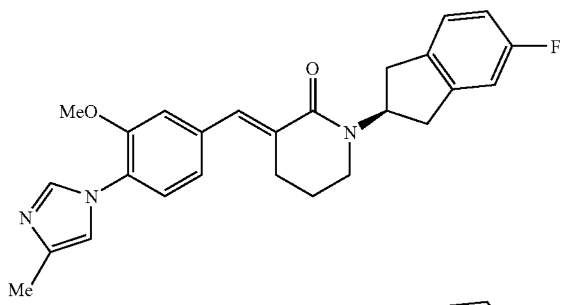

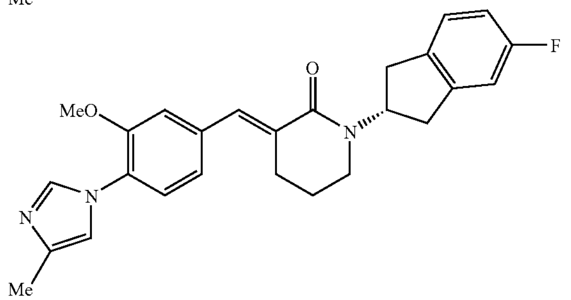

IPEA (0.58 mL), EDC (0.38 g) and HOBT (0.27 g) were added to a suspension of (E)-5-chloro-2-(3-methoxy-4-(4-methyl-1H-imidazol-1-yl)benzylidene)valeric acid trifluoroacetate (300 mg) and 5-fluoroindan-2-ylamine (CAS #2340-06-9, 151 mg) in DMF (10 mL) at room temperature, and the reaction solution was stirred at room temperature for 14 hours. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (elution solvent:ethyl acetate-methanol system) to obtain (E)-5-chloro-2-(3-methoxy-4-(4-methyl-1H-imidazol-1-yl)benzylidene)valeric acid (5-fluoroindan-2-yl)amide (318 mg). Sodium hydride (containing mineral oil at 40%, 60 mg) was added to a solution of (E)-5-chloro-2-(3-methoxy-4-(4-methyl-1H-imidazol-1-yl)benzylidene)valeric acid (5-fluoroindan-2-yl)amide (318 mg) in DMF (6 mL) at room temperature, and the reaction solution was stirred at room temperature for 30 minutes. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (Carrier: Chromatorex™ NH, elution solvent:heptane-ethyl acetate system) to obtain (E)-1-(5-fluoroindan-2-yl)-3-(3-methoxy-4-(4-methyl-1H-imidazol-1-yl)benzylidene)piperidin-2-one as a racemate (170 mg). The compound (10 mg) was fractionated using CHIRALPAK™ AD-H manufactured by Daicel Chemical Industries, Ltd. (2 cm×25 cm: mobile phase: ethanol) to obtain the title optically active substance with a retention time of 9.1 minutes (Example 991, 4 mg; >95% ee) and the title optically active substance with a retention time of 9.8 minutes (Example 992, 4 mg; >94% ee). The physical properties of the compounds are as follows.

$^{1}$H-NMR ($CDCl_3$) δ (ppm): 1.82-1.90 (m, 2H), 2.29 (s, 3H), 2.77-2.84 (m, 2H), 2.91-3.04 (m, 2H), 3.18-3.30 (m, 4H), 3.85 (s, 3H), 5.72-5.81 (m, 1H), 6.83-6.94 (m, 3H), 7.00-7.05 (m, 2H), 7.15 (dd, J=5.2 Hz, 8.0 Hz, 1H), 7.22-7.26 (m, 1H), 7.70 (d, J=1.6 Hz, 1H), 7.82-7.85 (m, 1H).

Example 993 and Example 994

Synthesis of (E)-1-[(1R and 1S)-6-fluoroindan-1-yl]-3-[3-methoxy-4-(4-methyl-1H-imidazol-1-yl)benzyliden])piperidin-2-one

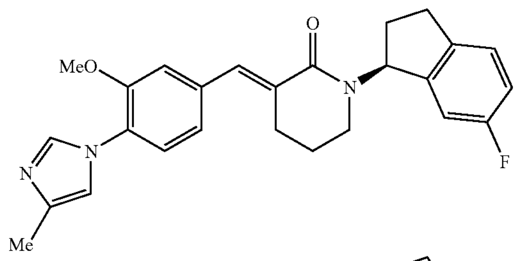

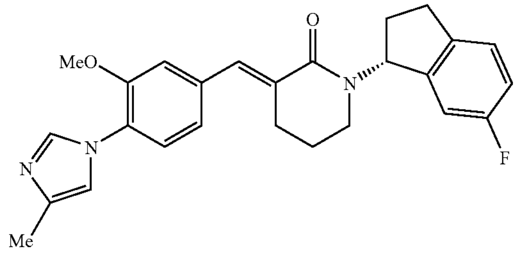

IPEA (0.58 mL), EDC (0.38 g) and HOBT (0.27 g) were added to a suspension of (E)-5-chloro-2-(3-methoxy-4-(4-methyl-1H-imidazol-1-yl)benzylidene)valeric acid trifluoroacetate (300 mg) and 6-fluoroindan-1-ylamine (CAS #168902-77-0, 151 mg) in DMF (10 mL) at room temperature, and the reaction solution was stirred at room temperature for 12 hours. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (Carrier: Chromatorex™ NH, elution solvent:heptane-ethyl acetate system) to obtain (E)-5-chloro-2-(3-methoxy-4-(4-methyl-1H-imidazol-1-yl)benzylidene) valeric acid (6-fluoroindan-1-yl)amide (270 mg). Sodium hydride (containing mineral oil at 40%, 60 mg) was added to a solution of (E)-5-chloro-2-(3-methoxy-4-(4-methyl-1H-imidazol-1-yl)benzylidene)valeric acid (6-fluoroindan-1-yl) amide (270 mg) in DMF (5 mL) at room temperature, and the reaction solution was stirred at room temperature for 30 minutes. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (Carrier: Chromatorex™ NH, elution solvent: heptane-ethyl acetate system) to obtain (E)-1-(6-fluoroindan-1-yl)-3-(3-methoxy-4-(4-methyl-1H-imidazol-1-yl) benzylidene)piperidin-2-one as a racemate (200 mg). The compound (200 mg) was fractionated using CHIRALPAK™ AD-H manufactured by Daicel Chemical Industries, Ltd. (2 cm×25 cm: mobile phase: ethanol) to obtain the title optically active substance with a retention time of 7.4 minutes (Example 994, 72 mg; >99% ee) and the title optically active substance with a retention time of 8.4 minutes (Example 993, 68 mg; >96% ee). The physical properties of the compounds are as follows.

$^{1}$H-NMR ($CDCl_3$) δ (ppm): 1.75-1.92 (m, 2H), 1.97-2.10 (m, 1H), 2.30 (s, 3H), 2.48-2.57 (m, 1H), 2.74-3.22 (m, 6H), 3.87 (s, 3H), 6.44-6.50 (m, 1H), 6.83-6.88 (m, 1H), 6.90-6.96 (m, 2H), 7.03-7.08 (m, 2H), 7.16-7.21 (m, 1H), 7.23-7.28 (m, 1H), 7.71 (d, J=0.8 Hz, 1H), 7.87-7.91 (m, 1H).

Example 995

Synthesis of (E)-1-[1-(4-fluorophenyl)-1-methylethyl]-3-[3-methoxy-4-(4-methyl-1H-imidazol-1-yl) benzylidene]piperidin-2-one

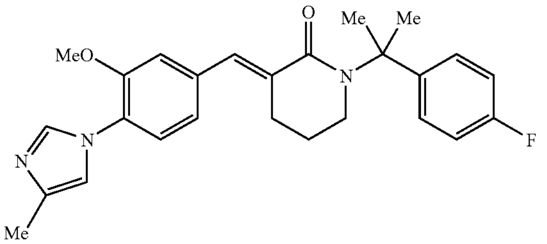

43 mg of the title compound was obtained from (E)-5-chloro-2-(3-methoxy-4-(4-methyl-1H-imidazol-1-yl)benzylidene)valeric acid trifluoroacetate (100 mg) and 1-(4-fluorophenyl)-1-methylethylamine (CAS #17797-10-3, 51 mg) in the same manner as in Example 418. The physical properties of the compound are as follows.

$^{1}$H-NMR ($CDCl_3$) δ (ppm): 1.75 (s, 6H), 1.90-2.00 (m, 2H), 2.32 (s, 3H), 2.76-2.85 (m, 2H), 3.57-3.64 (m, 2H), 3.83 (s, 3H), 6.91-7.05 (m, 5H), 7.20-7.33 (m, 3H), 7.63 (brs, 1H), 7.79 (brs, 1H).

Example 996

Synthesis of (E)-3-[3-methoxy-4-(4-methyl-1H-imidazol-1-yl)benzylidene]-1-[(1S)-1,2,3,4-tetrahydronaphthalen-1-yl]piperidin-2-one

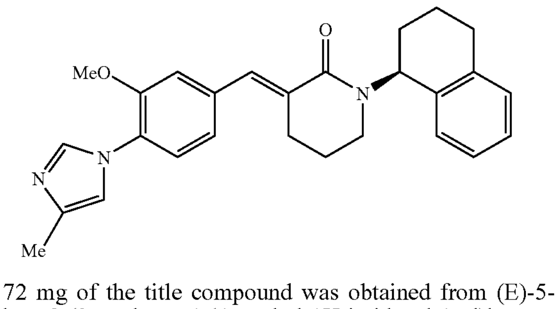

72 mg of the title compound was obtained from (E)-5-chloro-2-(3-methoxy-4-(4-methyl-1H-imidazol-1-yl)benzylidene)valeric acid trifluoroacetate (150 mg) and (1S)-1,2,3,4-tetrahydronaphthalen-1-ylamine (74 mg) in the same manner as in Example 418. The physical properties of the compound are as follows.

$^{1}$H-NMR ($CDCl_3$) δ (ppm): 1.70-1.96 (m, 4H), 1.98-2.16 (m, 2H), 2.30 (s, 3H), 2.73-2.98 (m, 4H), 3.03-3.10 (m, 1H), 3.17-3.26 (m, 1H), 3.87 (s, 3H), 6.10-6.17 (m, 1H), 6.93 (s, 1H), 7.04-7.18 (m, 6H), 7.22-7.28 (m, 1H), 7.71 (d, J=1.2 Hz, 1H), 7.91 (brs, 1H).

Example 997

Synthesis of (E)-3-[3-methoxy-4-(4-methyl-1H-imidazol-1-yl)benzylidene]-1-(2-methylindan-2-yl)piperidin-2-one

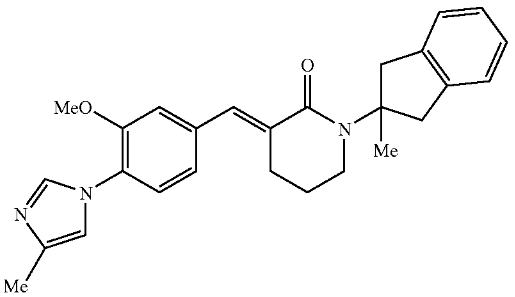

80 mg of the title compound was obtained from (E)-5-chloro-2-(3-methoxy-4-(4-methyl-1H-imidazol-1-yl)benzylidene)valeric acid trifluoroacetate (150 mg) and 2-methylindan-2-ylamine (CAS #312753-94-9, 98 mg) in the same manner as in Example 418. The physical properties of the compound are as follows.

$^1$H-NMR ($CDCl_3$) δ (ppm): 1.42 (s, 3H), 1.88-1.96 (m, 2H), 2.30 (s, 3H), 2.76-2.83 (m, 2H), 3.39 (s, 4H), 3.53-3.59 (m, 2H), 3.85 (s, 3H), 6.91-6.93 (m, 1H), 7.00-7.05 (m, 2H), 7.13-7.25 (m, 5H), 7.70 (d, J=1.6 Hz, 1H), 7.76-7.78 (m, 1H).

Example 998 and Example 999

Synthesis of (E)-1-[(2R and 2S)-5-methoxyindan-2-yl]-3-[3-methoxy-4-(4-methyl-1H-imidazol-1-yl)benzylidene]piperidin-2-one

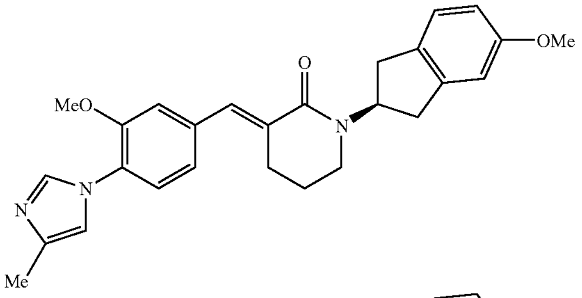

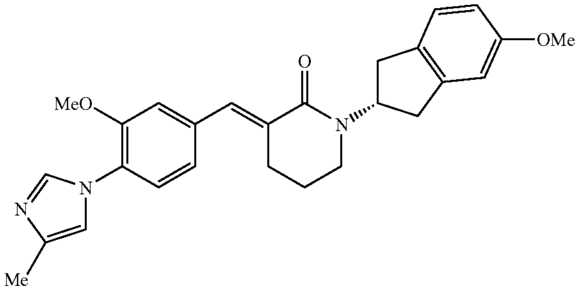

135 mg of the title compound as a racemate was obtained from (E)-5-chloro-2-(3-methoxy-4-(4-methyl-1H-imidazol-1-yl)benzylidene)valeric acid trifluoroacetate (300 mg) and 5-methoxyindan-2-ylamine (CAS #73305-09-6, 164 mg) in the same manner as in Example 418. The compound (8 mg) was fractionated using CHIRALCEL™ OJ manufactured by Daicel Chemical Industries, Ltd. (2 cm×25 cm: mobile phase: ethanol) to obtain the title optically active substance with a retention time of 8.8 minutes (Example 999, 1.3 mg, >99% ee) and the title optically active substance with a retention time of 11.7 minutes (Example 998, 1.9 mg, >99% ee). The physical properties of the compounds are as follows.

$^1$H-NMR ($CDCl_3$) δ (ppm): 1.81-1.89 (m, 2H), 2.37 (s, 3H), 2.75-2.82 (m, 2H), 2.88-3.00 (m, 2H), 3.18-3.30 (m, 4H), 3.79 (s, 3H), 3.87 (s, 3H), 5.73-5.82 (m, 1H), 6.72-6.80 (m, 2H), 6.97 (s, 1H), 7.02-7.14 (m, 3H), 7.24-7.28 (m, 1H), 7.83 (s, 1H), 8.08 (s, 1H).

Example 1000 and Example 1001

Synthesis of (E)-1-[(2R and 2S)-4-methoxyindan-2-yl]-3-[3-methoxy-4-(4-methyl-1H-imidazol-1-yl)benzylidene]piperidin-2-one

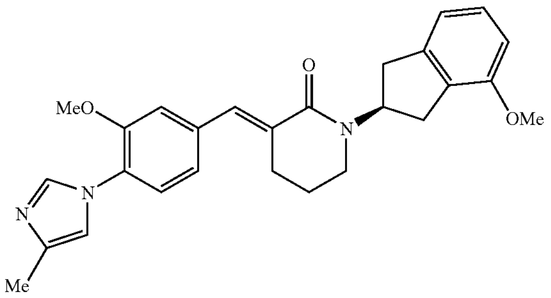

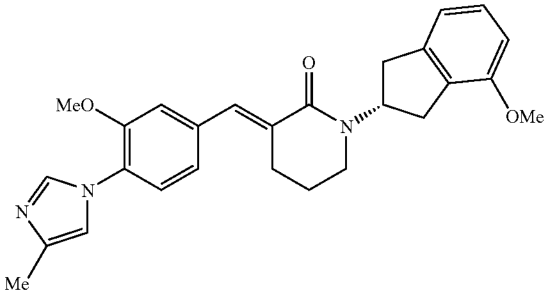

205 mg of the title compound as a racemate was obtained from (E)-5-chloro-2-(3-methoxy-4-(4-methyl-1H-imidazol-1-yl)benzylidene)valeric acid trifluoroacetate (300 mg) and 4-methoxyindan-2-ylamine (CAS #76413-92-8, 164 mg) in the same manner as in Example 418. The compound (3 mg) was fractionated using CHIRALPAK™ AD-H manufactured by Daicel Chemical Industries, Ltd. (2 cm×25 cm: mobile phase: ethanol) to obtain the title optically active substance with a retention time of 10.3 minutes (Example 1000, 1.1 mg, >99% ee) and the title optically active substance with a retention time of 10.9 minutes (Example 1001, 1.2 mg, >93% ee). The physical properties of the compounds are as follows.

$^1$H-NMR ($CDCl_3$) δ (ppm): 1.80-1.88 (m, 2H), 2.30 (s, 3H), 2.77-2.82 (m, 2H), 2.87-3.00 (m, 2H), 3.20-3.35 (m, 4H), 3.83 (s, 3H), 3.87 (s, 3H), 5.77-5.86 (m, 1H), 6.69 (d, J=8.0 Hz, 1H), 6.84 (d, J=7.6 Hz, 1H) 6.91-6.93 (m, 1H), 7.00-7.05 (m, 2H), 7.16 (dd, J=7.6 Hz, 8.0 Hz, 1H), 7.22-7.26 (m, 1H), 7.70 (d, J=1.2 Hz, 1H), 7.82-7.85 (m, 1H).

Example 1002 and Example 1003

Synthesis of (E)-1-[(2R and 2S)-4-fluoroindan-2-yl]-3-[3-methoxy-4-(4-methyl-1H-imidazol-1-yl)benzylidene]piperidin-2-one

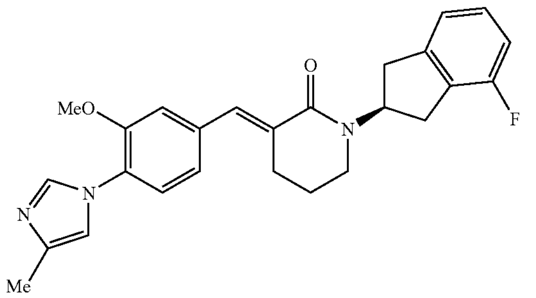

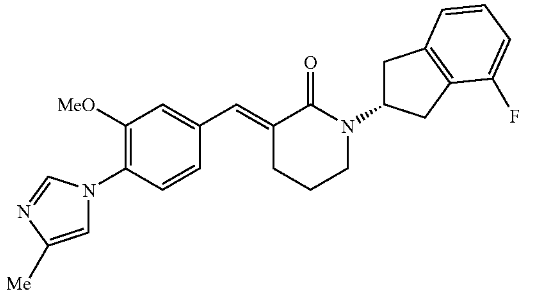

97 mg of the title compound as a racemate was obtained from (E)-5-chloro-2-(3-methoxy-4-(4-methyl-1H-imidazol-1-yl)benzylidene)valeric acid trifluoroacetate (500 mg) and 4-fluoroindan-2-ylamine (CAS #162752-09-2, 230 mg) in the same manner as in Example 418. The compound (8 mg) was fractionated using CHIRALCEL™ OJ manufactured by Daicel Chemical Industries, Ltd. (2 cm×25 cm: mobile phase: ethanol-hexane system) to obtain the title optically active substance with a retention time of 18.2 minutes (Example 1003, 1.2 mg, >99% ee) and the title optically active substance with a retention time of 22.8 minutes (Example 1002, 1.0 mg, >99% ee). The physical properties of the compounds are as follows.

$^1$H-NMR ($CDCl_3$) δ (ppm): 1.82-1.90 (m, 2H), 2.30 (s, 3H), 2.78-2.83 (m, 2H), 2.97-3.06 (m, 2H), 3.25-3.36 (m, 4H), 3.85 (s, 3H), 5.76-5.84 (m, 1H), 6.84-6.94 (m, 2H), 6.98-7.05 (m, 3H), 7.12-7.18 (m, 1H), 7.22-7.26 (m, 1H), 7.71 (d, J=1.6 Hz, 1H), 7.84 (brs, 1H)

Example 1004 and Example 1005

Synthesis of (E)-1-[(1R and 1S)-5-fluoroindan-1-yl]-3-[3-methoxy-4-(4-methyl-1H-imidazol-1-yl)benzylidene]piperidin-2-one

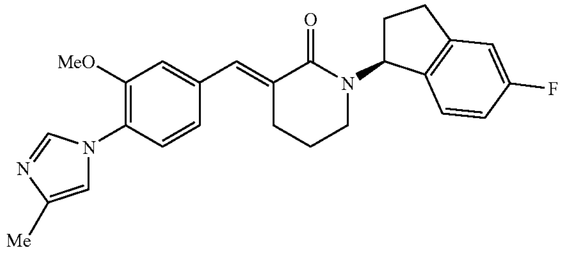

-continued

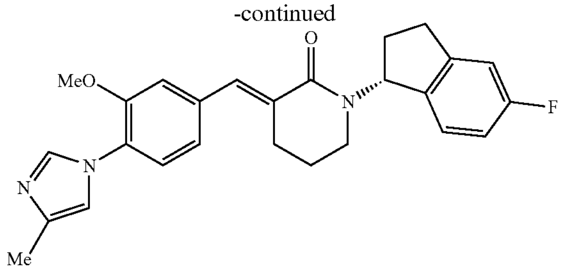

26 mg of the title compound as a racemate was obtained from (E)-5-chloro-2-(3-methoxy-4-(4-methyl-1H-imidazol-1-yl)benzylidene)valeric acid trifluoroacetate (80 mg) and 5-fluoroindan-1-ylamine (CAS #148960-33-2, 54 mg) in the same manner as in Example 418. The compound (20 mg) was fractionated using CHIRALCEL™ AD-H manufactured by Daicel Chemical Industries, Ltd. (2 cm×25 cm: mobile phase: ethanol) to obtain the title optically active substance with a retention time of 8.0 minutes (Example 1005, 6.9 mg, >99% ee) and the title optically active substance with a retention time of 8.8 minutes (Example 1004, 5.3 mg, >95% ee). The physical properties of the compounds are as follows.

$^1$H-NMR ($CDCl_3$) δ (ppm): 1.72-2.08 (m, 3H), 2.30 (s, 3H), 2.49-2.58 (m, 1H), 2.75-3.20 (m, 6H), 3.86 (s, 3H), 6.42-6.48 (m, 1H), 6.86-6.97 (m, 3H), 7.04-7.14 (m, 3H), 7.24-7.28 (m, 1H), 7.71 (s, 1H), 7.89 (brs, 1H).

Example 1006 and Example 1007

Synthesis of (E)-1-[(1R and 1S)-5-methoxyindan-1-yl]-3-[3-methoxy-4-(4-methyl-1H-imidazol-1-yl)benzylidene]piperidin-2-one

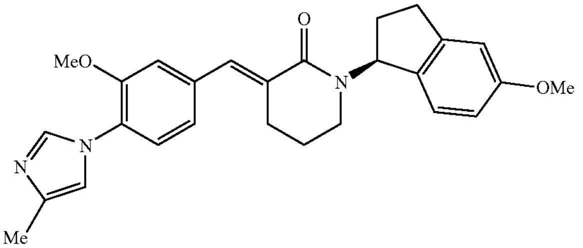

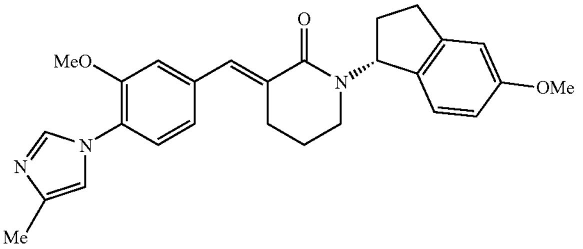

27 mg of the title compound as a racemate was obtained from (E)-5-chloro-2-(3-methoxy-4-(4-methyl-1H-imidazol-1-yl)benzylidene)valeric acid trifluoroacetate (80 mg) and 5-methoxyindan-1-ylamine (CAS #52372-95-9, 58 mg) in the same manner as in Example 418. The compound (27 mg) was fractionated using CHIRALPAK™ AD-H manufactured by Daicel Chemical Industries, Ltd. (2 cm×25 cm: mobile phase: hexane-ethanol system) to obtain the title optically active substance with a retention time of 16.0 minutes (Example 1007, 3.5 mg, >99% ee) and the title optically active substance with a retention time of 17.2 minutes (Example 1006, 2.1 mg, >95% ee). The physical properties of the compounds are as follows.

$^1$H-NMR ($CDCl_3$) δ (ppm): 1.75-2.05 (m, 3H), 2.37 (s, 3H), 2.47-2.58 (m, 1H), 2.76-3.18 (m, 6H), 3.80 (s, 3H), 3.88

(s, 3H), 6.39-6.45 (m, 1H), 6.74-6.81 (m, 2H), 6.97 (s, 1H), 7.04-7.10 (m, 3H), 7.24-7.29 (m, 1H), 7.88 (s, 1H), 8.07 (brs, 1H).

Example 1008 and Example 1009

Synthesis of (E)-1-[(1R and 1S)-4-fluoroindan-1-yl]-3-[3-methoxy-4-(4-methyl-1H-imidazol-1-yl)benzylidene]piperidin-2-one

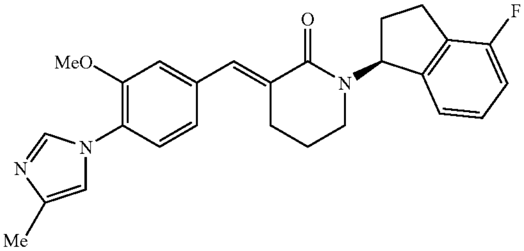

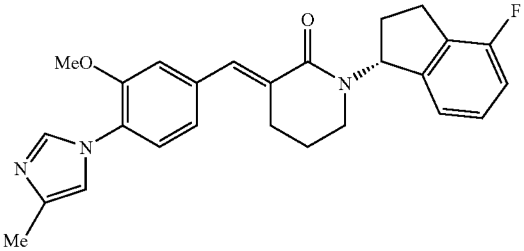

178 mg of the title compound as a racemate was obtained from (E)-5-chloro-2-(3-methoxy-4-(4-methyl-1H-imidazol-1-yl)benzylidene)valeric acid trifluoroacetate (300 mg) and 4-fluoroindan-1-ylamine (CAS #148960-34-3, 151 mg) in the same manner as in Example 418. The compound (178 mg) was fractionated using CHIRALPAK™ AD-H manufactured by Daicel Chemical Industries, Ltd. (2 cm×25 cm: mobile phase: ethanol) to obtain the title optically active substance with a retention time of 7.2 minutes (Example 1009, 71 mg, >99% ee) and the title optically active substance with a retention time of 9.5 minutes (Example 1008, 72 mg, >99% ee). The physical properties of the compounds are as follows.

$^1$H-NMR ($CDCl_3$) δ (ppm): 1.72-1.90 (m, 2H), 1.98-2.08 (m, 1H), 2.30 (s, 3H), 2.50-2.60 (m, 1H), 2.75-2.98 (m, 3H), 3.02-3.21 (m, 3H), 3.86 (s, 3H), 6.49-6.55 (m, 1H), 6.90-7.00 (m, 3H), 7.02-7.08 (m, 2H), 7.16-7.28 (m, 2H), 7.71 (s, 1H), 7.89 (brs, 1H).

Example 1010 and Example 1011

Synthesis of (E)-1-[(1R and 1S)-5,6-dimethoxyindan-1-yl]-3-[3-methoxy-4-(4-methyl-1H-imidazol-1-yl)benzylidene]piperidin-2-one

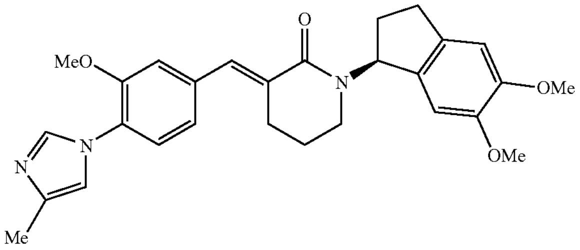

-continued

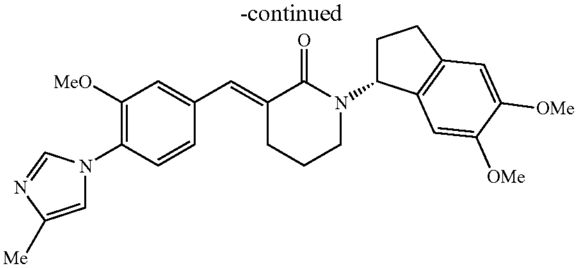

178 mg of the title compound as a racemate was obtained from (E)-5-chloro-2-(3-methoxy-4-(4-methyl-1H-imidazol-1-yl)benzylidene)valeric acid trifluoroacetate (300 mg) and 5,6-dimethoxyindan-1-ylamine (CAS #91247-06-2, 151 mg) in the same manner as in Example 418. The compound (178 mg) was fractionated using CHIRALPAK™ AD-H manufactured by Daicel Chemical Industries, Ltd. (2 cm×25 cm: mobile phase: ethanol) to obtain the title optically active substance with a retention time of 9.3 minutes (Example 1011, 71 mg, >99% ee) and the title optically active substance with a retention time of 10.9 minutes (Example 1010, 72 mg, >93% ee). The physical properties of the compounds are as follows.

$^1$H-NMR ($CDCl_3$) δ (ppm): 1.70-1.89 (m, 2H), 1.93-2.03 (m, 1H), 2.30 (s, 3H), 2.49-2.59 (m, 1H), 2.75-3.07 (m, 5H), 3.11-3.20 (m, 1H), 3.84 (s, 3H), 3.87 (s, 3H), 3.88 (s, 3H), 6.47 (dd, J=6.4 Hz, 8.4 Hz, 1H), 6.69 (s, 1H), 6.78 (s, 1H), 6.94 (brs, 1H), 7.04-7.10 (m, 2H), 7.24-7.30 (m, 1H), 7.72 (brs, 1H), 7.91 (brs, 1H)

Example 1012 and Example 1013

Synthesis of (E)-3-[3-methoxy-4-(4-methyl-1H-imidazol-1-yl)benzylidene]-1-[(1R and 1S)-5-trifluoromethoxyindan-1-yl]piperidin-2-one

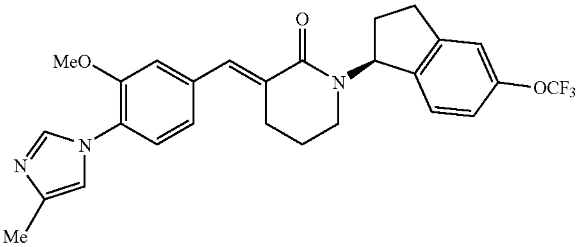

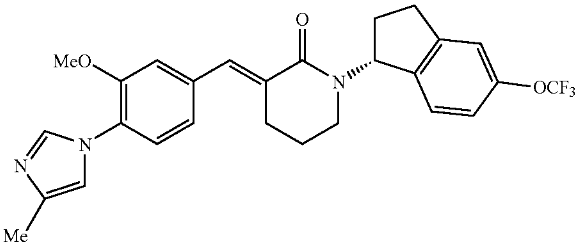

6.8 mg of the title compound as a racemate was obtained from 5-trifluoromethoxyindanone (CAS #173252-76-1, 1 g) in the same manner as in Example 973. The compound (6.8 mg) was fractionated using CHIRALCEL™ OJ manufactured by Daicel Chemical Industries, Ltd. (2 cm×25 cm: mobile phase: hexane-ethanol system) to obtain the title optically active substance with a retention time of 10.2 minutes (Example 1012, 1.9 mg, >99% ee) and the title optically active substance with a retention time of 17.3 minutes (Example 1013, 1.9 mg, >99% ee). The physical properties of the compounds are as follows.

$^1$H-NMR ($CDCl_3$) δ (ppm): 1.72-2.10 (m, 3H), 2.30 (s, 3H), 2.50-2.60 (m, 1H), 2.75-3.22 (m, 6H), 3.86 (s, 3H), 6.48 (dd, J=8.0 Hz, 8.4 Hz, 1H), 6.92-6.94 (m, 1H), 7.02-7.08 (m, 3H), 7.10 (brs, 1H), 7.17 (d, J=8.4 Hz, 1H), 7.24-7.28 (m, 1H), 7.71 (d, J=0.8 Hz, 1H), 7.89 (brs, 1H).

Example 1014 and Example 1015

Synthesis of (E)-3-[3-methoxy-4-(4-methyl-1H-imidazol-1-yl)benzylidene]-1-[(2R and 2S)-1,2,3,4-tetrahydronaphthalen-2-yl]piperidin-2-one

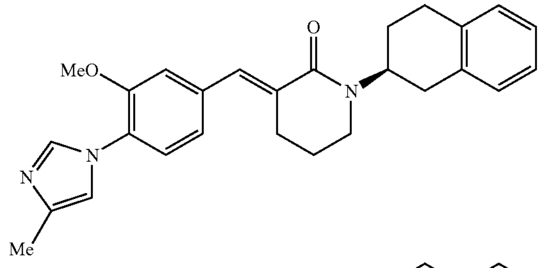

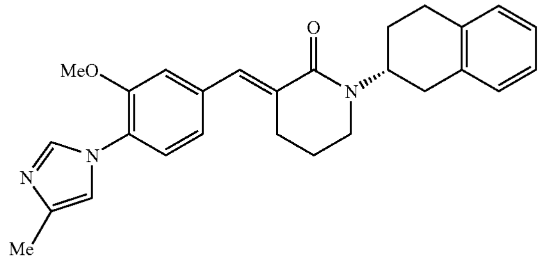

IPEA (0.58 mL), EDC (0.38 g) and HOBT (0.27 g) were added to a suspension of (E)-5-chloro-2-(3-methoxy-4-(4-methyl-1H-imidazol-1-yl)benzylidene)valeric acid trifluoroacetate (300 mg) and 1,2,3,4-tetrahydronaphthalen-2-ylamine (148 mg) in DMF (10 mL) at room temperature, and the reaction solution was stirred at room temperature for 1 hour. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (Carrier: Chromatorex™ NH, elution solvent: heptane-ethyl acetate system) to obtain (E)-5-chloro-2-(3-methoxy-4-(4-methyl-1H-imidazol-1-yl)benzylidene) valeric acid (1,2,3,4-tetrahydronaphthalen-2-yl)amide (255 mg). Sodium hydride (containing mineral oil at 40%, 50 mg) was added to a solution of (E)-5-chloro-2-(3-methoxy-4-(4-methyl-1H-imidazol-1-yl)benzylidene)valeric acid (1,2,3,4-tetrahydronaphthalen-2-yl)amide (255 mg) in DMF (6 mL) at room temperature, and the reaction solution was stirred at room temperature for 30 minutes. A saturated aqueous solution of sodium bicarbonate and ethyl acetate were added to the reaction solution and the organic layer was partitioned. The organic layer was washed sequentially with a saturated aqueous solution of ammonium chloride, water and a saturated aqueous solution of sodium chloride. The organic layer was dried over anhydrous magnesium sulfate, and then concentrated under reduced pressure. The resulting residue was purified by silica gel chromatography (Carrier: Chromatorex™ NH, elution solvent:heptane-ethyl acetate system) to obtain (E)-3-(3-methoxy-4-(4-methyl-1H-imidazol-1-yl) benzylidene)-1-(1,2,3,4-tetrahydronaphthalen-2-yl)piperidin-2-one as a racemate (210 mg). The compound (12 mg) was fractionated using CHIRALPAK™ AD-H manufactured by Daicel Chemical Industries, Ltd. (2 cm×25 cm: mobile phase: ethanol) to obtain the title optically active substance with a retention time of 9.5 minutes (Example 1014, 6.0 mg; >99% ee) and the title optically active substance with a retention time of 13.0 minutes (Example 1015, 5.9 mg; >99% ee). The physical properties of the compounds are as follows.

$^1$H-NMR ($CDCl_3$) δ (ppm): 1.80-2.05 (m, 4H), 2.31 (s, 3H), 2.76-3.10 (m, 6H), 3.41 (t, J=5.6 Hz, 2H), 3.86 (s, 3H), 5.03-5.13 (m, 1H), 6.94 (s, 1H), 7.02-7.15 (m, 6H), 7.22-7.28 (m, 1H), 7.74 (s, 1H), 7.85 (brs, 1H).

Example 1016 and Example 1017

Synthesis of (E)-1-[(4R and 4S)-7-methoxychroman-4-yl]-3-[3-methoxy-4-(4-methyl-1H-imidazol-1-yl)benzylidene]piperidin-2-one

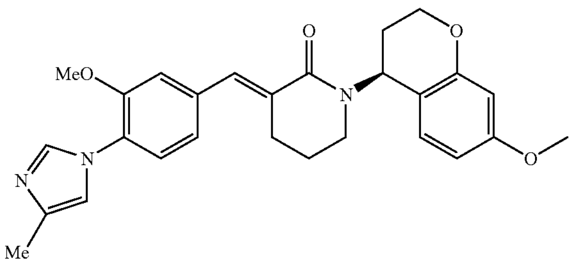

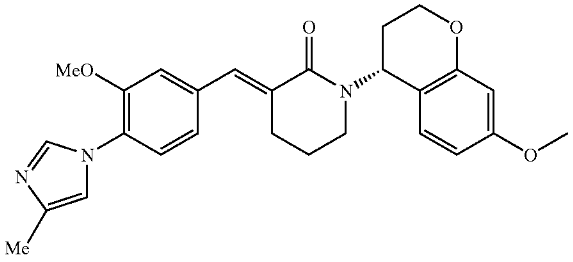

285 mg of the title compound as a racemate was obtained from (E)-5-chloro-2-(3-methoxy-4-(4-methyl-1H-imidazol-1-yl)benzylidene)valeric acid trifluoroacetate (300 mg) and 7-methoxychroman-4-ylamine (CAS #802037-18-9, 180 mg) in the same manner as in Example 418. The compound (10 mg) was fractionated using CHIRALPAK™ AD-H manufactured by Daicel Chemical Industries, Ltd. (2 cm×25 cm: mobile phase: ethanol) to obtain the title optically active substance with a retention time of 12.9 minutes (Example 1016, 2.3 mg, >99% ee) and the title optically active substance with a retention time of 20.5 minutes (Example 1017, 2.8 mg, >99% ee). The physical properties of the compounds are as follows.

$^1$H-NMR ($CDCl_3$) δ (ppm): 1.71-1.91 (m, 2H), 2.08-2.22 (m, 2H), 2.30 (s, 3H), 2.74-2.84 (m, 1H), 2.87-2.96 (m, 1H), 3.07-3.23 (m, 2H), 3.77 (s, 3H), 3.87 (s, 3H), 4.18-4.27 (m, 1H), 4.30-4.37 (m, 1H), 6.12-6.18 (m, 1H), 6.40 (d, J=2.4 Hz, 1H), 6.50 (dd, J=2.4 Hz, 8.8 Hz, 1H), 6.92-6.97 (m, 2H), 7.05-7.10 (m, 2H), 7.23-7.29 (m, 1H), 7.73 (d, J=1.6 Hz, 1H), 7.91 (brs, 1H).

Example 1018 and Example 1019

Synthesis of (E)-1-[(4R and 4S)-6-methoxychroman-4-yl]-3-[3-methoxy-4-(4-methyl-1H-imidazol-1-yl)benzylidene]piperidin-2-one

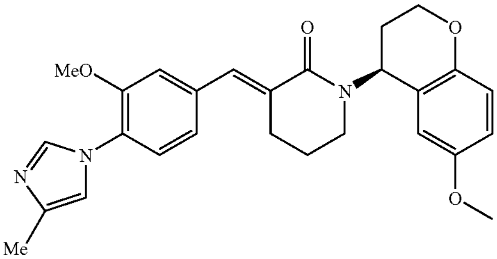

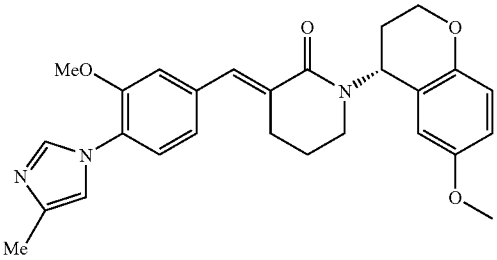

215 mg of the title compound as a racemate was obtained from (E)-5-chloro-2-(3-methoxy-4-(4-methyl-1H-imidazol-1-yl)benzylidene)valeric acid trifluoroacetate (300 mg) and 6-methoxychroman-4-ylamine (CAS #81816-60-6, 180 mg) in the same manner as in Example 418. The compound (12 mg) was fractionated using CHIRALCEL™ AD-H manufactured by Daicel Chemical Industries, Ltd. (2 cm×25 cm: mobile phase: ethanol) to obtain the title optically active substance with a retention time of 10.7 minutes (Example 1018, 5.8 mg, >99% ee) and the title optically active substance with a retention time of 15.3 minutes (Example 1019, 5.5 mg, >99% ee). The physical properties of the compounds are as follows.

$^1$H-NMR ($CDCl_3$) δ (ppm): 1.70-1.93 (m, 2H), 2.10-2.24 (m, 2H), 2.31 (s, 3H), 2.75-2.85 (m, 1H), 2.89-2.98 (m, 1H), 3.08-3.27 (m, 2H), 3.73 (s, 3H), 3.88 (s, 3H), 4.15-4.22 (m, 1H), 4.28-4.35 (m, 1H), 6.18-6.25 (m, 1H), 6.59 (d, J=3.2 Hz, 1H), 6.73-6.82 (m, 2H), 6.95 (s, 1H), 7.05-7.11 (m, 2H), 7.25-7.29 (m, 1H), 7.73 (d, J=1.2 Hz, 1H), 7.91 (brs, 1H).

Example 1020 and Example 1021

Synthesis of (E)-1-[(4R and 4S)-6-fluorochroman-4-yl]-3-[3-methoxy-4-(4-methyl-1H-imidazol-1-yl)benzylidene]piperidin-2-one

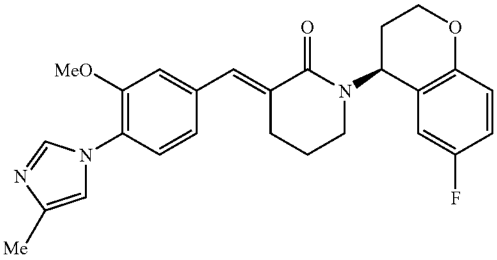

-continued

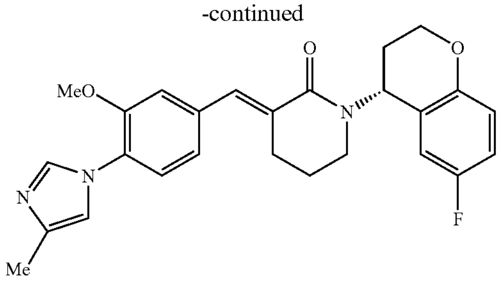

207 mg of the title compound as a racemate was obtained from (E)-5-chloro-2-(3-methoxy-4-(4-methyl-1H-imidazol-1-yl)benzylidene)valeric acid trifluoroacetate (300 mg) and 6-fluorochroman-4-ylamine (CAS #238764-22-2, 220 mg) in the same manner as in Example 418. The compound (11 mg) was fractionated using CHIRALCEL™ AD-H manufactured by Daicel Chemical Industries, Ltd. (2 cm×25 cm: mobile phase: ethanol) to obtain the title optically active substance with a retention time of 9.4 minutes (Example 1020, 4.0 mg, >99% ee) and the title optically active substance with a retention time of 12.8 minutes (Example 1021, 3.9 mg, >99% ee). The physical properties of the compounds are as follows.

$^1$H-NMR ($CDCl_3$) δ (ppm): 1.75-1.94 (m, 2H), 2.07-2.26 (m, 2H), 2.31 (s, 3H), 2.74-2.84 (m, 1H), 2.91-3.01 (m, 1H), 3.07-3.15 (m, 1H), 3.19-3.28 (m, 1H), 3.88 (s, 3H), 4.17-4.26 (m, 1H), 4.32-4.40 (m, 1H), 6.19-6.25 (m, 1H), 6.75-6.82 (m, 2H), 6.84-6.90 (m, 1H), 6.95 (s, 1H), 7.05-7.11 (m, 2H), 7.25-7.30 (m, 1H), 7.74 (d, J=1.2 Hz, 1H), 7.92 (brs, 1H).

Example 1022 and Example 1023

Synthesis of (E)-1-[(4R and 4S)-2,2-dimethylchroman-4-yl]-3-[3-methoxy-4-(4-methyl-1H-imidazol-1-yl)benzylidene]piperidin-2-one

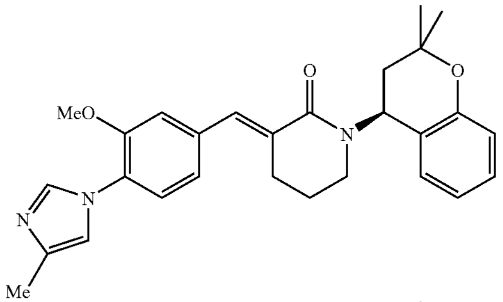

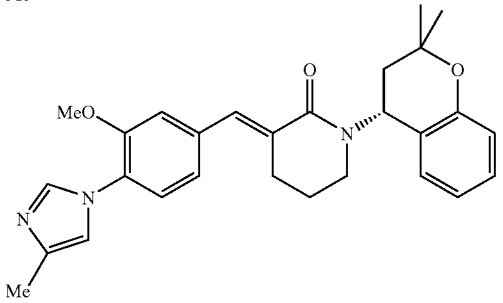

217 mg of the title compound as a racemate was obtained from (E)-5-chloro-2-(3-methoxy-4-(4-methyl-1H-imidazol-1-yl)benzylidene)valeric acid trifluoroacetate (300 mg) and 2,2-dimethylchroman-4-ylamine (CAS #220634-41-3, 145 mg) in the same manner as in Example 418. The compound (20 mg) was fractionated using CHIRALCEL™ AD-H manufactured by Daicel Chemical Industries, Ltd. (2 cm×25 cm: mobile phase: ethanol) to obtain the title optically active substance with a retention time of 8.2 minutes (Example 1022, 8.1 mg, >99% ee) and the title optically active substance with a retention time of 9.6 minutes (Example 1023, 8.0 mg, >99% ee). The physical properties of the compounds are as follows.

$^1$H-NMR ($CDCl_3$) δ (ppm): 1.37 (s, 3H), 1.48 (s, 3H), 1.73-2.04 (m, 4H), 2.31 (s, 3H), 2.74-2.83 (m, 1H), 2.89-2.98 (m, 1H), 3.04-3.22 (m, 2H), 3.88 (s, 3H), 6.23-6.33 (m, 1H), 6.83 (dd, J=1.2 Hz, 8.4 Hz, 1H), 6.86-6.91 (m, 1H), 6.95 (s, 1H), 7.05-7.12 (m, 3H), 7.14-7.19 (m, 1H), 7.24-7.30 (m, 1H), 7.73 (s, 1H), 7.92 (brs, 1H).

Example 1024 and Example 1025

Synthesis of (E)-1-[(4R) and (4S)-7-fluorochroman-4-yl]-3-[3-methoxy-4-(4-methyl-1H-imidazol-1-yl)benzylidene]piperidin-2-one

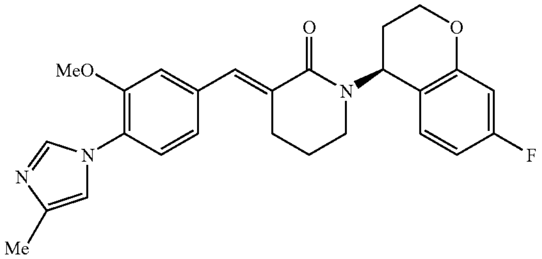

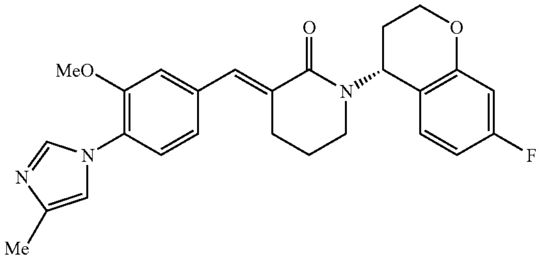

217 mg of the title compound as a racemate was obtained from (E)-5-chloro-2-(3-methoxy-4-(4-methyl-1H-imidazol-1-yl)benzylidene)valeric acid trifluoroacetate (300 mg) and 7-fluorochroman-4-ylamine (CAS #774163-31-4, 168 mg) in the same manner as in Example 418. The compound (20 mg) was fractionated using CHIRALPAK™ AD-H manufactured by Daicel Chemical Industries, Ltd. (2 cm×25 cm: mobile phase: ethanol) to obtain the title optically active substance with a retention time of 9.6 minutes (Example 1024, 8.1 mg, >99% ee) and the title optically active substance with a retention time of 14.0 minutes (Example 1025, 8.0 mg, >99% ee). The physical properties of the compounds are as follows.

$^1$H-NMR ($CDCl_3$) δ (ppm): 1.72-1.93 (m, 2H), 2.10-2.25 (m, 2H), 2.30 (s, 3H), 2.74-2.83 (m, 1H), 2.89-2.97 (m, 1H), 3.04-3.11 (m, 1H), 3.17-3.25 (m, 1H), 3.87 (s, 3H), 4.21-4.28 (m, 1H), 4.33-4.40 (m, 1H), 6.15-6.21 (m, 1H), 6.57 (dd, J=2.4 Hz, 9.6 Hz, 1H), 6.62 (ddd, J=2.4 Hz, 8.4 Hz, 8.4 Hz, 1H), 6.93-7.04 (m, 2H), 7.05-7.10 (m, 2H), 7.25-7.30 (m, 1H), 7.74 (brs, 1H), 7.91 (brs, 1H).

Example 1026 and Example 1027

Synthesis of (E)-1-[(3R and 3S)-chroman-3-yl]-3-[3-methoxy-4-(4-methyl-1H-imidazol-1-yl)benzylidene]piperidin-2-one

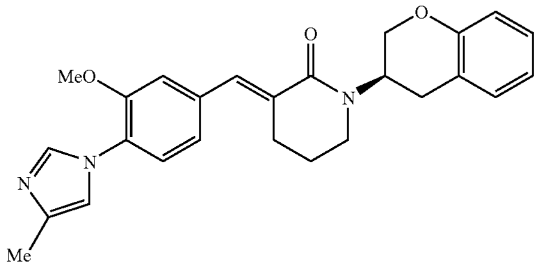

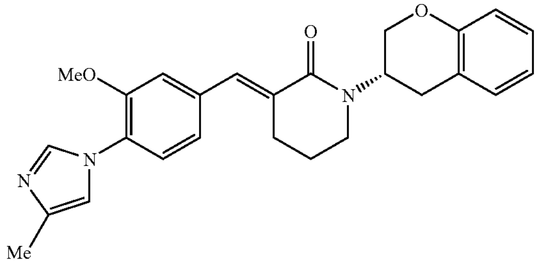

171 mg of the title compound as a racemate was obtained from (E)-5-chloro-2-(3-methoxy-4-(4-methyl-1H-imidazol-1-yl)benzylidene)valeric acid trifluoroacetate (250 mg) and chroman-3-ylamine (CAS #60575-19-1, 75 mg) in the same manner as in Example 418. The compound (10 mg) was fractionated using CHIRALCEL™ AD-H manufactured by Daicel Chemical Industries, Ltd. (2 cm×25 cm: mobile phase: ethanol) to obtain the title optically active substance with a retention time of 11.6 minutes (Example 1026, 4.3 mg, >99% ee) and the title optically active substance with a retention time of 13.9 minutes (Example 1027, 4.3 mg, >99% ee). The physical properties of the compounds are as follows.

$^1$H-NMR ($CDCl_3$) δ (ppm): 1.75-1.94 (m, 2H), 2.31 (s, 3H), 2.78-2.84 (m, 2H), 3.04 (dd, J=6.8 Hz, 17.2 Hz, 1H), 3.15 (dd, J=6.4 Hz, 17.2 Hz, 1H), 3.40 (t, J=6.0 Hz, 2H), 3.86 (s, 3H), 4.21-4.32 (m, 2H), 5.09-5.16 (m, 1H), 6.86 (d, J=8.0 Hz, 1H), 6.89-6.95 (m, 2H), 7.01-7.16 (m, 1H), 7.24-7.28 (m, 1H), 7.74 (s, 1H), 7.84 (brs, 1H).

Example 1028 and Example 1029

Synthesis of (E)-1-[(1R,2R and 1S,2S)-1-hydroxyindan-2-yl]-3-[3-methoxy-4-(4-methyl-1H-imidazol-1-yl)benzylidene]piperidin-2-one

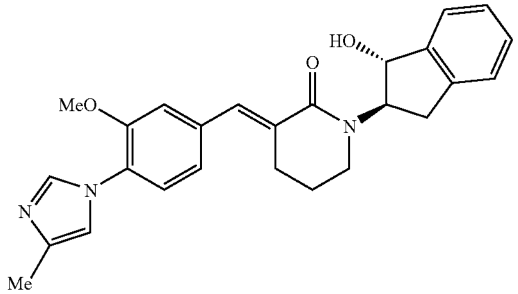

-continued

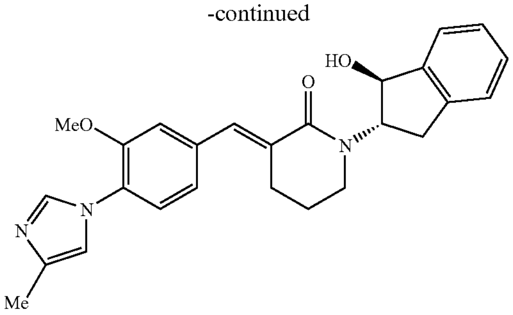

125 mg of the title compound as a racemate was obtained from (E)-5-chloro-2-(3-methoxy-4-(4-methyl-1H-imidazol-1-yl)benzylidene)valeric acid trifluoroacetate (800 mg) and trans-2-aminoindan-1-ol (CAS #13575-72-9, 446 mg) in the same manner as in Example 418. The compound (13 mg) was fractionated using CHIRALCEL™ AD-H manufactured by Daicel Chemical Industries, Ltd. (2 cm×25 cm: mobile phase: ethanol-hexane system) to obtain the title optically active substance with a retention time of 11.1 minutes (Example 1028, 5.7 mg, >99% ee) and the title optically active substance with a retention time of 13.7 minutes (Example 1029, 5.4 mg, >99% ee). The physical properties of the compounds are as follows.

$^1$H-NMR ($CDCl_3$) δ (ppm): 1.90-2.03 (m, 2H), 2.32 (s, 3H), 2.76-2.95 (m, 2H), 3.06-3.22 (m, 2H), 3.46-3.57 (m, 2H), 3.87 (s, 3H), 5.14-5.22 (m, 1H), 5.34 (d, J=7.6 Hz, 1H), 6.95 (s, 1H), 7.02-7.07 (m, 2H), 7.22-7.33 (m, 4H), 7.43-7.48 (m, 1H), 7.76 (s, 1H), 7.86 (s, 1H).

Example 1030 and Example 1031

Synthesis of (E)-1-[(3R,4S and 3S,4R)-3-hydroxychroman-4-yl]-3-[3-methoxy-4-(4-methyl-1H-imidazol-1-yl)benzylidene]piperidin-2-one

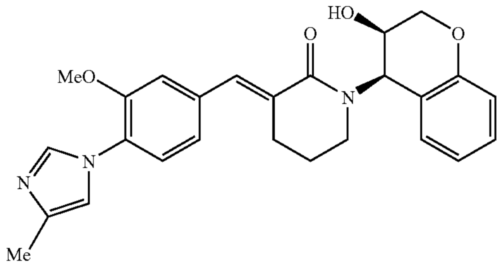

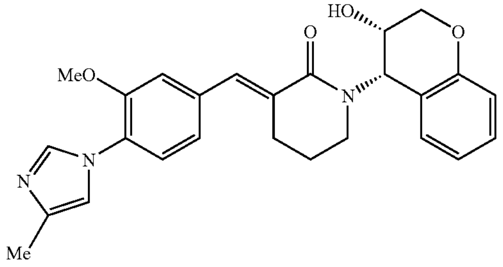

198 mg of the title compound as a racemate was obtained from (E)-5-chloro-2-(3-methoxy-4-(4-methyl-1H-imidazol-1-yl)benzylidene)valeric acid trifluoroacetate (600 mg) and cis-4-aminochroman-3-ol (CAS #58810-67-6, 332 mg) in the same manner as in Example 418. The compound (12 mg) was fractionated using CHIRALCEL™ AD-H manufactured by Daicel Chemical Industries, Ltd. (2 cm×25 cm: mobile phase: ethanol-hexane system) to obtain the title optically active substance with a retention time of 9.6 minutes (Example 1030, 5.4 mg, >99% ee) and the title optically active substance with a retention time of 12.6 minutes (Example 1031, 5.3 mg, >97% ee). The physical properties of the compounds are as follows.

$^1$H-NMR ($CDCl_3$) δ (ppm): 1.70-1.95 (m, 2H), 2.31 (s, 3H), 2.78-2.92 (m, 2H), 3.15-3.23 (m, 1H), 3.30-3.39 (m, 1H), 3.85-3.97 (m, 1H), 3.87 (s, 3H), 4.02 (dd, J=8.0 Hz, 11.2 Hz, 1H), 4.26-4.32 (m, 1H), 4.43-4.48 (m, 1H), 6.00 (d, J=4.4 Hz, 1H), 6.91-7.01 (m, 3H), 7.05-7.13 (m, 3H), 7.22-7.29 (m, 2H), 7.75 (d, J=1.2 Hz, 1H), 7.89 (brs, 1H).

Example 1032 and Example 1033

Synthesis of (E)-1-[(1S,2R and 1R,2S)-1-hydroxyindan-2-yl]-3-[3-methoxy-4-(4-methyl-1H-imidazol-1-yl)benzylidene]piperidin-2-one

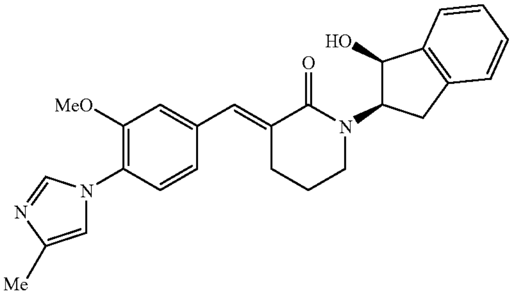

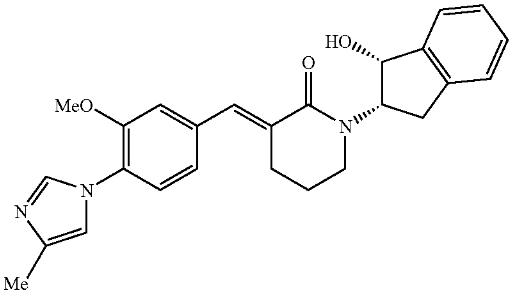

198 mg of the title compound as a racemate was obtained from (E)-5-chloro-2-(3-methoxy-4-(4-methyl-1H-imidazol-1-yl)benzylidene)valeric acid trifluoroacetate (400 mg) and cis-2-aminoindan-1-ol (CAS #23337-80-6, 188 mg) in the same manner as in Example 418. The compound (12 mg) was fractionated using CHIRALCEL™ OJ manufactured by Daicel Chemical Industries, Ltd. (2 cm×25 cm: mobile phase: ethanol) to obtain the title optically active substance with a retention time of 5.4 minutes (Example 1032, 3.5 mg, >99% ee) and the title optically active substance with a retention time of 7.9 minutes (Example 1033, 2.8 mg, >97% ee). The physical properties of the compound are as follows.

$^1$H-NMR ($CDCl_3$) δ (ppm): 1.83-1.91 (m, 2H), 2.34 (s, 3H), 2.72-2.89 (m, 2H), 3.18 (dd, J=8.4 Hz, 16.4 Hz, 1H), 3.30-3.45 (m, 3H), 3.87 (s, 3H), 5.17-5.24 (m, 1H), 5.39 (d, J=5.2 Hz, 1H), 6.95 (s, 1H), 7.02-7.07 (m, 2H), 7.24-7.34 (m, 4H), 7.44-7.48 (m, 1H), 7.80-7.85 (m, 2H).

Example 1034 and Example 1035

Synthesis of (E)-(3S)-(4-fluorophenyl)-6-[3-methoxy-4-(4-methyl-1H-imidazol-1-yl)benzylidene]-(9R)-hexahydroindolizin-5-one and (E)-(3R)-(4-fluorophenyl)-6-[3-methoxy-4-(4-methyl-1H-imidazol-1-yl)benzylidene]-(9S)-hexahydroindolizin-5-one

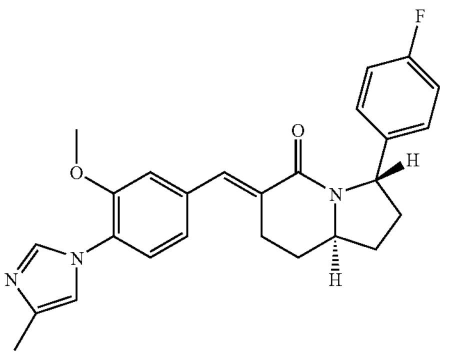

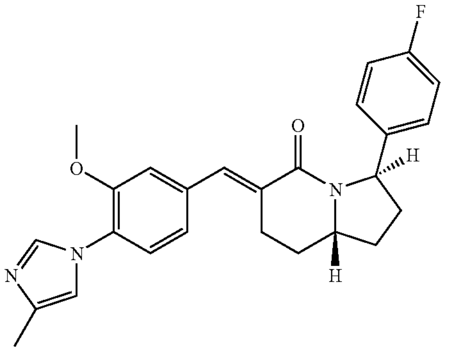

Synthesis of 6-chloro-(3S*)-(4-fluorophenyl)-(9S*)-hexahydroindolizin-5-one

Sec-butyl lithium (1 M cyclohexane solution, 0.65 mL) was added to a solution of (3S*)-(4-fluorophenyl)-(9R*)-hexahydroindolizin-5-one (130 mg) synthesized in accordance with the method described in The Journal of Organic Chemistry, 2001, vol. 66, p. 886 in THF (5 mL) at −40° C., and the reaction solution was stirred at −40° C. for 1 hour. The reaction solution was added dropwise to a solution of p-toluenesulfonic acid chloride (117 mg) in THF (2 mL) at −40° C. The reaction solution was stirred at −40° C. for 30 minutes, and further stirred at room temperature for 1 hour. Then, a saturated aqueous solution of ammonium chloride and ethyl acetate were added to the reaction solution and the organic layer was partitioned. The resulting organic layer was dried over magnesium sulfate, and concentrated under reduced pressure. The residue was purified by silica gel column chromatography (elution solvent:heptane:ethyl acetate=1:1→ethyl acetate) to obtain 84 mg of the title compound. Properties data of the compound are as follows.

$^1$H-NMR ($CDCl_3$) δ (ppm): 1.44-1.63 (m, 2H), 1.75-1.85 (m, 1H), 2.12-2.30 (m, 3H), 2.40-2.56 (m, 2H), 3.87-3.96 (m, 1H), 4.36 (dd, J=9.6, 6.8 Hz, 1H), 5.12 (t, J=8.0 Hz, 1H), 6.96-7.02 (m, 2H), 7.15-7.20 (m, 2H).

Synthesis of diethyl [(3S*)-(4-fluorophenyl)-5-oxo-(9S*)-octahydroindolizin-6-yl]phosphonate A mixture of 6-chloro-(3S*)-(4-fluorophenyl)-(9S*)-hexahydroindolizin-5-one (84 mg) with triethyl phosphite (1 mL) was stirred at 170° C. for 10 hours. After allowing the reaction solution to be cooled to room temperature, the reaction solution was concentrated under reduced pressure. The residue was purified by silica gel column chromatography (elution solvent:ethyl acetate→ethyl acetate:methanol=9:1) to obtain 86 mg of the title compound. Properties data of the compound are as follows.

$^1$H-NMR ($CDCl_3$) δ (ppm): 1.22-1.38 (m, 6H), 1.49-1.79 (m, 2H), 2.07-2.29 (m, 4H), 2.36-2.54 (m, 1H), 3.70-3.88 (m, 1H), 4.02-4.25 (m, 5H), 5.13 (t, J=8.0 Hz, 1H), 6.93-6.99 (m, 2H), 7.15-7.27 (m, 2H).

Synthesis of (E)-(3S*)-(4-fluorophenyl)-6-[3-methoxy-4-(4-methyl-1H-imidazol-1-yl)benzylidene]-(9R*)-hexahydroindolizin-5-one Lithium hydroxide monohydrate (29 mg) was added to a solution of diethyl ((3S*)-(4-fluorophenyl)-5-oxo-(9S*)-octahydroindolizin-6-yl)phosphonate (86 mg) and 3-methoxy-4-(4-methyl-1H-imidazol-1-yl)benzaldehyde (51 mg) obtained in Example 1 in THF (2 mL) and ethanol (0.4 mL), and the reaction solution was stirred at room temperature for 19 hours. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent: heptane:ethyl acetate=1:1→ethyl acetate) to obtain 74 mg of the title compound. Properties data of the compound are as follows.

$^1$H-NMR ($CDCl_3$) δ (ppm): 1.43-1.55 (m, 1H), 1.56-1.67 (m, 1H), 1.78-1.89 (m, 1H), 2.21-2.33 (m, 5H), 2.44-2.53 (m, 1H), 2.69 (tt, J=16.0, 3.6 Hz, 1H), 3.10 (dt, J=16.0, 2.8 Hz, 1H), 3.84 (S, 3H), 3.92-4.02 (m, 1H), 5.20 (t, J=8.4 Hz, 1H), 6.93 (brs, 1H), 6.98-7.06 (m, 4H), 7.23-7.28 (m, 3H), 7.72 (brs, 1H), 7.73 (d, J=2.4 Hz, 1H).

Synthesis of (E)-(3S)-(4-fluorophenyl)-6-[3-methoxy-4-(4-methyl-1H-imidazol-1-yl)benzylidene]-(9R)-hexahydroindolizin-5-one and (E)-(3R)-(4-fluorophenyl)-6-[3-methoxy-4-(4-methyl-1H-imidazol-1-yl)benzylidene]-(9S)-hexahydroindolizin-5-one (E)-(3S*)-(4-fluorophenyl)-6-(3-methoxy-4-(4-methyl-1H-imidazol-1-yl)benzylidene)-(9R*)-hexahydroindolizin-5-one as a racemate (50 mg) was fractionated using CHIRALPAK™ AD-H manufactured by Daicel Chemical Industries, Ltd. (2 cm×25 cm: mobile phase:hexane:ethanol=3:7) to obtain the title optically active substance with a retention time of 16 minutes (22.7 mg; >99% ee) and the title optically active substance with a retention time of 33 minutes (17.2 mg; >99% ee).

The physical properties of the optically active substance with a retention time of 16 minutes (Example 1034) are as follows.

$^1$H-NMR ($CDCl_3$) δ (ppm): 1.43-1.55 (m, 1H), 1.56-1.67 (m, 1H), 1.78-1.89 (m, 1H), 2.21-2.33 (m, 5H), 2.44-2.53 (m, 1H), 2.69 (tt, J=16.0, 3.6 Hz, 1H), 3.10 (dt, J=16.0, 2.8 Hz, 1H), 3.84 (S, 3H), 3.92-4.02 (m, 1H), 5.20 (t, J=8.4 Hz, 1H), 6.93 (brs, 1H), 6.98-7.06 (m, 4H), 7.23-7.28 (m, 3H), 7.72 (brs, 1H), 7.73 (d, J=2.4 Hz, 1H).

The physical properties of the optically active substance with a retention time of 33 minutes (Example 1035) are as follows.

$^1$H-NMR ($CDCl_3$) δ (ppm): 1.43-1.55 (m, 1H), 1.56-1.67 (m, 1H), 1.78-1.89 (m, 1H), 2.21-2.33 (m, 5H), 2.44-2.53 (m, 1H), 2.69 (tt, J=16.0, 3.6 Hz, 1H), 3.10 (dt, J=16.0, 2.8 Hz, 1H), 3.84 (S, 3H), 3.92-4.02 (m, 1H), 5.20 (t, J=8.4 Hz, 1H), 6.93 (brs, 1H), 6.98-7.06 (m, 4H), 7.23-7.28 (m, 3H), 7.72 (brs, 1H), 7.73 (d, J=2.4 Hz, 1H).

Example 1036 and Example 1037

Synthesis of (E)-(3S)-(4-fluorophenyl)-6-[3-methoxy-4-(4-methyl-1H-imidazol-1-yl)benzylidene]-(9S)-hexahydroindolizin-5-one and (E)-(3R)-(4-fluorophenyl)-6-[3-methoxy-4-(4-methyl-1H-imidazol-1-yl)benzylidene]-(9R)-hexahydroindolizin-5-one

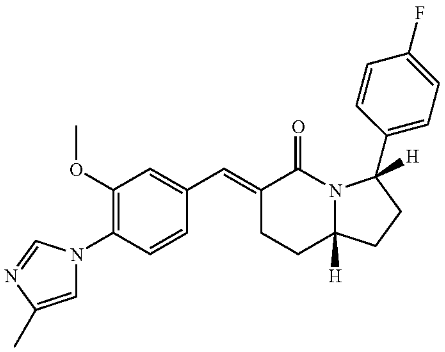

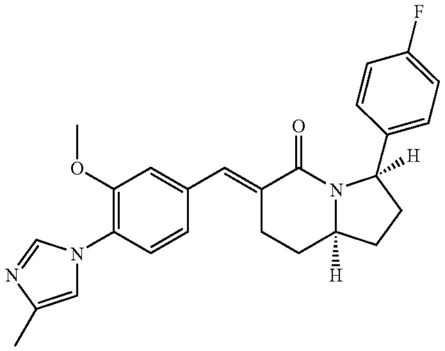

Synthesis of (E)-(3S*)-(4-fluorophenyl)-6-[3-methoxy-4-(4-methyl-1H-imidazol-1-yl)benzylidene]-(9S*)-hexahydroindolizin-5-one 43 mg of the title compound as a racemate was obtained from (3S*)-(4-fluorophenyl)-(9S*)-hexahydroindolizin-5-one (115 mg) in the same manner as in Example 1034. Properties data of the compound are as follows.

$^1$H-NMR ($CDCl_3$) δ (ppm): 1.72-1.88 (m, 3H), 2.05-2.11 (m, 1H), 2.27-2.37 (m, 5H), 2.70-2.81 (m, 1H), 3.15 (dt, J=16.8, 2.4 Hz, 1H), 3.76-3.84 (m, 1H), 3.85 (s, 3H), 5.21 (d, J=8.8 Hz, 1H), 6.94 (brs, 1H), 7.00 (t, J=8.8 Hz, 2H), 7.05 (d, J=1.2 Hz, 1H), 7.09 (dd, J=8.4, 1.2 Hz, 1H), 7.16 (dd, J=8.8, 5.2 Hz, 2H), 7.25 (d, J=8.4 Hz, 1H), 7.74 (s, 1H), 7.76 (d, J=2.0 Hz, 1H).

Synthesis of (E)-(3S)-(4-fluorophenyl)-6-[3-methoxy-4-(4-methyl-1H-imidazol-1-yl)benzylidene]-(9S)-hexahydroindolizin-5-one and (E)-(3R)-(4-fluorophenyl)-6-[3-methoxy-4-(4-methyl-1H-imidazol-1-yl)benzylidene]-(9R)-hexahydroindolizin-5-one (E)-(3S*)-(4-fluorophenyl)-6-(3-methoxy-4-(4-methyl-1H-imidazol-1-yl)benzylidene)-(9S*)-hexahydroindolizin-5-one as a racemate (30 mg) was fractionated using CHIRALPAK™ AD-H manufactured by Daicel Chemical Industries, Ltd. (2 cm×25 cm: mobile phase:hexane:ethanol=1:1) to obtain the title optically active substance with a retention time of 19 minutes (12.5 mg; >99% ee) and the title optically active substance with a retention time of 26 minutes (11.3 mg; >99% ee).

The physical properties of the optically active substance with a retention time of 19 minutes (Example 1036) are as follows.

$^1$H-NMR ($CDCl_3$) δ (ppm): 1.72-1.88 (m, 3H), 2.05-2.11 (m, 1H), 2.27-2.37 (m, 5H), 2.70-2.81 (m, 1H), 3.15 (dt, J=16.8, 2.4 Hz, 1H), 3.76-3.84 (m, 1H), 3.85 (s, 3H), 5.21 (d, J=8.8 Hz, 1H), 6.94 (brs, 1H), 7.00 (t, J=8.8 Hz, 2H), 7.05 (d, J=1.2 Hz, 1H), 7.09 (dd, J=8.4, 1.2 Hz, 1H), 7.16 (dd, J=8.8, 5.2 Hz, 2H), 7.25 (d, J=8.4 Hz, 1H), 7.74 (s, 1H), 7.76 (d, J=2.0 Hz, 1H).

The physical properties of the optically active substance with a retention time of 26 minutes (Example 1037) are as follows.

$^1$H-NMR ($CDCl_3$) δ (ppm): 1.72-1.88 (m, 3H), 2.05-2.11 (m, 1H), 2.27-2.37 (m, 5H), 2.70-2.81 (m, 1H), 3.15 (dt, J=16.8, 2.4 Hz, 1H), 3.76-3.84 (m, 1H), 3.85 (s, 3H), 5.21 (d, J=8.8 Hz, 1H), 6.94 (brs, 1H), 7.00 (t, J=8.8 Hz, 2H), 7.05 (d, J=1.2 Hz, 1H), 7.09 (dd, J=8.4, 1.2 Hz, 1H), 7.16 (dd, J=8.8, 5.2 Hz, 2H), 7.25 (d, J=8.4 Hz, 1H), 7.74 (s, 1H), 7.76 (d, J=2.0 Hz, 1H).

Example 1038

Synthesis of (E)-3-[2-fluoro-5-methoxy-4-(4-methyl-1H-imidazol-1-yl)benzylidene]-1-((1S)-(4-fluorophenyl)ethyl)piperidin-2-one

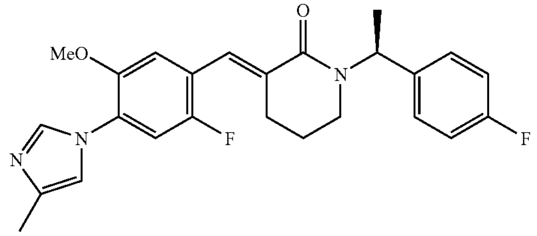

Synthesis of 2-fluoro-5-methoxy-4-(4-methyl-1H-imidazol-1-yl)benzonitrile

Zinc cyanide (4.05 g), tris(dibenzylideneacetone)dipalladium (527 mg) and 1,1'-bis(diphenylphosphino)ferrocene (638 mg) were added to a solution of 1-(4-bromo-5-fluoro-2-methoxyphenyl)-4-methyl-1H-imidazole (16.7 g) obtained in Example 18 in DMF (100 mL) at room temperature, and the reaction solution was stirred with heat in a nitrogen atmosphere at 120° C. for 7 hours. Further, zinc cyanide (4.05 g), tris(dibenzylideneacetone)dipalladium (527 mg) and 1,1'-bis(diphenylphosphino)ferrocene (638 mg) were added to the reaction solution, and the reaction solution was stirred with heat for 7 hours. After allowing the reaction solution to be cooled, concentrated aqueous ammonia and ethyl acetate were added to the reaction solution and the organic layer was partitioned. The resulting organic layer was washed with brine, and then dried over anhydrous magnesium sulfate and concentrated under reduced pressure. The residue was recrystallized from ethyl acetate to obtain 9.5 g of the title compound. Properties data of the compound are as follows.

$^1$H-NMR ($CDCl_3$) δ (ppm): 2.35 (s, 3H), 3.93 (s, 3H), 6.98 (s, 1H), 7.20 (d, J=8.8 Hz, 1H), 7.23 (d, J=5.6 Hz, 1H), 7.80 (s, 1H).

Synthesis of 2-fluoro-5-methoxy-4-(4-methyl-1H-imidazol-1-yl)benzaldehyde

Sodium bis(2-methoxyethoxy)aluminum hydride (65% solution in toluene, 11.4 mL) was added dropwise to a suspension of 2-fluoro-5-methoxy-4-(4-methyl-1H-imidazol-1-yl)benzonitrile (8.85 g) in THF (180 mL) in a nitrogen atmosphere at −15° C., and the reaction solution was stirred for 1 hour. Water was added to the reaction mixture, and the mixture was stirred at room temperature for 10 minutes. Then, a 5 N aqueous solution of sodium hydroxide and ethyl acetate were added to the mixture and the organic layer was partitioned. The resulting organic layer was made acidic with 5 N aqueous hydrochloric acid, and the mixture was stirred. Then, the mixture was neutralized with 5 N aqueous sodium hydroxide and the organic layer was partitioned. The organic layer was dried over anhydrous magnesium sulfate and concentrated under reduced pressure. The residue was purified by silica gel column chromatography (elution solvent:ethyl acetate) to obtain 3.32 g of the title compound. Properties data of the compound are as follows.

$^1$H-NMR ($CDCl_3$) δ (ppm): 2.30 (s, 3H), 3.94 (s, 3H), 7.00 (t, J=1.2 Hz, 1H), 7.14 (d, J=10 Hz, 1H), 7.49 (d, J=5.6 Hz, 1H), 7.88 (d, J=1.2 Hz, 1H), 10.35 (s, 1H).

Synthesis of (E)-5-chloro-2-[2-fluoro-5-methoxy-4-(4-methyl-1H-imidazol-1-yl)benzylidene]valeric acid trifluoroacetate Sodium hydride (containing mineral oil at 40%, 0.68 g) was added to a solution of tert-butyl 5-chloro-2-(diethoxyphosphoryl)valerate (5.59 g) in THF (50 mL) in a nitrogen atmosphere at room temperature, and the reaction solution was stirred at room temperature for 30 minutes. A solution of 2-fluoro-5-methoxy-4-(4-methyl-1H-imidazol-1-yl)benzaldehyde (3.19 g) in THF (10 mL) was added to the reaction mixture, and the reaction solution was stirred at room temperature for 4 hours. Water and ethyl acetate were added to the reaction mixture and the organic layer was partitioned. The organic layer was washed with brine, and then dried over anhydrous magnesium sulfate and concentrated under reduced pressure. The resulting residue was purified by silica gel chromatography (elution solvent:heptane-ethyl acetate system) to obtain tert-butyl (E)-5-chloro-2-(2-fluoro-5-methoxy-4-(4-methyl-1H-imidazol-1-yl)benzylidene)valerate (5.93 g). A solution of tert-butyl (E)-5-chloro-2-(2-fluoro-5-methoxy-4-(4-methyl-1H-imidazol-1-yl)benzylidene)valerate in trifluoroacetic acid (30 mL) was stirred while cooling with ice. After 2 hours, the reaction solution was concentrated under reduced pressure. Tert-butyl methyl ether was added to the resulting residue, and the resulting deposited solid was filtered to obtain 3 g of the title compound. Properties data of the compound are as follows.

$^1$H-NMR ($CDCl_3$) δ (ppm): 2.03-2.10 (m, 2H), 2.52 (s, 3H), 2.65-2.69 (m, 2H), 3.60 (t, J=6.4 Hz, 2H), 3.94 (s, 3H), 7.08 (d, J=6.4 Hz, 1H), 7.10 (t, J=1.6 Hz, 1H), 7.21 (d, J=8.8 Hz, 1H), 7.78 (s, 1H), 7.88 (d, J=2 Hz, 1H).

Synthesis of (E)-3-[2-fluoro-5-methoxy-4-(4-methyl-1H-imidazol-1-yl)benzylidene]-1-[(1S)-(4-fluorophenyl)ethyl]piperidin-2-one 0.57 g of the title compound was obtained from (E)-5-chloro-2-(2-fluoro-5-methoxy-4-(4-methyl-1H-imidazol-1-yl)benzylidene)valeric acid trifluoroacetate (1.0 g) and (S)-1-(4-fluorophenyl)ethylamine (447 mg) in the same manner as in Example 418. Properties data of the compound are as follows.

$^1$H-NMR ($CDCl_3$) δ: 1.56 (d, J=7.2 Hz, 3H), 1.65-1.74 (m, 1H), 1.78-1.87 (m, 1H), 2.30 (s, 3H), 2.62-2.66 (m, 2H), 2.91-2.96 (m, 1H), 3.22-3.28 (m, 1H), 3.83 (s, 3H), 6.23 (q, J=7.2 Hz, 1H), 6.92-6.93 (m, 2H), 7.01-7.06 (m, 3H), 7.30-7.35 (m, 2H), 7.75 (s, 1H), 7.84 (s, 1H).

Example 1039

Synthesis of (E)-1-[(4S)-chroman-4-yl]-3-[2-fluoro-5-methoxy-4-(4-methyl-1H-imidazol-1-yl)benzylidene]piperidin-2-one

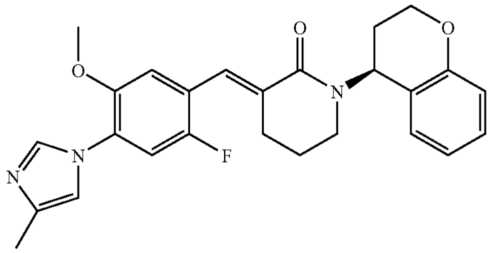

14 mg of the title compound was obtained from (E)-5-chloro-2-(2-fluoro-5-methoxy-4-(4-methyl-1H-imidazol-1-yl)-benzylidene)valeric acid trifluoroacetate (20 mg) and (4S)chroman-4-ylamine (10 mg) in the same manner as in Example 418. Properties data of the compound are as follows.

$^1$H-NMR ($CDCl_3$) δ (ppm): 1.70-1.90 (m, 2H), 2.12-2.25 (m, 2H), 2.30 (s, 3H), 2.64-2.80 (m, 2H), 3.07-3.13 (m, 1H), 3.05-3.14 (m, 1H), 3.85 (s, 3H), 4.22-4.28 (m, 1H), 4.35-4.39 (m, 1H), 6.23 (dd, J=6.4, 9.6 Hz, 1H), 6.84-6.96 (m, 4H), 7.05 (s, 1H), 7.08 (s, 1H), 7.15-7.19 (m, 1H), 7.76 (d, J=1.2 Hz, 1H), 7.87 (s, 1H).

Example 1040

Synthesis of (E)-1-[2,3-dihydrobenzo[1,4]dioxin-5-ylmethyl]-3-[2-fluoro-5-methoxy-4-(4-methyl-1H-imidazol-1-yl)benzylidene]piperidin-2-one

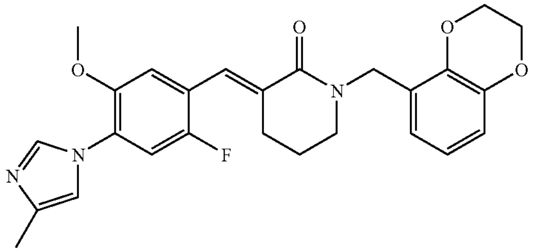

10 mg of the title compound was obtained from (E)-5-chloro-2-(2-fluoro-5-methoxy-4-(4-methyl-1H-imidazol-1-yl)benzylidene)valeric acid trifluoroacetate (20 mg) and 2,3-dihydro-1,4-benzodioxin-5-ylmethylamine hydrochloride (14 mg) in the same manner as in Example 418. Properties data of the compound are as follows.

$^1$H-NMR ($CDCl_3$) δ (ppm): 1.85-1.91 (m, 2H), 2.30 (s, 3H), 2.68 (t, J=6.4 Hz, 2H), 3.43 (t, J=6.0 Hz, 1H), 3.83 (s, 3H), 4.26-4.32 (m, 4H), 4.73 (s, 2H), 6.78-6.86 (m, 3H), 6.92 (d, J=6.4 Hz, 1H), 6.93 (s, 1H), 7.05 (d, J=9.6 Hz, 1H), 7.75 (d, J=1.2 Hz, 1H), 7.89 (s, 1H).

Example 1041

Synthesis of (E)-3-[2-fluoro-5-methoxy-4-(4-methyl-1H-imidazol-1-yl)benzylidene]-1-((1S)-phenylethyl)piperidin-2-one

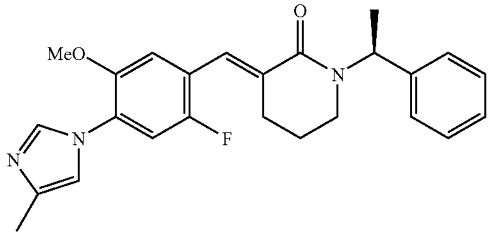

8 mg of the title compound was obtained from (E)-5-chloro-2-(2-fluoro-5-methoxy-4-(4-methyl-1H-imidazol-1-yl)-benzylidene)valeric acid trifluoroacetate (20 mg) and (S)-1-phenylethylamine (10 mg) in the same manner as in Example 418. Properties data of the compound are as follows.

$^1$H-NMR ($CDCl_3$) δ: 1.58 (d, J=7.2 Hz, 3H), 1.65-1.74 (m, 1H), 1.65-1.84 m, 3H), 2.32 (s; 3H), 2.62-2.65 (m, 2H), 2.92-2.98 (m, 1H), 3.22-3.28 (m, 1H), 3.84 (s, 3H), 6.25 (q, J=7.2 Hz, 1H), 6.93-6.95 (m, 2H), 6.25 (q, J=8.8 Hz, 1H), 7.26-7.36 (m, 5H), 7.84 (s, 1H).

Example 1042

Synthesis of (E)-3-[3-methoxy-4-(4-methyl-1H-imidazol-1-yl)benzylidene]-1-methyl-6-phenylpiperidin-2-one

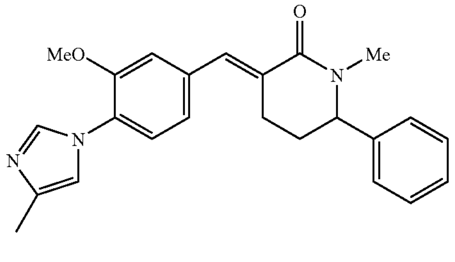

Lithium bis(trimethylsilyl)amide (1.0 M solution in THF, 1.59 mL) was added dropwise to a solution of 1-methyl-6-phenylpiperidin-2-one (200 mg) synthesized in accordance with a technique described in a document (see N. P. Baens et al., "Tetrahedron", 1993, vol. 49, pp. 3193-3202, for example) in THF (5 mL) at −78° C., and the reaction solution was stirred at room temperature for 30 minutes. This solution was added dropwise to a solution of 3-methoxy-4-(4-methyl-1H-imidazol-1-yl)benzaldehyde (248 mg) and a boron trifluoride-dimethyl ether complex (134 μL) in THF at −78° C., and the reaction solution was stirred overnight while heating to room temperature. A saturated aqueous solution of ammonium chloride and ethyl acetate were added to the reaction solution and the organic layer was partitioned. The organic layer was washed with brine, and then dried over anhydrous magnesium sulfate and concentrated under reduced pressure. The residue was purified by silica gel column chromatography (elution solvent:heptane-ethyl acetate system) to collect the part in which an aldol derivative eluted. The elution part was concentrated under reduced pressure. Methanesulfonyl chloride (33.9 mg), triethylamine (206 μL) and methylene chloride (25 mL) were added to the residue, and the reaction solution was stirred at room temperature for 3 days. Water and ethyl acetate were added to the reaction solution and the organic layer was partitioned. The organic layer was washed with brine, and then dried over anhydrous magnesium sulfate and concentrated under reduced pressure. The residue was purified by LC-MS to obtain 4.54 mg of the title compound. Properties data of the compound are as follows.

$^1$H-NMR ($CDCl_3$) δ: 1.94-2.01 (m, 1H), 2.24-2.33 (m, 1H), 2.29 (s, 3H), 2.53-2.62 (m, 1H), 2.73-2.79 (m, 1H), 3.02 (s, 3H), 3.84 (s, 3H), 4.67 (t, J=4.4 Hz, 1H), 6.92 (s, 1H), 6.93-7.02 (m, 2H), 7.21-7.23 (m, 2H), 7.29-7.36 (m, 2H), 7.38-7.44 (m, 2H), 7.71 (s, 1H), 7.90 (s, 1H).

ESI-MS; m/z388 [$M^+$+H].

Example 1043 and Example 1044

Synthesis of (E)-1-(4-fluorobenzyl)-3-[3-methoxy-4-(4-methyl-1H-imidazol-1-yl)benzylidene]-(6R and S)-methylpiperidin-2-one

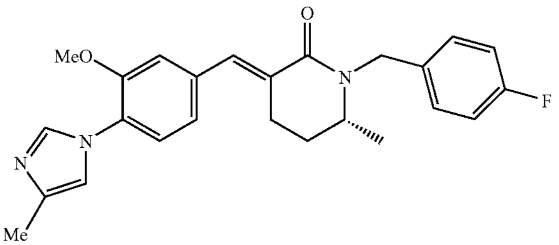

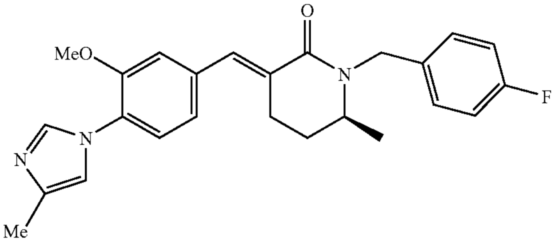

28.7 mg of the title compound as a racemate was obtained from 1-(4-fluorobenzyl)-6-methylpiperidin-2-one (198 mg) and 3-methoxy-4-(4-methyl-1H-imidazol-1-yl)benzaldehyde (194 mg) in the same manner as in Example 1042. The racemate (28.7 mg) was fractionated using CHIRALPAK™ AD-H manufactured by Daicel Chemical Industries, Ltd. (2 cm×25 cm: mobile phase:hexane:ethanol=60:40) to obtain the title optically active substance with a retention time of 29 minutes (Example 1043, 5.97 mg; >99% ee) and the title optically active substance with a retention time of 31 minutes (Example 1044, 6.76 mg; >95% ee). The physical properties of the optically active compounds are as follows.

ESI-MS; m/z420 [$M^+$+H]. $^1$H-NMR ($CDCl_3$) δ: 1.31 (d, J=6.8 Hz, 3H), 1.74-1.80 (m, 1H), 1.86-1.95 (m, 1H), 2.31 (s,

3H), 2.87-2.96 (m, 2H), 3.58-3.62 (m, 1H), 3.88 (s, 3H), 4.11 (d, J=14.8 Hz, 1H), 5.33 (d, J=14.8 Hz, 1H), 6.95 (s, 1H), 6.99-7.11 (m, 4H), 7.24-7.31 (m, 3H), 7.74 (s, 1H), 7.88 (s, 1H).

Example 1045, Example 1046, Example 1047 and Example 1048

Synthesis of (E)-1-(4-fluorobenzyl)-3-[3-methoxy-4-(4-methyl-1H-imidazol-1-yl)benzylidene]-(4R,6S)-dimethylpiperidin-2-one, (E)-1-(4-fluorobenzyl)-3-[3-methoxy-4-(4-methyl-1H-imidazol-1-yl)benzylidene]-(4S,6R)-dimethylpiperidin-2-one, (E)-1-(4-fluorobenzyl)-3-[3-methoxy-4-(4-methyl-1H-imidazol-1-yl)benzylidene]-(4S,6S)-dimethylpiperidin-2-one and (E)-1-(4-fluorobenzyl)-3-[3-methoxy-4-(4-methyl-1H-imidazol-1-yl)benzylidene]-(4R,6R)-dimethylpiperidin-2-one

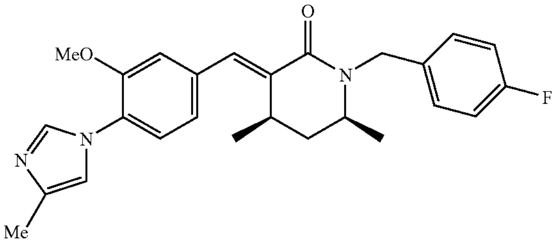

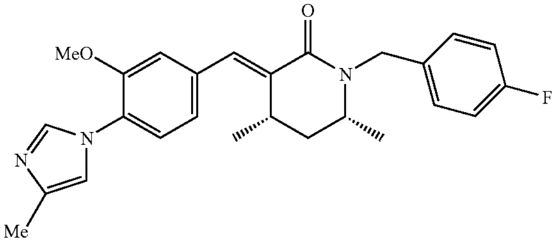

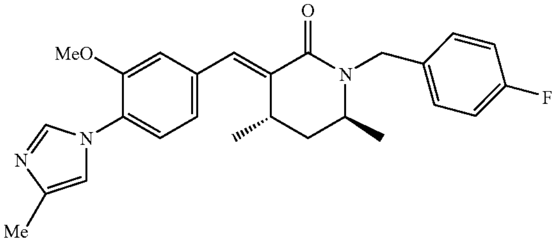

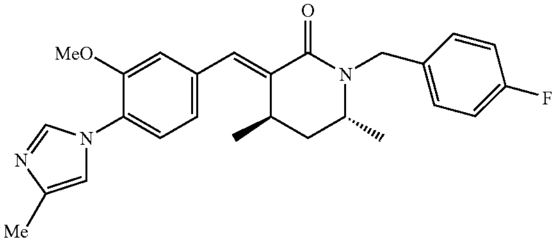

Synthesis of diethyl[1-(4-fluorobenzyl)-4,6-dimethyl-2-oxopiperidin-3-yl]phosphonate A solution of tert-butyl 2-diethoxyphosphoryl-3-methyl-5-oxohexanoate (500 mg) synthesized in accordance with a technique described in a document (see A. N. Pudovik et al., “Chemical Abstracts”, 1956, vol. 50, p. 2429, for example) and trifluoroacetic acid (5.0 mL) in chloroform (5.0 mL) was stirred at room temperature for 4 hours, and then concentrated under reduced pressure. 4-fluorobenzylamine (170 μL), acetic acid (512 μL), and sodium triacetoxyborohydride (947 mg) were added to a solution of the residue in THF (10 mL). The reaction solution was stirred at room temperature overnight, and further stirred with heat at 50° C. for 10 hours. Ethyl acetate and water were added to the reaction solution, and the solution was adjusted to about pH 8 with a 5 N aqueous solution of sodium hydroxide and the organic layer was partitioned. The organic layer was washed with brine, and then dried over anhydrous magnesium sulfate and concentrated under reduced pressure. The residue was purified by silica gel column chromatography (elution solvent:hexane-ethyl acetate system) to obtain 292.8 mg of the title compound as a low-polar diastereomer and 88.4 mg of the title compound as a high-polar diastereomer.

Properties data of the low-polar diastereomer are as follows.

ESI-MS; m/z372 $[M^++H]$. $^1H$-NMR ($CDCl_3$) δ: 1.17 (d, J=6.8 Hz, 3H), 1.20 (d, J=6.4 Hz, 3H), 1.33 (d, J=7.6 Hz, 3H), 1.37 (d, J=7.2 Hz, 3H) 1.95-2.01 (m, 1H), 2.32-2.48 (m, 1H), 2.80 (dd, J=26.8, 8.0 Hz, 1H), 3.54-3.62 (m, 1H), 4.14-4.26 (m, 4H), 4.38 (d, J=19.2 Hz, 1H), 4.44 (d, J=19.2 Hz, 1H), 5.39 (d, J=15.6 Hz, 1H), 6.97-7.04 (m, 2H), 7.23-7.31 (m, 2H).

Properties data of the high-polar diastereomer are as follows.

ESI-MS; m/z372 $[M^++H]$. $^1H$-NMR ($CDCl_3$) δ: 1.13 (d, J=6.8 Hz, 3H), 1.22 (d, J=6.4 Hz, 3H), 1.34 (d, J=6.8 Hz, 3H), 1.38 (d, J=6.8 Hz, 3H), 1.48-1.56 (m, 1H), 1.86-1.93 (m, 1H), 2.55-2.68 (m, 1H), 2.78 (dd, J=27.6, 6.0 Hz, 1H), 3.42-3.51 (m, 1H), 4.16-4.26 (m, 5H), 5.04 (d, J=14.8 Hz, 1H), 5.04 (d, J=14.8 Hz, 1H), 6.96-7.01 (m, 2H), 7.23-7.27 (m, 2H).

Synthesis of (E)-1-(4-fluorobenzyl)-3-[3-methoxy-4-(4-methyl-1H-imidazol-1-yl)benzylidene]-4,6-dimethylpiperidin-2-one Lithium hydroxide (175 mg) was added to a solution of low-polar diethyl[1-(4-fluorophenyl)-4,6-dimethyl-2-oxopiperidin-3-yl]phosphorate (292.8 mg) obtained as above and 3-methoxy-4-(4-methyl-1H-imidazol-1-yl)benzaldehyde (150 mg) in a mixture of THF (3.0 mL) with ethanol (1.0 mL), and the reaction solution was stirred at room temperature. After 1 hour, the reaction solution was diluted with water and ethyl acetate and the organic layer was partitioned. The resulting organic layer was washed with brine, dried over anhydrous magnesium sulfate, and then concentrated under reduced pressure. The residue was purified by silica gel column chromatography (Carrier: Chromatorex™ NH, elution solvent:hexane-ethyl acetate system) to obtain 309.5 mg of the title compound as a single diastereomer. The diastereomer was fractionated using CHIRALPAK™ AD-H manufactured by Daicel Chemical Industries, Ltd. (2 cm×50 cm; mobile phase: ethanol) to obtain an optically active substance with a retention time of 52 minutes (Example 1045, 36.8 mg; >99% ee) and an optically active substance with a retention time of 56 minutes (Example 1046, 15.3 mg; >85% ee). The physical properties of the optically active compounds are as follows.

ESI-MS; m/z434 $[M^++H]$. $^1H$-NMR ($CDCl_3$) δ: 1.35 (d, J=7.6 Hz, 3H), 1.41 (d, J=6.8 Hz, 3H), 1.64-1.70 (m, 1H), 2.11-2.18 (m, 1H), 2.32 (s, 3H), 3.34-3.41 (m, 1H), 3.57-3.66 (m, 1H), 3.86 (s, 3H), 4.33 (d, J=15.6 Hz, 1H), 5.26 (d, J=15.6 Hz, 1H), 6.95 (s, 1H), 6.99-7.08 (m, 5H), 7.24-7.28 (m, 2H), 7.75 (s, 1H), 7.76 (s, 1H).

Lithium hydroxide (52.5 mg) was added to a solution of high-polar diethyl[1-(4-fluorophenyl)-4,6-dimethyl-2-oxopiperidin-3-yl]phosphorate (88.4 mg) obtained as above and 3-methoxy-4-(4-methyl-1H-imidazol-1-yl)benzaldehyde (45 mg) in a mixture of THF (1.0 mL) with ethanol (0.3 mL), and the reaction solution was stirred at room temperature. After 1 hour, the reaction solution was diluted with water and ethyl acetate and the organic layer was partitioned. The resulting organic layer was washed with brine, dried over anhydrous magnesium sulfate, and then concentrated under reduced pressure. The residue was purified by silica gel column chromatography (Carrier: Chromatorex™ NH, elution solvent:hexane-ethyl acetate system) to obtain 102.8 mg of the title compound as a single diastereomer. The diastereomer was fractionated using CHIRALPAK™ AD-H manufactured by Daicel Chemical Industries, Ltd. (2 cm×50 cm; mobile phase: ethanol) to obtain an optically active substance with a retention time of 47 minutes (Example 1047, 41.5 mg; >97% ee) and an optically active substance with a retention time of 55 minutes (Example 1048, 45.4 mg; >86% ee). The physical properties of the optically active compounds are as follows.

ESI-MS; m/z434 $[M^++H]$. $^1$H-NMR ($CDCl_3$) δ: 1.19 (d, J=6.8 Hz, 3H), 1.22 (d, J=6.4 Hz, 3H), 1.76-1.81 (m, 2H), 2.35 (s, 3H), 3.22-3.32 (m, 1H), 3.58-3.64 (m, 1H), 3.87 (s, 3H), 4.32 (d, J=15.2 Hz, 1H), 5.31 (d, J=15.2 Hz, 1H), 6.96 (s, 1H), 7.00-7.06 (m, 5H), 7.25-7.31 (m, 2H), 7.68 (s, 1H), 7.86 (s, 1H).

Example 1049 and Example 1050

Synthesis of (E)-1-[(1S)-(4-fluorophenyl)ethyl]-3-[3-methoxy-4-(4-methyl-1H-imidazol-1-yl)benzylidene]-(6R and S)-methylpiperidin-2-one

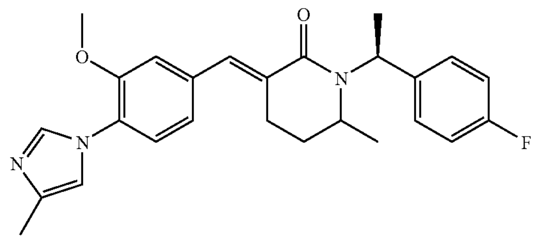

Synthesis of tert-butyl (E)-2-[3-methoxy-4-(4-methyl-1H-imidazol-1-yl)benzylidene]-5-oxohexanoate 5 N aqueous hydrochloric acid (1.0 mL) was added to a solution of tert-butyl 2-diethoxyphosphoryl-4-(2-methyl-[1,3]dioxolan-2-yl)butyrate (500 mg) synthesized in the same manner as in Example 425 in THF (5.0 mL), and the reaction solution was stirred at room temperature for 6 hours. Water and ethyl acetate were added to the reaction solution and the organic layer was partitioned. The organic layer was washed with brine, and then dried over anhydrous magnesium sulfate and concentrated under reduced pressure. 3-methoxy-4-(4-methyl-1H-imidazol-1-yl)benzaldehyde (278 mg) and lithium hydroxide (93 mg) were added to a solution of the residue in a mixture of THF (6.0 mL) with ethanol (2.0 mL), and the reaction solution was stirred at room temperature overnight. Water and ethyl acetate were added to the reaction solution and the organic layer was partitioned. The resulting organic layer was washed with brine, dried over anhydrous magnesium sulfate, and then concentrated under reduced pressure. The residue was purified by silica gel column chromatography (elution solvent:hexane-ethyl acetate system) to obtain 250 mg of the title compound.

ESI-MS; m/z385 $[M^++H]$. $^1$H-NMR ($CDCl_3$) δ: 1.56 (s, 9H), 2.17 (s, 3H), 2.31 (s, 3H), 2.68-2.72 (m, 2H), 2.76-2.81 (m, 2H), 3.87 (s, 3H), 6.94 (s, 1H), 6.98 (d, J=8.0 Hz, 1H), 7.02 (s, 1H), 7.26 (d, J=8.0 Hz, 1H), 7.58 (s, 1H), 7.74 (s, 1H).

Synthesis of (E)-1-[(1S)-(4-fluorophenyl)ethyl]-3-[3-methoxy-4-(4-methyl-1H-imidazol-1-yl)benzylidene]-(6S and R)-methylpiperidin-2-one (1S)-(4-fluorophenyl)ethylamine (90.5 mg), acetic acid (223 μL) and sodium triacetoxyborohydride (413 mg) were added to a solution of tert-butyl (E)-2-(3-methoxy-4-(4-methyl-1H-imidazol-1-yl)benzylidene)-5-oxohexanoate (250 mg) in THF (5.0 mL), and the reaction solution was stirred at room temperature overnight. Water and ethyl acetate were added to the reaction solution, and the reaction solution was adjusted to about pH 8 with a 5 N aqueous solution of sodium hydroxide and the organic layer was partitioned. The organic layer was concentrated under reduced pressure, and then the residue was purified by silica gel column. chromatography (elution solvent:chloroform-methanol system) to obtain 224 mg of an amino derivative. Trifluoroacetic acid (2.0 mL) was added to a solution of the amino derivative in chloroform (1.0 mL), and the reaction solution was stirred at room temperature for 6 hours. IPEA (167 μL), EDC (137 mg) and HOBT (132 mg) were sequentially added to a solution of the residue obtained by concentrating the reaction solution under reduced pressure in DMF (20 mL), and the reaction solution was stirred at room temperature for 5.5 hours. Water and ethyl acetate were added to the reaction solution and the organic layer was partitioned. The resulting organic layer was washed with brine, and then dried over anhydrous magnesium sulfate and concentrated under reduced pressure. The residue was purified by silica gel column chromatography (Carrier: Chromatorex™ NH, elution solvent:hexane-ethyl acetate system) to obtain 68.5 mg of the title compound as a racemate. The racemate (68.5 mg) was fractionated using CHIRALPAK™ IA manufactured by Daicel Chemical Industries, Ltd. (2 cm×25 cm: mobile phase:hexane:ethanol=50:50) to obtain the title optically active substance with a retention time of 28 minutes (Example 1049, 19.9 mg; >99% de) and the title optically active substance with a retention time of 31 minutes (Example 1050, 23.44 mg; >91% de).

Title optically active substance with a retention time of 28 minutes (Example 1049)

$^1$H-NMR ($CDCl_3$) δ: 0.74 (d, J=6.8 Hz, 3H), 1.61 (d, J=7.2 Hz, 3H), 1.78-1.91 (m, 2H), 2.34 (s, 3H), 2.85-2.88 (m, 2H), 3.68-3.71 (m, 1H), 3.87 (s, 3H), 5.99 (q, J=7.2 Hz, 1H), 6.96 (s, 1H), 6.99-7.07 (m, 2H), 7.10 (s, 1H), 7.14 (d, J=8.4 Hz, 1H), 7.27 (d, J=8.4 Hz, 1H), 7.38-7.42 (m, 2H), 7.81 (s, 1H), 7.84 (s, 1H).

ESI-MS; m/z434 $[M^++H]$.

Title optically active substance with a retention time of 31 minutes (Example 1050)

ESI-MS; m/z434 $[M^++H]$. $^1$H-NMR ($CDCl_3$) δ: 1.31 (d, J=6.8 Hz, 3H), 1.52-1.69 (m, 2H), 1.64 (d, J=7.6 Hz, 3H), 2.34 (s, 3H), 2.79-3.00 (m, 2H), 3.40-3.45 (m, 1H), 3.88 (s, 3H), 6.13 (q, J=7.6 Hz, 1H), 6.96 (s, 1H), 7.00-7.07 (m, 2H), 7.12 (s, 1H), 7.15 (d, J=8.0 Hz, 1H), 7.27 (d, J=8.0 Hz, 1H), 7.33-7.37 (m, 2H), 7.81 (s, 1H), 7.83 (s, 1H).

Example 1051 and Example 1052

Synthesis of (Z)-[(R) and (S)-chroman-4-yl]-2-[3-methoxy-4-(4-methyl-1H-imidazol-1-yl)benzylidene]morpholin-3-one

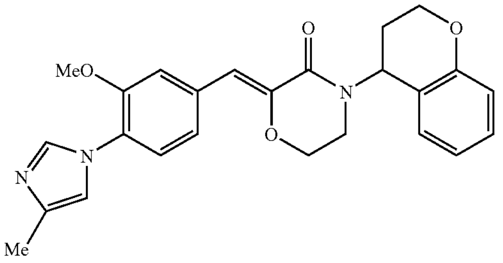

8.49 mg of the title compound as a racemate was obtained from 4-chroman-4-yl-morpholin-3-one (200 mg) synthesized in accordance with a technique described in a document (see T. Morie et al., "J. Heterocycles", 1994, vol. 38, p. 1033, for example) and 3-methoxy-4-(4-methyl-1H-imidazol-1-yl) benzaldehyde (185 mg) in the same manner as in Example 1042. The racemate (8.49 mg) was fractionated using CHIRALPAK™ AD-H manufactured by Daicel Chemical Industries, Ltd. (2 cm×25 cm: mobile phase: ethanol) to obtain the title optically active substance with a retention time of 23 minutes (Example 1051, 1.47 mg; >99% ee) and the title optically active substance with a retention time of 31 minutes (Example 1052, 1.72 mg; >99% ee). The physical properties of the optically active compounds are as follows.

ESI-MS; m/z432 [$M^+$+H]. $^1$H-NMR ($CDCl_3$) δ: 2.17-2.22 (m, 2H), 2.32 (s, 3H), 3.21-3.26 (m, 1H), 3.43-3.49 (m, 1H), 3.87 (s, 3H), 4.16-4.28 (m, 3H), 4.32-4.35 (m, 1H), 6.13 (t, J=8.4 Hz, 1H), 6.87 (d, J=7.6 Hz, 1H), 6.91-6.95 (m, 3H), 7.07 (d, J=7.6 Hz, 1H), 7.19 (t, J=7.6 Hz, 1H), 7.22 (d, J=8.0 Hz, 1H), 7.39-7.44 (m, 2H), 7.77 (s, 1H).

Example 1053

Synthesis of (Z)-4-[(1S)-(4-fluorophenyl)ethyl]-2-[3-methoxy-4-(4-methyl-1H-imidazol-1-yl)benzylidene]morpholin-3-one

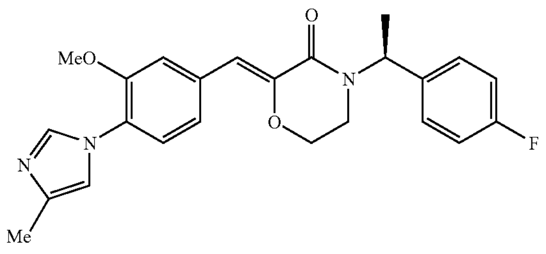

1.4 mg of the title compound was obtained from 4-((1S)-(4-fluorophenyl)ethyl)morpholin-3-one (200 mg) synthesized in accordance with a technique described in a document (see T. Morie et al., "J. Heterocycles", 1994, vol. 38, p. 1033, for example) and 3-methoxy-4-(4-methyl-1H-imidazol-1-yl) benzaldehyde (194 mg) in the same manner as in Example 1042. Properties data of the compound are as follows.

ESI-MS; m/z422 [$M^+$+H]. $^1$H-NMR ($CDCl_3$) δ: 1.58 (d, J=7.6 Hz, 3H), 2.30 (s, 3H), 3.05-3.11 (m, 1H), 3.44-3.50 (m, 1H), 3.86 (s, 3H), 4.04-4.09 (m, 1H), 4.20-4.25 (m, 1H), 6.14 (q, J=7.6 Hz, 1H), 6.91 (s, 1H), 6.93 (s, 1H), 7.04-7.08 (m, 2H), 7.21 (d, J=88.0 Hz, 1H), 7.32-7.41 (m, 4H), 7.73 (s, 1H).

(Z)-4-[(1S)-(4-fluorophenyl)ethyl]-2-[3-methoxy-4-(4-methyl-1H-imidazol-1-yl)benzylidene]morpholin-3-one can also be separately synthesized by the following method.

Synthesis of (Z)-4-[(1S)-(4-fluorophenyl)ethyl]-2-[3-methoxy-4-(4-methyl-1H-imidazol-1-yl)benzylidene]morpholin-3-one

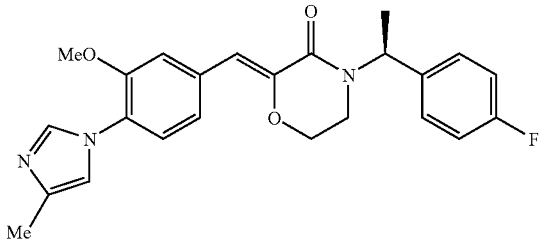

Synthesis of tert-butyl (Z)-2-(2-chloroethoxy)-3-[3-methoxy-4-(4-methyl-1H-imidazol-1-yl)phenyl] acrylate Lithium hydroxide (52.1 mg) was added to a solution of tert-butyl 2-chloroethoxy-(diethoxyphosphoryl)acetate (240 mg) synthesized by a technique described in a document (see C. J. Moody et al., "Tetrahedron", 1992, vol. 48, p. 3991, for example) and 3-methoxy-4-(4-methyl-1H-imidazol-1-yl) benzaldehyde (173 mg) in a mixture of THF (5.0 mL) with ethanol (1.0 mL), and the reaction solution was stirred at room temperature for 2.5 hours. Water and ethyl acetate were added to the reaction solution and the organic layer was partitioned. The resulting organic layer was washed with brine, dried over anhydrous magnesium sulfate, and then concentrated under reduced pressure. The residue was purified by silica gel column chromatography (Carrier: Chromatorex™ NH, elution solvent:heptane-ethyl acetate system) to obtain 51 mg of the title compound.

ESI-MS; m/z393 [$M^+$+H]. $^1$H-NMR ($CDCl_3$) δ: 1.58 (s, 9H), 2.30 (s, 3H), 3.79 (t, J=5.2 Hz, 2H), 3.90 (s, 3H), 4.25 (t, J=5.2 Hz, 2H) 6.89 (s, 1H), 6.96 (s, 1H), 7.24 (d, J=8.4 Hz, 1H), 7.32 (dd, J=8.4, 2.0 Hz, 1H), 7.64 (d, J=2.0 Hz, 1H), 7.76 (s, 1H).

Synthesis of (Z)-4-[(1S)-(4-fluorophenyl)ethyl]-2-[3-methoxy-4-(4-methyl-1H-imidazol-1-yl)benzylidene]morpholin-3-one 44.3 mg of the title compound was obtained from tert-butyl (Z)-2-(2-chloroethoxy)-3-(3-methoxy-4-(4-methyl-1H-imidazol-1-yl)phenyl)acrylate (51 mg) obtained as above and (S)-1-(4-fluorophenyl)ethylamine (26.3 μL) in the same manner as in Example 418. Properties data of the compound are as follows.

ESI-MS; m/z422 [$M^+$+H]. $^1$H-NMR ($CDCl_3$) δ: 1.58 (d, J=7.6 Hz, 3H), 2.30 (s, 3H), 3.05-3.11 (m, 1H), 3.44-3.50 (m, 1H), 3.86 (s, 3H), 4.04-4.09 (m, 1H), 4.20-4.25 (m, 1H), 6.14 (q, J=7.6 Hz, 1H), 6.91 (s, 1H), 6.93 (s, 1H), 7.04-7.08 (m, 2H), 7.21 (d, J=8.0 Hz, 1H), 7.32-7.41 (m, 4H), 7.73 (s, 1H).

Example 1054

Synthesis of (E)-1-[(1S)-(4-fluorophenyl)ethyl]-3-[3-methoxy-4-(4-methyl-1H-imidazol-1-yl)benzylidene]pyrrolidin-2-one

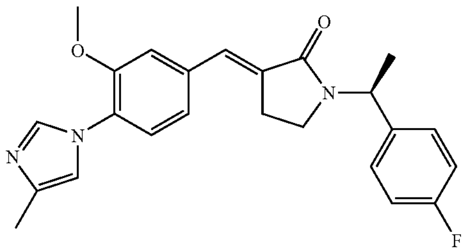

Synthesis of diethyl {1-[(1S)-(4-fluorophenyl)ethyl]-2-oxo-pyrrolidin-3-yl}phosphonate A mixture of 3-bromo-1-((1S)-(4-fluorophenyl)ethyl)pyrrolidin-2-one (117 mg) synthesized in accordance with the method described in Journal of Medicinal Chemistry, 1987, vol. 30, p. 1995 with triethyl phosphite (0.71 mL) was stirred at 150° C. for 2 hours. The reaction solution was allowed to be cooled to room temperature, and concentrated under reduced pressure. The resulting residue was purified by silica gel column chromatography (elution solvent:ethyl acetate: methanol=9:1) to obtain 60 mg of the title compound. Properties data of the compound are as follows.

ESI-MS; m/z344 $[M^{+}+H]$

Synthesis of (E)-1-[(1S)-(4-fluorophenyl)ethyl]-3-[3-methoxy-4-(4-methyl-1H-imidazol-1-yl)benzylidene]pyrrolidin-2-one Lithium hydroxide monohydrate (12.5 mg) was added to a solution of 3-methoxy-4-(4-methyl-1H-imidazol-1-yl)benzaldehyde (21 mg) obtained in Example 1 and diethyl (1-((1S)-(4-fluorophenyl)ethyl)-2-oxopyrrolidin-3-yl)phosphonate (34 mg) in a mixture of THF (2 mL) and ethanol (0.4 mL), and the reaction solution was stirred at room temperature for 14 hours. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent:heptane:ethyl acetate=1:1→ethyl acetate) to obtain 26 mg of the title compound. Properties data of the compound are as follows.

$^{1}H$-NMR ($CDCl_3$) δ (ppm): 1.60 (d, J=7.2 Hz, 3H), 2,30 (s, 3H), 2.92-3.15 (m, 3H), 3.44-3.51 (m, 1H), 3.87 (s, 3H), 5.68 (q, J=7.2 Hz, 1H), 6.93 (brs, 1H), 7.00-7.05 (m, 2H), 7.09 (d, J=1.6 Hz, 1H), 7.12 (dd, J=8.0, 1.6 Hz, 1H), 2.78 (d, J=8.0 Hz, 1H), 7.30-7.34 (m, 2H), 7.37 (t, J=2.8 Hz, 1H), 7.73 (d, J=1.2 Hz, 1H).

Example 1055 and Example 1056

Synthesis of (E) and (Z)-3-fluoro-N-(indan-1-yl)-3-[3-methoxy-4-(4-methyl-1H-imidazol-1-yl)phenyl]-2-methylacrylamide

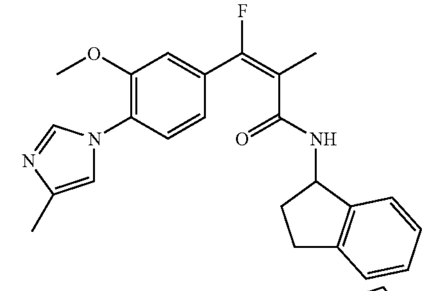

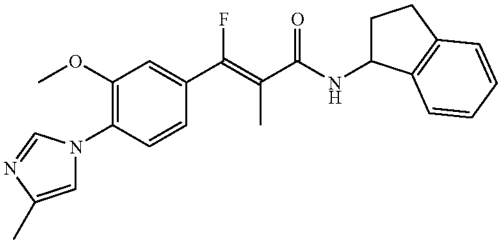

Synthesis of methyl 3-fluoro-3-[3-methoxy-4-(4-methyl-1H-imidazol-1-yl)phenyl]-2-methylacrylate Diethyl (fluoro-(3-methoxy-4-(4-methyl-1H-imidazol-1-yl)phenyl)methyl)phosphonate (1.1 g) was obtained from 3-methoxy-4-(4-methyl-1H-imidazol-1-yl)benzaldehyde (1 g) in accordance with the method described in Tetrahedron Letters, 1996, vol. 37, no. 5, p. 629. Lithium diisopropylamide (1.5 M solution in THF, 0.25 mL) was added to a solution of the resulting diethyl (fluoro-(3-methoxy-4-(4-methyl-1H-imidazol-1-yl)phenyl)methyl)phosphonate (110 mg) in THF at −78° C., and the reaction solution was stirred at −78° C. for 2 hours. Methyl pyruvate (32 mg) was added to the reaction solution at −78° C. The reaction solution was stirred at −78° C. for 15 minutes, and then further stirred at room temperature for 45 minutes. Saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (elution solvent:heptane: ethyl acetate=1:1→ethyl acetate) to obtain 39 mg of methyl 3-fluoro-3-(3-methoxy-4-(4-methyl-1H-imidazol-1-yl)phenyl)-2-methylacrylate as a mixture of isomers (E) and (Z). Properties data of the compounds are as follows.

ESI-MS; m/z305 $[M^{+}+H]$. $^{1}H$-NMR ($CDCl_3$) δ (ppm): 2.02 (d, J=3.2 Hz, 1.5H), 2.07 (d, J=4.0 Hz, 1.5H), 2.31 (s, 3H), 3.66 (s, 1.5H), 3.86 (s, 1.5H), 3.87 (s, 1.5H), 3.89 (s, 1.5H), 6.96 (s, 1H), 7.09 (brd, J=8.8 Hz, 0.5H), 7.13 (brs, 1H), 7.16 (brd, J=8.8 Hz, 0.5H), 1.18 (brs, 1H), 7.26 (d, J=8.8 Hz, 0.5H), 7.31 (d, J=8.8 Hz, 0.5H), 7.77 (brs, 1H).

Synthesis of (E) and (Z)-3-fluoro-N-indan-1-yl-3-[3-methoxy-4-(4-methyl-1H-imidazol-1-yl)phenyl]-2-methylacrylamide A 1 N aqueous solution of sodium hydroxide (1.3 mL) was added to a solution of methyl 3-fluoro-3-(3-methoxy-4-(4- methyl-1H-imidazol-1-yl)phenyl)-2-methylacrylate (39 mg) in methanol (3 mL), and the reaction solution was stirred at room temperature for 18 hours. 5 N hydrochloric acid (0.26 mL) was added to the reaction solution, and the solution was concentrated under reduced pressure. IPEA (0.09 mL) was added to a solution of the resulting residue in DMF (5 mL). Further, 1-aminoindan (0.032 mL), HOBT (34.5 mg) and EDC (49 mg) were sequentially added thereto. The reaction solution was stirred at room temperature for 3 hours, and saturated sodium bicarbonate water and ethyl acetate were added to the reaction solution and the organic layer was partitioned. The resulting organic layer was dried over magnesium sulfate, and concentrated under reduced pressure. The residue was purified by silica gel column chromatography (Carrier: Chromatorex™ NH, elution solvent:heptane:ethyl acetate=1:1→ethyl acetate) to obtain 16.8 mg of an isomer (E) of the title compound and 21.9 mg of an isomer (Z) of the title compound. Properties data of the compounds are as follows.

(E)-3-fluoro-N-(indan-1-yl)-3-(3-methoxy-4-(4-methyl-1H-imidazol-1-yl)phenyl)-2-methylacrylamide (Example 1055)

$^1$H-NMR ($CDCl_3$) δ (ppm): 1.52-1.63 (m, 1H), 2.11 (d, J=3.2 Hz, 3H), 2.33 (s, 3H), 2.45-2.54 (m, 1H), 2.80 (t, J=6.8 Hz, 2H), 3.86 (s, 3H), 5.40 (q, J=3.2 Hz, 1H), 5.55 (d, J=8.4 Hz, 1H), 6.87 (d, J=7.2 Hz, 1H), 6.93 (brs, 1H), 7.06-7.29 (m, 7H).

(Z)-3-fluoro-N-(indan-1-yl)-3-(3-methoxy-4-(4-methyl-1H-imidazol-1-yl)phenyl)-2-methylacrylamide (Example 1056)

$^1$H-NMR ($CDCl_3$) δ (ppm): 1.87-1.97 (m, 1H), 2.08 (d, J=2.8 Hz, 3H), 2.30 (s, 3H), 2.65-2.74 (m, 1H), 2.88-2.97 (m, 1H), 2.99-3.08 (m, 1H), 3.87 (s, 3H), 5.64 (q, J=2.8 Hz, 1H), 6.59 (t, J=8.4 Hz, 1H), 6.94 (brs, 1H), 7.11-7.40 (m, 7H), 7.74 (brs, 1H).

The compounds shown in Tables 27 and 28 were synthesized as in Example 418. The structural formulae and physical properties are shown in Table 27 and 28, respectively. The separation conditions in the notes to the table are as follows:

Separation Condition A: CHIRALPAK™ AD-H available from Daicel Chemical Industries, Ltd. (2 cm×25 cm: mobile phase:hexane-ethanol system)

Separation Condition B: CHIRALCEL™ OJ-H available from Daicel Chemical Industries, Ltd. (2 cm×25 cm: mobile phase:hexane-ethanol)

Separation Condition C: CHIRALCEL™ OD-H available from Daicel Chemical Industries, Ltd. (2 cm×25 cm: mobile phase; hexane-ethanol)

Separation Condition D: CHIRALCEL™ IA available from Daicel Chemical Industries, Ltd. (2 cm×25 cm: mobile phase; hexane-ethanol)

Separation Condition E: CHIRALCEL™ OD available from Daicel Chemical Industries, Ltd. (2 cm×25 cm: mobile phase; hexane-ethanol)

TABLE 27

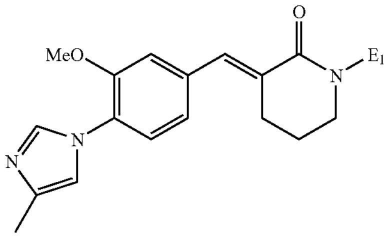

| Example | $E_1$ | DATA: MS m/z | Note |
|---|---|---|---|
| 1057 | 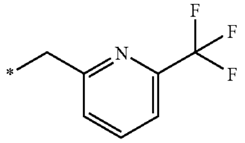 | $M^+$ + H:457(ESI) | |
| 1058 | 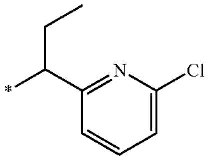 | $M^+$ + H:451(ESI) | |
| 1059 | 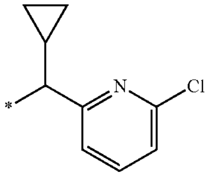 | $M^+$ + H:463(ESI) | |

TABLE 27-continued
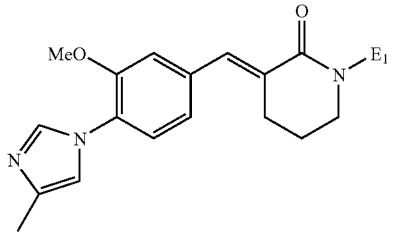
| Example | $E_1$ | DATA: MS m/z | Note |
|---|---|---|---|
| 1060 | 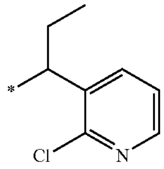 | $M^+$ + H:451(ESI) | |
| 1061 | 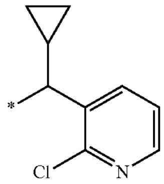 | $M^+$ + H:463(ESI) | |
| 1062 | 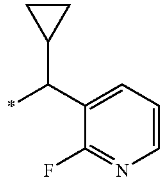 | $M^+$ + H:447(ESI) | |
| 1063 | 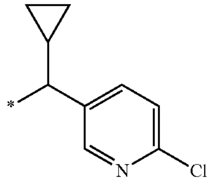 | $M^+$ + H:463(ESI) | |
| 1064 | 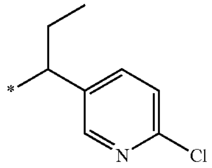 | $M^+$ + H:451(ESI) | |
| 1065 | 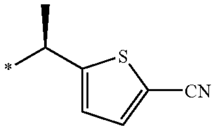 | $M^+$ + H:433(ESI) | optically active substance (separation condition E: retention time: 48 minutes; absolute configuration: unknown) |
| 1066 | 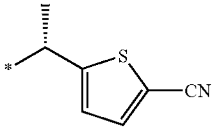 | $M^+$ + H:433(ESI) | optically active substance (separation condition E: retention time: 55 minutes: absolute configuration: unknown) |

TABLE 27-continued

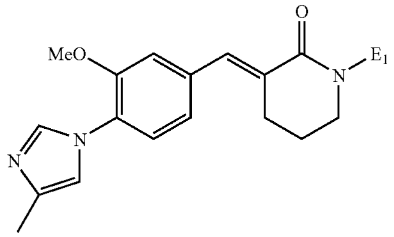

| Example | $E_1$ | DATA: MS m/z | Note |
|---|---|---|---|
| 1067 | 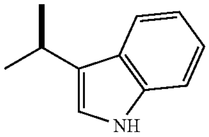 | $M^+$ + H:441(ESI) | optically active substance (separation condition A: retention time: 5.1 minutes; absolute configuration: unknown) |
| 1068 | 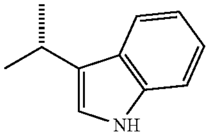 | $M^+$ + H:441(ESI) | optically active substance (separation condition A: retention time: 7.3 minutes; absolute configuration: unknown) |
| 1069 | 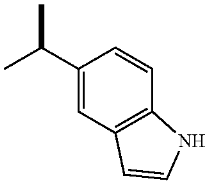 | $M^+$ + H:441(ESI) | optically active substance (separation condition C: retention time: 16.1 minutes; absolute configuration: unknown) |
| 1070 | 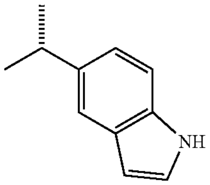 | $M^+$ + H:441(ESI) | optically active substance (separation condition C: retention time: 19.2 minutes; absolute configuration: unknown) |
| 1071 | 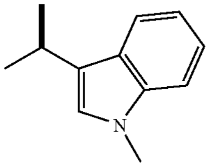 | $M^+$ + Na:477(ESI) | optically active substance (separation condition C: retention time: 13.6 minutes; absolute configuration: unknown) |
| 1072 | 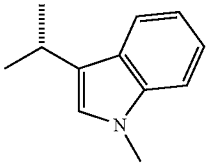 | $M^+$ + Na:477(ESI) | optically active substance (separation condition C: retention time: 15.9 minutes; absolute configuration: unknown) |
| 1073 | 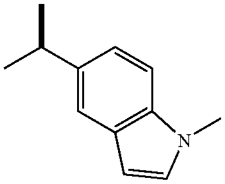 | $M^+$ + H:455(ESI) | optically active substance (separation condition D: retention time: 8.9 minutes; absolute configuration: unknown) |

TABLE 27-continued

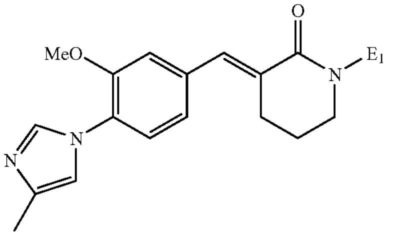

| Example | $E_1$ | DATA: MS m/z | Note |
|---|---|---|---|
| 1074 | 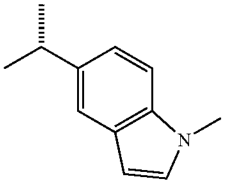 | $M^+$ + H:45 5(ESI) | optically active substance (separation condition D: retention time: 11.5 minutes; absolute configuration: unknown) |
| 1075 | 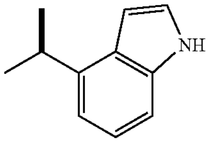 | $M^+$ + Na:4 5(ESI) | optically active substance (separation condition C: retention time: 13.3 minutes; absolute configuration: unknown) |
| 1076 | 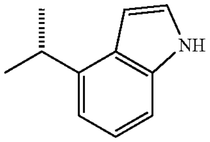 | $M^+$ + Na:4 63(ESI) | optically active substance (separation condition C: retention time: 16.5 minutes; absolute configuration: unknown) |
| 1077 | 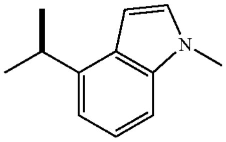 | $M^+$ + Na:4 77(ESI) | optically active substance (separation condition D: retention time: 8.4 minutes; absolute configuration: unknown) |
| 1078 | 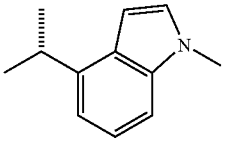 | $M^+$ + Na:4 77(ESI) | optically active substance (separation condition D; retention time: 10.5 minutes; absolute configuration: unknown) |
| 1079 | 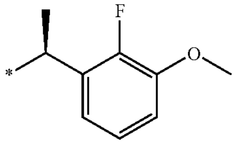 | $M^+$ + H:45 0(ESI) | optically active substance |
| 1080 | 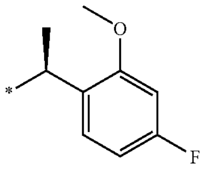 | $M^+$ + H:45 0(ESI) | optically active substance |
| 1081 | 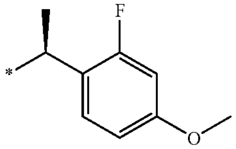 | $M^+$ + H:45 0(ESI) | optically active substance |

TABLE 27-continued
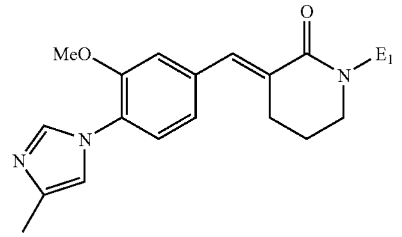
| Example | $E_1$ | DATA: MS m/z | Note |
|---|---|---|---|
| 1082 | 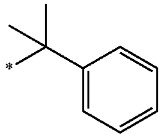 | $M^+$ + H:416(ESI) | |
| 1083 | 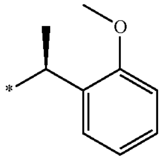 | $M^+$ + H:432(ESI) | optically active substance |
| 1084 | 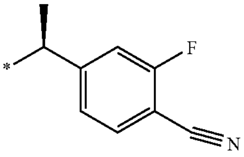 | $M^+$ + H:445(ESI) | optically active substance |
| 1085 | 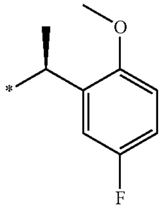 | $M^+$ + H:450(ESI) | optically active substance |
| 1086 | 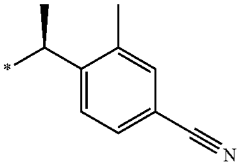 | $M^+$ + H:441(ESI) | optically active substance |
| 1087 | 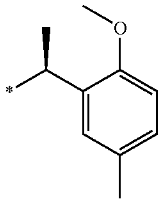 | $M^+$ + H:446(ESI) | optically active substance |
| 1088 | 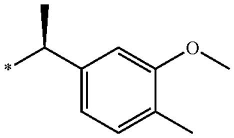 | $M^+$ + H:446(ESI) | optically active substance |

TABLE 27-continued

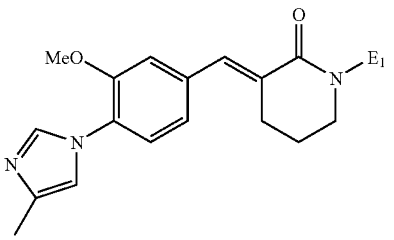

| Example | $E_1$ | DATA: MS m/z | Note |
|---|---|---|---|
| 1089 | 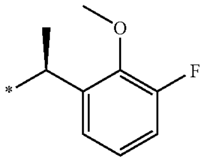 | $M^+$ + H:450(ESI) | optically active substance |
| 1090 | 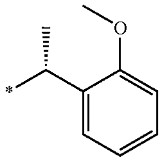 | $M^+$ + H:432(ESI) | optically active substance |
| 1091 | 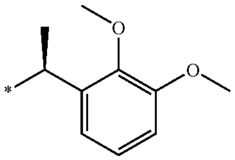 | $M^+$ + H:463(ESI) | optically active substance |
| 1092 | 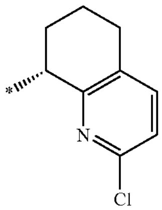 | $M^+$ + H:460(ESI) | optically active substance (separation condition C: retention time: 15.9 minutes; absolute configuration: unknown) |
| 1093 | 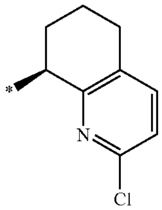 | $M^+$ + H:463(ESI) | optically active substance (separation condition C: retention time: 19.7 minutes; absolute configuration: unknown) |
| 1094 | 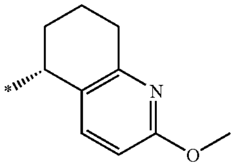 | $M^+$ + H:459(ESI) | optically active substance (separation condition C: retention time: 7.5 minutes; absolute configuration: unknown) |
| 1095 | 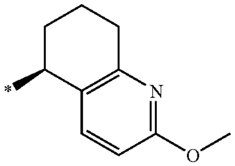 | $M^+$ + H:459(ESI) | optically active substance (separation condition A: retention time: 8.5 minutes; absolute configuration: unknown) |

TABLE 27-continued

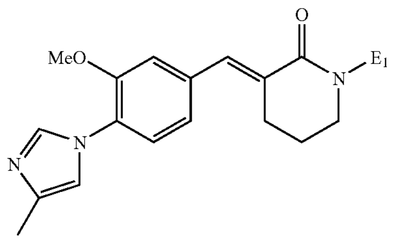

| Example | $E_1$ | DATA: MS m/z | Note |
|---|---|---|---|
| 1096 | 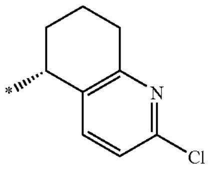 | $M^+ + H$:463(ESI) | optically active substance (separation condition C: retention time: 15.8 minutes; absolute configuration: unknown) |
| 1097 | 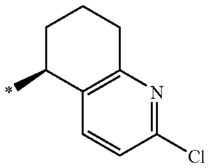 | $M^+ + H$:463(ESI) | optically active substance (separation condition C: retention time: 18.5 minutes; absolute configuration: unknown) |
| 1098 | 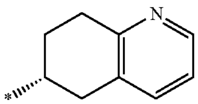 | $M^+ + H$:429(ESI) | optically active substance (separation condition B: retention time: 5.4 minutes; absolute configuration: unknown) |
| 1099 | 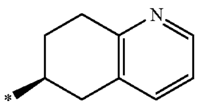 | $M^+ + H$:429(ESI) | optically active substance (separation condition B: retention time: 6.6 minutes; absolute configuration: unknown) |
| 1100 | 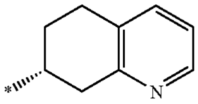 | $M^+ + H$:429(ESI) | optically active substance (separation condition C: retention time: 7.6 minutes; absolute configuration: unknown) |
| 1101 | 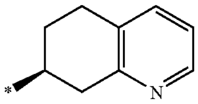 | $M^+ + H$:429(ESI) | optically active substance (separation condition C: retention time: 8.9 minutes; absolute configuration: unknown) |
| 1102 | 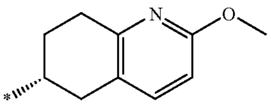 | $M^+ + H$:459(ESI) | optically active substance (separation condition B: retention time: 5.8 minutes; absolute configuration: unknown) |
| 1103 | 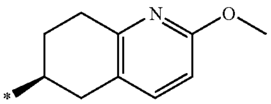 | $M^+ + H$:459(ESI) | optically active substance (separation condition B: retention time: 7.8 minutes; absolute configuration: unknown) |

TABLE 27-continued

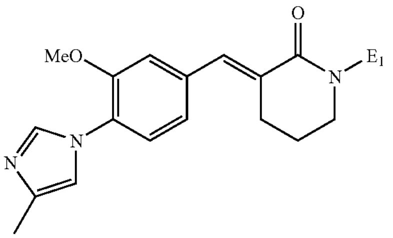

| Example | $E_1$ | DATA: MS m/z | Note |
|---|---|---|---|
| 1104 | 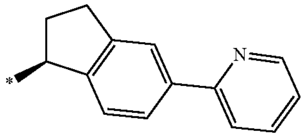 | $M^+$ + H:491(ESI) | optically active substance (separation condition A: retention time: 18.7 minutes; absolute configuration: unknown) |
| 1105 | 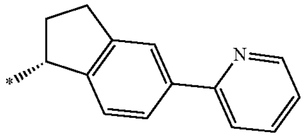 | $M^+$ + H:491(ESI) | optically active substance (separation condition A: retention time: 20.5 minutes; absolute configuration: unknown) |
| 1106 | 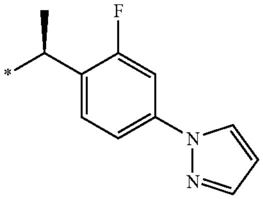 | $M^+$ + H:491(ESI) | optically active substance (separation condition B: retention time: 11.8 minutes; absolute configuration: unknown) |
| 1107 | 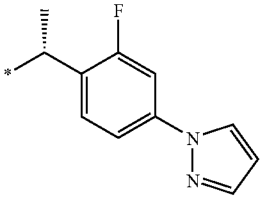 | $M^+$ + H:486(ESI) | optically active substance (separation condition B: retention time: 13.6 minutes; absolute configuration: unknown) |
| 1108 | 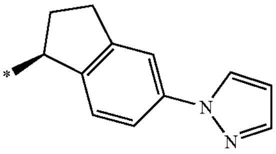 | $M^+$ + H:480(ESI) | optically active substance (separation condition B: retention time: 4.3 minutes; absolute configuration: unknown) |
| 1109 | 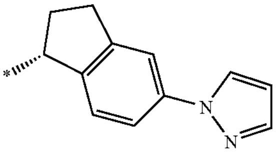 | $M^+$ + H:480(ESI) | optically active substance (separation condition C: retention time: 7.4 minutes; absolute configuration: unknown) |
| 1110 | 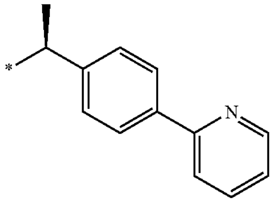 | $M^+$ + H:479(ESI) | optically active substance (separation condition A: retention time: 13.2 minutes; absolute configuration: unknown) |

TABLE 27-continued

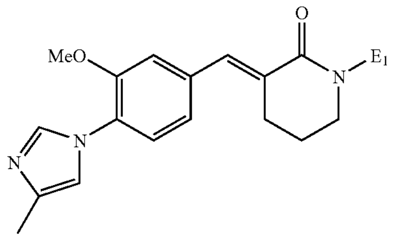

| Example | $E_1$ | DATA: MS m/z | Note |
|---|---|---|---|
| 1111 | 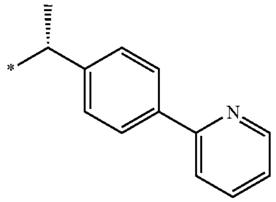 | $M^+$ + H:479(ESI) | optically active substance (separation condition A: retention time: 16.6 minutes; absolute configuration: unknown) |
| 1112 | 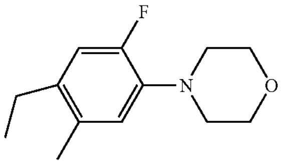 | $M^+$ + H:517(ESI) | racemate |
| 1113 | 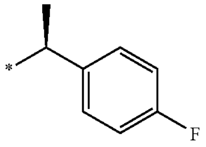 | $M^+$ + H:434(ESI) | optically active substance absolute configuration: unknown) |

TABLE 28

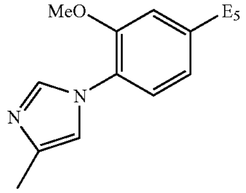

| Example | E5 | DATA: MS m/z | Note |
|---|---|---|---|
| 1114 | 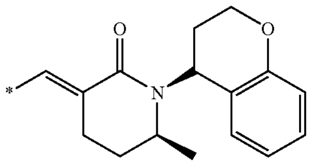 | $M^+$ + H:444(ESI) | optically active substance (separation condition A: retention time: 20.7 minutes; absolute configuration: unknown) |
| 1115 | 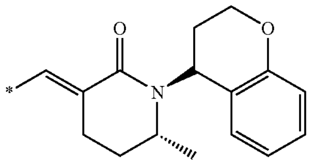 | $M^+$ + H:444(ESI) | optically active substance (separation condition A: retention time: 23.5 minutes; absolute configuration: unknown) |

TABLE 28-continued

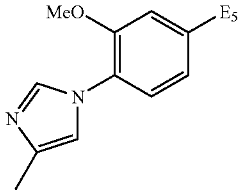

| Example | E5 | DATA: MS m/z | Note |
|---|---|---|---|
| 1116 | 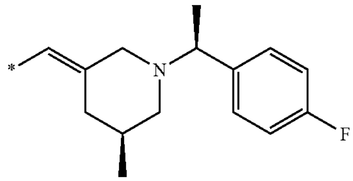 | M+ + H:434(ESI) | optically active substance (separation condition D: retention time: 60 minutes; absolute configuration: unknown) |
| 1117 | 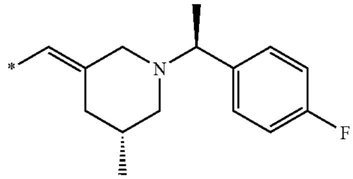 | M+ + H:434(ESI) | optically active substance (separation condition D: retention time: 67 minutes; absolute configuration: unknown) |
| 1118 | 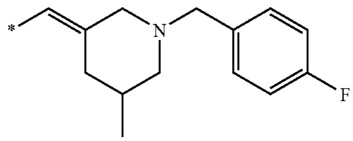 | M+ + H:420(ESI) | racemate |

Example 1119

Synthesis of (E)-1-[1-(4-fluorophenyl)-(1R,2R)-2-hydroxy propyl]-3-[3-methoxy-4-(4-methyl-1H-imidazol-1-yl)benzylidene]piperidin-2-one

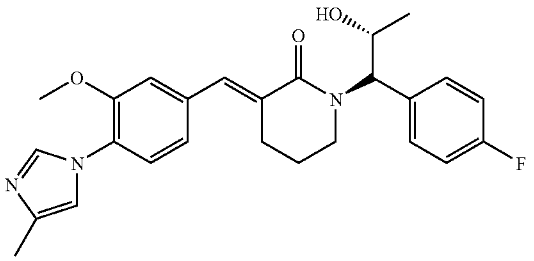

By the same method as in Example 418, 8 mg of the title compound was obtained from (E)-5-chloro-2-(3-methoxy-4-(4-methyl-1H-imidazol-1-yl)benzylidene)valeric acid trifluoroacetic acid salt (17 mg) and (1R,2R)-1-amino-1-(4-fluorophenyl)propan-2-ol 1 trifluoroacetic-acid salt (8.4 mg) synthesized according to the method described in Tetrahedoron: Asymmetry, 2000, vol. 11, p. 3079.

The physical properties of the compound are as follows.

ESI-MS; m/z450 [M$^+$+H]. $^1$H-NMR ($CDCl_3$) δ (ppm): 1.29 (d, J=6.4 Hz, 3H), 1.72-1.93 (m, 2H), 2.31 (s, 3H), 2.69-2.88 (m, 2H), 3.15-3.23 (m, 1H), 3.44-3.53 (m, 1H), 3.86 (s, 3H), 4.51 (dq, J=8.4, 6.4 Hz, 1H), 5.44 (d, J=8.4 Hz, 1H), 6.94 (s, 1H), 7.02-7.09 (m, 4H), 7.25 (d, J=8.0 Hz, 1H), 7.34-7.40 (m, 2H), 7.77 (d, J=0.8 Hz, 1H), 7.86 (brs, 1H).

Example 1120

Synthesis of (E)-1-[1-(4-fluorophenyl)-(1R,2R)-2-methoxypropyl]-3-[3-methoxy-4-(4-methyl-1H-imidazol-1-yl)benzylidene]piperidin-2-one

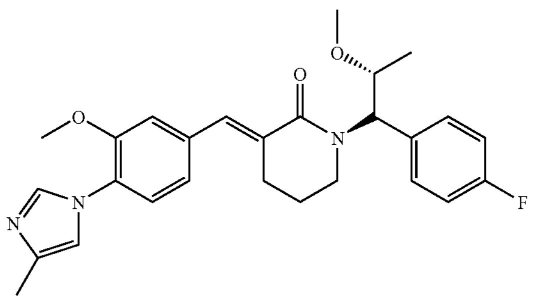

To a THF (1 mL) solution of (E)-1-(1-(4-fluorophenyl)-(1R,2R)-2-hydroxy propyl)-3-(3-methoxy-4-(4-methyl-1H-imidazol-1-yl)benzylidene)piperidin-2-one(4 mg) obtained in Example 1119, sodium hydride (40% mineral oil content, 0.5 mg) was added, and the reaction solution was agitated at room temperature for 30 minutes. Methyl iodide (2 mg) was added to the reaction solution, and the reaction solution was agitated at room temperature for 2 hours. Saturated sodium bicarbonate water and ethyl acetate were added to the reaction solution, and the organic layer was partitioned. The organic layer obtained was dried over magnesium sulfate and concentrated under reduced pressure. By purifying the residue with silica gel chromatography (Carrier: Chromatorex™ NH, elution solvent:ethyl acetate→ethyl acetate: methanol 9:1), 3 mg of the title compound was obtained. The physical properties of the compound are as follows.

ESI-MS; m/z464 [$M^{+}$+H].

Example 1121

Synthesis of (E)-1-[1-(4-fluorophenyl)-(1R,2S)-2-hydroxy propyl]-3-[3-methoxy-4-(4-methyl-1H-imidazol-1-yl)benzylidene]piperidin-2-one

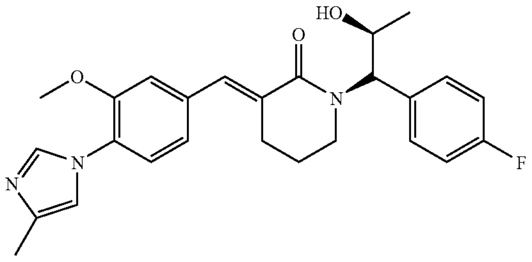

By the same method as in Example 418, 15 mg of the title compound was obtained from (E)-5-chloro-2-(3-methoxy-4-(4-methyl-1H-imidazol-1-yl)benzylidene)valeric acid trifluoroacetic acid salt (126 mg) and (1R,2S)-1-amino-1-(4-fluorophenyl)propan-2-ol 1 trifluoroacetic-acid salt (63 mg) synthesized according to the method described in Tetrahedoron: Asymmetry, 2000, vol. 11, p. 3079.

The physical properties of the compound are as follows.

ESI-MS; m/z450 [$M^{+}$+H]. $^{1}$H-NMR ($CDCl_3$) δ (ppm): 1.36 (d, J=6.0 Hz, 3H), 1.68-1.84 (m, 2H), 2.30 (s, 3H), 2.67-2.85 (m, 2H), 3.15-3.20 (m, 1H), 3.25-3.35 (m, 1H), 3.84 (s, 3H), 4.55 (dq, J=7.6, 6.0 Hz, 1H), 5.44 (d, J=7.6 Hz, 1H), 6.92 (s, 1H), 7.02-7.09 (m, 4H), 7.24 (d, J=8.0 Hz, 1H), 7.45-7.50 (m, 2H), 7.72 (d, J=0.8 Hz, 1H), 7.86 (brs, 1H).

Examples 1122 and 1123

Synthesis of (E)-1-[(1R and 1S)-1-(4-fluorophenyl)-2-hydroxy-1-methylethyl]-3-[3-methoxy-4-(4-methyl-1H-imidazol-1-yl)benzylidene]piperidin-2-one

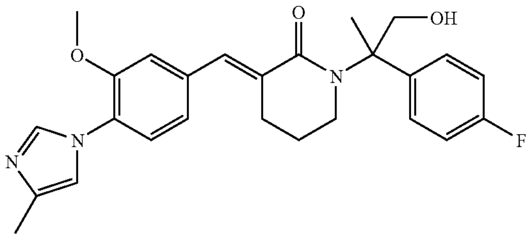

Synthesis of 2-(4-fluorophenyl)-3-methoxymethoxy-2-methylpropionic acid

To a methyl chloride (10 mL)-and-THF (5 mL) solution of 2-(4-fluorophenyl)-3-hydroxy-2-methylpropionic acid methyl ester (825 mg) synthesized according to the method described in Tetrahedron Letters, 1999, vol. 40, p. 5467, IPEA (2 mL) and chloromethyl methyl ether (0.74 mL) were added at 0° C. The reaction solution was agitated at 0° C. for 1 hour, and then at room temperature for 10 hours. 1N hydrochloric acid and ethyl acetate were added to the reaction solution, and the organic layer was partitioned. The organic layer obtained was washed with saturated sodium bicarbonate water, dried over magnesium sulfate, and then concentrated under reduced pressure. To a methanol (5 mL) solution of the obtained residue, 5N sodium hydroxide aqueous solution (4 mL) was added, and the reaction solution was agitated at room temperature for 10 hours. 5N hydrochloric acid (4 mL) and ethyl acetate were added to the reaction solution, and the organic layer was partitioned. The organic layer obtained was dried over magnesium sulfate and concentrated under reduced pressure to obtain 850 mg of the title compound. The physical properties of the compound are as follows.

$^{1}$H-NMR ($CDCl_3$) δ (ppm): 1.60 (s, 3H), 3.25 (s, 3H), 3.69 (d, J=9.2 Hz, 1H), 4.00 (d, J=9.2 Hz, 1H), 4,55 (d, J=6.4 Hz, 1H), 4.60 (d, J=6.4 Hz, 1H), 6.97 (t, J=8.4 Hz, 2H), 7.31 (dd, J=8.4, 4.8 Hz, 2H).

Synthesis of [1-(4-fluorophenyl)-2-hydroxy-1-methylethyl]carbamic acid tertiary butyl ester 252 mg of the title compound was obtained from 2-(4-fluorophenyl)-3-methoxymethoxy-2-methylpropionic acid (850 mg) obtained above according to the method described in Tetrahedron Letters, 1998, vol. 39, p. 3749. The physical properties of the compound are as follows.

ESI-MS; m/z270 [$M^{+}$+H].

Synthesis of 2-amino-2-(4-fluorophenyl)propan-1-ol hydrochloric acid salt

To an ethyl acetate (1 mL) solution of (1-(4-fluorophenyl)-2-hydroxy-1-methylethyl)carbamic acid tertiary butyl ester (252 mg), 4 N hydrochloric acid ethyl acetate solution (3 mL) was added, and the reaction solution was agitated at room temperature for 3 hours. The reaction solution was concentrated under reduced pressure to obtain 192 mg of the title compound. The physical properties of the compound are as follows.

$^{1}$H-NMR ($CDCl_3$) δ (ppm): 1.69 (s, 3H), 3.72 (d, J=11.6 Hz, 1H), 3.81 (d, J=11.6 Hz, 1H), 7.16-7.29 (m, 2H), 7.48-7.56 (m, 2H).

Synthesis of (E)-1-[(1R and 1S)-1-(4-fluorophenyl)-2-hydroxy-1-methylethyl]-3-[3-methoxy-4-(4-methyl-1H-imidazol-1-yl)benzylidene]piperidin-2-one By the same method as in Example 418, 36 mg of the racemic title compound was obtained from 2-amino-2-(4-fluorophenyl)propan-1-ol hydrochloric acid salt (192 mg) and (E)-5-chloro-2-(3-methoxy-4-(4-methyl-1H-imidazol-1-yl)benzylidene)valeric acid trifluoroacetic acid salt (526 mg). The racemate obtained (36 mg) was separated by CHIRALPAK™ AD-H available from Daicel Chemical Industries, Ltd. (2 cm×25 cm: mobile phase; IPA) to obtain the title optically-active substance with a retention time of 11 minutes (Example 1122, 15 mg; >99% ee) the title optically-active substance with a retention time of 12 minutes (Example 1123, 15 mg; >99% ee).

The physical properties of the title optically-active substance with a retention time of 11 minutes (Example 1122) are as follows.

ESI-MS; m/z450 $[M^{+}+H]$. $^{1}H$-NMR ($CDCl_3$) δ (ppm): 1.65-1.78 (m, 4H), 1.82-1.96 (m, 1H), 2.31 (s, 3H), 2.76-2.82 (m, 2H), 2.94-3.02 (m, 1H), 3.13-3.21 (m, 1H), 3.51 (brd, J=11.2 Hz, 1H), 3.86 (s, 3H), 4.29 (d, J=11.2 Hz, 1H), 5.37 (brs, 1H), 6.93 (d, J=1.2 Hz, 1H), 7.03-7.09 (m, 4H), 7.26 (d, J=7.6 Hz, 1H), 7.32 (dd, J=8.0, 5.2 Hz, 2H), 7.73 (s, 1H), 7.82 (brs, 1H) The physical properties of the title optically-active substance with a retention time of 12 minutes (Example 1123) are as follows.

ESI-MS; m/z450 $[M^{+}+H]$. $^{1}H$-NMR ($CDCl_3$) δ (ppm): 1.65-1.78 (m, 4H), 1.82-1.96 (m, 1H), 2.31 (s, 3H), 2.76-2.82 (m, 2H), 2.94-3.02 (m, 1H), 3.13-3.21 (m, 1H), 3.51 (brd, J=11.2 Hz, 1H), 3.86 (s, 3H), 4.29 (d, J=11.2 Hz, 1H), 5.37 (brs, 1H), 6.93 (d, J=1.2 Hz, 1H), 7.03-7.09 (m, 4H), 7.26 (d, J=7.6 Hz, 1H), 7.32 (dd, J=8.0, 5.2 Hz, 2H), 7.73 (s, 1H), 7.82 (brs, 1H).

Examples 1124 and 1125

Synthesis of (E)-1-[(1R and 1S)-1-(4-fluorophenyl)-2-methoxy-1-methylethyl]-3-[3-methoxy-4-(4-methyl-1H-imidazol-1-yl)benzylidene]piperidin-2-one

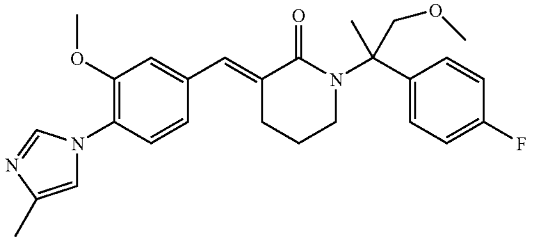

By the same method as in Examples 1122 and 1123, 10 mg of the racemic title compound was obtained from 1-(4-fluorophenyl)-2-methoxy-1-methylethylamine (11 mg) and (E)-5-chloro-2-(3-methoxy-4-(4-methyl-1H-imidazol-1-yl)benzylidene)valeric acid trifluoroacetic acid salt (33 mg). The racemate obtained (5 mg) was separated by CHIRALPAK™ AD-H available from Daicel Chemical Industries, Ltd. (2 cm×25 cm: mobile phase; hexane:IPA 8:1) to obtain the title optically-active substance with a retention time of 41 minutes (Example 1124, 2.3 mg; >99% ee) and the title optically-active substance with a retention time of 50 minutes (Example 1125, 1.6 mg; >99% ee).

The physical properties of the title optically-active substance with a retention time of 41 minutes (Example 1124) are as follows.

ESI-MS; m/z464 $[M^{+}+H]$. $^{1}H$-NMR ($CDCl_3$) δ (ppm): 1.78 (s, 3H), 1.90-1.98 (m, 2H), 2.31 (s, 3H), 2.76-2.83 (m, 2H), 3.36(s, 3H), 3.63-3.67 (m, 2H), 3.76 (brd, J=10.0 Hz, 1H), 3.83 (s, 3H), 4.07 (d, J=10.0 Hz, 1H), 6.93 (brs, 1H), 6.97-7.07 (m, 4H), 7.22-7.28 (m, 3H), 7.62 (brs, 1H), 7.75 (s, 1H).

The physical properties of the title optically-active substance with a retention time of 50 minutes (Example 1125) are as follows.

ESI-MS; m/z464 $[M^{+}+H]$. $^{1}H$-NMR ($CDCl_3$) δ (ppm): 1.78 (s, 3H), 1.90-1.98 (m, 2H), 2.31 (s, 3H), 2.76-2.83 (m, 2H), 3.36 (s, 3H), 3.63-3.67 (m, 2H), 3.76 (brd, J=10.0 Hz, 1H), 3.83 (s, 3H), 4.07 (d, J=10.0 Hz, 1H), 6.93 (brs, 1H), 6.97-7.07 (m, 4H), 7.22-7.28 (m, 3H), 7.62 (brs, 1H), 7.75 (s, 1H).

Examples 1126 and 1127

Synthesis of (E)-1-[(1S)-2-hydroxy-1-(3,4,5-trifluorophenyl)ethyl]-3-[3-methoxy-4-(4-methyl-1H-imidazol-1-yl)benzylidene]piperidin-2-one and (E)-1-[(1R)-2-hydroxy-1-(3,4,5-trifluorophenyl)ethyl]-3-[3-methoxy-4-(4-methyl-1H-imidazol-1-yl)-benzylidene]piperidin-2-one

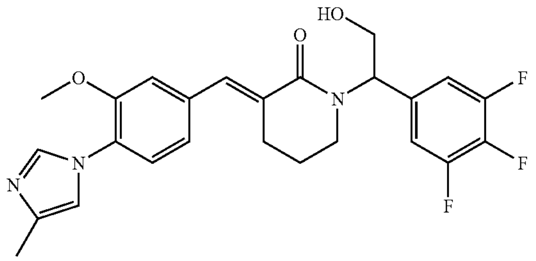

Synthesis of amino-(3,4,5-trifluorophenyl)acetonitrile

To a THF solution (20 mL) of 3,4,5-trifluorobenzaldehyde (1.3 g), trimethylsilylcyanide (1.35 mL) and zinc iodide (259 mg) were added, and the reaction solution was agitated at room temperature for 40 minutes. 2N ammonia solution in ethanol (15 mL) was added to the reaction solution, and the reaction solution was agitated at 50° C. for 4 hours. The reaction mixture was allowed to cool to room temperature, and the solvent was removed under reduced pressure. Ethyl acetate and saturated sodium bicarbonate water were added to the residue, and the organic layer was partitioned. The organic layer obtained was dried over magnesium sulfate, the solvent was removed under reduced pressure, and 780 mg of the title compound was obtained by purifying the residue with silica gel chromatography (Carrier: Chromatorex, elution solvent: heptane-ethyl acetate system). The physical properties of the compound are as follows.

$^{1}H$-NMR ($CD_3OD$) δ (ppm): 5.02 (s, 1H), 7.32-7.37 (m, 2H).

Synthesis of amino-(3,4,5-trifluorophenyl)acetic acid hydrochloric acid salt To amino-(3,4,5-trifluorophenyl)acetonitrile (780 mg), 5N hydrochloric acid (10 mL) was added and the reaction solution was heated under reflux overnight. The reaction mixture was allowed to cool to room temperature, washed with ether, and then the aqueous layer was separated. The aqueous layer obtained was concentrated under reduced pressure to obtain 933 mg of the title compound. The physical properties of the compound are as follows.

$^{1}H$-NMR (DMSO-$d_6$) δ (ppm): 7.18-7.46 (m, 2H), 7.54-7.58 (m, 1H), 9.10 (brs, 1H).

Synthesis of 2-amino-2-(3,4,5-trifluorophenyl)ethanol

To a THF suspension (10 mL) of LAH (641 mg), THF suspension (15 mL) of amino-(3,4,5-trifluorophenyl)acetic acid hydrochloric acid salt (933 mg) was added dropwise under cooling with ice. The reaction mixture was warmed to room temperature, and then agitated at room temperature for 7 hours. The reaction solution was once again cooled with ice, and methanol (4 mL) and water (2 mL) were consecutively added to the reaction solution. The insoluble matter formed in the reaction solution was filtered off by celite, and the insoluble matter was further washed with ether. The filtrate collected was dried over magnesium sulfate and the solvent was removed under reduced pressure to obtain 587 mg of the title compound. The physical properties of the compound are as follows.

$^1$H-NMR ($CDCl_3$) δ (ppm): 3.50 (dd, J=10.8, 8.0 Hz, 1H), 3.71 (dd, J=10.8, 4.0 Hz, 1H), 4.03 (dd, J=8.0, 4.0 Hz, 1H), 6.97-7.02 (m, 2H).

Synthesis of (E)-1-[(1S)-2-hydroxy-1-(3,4,5-trifluorophenyl)ethyl]-3-[3-methoxy-4-(4-methyl-1H-imidazol-1-yl)benzylidene]piperidin-2-one and (E)-1-[(1R)-2-hydroxy-1-(3,4,5-trifluorophenyl)ethyl]-3-[3-methoxy-4-(4-methyl-1H-imidazol-1-yl)benzylidene]piperidin-2-one By the same method as in Example 418, 140 mg of the racemic title compound was obtained from (E)-5-chloro-2-(3-methoxy-4-(4-methyl-1H-imidazol-1-yl)benzylidene)valeric acid trifluoroacetic acid salt (400 mg) and 2-amino-2-(3,4,5-trifluorophenyl)ethanol (180 mg). The racemate obtained (15 mg) was separated by CHIRALPAK™ AD-H available from Daicel Chemical Industries, Ltd. (2 cm×25 cm:

Examples 1128 and 1129

Synthesis of (E)-3-[3-methoxy-4-(4-methyl-1H-imidazol-1-yl)benzylidene]-1-[(1S)-2-methoxy-1-(3,4,5-trifluorophenyl)ethyl]piperidin-2-one and (E)-3-[3-methoxy-4-(4-methyl-1H-imidazol-1-yl)benzylidene]-1-[(1R)-2-methoxy-1-(3,4,5-trifluorophenyl)ethyl]piperidin-2-one

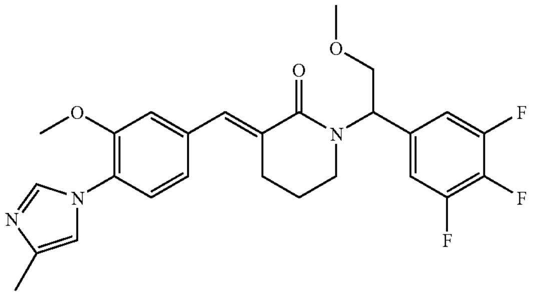

To a THF (2 mL) solution of racemic (E)-1-(2-hydroxy-1-(3,4,5-trifluorophenyl)ethyl)-3-(3-methoxy-4-(4-methyl-1H-imidazol-1-yl-benzylidene)piperidin-2-one (85 mg) obtained in Examples 1126 and 1127, sodium hydride (40% mineral oil content, 9.5 mg) was added under cooling with ice, and the reaction solution was agitated for 30 minutes. Then, methyl iodide (12.3 μL) was added to the reaction solution, and the reaction mixture was further agitated at room temperature for 3 hours. Water and ethyl acetate were added to the reaction solution, and the organic layer was partitioned. The organic layer obtained was dried over magnesium sulfate, and the solvent was removed under reduced pressure. The residue was purified by silica gel chromatography (Carrier: Chromatorex NH, elution solvent:heptane-ethyl acetate system→ethyl acetate-methanol system) to obtain 50 mg of the racemic title compound. The racemate obtained (50 mg) was separated by CHIRALPAK™ AD-H available from Daicel Chemical Industries, Ltd. (2 cm×25 cm: mobile phase; ethanol), and the title optically-active substance with a retention time of 43 minutes (Example 1128, 10.5 mg; >99% ee) and the title optically-active substance with a retention time of 50 minutes (Example 1129, 6.9 mg; 95% ee) of the title compound were obtained. The physical properties of these title compounds are as follows.

ESI-MS; m/z486 [$M^+$+H]. $^1$H-NMR ($CDCl_3$) δ (ppm): 1.71-1.92 (m, 2H), 2.30 (s, 3H), 2.74-2.90 (m, 2H), 3.10-3.17 (m, 1H), 3.36-3.43 (m, 1H), 3.43 (s, 3H), 3.82-3.92 (m, 2H), 3.85 (s, 3H), 6.03 (t, J=6.0 Hz, 1H), 6.93 (s, 1H), 6.98-7.05 (m, 4H), 7.25 (d, J=8.0 Hz, 1H), 7.74 (s, 1H), 7.86 (s, 1H).

Example 1130

Synthesis of (E)-2-(4-fluorobenzyl)-4-[3-methoxy-4-(4-methyl-1H-imidazol-1-yl)benzylidene]tetrahydropyrazine-3-one

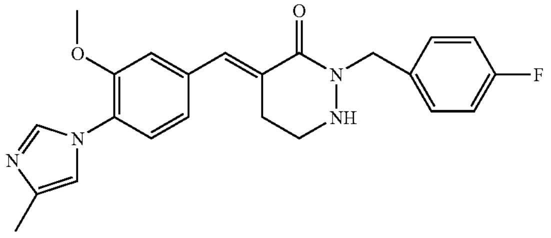

Synthesis of 4-bromo-2-(4-fluorobenzyl)-3-oxotetrahydropyrazine-1-carboxylic acid tertiary butyl ester N'-(4-fluorobenzyl)hydrazine carboxylic acid tertiary butyl ester (1.5 g) synthesized according to the method described in the literature (see, for example, H. L. Sham et al., J. Chem. Soc., Chem. Commun., 1993, vol. 13, p. 1052-1053) and 2,4-dibromo dibromobutyrylchloride (908 uL) in a mixture of dichloromethane (30 mL)-and-2N sodium hydroxide aqueous solution (5.0 mL) mixture of were vigorously agitated at room temperature. After 4.5 hours, the organic layer was separated. The organic layer obtained was washed with aqueous saline solution, dried over anhydrous magnesium sulfate, and then concentrated under reduced pressure. The residue was diluted with acetonitrile (21 mL), potassium carbonate (1.55 g) was added, and the reaction mixture was agitated at room temperature for 3.5 hours. Water and ethyl acetate were added to reaction solution and the organic layer was partitioned. The organic layer was washed with saturated saline solution, dried over anhydrous magnesium sulfate, and then concentrated under reduced pressure. By purifying the residue with silica gel chromatography (elution solvent:heptane-ethyl acetate system), 614 mg of the title compound was obtained. The physical properties of the compound are as follows.

ESI-MS; m/z331 [$M^+$-tert-butyl].

Synthesis of (E)-2-(4-fluorobenzyl)-4-[3-methoxy-4-(4-methyl-1H-imidazol-1-yl)benzylidene]-3-oxotetrahydropyrazine-1-carboxylic acid tertiary butyl ester A mixture of 4-bromo-2-(4-fluorobenzyl)-3-oxotetrahydropyrazine-1-carboxylic acid tertiary butyl ester (500 mg) and triethyl phosphite (3 mL) was agitated under heating overnight at 120° C. The reaction solution was concentrated under reduced pressure, the residue was diluted with THF (20 mL) and ethanol (2 mL), lithium hydroxide (271 mg) and 3-methoxy-4-(4-methyl-1H-imidazol-1-yl)benzaldehyde (279 mg) were added, and the reaction mixture was agitated at room temperature for 4 hours. Water and ethyl acetate were added to the reaction solution and the organic layer was partitioned. The organic layer was washed with saturated saline solution, dried over anhydrous magnesium sulfate, and then concentrated under reduced pressure. The residue was purified by silica gel chromatography (elution solvent:hexane-ethyl acetate system) to obtain 614 mg of the title compound. The physical properties of the compound are as follows.

ESI-MS; m/z507 [$M^+$+H]

Synthesis of (E)-2-(4-fluorobenzyl)-4-[3-methoxy-4-(4-methyl-1H-imidazol-1-yl)benzylidene]tetrahydropyrazine-3-one A mixture of (E)-2-(4-fluorobenzyl)-4-(3-methoxy-4-(4-methyl-1H-imidazol-1-yl)benzylidene)-3-oxotetrahydropyrazine-1-carboxylic acid tertiary butyl ester (582 mg) and trifluoroacetic acid (5 mL) was agitated at room temperature for 1 hour, and then concentrated under reduced pressure. Saturated sodium bicarbonate water and ethyl acetate were added to the residue and the organic layer was partitioned. The organic layer obtained was washed with saturated saline solution, dried over anhydrous magnesium sulfate, and then concentrated under reduced pressure. The residue was purified by silica gel chromatography (elution solvent:hexane-ethyl acetate system), and 385 mg of the title compound was obtained. The physical properties of the compound are as follows.

ESI-MS; m/z407 [$M^+$+H]. $^1$H-NMR ($CDCl_3$) δ: 3.31 (s, 3H), 2.91-2.95 (m, 2H), 3.15-3.21 (m, 2H), 3.87 (s, 3H), 4.08 (t, J=7.6 Hz, 1H), 4.78 (s, 2H), 6.94 (s, 1H), 7.00-7.05 (m, 2H), 7.07 (s, 1H), 7.08 (d, J=8.0 Hz, 1H), 7.27 (d, J=8.0 Hz, 1H), 7.36-7.40 (m, 2H), 7.76 (s, 1H), 7.86 (s, 1H).

Example 1131

Synthesis of (E)-1-acetyl-2-(4-fluorobenzyl)-4-[3-methoxy-4-(4-methyl-1H-imidazol-1-yl)benzylidene]tetrahydropyrazine-3-one

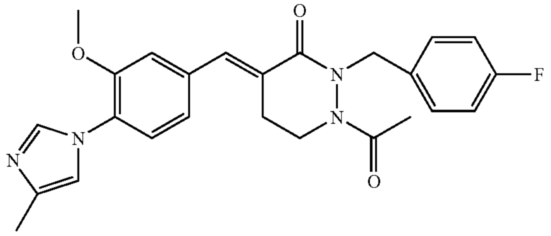

(E)-2-(4-fluorobenzyl)-4-(3-methoxy-4-(4-methyl-1H-imidazol-1-yl)benzylidene)tetrahydropyrazine-3-one (31 mg) and a mixture of acetic anhydride (1 mL) and pyridine (1 mL) were agitated for 1 hour at room temperature. The reaction solution was concentrated under reduced pressure, saturated sodium bicarbonate water and ethyl acetate were added to the residue, and the organic layer was partitioned. The organic layer obtained was washed with saturated saline solution, dried over anhydrous magnesium sulfate, and then concentrated under reduced pressure. The residue was purified by silica gel chromatography (elution solvent:chloroform-2-propanol system) to obtain 26.0 mg of the title compound. The physical properties of the compound are as follows.

ESI-MS; m/z449 [$M^+$+H]. $^1$H-NMR ($CDCl_3$) δ: 2.13 (s, 3H), 2.33 (s, 3H), 2.44-2.52 (m, 1H), 2.61-2.66 (m, 1H), 3.15-3.26 (m, 1H), 3.87 (s, 3H), 4.19 (d, J=14.4 Hz, 1H), 4.49-4.55 (m, 1H), 5.51 (d, J=14.4 Hz, 1H), 6.95 (s, 1H), 6.99-7.11 (m, 4H), 7.27 (d, J=8.4 Hz, 1H), 7.38-7.42 (m, 2H), 7.67 (s, 1H), 7.84 (s, 1H).

Example 1132

Synthesis of (E)-2-(4-fluorobenzyl)-4-[3-methoxy-4-(4-methyl-1H-imidazol-1-yl)benzylidene]-1-methyltetrahydropyrazine-3-one

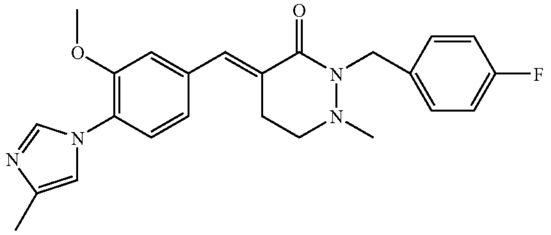

(E)-2-(4-fluorobenzyl)-4-(3-methoxy-4-(4-methyl-1H-imidazol-1-yl)benzylidene)tetrahydropyrazine-3-one (50 mg) and a mixture of formic acid (2 mL) and formalin (2 mL) were heated under reflux for 2 hours. Saturated sodium bicarbonate water and ethyl acetate were added to the reaction solution, and the organic layer was partitioned. The organic layer obtained was washed with saturated saline solution, dried over anhydrous magnesium sulfate, and then concentrated under reduced pressure. The residue was purified by silica gel chromatography (elution solvent:chloroform-2-propanol system) to obtain 36.7 mg of the title compound. The physical properties of the compound are as follows.

ESI-MS; m/z421 [$M^+$+H]. $^1$H-NMR ($CDCl_3$) δ: 2.31 (s, 3H), 2.68 (s, 3H), 3.04-3.07 (m, 2H), 3.13-3.17 (m, 2H), 3.87 (s, 3H), 4.70 (s, 2H), 6.95 (s, 1H), 6.98-7.03 (m, 2H), 7.11 (d, J=1.6 Hz, 1H), 7.15 (dd, J=8.0, 1.6 Hz, 1H), 7.28 (d, J=8.0 Hz, 1H), 7.37-7.41 (m, 2H), 7.75 (s, 1H), 7.80 (s, 1H).

Example 1133

Synthesis of (E)-1-ethyl-2-(4-fluorobenzyl)-4-(3-methoxy-4-[4-methyl-1H-imidazol-1-yl)benzylidene]tetrahydropyrazine-3-one

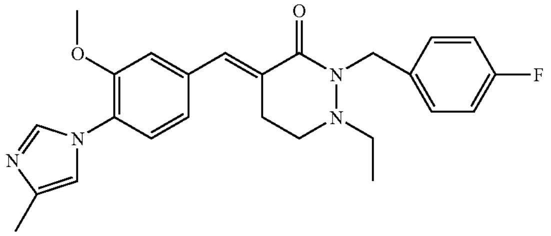

(E)-2-(4-fluorobenzyl)-4-(3-methoxy-4-(4-methyl-1H-imidazol-1-yl)benzylidene)tetrahydropyrazine-3-one (50 mg) and a mixture of acetaldehyde (20.7 μL) and acetic acid (42.2 μL) and triacetoxy sodium borohydride (78.2 mg) were agitated overnight at room temperature. Ethyl acetate and water were added to the reaction solution, the solution was adjusted to around pH 8 with 5N sodium hydroxide aqueous solution, and the organic layer was separated. The organic layer was washed with saturated saline solution, dried over anhydrous magnesium sulfate, and then concentrated under reduced pressure. The residue was purified by silica gel chromatography (elution solvent:chloroform-2-propanol system), and 38.8 mg of the title compound was obtained. The physical properties of the compound are as follows.

ESI-MS; m/z435 $[M^{+}+H]$. $^{1}$H-NMR ($CDCl_3$) δ: 1.13 (t, J=7.2 Hz, 3H), 2.34 (s, 3H), 2.93 (q, J=7.2 Hz, 2H), 2.90-2.98 (m, 2H), 3.11-3.15 (m, 2H), 3.88 (s, 3H), 4.70 (s, 2H), 6.96 (s, 1H), 6.98-7.03 (m, 2H), 7.11 (s, 1H), 7.15 (d, J=8.0 Hz, 1H), 7.27 (d, J=8.0 Hz, 1H), 7.39-7.43 (m, 2H), 7.74 (s, 1H), 7.85 (s, 1H).

Example 925

Synthesis of (E)-1-[(1R)-1-(3-fluorophenyl)ethyl)-3-(3-methoxy-4-(4-methyl-1H-imidazol-1-yl)benzylidene]piperidin-2-one

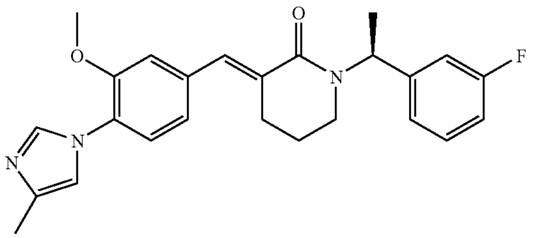

To a DMF (3 mL) solution of (E)-5-chloro-2-(3-methoxy-4-(4-methyl-1H-imidazol-1-yl)benzylidene)valeric acid trifluoroacetic acid salt (100 mg) obtained according to the method described in Example 418 and (S)-1-(3-fluorophenyl)ethylamine hydrochloric acid salt(31 mg), IPEA (0.2 mL) and HOBT (36 mg) and EDC (51 mg) were added, and the reaction solution was agitated at room temperature for 3 hours. Saturated sodium bicarbonate water and ethyl acetate were added to the reaction solution, and the organic layer was partitioned. The organic layer obtained was dried over magnesium sulfate and concentrated under reduced pressure. By purifying the residue with silica gel chromatography (Carrier: Chromatorex™ NH, elution solvent:heptane:ethyl acetate 1:1→ethyl acetate), 79 mg of 5-chloro-2-(3-methoxy-4-(4-methyl-1H-imidazol-1-yl)benzylidene)valeric acid ((1S)-1-(3-fluorophenyl)ethyl)amide was obtained. Sodium hydride (40% mineral oil content, 8 mg) was added to the DMF (3 mL) solution of 5-chloro-2-(3-methoxy-4-(4-methyl-1H-imidazol-1-yl)benzylidene)valeric acid ((1S)-1-(3-fluorophenyl)ethyl)amide obtained, and the reaction solution was agitated at room temperature for 5 minutes. Water and ethyl acetate were added to the reaction solution, and the organic layer was partitioned. The organic layer obtained was dried over anhydrous magnesium sulfate, and the solvent was removed under reduced pressure. The residue was purified by silica gel chromatography (Carrier: Chromatorex™ NH, elution solvent:heptane:ethyl acetate system 1:1→ethyl acetate) to obtain 48 mg of the racemic title compound. The physical properties of the compound are as follows.

$^{1}$H-NMR ($CDCl_3$) δ (ppm): 1.56 (d, J=7.2 Hz, 3H), 1.60-1.80 (m, 2H), 2.32 (s, 3H), 2.72-2.90 (m, 2H), 2.94-3.00 (m, 1H), 3.22-3.30 (m, 1H), 3.86 (s, 3H), 6.23 (d, J=7.2, 1H), 6.92-7.00 (m, 2H), 7.02-7.07 (m, 3H), 7.12 (dd, J=7.2, 0.8 Hz, 1H), 7.25 (d, J=7.2 Hz, 1H), 7.28-7.34 (m, 2H), 7.76 (d, J=1.2 Hz, 1H), 7.89 (s, 1H).

Example 1134

Synthesis of (E)-N-[(1S)-indan-1-yl-3-[4-methoxy-5-(4-methyl-1H-imidazol-1-yl) pyrimidin-2-yl]acrylamide

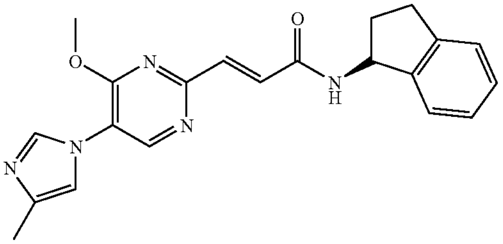

Synthesis of 4-methoxy-5-nitro-2-pyrimidine

To a solution of 2-chloro-3-methoxy-5-nitropyrimidine (CASNo. 282102-07-02, 670 mg), vinyl tri-n-butyltin (2.07 mL) and 2,6-di-t-butyl-4-methylphenol (30 mg) in DMF (15 mL) was added bis(triphenylphosphine)palladium (II) dichloride (124 mg), and the reaction mixture was stirred at 35° C. for 2 hrs. To the reaction mixture was added water and ethyl acetate, and the organic layer was separated. The obtained organic layer was sequentially washed with water and saturated saline solution, dried over anhydrous sodium sulfate, and concentrated under reduced pressure. The obtained residue was purified by silica gel column chromatography (eluting solvent:heptane/ethyl acetate) to give the title compound (261 mg). The physical data of the title compound was described as below.

ESI-MS; m/z182 $[M^{+}+H]$. $^{1}$H-NMR($CDCl_3$) δ (ppm): 4.21 (s, 3H), 5.94 (dd, J=9.6, 2.8 Hz, 1H), 6.75-6.88 (m, 2H), 9.15 (s, 1H).

Synthesis of (E)-3-(4-methoxy-5-nitropyrimidin-2-yl)acrylic acid ethyl ester A solution of 4-methoxy-5-nitro-2-vinylpyrimidine (260 mg) in methylene chloride (15 mL) was stirred with an ozone stream of bubbling at −50° C. for 1 hr. After the reaction mixture was warmed to −20° C., the ozone stream was stopped and dimethyl sulfide (1.06 mL) was added to the reaction mixture. The reaction mixture was gradually warmed up to room temperature with stirring for 30 min. The reaction mixture was concentrated under reduced pressure to obtain the corresponding crude aldehyde. To a solution of the crude aldehyde and triethyl phosphonoacetate (0.432 mL) in THF (5 mL) was added lithium hydroxide monohydrate (90.6 mg) at 0° C. After stirring for 1.5 hr at room temperature, water and ethyl acetate was added to the reaction mixture and an organic layer was separated. The obtained organic layer was sequentially washed with water and saturated saline solution, dried over anhydrous sodium sulfate, and concentrated under reduced pressure. The residue was purified by silica gel column chromatography (eluting solvent:heptane/ethyl acetate) to give the title compound (100 mg). The physical data of the title compound was described as below.

$^1$H-NMR($CDCl_3$) δ (ppm): 1.37 (t, J=6.8 Hz, 3H), 4.23 (s, 3H), 4.32 (q, J=6.8 Hz, 2H), 7.25 (d, J=15.6 Hz, 1H), 7.60 (d, J=15.6 Hz, 1H), 9.18 (s, 1H).

Synthesis of (E)-3-[4-methoxy-5-(4-methyl-1H-imidazol-1-yl)pyrimidin-2-yl]acrylic acid ethyl ester According to the method described in Example 23, the title compound (27.8 mg) was obtained from (E)-3-(4-methoxy-5-nitropyrimidin-2-yl)acrylic acid ethyl ester (100 mg). The physical-data of the title compound was described as below.

$^1$H-NMR($CDCl_3$) δ(ppm): 1.37 (t, J=7.2 Hz, 3H), 2.31 (s, 3H), 4.14 (s, 3H), 4.31 (q, J=7.2 Hz, 2H), 6.99 (d, J=1.6 Hz, 1H), 7.15 (d, J=15.6 Hz, 1H), 7.61 (d, J=15.6 Hz, 1H), 7.82 (d, J=1.6 Hz, 1H), 8.50 (s, 1H).

Synthesis of (E)-[(1S)-N-indan-1-yl]-3-[4-methoxy-5-(4-methyl-1H-imidazol-1-yl)pyrimidin-2-yl]acrylamide To a solution of (E)-3-[4-methoxy-5-(4-methyl-1H-imidazol-1-yl)pyrimidin-2-yl]acrylic acid ethyl ester (27.8 mg) in THF (1 mL) and ethanol (0.5 mL) was added 1N sodium hydroxide aqueous solution (1.0 mL) at 0° C. After the reaction mixture was stirred at room temperature for 2 hrs, saturated aqueous ammonium chloride was added to the reaction mixture, and the reaction mixture was concentrated under reduced pressure. The residue was diluted with MeOH, and the diluted solution was filtrated on florisil. The filtrate was concentrated under reduced pressure to give the corresponding crude carboxylic acid. According to the method described in Example 23, the title compound (7.1 mg) was obtained from the crude carboxylic acid and (S)-1-aminoindan (61.8 μL). The physical data of the title compound was described as below.

ESI-MS; m/z376 [$M^+$+H]. $^1$H-NMR($CDCl_3$) δ(ppm): 1.87-1.96 (m, 1H), 2.30 (s, 3H), 2.64-2.73 (m, 1H), 2.88-3.06 (m, 2H), 4.11 (s, 3H), 5.65 (dd, J=15.2, 7.6 Hz, 1H), 6.08 (d, J=7.6 Hz, 1H), 6.98 (s, 1H), 7.18 (d, J=15.2 Hz, 1H), 7.20-7.36 (m, 4H), 7.60 (d, J=15.2 Hz, 1H), 7.81 (s, 1H), 8.47 (s, 1H).

The compounds shown in Table 29 were synthesized as in Example 121. The structural formulae and physical properties are shown in Table 29, respectively.

TABLE 29

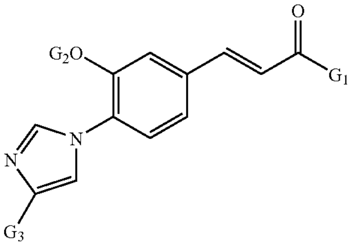

| Example | G1 | G2 | G3 | DATA: MS m/z |
|---|---|---|---|---|
| 1135 | 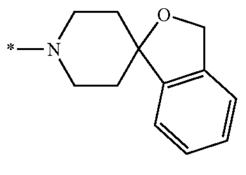 | Me | Me | $M^+$ + H:430 (ESI) |

TABLE 29-continued

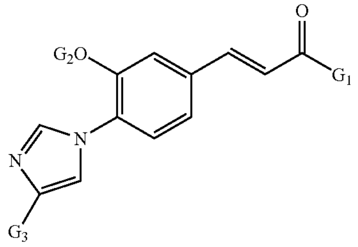

| Example | G1 | G2 | G3 | DATA: MS m/z |
|---|---|---|---|---|
| 1136 | 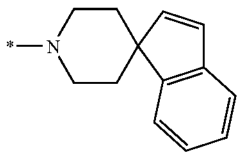 | Me | Me | $M^+$ + H:426 (ESI) |
| 1137 | 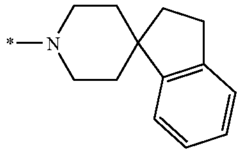 | Me | Me | $M^+$ + H:428 (ESI) |
| 1138 | 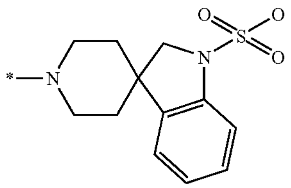 | Me | Me | $M^+$ + H:50 (ESI) |
| 1139 | 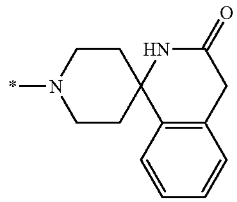 | Me | Me | $M^+$ + H:457 (ESI) |

The compounds shown in Tables 30 and 31 were synthesized as in Example 403. The structural formulae and physical properties are shown in Tables 30 and 31, respectively.

TABLE 30

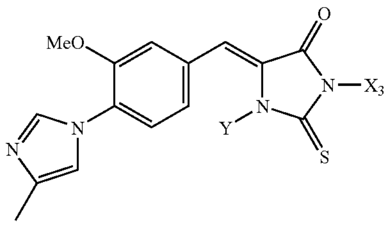

| Example | X3 | Y | DATA: MS m/z |
|---|---|---|---|
| 1140 | 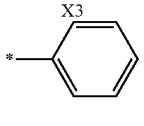 | H | $M^+$ + H:39 1 (ESI) |

TABLE 30-continued
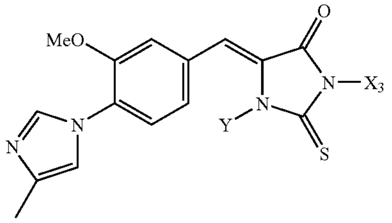
| Example | X3 | Y | DATA: MS m/z |
|---|---|---|---|
| 1141 | 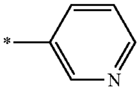 | H | $M^+$ + H:392 (ESI) |
| 1142 | 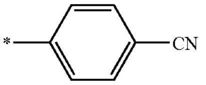 | H | $M^+$ + H:416 (ESI) |
| 1143 | 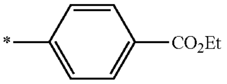 | H | $M^+$ + H:463 (ESI) |
| 1144 | 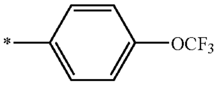 | H | $M^+$ + H:475 (ESI) |
| 1145 | 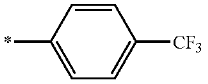 | H | $M^+$ + H:459 (ESI) |
| 1146 | 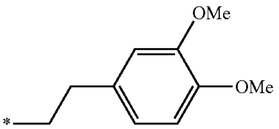 | H | $M^+$ + H:479 (ESI) |
| 1147 | 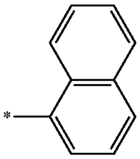 | H | $M^+$ + H:441 (ESI) |
| 1148 | 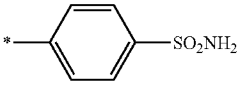 | H | $M^+$ + H:470 (ESI) |
| 1149 | 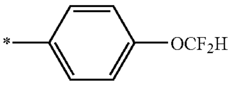 | H | $M^+$ + H:457 (ESI) |
| 1150 | 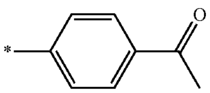 | H | $M^+$ + H:433 (ESI) |
| 1151 | 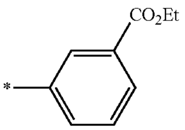 | H | $M^+$ + H:463 (ESI) |
TABLE 30-continued
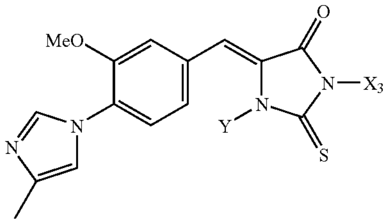
| Example | X3 | Y | DATA: MS m/z |
|---|---|---|---|
| 1152 | 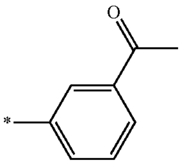 | H | $M^+$ + H:433 (ESI) |
| 1153 | 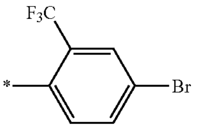 | H | $M^+$ + H:537 (ESI) |
| 1154 | 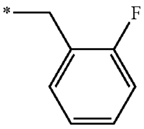 | H | $M^+$ + H:423 (ESI) |
| 1155 | 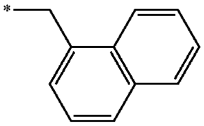 | H | $M^+$ + H:455 (ESI) |
| 1156 | 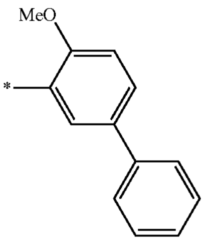 | H | $M^+$ + H:497 (ESI) |
| 1157 | 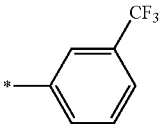 | H | $M^+$ + H:459 (ESI) |
| 1158 | 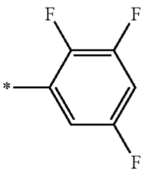 | H | $M^+$ + H:445 (ESI) |
| 1159 | 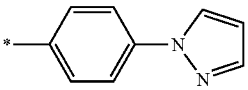 | H | $M^+$ + H:457 (ESI) |

TABLE 30-continued
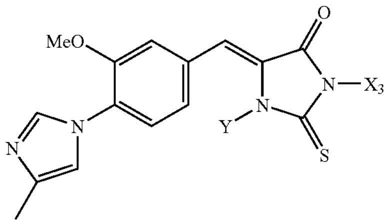
| Example | X3 | Y | DATA: MS m/z |
| --- | --- | --- | --- |
| 1160 | 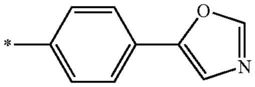 | H | $M^+$ + H:458 (ESI) |
| 1161 | 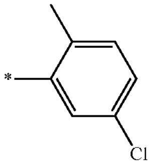 | H | $M^+$ + H:439 (ESI) |
| 1162 | 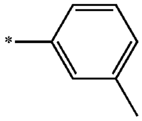 | H | $M^+$ + H:405 (ESI) |
| 1163 | 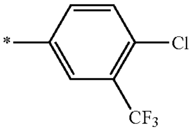 | H | $M^+$ + H:493 (ESI) |
| 1164 | 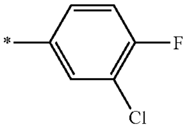 | H | $M^+$ + H:443 (ESI) |
| 1165 | 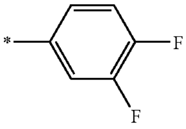 | H | $M^+$ + H:427 (ESI) |
| 1166 | 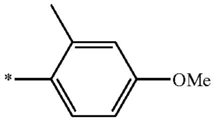 | H | $M^+$ + H:435 (ESI) |
TABLE 31
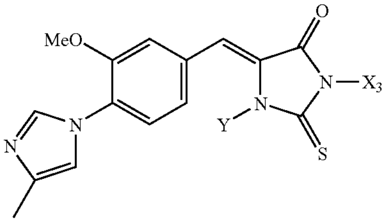
| Example | X3 | Y | DATA: MS m/z |
| --- | --- | --- | --- |
| 1167 | 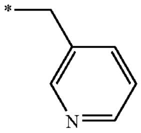 | H | $M^+$ + H:406 (ESI) |
| 1168 | 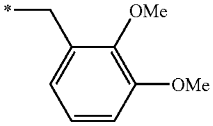 | H | $M^+$ + H:465 (ESI) |
| 1169 | 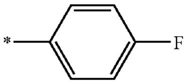 | H | $M^+$ + H:409 (ESI) |
| 1170 | 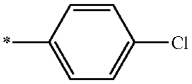 | H | $M^+$ + H:425 (ESI) |
| 1171 | 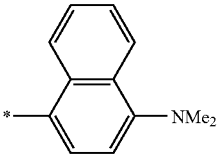 | H | $M^+$ + H:484 (ESI) |
| 1172 | 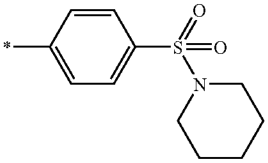 | H | $M^+$ + H:538 (ESI) |
| 1173 | 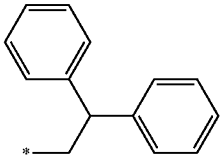 | H | $M^+$ + H:495 (ESI) |
| 1174 | 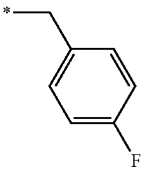 | H | $M^+$ + H:423 (ESI) |
| 1175 | 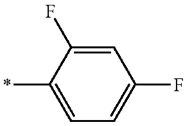 | H | $M^+$ + H:427 (ESI) |

TABLE 31-continued

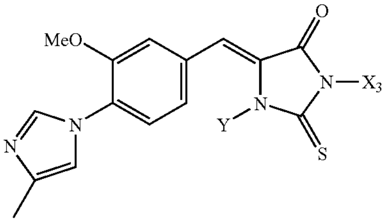

| Example | X3 | Y | DATA: MS m/z |
|---|---|---|---|
| 1176 | 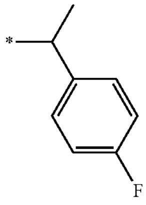 | H | $M^+ + H$:437 (ESI) |

The compounds shown in Tables 32, 33 and 34 were synthesized as in Example 418. The structural formulae and physical properties are shown in Tables 32, 33 and 34, respectively. Separation Condition A: CHIRALPAK™ AD-H available from Daicel Chemical Industries, Ltd. (2 cm×25 cm: mobile phase:hexane-ethanol system)

Separation Condition B: CHIRALCEL™ OJ-H available from Daicel Chemical Industries, Ltd. (2 cm×25 cm: mobile phase: hexane-ethanol)

Separation Condition C: CHIRALCEL™ OD-H available from Daicel Chemical Industries, Ltd. (2 cm×25 cm: mobile phase; hexane-ethanol)

Separation Condition D: CHIRALCEL™ IA available from Daicel Chemical Industries, Ltd. (2 cm×25 cm: mobile phase; hexane-ethanol)

Separation Condition E: CHIRALCEL™ OD available from Daicel Chemical Industries, Ltd. (2 cm×25 cm: mobile phase; hexane-ethanol)

TABLE 32

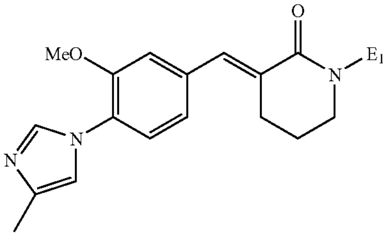

| Example | $E_1$ | DATA: MS m/z | Notes |
|---|---|---|---|
| 1177 | 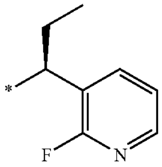 | $M^+ + H$:435 (ESI) | optically active substance (separation condition C: retention tine: 11.2 minutes; absolute configuration: unknown) |
| 1178 | 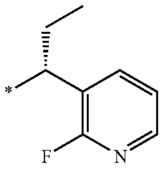 | $M^+ + H$:435 (ESI) | optically active substance (separation condition C: retention time: 12.4 minutes; absolute configuration: unknown) |
| 1179 | 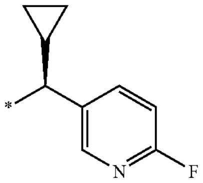 | $M^+ + H$:447 (ESI) | optically active substance (separation condition A: retention time: 6.5 minutes; absolute configuration: unknown) |
| 1180 | 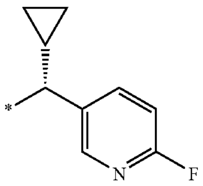 | $M^+ + H$:447 (ESI) | optically active substance (separation condition A: retention time. 7.4 minutes; absolute configuration: unknown) |

TABLE 32-continued

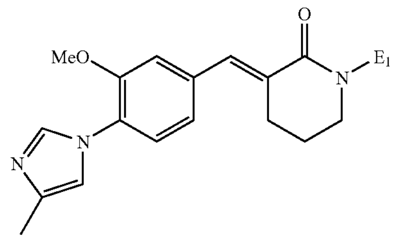

| Example | $E_1$ | DATA: MS m/z | Notes |
| --- | --- | --- | --- |
| 1181 | 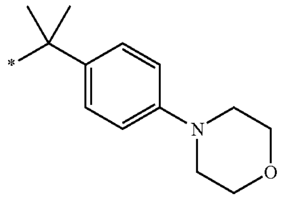 | $M^+$ + H:501 (ESI) | |
| 1182 | 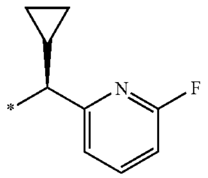 | $M^+$ + H:447 (ESI) | optically active substance (separation condition A: retention time: 5.5 minutes; absolute configuration: unknown) |
| 1183 | 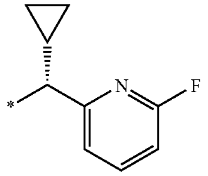 | $M^+$ + H:447 (ESI) | optically active substance (separation condition A: retention time: 6.6 minutes; absolute configuration: unknown) |
| 1184 | 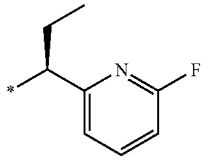 | $M^+$ + H:435 (ESI) | optically active substance (separation condition A: retention time: 7.2 minutes; absolute configuration: unknown) |
| 1185 | 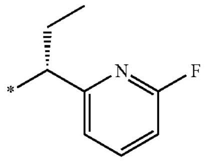 | $M^+$ + H:435 (ESI) | optically active substance (separation condition A: retention time: 8.0 minutes; absolute configuration: unknown) |
| 1186 | 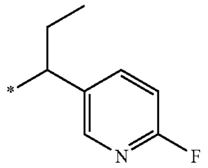 | $M^+$ + H:435 (ESI) | Racemate |
| 1187 | 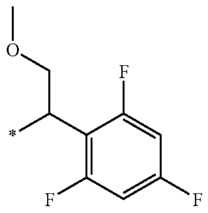 | $M^+$ + H:486 (ESI) | racemate |

TABLE 32-continued
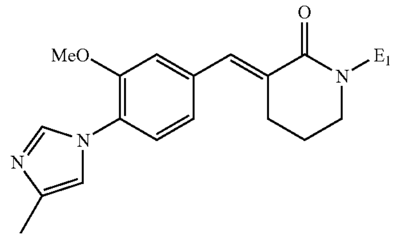
| Example | $E_1$ | DATA: MS m/z | Notes |
|---|---|---|---|
| 1188 | 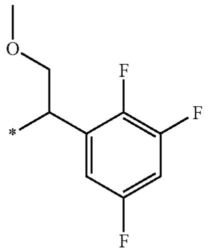 | $M^+$ + H:486 (ESI) | racemate |
| 1189 | 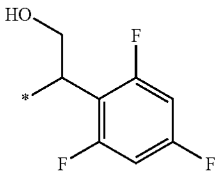 | $M^+$ + H:472 (ESI) | racemate |
| 1190 | 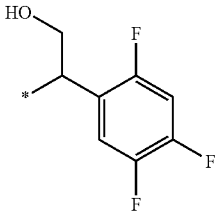 | $M^+$ + H:472 (ESI) | racemate |
| 1191 | 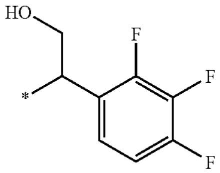 | $M^+$ + H:472 (ESI) | racemate |
| 1192 | 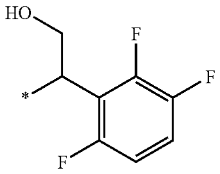 | $M^+$ + H:472 (ESI) | racemate |
| 1193 | 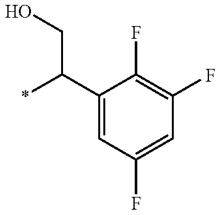 | $M^+$ + H:472 (ESI) | racemate |

TABLE 32-continued

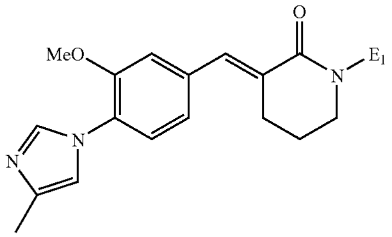

| Example | $E_1$ | DATA: MS m/z | Notes |
|---|---|---|---|
| 1194 | 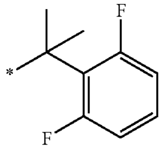 | $M^+$ + H:452 (ESI) | |
| 1195 | 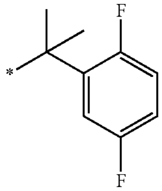 | $M^+$ + H:452 (ESI) | |
| 1196 | 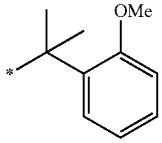 | $M^+$ + H:446 (ESI) | |
| 1197 | 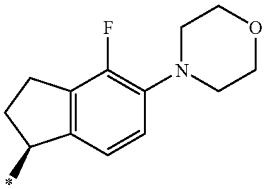 | $M^+$ + H:517 (ESI) | optically acitve substance (separation condition C: retention time: 7.7 minutes; absolute configuration: unknown) |
| 1198 | 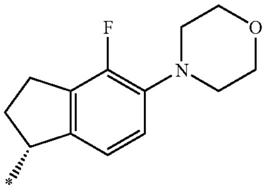 | $M^+$ + H:517 (ESI) | optically active substance (separation condition C: retention time: 9.6 minutes; absolute configuration: unknown) |
| 1199 | 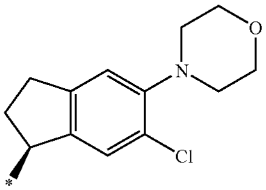 | $M^+$ + H:533 (ESI) | optically active substance (separation condition C: retention time: 6.9 minutes; absolute configuration: unknown) |

TABLE 32-continued

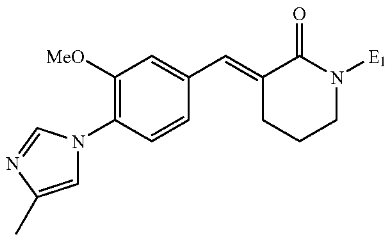

| Example | $E_1$ | DATA: MS m/z | Notes |
|---|---|---|---|
| 1200 | 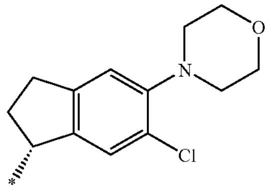 | $M^+ + H$:533 (ESI) | optically active substance (separation condition C: retention time: 8.6 minutes; absolute configuration: unknown) |
| 1201 | 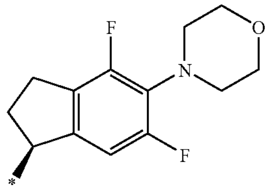 | $M^+ + H$:535 (ESI) | optically active substance (separation condition A: retention time: 8.4 minutes; absolute configuration: unknown) |
| 1202 | 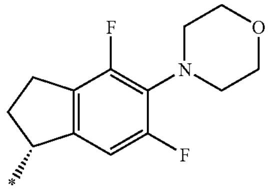 | $M^+ + H$:535 (ESI) | optically active substance (separation condition A: retention time: 10.2 minutes; absolute configuration: unknown) |
| 1203 | 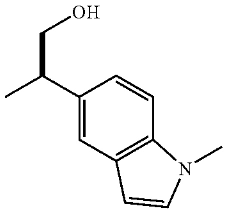 | $M^+ + Na$:493 (ESI) | optically active substance (separation condition D: retention time: 8.2 minutes; absolute configuration: unknown) |
| 1204 | 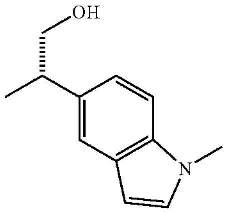 | $M^+ + Na$:493 (ESI) | optically active substance (separation condition D: retention time: 10.4 minutes; absolute configuration: unknown) |
| 1205 | 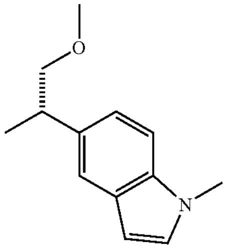 | $M^+ + Na$:507 (ESI) | optically active substance (separation condition C: retention time: 17.8 minutes; absolute configuration: unknown) |

TABLE 32-continued

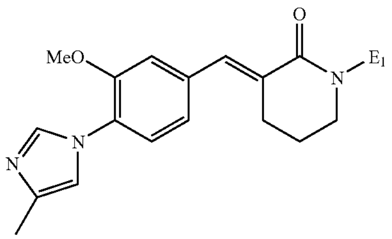

| Example | $E_1$ | DATA: MS m/z | Notes |
| --- | --- | --- | --- |
| 1206 | 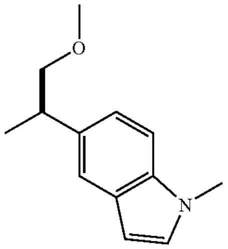 | $M^+$ + Na:507 (ESI) | optically active substance (separation condition C: retention time: 21.7 minutes; absolute configuration: unknown) |
| 1207 | 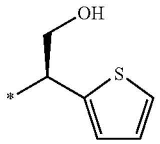 | $M^+$ + H:424 (ESI) | optically active substance |
| 1208 | 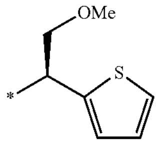 | $M^+$ + H:438 (ESI) | optically active substance |
| 1209 | 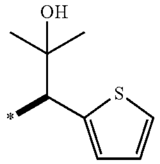 | $M^+$ + H:452 (ESI) | optically active substance |
| 1210 | 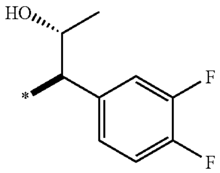 | $M^+$ + H:468 (ESI) | optically active substance |
| 1211 | 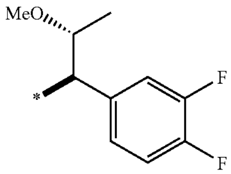 | $M^+$ + H:482 (ESI) | optically active substance |
| 1212 | 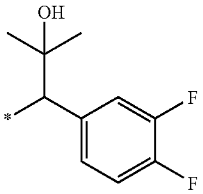 | $M^+$ + H:482 (ESI) | racemate |

TABLE 32-continued

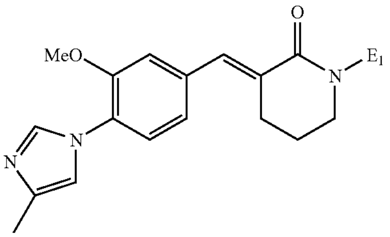

| Example | $E_1$ | DATA: MS m/z | Notes |
|---|---|---|---|
| 1213 | 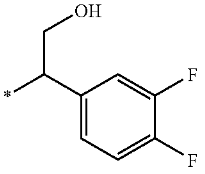 | $M^+$ + H:454 (ESI) | racemate |
| 1214 | 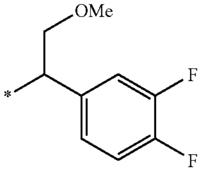 | $M^+$ + H:468 (ESI) | racemate |
| 1215 | 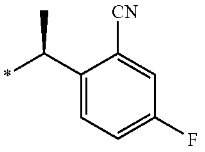 | $M^+$ + H:445 (ESI) | racemate |
| 1216 | 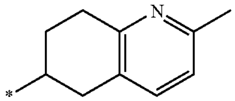 | $M^+$ + H:443 (ESI) | racemate |
| 1217 | 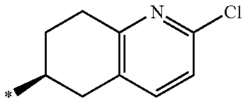 | $M^+$ + H:463 (ESI) | optically active substance (separation condition A: retention time: 11.7 minutes; absolute configuration: unknonw) |
| 1218 | 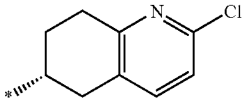 | $M^+$ + H:463 (ESI) | optically active substance (separation condition A: retention time: 15.4 minutes; absolute configuration: unknonw) |
| 1219 | 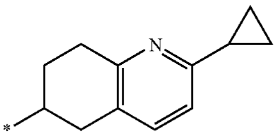 | $M^+$ + H:469 (ESI) | racemate |

TABLE 32-continued
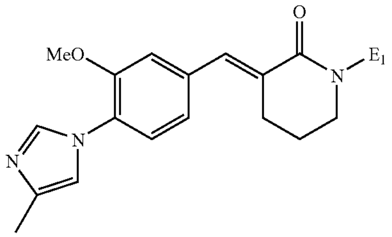
| Example | $E_1$ | DATA: MS m/z | Notes |
|---|---|---|---|
| 1220 | 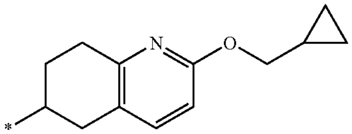 | $M^+$ + H:499 (ESI) | racemate |
| 1235 | 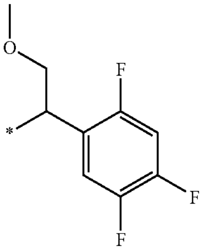 | $M^+$ + H:486 (ESI) | racemate |
| 1236 | 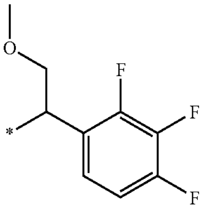 | $M^+$ + H:486 (ESI) | racemate |
| 1237 | 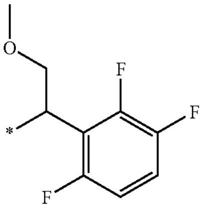 | $M^+$ + H:486 (ESI) | racemate |
| 1238 | 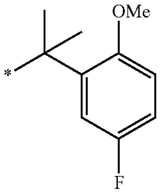 | $M^+$ + H:464 (ESI) | |

TABLE 33

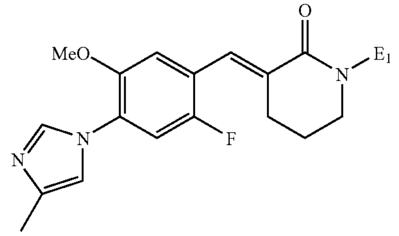

| Example | $E_1$ | DATA: MS m/z | Notes |
|---|---|---|---|
| 1221 | 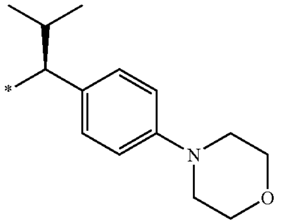 | $M^+$ + H:533 (ESI) | optically active substance (separation condition A: retention time: 11 minutes; absolute configuration: unknonw) |
| 1222 | 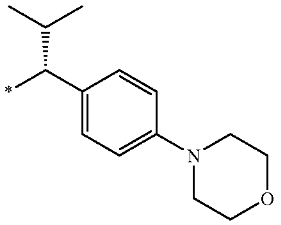 | $M^+$ + H:533 (ESI) | optically active substance (separation condition A: retention time: 25 minutes; absolute configuration: unknonw) |

TABLE 34

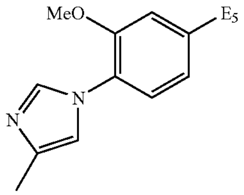

| Example | E5 | DATA: MS m/z | Notes |
|---|---|---|---|
| 1223 | 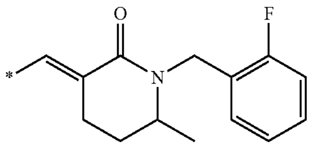 | $M^+$ + H:420 (ESI) | racemate |
| 1224 | 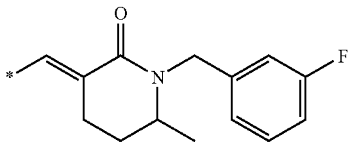 | $M^+$ + H:420 (ESI) | racemate |
| 1225 | 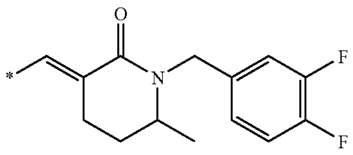 | $M^+$ + H:438 (ESI) | racemate |

TABLE 34-continued
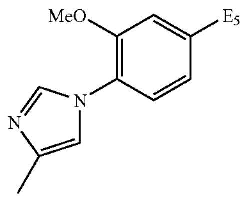
| Example | E5 | DATA: MS m/z | Notes |
|---|---|---|---|
| 1226 | 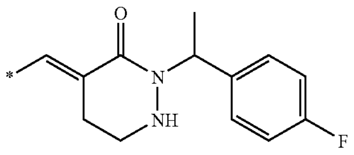 | $M^+ + H$:421 (ESI) | racemate |
| 1227 | 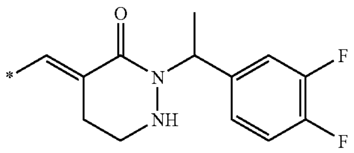 | $M^+ + H$:439 (ESI) | racemate |
| 1228 | 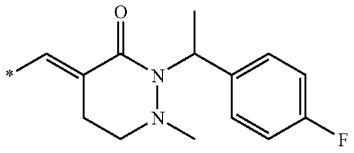 | $M^+ + H$:435 (ESI) | racemate |
| 1229 | 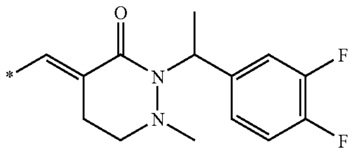 | $M^+ + H$:453 (ESI) | racemate |
| 1230 | 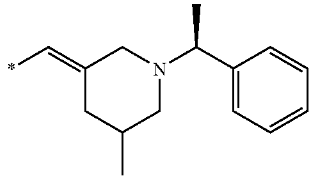 | $M^+ + H$:416 (ESI) | racemate |
| 1231 | 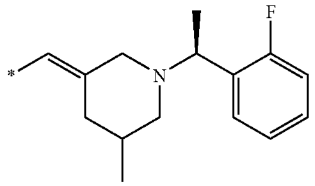 | $M^+ + H$:434 (ESI) | racemate |
| 1232 | 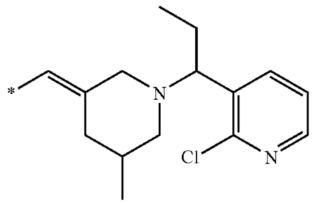 | $M^+ + H$:466 (ESI) | diasteromers-containing racemate |

TABLE 34-continued

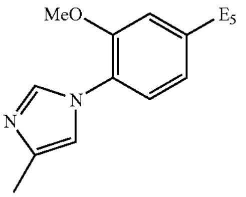

| Example | E5 | DATA: MS m/z | Notes |
|---|---|---|---|
| 1233 | 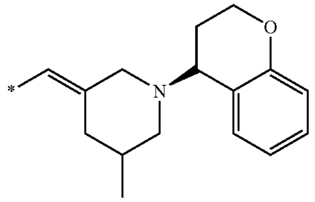 | $M^+ + H$:444 (ESI) | racemate |
| 1234 | 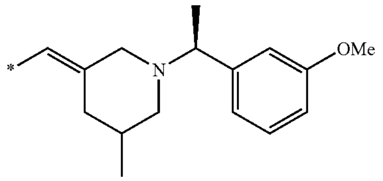 | $M^+ + H$:446 (ESI) | racemate |

The compound of the general formula (I) of the present invention has an effect to reduce the production of Aβ40 and Aβ42, hence is useful as a preventive or therapeutic agent for neurodegenerative diseases caused by Aβ, such as in particular Alzheimer's disease and Down syndrome.

What is claimed is:

1. A compound of the following formula or a pharmacologically acceptable salt thereof:

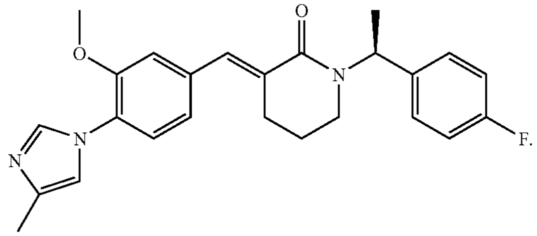

2. The pharmacologically acceptable salt of the compound of claim 1.

3. The compound of claim 1.

4. A pharmaceutical composition comprising: the compound or pharmaceutically acceptable salt thereof of claim 1; and a pharmaceutically acceptable carrier.

* * * * *

UNITED STATES PATENT AND TRADEMARK OFFICE

CERTIFICATE OF CORRECTION

PATENT NO. : 7,667,041 B2
APPLICATION NO. : 11/136355
DATED : February 23, 2010
INVENTOR(S) : Kimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this

Twenty-eighth Day of December, 2010

David J. Kappos

*Director of the United States Patent and Trademark Office*